US009617256B2

(12) United States Patent
Moser et al.

(10) Patent No.: US 9,617,256 B2
(45) Date of Patent: Apr. 11, 2017

(54) ANTIBACTERIAL AGENTS

(71) Applicant: Achaogen, Inc., South San Francisco, CA (US)

(72) Inventors: Heinz E. Moser, San Mateo, CA (US); Qing Lu, Foster City, CA (US); Phillip A. Patten, Portola Valley, CA (US); Dan Wang, Fremont, CA (US); Ramesh Kasar, Bellevue, WA (US); Stephen Kaldor, San Diego, CA (US); Brian D. Patterson, San Francisco, CA (US)

(73) Assignee: Achaogen, Inc., South San Francisco, CA (US)

( * ) Notice: Subject to any disclaimer, the term of this patent is extended or adjusted under 35 U.S.C. 154(b) by 0 days.

(21) Appl. No.: 14/223,971

(22) Filed: Mar. 24, 2014

(65) Prior Publication Data
US 2015/0018331 A1 Jan. 15, 2015

Related U.S. Application Data

(63) Continuation of application No. 12/635,551, filed on Dec. 10, 2009, now abandoned, which is a
(Continued)

(51) Int. Cl.
*C07D 471/04* (2006.01)
*C07C 259/06* (2006.01)
(Continued)

(52) U.S. Cl.
CPC .......... *C07D 471/04* (2013.01); *C07C 259/06* (2013.01); *C07D 205/04* (2013.01); *C07D 207/08* (2013.01); *C07D 207/09* (2013.01); *C07D 207/10* (2013.01); *C07D 207/12* (2013.01); *C07D 207/16* (2013.01); *C07D 207/32* (2013.01); *C07D 207/337* (2013.01); *C07D 207/46* (2013.01); *C07D 207/48* (2013.01); *C07D 209/46* (2013.01); *C07D 211/08* (2013.01); *C07D 211/26* (2013.01); *C07D 211/34* (2013.01); *C07D 211/38* (2013.01); *C07D 211/46* (2013.01); *C07D 211/94* (2013.01); *C07D 213/36* (2013.01); *C07D 213/38* (2013.01); *C07D 213/56* (2013.01); *C07D 213/61* (2013.01); *C07D 213/74* (2013.01); *C07D 217/22* (2013.01); *C07D 217/24* (2013.01); *C07D 231/12* (2013.01); *C07D 231/14* (2013.01); *C07D 231/56* (2013.01); *C07D 233/26* (2013.01); *C07D 233/36* (2013.01); *C07D 233/64* (2013.01); *C07D 239/26* (2013.01); *C07D 239/42* (2013.01); *C07D 239/70* (2013.01); *C07D 239/88* (2013.01); *C07D 239/90* (2013.01); *C07D 241/12* (2013.01); *C07D 241/52* (2013.01); *C07D 249/08* (2013.01); *C07D 261/08* (2013.01); *C07D 261/20* (2013.01); *C07D 263/32* (2013.01); *C07D 263/34* (2013.01); *C07D 263/58* (2013.01); *C07D 267/10* (2013.01); *C07D 271/107* (2013.01); *C07D 275/02* (2013.01); *C07D 277/30* (2013.01); *C07D 277/40* (2013.01); *C07D 277/46* (2013.01); *C07D 277/82* (2013.01); *C07D 285/12* (2013.01); *C07D 295/092* (2013.01); *C07D 295/096* (2013.01); *C07D 295/135* (2013.01); *C07D 295/155* (2013.01); *C07D 295/26* (2013.01); *C07D 307/14* (2013.01); *C07D 309/04* (2013.01); *C07D 309/12* (2013.01); *C07D 333/06* (2013.01); *C07D 333/24* (2013.01);
(Continued)

(58) Field of Classification Search
None
See application file for complete search history.

(56) References Cited

U.S. PATENT DOCUMENTS 2,772,281 A 11/1956 Holly et al.
5,925,659 A 7/1999 Patchett et al.
(Continued)

FOREIGN PATENT DOCUMENTS

CN 1777577 A 5/2006
CN 101209974 A 7/2008
(Continued)

OTHER PUBLICATIONS

Williams et al (Foye's Principles of Medicinal Chemistry, 5th Edition, pp. 59-61, 2002).*
(Continued)

*Primary Examiner* — Craig Ricci
(74) *Attorney, Agent, or Firm* — Cooley LLP

(57) ABSTRACT

Antibacterial compounds of formula (I) are provided:

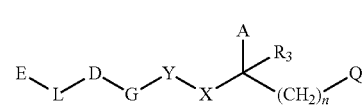

as well as stereoisomers, pharmaceutically acceptable salts, esters, and prodrugs thereof; pharmaceutical compositions comprising such compounds; methods of treating bacterial infections by the administration of such compounds; and processes for the preparation of such compounds.

7 Claims, No Drawings

Related U.S. Application Data continuation of application No. PCT/US2008/066766, filed on Jun. 12, 2008.

(60) Provisional application No. 60/943,494, filed on Jun. 12, 2007.

(51) Int. Cl.

| | | |
|---|---|---|
| C07D 205/04 | (2006.01) |
| C07D 207/08 | (2006.01) |
| C07D 207/09 | (2006.01) |
| C07D 207/10 | (2006.01) |
| C07D 207/12 | (2006.01) |
| C07D 207/16 | (2006.01) |
| C07D 207/32 | (2006.01) |
| C07D 207/337 | (2006.01) |
| C07D 207/46 | (2006.01) |
| C07D 207/48 | (2006.01) |
| C07D 209/46 | (2006.01) |
| C07D 211/08 | (2006.01) |
| C07D 211/26 | (2006.01) |
| C07D 211/34 | (2006.01) |
| C07D 211/38 | (2006.01) |
| C07D 211/46 | (2006.01) |
| C07D 211/94 | (2006.01) |
| C07D 213/36 | (2006.01) |
| C07D 213/38 | (2006.01) |
| C07D 213/56 | (2006.01) |
| C07D 213/61 | (2006.01) |
| C07D 217/22 | (2006.01) |
| C07D 217/24 | (2006.01) |
| C07D 231/12 | (2006.01) |
| C07D 231/14 | (2006.01) |
| C07D 231/56 | (2006.01) |
| C07D 233/26 | (2006.01) |
| C07D 233/36 | (2006.01) |
| C07D 233/64 | (2006.01) |
| C07D 239/26 | (2006.01) |
| C07D 239/42 | (2006.01) |
| C07D 239/88 | (2006.01) |
| C07D 239/90 | (2006.01) |
| C07D 241/12 | (2006.01) |
| C07D 241/52 | (2006.01) |
| C07D 249/08 | (2006.01) |
| C07D 261/08 | (2006.01) |
| C07D 261/20 | (2006.01) |
| C07D 263/32 | (2006.01) |
| C07D 263/34 | (2006.01) |
| C07D 263/58 | (2006.01) |
| C07D 267/10 | (2006.01) |
| C07D 271/107 | (2006.01) |
| C07D 275/02 | (2006.01) |
| C07D 277/30 | (2006.01) |
| C07D 277/40 | (2006.01) |
| C07D 277/46 | (2006.01) |
| C07D 277/82 | (2006.01) |
| C07D 285/12 | (2006.01) |
| C07D 295/092 | (2006.01) |
| C07D 295/096 | (2006.01) |
| C07D 295/135 | (2006.01) |
| C07D 295/155 | (2006.01) |
| C07D 295/26 | (2006.01) |
| C07D 307/14 | (2006.01) |
| C07D 309/04 | (2006.01) |
| C07D 309/12 | (2006.01) |
| C07D 333/06 | (2006.01) |
| C07D 333/24 | (2006.01) |
| C07D 333/34 | (2006.01) |
| C07D 333/36 | (2006.01) |
| C07D 335/02 | (2006.01) |
| C07D 413/04 | (2006.01) |
| C07D 213/74 | (2006.01) |
| C07D 239/70 | (2006.01) |

(52) U.S. Cl.
CPC ......... *C07D 333/34* (2013.01); *C07D 333/36* (2013.01); *C07D 335/02* (2013.01); *C07D 413/04* (2013.01)

(56) References Cited

U.S. PATENT DOCUMENTS

| | | |
|---|---|---|
| 6,218,389 B1 | 4/2001 | Almstead et al. |
| 6,228,988 B1 | 5/2001 | Floyd et al. |
| 6,281,245 B1 | 8/2001 | Patel et al. |
| 6,358,987 B1 | 3/2002 | Beckett et al. |
| 6,541,276 B2 | 4/2003 | Patel et al. |
| 7,358,359 B2 | 4/2008 | Andersen et al. |
| 7,691,843 B2 | 4/2010 | Raju et al. |
| 7,989,660 B2 | 8/2011 | Andersen et al. |
| 8,084,615 B2 | 12/2011 | Andersen et al. |
| 8,101,640 B2 | 1/2012 | Andersen et al. |
| 8,153,843 B2 | 4/2012 | Andersen et al. |
| 2001/0053555 A1 | 12/2001 | Patel et al. |
| 2004/0229955 A1* | 11/2004 | Andersen ............... C07C 233/83 514/616 |
| 2006/0154988 A1 | 7/2006 | Andersen et al. |
| 2007/0066646 A1 | 3/2007 | Clauzel et al. |
| 2007/0244197 A1 | 10/2007 | Andersen et al. |
| 2008/0269221 A1 | 10/2008 | Andersen et al. |
| 2009/0163496 A1 | 6/2009 | Andersen et al. |
| 2009/0247506 A1 | 10/2009 | Andersen et al. |
| 2010/0120872 A1 | 5/2010 | Dobler et al. |
| 2010/0190766 A1 | 7/2010 | Moser et al. |
| 2010/0324025 A1 | 12/2010 | Andersen et al. |
| 2011/0172174 A1 | 7/2011 | Andersen et al. |
| 2012/0283175 A1 | 11/2012 | Patten et al. |
| 2015/0175530 A1 | 6/2015 | Patterson et al. |
| 2015/0203444 A1 | 7/2015 | Trend et al. |

FOREIGN PATENT DOCUMENTS

| | | |
|---|---|---|
| JP | 3155536 | 2/2001 |
| TW | 200706534 A | 5/1995 |
| WO | WO 96/26223 A1 | 8/1996 |
| WO | WO 97/05105 A1 | 2/1997 |
| WO | WO 97/42179 A1 | 11/1997 |
| WO | WO 98/15525 A1 | 4/1998 |
| WO | WO 98/18754 A1 | 5/1998 |
| WO | WO 98/22494 A2 | 5/1998 |
| WO | WO 99/06340 A2 | 2/1999 |
| WO | WO 99/19296 A1 | 4/1999 |
| WO | WO 99/39704 A1 | 8/1999 |
| WO | WO 99/57097 A2 | 11/1999 |
| WO | WO 00/02904 A1 | 1/2000 |
| WO | WO 00/44373 A1 | 8/2000 |
| WO | WO 00/59874 A1 | 10/2000 |
| WO | WO 00/61134 A1 | 10/2000 |
| WO | WO 02/26696 A1 | 4/2002 |
| WO | WO 02/30873 A1 | 4/2002 |
| WO | WO 02/50081 A2 | 6/2002 |
| WO | WO 03/004488 A1 | 1/2003 |
| WO | WO 03/101382 A2 | 12/2003 |
| WO | WO 2004/007444 A2 | 1/2004 |
| WO | WO 2004/035525 A1 | 4/2004 |
| WO | WO 2004/062601 A2 | 7/2004 |
| WO | WO 2006/127576 A2 | 11/2006 |
| WO | WO 2006/131303 A2 | 12/2006 |
| WO | WO 2007/064732 A1 | 6/2007 |
| WO | WO 2007/069020 A2 | 6/2007 |
| WO | WO 2008/027466 A1 | 3/2008 |

(56) References Cited

FOREIGN PATENT DOCUMENTS

| WO | WO 2008/105515 A1 | 9/2008 |
|---|---|---|
| WO | WO 2008/154642 A2 | 12/2008 |
| WO | WO 2009/158369 A1 | 12/2009 |
| WO | WO 2010/017060 A1 | 2/2010 |
| WO | WO 2010/024356 A1 | 3/2010 |
| WO | WO 2010/031750 A1 | 3/2010 |
| WO | WO 2010/032147 A2 | 3/2010 |
| WO | WO 2010/100475 A1 | 9/2010 |
| WO | WO 2011/005355 A1 | 1/2011 |
| WO | WO 2011/045703 A2 | 4/2011 |
| WO | WO 2011/073845 A1 | 6/2011 |
| WO | WO 2011/132712 A1 | 10/2011 |
| WO | WO 2012/154204 A1 | 11/2012 |
| WO | WO 2013/039947 A1 | 3/2013 |
| WO | WO 2013/170030 A1 | 11/2013 |
| WO | WO 2013/170165 A1 | 11/2013 |

OTHER PUBLICATIONS

CAS RN 728865-32-5 (entered into STN on Aug. 19, 2004).*
CAS Registry Database, CAS Registry 202273-66-3, Mar. 5, 1998 (1 page).
Database CAPLUS on STN, Acc. No. 1999:113626, Almstead et al., WO 9906340 (Feb. 11, 1999) abstract (2 pages).
Anderson, "The Process of Structure-Based Drug Design," *Chemistry & Biology*, vol. 10, 787-797, Sep. 2003.
Angus et al., "Outer Membrane Permeability in *Pseudomonas aeruginosa*: Comparison of a Wild-type with an Antibiotic-Supersusceptible Mutant," *Antimicrobial Agents and Chemotherapy*. 21(2):299-309, Feb. 1982.
Arcadi et al., "Synthesis of New Cardanol Derivatives through Combined Iodination/Palladium-Catalysed Cross-Coupling Reactions," *Synthesis* 15:2523-2530, 2006.
Baker et al., "An Antimalarial Alkaloid From Hydrangea. XV. Synthesis of 5-, 6-, 7-, and 8 Derivatives With Two Identical Substituents," *J. Org. Chem.* 17(1):149-156, Jan. 1952.
Barb et al., "Inhibition of Lipid A Biosynthesis as the Primary Mechanism of CHIR-090 Antibiotic Activity in *Escherichia coli*," *Biochemistry* 46(12):3793-3802, 2007.
Bergeron et al., "Effects of C-4 Stereochemistry and C-4' Hydroxylation on the Iron Clearing Efficiency and Toxicity of Desferrithiocin Analogues," *J. Med. Chem.* 42(13):2432-2440, 1999.
Boyce et al., "Total Synthesis of Thiangazole, A Novel Naturally Occurring HIV-1 Inhibitor from *Polyangium* sp," *Tetrahedron* 51(26):7321-7330, 1995.
Brooks et al., "Modulators of Leukotriene Biosynthesis and Receptor Activation," *Journal of Medicinal Chemistry* 39(14):2629-2654, 1996.
Brown et al., "Potent Inhibitors of LpxC for the Treatment of Gram-Negative Infections," *J. Med. Chem.* 55(2):914-923 (2012).
Burger's Medicinal Chemistry and Drug Discovery, 5$^{th}$ Ed., vol. 1, Manfred E. Wolff ed., John Wiley & Sons, New York, pp. 975-977, 1995.
Byrne et al., "Antibiotic Treatment of Experimental Pneumonic Plague in Mice," *Antimicrobial Agents and Chemotherapy* 42(3):675-681, Mar. 1998.
CAS Registry Database, CAS Registry 71972-38-8, Nov. 16, 1984.
Charette et al., "Mild Method for the Synthesis of Thiazolines from Secondary and Tertiary Amides," *J. Org. Chem.* 63(4):908-909, 1998.
Chen et al "Carbohydroxamido-Oxazolidines: Antibacterial Agents That Target Lipid A Biosynthesis," *Bioorganic & Medicinal Chemistry Letters* 9:313-318, 1999.
Clements et al., "Antibacterial Activities and Characterization of Novel Inhibitors of LpxC," *Antimicrobial Agents and Chemotherapy* 46(6):1793-1799, Jun. 2002.
Coghlan et al., "A one-pot three-component synthesis of β-nitro-α-amino acids and their N-alkyl derivatives," *J. Chem. Soc., Perkin Trans.* 1:2659-2660, 1999.
Cuny, G. D., "A new class of UDP-3-O-(R-3-hydroxymyristol)-N-acetylglucosamine deacetylase (LpxC) inhibitors for the treatment of Gram-negative infections: PCT application WO 2008027466," *Expert Opin. Ther. Patents* 19(6):893-899, 2009.
Daku et al., "Suzuki cross-coupling reactions using reverse-phase glass beads in aqueous media," *Tetrahedron Letters* 44:5095-5098, 2003.
Dong et al. "Total Synthesis of Exochelin MN and Analogues," *J. Org. Chem.* 67(14):4759-4770, 2002.
Farnum et al., "The Nuclear Magnetic Resonance Spectra of Cyclic 1,3-Diphenylallyl Cations. Some Observations on 1,3-Orbital Interaction," *J. Org. Chem.* 36(5):698-702, 1971.
Fernandez et al., "Novel synthesis of 2-thiazolines," *Tetrahedron Letters* 41:3381-3384, 2000.
Database CAPLUS on STN, Acc. No. 1911:22205, Fourneau, "Amino Alcohols and Derivatives with Therapeutic Properties. II," *Journal de Pharmacie et de Chimie*, 2:109-17, 1911.
Fushiya et al., "4-N-Hydroxy-L-2,4-diaminobutyric Acid. A Strong Inhibitor of Glutamine Synthetase," *J. Med. Chem.* 31(2):480-483, 1988.
Galéotti et al., "Synthesis of Peptidyl Aldehydes from Thiazolidines," *Tetrahedron Letters* 38(14):2459-2462, 1997.
Gallant et al., "Structure—Activity Relationship of Triaryl Propionic Acid Analogues on the Human EP$_3$ Prostanoid Receptor," *Bioorganic & Medicinal Chemistry Letters* 13(21):3813-3816, 2003.
Goodman & Gilman, "The Pharmacological Basis of Therapeutics," Sixth Edition, Alfred Goodman Gilman et al., eds., Macmillan, New York, pp. 1097-1098, 1980.
Greco et al., "The Search for Synergy: A Critical Review from a Response Surface Perspective," *Pharmacological Reviews* 47(2):331-385, 1995.
Guyton A.C., "Measurement of the Respiratory Volume of Laboratory Animals," *Am. J. Physiol.* 150:70-77, 1947.
Hartings et al., "The automated bioaerosol exposure system: Preclinical platform development and a respiratory dosimetry application with nonhuman primates," *Journal of Pharmacological and Toxicological Methods* 49:39-55, 2004.
Hyland et al., "Cloning, Expression, and Purification of UDP-3-O-Acyl-GlcNAc Deacetylase from *Pseudomonas aeruginosa*: a Metalloamidase of the Lipid A Biosynthesis Pathway," *Journal of Bacteriology* 179(6):2029-2037, Mar. 1997.
Ito et al., "Synthetic Reactions by Complex Catalysts. XXXI. A Novel and Versatile Method of Heterocycle Synthesis," *Journal of the American Chemical Society* 95(13):4447-4448, Jun. 27, 1973.
Ito et al., "Synthetic Reactions by Complex Catalysts. XXXV. A Facile Synthetic Method of Cyclic Imino Ethers and Imino Thioethers," *Synthetic Communications* 4(2):97-103, 1974.
Jackman et al., "Antibacterial Agents that Target Lipid A Biosynthesis in Gram-Negative Bacteria," *The Journal of Biological Chemistry* 275(15):11002-11009, Apr. 14, 2000.
Jeng et al., "Endothelin Converting Enzyme Inhibitors," *Current Pharmaceutical Design* 3(6):597-614, 1997.
Jones, R. N., "Resistance Patterns Among Nosocomial Pathogens. Trends Over the Past Few Years," *Chest.* 119(Suppl 2):397S-404S, 2001.
Juaristi et al., "Use of Hexamethylphosphoramide (HMPA) in the Alkylation of Aromatic Amines: Synthesis of Azetidines, Pyrrolidines, Piperidines and Hexahydroazephines," *Tetrahedron* 45(3):629-636, 1989.
Khan et al., "An Alternative Method for the Synthesis of γ-Lactones by Using Cesium Fluoride-Celite/Acetonitrile Combination," *Synthetic Communications* 33(19):3435-3453, 2003.
Khan et al., "A Facile and Convenient Solid-Phase Procedure for Synthesizing Nucleoside Hydroxamic Acids," *Tetrahedron Letters* 39:8031-8034, 1998.
Database CAPLUS on STN, Acc. No. 1997:224101, Kleinman, WO 9705105 (Feb. 13, 1997) abstract (1 page).
Database CAPLUS on STN, Acc. No. 2002:429779, Kline et al., *Journal of Medicinal Chemistry* (2002), 45(14), 3112-3129, abstract (1 page).

(56) References Cited

OTHER PUBLICATIONS

Kline et al., "Potent, Novel in Vitro Inhibitors of the *Pseudomonas aeruginosa* Deacetylase LpxC," *J. Med. Chem.* 45(14):3112-3129, 2002.
Krasovitskii et al., "4-(5-Aryl-2-Oxazolyl)Phthalic Anhydrides," *Chemistry of Heterocyclic Compounds* 15(1):28-31, Jul. 1979.
Lee et al., "Species-Specific and Inhibitor-Dependent Conformations of LpxC: Implications for Antibiotic Design," *Chemistry & Biology* 18:38-47, Jan. 28, 2011.
Liang et al., "Syntheses, structures and antibiotic activities of LpxC inhibitors based on the diacetylene scaffold," *Bioorganic & Medicinal Chemistry* 19:852-860, 2011.
Lopez et al., "Potency and Efficacy of Small Molecule Inhibitors of the Gram-Negative Bacterial Enzyme LpxC Against Yersinia Pestis and Other Enterobacteriaceae," Poster W032, Poster presentation, the Chemical and Biological Defense Science and Technology (CBD S&T) Conference, Dallas, Texas, Nov. 2009 (1 page).
Lopez et al., "Small Molecule LpxC Inhibitors of Burkholderia Mallei and Burkholderia Psuedomallei: In Vitro and In Vivo Potency and Efficacy," Poster WO33, Poster presentation, the Chemical and Biological Defense Science and Technology (CBD S&T) Conference, Dallas, Texas, Nov. 2009 (1 page).
Matier et al., "Antihypertensive Agents. Synthesis and Biological Properties of 2-Amino-4-aryl-2-imidazolines," *Journal of Medicinal Chemistry* 16(8):901-908, 1973.
Matsuda et al., "Nucleosides and Nucleotides. 95. Improved Synthesis of 1-(2-Azido-2-deoxy-β-D-arabinofuranosyl)cytosine (Cytarazid) and -thymine. Inhibitory Spectrum of Cytarazid on the Growth of Various Human Tumor Cells in Vitro," *J. Med. Chem.* 34(3):999-1002, 1991.
May, K.R., "The Collison Nebulizer: Description, Performance and Application," *Aerosol Science* 4:235-243, 1973.
McClerren et al., "A Slow, Tight-Binding Inhibitor of the Zinc-Dependent Deacetylase LpxC of Lipid A Biosynthesis with Antibiotic Activity Comparable to Ciprofloxacin," *Biochemistry* 44(50):16574-16583 (XP-002499759), 2005.
Mellor et al., "N-Fmoc-aminooxy-2-chlortrityl polystyrene resin: A facile solid-phase methodology for the synthesis of hydroxamic acids," *Tetrahedron Letters* 38(18):3311-3314, 1997.
Metcalf et al., "Catalytic Irreversible Inhibition of Mammalian Ornithine Decarboxylase (E.C. 4.1.1.17) by Substrate and Product Analogues," *Journal of the American Chemical Society* 100(8):2551-2553, Apr. 12, 1978.
"Modern Pharmaceutics," 3rd Ed., Gilbert S. Banker et al., ed., Marcel Dekker, Inc., New York, p. 596, 1996.
Montgomery et al., "Pyridone Methylsulfone Hydroxamate LpxC Inhibitors for the Treatment of Serious Gram-Negative Infections," *J. Med Chem* 44(4):1662-70 (2012).
Mori et al., "Sonogashira Coupling with Aqueous Ammonia," *Chemistry Letters* 31(7):756-757, 2002.
Neset et al., "Synthesis of Cyclic Hydroxamic Acids by Oxidation of Secondary Amines with Dimethyldioxirane," *Acta Chemica Scandinavica* 47:1141-1143, 1993.
Neumeyer et al., "Isoquinolines. 2. 3-(Dialkylaminoalkylamino)isoquinolines as Potential Antimalarial Drugs," *Journal of Medicinal Chemistry* 13(5):999-1002, 1970.
Ngu et al., "A New and Efficient Solid Phase Synthesis of Hydroxamic Acids," *J. Org. Chem.* 62(21):7088-7089, 1997.
Nicolaus, J. R., "Symbiotic Approach to Drug Design," in Decision Making in Drug Research, Franz Gross, ed., Raven Press, New York, pp. 173-186, 1983.
Nikaido, H., "Antibacterial Resistance Caused by Gram-Negative Multidrug Efflux Pumps," *Clinical Infectious Diseases* 27(Supp 1):S32-S41, 1998.
Numata et al., "General Synthetic Method for Naphthyridines and Their N-Oxides Containing Isoquinolinic Nitrogen," *Synthesis* 2:306-3011, 1999.
Onishi et al., "Antibacterial Agents That Inhibit Lipid A Biosynthesis," *Science* 274:980-982, Nov. 8, 1996.
O'Shea et al., "Physicochemical Properties of Antibacterial Compounds: Implications for Drug Discovery," *Journal of Medicinal Chemistry* 51(10):2871-2878, May 22, 2008.
Padwa et al., "1,3-Dipolar Cycloadditions of Nitrones Derived from the Reaction of Acetylenes with Hydroxylamines," *J. Org. Chem.* 51(16):3125-3133, 1986.
Patani et al., "Bioisosterism: A Rational Approach in Drug Design," *Chem. Rev.* 96:3147-3176, 1996.
Database CAPLUS on STN, Acc. No. 1997:746038, Patchett et al., WO 9742179 (Nov. 13, 1997) abstract (2 pages).
Pattenden et al., "Naturally Occurring Linear Fused Thiazoline-Thiazole Containing Metabolites: Total Synthesis of (−)—Didehydromirabazole A, a Cytotoxic Alkaloid from Blue-Green Algae," *J. Chem. Soc. Perkin Trans.* 1:1629-1636, 1993.
Pirrung et al., "A Convenient Procedure for the Preparation of Amino Acid Hydroxamates from Esters," *J. Org. Chem.* 60(24):8084-8085, 1995.
Pirrung et al., "Inhibition of the Antibacterial Target UDP-(3-O-acyl)-N-acetylglucosamine Deacetylase (LpxC): Isoxazoline Zinc Amidase Inhibitors Bearing Diverse Metal Binding Groups," *J. Med. Chem.* 45(19):4359-4370, 2002.
Pirrung et al., "High-Throughput Catch-and-Release Synthesis of Oxazoline Hydroxamates. Structure—Activity Relationships in Novel Inhibitors of *Escherichia coli* LpxC: In Vitro Enzyme Inhibition and Antibacterial Properties," *J. Am. Chem. Soc.* 125(6):1575-1586, 2003.
Powell et al., "Practical Sythesis of 1-Aryl-6-(hydroxymethyl)-2-ketopiperazines via a 6-*exo* Amide—Epoxide Cyclization," *Org. Lett.* 6(22):4069-4072, 2004.
Raman et al., "Titanium(IV)-Mediated Tandem Deprotection-Cyclodehydration of Protected Cysteine N-Amides: Biomimetic Syntheses of Thiazoline- and Thiazole-Containing Heterocycles," *Org. Lett.* 2(21):3289-3292, 2000.
Righi et al., "Solution- and Solid-Phase Synthesis of 4-Hydroxy-4,5-dihydroisoxazole Derivatives from Enantiomerically Pure N-Tosyl-2,3-aziridine Alcohols," *Org. Lett.* 4(4):497-500, 2002.
Sahm et al., "Evaluation of Current Activities of Fluoroquinolones against Gram-Negative Bacilli Using Centralized In Vitro Testing and Electronic Surveillance," *Antimicrobial Agents and Chemotherapy* 45(1):267-274, Jan. 2001.
Sam et al., "Benzoxazoles: Potent Skeletal Muscle Relaxants," *Journal of Pharmaceutical Sciences* 53(5):538-544, May 1964.
Scribner et al., "Activities of Various β-Lactams and Aminoglycosides Along and in Combination, Against Isolates of *Pseudomonas aeruginosa* from Patients with Cystic Fibrosis," *Antimicrobial Agents and Chemotherapy* 21(6):939-943, Jun. 1982.
Shen et al., "Synthesis of 1,3-Diynes via Palladium-Catalyzed Reaction of 1,1-Dibromo-1-alkenes," *Org. Lett.* 2(18):2857-2860, 2000.
Shen et al., "The Stille Reaction of 1,1-Dibromo-1-alkenes: Preparation of Trisubstituted Alkenes and Internal Alkynes," *J. Org. Chem.* 64(24):8873-8879, 1999.
Sigman et al., "Free Energy and Structure Dependence of Intramolecular Triplet Energy Transfer in Organic Model Compounds," *J. Phys. Chem.* 95(13):5012-5017, 1991.
Skotnicki et al., "Design strategies for the identification of MMP-13 and TACE Inhibitors," *Current Opinion in Drug Discovery & Development* 6(5):742-759, 2003.
Stella et al., "Prodrugs: Challenges and Rewards. Part 1," *Biotechnology: Pharmaceutical Aspects*, 2007.
Stobbe et al., "Lichtreaktionen der *trans*- und *cis*-Zimtsäuren," *Berichte der Deutschen Chemischen Gesellschaft* 55(8):2225-2245, Sep. 16, 1922.
Süsse et al., "Chinazolincarbonsäuren. VII. Mitteilung. Ein einfacher Zugang zu (4-Oxo-3,4-dihydrochinazolin-3-yl)-alkansäuren, (4-Oxo-3,4-dihydro-1,2,3-benzotriazin-3-yl)-alkansäuren und deren Estern," *Helvetica Chimica Acta* 68:892-899, 1985.
Thiel, "Structure-aided drug design's next generation," *Nature Biotechnology* 22(5):513-519, May 2004.
Vaara et al., "Antibiotic-Supersusceptible Mutants of *Escherichia coli* and *Salmonella typhimurium*," *Antimicrobial Agents and Chemotherapy* 37(11):2255-2260, Nov. 1993.

(56) References Cited

OTHER PUBLICATIONS

Vachal et al. "General facile synthesis of 2,5-diarylheteropentalenes," *Tetrahedron Letters* 45:7157-7161, 2004.
van den Haak et al., "Chichibabin Amination of 1,X-Naphthyridines. Nuclear Magnetic Resonance Studies on the σ Adducts of Heterocyclic Systems with Nucleophiles," *J. Org. Chem.* 46(10):2134-2137, 1981.
Williams et al., "Foye's Principles of Medicinal Chemistry," Fifth Edition, Lippincott Williams & Wilkins, pp. 59-63, 2002.
Wipf et al., "Thiolysis of Oxazolines: A New, Selective Method for the Direct Conversion of Peptide Oxazolines Into Thiazolines," *Tetrahedron Letters* 36(36):6395-6398, 1995.
Witte et al., "Cyclische Imidsäureester aus Nitrilen und Aminoalkoholen," *Liebigs Ann. Chem.* 996-1009, 1974.
Wyckoff et al., "Antibacterial and anti-inflammatory agents that target endotoxin," *Trends in Microbiology* 6(4):154-159, Apr. 1998.
Yoon et al., "Oxygen-Promoted Palladium(II) Catalysis: Facile $C(sp^2)$—$C(sp^2)$ Bond Formation via Cross Coupling of Alkenylboronic Compounds and Olefins," *Org. Lett.* 6(22):4037-4039, 2004.
Young et al., "Leakage of Periplasmic Enzymes from *envA1* Strains of *Escherichia coli*," *Journal of Bacteriology* 173(12):3609-3614, Jun. 1991.
Youngman et al., "The Synthesis of Novel *cis*-α-Substituted-β-aminotetralins," *Synthetic Communications* 33(13):2215-2227, 2003.
Zask et al., "Inhibition of Matrix Metalloproteinases: Structure Based Design," *Current Pharmaceutical Design* 2(6):624-661, 1996.
Zhang et al., "Design, Combinatorial Chemical Synthesis, and In Vitro Characterization of Novel Urea Based Gelatinase Inhibitors," *Bioorganic & Medicinal Chemistry Letters* 9:2823-2826, 1999.
Zhu et al., "Isoquinoline—pyridine-based protein kinase B/Akt antagonists: SAR and in vivo antitumor activity," *Bioorganic & Medicinal Chemistry Letters* 16(12):3150-3155, Jun. 15, 2006.
Supplementary Partial European Search Report for European Patent Application No. 04700887.5, dated Sep. 27, 2006.
Supplementary Partial European Search Report for European Patent Application No. 04700887.5, dated Jan. 2, 2007.
Extended European Search Report for European Patent Application No. 10179798.3, dated Jul. 4, 2011.
Invitation to Pay Additional Fees for PCT/US2013/040571, mailed Jul. 29, 2013.
International Search Report for PCT/US2004/000433, dated Jan. 19, 2005.
International Search Report for PCT/US2008/066766, dated May 29, 2009.
International Search Report for PCT/US2010/033910, dated Dec. 3, 2010.
Written Opinion of the International Searching Authority for PCT/US2004/000433, dated Jan. 19, 2005.
Written Opinion of the International Searching Authority for PCT/US2008/066766, dated May 29, 2009.
Written Opinion of the International Searching Authority for PCT/US2010/033910, dated Dec. 3, 2010.
International Preliminary Report on Patentability for PCT/US2004/000433, dated Jul. 8, 2005.
International Preliminary Report on Patentability for PCT/US2008/066766, dated Dec. 17, 2009.
International Preliminary Report on Patentability for PCT/US2010/033910, dated Nov. 9, 2011.
International Preliminary Report on Patentability for PCT/US2011/059280, dated May 14, 2013.
International Preliminary Report on Patentability for PCT/US2012/054718, dated Mar. 20, 2014.
International Search Report and Written Opinion for PCT/US2011/059280, dated Sep. 5, 2012.
International Search Report and Written Opinion for PCT/US2012/054718, dated Nov. 27, 2012.
International Search Report and Written Opinion for PCT/US2013/040571, dated Sep. 25, 2013.
Non-Final Office Action received for U.S. Appl. No. 10/754,928, dated Jun. 23, 2005.
Non-Final Office Action received for U.S. Appl. No. 10/754,928, dated Aug. 11, 2005.
Final Rejection received for U.S. Appl. No. 10/754,928, dated Apr. 21, 2006.
Final Rejection received for U.S. Appl. No. 10/754,928, dated Jul. 13, 2006.
Non-Final Office Action received for U.S. Appl. No. 11/187,708, dated Mar. 29, 2007.
Non-Final Office Action received for U.S. Appl. No. 11/187,708, dated Aug. 10, 2007.
Notice of Allowance received for U.S. Appl. No. 11/187,708, dated Oct. 25, 2007.
Notice of Allowance received for U.S. Appl. No. 11/187,708, dated Jan. 7, 2008.
Non-Final Office Action received for U.S. Appl. No. 11/417,346, dated Sep. 17, 2007.
Non-Final Office Action received for U.S. Appl. No. 11/417,346, dated May 22, 2008.
Notice of Allowance received for U.S. Appl. No. 11/417,346, dated Nov. 17, 2008.
Non-Final Office Action received for U.S. Appl. No. 11/417,346, dated Mar. 20, 2009.
Non-Final Office Action received for U.S. Appl. No. 11/894,208, dated Apr. 6, 2010.
Final Rejection received for U.S. Appl. No. 11/894,208, dated Nov. 15, 2010.
Non-Final Office Action received for U.S. Appl. No. 11/894,208, dated May 31, 2012.
Notice of Abandonment received for U.S. Appl. No. 11/894,208, dated Dec. 6, 2012.
Non-Final Office Action received for U.S. Appl. No. 11/928,122, dated Aug. 6, 2008.
Non-Final Office Action received for U.S. Appl. No. 11/928,122, dated Dec. 3, 2008.
Non-Final Office Action received for U.S. Appl. No. 11/928,122, dated Aug. 11, 2009.
Final Rejection received for U.S. Appl. No. 11/928,122, dated May 13, 2010.
Advisory Action received for U.S. Appl. No. 11/928,122, dated Jul. 14, 2010.
Notice of Allowance received for U.S. Appl. No. 11/928,122, dated Jul. 21, 2011.
Notice of Allowance received for U.S. Appl. No. 11/928,122, dated Oct. 4, 2011.
Non-Final Office Action received for U.S. Appl. No. 11/837,327, dated May 5, 2008.
Non-Final Office Action received for U.S. Appl. No. 11/837,327, dated Jul. 10, 2008.
Final Rejection received for U.S. Appl. No. 11/837,327, dated Jan. 27, 2009.
Non-Final Office Action received for U.S. Appl. No. 11/837,327, dated Mar. 4, 2010.
Final Rejection received for U.S. Appl. No. 11/837,327, dated Jul. 14, 2010.
Advisory Action received for U.S. Appl. No. 11/837,327, dated Sep. 21, 2010.
Notice of Allowance received for U.S. Appl. No. 11/837,327, dated Dec. 17, 2010.
Notice of Allowance received for U.S. Appl. No. 11/837,327, dated Mar. 23, 2011.
Non-Final Office Action received for U.S. Appl. No. 12/563,697, dated Jan. 4, 2011.
Non-Final Office Action received for U.S. Appl. No. 12/563,697, dated Aug. 8, 2011.
Notice of Allowance received for U.S. Appl. No. 12/563,697, dated Nov. 23, 2011.
Non-Final Office Action received for U.S. Appl. No. 11/981,279, dated Apr. 18, 2011.

(56) References Cited

OTHER PUBLICATIONS

Non-Final Office Action received for U.S. Appl. No. 11/981,279, dated Jul. 21, 2011.
Notice of Allowance received for U.S. Appl. No. 11/981,279, dated Oct. 31, 2011.
Non-Final Office Action received for U.S. Appl. No. 12/635,551, dated Jan. 5, 2012.
Non-Final Office Action received for U.S. Appl. No. 12/635,551, dated Apr. 3, 2012.
Non-Final Office Action received for U.S. Appl. No. 12/635,551, dated Mar. 27, 2013.
Final Rejection received for U.S. Appl. No. 12/635,551, dated Sep. 25, 2012.
Final Rejection received for U.S. Appl. No. 12/635,551, dated Oct. 24, 2013.
Non-Final Office Action received for U.S. Appl. No. 12/638,525, dated Dec. 22, 2010.
Non-Final Office Action received for U.S. Appl. No. 12/638,525, dated Feb. 16, 2011.
Non-Final Office Action received for U.S. Appl. No. 12/638,525, dated Aug. 12, 2011.
Non-Final Office Action received for U.S. Appl. No. 13/248,782, dated Mar. 28, 2012.
Non-Final Office Action received for U.S. Appl. No. 13/248,782, dated Jul. 31, 2012.
Non-Final Office Action received for U.S. Appl. No. 13/289,212, dated Oct. 17, 2012.
Non-Final Office Action received for U.S. Appl. No. 13/289,212, dated Jan. 16, 2013.
Non-Final Office Action received for U.S. Appl. No. 13/289,212, dated Jul. 17, 2013.
Notice of Abandonment received for U.S. Appl. No. 13/289,212, dated Jan. 31, 2014.
Nakatani, S. et al., "Design and synthesis of novel metalloproteinase inhibitors", *Bioorganic & Medicinal Chemistry*, 14: 5402-5422 (2006).
Restriction Requirement for U.S. Appl. No. 14/536,286, dated Jul. 30, 2015 (10 pages).
Restriction Requirement for U.S. Appl. No. 13/611,149, dated Jul. 31, 2015 (6 pages).
Oslo (editor), Remington's Pharmaceutical Sciences, 1990, Philadephia College of Pharmaceutical Science, Chapter 27: Structure-Activity Relationship and Drug Design, pp. 420-435.
Restriction Requirement received for U.S. Appl. No. 13/289,209, dated Aug. 1, 2014 (15 pages).
Office Action received for U.S. Appl. No. 13/289,209, dated Feb. 27, 2015 (18 pages).
Invitation to Pay Additional Fees for PCT/US2014/024304 mailed Jul. 1, 2014, 5 pages.
International Search Report and Written Opinion for PCT/US2013/040350 mailed Sep. 2, 2013, 10 pages.
International Search Report and Written Opinion for PCT/US2014/024304 mailed Sep. 12, 2014, 12 pages.
International Preliminary Report on Patentability for PCT/US2013/040350 mailed Nov. 20, 2014, 9 pages.
International Preliminary Report on Patentability for PCT/US2013/040571 mailed Nov. 20, 2014, 11 pages.
Auwers et al., "Über halogenierte Indazole und Raumisomerie bei freien Indazolen," *Berichte der Deutschen Chemischen Gesellschaft* 55(3):1139-1173, Mar. 11, 1922.
U.S. Appl. No. 13/289,209, filed Nov. 4, 2011, which is pending (not yet published).
U.S. Appl. No. 13/611,149, filed Sep. 12, 2012, which is pending (not yet published).
U.S. Appl. No. 14/536,286, filed Nov. 7, 2014, which is pending (not yet published).
U.S. Appl. No. 14/537,048, filed Nov. 10, 2014, which is pending (not yet published).

\* cited by examiner

ANTIBACTERIAL AGENTS

CROSS-REFERENCE TO RELATED APPLICATIONS

This application is a continuation of U.S. patent application Ser. No. 12/635,551, filed Dec. 10, 2009, now pending, which is a continuation of International PCT Application No. PCT/US2008/066766, filed Jun. 12, 2008, which claims the benefit under 35 U.S.C. §119(e) of U.S. Provisional Patent Application No. 60/943,494, filed Jun. 12, 2007. The foregoing applications are incorporated herein by reference in their entireties.

STATEMENT OF GOVERNMENT INTEREST

This invention was made with government support under Contract No. HDTRA1-07-C-0079 awarded by the United States Department of Defense. The government has certain rights in this invention.

BACKGROUND OF THE INVENTION

Field of the Invention

This invention pertains generally to treating infections caused by gram-negative bacteria. More specifically, the invention described herein pertains to treating gram-negative infections by inhibiting activity of UDP-3-O—(R-3-hydroxydecanoyl)-N-acetylglucosamine deacetylase (LpxC). The present invention provides small molecule inhibitors of LpxC, pharmaceutical formulations containing such inhibitors, methods of treating patients with such pharmaceutical formulations, and methods of preparing such pharmaceutical formulations and inhibitors. The inhibitors can be used to treat gram-negative infections of patients alone and in combination with other antibacterials.

Description of the Related Art

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial infections occurring each year in the United States, 50 to 60% are caused by antimicrobial-resistant strains of bacteria. This high rate of resistance increases the morbidity, mortality, and costs associated with nosocomial infections. In the United States, nosocomial infections are thought to contribute to or cause more than 77,000 deaths per year and cost approximately $5 to $10 billion annually. Among gram-positive organisms, the most important resistant pathogens are methicillin-(oxacillin-)resistant *Staphylococcus aureus*, β-lactam-resistant and multidrug-resistant pneumococci, and vancomycin-resistant enterococci. Important causes of gram-negative resistance include extended-spectrum β-lactamases (ESBLs) in *Klebsiella pneumoniae*, *Escherichia coli*, and *Proteus mirabilis*, high-level third-generation cephalosporin (Amp C) β-lactamase resistance among *Enterobacter* species and *Citrobacter freundii*, and multidrug-resistance genes observed in *Pseudomonas aeruginosa, Acinetobacter*, and *Stenotrophomonas maltophilia* (see Jones, R. N., "Resistance patterns among nosocomial pathogens: Trends over the past few years" *Chest.*, 2001, 119 (Supp 2), 397S-404S).

The problem of antibacterial resistance is compounded by the existence of bacterial strains resistant to multiple antibacterials. For example, *Pseudomonas aeruginosa* isolates resistant to fluoroquinolones are virtually all resistant to additional antibacterials (see Sahm, D. F. et al., "Evaluation of current activities of fluoroquinolones against gram-negative bacilli using centralized in vitro testing and electronic surveillance" *Antimicrobial Agents and Chemotherapy*, 2001, 45, 267-274).

Thus there is a need for new antibacterials, particularly antibacterials with novel mechanisms of action. Most of the antibacterial discovery effort in the pharmaceutical industry is aimed at development of drugs effective against gram-positive bacteria. However, there is also a need for new gram-negative antibacterials. Gram-negative bacteria are in general more resistant to a large number of antibacterials and chemotherapeutic agents than are gram-positive bacteria. A survey of recently reported antibacterials of natural origin showed that over 90% lacked activity against *Escherichia coli*, although they were active against gram-positive bacteria. The outer membrane of gram-negative bacteria contributes to this intrinsic resistance by acting as an efficient permeability barrier, because the narrow porin channels limit the penetration of hydrophilic solutes and the low fluidity of the lipopolysaccharide leaflet slows down the inward diffusion of lipophilic solutes. A second mechanism also contributes to the intrinsic resistance of gram-negative bacteria. Recent studies showed that multiple drug efflux pumps, sometimes with unusually broad specificity, act as this second factor to create the general intrinsic resistance of gram-negative bacteria. When their expression levels are elevated as a consequence of physiological regulation or genetic alteration, they can frequently produce impressive levels of resistance to a wide variety of antimicrobial agents (see Nikaido H., "Antibacterial resistance caused by gram-negative multidrug efflux pumps" *Clinical Infectious Diseases*, 1998, 27 (Supp 1), S32-41).

Historically, most development of antimicrobial agents has been relatively empirical. Active compounds have generally been found via screening soil, sewage, water, and other natural substances to detect antimicrobial-producing organisms, or by screening various chemical compounds. Once a leading candidate has been found and its chemical structure determined, a series of analogs is made to identify an optimal compound for further clinical development. A more rational approach involves the defining of new targets, such as genes or enzymatic functions, responsible for a crucial cellular essential activity. Once this has been done, inhibitors or blockers of the function or gene product can be developed.

In order to identify potential targets for novel gram-negative antibacterial agents, studies aimed at identifying all essential and important genes in *Pseudomonas aeruginosa* have been performed. Among the essential genes identified was LpxC, that encodes the enzyme uridyldiphospho-3-O—(R-hydroxydecanoyl)-N-acetylglucosamine deacetylase (LpxC). This enzyme is the first committed step in the synthesis of lipid A, the lipid moiety of lipopolysaccharide, that is an essential component of all gram-negative bacteria. It therefore is an attractive target for novel antibacterials. In order to be useful as antibacterial agents, LpxC inhibitors would not only have to inhibit the enzymatic activity of LpxC from a variety of bacteria, but would have to defeat the intrinsic resistance mechanisms of gram-negative bacteria, as described above (i.e., they would have to penetrate the outer membrane and be relatively unsusceptible to multidrug efflux pumps).

To date, researchers have identified a few compounds with antibacterial activity that target lipid A biosynthesis.

For example, International PCT Publication No. WO 97/42179 to Patchett et al. discloses compounds of the formula:

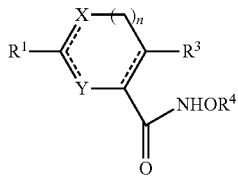

The compounds possess activity against certain gram-negative organisms, for example *Escherichia coli*, but are not active against other medically important gram-negative bacteria, for example *Pseudomonas aeruginosa*. Subsequent studies have found that the primary reason for their inactivity against particular, medically important gram-negative bacteria is their poor ability to inhibit *P. aeruginosa* LpxC; efflux by the major multidrug efflux pump or inability to penetrate the outer membrane were not the critical factors.

Jackman et al. (*J. Biol. Chem.*, 2000, 275(15), 11002-11009) discuss the mechanism of lipid A biosynthesis in the context of gram-negative bacteria and disclose a new class of hydroxamate-containing inhibitors of LpxC. Wyckoff et al. (*Trends in Microbiology*, 1998, 6(4), 154-159) discuss the role of LpxC in lipid A biosynthesis and its role in regulation and disclose a few oxazoline hydroxamic acids that inhibit bacterial growth. However, Wyckoff et al. also discuss the shortcomings of the available deacetylase inhibitors as bactericidal agents against *Pseudomonas* and note that more work is needed to be done in the area.

U.S. Patent Application Publication No. 2001/0053555 (published Dec. 20, 2001, corresponding to International PCT Publication No. WO 98/18754 published May 7, 1998) discloses a combinatorial library of hydroxylamine, hydroxamic acid, hydroxyurea and hydroxylsulfonamide compounds purported to be potentially useful as inhibitors of metalloproteases, and U.S. Pat. No. 6,281,245 claims a method of inhibiting a deformylase enzyme by administering one of the hydroxylamine compounds from the combinatorial library disclosed in U.S. Patent Application Publication No. 2001/0053555. Related to the foregoing patent publications is International PCT Publication No. WO 99/57097 (published Nov. 11, 1999) that discloses a method of solid phase synthesis of the hydroxyl amine library of compounds.

International PCT Publication No. WO 00/61134 to British Biotech Pharmaceuticals Limited (published Oct. 19, 2000) discloses compounds of the formula:

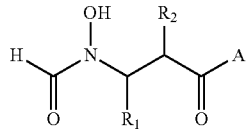

The compounds are useful as antimicrobial agents and are believed to have bactericidal activity due, at least in part, to intracellular inhibition of bacterial polypeptide deformylase.

In earlier International PCT Publication No. WO 99/39704 to British Biotech Pharmaceuticals Limited (published Aug. 12, 1999), compounds of the following formula were disclosed:

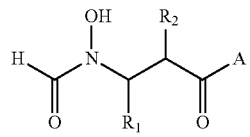

The compounds are useful as antimicrobial agents useful against gram-negative and gram positive bacteria.

De Novo Pharmaceuticals LTD disclosed in International PCT Publication No. WO 02/50081 (published Jun. 27, 2002), certain antibacterial and antiprotozoal agents having the formulae shown below:

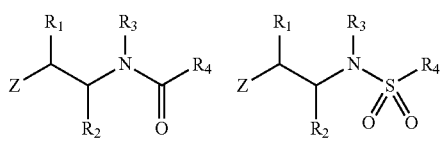

The patent publication discusses that the antibacterial activity is due, at least in part, to intracellular inhibition of bacterial polypeptide deformylase.

More recently, certain compounds having activity against gram-negative bacterial infections were disclosed in U.S. Patent Application Publication No. 2004/0229955 (published Nov. 18, 2004).

Although there have been advances in the field, there remains a need for LpxC inhibitors that have activity as bactericidal agents against gram-negative bacteria. It is, accordingly, an object of this invention to provide compounds and combinations of such compounds for use in the preparation of antibacterials and other pharmaceuticals capable of inhibiting gram-negative bacterial infections.

BRIEF SUMMARY OF THE INVENTION

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections.

In one aspect, the present invention provides compounds having the following formula (I):

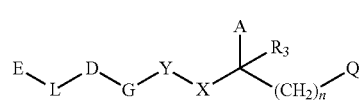

I including stereoisomers, pharmaceutically acceptable salts, esters, and prodrugs thereof.

In a first embodiment, the present invention provides compounds of formula (I) wherein:

E is selected from the group consisting of
(1) H,
(2) substituted or unsubstituted $C_1$-$C_6$-alkyl,
(3) substituted or unsubstituted $C_2$-$C_6$-alkenyl,
(4) substituted or unsubstituted $C_2$-$C_6$-alkynyl,
(5) substituted or unsubstituted $C_3$-$C_{10}$-cycloalkyl,
(6) substituted or unsubstituted aryl,
(7) substituted or unsubstituted heterocyclyl, and
(8) substituted or unsubstituted heteroaryl;

L is absent or selected from the group consisting of
(1) substituted or unsubstituted $C_1$-$C_6$-alkyl,
(2) —$(NR^{3L})_{0-1}$—$(CH_2)_{0-4}$—$NR^{3L}$—$(CH_2)_{0-4}$—,
(3) —$(NR^{3L})_{0-1}$—$C(R^{1L},R^{2L})$—$NR^{3L}$—$C(R^{1L},R^{2L})$—,
(4) —$C(R^{1L},R^{2L})$—O—$C(R^{1L},R^{2L})$—,
(5) —$(CH_2)_{0-4}$—$NR^{3L}$—$C(R^{1L},R^{2L})$—CONH—$(CH_2)_{0-4}$—,
(6) —CO—$C(R^{1L},R^{2L})$—NHCO—,
(7) —$CONR^{3L}$—,
(8) —$NR^{3L}CO$—,
(9) —$NR^{3L}$—,
(10) —$SO_2NR^{3L}$—,
(11) —$NR^{3L}$—C(=O)—$NR^{3L}$—,
(12) substituted or unsubstituted $C_3$-$C_{10}$-cycloalkyl,
(13) substituted or unsubstituted aryl,
(14) substituted or unsubstituted heterocyclyl, and
(15) substituted or unsubstituted heteroaryl,
wherein:
  each $R^{1L}$, $R^{2L}$, and $R^{3L}$ is independently selected from the group consisting of:
    (a) H,
    (b) substituted or unsubstituted $C_1$-$C_6$-alkyl,
    (c) $C_1$-$C_6$-alkyl substituted with aryl,
    (d) $C_1$-$C_6$-alkyl substituted with heterocyclyl, and
    (e) $C_1$-$C_6$-alkyl substituted with heteroaryl,
  or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring are selected from N, O and S;
D is absent or selected from the group consisting of:
(1) substituted or unsubstituted $C_3$-$C_{10}$-cycloalkyl,
(2) substituted or unsubstituted aryl,
(3) substituted or unsubstituted heterocyclyl, and
(4) substituted or unsubstituted heteroaryl;
G is selected from the group consisting of:
(1) —$NR^{1G}C(=O)$—,
(2) —$C(=O)NR^{1G}$—,
(3) —$(CH_2)_{0-4}NHCH_2C(=O)NR^{1G}$—,
(4) —$CR^{2G}$=$CR^{2G}$—,
(5) —S(=O)—,
(6) —$SO_2$—,
(7) —$C(R^{3G})_2$—S(=O)—,
(8) —S(=O)—$C(R^{3G})_2$—,
(9) —$C(R^{3G})_2$—$SO_2$—,
(10) —$SO_2$—$C(R^{3G})_2$—
(11) —$CR^{3G}$=$CR^{3G}$—$CR^{3G}$=$CR^{3G}$—,
(12) —$C(R^{3G})_2$—,
(13) —$CR^{3G}$=$CR^{3G}$—C≡C—,
(14) —C≡C—$CR^{3G}$=$CR^{3G}$—,
(15) —C(=O)—C≡C—,
(16) —C≡C—C(=O)—,
(17) substituted or unsubstituted $C_3$-$C_{10}$-cycloalkyl,
(18) substituted or unsubstituted aryl,
(19) substituted or unsubstituted heterocyclyl, and
(20) substituted or unsubstituted heteroaryl,
wherein:
  $R^{1G}$ is substituted or unsubstituted $C_1$-$C_6$-alkyl;
  each $R^{2G}$ is independently selected from the group consisting of H, a halogen atom, and substituted or unsubstituted $C_1$-$C_6$-alkyl, and at least one $R^{2G}$ is not H; and
  $R^{3G}$ is selected from the group consisting of H, a halogen atom, and substituted or unsubstituted $C_1$-$C_6$-alkyl;

Y is absent or selected from the group consisting of:
(1) substituted or unsubstituted $C_3$-$C_{10}$-cycloalkyl,
(2) substituted or unsubstituted aryl,
(3) substituted or unsubstituted heterocyclyl, and
(4) substituted or unsubstituted heteroaryl;
X is selected from the group consisting of
(1) —C(=O)$NR_4$—,
(2) —$C_1$-$C_6$-alkyl-(C=O)$NR_4$—,
(3) —$C_2$-$C_6$-alkenyl-(C=O)$NR_4$—,
(4) —$C_2$-$C_6$-alkynyl-(C=O)$NR_4$—,
(5) —$CH_2NR_4$—,
(6) —$SO_2NR_4$—,
(7) —S(=O)$NR_4$—,
(8) —$NR_4$C(=O)—, and
(9) —$NR_4$—,
or X and A, together with the atoms to which they are attached can form a heterocyclic ring, having from 5 to 8 ring atoms, wherein 1-2 ring atoms of the heterocyclic ring are selected from N, O and S,
or when Y is a bicyclic substituted or unsubstituted heterocyclyl or heteroaryl, then X is absent;
$R_3$ is H or substituted or unsubstituted $C_1$-$C_6$-alkyl, or $R_3$ and A, together with the atom to which they are attached can form a substituted or unsubstituted 3-10 membered cycloalkyl or a heterocyclic ring, having from 3 to 10 ring atoms, wherein 1-4 ring atoms of the heterocyclic ring are selected from N, O and S;
$R_4$ is (1) H or substituted or unsubstituted $C_1$-$C_6$-alkyl, or (2) $R_4$ and A, together with the atoms to which they are attached can form a substituted or unsubstituted heterocyclic ring, having from 3 to 8 ring atoms, wherein 1-2 ring atoms of the heterocyclic ring are selected from N, O and S, or (3) $R_4$ and Y, together with the atoms to which they are attached, form a bicyclic substituted or unsubstituted heterocyclyl or heteroaryl;
n is an integer from 0-6;
A is selected from the group consisting of:
(1) H,
(2) —$(CH_2)_{0-4}C(R^{1a},R^{2a})(CH_2)_{0-4}OR^{3a}$,
(3) —$(CH_2)_{0-4}C(R^{1a},R^{2a})N(R^{4a},R^{5a})$,
(4) —$(CH_2)_{0-4}C(R^{1a},R^{2a})N(R^{4a})COR^{3a}$,
(5) —$(CH_2)_{0-4}C(R^{1a},R^{2a})NHCON(R^{4a},R^{5a})$,
(6) —$(CH_2)_{0-4}C(R^{1a},R^{2a})NHC(NH)N(R^{4a},R^{5a})$,
(7) —$CH(R^{1a},R^{2a})$,
(8) —C≡CH,
(9) —$(CH_2)_{0-4}C(R^{1a},R^{2a})CN$,
(10) —$(CH_2)_{0-4}C(R^{1a},R^{2a})CO_2R^{3a}$,
(11) —$(CH_2)_{0-4}C(R^{1a},R^{2a})CON(R^{4a},R^{5a})$,
(12) substituted or unsubstituted $C_3$-$C_{10}$-cycloalkyl,
(13) substituted or unsubstituted aryl,
(14) substituted or unsubstituted heterocyclyl, and
(15) substituted or unsubstituted heteroaryl,
wherein:
  each $R^{1a}$, $R^{2a}$, $R^{3a}$, $R^{4a}$, and $R^{5a}$ is independently selected from the group consisting of:
    (a) H,
    (b) a halogen atom,
    (c) substituted or unsubstituted $C_1$-$C_6$-alkyl,
    (d) substituted or unsubstituted aryl,
    (e) substituted or unsubstituted heterocyclyl, and
    (f) substituted or unsubstituted heteroaryl,
  or $R^{4a}$ and $R^{5a}$ together with the N atom to which they are attached can form a substituted or unsubstituted heterocyclic ring, having from 5 to 8 ring atoms, wherein 1-2 ring atoms of the heterocyclic ring are selected from N, O and S;
Q is absent or selected from the group consisting of:
(1) —C(=O)$N(R_1,R_2)$,
(2) —NHC(=O)$N(R_1,R_2)$, (3) —N(OH)C(=O)N($R_1$,$R_2$),
(4) —CH(OH)C(=O)N($R_1$,$R_2$),
(5) —CH[N($R^{2q}$,$R^{3q}$)]C(=O)N($R_1$,$R_2$),
(6) —CH$R^{1q}$C(=O)N($R_1$,$R_2$),
(7) —CO$_2$H,
(8) —C(=O)NHSO$_2$$R^{4q}$,
(9) —SO$_2$NH$_2$,
(10) —N(OH)C(=O)$R^{1q}$,
(11) —N(OH)SO$_2$$R^{4q}$,
(12) —NHSO$_2$$R^{4q}$,
(13) —SH,
(14) —CH(SH)(CH$_2$)$_{0-1}$C(=O)N($R_1$,$R_2$),
(15) —CH(SH)(CH$_2$)$_{0-1}$CO$_2$H,
(16) —CH(OH)(CH$_2$)$_{0-1}$CO$_2$H,
(17) —CH(SH)CH$_2$CO$_2$$R^{1q}$,
(18) —CH(OH)(CH$_2$)SO$_2$NH$_2$,
(19) —CH(CH$_2$SH)NHCOR$^{1q}$,
(20) —CH(CH$_2$SH)NHSO$_2$$R^{4q}$,
(21) —CH(CH$_2$S$R^{5q}$)CO$_2$H,
(22) —CH(CH$_2$SH)NHSO$_2$NH$_2$,
(23) —CH(CH$_2$OH)CO$_2$H,
(24) —CH(CH$_2$OH)NHSO$_2$NH$_2$,
(25) —C(=O)CH$_2$CO$_2$H,
(26) —C(=O)(CH$_2$)$_{0-1}$CONH$_2$,
(27) —OSO$_2$NH$R^{5q}$,
(28) —SO$_2$NHNH$_2$,
(29) —P(=O)(OH)$_2$,

(30) 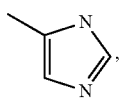

(31) 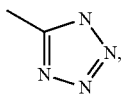

(32) 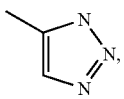

and
(33) —N(OH)C(=O)C$R_1$$R_2$,
wherein:
$R_1$ is selected from the group consisting of:
(1) —H,
(2) —OH,
(3) —OC$_1$—C$_6$-alkyl,
(4) —N($R^{2q}$,$R^{3q}$), and
(5) substituted or unsubstituted C$_1$-C$_6$-alkyl;
$R_2$ is selected from the group consisting of:
(1) H,
(2) substituted or unsubstituted
(3) substituted or unsubstituted C$_2$-C$_6$-alkenyl,
(4) substituted or unsubstituted C$_2$-C$_6$-alkenyl,
(5) substituted or unsubstituted aryl,
(6) substituted or unsubstituted heterocyclyl, and
(7) substituted or unsubstituted heteroaryl,
or $R_1$ and $R_2$, together with the N atom to which they are attached can form a substituted or unsubstituted heterocyclic ring, having from 3 to 10 ring atoms, wherein 1-4 ring atoms of the heterocyclic ring are selected from N, O and S; and each $R^{1q}$, $R^{2q}$, $R^{3q}$, $R^{4q}$, and $R^{5q}$ is independently selected from the group consisting of H and C$_1$-C$_6$ alkyl.

In a second embodiment, the present invention provides compounds of formula (I) wherein:
E is selected from the group consisting of
(1) H,
(2) substituted or unsubstituted C$_1$-C$_6$-alkyl,
(3) substituted or unsubstituted C$_2$-C$_6$-alkenyl,
(4) substituted or unsubstituted C$_2$-C$_6$-alkynyl,
(5) substituted or unsubstituted C$_3$-C$_{10}$-cycloalkyl,
(6) substituted or unsubstituted aryl,
(7) substituted or unsubstituted heterocyclyl, and
(8) substituted or unsubstituted heteroaryl;
L is absent or selected from the group consisting of:
(1) substituted or unsubstituted C$_1$-C$_6$-alkyl,
(2) —(N$R^{3L}$)$_{0-1}$—(CH$_2$)$_{0-4}$—N$R^{3L}$—(CH$_2$)$_{0-4}$—,
(3) —(N$R^{3L}$)$_{0-1}$—C($R^{1L}$,$R^{2L}$)—N$R^{3L}$—C($R^{1L}$,$R^{2L}$)—,
(4) —C($R^{1L}$,$R^{2L}$)—O—C($R^{1L}$,$R^{2L}$)—,
(5) —(CH$_2$)$_{0-4}$—N$R^{3L}$—C($R^{1L}$,$R^{2L}$)—CONH—(CH$_2$)$_{0-4}$—,
(6) —CO—C($R^{1L}$,$R^{2L}$)—NHCO—,
(7) —CON$R^{3L}$—,
(8) —N$R^{3L}$CO—,
(9) —N$R^{3L}$—,
(10) —SO$_2$N$R^{3L}$—,
(11) —N$R^{3L}$—C(=O)—N$R^{3L}$—,
(12) substituted or unsubstituted C$_3$-C$_{10}$-cycloalkyl,
(13) substituted or unsubstituted aryl,
(14) substituted or unsubstituted heterocyclyl, and
(15) substituted or unsubstituted heteroaryl,
wherein:
each $R^{1L}$, $R^{2L}$, and $R^{3L}$ is independently selected from the group consisting of
(a) H,
(b) substituted or unsubstituted C$_1$-C$_6$-alkyl,
(c) C$_1$-C$_6$-alkyl substituted with aryl,
(d) C$_1$-C$_6$-alkyl substituted with heterocyclyl, and
(e) C$_1$-C$_6$-alkyl substituted with heteroaryl,
or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring are selected from N, O and S;
D is absent or selected from the group consisting of:
(1) substituted or unsubstituted C$_3$-C$_{10}$-cycloalkyl,
(2) substituted or unsubstituted aryl,
(3) substituted or unsubstituted heterocyclyl, and
(4) substituted or unsubstituted heteroaryl;
G is selected from the group consisting of:
(1) —(CH$_2$)$_{0-4}$—O—(CH$_2$)$_{0-4}$—,
(2) —(CH$_2$)$_{0-4}$—S—(CH$_2$)$_{0-4}$—,
(3) —(CH$_2$)$_{0-4}$—N$R^{1G}$—(CH$_2$)$_{0-4}$—,
(4) —C(=O)—,
(5) —N$R^{1G}$C(=O)—,
(6) —C(=O)N$R^{1G}$—,
(7) —(CH$_2$)$_{0-4}$NHCH$_2$C(=O)N$R^{1G}$—,
(8) —C≡C—,
(9) —C≡C—C≡C—,
(10) —C$R^{2G}$=C$R^{2G}$—,
(11) —S(=O)—,
(12) —SO$_2$—,
(13) —C($R^{3G}$)$_2$—S(=O)—,
(14) —S(=O)—C($R^{3G}$)$_2$—,
(15) —C($R^{3G}$)$_2$—SO$_2$—,
(16) —SO$_2$—C($R^{3G}$)$_2$—,
(17) —C$R^{3G}$=C$R^{3G}$—C$R^{3G}$=C$R^{3G}$—,

(18) —C(R$^{3G}$)$_2$—,
(19) —CR$^{3G}$=CR$^{3G}$—C≡C—,
(20) —C≡C—CR$^{3G}$=CR$^{3G}$—,
(21) —C(=O)—C≡C—,
(22) —C≡C—C(=O)—,
(23) substituted or unsubstituted C$_3$-C$_{10}$-cycloalkyl,
(24) substituted or unsubstituted aryl,
(25) substituted or unsubstituted heterocyclyl, and
(26) substituted or unsubstituted heteroaryl,
wherein:
  R$^{1G}$ is substituted or unsubstituted C$_1$-C$_6$-alkyl;
  each R$^{2G}$ and R$^{3G}$ is independently selected from the group consisting of H, a halogen atom, and substituted or unsubstituted C$_1$-C$_6$-alkyl;
Y is absent or selected from the group consisting of:
(1) substituted or unsubstituted C$_3$-C$_{10}$-cycloalkyl,
(2) substituted or unsubstituted aryl,
(3) substituted or unsubstituted heterocyclyl, and
(4) substituted or unsubstituted heteroaryl;
X is selected from the group consisting of
(1) —(C=O)NR$_4$—,
(2) —C$_1$-C$_6$-alkyl-(C=O)NR$_4$—,
(3) —C$_2$-C$_6$-alkenyl-(C=O)NR$_4$—,
(4) —C$_2$-C$_6$-alkynyl-(C=O)NR$_4$—,
(5) —CH$_2$NR$_4$—,
(6) —SO$_2$NR$_4$—,
(7) —S(=O)NR$_4$—,
(8) —NR$_4$C(=O)—, and
(9) —NR$_4$—,
or X and A, together with the atoms to which they are attached can form a heterocyclic ring, having from 5 to 8 ring atoms, wherein 1-2 ring atoms of the heterocyclic ring are selected from N, O and S,
or when Y is a bicyclic substituted or unsubstituted heterocyclyl or heteroaryl, then X is absent;
R$_3$ is H or substituted or unsubstituted C$_1$-C$_6$-alkyl, or R$_3$ and A, together with the atom to which they are attached can form a substituted or unsubstituted 3-10 membered cycloalkyl or a heterocyclic ring, having from 3 to 10 ring atoms, wherein 1-4 ring atoms of the heterocyclic ring are selected from N, O and S;
R$_4$ is (1) H or substituted or unsubstituted C$_1$-C$_6$-alkyl, or (2) R$_4$ and A, together with the atoms to which they are attached can form a substituted or unsubstituted heterocyclic ring, having from 3 to 8 ring atoms, wherein 1-2 ring atoms of the heterocyclic ring are selected from N, O and S, or (3) R$_4$ and Y, together with the atoms to which they are attached, form a bicyclic substituted or unsubstituted heterocyclyl or heteroaryl;
n is an integer from 0-6;
A is selected from the group consisting of
(1) —C(R$^{1a}$,R$^{2a}$)OR$^{3a}$,
(2) —C(R$^{1a}$,R$^{2a}$)N(R$^{4a}$,R$^{5a}$),
(3) substituted or unsubstituted C$_3$-C$_{10}$-cycloalkyl,
(4) substituted or unsubstituted aryl,
(5) substituted or unsubstituted heterocyclyl, and
(6) substituted or unsubstituted heteroaryl,
wherein:
  each R$^{1a}$ and R$^{2a}$ is independently selected from the group consisting of substituted or unsubstituted C$_1$-C$_6$-alkyl;
  each R$^{3a}$, R$^{4a}$, and R$^{5a}$ is independently selected from the group consisting of:
    (a) H,
    (b) a halogen atom,
    (c) substituted or unsubstituted C$_1$-C$_6$-alkyl,
    (d) substituted or unsubstituted aryl,
    (e) substituted or unsubstituted heterocyclyl, and
    (f) substituted or unsubstituted heteroaryl,
  or R$^{4a}$ and R$^{5a}$ together with the N atom to which they are attached can form a substituted or unsubstituted heterocyclic ring, having from 5 to 8 ring atoms, wherein 1-2 ring atoms of the heterocyclic ring are selected from N, O and S; and
  when A is —C(R$^{1a}$,R$^{2a}$)OR$^{3a}$, the compound is not 2-{[(4'-ethyl-1,1'-biphenyl-4-yl)carbonyl]amino}-3-hydroxy-3-methylbutanoic acid, 4'-ethyl-N-{2-hydroxy-1-[(hydroxyamino) carbonyl]-2-methylpropyl}-1,1'-biphenyl-4-carboxamide or N-{2-hydroxy-1-[(hydroxyamino)carbonyl]-2-methylpropyl}-4-(phenylethynyl)benzamide;
Q is absent or selected from the group consisting of:
(1) —C(=O)N(R$_1$,R$_2$),
(2) —NHC(=O)N(R$_1$,R$_2$),
(3) —N(OH)C(=O)N(R$_1$,R$_2$),
(4) —CH(OH)C(=O)N(R$_1$,R$_2$),
(5) —CH[N(R$^{2q}$,R$^{3q}$)]C(=O)N(R$_1$,R$_2$),
(6) —CHR$^{1q}$C(=O)N(R$_1$,R$_2$),
(7) —CO$_2$H,
(8) —C(=O)NHSO$_2$R$^{4q}$,
(9) —SO$_2$NH$_2$,
(10) —N(OH)C(=O)R$^{1q}$,
(11) —N(OH)SO$_2$R$^{4q}$,
(12) —NHSO$_2$R$^{4q}$,
(13) —SH,
(14) —CH(SH)(CH$_2$)$_{0-1}$C(=O)N(R$_1$,R$_2$),
(15) —CH(SH)(CH$_2$)$_{0-1}$CO$_2$H,
(16) —CH(OH)(CH$_2$)$_{0-1}$CO$_2$H,
(17) —CH(SH)CH$_2$CO$_2$R$^{1q}$,
(18) —CH(OH)(CH$_2$)SO$_2$NH$_2$,
(19) —CH(CH$_2$SH)NHCOR$^{1q}$,
(20) —CH(CH$_2$SH)NHSO$_2$R$^{4q}$,
(21) —CH(CH$_2$SR$^{5q}$)CO$_2$H,
(22) —CH(CH$_2$SH)NHSO$_2$NH$_2$,
(23) —CH(CH$_2$OH)CO$_2$H,
(24) —CH(CH$_2$OH)NHSO$_2$NH$_2$,
(25) —C(=O)CH$_2$CO$_2$H,
(26) —C(=O)(CH$_2$)$_{0-1}$CONH$_2$,
(27) —OSO$_2$NHR$^{5q}$,
(28) —SO$_2$NHNH$_2$,
(29) —P(=O)(OH)$_2$,

(30) 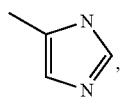

(31) 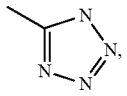

(32) 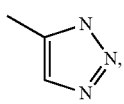

and
(33) —N(OH)C(=O)CR$_1$R$_2$, wherein:
R$_1$ is selected from the group consisting of
(1) —H,
(2) —OH,
(3) —OC$_1$—C$_6$-alkyl,
(4) —N(R$^{2q}$,R$^{3q}$), and
(5) substituted or unsubstituted C$_1$-C$_6$-alkyl;
R$_2$ is selected from the group consisting of:
(1) H,
(2) substituted or unsubstituted C$_1$-C$_6$-alkyl,
(3) substituted or unsubstituted C$_2$-C$_6$-alkenyl,
(4) substituted or unsubstituted C$_2$-C$_6$-alkenyl,
(5) substituted or unsubstituted aryl,
(6) substituted or unsubstituted heterocyclyl, and
(7) substituted or unsubstituted heteroaryl,
or R$_1$ and R$_2$, together with the N atom to which they are attached can form a substituted or unsubstituted heterocyclic ring, having from 3 to 10 ring atoms, wherein 1-4 ring atoms of the heterocyclic ring are selected from N, O and S; and
each R$^{1q}$, R$^{2q}$, R$^{3q}$, R$^{4q}$, and R$^{5q}$ is independently selected from the group consisting of H and C$_1$-C$_6$ alkyl.

In another aspect, the present invention provides a pharmaceutical composition comprising a compound of formula (I) and a pharmaceutically acceptable carrier or diluent.

In another aspect, the present invention provides a pharmaceutical composition or formulation comprising an effective amount of a compound of formula (I) and a pharmaceutically acceptable carrier or diluent.

In another aspect, the present invention provides a method of inhibiting a deacetylase enzyme in gram-negative bacteria, thereby affecting bacterial growth, comprising administering to a patient in need of such inhibition a compound of formula (I).

In another aspect, the present invention provides a method of inhibiting LpxC, thereby modulating the virulence of a bacterial infection, comprising administering to a patient in need of such inhibition a compound of formula (I).

In another aspect, the present invention provides a method for treating a subject with a gram-negative bacterial infection comprising administering to the subject in need thereof an antibacterially effective amount of a compound of formula (I) with a pharmaceutically acceptable carrier. In a more specific embodiment of the method of treatment, the subject is a mammal and in certain embodiments, a human.

In another aspect, the present invention provides a method of administering an inhibitory amount of a compound of formula (I) to a subject infected with a fermentative or non-fermentative gram-negative bacteria. In a more specific embodiment of the method of administering an inhibitory amount of a compound of formula (I) to a subject infected with a fermentative or non-fermentative gram-negative bacteria, the gram-negative bacteria are selected from the group consisting of *Pseudomonas aeruginosa, Stenotrophomonas maltophila, Burkholderia cepacia, Alcaligenes xylosoxidans, Acinetobacter, Enterobacteriaceae, Haemophilus, Franciscellaceae (Franciscella tularensis)* and *Neisseria* species.

In another aspect, the present invention provides a method of administering an inhibitory amount of a compound of formula (I) to a subject infected with gram-negative bacteria, such as a member of the Enterobacteriaceae which is selected from the group consisting of organisms such as *Serratia, Proteus, Klebsiella, Enterobacter, Citrobacter, Salmonella, Providencia, Yersinia (Yersinia pestis), Morganella, Cedecea*, and *Edwardsiella* species and *Escherichia coli*.

In another aspect, the present invention provides a method of co-administering a compound of formula (I) with other therapeutic agents that are selected for their particular usefulness against the condition that is being treated. For example, a compound of formula (I) is useful in combination with other anti-bacterial agents. The compound of formula (I) augments the sensitivity of gram-negative bacteria to existing classes of antibacterials. Combinations of the presently disclosed compounds with other anti-bacterial agents are within the scope of the invention. Such anti-bacterial agents include, but are not limited to, erythromycin, rifampicin, Nalidixic acid, carbenicillin, bacitracin, cycloserine, fosfomycin, and vancomycin.

These and other aspects of the invention will be evident upon reference to the following detailed description.

DETAILED DESCRIPTION OF THE INVENTION

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The present invention provides novel compounds, methods for inhibiting LpxC in gram-negative bacteria, and novel methods for treating bacterial infections. The compounds provided herein can be formulated into pharmaceutical formulations and medicaments that are useful in the methods of the invention. The invention also provides for the use of the compounds in preparing medicaments and pharmaceutical formulations, for use of the compounds in inhibiting LpxC, and for use of the compounds in treating bacterial infections in a subject.

The following abbreviations and definitions are used throughout this application:

"LpxC" is an abbreviation that stands for UDP-3-O—(R-3-hydroxydecanoyl)-N-acetylglucosamine deacetylase.

Generally, reference to a certain element such as hydrogen or H is meant to include all isotopes of that element. For example, if a substituent group is defined to include hydrogen or H, it also includes deuterium and tritium.

"Alkyl" refers to a straight or branched, saturated hydrocarbon chain radical consisting solely of carbon and hydrogen atoms, and having from one to twelve carbon atoms, preferably one to eight carbon atoms (C$_1$-C$_8$-alkyl) or one to six carbon atoms (C$_1$-C$_6$-alkyl). Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following, that are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, —CH(CH₂CH₃)CH(CH₃)CH(CH₃)(CH₂CH₃) and the like.

"Alkenyl" refers to a straight or branched, unsaturated hydrocarbon chain radical containing at least one double bond, consisting solely of carbon and hydrogen atoms and having from two to twelve carbon atoms, preferably two to eight carbon atoms ($C_2$-$C_8$-alkenyl) or two to six carbon atoms ($C_2$-$C_6$-alkenyl). Representative alkenyl radicals include, but are not limited to, vinyl, —CH=CH(CH₃), —CH=C(CH₃)₂, —C(CH₃)=CH₂, —C(CH₃)=CH(CH₃), —C(CH₂CH₃)=CH₂, cyclohexenyl, cyclopentenyl, cyclohexadienyl, butadienyl, pentadienyl, hexadienyl and the like.

"Alkynyl" refers to a straight or branched, unsaturated hydrocarbon chain radical containing at least one triple bond, and, optionally, at least one double bond, consisting solely of carbon and hydrogen atoms and having from two to twelve carbon atoms, preferably two to eight carbon atoms ($C_2$-$C_8$-alkynyl) or two to six carbon atoms ($C_2$-$C_6$-alkynyl). Representative alkynyl radicals include, but are not limited to —C≡CH, —C≡C(CH₃), —C≡C(CH₂CH₃), —CH₂C≡CH, —CH₂C≡C(CH₃), —CH₂C≡C(CH₂CH₃) and the like.

"Alkoxy" refers to a radical of the formula —OR$_a$ where R$_a$ is an alkyl, alkenyl or alkynyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl, alkenyl or alkynyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl, alkenyl or alkynyl radical as defined above containing one to twelve carbon atoms. Unless stated otherwise specifically in the specification, a thioalkyl group may be optionally substituted.

"Aryl" refers to aromatic monocyclic or multicyclic hydrocarbon ring systems consisting only of hydrogen and carbon atoms and containing from 6 to 19 carbon atoms, where the ring system may be partially or fully saturated, e.g., phenyl, biphenyl, anthracenyl, naphthyl, and the like.

"Cycloalkyl" refers to a non-aromatic monocyclic or polycyclic hydrocarbon radical consisting solely of carbon and hydrogen atoms, which may include fused or bridged ring systems, having from three to fifteen carbon atoms, preferably having from three to ten carbon atoms ($C_3$-$C_{10}$-cycloalkyl), and which is saturated or unsaturated. Monocyclic radicals include, for example, cyclopropyl, cyclobutyl, cyclopentyl, cyclohexyl, cycloheptyl, cyclooctyl, and the like. Polycyclic radicals include, for example, adamantine, norbornane, decalinyl, 7,7-dimethyl-bicyclo[2.2.1]heptanyl, and the like.

"Heteroaryl" or "heteroaryl ring" refers to a 5- to 18-membered aromatic ring radical which consists of three to seventeen carbon atoms and from one to ten heteroatoms selected from the group consisting of nitrogen, oxygen and sulfur. For purposes of this invention, the heteroaryl radical may be a monocyclic, bicyclic or polycyclic ring system, which may include fused or bridged ring systems; the nitrogen, carbon or sulfur atoms in the heteroaryl radical may be optionally oxidized; and the nitrogen atom may be optionally quaternized. Heteroaryl radicals include, for example, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzo-1,3-dioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, thiophenyl (i.e., thienyl), and the like.

"Heterocyclic ring" includes both "heterocyclyl" and "heteroaryl" groups.

"Heterocyclyl" refers to a 3- to 18-membered non-aromatic ring radical which consists of two to seventeen carbon atoms and from one to ten heteroatoms selected from the group consisting of nitrogen, oxygen and sulfur. Unless stated otherwise specifically in the specification, the heterocyclyl radical may be a monocyclic, bicyclic or polycyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Heterocyclyl radicals include, for example, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, oxiranyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

Representative heteroaryl and heterocyclyl radicals include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more 0 atoms, pyrrole, homopiperazine, oxazolidin-2-one, pyrrolidin-2-one, oxazole, quinuclidine, thiazole, isoxazole, furan, and tetrahydrofuran.

The term "substituted" used herein means any of the above groups (i.e., alkyl, alkenyl, alkynyl, alkylamino, alkoxy, alkylthio, aryl, cycloalkyl, heteroaryl and/or heterocyclyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more bonds are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. "Substituted" further means any of the above groups in which one or more bonds are replaced by a bond to an alkyl, alkenyl, alkynyl, amino, aryl, cyano, cycloalkyl, halogen, heteroaryl, heterocyclyl, hydroxyl, imino, nitro, oxo or thioxo group. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, alkylthio, aryl, cycloalkyl, heterocyclyl and/or heteroaryl. In addition, the foregoing substituents may also be optionally substituted with one or more of the above substituents.

For example, representative substituted alkyl groups include trifluoromethyl. Representative heteroaryl and heterocyclyl groups include 2-methylbenzimidazolyl, 5-methylbenzimidazolyl, 5-chlorobenzthiazolyl, 1-methylpiperazinyl, and 2-chloropyridyl. Representative substituted aryl groups include tolyl and hydroxyphenyl. Other representative substitutents include straight and branched chain alkyl groups, $-CH_3$, $-C_2H_5$, $-CH_2OH$, $-OH$, $-OCH_3$, $-OC_2H_5$, $-OCF_3$, $-CN$, $-NO_2$, $-CO_2H$, $-CO_2CH_3$, $-CONH_2$, $-NH_2$, $-F$, $-Cl$, $-Br$, $-CF_3$, $-N(CH_3)_2$, $-NHSO_2CH_3$, and $-NHCOCH_3$.

"Amino" refers to the $-NH_2$ radical.
"Cyano" refers to the $-CN$ radical.
"Halogen" refers to bromo, chloro, fluoro or iodo.
"Hydroxyl" refers to the $-OH$ radical.
"Imino" refers to the $=NH$ substituent.
"Nitro" refers to the $-NO_2$ radical.
"Oxo" refers to the $=O$ substituent.
"Thioxo" refers to the $=S$ substituent.

"Fused" refers to any ring structure described herein which is fused to an existing ring structure in the compounds of the present invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

The term "protected" with respect to hydroxyl groups, amine groups, and sulfhydryl groups refers to forms of these functionalities that are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) that can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The term "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "antibacterial agent" refers to agents synthesized or modified in the laboratory that have either bactericidal or bacteriostatic activity. An "active" agent in this context will inhibit the growth of P. aeruginosa and other gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The subject invention also includes isotopically-labeled LpxC inhibitors, that are structurally identical to those disclosed herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

As noted above, in one aspect, the present invention provides compounds having the following formula (I):

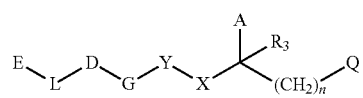

I including stereoisomers, pharmaceutically acceptable salts, esters, and prodrugs thereof.

In a first embodiment, the present invention provides compounds of formula (I) wherein:

E is selected from the group consisting of:
(1) H,
(2) substituted or unsubstituted $C_1$-$C_6$-alkyl,
(3) substituted or unsubstituted $C_2$-$C_6$-alkenyl,
(4) substituted or unsubstituted $C_2$-$C_6$-alkynyl,
(5) substituted or unsubstituted $C_3$-$C_{10}$-cycloalkyl,
(6) substituted or unsubstituted aryl,
(7) substituted or unsubstituted heterocyclyl, and
(8) substituted or unsubstituted heteroaryl;

L is absent or selected from the group consisting of:
(1) substituted or unsubstituted $C_1$-$C_6$-alkyl,
(2) —$(NR^{3L})_{0-1}$—$(CH_2)_{0-4}$—$NR^{3L}$—$(CH_2)_{0-4}$—,
(3) —$(NR^{3L})_{0-1}$—$C(R^{1L},R^{2L})$—$NR^{3L}$—$C(R^{1L},R^{2L})$—,
(4) —$C(R^{1L},R^{2L})$—O—$C(R^{1L},R^{2L})$—,
(5) —$(CH_2)_{0-4}$—$NR^{3L}$—$C(R^{1L},R^{2L})$—CONH—$(CH_2)_{0-4}$—,
(6) —CO—$C(R^{1L},R^{2L})$—NHCO—,
(7) —$CONR^{3L}$—,
(8) —$NR^{3L}CO$—,
(9) —$NR^{3L}$—,
(10) —$SO_2NR^{3L}$—,
(11) —$NR^{3L}$—C(=O)—$NR^{3L}$—,
(12) substituted or unsubstituted $C_3$-$C_{10}$-cycloalkyl,
(13) substituted or unsubstituted aryl,
(14) substituted or unsubstituted heterocyclyl, and
(15) substituted or unsubstituted heteroaryl, wherein:
each $R^{1L}$, $R^{2L}$, and $R^{3L}$ is independently selected from the group consisting of
(a) H,
(b) substituted or unsubstituted $C_1$-$C_6$-alkyl,
(c) $C_1$-$C_6$-alkyl substituted with aryl,
(d) $C_1$-$C_6$-alkyl substituted with heterocyclyl, and
(e) $C_1$-$C_6$-alkyl substituted with heteroaryl,
or $R^{1L}$ and $R^{3L}$, together with the atoms to which they are attached can form a substituted or unsubstituted heterocyclic ring, having from 3 to 8 ring atoms, wherein 1-2 ring atoms of the heterocyclic ring are selected from N, O and S;
D is absent or selected from the group consisting of:
(1) substituted or unsubstituted $C_3$-$C_{10}$-cycloalkyl,
(2) substituted or unsubstituted aryl,
(3) substituted or unsubstituted heterocyclyl, and
(4) substituted or unsubstituted heteroaryl;
G is selected from the group consisting of:
(1) —$NR^{1G}C(=O)$—,
(2) —$C(=O)NR^{1G}$—,
(3) —$(CH_2)_{0-4}NHCH_2C(=O)NR^{1G}$—,
(4) —$CR^{2G}=CR^{2G}$—,
(5) —$S(=O)$—,
(6) —$SO_2$—,
(7) —$C(R^{3G})_2$—$S(=O)$—,
(8) —$S(=O)$—$C(R^{3G})_2$—,
(9) —$C(R^{3G})_2$—$SO_2$—,
(10) —$SO_2$—$C(R^{3G})_2$—,
(11) —$CR^{3G}=CR^{3G}$—$CR^{3G}=CR^{3G}$—,
(12) —$C(R^{3G})_2$—,
(13) —$CR^{3G}=CR^{3G}$—$C\equiv C$—,
(14) —$C\equiv C$—$CR^{3G}=CR^{3G}$—,
(15) —$C(=O)$—$C\equiv C$—,
(16) —$C\equiv C$—$C(=O)$—,
(17) substituted or unsubstituted $C_3$-$C_{10}$-cycloalkyl,
(18) substituted or unsubstituted aryl,
(19) substituted or unsubstituted heterocyclyl, and
(20) substituted or unsubstituted heteroaryl,
wherein:
$R^{1G}$ is substituted or unsubstituted $C_1$-$C_6$-alkyl;
each $R^{2G}$ is independently selected from the group consisting of H, a halogen atom, and substituted or unsubstituted $C_1$-$C_6$-alkyl, and at least one $R^{2G}$ is not H; and
$R^{3G}$ is selected from the group consisting of H, a halogen atom, and substituted or unsubstituted $C_1$-$C_6$-alkyl;
Y is absent or selected from the group consisting of:
(1) substituted or unsubstituted $C_3$-$C_{10}$-cycloalkyl,
(2) substituted or unsubstituted aryl,
(3) substituted or unsubstituted heterocyclyl, and
(4) substituted or unsubstituted heteroaryl;
X is selected from the group consisting of:
(1) —$(C=O)NR_4$—,
(2) —$C_1$-$C_6$-alkyl-$(C=O)NR_4$—,
(3) —$C_2$-$C_6$-alkenyl-$(C=O)NR_4$—,
(4) —$C_2$-$C_6$-alkynyl-$(C=O)NR_4$—,
(5) —$CH_2NR_4$—,
(6) —$SO_2NR_4$—,
(7) —$S(=O)NR_4$—,
(8) —$NR_4C(=O)$—, and
(9) —$NR_4$—,
or X and A, together with the atoms to which they are attached can form a heterocyclic ring, having from 5 to 8 ring atoms, wherein 1-2 ring atoms of the heterocyclic ring are selected from N, O and S,
or when Y is a bicyclic substituted or unsubstituted heterocyclyl or heteroaryl, then X is absent;

$R_3$ is H or substituted or unsubstituted $C_1$-$C_6$-alkyl, or $R_3$ and A, together with the atom to which they are attached can form a substituted or unsubstituted 3-10 membered cycloalkyl or a heterocyclic ring, having from 3 to 10 ring atoms, wherein 1-4 ring atoms of the heterocyclic ring are selected from N, O and S;
$R_4$ is (1) H or substituted or unsubstituted $C_1$-$C_6$-alkyl, or (2) $R_4$ and A, together with the atoms to which they are attached can form a substituted or unsubstituted heterocyclic ring, having from 3 to 8 ring atoms, wherein 1-2 ring atoms of the heterocyclic ring are selected from N, O and S, or (3) $R_4$ and Y, together with the atoms to which they are attached, form a bicyclic substituted or unsubstituted heterocyclyl or heteroaryl;
n is an integer from 0-6;
A is selected from the group consisting of
(1) H,
(2) —$(CH_2)_{0-4}C(R^{1a},R^{2a})(CH_2)_{0-4}OR^{3a}$,
(3) —$(CH_2)_{0-4}C(R^{1a},R^{2a})N(R^{4a},R^{5a})$,
(4) —$(CH_2)_{0-4}C(R^{1a},R^{2a})N(R^{4a})COR^{3a}$,
(5) —$(CH_2)_{0-4}C(R^{1a},R^{2a})NHCON(R^{4a},R^{5a})$,
(6) —$(CH_2)_{0-4}C(R^{1a},R^{2a})NHC(=NH)N(R^{4a},R^{5a})$,
(7) —$CH(R^{1a},R^{2a})$,
(8) —$C\equiv CH$,
(9) —$(CH_2)_{0-4}C(R^{1a},R^{2a})CN$,
(10) —$(CH_2)_{0-4}C(R^{1a},R^{2a})CO_2R^{3a}$,
(11) —$(CH_2)_{0-4}C(R^{1a},R^{2a})CON(R^{4a},R^{5a})$,
(12) substituted or unsubstituted $C_3$-$C_{10}$-cycloalkyl,
(13) substituted or unsubstituted aryl,
(14) substituted or unsubstituted heterocyclyl, and
(15) substituted or unsubstituted heteroaryl,
wherein:
each $R^{1a}$, $R^{2a}$, $R^{3a}$, $R^{4a}$, and $R^{5a}$ is independently selected from the group consisting of
(a) H,
(b) a halogen atom,
(c) substituted or unsubstituted $C_1$-$C_6$-alkyl,
(d) substituted or unsubstituted aryl,
(e) substituted or unsubstituted heterocyclyl, and
(f) substituted or unsubstituted heteroaryl,
or $R^{4a}$ and $R^{5a}$ together with the N atom to which they are attached can form a substituted or unsubstituted heterocyclic ring, having from 5 to 8 ring atoms, wherein 1-2 ring atoms of the heterocyclic ring are selected from N, O and S;
Q is absent or selected from the group consisting of:
(1) —$C(=O)N(R_1,R_2)$,
(2) —$NHC(=O)N(R_1,R_2)$,
(3) —$N(OH)C(=O)N(R_1,R_2)$,
(4) —$CH(OH)C(=O)N(R_1,R_2)$,
(5) —$CH[N(R^{2q},R^{3q})]C(=O)N(R_1,R_2)$,
(6) —$CHR^{1q}C(=O)N(R_1,R_2)$,
(7) —$CO_2H$,
(8) —$C(=O)NHSO_2R^{4q}$,
(9) —$SO_2NH_2$,
(10) —$N(OH)C(=O)R^{1q}$,
(11) —$N(OH)SO_2R^{4q}$,
(12) —$NHSO_2R^{4q}$,
(13) —SH,
(14) —$CH(SH)(CH_2)_{0-1}C(=O)N(R_1,R_2)$,
(15) —$CH(SH)(CH_2)_{0-1}CO_2H$,
(16) —$CH(OH)(CH_2)_{0-1}CO_2H$,
(17) —$CH(SH)CH_2CO_2R^{1q}$,
(18) —$CH(OH)(CH_2)SO_2NH_2$,
(19) —$CH(CH_2SH)NHCOR^{1q}$,
(20) —$CH(CH_2SH)NHSO_2R^{4q}$,
(21) —$CH(CH_2SR^{5q})CO_2H$,

(22) —CH(CH₂SH)NHSO₂NH₂,
(23) —CH(CH₂OH)CO₂H,
(24) —CH(CH₂OH)NHSO₂NH₂,
(25) —C(═O)CH₂CO₂H,
(26) —C(═O)(CH₂)₀₋₁CONH₂,
(27) —OSO₂NHR$^{5q}$,
(28) —SO₂NHNH₂,
(29) —P(═O)(OH)₂,

(30) 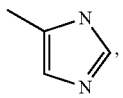

(31) 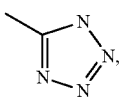

(32) 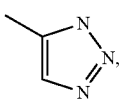

and
(33) —N(OH)C(═O)CR₁R₂,
wherein:
R₁ is selected from the group consisting of:
(1) —H,
(2) —OH,
(3) —OC₁—C₆-alkyl,
(4) —N(R$^{2q}$,R$^{3q}$), and
(5) substituted or unsubstituted C₁-C₆-alkyl;
R₂ is selected from the group consisting of:
(1) H,
(2) substituted or unsubstituted C₁-C₆-alkyl,
(3) substituted or unsubstituted C₂-C₆-alkenyl,
(4) substituted or unsubstituted C₂-C₆-alkenyl,
(5) substituted or unsubstituted aryl,
(6) substituted or unsubstituted heterocyclyl, and
(7) substituted or unsubstituted heteroaryl,
or R₁ and R₂, together with the N atom to which they are attached can form a substituted or unsubstituted heterocyclic ring, having from 3 to 10 ring atoms, wherein 1-4 ring atoms of the heterocyclic ring are selected from N, O and S; and
each R$^{1q}$, R$^{2q}$, R$^{3q}$, R$^{4q}$, and R$^{5q}$ is independently selected from the group consisting of H and C₁-C₆ alkyl.

In certain embodiments of the above embodiment, G is selected from the group consisting of:
(1) —C≡C—,
(2) —C≡C—C≡C—,
(3) —CR$^{3G}$═CR$^{3G}$—C≡C—, and
(4) —C≡C—CR$^{3G}$═CR$^{3G}$—.

For example, G may be —CH═CH—, —C≡C—C≡C—, —CH═CH—C≡C— or —C≡C—CH═CH—. In embodiments wherein G is —CH═CH—C≡C—, G may have one of the following structures:

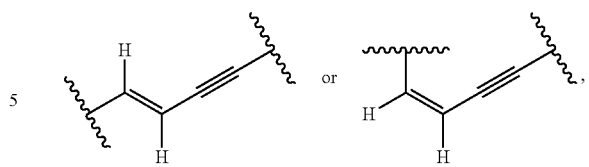

and in embodiments wherein G is —C≡C—CH═CH—, G may have one of the following structures:

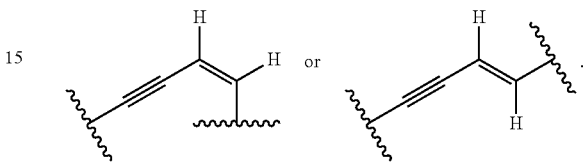

In certain embodiments of the above embodiments, X is —(C═O)NR₄—. For example, X may be —(C═O)NH—.
In certain embodiments of the above embodiments, Q is —(C═O)N(R₁,R₂). For example, Q may be —(C═O)NHOH.
In certain embodiments of the above embodiments, n is 0.
In certain embodiments of the above embodiments, R₃ is H.
In certain embodiments of the above embodiments, Y is substituted or unsubstituted aryl. For example, Y may be substituted or unsubstituted phenyl.
In certain embodiments of the above embodiments, A is selected from the group consisting of
(1) —(CH₂)₀₋₄C(R$^{1a}$,R$^{2a}$)(CH₂)₀₋₄OR$^{3a}$,
(2) —(CH₂)₀₋₄C(R$^{1a}$,R$^{2a}$)N(R$^{4a}$,R$^{5a}$), and
(3) —CH(R$^{1a}$,R$^{2a}$).

For example, A may be —CH(CH₃)₂, —CH₂OH, —CH₂NH₂, —CHCH₃OH, —CHCH₃NH₂ or —C(CH₃)₂OH, or A may be —C(CH₃)₂NH₂.

In other certain embodiments of the above embodiments, A is selected from the group consisting of:
(1) substituted or unsubstituted C₃-C₁₀-cycloalkyl,
(2) substituted or unsubstituted aryl,
(3) substituted or unsubstituted heterocyclyl, and
(4) substituted or unsubstituted heteroaryl.

For example, A may be:

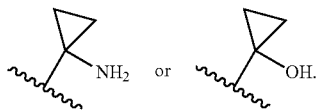 [SMILES: *C1(N)CC1 ; *C1(O)CC1]

In certain embodiments of the above embodiments, R₃ is H and

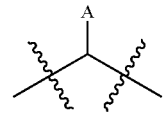

has the following structure:

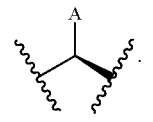

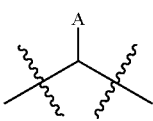

For example, when A is —CHCH$_3$OH or —CHCH$_3$NH$_2$, has one of the following structures:

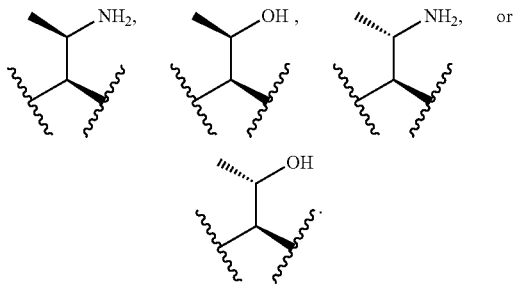

In certain embodiments of the above embodiments, D is present. For example, D may be substituted or unsubstituted heteroaryl (such as, for example, a heteroaryl is selected from the group consisting of:

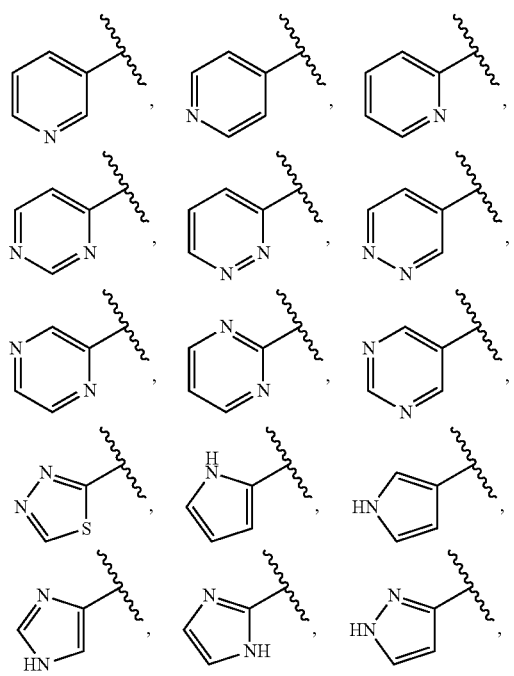

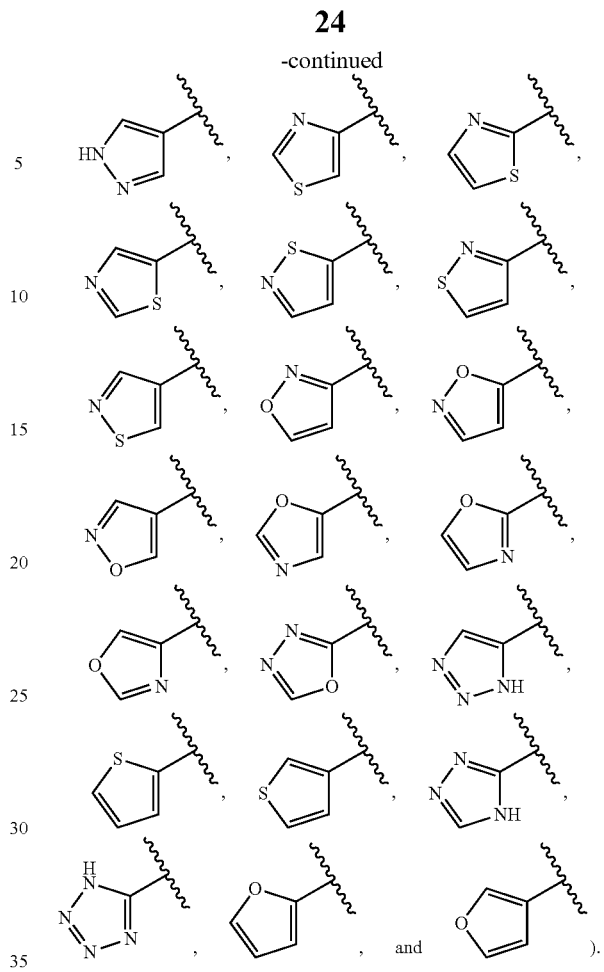

Alternatively, D may be substituted or unsubstituted aryl (such as, for example, substituted or unsubstituted phenyl), In other certain embodiments of the above embodiments, D is absent.

In certain embodiments of the above embodiments, L is present. For example, L may be substituted or unsubstituted alkyl (such as —CH$_3$—) or L may be —CH$_2$—NH—.

In other certain embodiments of the above embodiments, L is absent.

In a second embodiment, the present invention provides compounds of formula (I) wherein:

E is selected from the group consisting of:
(1) H,
(2) substituted or unsubstituted C$_1$-C$_6$-alkyl,
(3) substituted or unsubstituted C$_2$-C$_6$-alkenyl,
(4) substituted or unsubstituted C$_2$-C$_6$-alkynyl,
(5) substituted or unsubstituted C$_3$-C$_{10}$-cycloalkyl,
(6) substituted or unsubstituted aryl,
(7) substituted or unsubstituted heterocyclyl, and
(8) substituted or unsubstituted heteroaryl;

L is absent or selected from the group consisting of:
(1) substituted or unsubstituted C$_1$-C$_6$-alkyl,
(2) —(NR$^{3L}$)$_{0-1}$—(CH$_2$)$_{0-4}$—NR$^{3L}$—(CH$_2$)$_{0-4}$—,
(3) —(NR$^{3L}$)$_{0-1}$—C(R$^{1L}$,R$^{2L}$)NR$^{3L}$—C(R$^{1L}$,R$^{2L}$)—,
(4) —C(R$^{1L}$,R$^{2L}$)—O—C(R$^{1L}$,R$^{2L}$)—,
(5) —(CH$_2$)$_{0-4}$—NR$^{3L}$—C(R$^{1L}$,R$^{2L}$)CONH—(CH$_2$)$_{0-4}$—,
(6) —CO—C(R$^{1L}$, R$^{2L}$)—NHCO—,
(7) —CONR$^{3L}$—,
(8) —NR$^{3L}$CO—, (9) —NR$^{3L}$—,
(10) —SO$_2$NR$^{3L}$—,
(11) —NR$^{3L}$—C(=O)—NR$^{3L}$—,
(12) substituted or unsubstituted C$_3$-C$_{10}$-cycloalkyl,
(13) substituted or unsubstituted aryl,
(14) substituted or unsubstituted heterocyclyl, and
(15) substituted or unsubstituted heteroaryl,
wherein:
  each R$^{1L}$, R$^{2L}$, and R$^{3L}$ is independently selected from the group consisting of:
    (a) H,
    (b) substituted or unsubstituted C$_1$-C$_6$-alkyl,
    (c) C$_1$-C$_6$-alkyl substituted with aryl,
    (d) C$_1$-C$_6$-alkyl substituted with heterocyclyl, and
    (e) C$_1$-C$_6$-alkyl substituted with heteroaryl,
  or R$^{1L}$ and R$^{3L}$, together with the atoms to which they are attached can form a substituted or unsubstituted heterocyclic ring, having from 3 to 8 ring atoms, wherein 1-2 ring atoms of the heterocyclic ring are selected from N, O and S;
D is absent or selected from the group consisting of
(1) substituted or unsubstituted C$_3$-C$_{10}$-cycloalkyl,
(2) substituted or unsubstituted aryl,
(3) substituted or unsubstituted heterocyclyl, and
(4) substituted or unsubstituted heteroaryl;
G is selected from the group consisting of:
(1) —(CH$_2$)$_{0-4}$—O—(CH$_2$)$_{0-4}$—,
(2) —(CH$_2$)$_{0-4}$—S—(CH$_2$)$_{0-4}$—,
(3) —(CH$_2$)$_{0-4}$—NR$^{1G}$—(CH$_2$)$_{0-4}$—,
(4) —C(=O)—,
(5) —NR$^{1G}$C(=O)—,
(6) —C(=O)NR$^{1G}$—,
(7) —(CH$_2$)$_{0-4}$NHCH$_2$C(=O)NR$^{1G}$—,
(8) —C≡C—,
(9) —C≡C—C≡C—,
(10) —CR$^{2G}$=CR$^{2G}$—,
(11) —S(=O)—,
(12) —SO$_2$—,
(13) —C(R$^{3G}$)$_2$—S(=O)—,
(14) —S(=O)—C(R$^{3G}$)$_2$—,
(15) —C(R$^{3G}$)$_2$—SO$_2$—,
(16) —SO$_2$—C(R$^{3G}$)$_2$—
(17) —CR$^{3G}$=CR$^{3G}$—CR$^{3G}$=CR$^{3G}$—,
(18) —C(R$^{3G}$)$_2$—,
(19) —CR$^{3G}$=CR$^{3G}$—C≡C—,
(20) —C≡C—CR$^{3G}$=CR$^{3G}$—,
(21) —C(=O)—C≡C—,
(22) —C≡C—C(=O)—,
(23) substituted or unsubstituted C$_3$-C$_{10}$-cycloalkyl,
(24) substituted or unsubstituted aryl,
(25) substituted or unsubstituted heterocyclyl, and
(26) substituted or unsubstituted heteroaryl,
wherein:
  R$^{1G}$ is substituted or unsubstituted C$_1$-C$_6$-alkyl;
  each R$^{2G}$ and R$^{3G}$ is independently selected from the group consisting of H, a halogen atom, and substituted or unsubstituted C$_1$-C$_6$-alkyl;
Y is absent or selected from the group consisting of
(1) substituted or unsubstituted C$_3$-C$_{10}$-cycloalkyl,
(2) substituted or unsubstituted aryl,
(3) substituted or unsubstituted heterocyclyl, and
(4) substituted or unsubstituted heteroaryl;
X is selected from the group consisting of:
(1) —(C=O)NR$_4$—,
(2) —C$_1$-C$_6$-alkyl-(C=O)NR$_4$—,
(3) —C$_2$-C$_6$-alkenyl-(C=O)NR$_4$—,
(4) —C$_2$-C$_6$-alkynyl-(C=O)NR$_4$—,
(5) —CH$_2$NR$_4$—,
(6) —SO$_2$NR$_4$—,
(7) —S(=O)NR$_4$—,
(8) —NR$_4$C(=O)—, and
(9) —NR$_4$—,
or X and A, together with the atoms to which they are attached can form a heterocyclic ring, having from 5 to 8 ring atoms, wherein 1-2 ring atoms of the heterocyclic ring are selected from N, O and S,
or when Y is a bicyclic substituted or unsubstituted heterocyclyl or heteroaryl, then X is absent;
R$_3$ is H or substituted or unsubstituted C$_1$-C$_6$-alkyl, or R$_3$ and A, together with the atom to which they are attached can form a substituted or unsubstituted 3-10 membered cycloalkyl or a heterocyclic ring, having from 3 to 10 ring atoms, wherein 1-4 ring atoms of the heterocyclic ring are selected from N, O and S;
R$_4$ is (1) H or substituted or unsubstituted C$_1$-C$_6$-alkyl, or (2) R$_4$ and A, together with the atoms to which they are attached can form a substituted or unsubstituted heterocyclic ring, having from 3 to 8 ring atoms, wherein 1-2 ring atoms of the heterocyclic ring are selected from N, O and S, or (3) R$_4$ and Y, together with the atoms to which they are attached, form a bicyclic substituted or unsubstituted heterocyclyl or heteroaryl;
n is an integer from 0-6;
A is selected from the group consisting of
(1) —C(R$^{1a}$,R$^{2a}$)OR$^{3a}$,
(2) —C(R$^{1a}$,R$^{2a}$)N(R$^{4a}$,R$^{5a}$),
(3) substituted or unsubstituted C$_3$-C$_{10}$-cycloalkyl,
(4) substituted or unsubstituted aryl,
(5) substituted or unsubstituted heterocyclyl, and
(6) substituted or unsubstituted heteroaryl,
wherein:
  each R$^{1a}$ and R$^{2a}$ is independently selected from the group consisting of substituted or unsubstituted C$_1$-C$_6$-alkyl;
  each R$^{3a}$, R$^{4a}$, and R$^{5a}$ is independently selected from the group consisting of:
    (a) H,
    (b) a halogen atom,
    (c) substituted or unsubstituted C$_1$-C$_6$-alkyl,
    (d) substituted or unsubstituted aryl,
    (e) substituted or unsubstituted heterocyclyl, and
    (f) substituted or unsubstituted heteroaryl,
  or R$^{4a}$ and R$^{5a}$ together with the N atom to which they are attached can form a substituted or unsubstituted heterocyclic ring, having from 5 to 8 ring atoms, wherein 1-2 ring atoms of the heterocyclic ring are selected from N, O and S; and
  when A is —C(R$^{1a}$,R$^{2a}$)OR$^{3a}$, the compound is not 2-{[(4'-ethyl-1,1'-biphenyl-4-yl)carbonyl]amino}-3-hydroxy-3-methylbutanoic acid, 4'-ethyl-N-{2-hydroxy-1-[(hydroxyamino) carbonyl]-2-methylpropyl}-1,1'-biphenyl-4-carboxamide or N-{2-hydroxy-1-[(hydroxyamino)carbonyl]-2-methylpropyl}-4-(phenylethynyl)benzamide;
Q is absent or selected from the group consisting of
(1) —C(=O)N(R$_1$,R$_2$),
(2) —NHC(=O)N(R$_1$,R$_2$),
(3) —N(OH)C(=O)N(R$_1$,R$_2$),
(4) —CH(OH)C(=O)N(R$_1$,R$_2$),
(5) —CH[N(R$^{2q}$,R$^{3q}$)]C(=O)N(R$_1$,R$_2$),
(6) —CHR$^{1q}$C(=O)N(R$_1$,R$_2$),
(7) —CO$_2$H,
(8) —C(=O)NHSO$_2$R$^{4q}$,
(9) —SO$_2$NH$_2$,

(10) —N(OH)C(=O)R$^{1q}$,
(11) —N(OH)SO$_2$R$^{4q}$,
(12) —NHSO$_2$R$^{4q}$,
(13) —SH,
(14) —CH(SH)(CH$_2$)$_{0-1}$C(=O)N(R$_1$,R$_2$),
(15) —CH(SH)(CH$_2$)$_{0-1}$CO$_2$H,
(16) —CH(OH)(CH$_2$)$_{0-1}$CO$_2$H,
(17) —CH(SH)CH$_2$CO$_2$R$^{1q}$,
(18) —CH(OH)(CH$_2$)SO$_2$NH$_2$,
(19) —CH(CH$_2$SH)NHCOR$^{1q}$,
(20) —CH(CH$_2$SH)NHSO$_2$R$^{4q}$,
(21) —CH(CH$_2$SR$^{5q}$)CO$_2$H,
(22) —CH(CH$_2$SH)NHSO$_2$NH$_2$,
(23) —CH(CH$_2$OH)CO$_2$H,
(24) —CH(CH$_2$OH)NHSO$_2$NH$_2$,
(25) —C(=O)CH$_2$CO$_2$H,
(26) —C(=O)(CH$_2$)$_{0-1}$CONH$_2$,
(27) —OSO$_2$NHR$^{5q}$,
(28) —SO$_2$NHNH$_2$,
(29) —P(=O)(OH)$_2$,

(30) 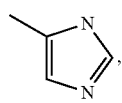

(31) 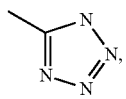

(32) 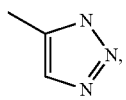

and
(33) —N(OH)C(=O)CR$_1$R$_2$,
wherein:
R$_1$ is selected from the group consisting of
  (1) —H,
  (2) —OH,
  (3) —OC$_1$—C$_6$-alkyl,
  (4) —N(R$^{2q}$,R$^{3q}$), and
  (5) substituted or unsubstituted C$_1$-C$_6$-alkyl;
R$_2$ is selected from the group consisting of:
  (1) H,
  (2) substituted or unsubstituted C$_1$-C$_6$-alkyl,
  (3) substituted or unsubstituted C$_2$-C$_6$-alkenyl,
  (4) substituted or unsubstituted C$_2$-C$_6$-alkenyl,
  (5) substituted or unsubstituted aryl,
  (6) substituted or unsubstituted heterocyclyl, and
  (7) substituted or unsubstituted heteroaryl,
  or R$_1$ and R$_2$, together with the N atom to which they are attached can form a substituted or unsubstituted heterocyclic ring, having from 3 to 10 ring atoms, wherein 1-4 ring atoms of the heterocyclic ring are selected from N, O and S; and
  each R$^{1q}$, R$^{2q}$, R$^{3q}$, R$^{4q}$, and R$^{5q}$ is independently selected from the group consisting of H and C$_1$-C$_6$ alkyl.
In certain embodiments of the above embodiment, A is —C(R$^{1a}$,R$^{2a}$)N(R$^{4a}$,R$^{5a}$). For example, A may be —C(CH$_3$)$_2$NH$_2$.

In other certain embodiments of the above embodiment, A is —C(R$^{1a}$,R$^{2a}$)OR$^{3a}$.
In other certain embodiments of the above embodiments, A is selected from the group consisting of:
  (1) substituted or unsubstituted C$_3$-C$_{10}$-cycloalkyl,
  (2) substituted or unsubstituted aryl,
  (3) substituted or unsubstituted heterocyclyl, and
  (4) substituted or unsubstituted heteroaryl.
For example, A may be:

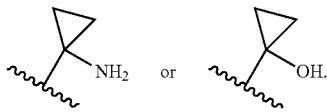 [SMILES: *C1(N)CC1 ; *C1(O)CC1]

In certain embodiments of the above embodiments, R$_3$ is H and

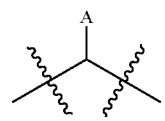

has the following structure:

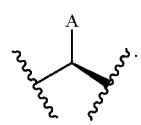

In certain embodiments of the above embodiments, G is selected from the group consisting of
  (1) —C≡C—,
  (2) —C≡C—C≡C—,
  (3) —CR$^{3G}$=CR$^{3G}$—C≡C—, and
  (4) —C≡C—CR$^{3G}$=CR$^{3G}$—.
For example, G may be —C≡C—, —C≡C—C≡C—, —CH=CH—C≡C—, or —C≡C—CH=CH—. In embodiments wherein G is —CH=CH—C≡C—, G may have one of the following structures:

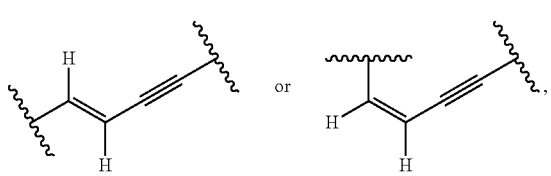 [SMILES: *C#C/C=C/* ; *C#C/C=C\*]

and in embodiments wherein G is —C≡C—CH=CH—, G may have one of the following structures:

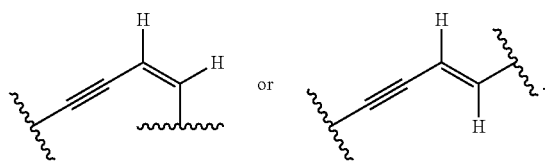 [SMILES: *C#C/C=C\* ; *C#C/C=C/*]

In certain embodiments of the above embodiments, X is —(C=O)NR$_4$—. For example, X may be —(C=O)NH—.

In certain embodiments of the above embodiments, Q is —(C=O)N(R$_1$,R$_2$). For example, Q may be —(C=O)NHOH.

In certain embodiments of the above embodiments, n is 0.

In certain embodiments of the above embodiments, R$_3$ is H.

In certain embodiments of the above embodiments, Y is substituted or unsubstituted aryl. For example, Y may be substituted or unsubstituted phenyl.

In certain embodiments of the above embodiments, D is present. For example, D may be substituted or unsubstituted heteroaryl (such as, for example, a heteroaryl is selected from the group consisting of:

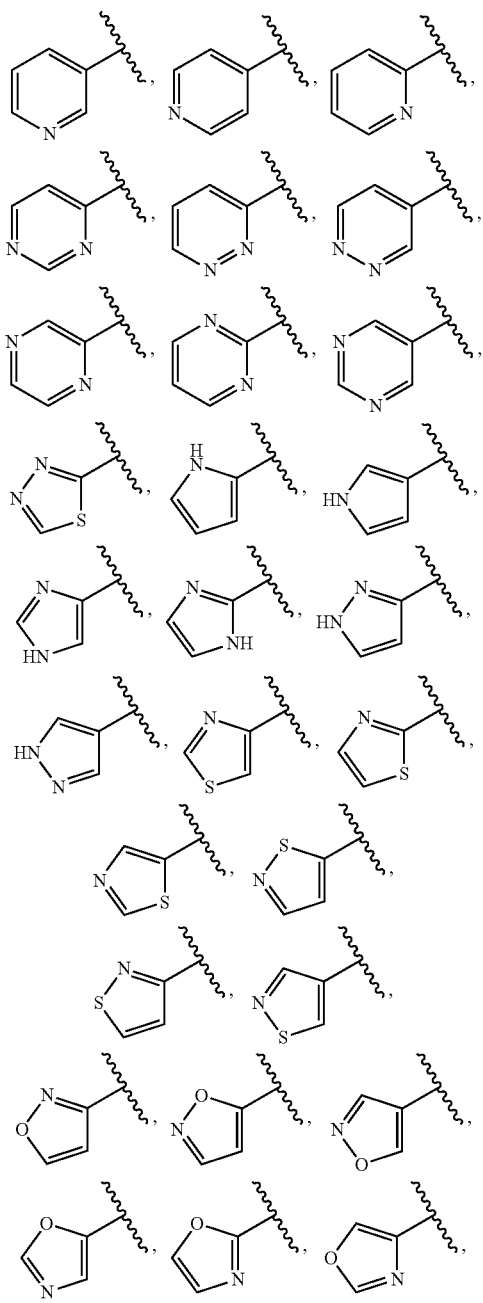

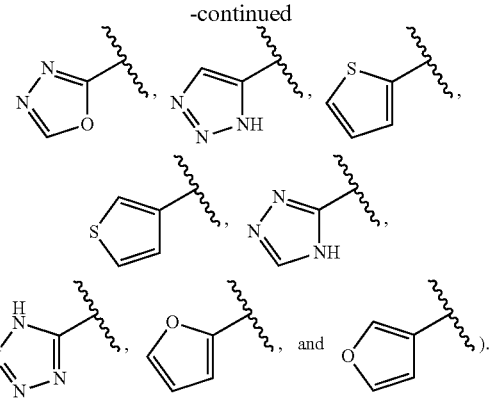

Alternatively, D may be substituted or unsubstituted aryl (such as, for example, substituted or unsubstituted phenyl), In other certain embodiments of the above embodiments, D is absent.

In certain embodiments of the above embodiments, L is present. For example, L may be substituted or unsubstituted alkyl (such as —CH$_3$—) or L may be —CH$_2$—NH—.

In other certain embodiments of the above embodiments, L is absent.

In various other embodiments of all of the foregoing embodiments, E-L-D-G-Y taken together, may be selected from the group consisting of:

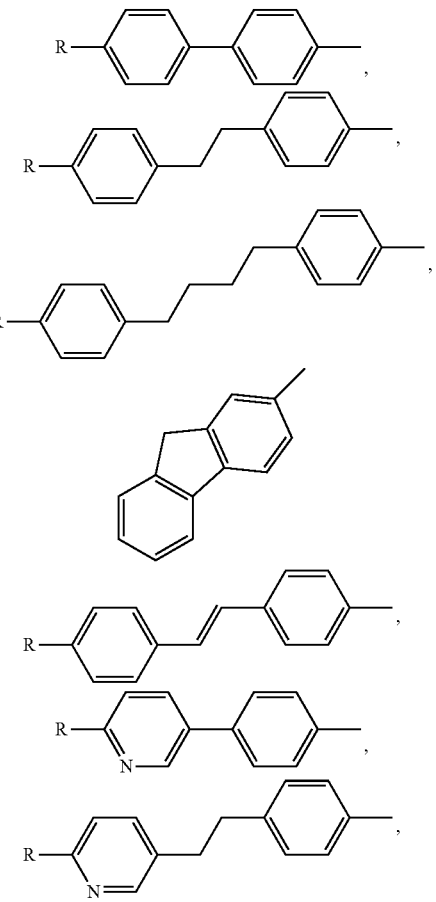

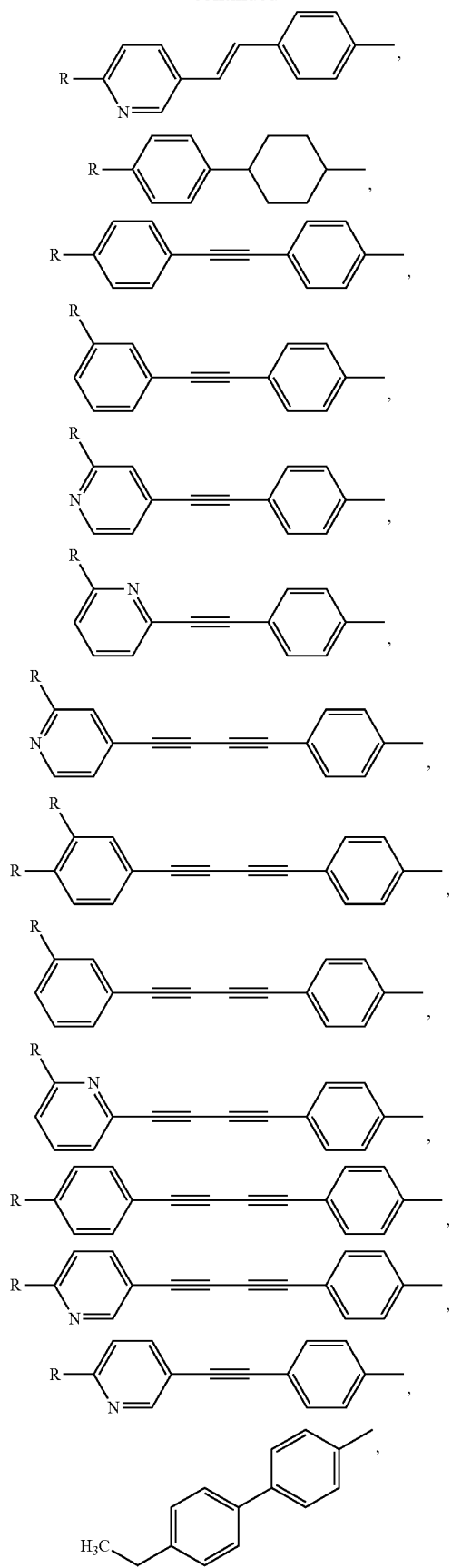
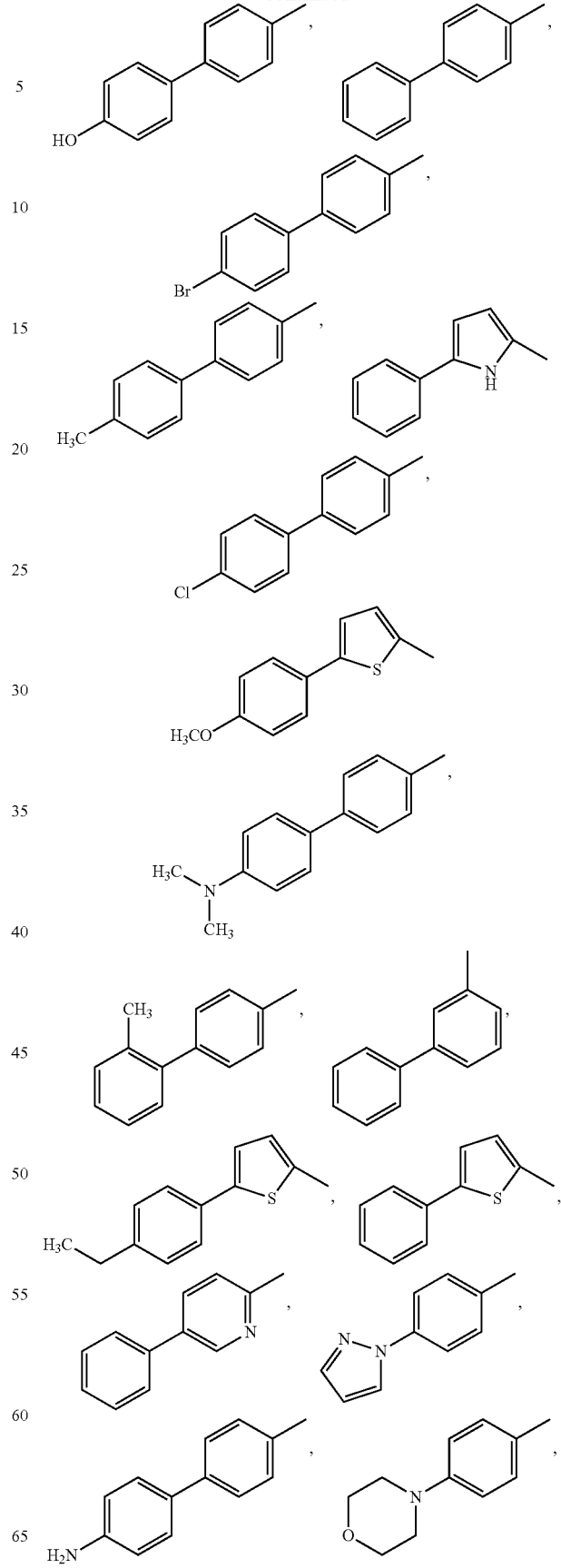

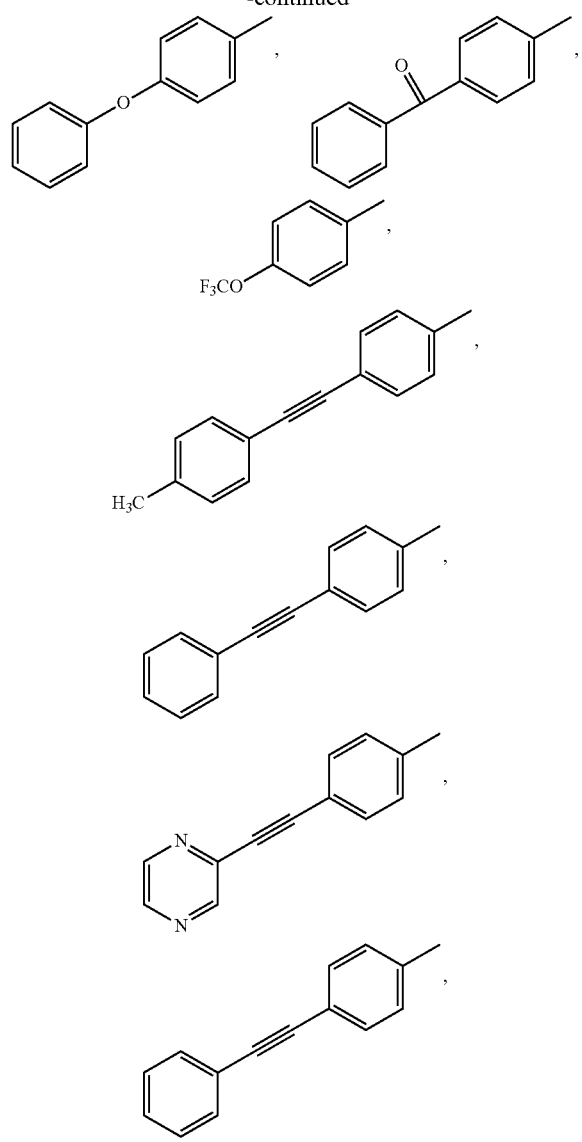
wherein R is selected from the group consisting of —CH$_3$, —C$_2$H$_5$, —CH$_2$OH, —OH, —OCH$_3$, —OC$_2$H$_5$, —OCF$_3$, —CN, —NO$_2$, —CO$_2$, —CO$_2$CH$_3$, —CONH$_2$, —NH$_2$, —F, —Cl, —Br, —CF$_3$, —N(CH$_3$)$_2$, —NHSO$_2$CH$_3$, and —NHCOCH$_3$.
In various other embodiments of all of the foregoing embodiments, G may be selected from the group consisting of:

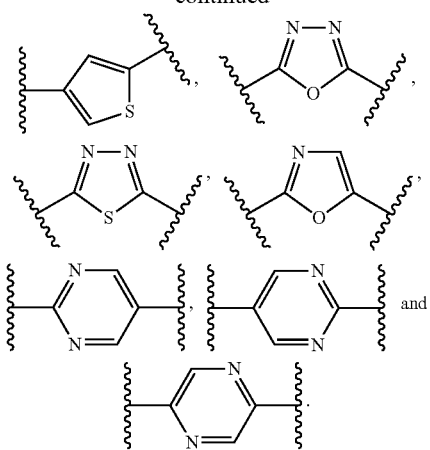

In various other embodiments of all of the foregoing embodiments, A may be:

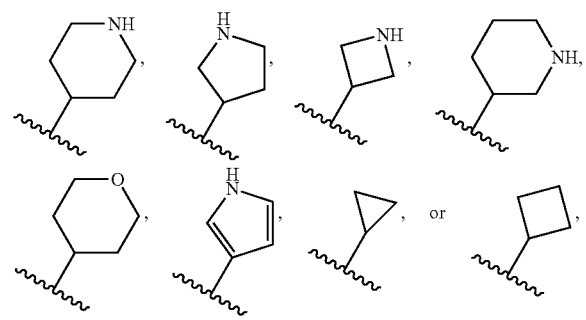

In various other embodiments of all of the foregoing embodiments, the compound may have the structure:

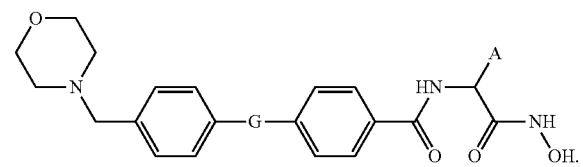

In various other embodiments of all of the foregoing embodiments, X is —(C=O)NR$_4$—, and R$_4$ and A, together with the atoms to which they are attached, form a substituted heterocyclic ring, and the compounds have the following structure:

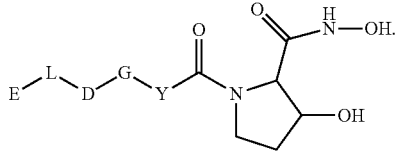

In various other embodiments of all of the foregoing embodiments, X is —(C=O)NR$_4$—, and the compounds have the following structure:

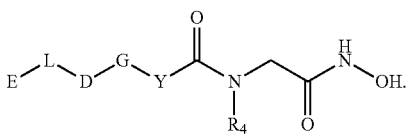

In various other embodiments of all of the foregoing embodiments, X and A, together with the atoms to which they are attached form a heterocyclic ring, and the compounds have the following structure:

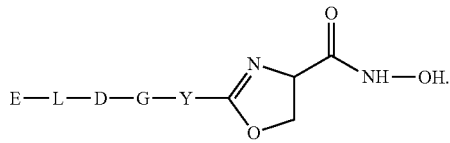

In various other embodiments of all of the foregoing embodiments, Q is —N(OH)C(=O)CR$_1$R$_2$ and at least one of R$_1$ and R$_2$ is not H or C$_1$-C$_6$-alkyl.

In various other embodiments of all of the foregoing embodiments, X is selected from the group consisting of
(1) —SO$_2$NR$_4$—,
(2) —S(=O)NR$_4$—,
(3) —NR$_4$C(=O)—, and
(4) —NR$_4$—,
wherein R$_4$ is H or substituted or unsubstituted C$_1$-C$_6$-alkyl, or R$_4$ and A, together with the atoms to which they are attached can form a substituted or unsubstituted heterocyclic ring, having from 3 to 8 ring atoms, wherein 1-2 ring atoms of the heterocyclic ring are selected from N, O and S, or X is selected from the group consisting of
(1) —(C=O)NR$_4$—,
(2) —C$_1$-C$_6$-alkyl-(C=O)NR$_4$—,
(3) —C$_2$-C$_6$-alkenyl-(C=O)NR$_4$—,
(4) —C$_2$-C$_6$-alkynyl-(C=O)NR$_4$—,
(5) —CH$_2$NR$_4$—,
(6) —SO$_2$NR$_4$—,
(7) —S(=O)NR$_4$—,
(8) —NR$_4$C(=O)—, and
(9) —NR$_4$—,
wherein R$_4$ and Y, together with the atoms to which they are attached, form a bicyclic substituted or unsubstituted heterocyclyl or heteroaryl, or when Y is a bicyclic substituted or unsubstituted heterocyclyl or heteroaryl, then X is absent.

For example, in more specific embodiments, X may be —NH— and Y may be a bicyclic substituted or unsubstituted heterocyclyl or heteroaryl. In such embodiments, Y may be selected from the group consisting of

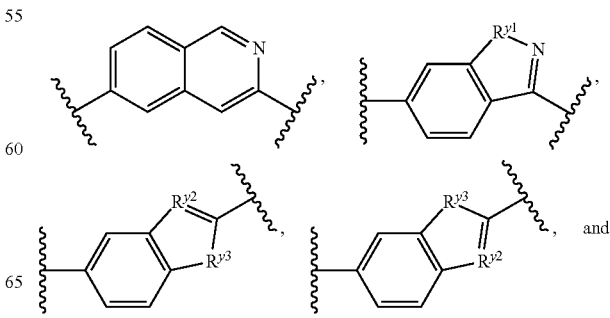

-continued

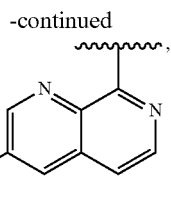

wherein: $R^{y1}$ is S, O, NH or N($C_1$-$C_6$-alkyl); $R^{y2}$ is N, CH, or C($C_1$-$C_6$-alkyl); and $R^{y3}$ is S or O.

In other more specific embodiments, X may be —(C=O)NR$_4$— and R$_4$ and Y, together with the atoms to which they are attached, may form a bicyclic substituted or unsubstituted heterocyclyl or heteroaryl. In such embodiments, R$_4$ and Y may form:

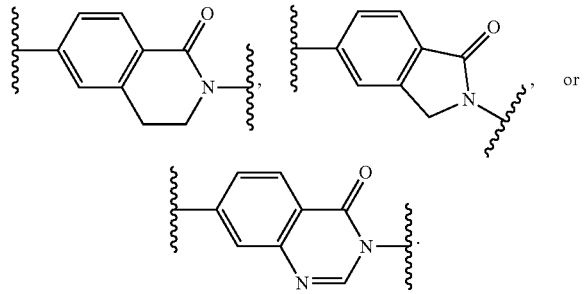

In other more specific embodiments, Y may be a bicyclic substituted or unsubstituted heterocyclyl or heteroaryl and X may be absent. In such embodiments, Y may be:

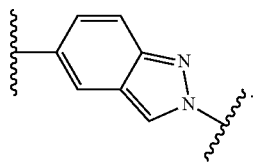 [SMILES: *c1ccc2nn(*)cc2c1]

In various other embodiments of all of the foregoing embodiments, —X—C(AR$_3$)—(CH$_2$)$_n$-Q is —X$_1$-Q$_1$ wherein:

X$_1$ is absent or selected from the group consisting of:
(1) —(C=O)—,
(2) —CR$^x$—,
(3) —(C=O)NR$^x$—, and
(4) —NR$^x$(C=O)—,
wherein R$^x$ is H or substituted or unsubstituted $C_1$-$C_6$-alkyl;

Q$_1$ is selected from the group consisting of:

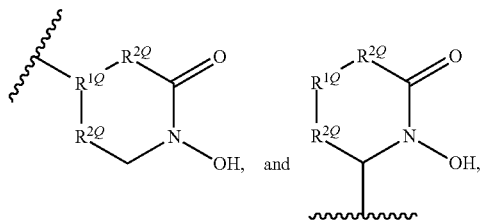

wherein:
R$^{1Q}$ is a carbon or a nitrogen ring atom,
each R$^{2Q}$ is absent or is a carbon ring atom,
R$^{1Q}$ and an adjacent R$^{2Q}$ optionally form a double bond, and
each carbon ring atom is optionally substituted with a substituted or unsubstituted $C_1$-$C_6$ alkyl, or an oxo substituent.

For example, —X$_1$-Q$_1$ may be:

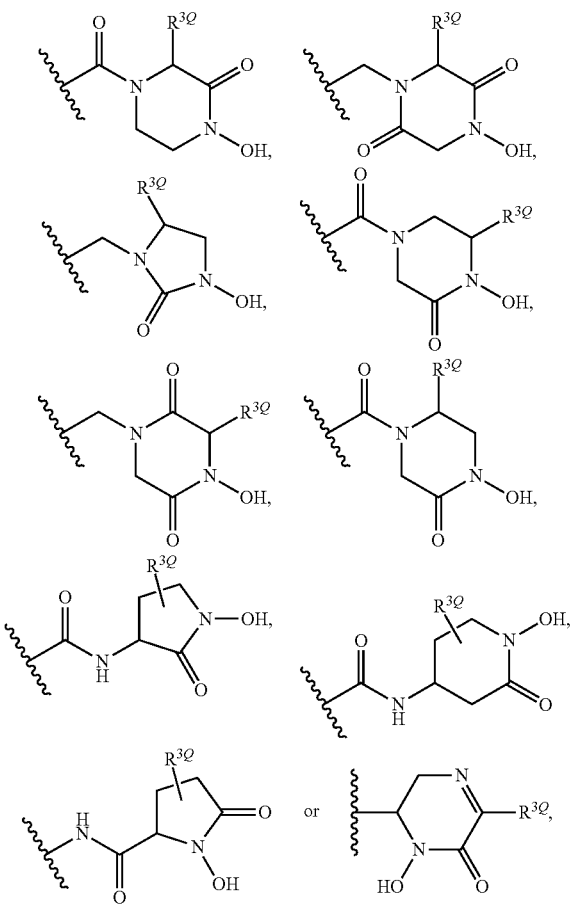

wherein R$^{3Q}$ is H or substituted or unsubstituted $C_1$-$C_6$ alkyl.

In various other embodiments or all of the foregoing embodiments, A contains at least one halogen atom.

In another aspect, the invention provides a method of inhibiting a deacetylase enzyme in a gram-negative bacteria, thereby affecting bacterial growth, comprising administering to a patient in need of such inhibition a compound of formula (I).

In another aspect, the invention provides a method of inhibiting LpxC, thereby modulating the virulence of a bacterial infection, comprising administering to a patient in need of such inhibition a compound of formula (I). In certain embodiments of the method of inhibiting LpxC using a compound of formula (I), the IC$_{50}$ value of the compound is less than or equal to 10 μM with respect to LpxC. In other embodiments, the IC$_{50}$ value is less than or equal to 1 μM, is less than or equal to 0.1 μM, is less than or equal to 0.050 μM, is less than or equal to 0.030 μM, is less than or equal to 0.025 μM, or is less than or equal to 0.010 μM.

In another aspect, the invention provides a method for treating a subject with a gram-negative bacterial infection comprising administering to the subject in need thereof an antibacterially effective amount of a compound of formula (I) with a pharmaceutically acceptable carrier. In certain embodiments, the subject may be a mammal, and in some embodiments, a human.

In another aspect, the invention provides a method of administering an inhibitory amount of a compound of formula (I) to fermentative or non-fermentative gram-negative bacteria. In a more specific embodiment of the method of administering an inhibitory amount of a compound of formula (I) to fermentative or non-fermentative gram-negative bacteria, the gram-negative bacteria are selected from the group consisting of *Pseudomonas aeruginosa, Stenotrophomonas maltophila, Burkholderia cepacia, Alcaligenes xylosoxidans, Acinetobacter, Enterobacteriaceae, Haemophilus, Franciscellaceae (Franciscella tularensis)* and *Neisseria* species.

In another aspect, the invention provides a method of administering an inhibitory amount of a compound of formula (I) to gram-negative bacteria, such as Enterobacteriaceae which is selected from the group consisting of organisms such as *Serratia, Proteus, Klebsiella, Enterobacter, Citrobacter, Salmonella, Providencia, Yersinia (Yersinia pestis), Morganella, Cedecea,* and *Edwardsiella* species and *Escherichia coli.*

In another aspect, the invention provides a pharmaceutical composition or formulation comprising an effective amount of a compound of formula (I) with a pharmaceutically acceptable carrier thereof.

In another aspect, the invention provides a method of co-administering a compound of formula (I) with other therapeutic agents that are selected for their particular usefulness against the condition that is being treated. For example, a compound of formula (I) is useful in combination with other anti-bacterial agents. The compound of formula (I) augments the sensitivity of gram-negative bacteria to existing classes of antibacterials. Combinations of the presently disclosed compounds with other anti-bacterial agents are within the scope of the invention. Such anti-bacterial agents include, but are not limited to, erythromycin, rifampicin, Nalidixic acid, carbenicillin, bacitracin, cycloserine, fosfomycin, and vancomycin.

A further aspect of the invention is the use of LpxC inhibitors for the treatment of an infection, particularly a bacterial infection. A bacterial infection treated with the compounds of the invention can be a primary infection or a co-infection caused by a species of bacteria and one or more additional infectious agents selected from the group consisting of bacteria, virus, parasite and fungus.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The compounds of the invention can be used for treating conditions caused by the bacterial production of endotoxin and, in particular, by gram-negative bacteria and bacteria that use LpxC in the biosynthesis of lipopolysaccharide (LPS) or endotoxin.

The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, anti-CD 14-binding protein antibodies, antilipopolysaccharide-binding protein antibodies and tyrosine kinase inhibitors.

In treatment of serious or chronic respiratory tract infections, the compounds of the present invention may also be used with second non-antibacterial agents administered via inhalation. Representative non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salmeterol, formoterol, indacaterol, bronchiodilators, mucolytics, calfactant, beractant, poractant alfa, surfaxin and pulmozyme (also called domase alfa).

The compounds of the invention can be used, alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter calcoaceticus, Alcaligenes xylosoxidans, Flavobacterium meningosepticum, Providencia stuartii* and *Citrobacter freundi*, community lung infections such as those caused by *Haemophilus Influenzae, Legionella* species, *Moraxella catarrhalis, Branhamella catarrhalis, Enterobacter* species, *Acinetobacter* species, *Klebsiella* species, and *Proteus* species, and infections caused by other bacterial species such as *Neisseria* species, *Shigella* species, *Salmonella* species, *Helicobacter pylori, Vibrionaceae* and *Bordetella* species as well as the infections is caused by a *Brucella* species, *Francisella tularensis* and/or *Yersinia Pestis*.

When used for treating subjects infected with gram-negative bacterial infections, the compounds of the present invention can be used to sensitize gram-negative bacteria to the effects of a second agent.

When the compounds of the present invention are used in combination with a second antibacterial agent, non-limiting examples of antibacterial agents may be selected from the following groups:

(1) Macrolides or ketolides such as erythromycin, azithromycin, clarithromycin and telithromycin;

(2) Beta-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;

(3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;

(4) Antibacterial sulfonamides and antibacterial sulphanilamides, including para-aminobenzoic acid, sulfadiazine, sulfisoxazole, sulfamethoxazole and sulfathalidine;

(5) Aminoglycosides such as streptomycin, neomycin, kanamycin, paromycin, gentamicin, tobramycin, amikacin, netilmicin, spectinomycin, sisomicin, dibekacin and isepamicin;

(6) Tetracyclines such as tetracycline, chlortetracycline, demeclocycline, minocycline, oxytetracycline, methacycline, tigecycline, doxycycline;

(7) Rifamycins such as rifampicin (also called rifampin), rifapentine, rifabutin, bezoxazinorifamycin and rifaximin;

(8) Lincosamides such as lincomycin and clindamycin;

(9) Glycopeptides such as telavancin, vancomycin and teicoplanin or lipopeptides such as daptomycin;

(10) Streptogramins such as quinupristin and dafloristin;

(11) Oxazolidinones such as linezolid;

(12) Polymyxin, colistin and colymycin; and

(13) Trimethoprim and bacitracin.

The second antibacterial agent may be administered in combination with the compounds of the present inventions, wherein the second antibacterial agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

When used for treating a serious or chronic respiratory tract infections, the compounds of the invention may be used alone or in combination with a second antibacterial agent administered via inhalation. In the case of inhalation, a preferred second antibacterial agent is selected from a group consisting of tobramycin, gentamicin, aztreonam, ciprofloxacin, polymyxin, colistin, colymycin, azithromycin and clarithromycin.

Pharmaceutical Compositions

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions that are compatible with body tissues.

Compositions for rectal or vaginal administration are preferably suppositories that can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μm. Predominantly in this application means that at least 70% but preferably more than 90% of all generated aerosol particles are 1 to 5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and UltraAire7 (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen that the tablets or capsules so specified should be ingested or a card that contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, that indicates the number of daily doses that has been dispensed. Another example of such a memory-aid is a battery-powered microchip memory coupled with a liquid crystal readout, or audible reminder signal that, for example, reads out the date that the last daily dose has been taken and/or reminds one when the next dose is to be taken.

The kits of the present invention may also include, in addition to LpxC inhibitors, one or more additional pharmaceutically active compounds. Preferably, the additional compound is another LpxC inhibitor or another compound useful to bacterial infections. The additional compounds may be administered in the same dosage form as the LpxC inhibitor or in different dosage forms. Likewise, the additional compounds can be administered at the same time as the LpxC inhibitor or at different times.

Compositions of the present compounds may also be used in combination with other known antibacterial agents of similar spectrum to (1) synergistically enhance treatment of severe Gram-negative infections covered by the spectrum of this compound or (2) add coverage in severe infections in which multiple organisms are suspected in which another agent of a different spectrum may be required in addition to this compound. Potential agents include members of the aminoglycosides, penicillins, cephalosporins, fluoroquinolones, macrolides, glycopeptides, lipopeptides and oxazolidinones. The treatment can involve administering a composition having both active agents or administration of the inventive compounds followed by or preceded by administration of an additional active antibacterial agent.

Characterization and Purification Methods

Referring to the examples that follow, compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1 B2-F flexible sheets. TLC results were readily detected visually under ultraviolet light, or by employing well known iodine vapor and other various staining techniques.

Mass spectrometric analysis was performed on one of two LCMS instruments: a Waters System. (Alliance HT HPLC and a Micromass ZQ mass spectrometer; Column: Eclipse XDB-C-18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses are reported as those of the protonated parent ions.

GCMS analysis was performed on a Hewlet Packard instrument (HP6890 Series gas chromatograph with a Mass Selective Detector 5973; injector volume: 1 µL; initial column temperature: 50° C.; final column temperature: 250 C; ramp time: 20 minutes; gas flow rate: 1 mL/min; column: 5% phenyl methyl siloxane, Model #HP 190915-443, dimensions: 30.0 m×25 m×0.25 m).

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (e.g. 75° C.) to promote increased sample solubility.

The purity of some of the invention compounds was assessed by elemental analysis (Desert Analytics, Tuscon, Ariz.)

Melting points were determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Compounds of the present invention can be readily synthesized using the methods described herein, or other methods, that are well known in the art. For example, the synthesis of hydroxamic acids or similar scaffolds having a wide variety of substituents are comprehensively reviewed in Kline, T., et al., "Potent, novel in vitro inhibitors of the *Pseudomonas aeruginosa* deacetylase LpxC" *J. Med Chem.* 2002, 45(14), 3112-29; U.S. Pat. No. 5,925,659; Pirrung, M. C., et al., "A Convenient Procedure for the Preparation of Amino Acid Hydrokamates from Esters" *J. Org. Chem.* 1995, 60, 8084-8085; Nhu, K., et al., "A New and Efficient Solid Phase Synthesis of Hydroxamic Acids" *J. Org. Chem.* 1997, 62, 7088-7089; Internationa PCT Publication No. WO98/18754; Mellor, S. L., et al., "N-Fmoc-aminoxy-2-chlortrityl Polystyrene Resin: A Facile Solid-phase Methodology for the Synthesis of Hydroxamic Acids" *Tetrahedron Lett.* 1997, 38, 3311-3314; Khan, S. I., et al., "A Facile and Convenient Solid-phase Procedure for Synthesizing Nucleoside Hydroxamic Acids" *Terahedron. Lett.* 1998, 39, 8031-8034; Zhang, Y., et al., "Design, Combinatorial Chemical Synthesis, and in vitro Characterization of Novel Urea Based Gelatinase Inhibitors" *Bioorg. Med. Chem. Lett.* 1999, 9, 2823-2826; Ito, Y., et al., "Synthetic Reactions by Complex Catalysts. XXXI, A Novel and Versatile Method of Heterocycle Synthesis" *J. Am Chem. Soc.* 1973, 95, 4447-4448; Ito, Y., et al., "Synthetic Reactions by Complex Catalysts XXXV" *Syn. Commun.* 1974, 4, 97-103; Witte, H., et al., "Cyclische Imidsaurester aus Nitrilen and Aminoalkoholen" *Liebigs Ann. Chem.* 1974, 996-1009; Pattenden, G., et al., "Naturally Occurring Linear Fused Thiazoline-Thiazole Containing Metabolites: Total Synthesis of (−) Didehydromirabazole A, a Cytotoxic Alkaloid from Blue-Green Algae" *J. Chem. Soc. Perkin Trans* 1993, 1, 1629-1636; Boyce, R. J., et al., "Total Synthesis of Thiangazole, A Novel Naturally Occurring HIV-1 Inhibitor from *Polyangium* sp." Tetrahedron 1995, 51, 7321-7330; Galeotti, N., et al., "Synthesis of Peptidyl Aldehydes from Thiazolines" *Tetrahedron. Lett.* 1997, 38, 2459-2462; Charette, A. B., et al., "Mild Method for the Synthesis of Thiazolines from Secondary and Tertiary Amides" *J. Org. Chem.* 1998, 63, 908-909; Bergeron, R. J., et al., "Effects of C-4 Stereochemistry and C-4' Hydroxylation on the Iron Clearing Efficiency and Toxicity of Desferrithiocin Analogues" *J. Med. Chem.* 1999, 42, 2432-2440; Raman, P., et al., "Titanium (IV)-mediated Tandem Deprotection-cyclodehydration of Protected Cysteine N-Amides: Biomimetic Synthesis of Thiazoline- and Thiazole-containing Heterocycles" *Org. Lett.* 2000, 2, 3289-3292; Fernandez, X., et al., "Novel Synthesis of 2-Thioazolines" *Tetrahedron Lett.* 2000, 41, 3381-3384; and Wipf, P., et al., "C. Thiolysis of Oxazolinenes: A New, Selective Method for the Direct Conversion of Peptide Oxazolines into Thiazolines" *Tetrahedron Lett.* 1995, 36, 6395-6398, which are incorporated herein by reference.

The synthesis of other non-hydroxamates compounds or more generally zinc binding groups are reviewed in Pirrung, M. C., et al., "Inhibition of the Antibacterial Target UDP-(3-O-acyl)-N-acetylglucosamine Deacetylase (LpxC): Isoxazoline Zinc Amidase Inhibitors Bearing Diverse Metal Binding Groups" *J. Med. Chem.* 2002, 45(19), 4359-4370; Jackman, J. E., et al., "Antibacterial agents that target lipid A biosynthesis in gram-negative bacteria: inhibition of diverse UDP-3-O—(R-3-hydroxymyristoyl)-N-acetylglucosamine deacetylases by substrate analogs containing zinc binding motifs" *J. Bio. Chem.* 2000, 275(15), 11002-11009; Brooks, C. D. W., et al, "Modulators of Leukotriene Biosynthesis and Receptor Activation" *J. Med. Chem.* 1996, 39(14), 2629-2654; Jeng, A. Y., et al., "Endothelin converting enzyme inhibitors" *Current Pharmaceutical Design* 1997, 3(6), 597-614; Zask, A., et al., "Inhibition of matrix metalloproteinases: structure based design" *Current Pharmaceutical Design* 1996, 2(6), 624-661; Skotnicki, J. S., et al., *Current Opinion in Drug Discovery & Development* 2003, 6(5), 742-759.

The foregoing may be better understood by reference to the following examples, that are presented for illustration and not to limit the scope of the inventive concepts.

EXAMPLES

The following are abbreviations used in the examples:
AcOH: Acetic acid
aq: Aqueous
ATP: Adenosine triphosphate
Boc: tert-butoxycarbonyl
Boc-Thr(OBn)-OH 3-(R)-Benzyloxy-2-(S)-tert-butoxycarbonylaminobutyric acid
DAP or Dap: Diaminopropionate
DCM: 4-(Dicyanomethylene)-2-methyl-6-(4-dimethylaminostyryl)-4H-pyran
DEAD: Diethyl azodicarboxylate
DIEA: Diisopropylethylamine
DME: 1,2-dimethoxyethane
DMF: N,N-Dimethylformamide
DMSO: Dimethyl sulfoxide
DPPA: Diphenyl phosphoryl azide
Et$_3$N: Triethylamine
EDC: N-(3-Dimethylaminopropyl)-N'-ethylcarbodiimide
EDCI: 1-(3-dimethylaminopropyl)-3-ethylcarbodiimide
EtOAc: Ethyl acetate
EtOH: Ethanol
Fmoc: 9-fluorenylmethoxycarbonyl
Gly-OH: glycine
HATU: O-(7-azabenzotriaazol-1-yl)-N,N,N'N'=tetramethyluronium hexafluorophophate
HBTU: 2-(1H-benzotriazol-1-yl)-1,1,3,3-tetramethyluronium hexafluorophosphate
Hex: hexane
HOBt: butyl alcohol
HOBT: 1-Hydroxybenzotriazole
HPLC: High Pressure Liquid Chromatography
IC$_{50}$ value: The concentration of an inhibitor that causes a 50% reduction in a measured activity.
iPrOH: Isopropanol
LC/MS: Liquid Chromatography/Mass Spectrometry
LRMS: Low Resolution Mass Spectrometry
MeOH: Methanol
NaOMe: sodium methoxide
nm: Nanometer
NMP: N-Methylpyrrolidone
PPh$_3$: triphenyl phosphine
RP-HPLC: Reversed-phase high-pressure liquid chromatography
RT: Room temperature
sat: Saturated
TEA: Triethylamine
TFA: Trifluoroacetic acid
THF: Tetrahydrofuran
Thr: Threonine
TLC: Thin Layer Chromatography
Trt-Br: Tert-butyl bromide Nomenclature for the Example compounds was provided using ACD Name version 5.07 software (Nov. 14, 2001) available from Advanced Chemistry Development, Inc. In addition, some of the compounds were named using ChemDraw Ultra 9.0 and ChemDraw Ultra 11.0 software available from CambridgeSoft Corporation. Some of the compounds and starting materials were named using standard IUPAC nomenclature.

Synthesis of N-Aryl Threonine Analogues and Formation of Hydroxamate

Example 1

Synthesis of 3-bromo-4-fluoro-N-{(1S,2R)-2-hydroxy-1-[(hydroxyamino)carbonyl]propyl}benzamide (3)

Preparation of (2S,3R)-2-(3-bromo-4-fluoro-benzoylamino)-3-hydroxy-butyric acid methyl ester (2)

Diisopropylethylamine (6.8 mL, 39.0 mmol) was added to a stirred solution of 3-bromo-4-fluorobenzoic acid (1) (2.152 g, 9.83 mmol), L-threonine methyl ester hydrochloride (1.968 g, 11.6 mmol), EDCI (2.218 g, 11.6 mmol) and HOBt (1.410 g, 10.4 mmol) in anhydrous DMF (60 mL) at 0° C. under N$_2$. The solution was stirred at 0° C. for 1 h and at room temperature for 20 h. The solution was diluted with EtOAc (300 mL) and washed with 1.0 M HCl (2×80 mL), saturated NaHCO$_3$ (2×80 mL), H$_2$O (4×80 mL), dried over MgSO$_4$, filtered and concentrated in vacuo to give a colorless syrup which solidified on standing to afford 3.280 g (100%) of (2) as a white solid, mp 73-74° C. MS(ES+) m/z 333.9 (C$_{12}$H$_{13}$BrFNO$_4$+H requires 334.00).

Preparation of 3-bromo-4-fluoro-N-{(1S,2R)-2-hydroxy-1-[(hydroxyamino)carbonyl]propyl}benzamide (3)

To a solution of hydroxylamine hydrochloride (66 mg, 0.95 mmol) in anhydrous MeOH (2.0 mL) at 0° C. under N$_2$ atmosphere was added sodium methoxide (25 wt % in MeOH, 360 mg, 1.67 mmol). A precipitate formed immediately and the cloudy white solution was stirred for 10 minutes at 0° C. A solution of (2) (284 mg, 0.850 mmol) in MeOH (2.0 mL) was added and the reaction stirred 2 h at 0° C. and then warmed gradually to room temperature overnight (17 h total). Aqueous 1.0 M HCl (10 mL) was added and the solution extracted with 4:1 chloroform/isopropyl alcohol (4×20 mL). The organic layers were combined, dried over Na$_2$SO$_4$ and concentrated to give a pink foam. The crude solid was triturated with diethyl ether (2×8 mL) and dried in vacuo to give (3) as a white foam: mp 152-153° C. Rf (10:1 CH$_2$Cl$_2$/MeOH on silica gel)=0.53.

Preparation of Hydroxamates

Example 2

Synthesis of 4-benzoyl-N-{(1S,2R)-2-hydroxy-1-[(hydroxyamino)carbonyl]propyl}benzamide (2)

To a solution of hydroxylamine hydrochloride (121 mg, 1.74 mmol) in anhydrous MeOH (2.0 mL) at 0° C. under N$_2$ atmosphere was added sodium methoxide (25 wt % in MeOH, 680 mg, 3.14 mmol). A precipitate was immediately observed and the cloudy white solution was stirred for 10 minutes at 0° C. A solution of methyl (2S,3R)-3-hydroxy-2-{[4-(phenylcarbonyl)phenyl]carbonylamino}butanoate (1) (534 mg, 1.56 mmol) in MeOH (3.0 nL) was added and the reaction stirred 3 h at 0° C., then warmed gradually to ambient temperature overnight (18 h total). Aqueous 0.5 M HCl (20 mL) was added and the solution extracted with 5:1 chloroform/isopropyl alcohol (4×40 mL). The organic layers were combined, dried over $Na_2SO_4$ and concentrated to give an orange foam. Purification by silica gel chromatography (increasing eluant polarity from 30:1 $CH_2Cl_2$/MeOH to 15:1 $CH_2Cl_2$/MeOH) afforded 228 mg (43%) of (2).

Example 3

Synthesis of (2R,3R)-3-hydroxy-1-{[4-(trifluoromethoxy)phenyl]carbonyl}pyrrolidine-2-carbohydroxamic acid (3)

Preparation of ((2R,3R)-3-hydroxy-1-{[4-(trifluoromethoxy)phenyl]carbonyl)}pyrrolidin-2-yl)-N-(phenylmethoxy)carboxamide (2)

To a solution of (2R,3R)-3-hydroxy-1-{[4-(trifluoromethoxy)phenyl]carbonyl}pyrrolidine-2-carboxylic acid (1) (405 mg, 1.27 mmol), benzylhydroxylamine hydrochloride (243 mg, 1.52 mmol), HATU (556 mg, 1.46 mmol), and HOBt (178 mg, 1.32 mmol) in DMF (10 mL) at 0° C. was added diisopropylethylamine (710 μL, 4.07 mmol) with stirring. The cooling bath was removed after one hour and the reaction mixture stirred at ambient temperature for 18 h and then diluted with EtOAc (200 mL). The organic layer was washed with 1.0 M HCl (2×60 mL), sat. $NaHCO_3$ (2×60 mL) and $H_2O$ (5×60 mL), dried over $MgSO_4$ and concentrated to give 493 mg (92%) of (2), a colorless oil that slowly crystallized upon standing. Rf (25:1 $CH_2Cl_2$/MeOH)=0.35.

Preparation of (2R,3R)-3-hydroxy-1-{[4-(trifluoromethoxy)phenyl]carbonyl}pyrrolidine-2-carbohydroxamic acid (3)

To a solution of (2) (143 mg, 0.337 mmol) in EtOH (10 mL) was added 20% $Pd(OH)_2$/C (50 mg). The solution was purged with hydrogen gas (approx. 0.5 L from a 1 L balloon) and then stirred under an atmosphere of $H_2$ (balloon pressure). TLC analysis showed no starting material after one hour. The solution was diluted with EtOAc (10 mL) and filtered through celite, washing with 20:1 EtOAc/EtOH (50 mL) The solution was concentrated and dried in vacuo to afford 90 mg (80%) of (3) as a sticky white foam: mp 64-65° C. Rf (10:1 $CH_2Cl_2$/MeOH)=0.29.

Synthesis of N-Benzyl Threonine Analogues by Reductive Amination

Example 4

Synthesis of (2S,3R-3-hydroxy-2-{[(4-phenylphenyl)methyl]amino}butanehydroxamic acid (3)

Triethylamine (1.70 mL, 12.1 mmol) was added to a stirred suspension of L-threonine methyl ester hydrochloride (1.030 g, 6.07 mmol) and 4-biphenylcarboxaldehyde (1) (1.104 g, 6.06 mmol) in THF (25 mL). After 20 min, $NaBH(OAc)_3$ (1.800 g, 8.49 mmol) was added and the suspension stirred for 20 h. The reaction was monitored by TLC (50:1 DCM/MeOH, $R_f$=0.4). The reaction mixture was quenched with saturated $NaHCO_3$ (50 mL), extracted with EtOAc (2×120 mL), dried over $MgSO_4$, filtered and concentrated to give a yellow oil. Purification by silica gel chromatography (150:1 DCM/MeOH) afforded 1.220 g (67% yield, 98% pure) of (2) as a pale yellow oil. HPLC (260 nm, 34 min run) 14.2 min; LRMS(ES+) m/z 299.9 ($C_{18}H_{21}NO_3$+H requires 300.10).

Compound (3) was then formed by the addition of $NH_2OH$ in MeOH/NaOMe at 0° C., warming to ambient temperature of the period of several hours. LCMS MH+301.15.

General Methods for Making Phenyl-Benzoic Acids and Phenyl-Benzoate Esters (See Example 5 Below)

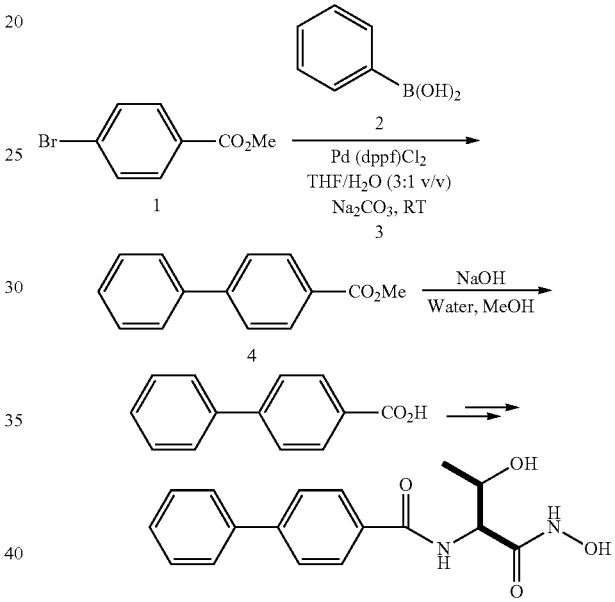

Suzuki Procedures Using $Pd(dppf)Cl_2$-DCM Catalyst and a THF/$H_2O$ Mixture

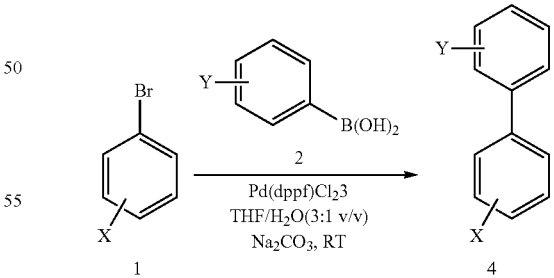

| Reagent | MW | Eq. | g/ml | mmol |
|---|---|---|---|---|
| BromoArene #1 | ~300 | 1 | 100 mg | ~0.33 |
| Boronic Acid #2 | — | 1.2 | — | ~0.40 |
| $Na_2CO_3$ | 105.99 | 3 | 104 m | ~0.99 |
| $Pd(dppf)Cl_2$ | 816.63 | 0.1-0.2 | 27-54 mg | ~0.033-0.066 |

| Reagent | MW | Eq. | g/ml | mmol |
|---|---|---|---|---|
| THF (3) (sparged with argon for 5 min.) | | | 0.75 ml | |
| water (1) (sparged with argon for 5 min.) | | | 0.25 ml | |

1 eq aryl halide (1) was added to 1.2 eq. (2) and Pd(dppf)Cl₂ in THF, followed by addition of water and stirred 8 hours at RT. Upon completion (usually over night), the reactions are diluted with ethyl acetate (5-10 ml) and water (1 ml). The organic layer is separated and washed with NaHCO₃ (2×3 ml), water (1×3 ml), brine (1×3 ml), dried with Na₂SO₄, filtered and concentrated in an 8 ml glass vial. The residue is dissolved in DMSO and injected on a preparatory HPLC reverse phase column to afford >80% yield.

Suzuki Procedures Using Pd(dppf)Cl₂-DCM Catalyst and DMF Solvent

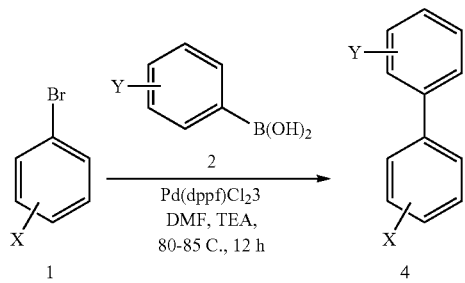

| Reagent | MW | Eq. | g/ml | mmol |
|---|---|---|---|---|
| BromoArene #1 | ~500 | 1 | 20 mg | ~0.04 |
| Boronic Acid #2 | ~200 | 2 | ~14 mg | ~0.08 |
| Pd(dppf)Cl₂ | 816.63 | 0.25 | 10 mg | ~0.01-0.02 |
| TEA | 101.19 | 5 | 28 μL | ~0.2 |
| DMF (dry & sparged with argon for 5 min.) | | | 0.5 ml | |

The haloarene (1) and boronic acid (2) were weighed out and placed in the reaction flask. The DMF was sparged with argon for 5-10 minutes, followed by TEA addition, and the reaction was lightly bubbled with argon. The solid Pd(dppf)Cl₂ catalyst was added in one portion. The vial was flushed with argon, capped tight and stirred or shaken at ~80° C. Upon reaching completion (over night), the reaction was filtered and injected on a preparatory HPLC reverse phase column (80% yield).

Synthesis of Methyl DAP Analogues

Example 5

3-(R)-Amino-2-(S)-[(4'-ethyl-biphenyl-4-carbonyl)-amino]-butyl-hydroxamic acid (8)

Preparation of N-triphenylmethyl allo-threonine Methyl Ester (2)

*For similar-procedures see: Righi, P., et al., B. *Organic Letters* 2002, 4(4), 497-500.

A solution of trityl bromide (3.2 g, 10.0 mmol) in CHCl₃ (40 ml) was added dropwise to a stirred solution of allo-threonine methyl ester HCl salt (1) (2.0 g, 12.0 mmol) and DIEA (5.2 ml, 30.0 mmol) in CHCl₃ (60 ml) at rt under N₂. The reaction could be followed by TLC eluting with EtOAc/Hex (40:60) (Rf=0.3). After stirring 12 h, the reaction was concentrated to a brown oil. The crude product was diluted with EtOAc (170 ml) and washed with 0.2 N citric acid (2×50 ml), water (2×50 ml), brine (50 ml), dried (Na₂SO₄), filtered and concentrated under reduced pressure to yield 3.73 g (85% yield, 95% pure) of (2) as a yellow solid. HPLC (220 nm, 41 min. run) 30.90 min.; HPLC (220 nm, 17 min. run) 14.86 min.; LCMS: LC (214 nm) 3.06 min., MS(ES+) m/z 376.2 (C₂₄H₂₅NO₃+H requires 376.18).

Preparation of 3-(R)-Azido-2-(S)-(trityl-amino)-butyric Acid Methyl Ester (3)

*For similar procedures see: Matsuda, A., et al., *J. Med. Chem.* 1991, 34, 999-1002.

A solution of pure DEAD (2.9 ml, 17.8 mmol) in THF (5 ml) was added slowly dropwise to a stirred solution of trt-allo-threonine methyl ester (2) (4.1 g, 10.9 mmol) and PPh₃ (2.9 g, 10.9 mmol) in THF (40 ml) at 0° C. under N₂. After 3 min., a solution of DPPA (6.4 ml, 29.7 mmol) in THF (5 ml) was added to the orange-yellow reaction solution at 0° C. After 1 h, the reaction was allowed to warm to rt. After 40 h, the reaction had reached completion by TLC (Hexane/DCM/EtOAc (64:20:16) (Rf=0.6)) and LCMS. The yellow solution was concentrated to give 18 g of crude material that was purified by column chromatography eluting with Hexane/EtOAc (88:12) giving 3.5 g of 70% pure product after evaporation. The product was purified again (to remove trityl alcohol and a crotyl side-product formed during the reaction by elimination) by column chromatography eluting with Hexane/DCM/EtOAc (76:20:4) giving 1.65 g (38% yield) of (3) as a pale yellow oil after concentration and drying in vacuo. Note that the trityl protecting group would hydrolyze when exposed to TFA while running the sample on HPLC.

Alternately, the reaction could be carried out in dry DCM. A reaction using 5.44 g (14.5 mmol) of trt-allo-threonine methyl ester (2) in DCM (100 ml) with PPh₃ (3.8 g, 14.5 mmol), pure DEAD (3.4 ml, 21.8 mmol) in DCM (5 ml) and DPPA (6.3 ml, 24.0 mmol) in DCM (10 ml) were combined following the procedure above. After 3 days, the reaction did not progress further by TLC and LCMS. After the same work up, 2.97 g of the product was obtained in 51% yield.

HPLC (220 nm, 41 min. run) 40.5 min.; HPLC (220 nm, 17 min. run) 16.32 min.; LCMS: LC (214 nm) 3.7 min., MS(ES+) m/z 401.2 (C₂₄H₂₅N₃O₂+H requires 401.15).

Preparation of 2-(S)-Amino-3-(R)-azido-butyric acid methyl ester HCl salt (4)

A solution of Trt-Azido-Thr-OMe (3) (4.8 g, 12.0 mmol) was dissolved in a 95% TFA/DCM solution (60 ml) at rt with stirring. After 2.5 h, the reaction was complete by LCMS. The bright yellow solution was diluted with 0.5 N aq. HCl (300 ml). The aqueous layer was extracted with DCM (2×30 ml) and then lyophilized to dryness. The white solid was dissolved in AcCN/water (50:50) (100 ml) and again lyophilized to dryness to produce a consistent powder and remove as much of the TFA as possible. The azido-Thr product (4), 2.26 g (97% yield, 95% pure) of a white solid, was obtained as the HCl salt. HPLC (220 nm, 41 min. run) 7.91 min.; HPLC (220 nm, 17 min·run) 3.36 min; LCMS:

LC (214 nm) 0.48 min., MS(ES+) m/z 159.3 ($C_5H_{10}N_4O_2$+H requires 159.08).

Preparation of 3-(R)-Azido-2-(S-[(4'-ethyl-biphenyl-4-carbonyl)-amino]-butyric acid methyl ester (6)

An EDC.HCl (249 mg, 1.3 mmol) was added to a stirred colorless solution of azido-Thr-OMe.HCl (4) (195 mg, 1.0 mmol), HOBT (158 mg, 1.0 mmol), 4'-Ethyl-biphenyl-4-carboxylic acid (5) (226 mg, 1.0 mmol) and DIEA (0.44 ml, 2.5 mmol) in DCM (10 ml) at rt under $N_2$. After 24 h, the reaction had reached completion by TLC (Hexane/EtOAc (60:40) (Rf=0.3)) and LCMS. The reaction was evaporated under reduced pressure to a brown tar. The crude product was dissolved in EtOAc (100 ml) and washed with 0.2N aq. HCl (2×50 ml), aq. sat. $NaHCO_3$ (50 ml), brine (50 ml), dried ($Na_2SO_4$), filtered and concentrated under reduced pressure to yield a crude brown solid. The crude material was further purified by column chromatography eluting with Hexane/EtOAc (70:30) giving 245 mg (67% yield) of pure product (6) after evaporation and drying in vacuo. HPLC (220 nn, 41 min. run) 33.87 min.; HPLC (220 nm, 17 min. run) 15.61 min; LCMS: LC (214 nm) 3.25 min., MS(ES+) m/z 367.2 ($C_{20}H_{22}N_4O_3$+H requires 367.17).

Preparation of 3-(R)-Amino-2-(S)-[(4'-ethyl-biphenyl-4-carbonyl)-amino]-butyric acid methyl ester (7)

A solution of biphenyl azido-Thr methyl ester (6) (244 mg, 0.67 mmol) in MeOH (10 ml) was made by sonicating until the milky precipitate cleared. After bubbling nitrogen through the reaction solution for 30 sec., 10% Pd/C was added in one portion. The reaction was stirred under nitrogen at RT. The reaction was exposed to aspirator vacuum to remove the nitrogen and then opened to the hydrogen gas at balloon pressure (~1 atm). The reaction stirred for 3 h at which time the hydrogen was exchanged for nitrogen. The reaction was filtered through a pad of celite to remove the palladium. The celite pad was washed with MeOH (30 ml). The combined fractions of MeOH were evaporated under reduced pressure and dried in vacuo to give 225 mg (99% yield) of pure product (7) as a white solid. HPLC (220 nm, 17 min. run) 10.79 min.; LCMS: LC (214 nm) 2.21 min., MS(ES+) m/z 341.2 ($C_{20}H_{24}N_2O_2$+H requires 341.18).

Preparation of 3-(R)-Amino-2-(S)-[(4'-ethyl-biphenyl-4-carbonyl)-amino]-butyl-hydroxamic acid (8)

To a stirred suspension of biphenyl-amino-Thr methyl ester (7) (225 mg, 0.6 mmol) and hydroxylamine HCl salt (460 mg, 6.6 mmol) in MeOH (7 ml) and DCM (5 ml) was added fresh solid NaOMe powder (430 mg, 7.92 mmol) in one portion. After stirring for 2 min. at rt under nitrogen, the pH of the reaction on wet pH paper was approximately 7-8. The suspension had change from larger particles of white solid to a finely-divided milky consistency. The pH of the reaction was checked after adding small portions of NaOMe (50-100 mg) and allowing 2 min. for the reaction to equilibrate. The pH of the reaction reached a stable 11-12 after the final portion of NaOMe was added (250 mg total). The reaction was initiated at pH 11 and proceeded quickly. After 30 min., the reaction reached 85% completion as determined by LCMS, and the reaction was placed in a −10° C. bath. The cold mixture filtered over fine filter paper on a Buchner funnel. The white residue was washed with MeOH (15 ml). The organic fractions were collected and concentrated under reduced pressure to give crude product (750 mg). The crude product (only one 150 mg portion) was dissolved in DMSO (1 ml), AcCN (1000 and water (100 µl), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness. The product as the TFA salt was dissolved in AcCN/water (50:50) (5 ml), 1N aq. HCl (1 equivalent) and lyophilized again to give 11.5 mg of (8) as a white powder as an HCl salt (23% yield). HPLC (220 nm, 41 min. run) 19.31 min.; HPLC (220 nm, 17 min. run) 9.39 min; LCMS: LC (214 nm) 1.98 min., MS(ES+) m/z 342.2 ($C_{19}H_{23}N_3O_3$+H requires 342.17).

Synthesis of 4'-Benzamide Biphenyl Threonine Hydroxamic Acid

Example 6

Biphenyl-4,4'-dicarboxylic acid 4'-[(3-Boc-amino-propyl)-amide]-4-[((2R)-hydroxy-(1S)-hydroxycarbamoyl-propyl)-amide] (6)

and

Example 7

Biphenyl-4,4'-dicarboxylic acid 4'-[(3-amino-propyl)-amide]-4-[((2R)-hydroxy-(1S)-hydroxycarbamoyl-propyl)-amide] (7)

Synthesis of (2S,3R)-2-amino-3-(phenylmethoxys)-N-(phenylmethoxy)butanamide (1)

To a suspension of benzylhydroxylamine hydrochloride (8.310 g, 52.06 mmol), Boc-Thr(OBn)-OH (14.01 g, 45.28 mmol), EDCI (10.01 g, 52.21 mmol), and HOBt (6.90 g, 51.06 mmol) in $CH_2Cl_2$ (300 mL) at 0° C. was added diisopropylethylamine (28.3 mL, 162 mmol) with stirring. The cooling bath was removed after one hour and the reaction mixture stirred at ambient temperature for 20 h and was then diluted with $CH_2Cl_2$ (300 mL). The organic layer was washed with 1.0 M HCl (2×200 mL), sat. $NaHCO_3$ (2×200 mL) and brine (200 mL), dried over $MgSO_4$ and concentrated to give 14.5 g of a white solid. The crude solid was treated with a solution of trifluoroacetic acid (90 mL) in $CH_2Cl_2$ (90 mL) and stirred for 2.5 h. The reaction mixture was concentrated by rotary evaporation and then diluted with $CH_2Cl_2$ (600 mL). The organic layer was washed with sat. $NaHCO_3$ (2×200 mL), dried over $MgSO_4$ and concentrated to give a dark orange oil. Purification by silica gel chromatography (50:1 $CH_2Cl_2$/MeOH) afforded (1) (8.9 g) as a pale yellow oil. Rf(50:1 $CH_2Cl_2$/MeOH on silica gel)=0.2.

Preparation of (1S,2R)-4'-(2-benzyloxy-1-benzyloxycarbamoyl-propyl carbamoyl)-biphenyl-4-carboxylic acid (3)

To a suspension of 4,4'-biphenyldicarboxylic acid (2) (1.360 g, 5.61 mmol) in DMF (180 mL) was added BOP (2.007 g, 4.54 mmol) and DIEA (1.7 mL, 9.8 mmol). A solution of (1) (944 mg, 3.00 mmol) in DMF (20 mL) was added and the reaction stirred for 18 h. The solution was diluted with EtOAc (250 mL) and washed with 1.0 M HCl (500 mL). The aqueous layer was extracted with EtOAc (250 mL) and the organic layers combined. The organic layer was washed with 1.0 M HCl (250 mL), dried over MgSO$_4$, and concentrated to give a crude yellow solid. Purification by silica gel chromatography (60:1 CH$_2$Cl$_2$/ MeOH) gave 210 mg (3) (13% yield) as a yellow solid. R$_f$=0.80 (10:1 CH$_2$Cl$_2$/MeOH); LRMS (ES+) m/z 539.1 (C$_{32}$H$_{30}$N$_2$O$_6$+H requires 539.22).

Preparation of biphenyl-4,4'-dicarboxylic acid 4'-[(3-(Boc)-amino-propyl)-amide]-4-[(2R)-benzyloxy-(1S)-benzyloxycarbamoyl-propyl)-amide] (5)

To a solution of (3) (200 mg, 0.371 mmol), EDCI (78 mg, 0.407 mmol), and HOBt (52 mg, 0.385 mmol) in DMF (2 mL) was added t-Butyl N-(3-aminopropyl)carbamate (4) (71 mg, 0.407 mmol) and DIEA (180 µL, 1.0 mmol). The reaction mixture was stirred 24 h, diluted with EtOAc (150 mL), washed with 1.0 M HCl (2×60 mL), saturated NaHCO$_3$ (2×60 mL), H$_2$O (3×60 mL), dried over MgSO$_4$ and concentrated to give a crude white solid. Purification by silica gel chromatography (25:1 CH$_2$Cl$_2$/MeOH) afforded 194 mg (75% yield) of (5) as a white solid. R$_f$=0.15 (50:1 CH$_2$Cl$_2$/ MeOH); LRMS (ES+) m/z 695.2 (C$_{40}$H$_{46}$N$_4$O$_7$+H requires 695.35).

Preparation of Biphenyl-4,4'-dicarboxylic acid 4'-[(3-Boc-amino-propyl)-amide]4-[((2R)-hydroxy-(1S)-hydroxycarbamoyl-propyl)-amide] (6)

A solution of (5) (190 mg, 0.273 mmol) in THF (5 mL) and MeOH (3 mL) was charged with Pd(OH)$_2$ (20%/C, 20 mg, 0.04 mmol) and stirred under a hydrogen atmosphere (balloon pressure) for 16 h. The crude mixture was filtered through a plug of celite eluting with 2:1 MeOH/THF (15 mL) and concentrated to give an orange syrup. Purification by silica gel chromatography (5:1:1 THF/MeOH/CH$_2$Cl$_2$) afforded 110 mg (78% yield) of (6) as a white foam, mp 75-77° C. R$_f$=0.20 (10:1 CH$_2$Cl$_2$/MeOH); LRMS (ES+) m/z 515.4 (C$_{26}$H$_{34}$N$_4$O$_7$+H requires 515.26).

Preparation of Biphenyl-4,4'-dicarboxylic acid 4'-[(3-amino-propyl)-amide]4-[((2R)-hydroxy-(1S)-hydroxycarbamoyl-propyl)-amide] (7)

A flask containing (6) (80 mg, 0.155 mmol) was treated with 50% TFA/CH$_2$Cl$_2$ (6.0 mL) and stirred for 2.5 h. The reaction mixture was concentrated by rotary evaporation to give a brown syrup. Purification by RP-HPLC(C$_{18}$ column, CH$_3$CN gradient 5-70%, 0.1% TFA, UV analysis 300 nm, 36 min) and lyophilization of the collected fractions afforded 14 mg (21% yield) of (7) as a white solid. LRMS (ES+) m/z 415.3 (C$_{21}$H$_{26}$N$_4$O$_5$+H requires 415.20); RP-HPLC (300 nm, 36 min run) 18.2 min.

Example 8

Synthesis of N-(2-(N-hydroxycarbamoyl)(2S)-2-{[4-(4-ethylphenyl)phenyl]carbonylamino}ethyl)acetamide (4)

Preparation of 3-Acetylamino-2-(9H-fluoren-9-ylmethoxycarbonylamino)-propionic acid (2)

Acetic anhydride (425 uL) in THF (5 ml) was added to a cloudy mixture of Fmoc-DAP-H (1) (980 mg, 3.0 mmol) and pyridine (483 uL, 6.0 mmol) in THF (15 ml) with stirring at rt. After 4 hours, the clear pale yellow solution had reacted completely by LCMS. The reaction was evaporated under reduced pressure. The residue was dissolved in EtOAc (150 ml) and washed with 0.1M NaHSO$_4$ (50 ml), water (50 ml), sat. brine (50 ml), dried with Na$_2$SO$_4$, filtered and concentrated under reduced pressure to give 1.1 g of crude product as a white solid. The crude product was purified by prep. HPLC to give 0.99 g (90% yield) of (2).

Preparation of (2-Acetylamino-1-hydroxycarbamoyl-ethyl)-carbamic acid 9H-fluoren-9-ylmethyl ester trityl resin (3)

A solution of (2) (980 mg, 0.56 mmol), HATU (0.146 g, 0.56 mmol) in NMP (1.7 ml) was made. After 2 min. of shaking, the activated acid was added to the deprotected H$_2$N—O-Trt Resin (120 mg, 0.113 mmol) at rt with shaking. Deprotection of the Fmoc group from the resin was accomplished using 20% piperizine in DMF (4 ml) for 2 hours twice. The resin was drained and washed with DMF (2×5 ml) and DCM (2×5 ml).] After shaking for 20 hours, the reaction was drained and washed with DMF (2×5 ml) and DCM (2×5 ml). The resin (3) was dried and used as is in the next reaction.

Preparation of N-(2-(N-hydroxycarbamoyl)(2S)-2-{[4-(4-ethylphenyl)phenyl]carbonylamino}ethyl)acetamide (4)

Resin (3) was treated with 20% piperizine in DMF (4 ml) for 2 hours twice. The resin was drained and washed with DMF (2×5 ml) and DCM (2×5 ml). The resin was dried in vacuo. A solution of 4'-Ethyl-biphenyl-4-carboxylic acid (91 mg, 0.4 mmol), HATU (152 g, 0.4 mmol) in NMP (1.0 ml) was made. After 2 min. of shaking, the activated acid was added to the deprotected H-DAP(Ac)-Trt resin (120 mg, 0.113 mmol) at rt with shaking. After shaking for 18 hours, the reaction was drained and washed with DMF (2×5 ml) and DCM (2×5 ml). The resin was dried in vacuo. The product was cleaved from the resin through treatment with a solution of TFA (500 uL), DCM (500 uL) and water (50 uL) for 25 min. The resin was filtered and washed with fresh DCM (2 ml). The combined TFA and DCM fractions are evaporated under reduced pressure. The residue was diluted with CH$_3$CN/water (1:1) (10 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness. The solid residue was lyophilized again from CH$_3$CN/water (1:1) (5 ml) give 8.6 mg of pure product (4) (~21% yield).

Example 9

Synthesis of 4'-Ethyl-biphenyl-4-carboxylic acid (1-hydroxycarbamoyl-2-methanesulfonylamino-ethyl)-amide (3)

Preparation of 4'-Ethyl-biphenyl-4-carboxylic acid (2-amino-1-hydroxycarbamoyl-ethyl)-amide trityl resin (2)

Pd(PPh$_3$)$_4$ (438 mg, 0.35 mmol) was added to a vial containing biphenyl-DAP(Alloc)-Trt Resin (1) (500 mg, 0.35 mmol), dimethyl barbituric acid (600 mg, 3.5 mmol)

and PPh₃ (438 mg, 0.35 mmol) in DCM (11 ml) at rt under argon. The mixture was sparged with argon and shaken for 16 hours. The bright yellow mixture was drained and washed with DMF (8×10 ml) and DCM (8×10). The resin was dried in vacuo to give the deprotected DAP resin (2).

Preparation of 4'-Ethyl-biphenyl-4-carboxylic acid (1-hydroxycarbamoyl-2-methane sulfonylamino-ethyl)-amide (3)

Methanesulfonyl chloride (85 uL, 1.1 mmol) was added to a mixture of deprotected DAP resin (2) (160 mg, 0.11 mmol) and lutidine (190 uL, 1.6 mmol) in DCM (1.5 ml). After shaking for 16 hours, the mixture was drained and washed with DMF 10×2 ml) and DCM (5×2 ml). The product was cleaved from the resin through treatment with TFA/water (4:1) (1.5 ml). After shaking for 45 min., the TFA solution was collected from the resin by filtration, and the resin was washed with TFA (1 ml) and TFA/water (1:1) (10 ml). The combined TFA fractions were concentrated under reduced pressure to a reddish-brown solid. The product, identified by LCMS, was purified by prep. HPLC using a 20×50 mm Ultro 120 C18 column running a 22 ml/min 4% gradient (AcCN/water, 0.1% TFA) for 16 min. The purified fractions were lyophilized to dryness. The solid residue was lyophilized again from CH₃CN/water (1:1) (5 ml) give 4 mg of pure product as a white solid (3) (~9% yield).

Example 10

Synthesis of 4'-Ethyl-biphenyl-4-carboxylic acid [2-(3,3-dimethyl-ureido)-1-hydroxycarbamoyl-ethyl]-amide (3) (Continued from (2) of Example 9 above)

Dimethylcarbamyl chloride (103 mg, 0.96 mmol) was added to a mixture of deprotected DAP resin (2) (125 mg, 0.096 mmol) and lutidine (225 uL, 1.92 mmol) in DCM (1.5 ml). After shaking at rt for 5 hours, the mixture was drained and washed with DCM (5×2 ml), DMF (5×2 ml) and DCM (5×2 ml). The product was cleaved from the resin through treatment with TFA/water (4:1) (1.5 ml). After shaking for 45 min., the TFA solution was collected from the resin by filtration, and the resin was washed with TFA/water (1:1) (2 ml). The combined TFA fractions were concentrated under reduced pressure to a reddish-brown solid. The product, identified by LCMS, was purified by prep. HPLC using a 20×50 mm Ultro 120 C18 column running a 22 mvmin 4% gradient (AcCN/water, 0.1% TFA) for 16 min. The purified fractions were lyophilized to dryness. The solid residue was lyophilized again from CH₃CN/water (1:1) (5 ml) give 5 mg of pure product as a white solid (3) (~13% yield).

Example 11

Synthesis of 4'-Ethyl-biphenyl-4-carboxylic acid [2-(2-amino-ethylamino)-1-hydroxycarbamoyl-ethyl]-amide (2)

NaBH₃CN (3.1 mg, 0.05 mmol) followed by acetic acid (6 uL, 1.0 mmol) were sequentially added to a stirred suspension of biphenyl-DAP-hydroxamate (1) (20 mg, 0.096 mmol) and Boc-amino-acetaldehyde (6.4 mg, 0.4 mmol) in MeOH (1.5 ml) in a 4 ml vial. The reaction was followed by LCMS. After stirring 12 hours, the cloudy reaction was only 50% complete. The reaction was concentrated under reduced pressure to a thick slurry that was dissolved in DMSO. The product was purified by prep. HPLC using a 20×50 mm Ultro 120 C18 column running a 22 ml/min 3% gradient (AcCN/water, 0.1% TFA) for 16 min. The purified fractions were lyophilized to dryness. The dried powder was dissolved in CH₃CN/water (1:1) (1 ml) and 1M HCl (700 uL). After heating at 50° C. for 75 min., the reaction mixture was again lyophilized to dryness to produce 7.1 mg of (2) as a 2×HCl salt white powder (~17% yield).

Example 12

Synthesis of N-(1-(N-hydroxycarbamoyl)1S,2R)-2-hydroxypropyl)[4-(2-phenylethynyl)phenyl]carbox-amide Preparation of 4-Phenylethynyl-benzoic acid (3)

4-iodo-benzoic acid methyl ester (1) (20.0 g, 76.34 mmol), ethynyl-benzene (2) (8.56 g, 83.96 mmol), PdCl₂(PPh₃)₂ (0.65 g, 0.92 mmol), and CuI (0.35 g, 1.83 mmol) were mixed with THF (110 ml) in a round bottom under argon. The dry THF was sparged with dry, oxygen-free argon for at least 5 min. immediately before use. The reaction was cooled to 10° C. and TEA (16 ml) was added. The cooling bath was removed and the reaction was stirred at RT under argon. After 2.5 h, the reaction was diluted with EtOAc (400 ml) and the solids were filtered off through a pad of celite. The organic filtrate was washed with 1M HCl (60 ml), sat. aq. NaHCO₃ (60 ml), water (60 ml), brine (60 ml), dried with Na₂SO₄, filtered and concentrated under reduced pressure. The crude solid methyl ester was dissolved in MeOH (400 ml), 6M NaOH (30 ml) and water (50 ml). The reaction was stirred at 70° C. until a clear solution was formed (about 1 h). The reaction could be followed by LCMS. The reaction was cooled and diluted with water (500 ml) and hexane (100 ml). The pH was adjusted to pH 6-7. The white solid that formed was collected and washed with water (3×60 ml) and hexane (3×60 ml). The solid (3) was dried in vacuo yielding 17.3 g (approximately quantitative yield in 99% purity).

Preparation of 3-hydroxy-2-(4-phenylethynyl-benzoylamino)-butyric acid methyl ester (4)

A solution of threonine methyl ester (1.66 g, 9.8 mmol) and DIEA (1.53 ml, 8.8 mmol) in DMF (10 ml) was added to a stirred solution of (3) (1.55 g, 7.0 mmol) and DIEA (1.53 ml, 8.8 mmol) in DMF (11 ml) at rt. After 12 h, the reaction was diluted with EtOAc (300 ml) and washed with 0.5M HCl (2×60 ml), sat. aq. NaHCO₃ (60 ml), 50% diluted brine (60 ml), sat. brine (60 ml), dried with Na₂SO₄, filtered and concentrated under reduced pressure. Upon drying in vacuo, 2.34 g of white solid (4) was obtained (approximately quantitative yield in 99% purity).

Preparation of N-(2-Hydroxy-1hydroxycarbamoyl-propyl)-4-phenylethynyl-benzamide (5)

A solution of (4) (2.34 g, 7.0 mmol) in MeOH (20 ml) and DCM (30 ml) was added to a cooled (−10° C. bath) suspension of hydroxylamine HCl salt (4.81 g, 70.0 mmol) and NaOMe (4.16 g, 77.0 mmol) in MeOH (30 ml). Follow reaction by LCMS. After stirring for 2 hours, the reaction seems to stall at 50% completion. Add an additional 1 equivalent of NaOMe (0.416 g). After 3 hours, the reaction was 75% complete. Add an additional 0.5 equivalent of NaOMe (0.21 g). After 4 hours, the reaction was 90% complete. Add an additional 0.15 equivalent of NaOMe (0.064 g) for a total of 12.65 equivalents of NaOMe. The pH of the reaction was between 11-12 and had reacted about 95% completion. The reaction was diluted with EtOAc (500 ml) and washed with sat. aq. NaHCO$_3$ (2×60 ml), 50% diluted brine (60 ml), sat. brine (60 ml), dried with Na$_2$SO$_4$, filtered and concentrated under reduced pressure. The residue was dissolved in minimal DMA. The product was purified by prep. HPLC using a reverse phase Ultro 120 C18 column running a 2% gradient (AcCN/water, 0.1% TFA). The purified fractions were lyophilized to dryness. The product as the TFA salt dissolved in AcCN/water (50:50) (80 ml), 1N aq. HCl (13 equivalent) and lyophilized again to give 1.3 g of white powder (5) in 55% yield and >97% purity.

Example 13

Synthesis of 3-(R)-Amino-2-(S)-(3-phenylethynyl-benzoylamino)-butyl-hydroxamic acid (10)

Preparation of 3-(R)-Azido-2-(S)-(3-phenylethynyl-benzoylamino)-butyric acid methyl ester (9)

Compound (9) was made by the same procedures as for compound (6) in Example 5 above using compound (3) from Example 12 above. The product (9) was obtained in 92% yield (952 mg). HPLC (220 nm, 41 min. run) 32.64 min.; HPLC (220 nm, 17 min. run) 15.08 min LCMS: LC (214 nm) 3.16 min., MS(ES+) m/z 363.1 (C$_{20}$H$_{18}$N$_4$O$_3$+H requires 363.14).

Preparation of 3-(R)-Amino-2-(S)-(3-phenylethynyl-benzoylamino)-butyl-hydroxamic acid (10)

Triphenylphosphine (526 mg, 2.0 mmol) was added to a stirred solution of (9) (726 mg, 2.0 mmol) at rt. After 3 days the reaction reached completion as judged by TLC (EtOAc/Hex (2:1)) and LCMS. The reaction was concentrated under reduced pressure to give an ivory colored solid. The crude amino-phosphine was dissolved in MeOH (20 ml) to give a pale yellow solution. To the solution of amino-phosphine was added sequentially hydroxylamine HCl salt (1.4 g, 20.0 mmol) followed by fresh solid NaOMe powder (1.3 g, 24.0 mmol) to make a milky pH 10 suspension. After 36 h, the reaction was complete by LCMS. The reaction was evaporated under reduced pressure to give a yellow solid that was dried in vacuo. The crude product (2.75 g) was triturated with ether (3×50 ml) to remove impurities (P(O)Ph$_3$) and then was dissolved in abs. EtOH (120 ml) with sonication for 15 min. A fine white powder was suction filtered off, and the clear yellow ethanolic portion was concentrated to a small volume. The crude product was dissolved in DMSO (8 ml) and purified by preparative HPLC (Ultro 120 C18 75×300 mm column) running a gradient (AcCN/water, 0.1% TFA) from 5 to 70% for 55 min. The purified fractions were pooled together and lyophilized to dryness. The product as the TFA salt was dissolved in AcCN/water (50:50) (100 ml), 1N aq. HCl (1 equivalent) and lyophilized again to give 325 mg of (10) as a light yellow powder as the HCl salt (43% yield). HPLC (220 nm, 41 min·run) 18.31 min.; HPLC (220 nm, 17 min·run) 9.11 min; LCMS: LC (214 nm) 1.91 min., MS(ES+) m/z 338.1 (C$_{19}$H$_{19}$N$_3$O$_3$+H requires 338.14).

Synthesis of 4'-(N-Acylamino)-Tolan Dap Analogs

Example 14

Synthesis of 4-({4-[(aminoacetyl)amino]phenyl}ethynyl)-N-[(1S)-1-(aminomethyl)-2-(hydroxyamino)-2-oxoethyl]benzamide Preparation of 2-N-Boc-amino-N-(4-iodo-phenyl)-acetamide (2)

A solution of Boc-Gly-OH (1.752 g, 10.0 mmol) in DCM (18 mL) and DMF (1 mL) was treated with EDCI (1.994 g, 10.4 mmol) and HOBt (1.351 g, 10.0 mmol). After stirring 15 min, 4-iodoaniline (1) (2.290 g, 10.4 mmol) was added and the reaction monitored by TLC (25:1 DCM/MeOH (R$_1$=0.6)). After 24 h the solution was diluted with EtOAc (250 mL), washed with 1.0 M HCl (3×100 mL), sat. NaHCO$_3$ (3×100 mL), brine (3×100 mL), dried over MgSO$_4$, filtered and concentrated in vacuo to afford 2.900 g (77% yield) of (2) as a white solid.

Preparation of (2S)-3-N-Boc-amino-(4-ethynyl-benzoylamino)-propionic acid methyl ester (4)

Diethylamine (3.5 mL, 20.0 mmol) was added to a stirred solution of 4-ethynylbenzoic acid (3) (910 mg, 6.22 mmol), H-Dap(Boc)-OMe hydrochloride (1.903 g, 7.47 mmol), EDCI (1.432 g, 7.47 mmol), and HOBt (910 mg, 6.73 mmol) in DMF (50.0 mL). After stirring 20 h, the reaction mixture was diluted with EtOAc (400 mL), washed with 1.0 M HCl (2×100 mL), saturated NaHCO$_3$ (2×100 mL), H$_2$O (4×100 mL), dried over MgSO$_4$, filtered and concentrated in vacuo to give 2.140 g (99% yield) of (4) as a tan solid, mp=110-111° C. LRMS(ES+) m/z 346.9 (C$_{18}$H$_{22}$N$_2$O$_5$+H requires 347.10).

Preparation of Methyl (2S)-3-[(tert-butoxy)carbonylamino]-2-({4-[2-(4-{2-[(tert-butoxy)carbonyl amino]acetylamino}phenyl)ethynyl]phenyl}carbonylamino) propanoate (5)

To a suspension of methyl (2S)-3-[(tert-butoxy)carbonylamino]-2-[(4-ethynylphenyl)carbonylamino]propanoate (4) (200 mg, 0.577 mmol) and 2-[(tert-butoxy)carbonylamino]-N-(4-iodophenyl)acetamide (2) (476 mg, 1.26 mmol) was added Et$_3$N (350 μL, 2.5 mmol). The solution was purged with a stream of N$_2$ for several minutes and PdCl$_2$(PPh$_3$)$_2$ (20 mg, 0.028 mmol) and CuI (10.6 mg, 0.055 mmol) were added. The reaction mixture was stirred at ambient temperature for 22 h and then concentrated by rotary evaporation. The crude black residue was chromatographed twice by silica gel chromatography (30:1 CH$_2$Cl$_2$/MeOH) to give 285 mg (83%) of (5) as a yellow foam.

Preparation of N-(4-{2-[4-(N-{1-(N-hydroxycarbamoyl)(1S)-2-[(tert-butoxy)carbonyl amino]ethyl}carbamoyl)phenyl]ethynyl}phenyl)-2-[(tert-butoxy)carbonylamino]acetamide (6)

To a solution of hydroxylamine hydrochloride (98 mg, 1.41 mmol) in MeOH (1.3 mL) at 0° C. was added 25 wt % NaOMe (460 mg, 2.13 mmol). The solution was stirred at 0° C. for 15 min and then charged with a solution of (5) (279 mg, 0.469 mmol) in THF (1.5 mL) and MeOH (0.6 mL). The reaction was stirred at 0° C. for 30 min and at room temperature for 2.5 h. The reaction mixture was diluted with 4:1 CHCl₃/iPrOH (50 ml) and washed with 0.1 M HCl (30 mL). The layers were separated and the aqueous layer extracted once more with 4:1 CHCl₃/iPrOH (30 ml). The organic layers were combined, dried over Na₂SO₄, filtered and concentrated. The crude residue was suspended in 10:1 CH₂Cl₂/MeOH (4 mL), filtered, and washed with 50:1 CH₂Cl₂/MeOH (2 mL) and Et₂O (10 mL) to afford 180 mg (64%) of (6) as a white powder.

Preparation of 4-({4-[(aminoacetyl)amino]phenyl}ethynyl)-N-[(1S)-1-(aminomethyl)-2-(hydroxyamino)-2-oxoethyl]benzamide (7)

To an oven-dried flask containing (6) (130 mg, 0.218 mmol) was added 1:1 TFA/CH₂Cl₂ (2.5 mL). The resulting pink solution was stirred for 2 h and concentrated to give a pink gum. The crude residue was rinsed with CH₂Cl₂ (4 mL), concentrated by rotary evaporation and dissolved in THF (2 mL) and MeOH (0.4 mL). A solution of 4 M HCl in dioxane (200 µL) was added and the resulting precipitate filtered and washed with Et₂O (10 mL) to afford 90 mg of (7) as a pale tan powder.

Reaction of Iodoaniline with Bromoacetyl Bromide

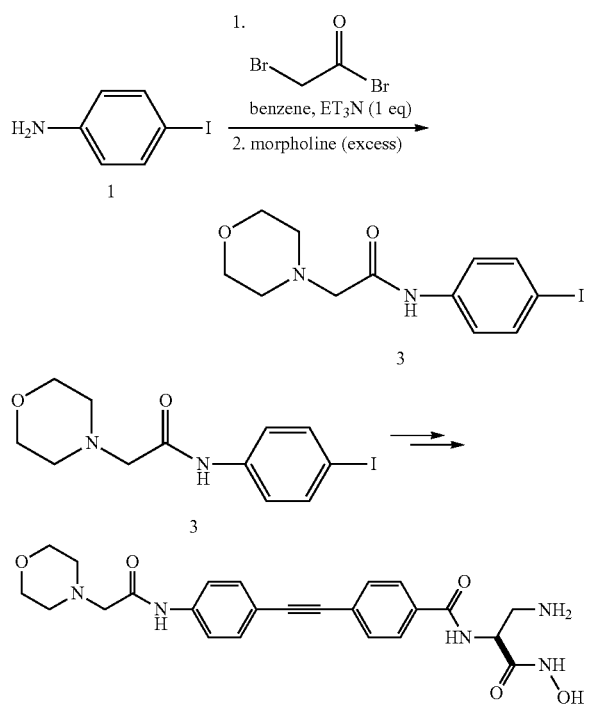

Bromoacetyl bromide (175 µL, 2.00 mmol) was added dropwise over 5 minutes to a solution of 4-iodoaniline (438 mg, 2.00 mmol) and Et₃N (280 µl, 2.00 mmol) in benzene (5 mL). The reaction was stirred 1 hour, treated with morpholine (1.0 mL, 11.5 mmol) and stirred overnight. The reaction mixture was diluted with EtOAc (200 mL), washed with aqueous 0.1 M KOH (50 mL), H₂O (50 mL), dried over MgSO₄ and concentrated to give a yellow oil. Purification by silica gel chromatography (100:1 CH₂Cl₂/MeOH) afforded 630 mg (91%) of N-(4-iodophenyl)-2-morpholin-4-ylacetamide as a waxy tan solid. This product was converted to analogues in a similar manner as Example 14.

Example A

Preparation of 4-[4-(6-Chloro-pyridin-3-yl)-buta-1,3-diynyl]-benzoic acid methyl ester DIEA (9.7 ml, 55.1 mmol) was added to a stirred solution of 4-iodo-benzoic acid (5.49 g, 22.2 mmol), HOAT (3.08 g, 22.6 mmol), EDC (4.33 g, 22.6 mmol) in DMF (85 ml). After 2 min., H-DAP(Boc)-OMe (1) was added in one portion. After 12 hours, the reaction was found complete by LCMS. The reaction was diluted with EtOAc/hexane (1:1) (500 ml). The organic phase was washed with 1N HCl (2×80 ml), 1N NaOH (2×80 ml), water (2×80 ml), sat. brine (80 ml), dried with Na₂SO₄, filtered and concentrated under reduced pressure to give crude product. The residue was filtered through a filter plug of silica eluting with EtOAc/hexane (1:1). The fractions with product were evaporated to give 9.3 g of product (3-tert-Butoxycarbonylamino-2-(4-iodo-benzoylamino)-propionic acid methyl ester) in 93% yield. This product was converted to analogues in a similar manner as the aforementioned Examples.

Example 15

N-(1-(N-hydroxycarbamoyl)(1S,2R)-2-hydroxypropyl)(4-{2-[4-(morpholin-4-ylmethyl)phenyl]ethynyl}phenyl)carboxamide (5)

Preparation of (2S,3R)-2-[4-(4-formyl-phenylethynyl)-benzoylaminol-3-hydroxy-butyric acid methyl ester (3)

A solution of (2S,3R)-methyl-2-(4-ethynylbenzamido)-3-hydroxybutanoate (1) (745 mg, 2.85 mmol), 4-iodobenzaldehyde (2) (902 mg, 3.89 mmol), and Et₃N (900 µL, 6.5 mmol) in THF (50 mL) was purged with a stream of N₂ for two minutes and then treated with PdCl₂(PPh₃)₂ (70 mg, 0.10 mmol) and CuI (34 mg, 0.18 mmol). The reaction mixture was stirred 40 h, concentrated by rotary evaporation and purified by silica gel chromatography (40:1 DCM/MeOH) to give 0.833 g (80% yield) of (3) as a pale yellow powder, mp=143-144° C. R_f=0.3 (25:1 DCM/MeOH); LRMS(ES+) m/z 366.1 (C₂₁H₁₉NO₅+H requires 366.13); HPLC (300 nm, 47 min) 15.3 min.

Preparation of (2S,3R)-3-Hydroxy-2-[4-(4-morpholin-4-ylmethyl-phenylethynyl)-benzoylamino]-butyric acid methyl ester (4)

Sodium triacetoxyborohydride (0.670 g, 3.16 mmol) was added to a solution of benzaldehyde (3) (0.822 g, 2.25 mmol) and morpholine (260 µL, 2.97 mmol) in THF (15 mL) under N₂ atmosphere and the reaction monitored by TLC (25:1 DCM/MeOH, R_f=0.2). After stirring 4 h, the reaction mixture was quenched with saturated NaHCO₃ (150 mL), extracted with EtOAc (3×100 mL), dried over MgSO₄, filtered and concentrated to give a yellow syrup. Purification by silica gel chromatography (35:1 DCM/MeOH) afforded 0.844 g (86% yield) of (4) as a sticky white foam.

Preparation of (2S,3R)—N-(2-Hydroxy-1-hydroxycarbamoyl-propyl)-4-(4-morpholin-4-ylmethyl-phenylethynyl)-benzamide (5)

Sodium methoxide (25 wt % in MeOH, 1.860 g, 8.60 mmol) was added to a stirred solution of hydroxylamine hydrochloride (400 mg, 5.76 mmol) in anhydrous MeOH (5 mL) at 0° C. under N₂ atmosphere. After stirring 20 min, a solution of methyl ester (4) (829 mg, 1.90 mmol) in 1:1 MeOH/THF (6 mL) was added and the reaction mixture stirred at 0° C. for 1 h and at room temperature for 4 h. The reaction was quenched with 1.0 M HCl (6 mL), concentrated by rotary evaporation to remove organic solvents, and diluted with DMSO (4 mL). Analytical RP-HPLC($C_{18}$ column, $CH_3CN$ gradient 5-35%, 0.1% TFA, UV analysis 300 nm, 16 min) indicated a purity of 85% for the crude product mixture. Purification by preparative RP-HPLC and lyophilization of the collected fractions gave 701 mg (81%) of (5) as a fluffy white solid. LRMS(ES+) m/z 438.1 ($C_{24}H_{27}N_3O_5$+H requires 438.20); RP-HPLC (300 nm, 16 min run) 8.7 min.

Resin Procedures for Synthesizing Tolanyl Hydroxamates

Example 16

Synthesis of 4-[(4-{[(benzylamino)acetyl]amino}phenyl)ethynyl]-N-{(1S,2R)-2-hydroxy-1-[(hydroxyamino)carbonyl]propyl}benzamide

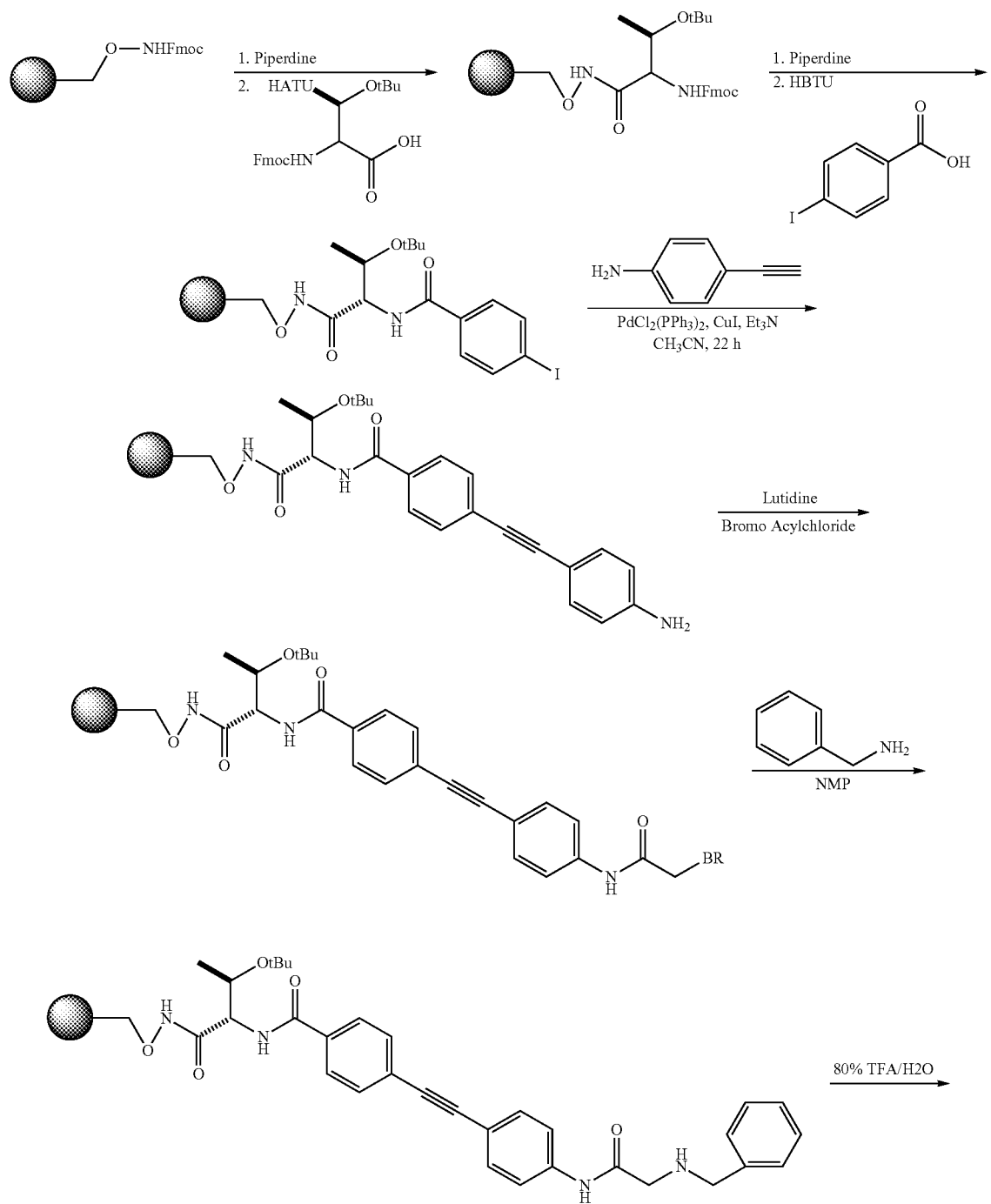

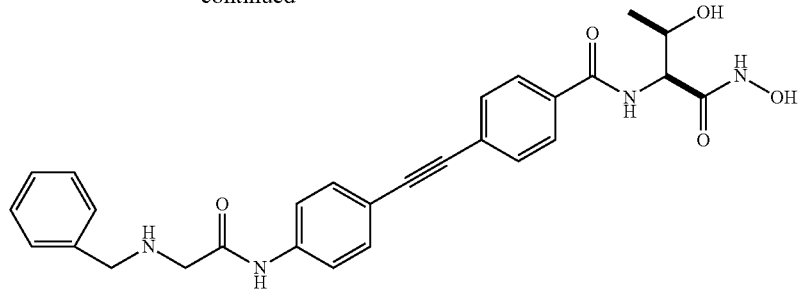

1. Coupling to Fmoc Hydroxylamine Resin

The resin was pre-swelled by adding DCM and shaking for 30 min. The resin was drained, 20% piperidine was added in DMF, the resin was shaken 1.25 hours, and finally drained and washed in 2×DMF and 2×DCM. After draining completely, 20% piperidine in DMF was added to attain cleavage in 1.25 hours. The resin was washed 4×DMF, 4×DCM and drained completely. In a separate flask, the amino acid (Fmoc-Thr tBu-OH, or Fmoc-DAP Boc-OH, 4 eq) was mixed, HATU (4 eq), DMF (60 ml) and Hunig's (8 eq) base were added and stirred for 2-3 min. The mixture was added to the resin and shaken 20-24 hours. Subsequently, the resin was drained and run with a standard wash (1×DCM, 4×DMF and 4×DCM). The Fmoc was removed from the amino acid by adding 20% piperidine in DMF and shaken 1.25 hours, drained, and given the standard wash (1×DCM, 4×DMF and 4×DCM).

2. Coupling of 4-Iodobenzoic Acid to Amino Acid Resin

A mixture of 4-iodobenzoic acid (4 eq), HBTU (4 eq), DMF (60 ml) was shaken for several minutes. Hunig's base (8 eq) was subsequently added and the mixture was shaken further for 2-3 min. The pre-activated mixture was then added to the prepared Thr or DAP resin (Fmoc removed, 7.5 g, 5.775 mmol). The reaction is shaken 12-16 hours followed by the standard wash (1×DCM, 4×DMF and 4×DCM).

3. Alkyne Coupling on Resin

To the 4-iodobenzoic resin (4 g, 3.08 mmol) was added 4-aminophenylacetylene (3 eq), Pd(PPh$_3$)$_2$Cl$_2$ (0.04 eq), CuI (0.08 eq) and THF (purged with Argon). After mixing for 1 min., TEA (4.5 eq) was added and the reaction was shaken 12 hours at RT under argon.

4. Aniline Coupling with Bromoacetyl Chloride on Resin

To aniline resin (4 g, 3.08 mmol) was added DCM (30 ml) lutidine (10 eq) and shaken for 1 min. Bromoacetyl chloride (8 eq) in DCM (5 ml) was added slowly. After the addition, the slurry was shaken for 1.5 to 1.75 hours. Subsequent draining and a wash with 2×DCM, 4×DMF and 4×DCM was then performed.

5. Displacement with Amines on Resin

To the bromoacetyl resin (125 mg), was added NMP (1.5 ml) followed by amine (0.2 g or ml, ie excess) and the slurry was shaken for 12-16 hours at RT. To neutralize the salt, TEA was added. The imidazole was heated at 38° C. for 24 h (in the case of anilines, they were heated at 38° C. for 48 h). The reaction mixture was drained and washed 4×DMF and 4×DCM.

6. Cleavage from Resin and Deprotection of Thr tBu and DAP Boc

The resin (125 mg) was soaked in TFA/water (80:20 v/v) (1.5 ml) at RT for 45 min. Upon cleavage the solution was collected and the resin was washed with more TFA/water mixture (0.75 ml). To the TFA/product solution was added acetonitrile/water solution (1:1 v/v, 10 ml) and pure water (2.5 ml). The mixture was frozen in liquid nitrogen for 15 min and lyophilized. The dry residue was dissolved in the acetonitrile/water solution (1:1 v/v, 10 ml) again followed by addition of 1M aq. HCl (1.2 eq per basic nitrogen), frozen, and lyophilized to a powder.

Synthesis of 3'-Nitro-Tolan Threonine Hydroxamic Acid

Example 17

(1S,2R)—N-(2-hydroxy-1-hydroxycarbamoyl-propyl)-4-(3-nitro-phenylethynyl)-benzamide Preparation of (1S,2R)—N-(2-tert-butoxy-1-hydroxycarbamoyl-propyl)-4-ethynyl-benzamide on Hydroxylamine 2-chlorotrityl Resin (3)

Fmoc-threonine resin (1) (0.522 g, 0.365 mmol, 0.70 mmol) was swelled in DCM (5 mL) for 2 h and drained. The resin was treated with 20% piperidine in DMF (6 mL) for 1 hour, washed with DMF (4×6 mL) and DCM (4×6 mL) and drained completely. In a separate flask, 4-ethynylbenzoic acid (2) (0.160 g, 1.10 mmol), DIC (0.280 mL, 1.79 mmol), HOBt (0.148 g, 1.10 mmol) and DIEA (0.4 mL, 2.30 mmol) were dissolved in DCM (1 mL) and DMF (4 mL), stirred 15 min and added to the resin. After shaking for 36 h, the mixture was drained, washed with DMF (4×6 mL) and DCM (4×6 mL) and dried in vacuo to give 0.495 g of (3) as a yellow resin.

Preparation of (1S,2R)—N-(2-hydroxy-1-hydroxycarbamoyl-propyl)-4-(3-nitro-phenylethynyl)-benzamide (5)

Resin (3) (100 mg, 0.070 mmol) was swelled in DCM (2 mL) for 1 h and drained. A solution of 1-iodo-3-nitrobenzene (4) (87.1 mg, 0.350 mmol) and Et$_3$N (150 µL, 1.10 mmol) in DMF (1.5 mL) was purged with a stream of N$_2$ bubbles for two minutes and added to the resin. After mixing for 5 min, PdCl$_2$(PPh$_3$)$_2$ (10.0 mg, 0.014 mmol) and CuI (7.0 mg, 0.036 mmol) were added and the mixture shaken for 26 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC (C$_{18}$ column, CH$_3$CN gradient 5-65%, 0.1% TFA, UV analysis 300 nm, 28 min) and lyophilization of the collected fractions afforded 6.0 mg (22% yield) of (5) as a white foam. LRMS(ES+) m/z 384.2 ($C_{19}H_{17}N_3O_6$+H requires 384.15); RP-HPLC (300 nm, 28 min run) 15.2 min.

Synthesis of 4'-Trifluoromethoxy-Tolan Dap Hydroxamic Acid

Example 18

(1S)—N-(2-amino-1-hydroxycarbamoyl-ethyl)-4-(4-tri fluoromethoxy-phenylethynyl)-benzamide (5)

Preparation of (1S)—N-(2-(Boc)-amino-1-hydroxy-carbamoyl-ethyl)-4-ethynyl-benz-amide on Hydroxylamine 2-chlorotrityl Resin (3)

Fmoc-Dap resin (1) (1.330 g, 0.931 mmol, 0.70 mmol/g) was swelled in DCM (15 mL) for 2 h and drained. The resin was treated with 20% piperidine in DMF (20 mL) for 1 hour, washed with DMF (3×15 mL) and DCM (3×15 mL) and drained completely. In a separate flask, 4-ethynylbenzoic acid (2) (0.408 g, 2.793 mmol), DIC (0.70 mL, 4.470 mmol), HOBt (0.377 g, 2.793 mmol) and DIEA (1.0 mL, 5.7 mmol) were dissolved in DCM (10 mL) and DMF (2 mL), stirred 15 min and added to the resin. After shaking for 36 h, the mixture was drained, washed with DMF (3×15 mL) and DCM (3×15 mL) and dried in vacuo to give 1.290 g of (3) as a yellow resin.

Preparation of (1S)—N-(2-amino-1-hydroxycarbamoyl-ethyl)-4-(4-trifluoromethoxy-phenylethynyl)-benzamide (5)

Resin (3) (120 mg, 0.084 mmol) was swelled in DCM (2 mL) for 1 h and drained. A solution of 4-(trifluoromethoxy) iodobenzene (4) (96.8 mg, 0.336 mmol) and Et$_3$N (150 µL, 1.10 mmol) in DMF (2.0 mL) was purged with a stream of N$_2$ bubbles for two minutes and added to the resin. After mixing for 5 min, PdCl$_2$(PPh$_3$)$_2$ (18.0 mg, 0.025 mmol) and CuI (8.0 mg, 0.042 mmol) were added and the mixture shaken for 24 h. The resin was drained, washed with DMF (3×2 mL), DCM (3×2 mL) and cleaved with 10% TFA/DCM (2.0 mL) for 20 min. The solution was collected and the resin was rinsed with additional 10% TFA/DCM (1.0 mL). The cleavage fractions were combined, treated with neat TFA (3.0 mL), stirred for 1 h at rt and concentrated by rotary evaporation to give a crude brown residue. Purification by RP-HPLC(C$_{18}$ column, CH$_3$CN gradient 5-55%, 0.1% TFA, UV analysis 300 nm, 28 min) and lyophilization of the collected fractions afforded 9.0 mg (25% yield) of (5) as a white solid. LRMS (ES+) m/z 408.0 ($C_{19}H_{16}F_3N_3O_4$+H requires 408.11); RP-HPLC (300 nm, 28 min run) 18.0 min.

Example 19

Synthesis of N-(1-(N-hydroxycarbamoyl)(1S,2R)-2-hydroxypropyl)[4-(4-phenylbuta-1,3-diynyl)phenyl] carboxamide 4-(2,2-Dibromo-vinyl)-benzoic acid methyl ester (2) was made by the method of Wang, S., et al., *J. Org. Chem.* 1999, 64, 8873-8879.

A solution of (2) (5.76 g, 18.0 mmol), ethynyl-benzene (3) (2.57 g, 25.2 mmol), Pd$_2$dba$_3$ (164 mg, 0.18 mmol), tris(4-methoxyphenyl) phosphine (TMPP) (253 mg, 0.72 mmol) were dissolved in argon sparged (5 min.) DMF (60 ml). The reaction was sparged with argon for 1 min. TEA (7.5 ml, 54.0 mmol) was added to the stirred reaction mixture that was then heated under argon at 85° C. for 3.5 hours. The reaction was found complete by LCMS. The reaction was cooled to rt and diluted with EtOAc/hexane (1:1) (300 ml). The organic phase was washed with 1M HCl (2×50 ml), 1M NaOH (3×50 ml), water (2×50 ml), sat. brine (50 ml), dried with Na$_2$SO$_4$, filtered and concentrated under reduced pressure to obtain 5.25 g of crude product as an oil. The oil was treated with approximately 20 ml of a solution of 20% EtOAc/hexane that was heated to dissolve the residue. The walls of the flask were washed with the 20% EtOAc/hexane solution (5 ml) that upon cooling gave 1.45 g of pure product (31% yield) as a white solid. The balance of the crude reaction product was purified by flash chromatography using EtOAc (8%)/hexane as eluant. The pure fractions were evaporated and dried in vacuo to give addition product typically 25-30% addition yield.

4-(4-Phenyl-buta-1,3-diynyl)-benzoic acid methyl ester (4) was made according to the method of Wang, S., et al., *Org. Lett.* 2000, 2(18), 2857-2860.

Preparation of 4-(4-Phenyl-buta-1,3-diynyl)-benzoic acid (5)

A 3M aq. solution of NaOH (20 ml) was added to a stirred solution of methyl ester (4) (1.45 g, 5.6 mmol) in MeOH (100 ml) at rt. The reaction solution was heated to reflux for 45 min. until the reaction turned clear. All of the starting material was gone by TLC and HPLC. The reaction was cooled to rt and some MeOH (~50 ml) was removed by evaporation under reduced pressure. Water (100 ml) was added to the mixture. Conc. HCl was added dropwise to the stirred solution until acidic by pH paper (pH2). The white precipitate that formed was collected by suction filtration. The solid was washed with water (3×20 ml) and hexane (2×20 ml) to give after drying 1.35 g of (5) in 99% yield.

Subsequent conversion of compound (5) to N-((2S,3R)-3-hydroxy-1-(hydroxyamino)-1-oxobutan-2-yl)-4-(penta-1,3-diynyl)benzamide (7) was performed according to the method described in Example 12 for the synthesis of N-(2-Hydroxy-1-hydroxycarbamoyl-propyl)-4-phenylethynyl-benzamide (compound 5). LCMS MH+363.13.

Example B

Synthesis of N-[(1S)-1-(aminomethyl)-2-(hydroxyamino)-2-oxoethyl]-4-[4-(4-aminophenyl)buta-1,3-diynyl]benzamide Preparation of 2-{4-[4-(4-Amino-phenyl)-buta-1,3-diynyl]-benzoylamino}-3-tert-butoxycarbonyl amino-propionic acid methyl ester (2)

DIEA (10.5 ml, 60.3 mmol) was added to a stirred solution of 4-[4-(4-Amino-phenyl)-buta-1,3-diynyl]-benzoic acid (1) (5.0 g, 19.1 mmol), HOBT (2.72 g, 20.1 mmol), EDC (3.85 g, 20.1 mmol) in DMF (80 ml). After 2 min., H-DAP(Boc)-OMe (5.12 g, 2.1 mmol) was added in one portion. After 12 hours at rt, the reaction was found complete by LCMS. The reaction was diluted with EtOAc/hexane (4:1) (500 ml). The organic phase was washed with 1N NaOH (2×80 ml), water (2×80 ml), sat. brine (80 ml), dried with Na$_2$SO$_4$, filtered and concentrated under reduced pressure to give crude product. The residue was filtered through a filter plug of silica eluting with EtOAc/hexane (4:1). The fractions with product were evaporated to give 8.02 g of (2)

in 91% yield. Subsequent conversion of (2) to the final hydroxamic acid was performed according to the method described in Example 12 for the synthesis of N-(2-Hydroxy-1-hydroxycarbamoyl-propyl)-4-phenylethynyl-benzamide (compound 5).

Synthesis of 4-(Buta-1,3-diynyl)-benzoic Acid (4) for making 1,3-diynyl analogues (such as Example 20 below)

Preparation of 4-(4-trimethylsilanyl-buta-1,3-diynyl)-benzoic acid methyl ester (3)

A solution of methyl 4-iodobenzoate (2) (4.510 g, 17.2 mmol), $PdCl_2(PPh_3)_2$ (483 mg, 0.690 mmol), and CuI (262 mg, 1.37 mmol) in $CH_3CN$ (50 mL) was cooled to 0° C. under $N_2$ atmosphere in the absence of light. Triethylamine (7.2 mL, 52.0 mmol) was added, followed by trimethylsilyl-1,3-butadiyne (1) (5.240 g, 42.8 mmol) and the reaction stirred 3 h at 0° C. and 30 h at ambient temperature. Removal of solvent by rotary evaporation afforded a crude black residue that was purified by silica gel chromatography (95:5 hexanes/EtOAc) to give 3.450 g (79% yield) of (3) as a brown solid, mp=67-68° C.

Preparation of 4-(buta-1,3-diynyl)-benzoic acid (4)

Potassium hydroxide (3.700 g, 65.9 mmol) was dissolved in $H_2O$ (10 mL) and added to a solution of (3) (3.420 g, 13.5 mmol) in THF (26 mL) in the absence of light. After stirring 16 h, the reaction was quenched with 1.0 M HCl (120 mL) and the resulting precipitate was filtered, washed with 1:1 hexanes/benzene (150 mL) and dried in vacuo to afford 2.100 g (91% yield, 98% pure) of (4) as a brown solid, mp>230° C. Although diyne (4) was found to be unstable at room temperature it could be stored for several weeks at 0° C. with only small amounts of decomposition observed by TLC. $R_f$=0.2 (4:1 Hexanes/EtOAc); HPLC (300 nm, 28 min run) 16.0 min; LRMS (ES+) m/z 171.0 ($C_{11}H_6O_2$+H requires 171.04).

Synthesis of a 3'-Nitrophenyl-Diacetylenic-Dap Hydroxamic Acid

Example 20

N-(1-(N-hydroxycarbamoyl)(1S)-2-aminoethyl){4-[4-(3-nitrophenyl)buta-1,3-diynyl] phenyl}carboxamide (6)

Preparation of Fmoc-Dap(Boc)-NHOH on hydroxylamine 2-chlorotrityl resin (2)

A suspension of N-Fmoc-hydroxylamine 2-chlorotrityl resin (1) (3.288 g, 2.53 mmol, 0.77 mmol/g, Novabiochem) in DCM (40 mL) was shaken for 2 h and drained. The resin was treated with 20% piperidine in DMF (40 mL) for 1 hour, washed with DMF (2×40 mL), treated a second time with 20% piperidine in DMF (40 mL), washed with DMF (3×40 mL) and DCM (3×40 mL) and drained completely. In a separate flask, Fmoc-Dap(Boc)-OH (3.175 g, 7.44 mmol), HATU (2.829 g, 7.44 mmol) and DIEA (4.3 mL, 24.7 mmol) were dissolved in DMF (35 mL), stirred three minutes and added to the resin. After shaking for 48 h, the mixture was drained, washed with DMF (4×40 mL) and DCM (4×40 mL) and dried in vacuo to give 3.530 g of (2) as a yellow resin.

Preparation of (S)—N-(2-N-Fmoc-amino-1-hydroxycarbamoyl-ethyl)-4-buta-1,3-diynyl-benzamide on hydroxylamine 2-chlorotrityl resin (4)

Resin (2) (3.530 g, 2.53 mmol, 0.71 mmol/g) was swelled in DCM (40 mL) for 2 h and drained. The resin was treated with 20% piperidine in DMF (40 mL) for 1 hour, washed with DMF (4×40 mL) and DCM (4×40 mL) and drained completely. In a separate flask, 4-buta-1,3-diynyl-benzoic acid (3) (1.076 g, 6.32 mmol), EDCI (1.457 g, 7.60 mmol), HOBt (1.048 g, 7.75 mmol) and DIEA (2.2 mL, 12.6 mmol) were dissolved in DCM (25 mL) and DMF (5 mL), stirred 45 min and added to the resin. After shaking for 48 h, the mixture was drained, washed with DMF (4×40 mL) and DCM (4×40 mL) and dried in vacuo to give 3.35 g of (4) as a pale brown resin.

Preparation of (S)—N-(2-amino-1-hydroxycarbamoyl-ethyl)-4-[4-(3-nitro-phenyl)-buta-1,3-diynyl]-benzamide (6)

Resin (4) (176 mg, 0.135 mmol) was swelled in DCM (3 mL) for 1 h and drained. A solution of 1-iodo-3-nitrobenzene (5) (118 mg, 0.474 mmol) and $Et_3N$ (200 μL, 1.43 mmol) in DMF (3.0 mL) was purged with a stream of $N_2$ bubbles for two minutes and added to the resin. After mixing for 5 min, $PdCl_2(PPh_3)_2$ (6.0 mg, 0.009 mmol) and CuI (10.0 mg, 0.052 mmol) were added and the mixture shaken for 36 h. The resin was drained, washed with DMF (4×3 mL), DCM (4×3 mL) and cleaved with 10% TFA/DCM (2 mL) for 20 min. The solution was collected and the resin was rinsed with additional 10% TFA/DCM (2 mL). The cleavage fractions were combined, treated with neat TFA (4.0 mL), stirred for 1 h at rt and concentrated by rotary evaporation to give a crude brown residue. Purification by RP-HPLC($C_{18}$ column, $CH_3CN$ gradient 5-65%, 0.1% TFA, UV analysis 300 nm, 30 min) and lyophilization of the collected fractions afforded 12.0 mg (22%) of 470 as a white solid. LRMS (ES+) m/z 392.9 ($C_{20}H_{16}N_4O_5$+H requires 393.11); RP-HPLC (300 nm, 30 min run) 14.9 min.

Synthesis of 4'-Benzamide Diacetylene Dap Hydroxamic Acid

Example 21

N-((2S)-amino-1-hydroxycarbamoyl-ethyl)-4-{4-[4-(2-amino-ethylcarbamoyl)-phenyl]-buta-1,3-diynyl}-benzamide (3)

(1S)—N-(2-(Boc)-amino-1-hydroxycarbamoyl-ethyl)-4-ethynyl-benz-amide on hydroxylamine-2-chloro resin (1) (145 mg, 0.111 mmol) was swelled in DCM (2 mL) for 1 h and drained. A solution of 4-ethynylbenzamide (2) (124 mg, 0.288 mmol) and $Et_3N$ (100 μL, 0.72 mmol) in DMF (2.0 mL) was added and the resin agitated for 5 min. A mixture of $PdCl_2(PPh_3)_2$ (21 mg, 0.030 mmol) and CuI (22 mg, 0.110 mmol) was added and the resin was agitated for 60 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC (C$_{18}$ column, CH$_3$CN gradient 5-55%, 0.1% TFA, UV analysis 300 nm, 26 min) and lyophilization of the collected fractions afforded 2.6 mg (5% yield) of (3). LRMS (ES+) m/z 434.0 (C$_{23}$H$_{23}$N$_5$O$_4$+H requires 434.19); RP-HPLC (300 nm, 26 min run) 15.3 min.

Synthesis of N-[4-Butadiynyl-benzoyl]-Thr(tBu) on Resin

Continued to Make Examples 22 and 23

Preparation of (2S,3R)-2-N-Fmoc-amino-3-tert-butoxy-N-hydroxy-butyramide on hydroxylamine 2-chlorotrityl resin (2)

A suspension of N-Fmoc-hydroxylamine 2-chlorotrityl resin (1) (3.188 g, 2.45 mmol, 0.77 mmol/g, Novabiochem) in DCM (40 mL) was shaken for 2 h and drained. The resin was treated with 20% piperidine in DMF (40 mL) for 1 hour, washed with DMF (2×40 mL), treated a second time with 20% piperidine in DMF (40 mL), washed with DMF (3×40 mL) and DCM (3×40 mL) and drained completely. In a separate flask, Fmoc-Thr(tBu)-OH (2.927 g, 7.36 mmol), HATU (2.798 g, 7.36 mmol) and DIEA (4.3 mL, 24.6 mmol) were dissolved in DMF (40 mL), stirred three minutes and added to the resin. After shaking for 24 h, the mixture was drained, washed with DMF (4×40 mL) and DCM (4×40 mL) and dried in vacuo to give 3.500 g of (2) as a yellow resin.

Preparation of 4-buta-1,3-diynyl-N-(2-tert-butoxy-1-hydroxycarbamoyl-propyl)-benzamide on hydroxylamine 2-chlorotrityl Resin (4)

Resin (2) (2.030 g, 1.56 mmol, 0.77 mmol/g) was swelled in DCM (20 mL) for 2 h and drained. The resin was treated with 20% piperidine in DMF (20 mL) for 1 hour, washed with DMF (4×20 mL) and DCM (4×20 mL) and drained completely. In a separate flask, 4-buta-1,3-diynyl-benzoic acid (3) (0.617 g, 3.63 mmol), EDCI (0.834 g, 4.35 mmol), HOBt (0.588 g, 4.35 mmol) and DIEA (1.0 mL, 5.7 mmol) were dissolved in DCM (15 mL) and DMF (4 mL), stirred 45 min and added to the resin. After shaking for 36 h, the mixture was drained, washed with DMF (4×20 mL) and DCM (4×20 mL) and dried in vacuo to give 1.900 g of (4) as a pale brown resin.

Synthesis of Diacetylenic Threonine Hydroxamic Acids

Example 22

(2S,3R)-4-[4-(3-aminomethyl-phenyl)-buta-1,3-diynyl]-N-(2-hydroxy-1-hydroxycarbamoyl-propyl)-benzamide (3)

Resin (1) (resin (4) obtained from previous synthesis) (100 mg, 0.077 mmol) was swelled in DCM (2 mL) for 1 h and drained. A solution of 3-iodobenzylamine hydrochloride (2) (83.0 mg, 0.308 mmol) and Et$_3$N (250 µL, 1.80 mmol) in DMF (1.5 mL) was purged with a stream of N$_2$ bubbles for two minutes and added to the resin. After mixing for 5 min, PdCl$_2$(PPh$_3$)$_2$ (11.0 mg, 0.016 mmol) and CuI (7.0 mg 0.037 mmol) were added and the mixture shaken for 36 h. The resin was drained, washed with DMF (4×2 mL), DCM (4×2 mL) and cleaved with 10% TFA/DCM (1.5 mL) for 20 min. The solution was collected and the resin was rinsed with additional 10% TFA/DCM (1.5 mL). The cleavage fractions were combined, treated with neat TFA (3.0 mL), stirred for 1 h at rt and concentrated by rotary evaporation to give a crude brown residue. Purification by RP-HPLC (C$_{18}$ column, CH$_3$CN gradient 5-65%, 0.1% TFA, UV analysis 300 nm, 28 min) and lyophilization of the collected fractions afforded 4.3 mg (14%) of (3) as a white solid. LRMS (ES+) m/z 392.0 (C$_{22}$H$_{21}$N$_3$O$_4$+H requires 392.15); RP-HPLC (300 nm, 28 min run) 10.0 min.

Synthesis of Diacetylenic Benzylamine Analogues

Example 23

(1S,2R)—N-2-hydroxy-1-hydroxycarbamoyl-propyl)-4-[4-(4-meorphoin-4-ylmethyl-phenyl)-buta-1,3-diynyl]-benzamide (4)

Preparation of Threonine Diacetylenic Benzaldehyde on Resin (3)

Resin (1) (resin (4) obtained from prior synthesis)) (1.00 g, 0.77 mmol) was pre-swelled in DCM (25 mL) for 14 h and drained. A solution of 4-iodobenzaldehyde (2) (715 mg, 3.08 mmol) and Et$_3$N (1.00 mL, 7.17 mmol) in DMF (20 mL) was purged with N$_2$ for two minutes and added to the resin. After mixing for 5 min, PdCl$_2$(PPh$_3$)$_2$ (40.0 mg, 0.057 mmol) and CuI (19.0 mg, 0.100 mmol) were added and the reaction shaken for 48 h. The resin was drained, washed with DMF (4×20 mL), DCM (4×20 mL) and dried in vacuo to give 1.100 g of (3) as a dark yellow resin.

Preparation of (1S,2R)—N-2-hydroxy-1-hydroxycarbamoyl-propyl)-4-[4-(4-morpholin-4-ylmethyl-phenyl)-buta-1,3-diynyl]-benzamide (4)

A solution of morpholine (75 µL, 0.860 mmol) and trimethyl orthoformate (100 µL, 0.914 mmol) in THF (3.0 mL) was added to a Teflon-lined screw-capped vial containing the resin-bound diacetylenic benzaldehyde (3). The resin was agitated for 10 min, treated successively with acetic acid (100 µL, 1.75 mmol) and a solution of NaCNBH$_3$ (40.0 mg, 0.637 mmol) in MeOH (1.0 mL) and shaken for 44 h. The resin was filtered, washed with DMF (3×3 mL) and DCM (3×3 mL) and drained. Cleavage from the resin was achieved by treatment with 10% TFA/DCM (2.0 mL) and shaking 20 min. The solution was collected and the resin was rinsed with additional 10% TFA/DCM (2.0 mL). The cleavage fractions were combined, treated with neat TFA (3.0 mL), stirred for 1 h at rt and concentrated by rotary evaporation to give a crude yellow residue. Purification by RP-HPLC (C$_{18}$ column, CH$_3$CN gradient 5-35%, 0.1% TFA, UV analysis 300 nm, 18 min) and lyophilization of the collected fractions afforded 19.0 mg (29%) of (4) as a fluffy yellow solid. LRMS (ES+) m/z 462.0 (C$_{26}$H$_{27}$N$_3$O$_5$+H requires 462.10); HPLC (300 nm, 18 min run) 10.3 min.

Synthesis of 4'-Benzamide Diacetylene Threonine Hydroxamic Acid

Example 24

(1S,2R)—N-(2-hydroxy-1-hydroxycarbamoyl-propyl)-4-{4-[4-(2-amino-ethylcarbamoyl)-phenyl]-buta-1,3-diynyl}-benzamide (5)

Preparation of N-(2-trityl-amino-ethyl)-4-ethynyl-benzamide (3)

To a solution of 4-ethynylbenzoic acid (1) (292 mg, 2.00 mmol), EDCI (382 mg, 2.00 mmol), and HOBt (270 mg, 2.00 mmol) in DMF (10 mL) was added N-trityl ethylenediamine (2) (810 mg, 2.67 mmol) and DIEA (1.4 mL, 8.0 mmol). The reaction mixture was stirred 24 h, diluted with EtOAc (200 mL), washed with 0.5 M HCl (60 mL), saturated NaHCO$_3$ (2×60 mL), H$_2$O (4×60 mL), dried over MgSO$_4$ and concentrated to give 836 mg (97% yield) of (3) as a white solid, mp 50-51° C. R$_f$=0.40 (1:1 Hexanes/EtOAc).

Preparation of (1S,2R)—N-(2-hydroxy-1-hydroxycarbamoyl-propyl)-4-{-4-[4-(2-amino-ethylcarbamoyl)-phenyl]-buta-1,3-diynyl}-benzamide (5)

Resin (4) (resin (1) from above syntheses) (150 mg, 0.116 mmol) was swelled in DCM (2 mL) for 1 h and drained. A solution of 4-ethynylbenzamide (3) (151 mg, 0.350 mmol) and Et$_3$N (150 µL, 1.10 mmol) in DMF (2.0 mL) was added and the resin agitated for 5 min. A mixture of PdCl$_2$(PPh$_3$)$_2$ (21 mg, 0.030 mmol) and CuI (28 mg, 0.147 mmol) was added and the resin was agitated for 60 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC(C$_{18}$ column, CH$_3$CN gradient 5-65%, 0.1% TFA, UV analysis 300 nm, 26 min) and lyophilization of the collected fractions afforded 2.0 mg (4% yield) of (5). LRMS (ES+) m/z 449.1 (C$_{24}$H$_{24}$N$_4$O$_5$+H requires 449.18); RP-HPLC (300 nm n, 26 min run) 17.0 min.

Synthesis of 3'-Pyridine Diacetylene Threonine Hydroxamic Acid

Example 25

N-((2R)-hydroxy-(1S)-hydroxycarbamoyl-propyl)-4-(4-pyridin-3-yl-buta-1,3-diynyl)-benzamide (3)

(1S,2R)—N-(2-tert-butoxy-1-hydroxycarbamoyl-propyl)-4-ethynyl-benzamide on hydroxylamine 2-chlorotrityl resin (1) (142 mg, 0.109 mmol) was swelled in DCM (2 mL) for 1 h and drained. A solution of 3-ethynylpyridine (2) (38 mg, 0.368 mmol) and Et$_3$N (200 µL, 1.4 mmol) in DMF (2 mL) was added and the resin agitated for 5 min. A mixture of PdCl$_2$(PPh$_3$)$_2$ (22 mg, 0.031 mmol) and CuI (25 mg, 0.131 mmol) was added and the resin was agitated for 72 h. The resin was drained, washed with DMF (3×2 mL), DCM (3×2 mL) and cleaved with 10% TFA/DCM (1.5 mL) for 20 min. The solution was collected and the resin was rinsed with additional 10% TFA/DCM (1.0 mL). The cleavage fractions were combined, treated with neat TFA (2.0 mL), stirred for 1 h at rt and concentrated by rotary evaporation to give a crude brown residue. Purification by RP-HPLC (C$_{18}$ column, CH$_3$CN gradient 5-65%, 0.1% TFA, UV analysis 300 nm, 24 min) and lyophilization of the collected fractions afforded 4.4 mg (11% yield) of (3). LRMS (ES+) m/z 364.0 (C$_{20}$H$_{17}$N$_3$O$_4$+H requires 364.13); RP-HPLC (300 nm, 24 min run) 11.2 min.

Example 26

Synthesis of N-(1-(N-hydroxycarbamoyl)(1S,2R)-2-hydroxy propyl) {4-[4-(6-morpholin-4-yl(3-pyridyl))buta-1,3-diynyl]phenyl}carboxamide (5)

Preparation of 4-[4-(6-Chloro-pyridin-3-yl)-buta-1,3-diynyl]-benzoic acid methyl ester 4-[4-(6-Chloro-pyridin-3-yl)-buta-1,3-diynyl]-benzoic acid was made according to the method of Wang Shen and Sheela A. Thomas in *Org. Lett.* 2000, 2(18), 2857-2860.

A solution of 4-(2,2-dibromo-vinyl)-benzoic acid methyl ester (1) (9.6 g, 30.0 mmol), 2-chloro-5-ethynyl-pyridine (2) (5.43 g, 39.0 mmol), Pd$_2$ dba$_3$ (274 mg, 0.3 mmol), tris(4-methoxyphenyl) phosphine (TMPP) (422 mg, 1.2 mmol) were dissolved in argon sparged (5 min.) DMF (60 ml). The reaction was sparged with argon for 1 min. TEA (12.5 ml, 90.0 mmol) was added to the stirred reaction mixture that was then heated under argon at 85° C. for 3 hours. The reaction was found complete by LCMS. The reaction was cooled to rt and diluted with EtOAc/hexane (1:1) (500 ml). The organic phase was washed with 1 M NaOH (2×80 ml), water (2×80 ml), sat. brine (80 ml), dried with Na$_2$SO$_4$, filtered concentrated under reduced pressure to give crude product. The residue was filtered through a filter plug of silica eluting with EtOAc/hexane (1:1). The fractions with product were evaporated to give 9.06 g of product in good purity (~96% pure). The material was taken on without further purification.

Preparation of 4-[4-(6-Chloro-pyridin-3-yl)-buta-1,3-diynyl]-benzoic Acid (3)

A 6M aq. solution of NaOH (15 ml) was added to a stirred solution of 4-[4-(6-Chloro-pyridin-3-yl)-buta-1,3-diynyl]-benzoic acid methyl ester (9.06 g, 30 mmol) in MeOH (350 ml) at rt. The reaction solution was heated to reflux for 3 hours. The reaction stayed a mixture and did not turn clear. HPLC and LCMS indicated that the reaction was forming side products. The reaction was cooled to rt and some MeOH (~200 ml) was removed by evaporation under reduced pressure. Water (400 ml) was added to the mixture. Conc. HCl was added dropwise to the stirred solution until acidic by pH paper (pH2). The yellow precipitate that formed was collected by suction filtration. The solid was washed with water (3×20 ml) and hexane (2×20 ml) to give the crude product. HPLC indicated that there was approximately 40% product in the mixture. The crude reaction product was purified by flash chromatography using EtOAc (8-10%)/hexane as eluant. The pure fractions were evaporated and dried in vacuo to give 4.2 g of product (3) in 50% yield.

Preparation of [4-[4-(6-chloro-pyridin-3-yl)-buta-1,3-diynyl]-benzoyl]-HN-Thr(OtBu)-hydroxamic acid trityl resin (4)

(3) was coupled to a tert-butyl protected threonine preloaded on hydroxylamine 2-chlorotrityl resin following the same procedure as used for Example 26. The coupling employed DIC and HOBT. [N-Fmoc-hydroxylamine 2-chlorotrityl resin was purchased from Novabiochem cat. #01-64-0165.]

Preparation of N-(2-Hydroxy-1-hydroxycarbamoyl-propyl)-4-[4-(6-morpholin-4-yl-pyridin-3-yl)-buta-1,3-diynyl]-benzamide (5)

A solution of morpholine (300 uL) in NMP (1 ml) was added to a vial containing (4) (150 mg, 0.12 mmol). The reaction mixture was purged with argon and heated to 85-90° C. for 24 hours. The resin was drained and washed with DMF and DCM alternately several times. The product was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with $CH_3CN$/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2.2 mg of pure product (5) as the TFA salt (~32% yield).

Example 27

Synthesis of 4-[4-(4-Amino-phenyl)-buta-1,3-diynyl]-N-(2-hydroxy-1-hydroxycarbamoyl-propyl)-benzamide (4)

Preparation of 2{4-[4-(4-Amino-phenyl)-buta-1,3-diynyl]-benzoylamino}-3-tert-butoxycarbonyl oxybutyric hydroxamic acid trityl resin (3)

DIEA (2.7 ml, 15.6 mmol) was added to a stirred solution of 4-[4-(4-Amino-phenyl)-buta-1,3-diynyl]-benzoic acid (2) (1.64 g, 6.3 mmol), HOBT (0.85 g, 6.3 mmol), DIC (0.98 ml, 6.3 mmol) in DMF (50 ml). After 2 min., H-Thr(Boc)-NHO-Trt resin (1) (5.8 g, 4.5 mmol) was added in one portion. [N-Fmoc-hydroxylamine 2-chlorotrityl resin was purchased from Novabiochem cat. #01-64-0165.] After 12 hours at rt, the reaction was found complete by LCMS. The resin was drained and washed with DMF and DCM alternately 3 times each. The product (3) was used as is in subsequent reactions without further treatment.

Preparation of 4-]4-(4-Amino-phenyl)-buta-1,3-diynyl]-N-(2-hydroxy-1-hydroxy carbamoyl-propyl)-benzamide (4)

The product (4) (120 mg, 0.09 mmol) was cleaved from resin (3) through treatment with a TFA/water solution (80:20) (1.5 ml) for 45 min. The resin was filtered and washed with fresh TFA/water solution (80:20) (0.5 ml). The combined TFA and organic fractions were diluted with $CH_3CN$/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2.2 mg of pure product as the TFA salt. The product was lyophilized again from $CH_3CN$/water with 10 equivalents of HCl to remove most of the TFA to yield 2 mg of (4) as the HCl salt (~53% yield).

Example 28

Synthesis of 4-{4-[4-(2-Dimethylamino-acetylamino)-phenyl]-buta-1,3-diynyl}-N-(2-hydroxy-1-hydroxycarbamoyl-propyl)-benzamide (6)

Continued from Compound (3) of Example 27 Above

Preparation of 2-{4-(4-[4-(2-Bromo-acetylamino)-phenyl]-buta-1,3-diynyl}-benzoylamino)-3-tert-butoxycarbonyloxy-butyric acid hydroxamate trityl resin (5)

A solution of bromo-acetyl chloride (0.75 g, 0.58 mmol) in DCM (2 ml) was added to a mixture of (3) (0.75 g, 0.58 mmol), lutidine (1.1 ml, 9.2 mmol) and DCM (4 ml) at rt with shaking. After shaking for 1.5 hours, the reaction was found complete by LCMS. The resin was drained and washed with DCM (2×10 ml), DMF (3×10 ml) and DCM (3×10 ml) again. The resin was drained and dried in vacuo. The product resin (5) was used as is in subsequent reactions without further treatment.

Preparation of 4-{4-[4-(2-Dimethylamino-acetylamino)-phenyl]-buta-1,3-diynyl}-N-(2-hydroxy-1-hydroxycarbamoyl-propyl)-benzamide (6)

A solution of dimethyl amine (0.2 ml) in NMP (1.2 ml) was added to (5) (125 mg, 0.09 mmol) at rt with shaking. After shaking for 12 hours, the reaction was found complete by LCMS. The resin was drained and washed with DCM (2×10), DMF (3×10) and DCM (3×10) again. The product (6 ml) was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with $CH_3CN$/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 2 mg of pure product (6) as the TFA salt (~37% yield).

Example 29

Synthesis of 4-{-4-[4-(2-Amino-4-methyl-pentanoylamino)-phenyl]-buta-1,3-diynyl}-N-(2-hydroxy-1-hydroxycarbamoyl-propyl)-benzamide (7)

Continued from Compound (3) of Example 27 Above

A solution of Fmoc-L-leucine (0.135 g, 0.38 mmol), HATU (0.146 g, 0.38 mmol) in DMF (1.5 ml) was made. After 2 min. of shaking, the activated acid was added to (3) (125 mg, 0.09 mmol) at rt with shaking. After shaking for 36 hours, the reaction was drained and washed with DCM (2×4 ml), DMF (3×4 ml) and DCM (3×4 ml) again. The resin was treated with 20% piperizine in DMF (4 ml) for 2 hours twice. The resin was drained and washed with DMF and DCM alternately several times. The product was cleaved from the resin through treatment with a TFA/water solution (80:20) (1.5 ml) for 45 min. The resin was filtered and washed with fresh TFA/water solution (80:20) (0.5 ml). The combined TFA and organic fractions were diluted with CH₃CN/water (1:1) (10 ml), water (2 ml) and lyophilized. The crude product was purified by prep. HPLC. The crude product was dissolved in DMSO (1 ml), passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 1.7 mg of pure product (7) as the TFA salt (~30% yield).

Example 30

Step 1

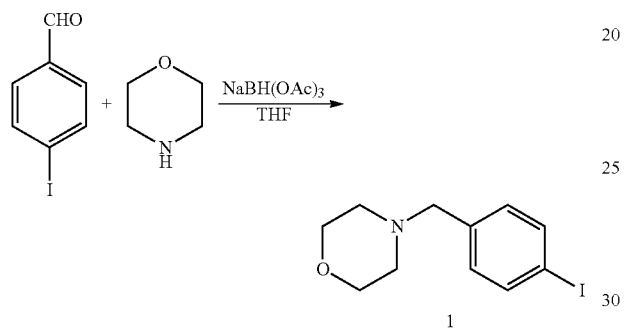

NaBH(OAc)₃ (1.38 g, 6.03 mmol) was added at 0° C. to a solution of 4-iodobenzylaldehyde (1.0 g, 4.31 mmol) and morpholine (462 mg, 5.37 mmol) in THF (30 mL). The reaction mixture was then warmed to rt and stirred overnight. The solvent was removed (RV) and the residue was extracted with EtOAc (2×) from aqueous NaHCO₃ (pH=8-9). The combined organic extracts were dried (NaSO₄) and concentrated to dryness (RV). Column chromatography (silica gel, EtOAc/DCM 0-100%) yielded compound (1) (980 mg, 74.8% yield, M+H⁺=304.0).

Step 2

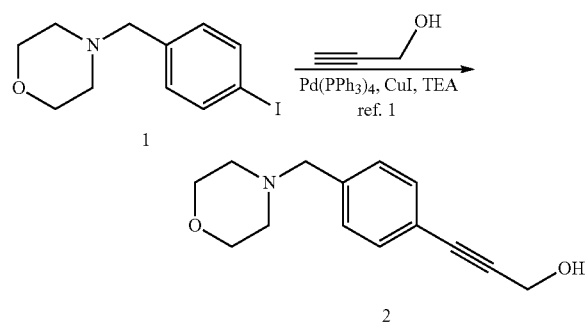

A solution of compound (1) (2.0 g, 6.6 mmol) and propargyl alcohol (407 mg, 7.26 mmol) in THF (20 mL) was purged by nitrogen for 30 min, followed by addition of PdCl₂(PPh₃)₂ (55.6 mg, 0.079 mmol) and CuI (30 mg, 0.158 mmol). The reaction mixture was cooled to 0° C. and triethyl amine (1.0 g, 9.9 mmol) was added. The reaction mixture was warmed to rt and stirred overnight under N₂. The reaction mixture was filtered through a plug of celit and the filtrate was concentrated. The residue was treated with water (200 mL) and extracted with EtOAc (200 mL×2). The combined organic layers were washed with water (200 mL×2), brine (200 mL) and dried (NaSO₄). The crude product was purified by chromatography on silica gel eluting with EtOAc/Hexane (0-50%) to give 1.5 g of the product (2) (98.7% yield, M+H⁺=232.0).

Step 3

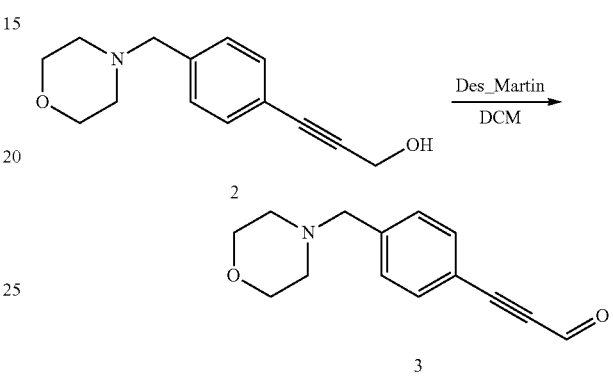

Dess-Martin reagent (1.37 g, 3.25 mmol) was added to a solution of compound (2) (500 mg, 2.1 mmol) in CH₂Cl₂ (5 mL) at 0° C. The reaction mixture was warmed to rt and stirred overnight. The reaction mixture was diluted with CH₂Cl₂ (200 mL), basified with NaHCO₃ (saturated) to pH=8-9 and then washed with water (200 mL) and brine (200 mL), dried (NaSO₄) and concentrated under reduced pressure. The crude product (3) (900 mg, MS+H⁺=230.0) was not very stable and used directly in the next reaction without further purification.

Step 4

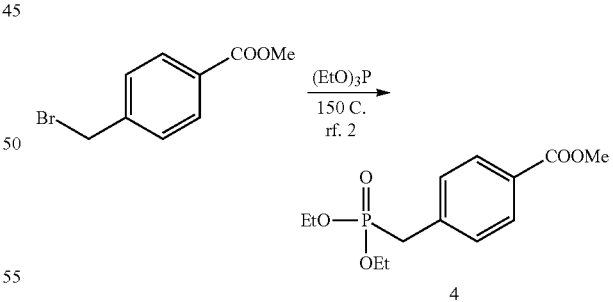

A mixture of 4-bromomethyl-benzoylic methyl ester (1.0 g, 4.37 mmol) and P(OEt)₃ (3 mL) in a sealed tube was heated at 150° C. overnight. Cooled to rt, the reaction mixture was diluted with EtOAc (200 mL), washed with water (100 mL×2) and brine (100 mL), dried (NaSO₄) and concentrated under reduced pressure. The crude product was purified by chromatography on silica gel eluting with EtOAc/Hexane (0-100%) to give compound (4) (800 mg, 64.0% yield, M+H⁺=286.9).

Step 5

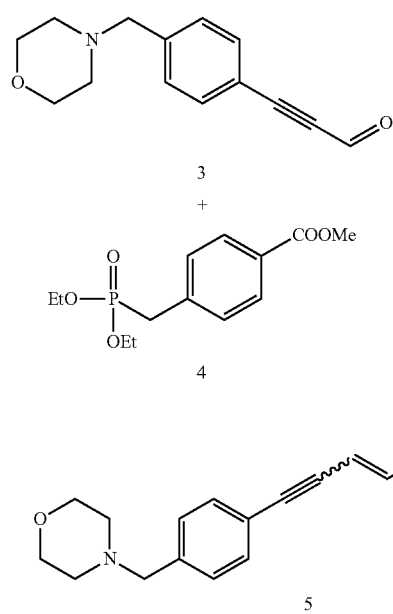

To a solution of compound (4) (741 mg, 2.59 mmol) in THF (5 mL) was added NaH (114 mg, 2.85 mmol). Stirred at rt for one hour, followed by addition of compound (3) (900 mg) in THF solution (5 mL), the resulting mixture was stirred at rt overnight and concentrated under reduced pressure. The residue was treated with EtOAc (300 mL), washed with water (200 ml×2) and brine (200 ml), dried (NaSO$_4$) and concentrated under reduced pressure. The crude product was purified by chromatography on silica gel eluting with EtOAc/Hexane (0-60%) to give compound (5) (188 mg, 20.0% yield, M+H$^+$=362.0).

Step 6

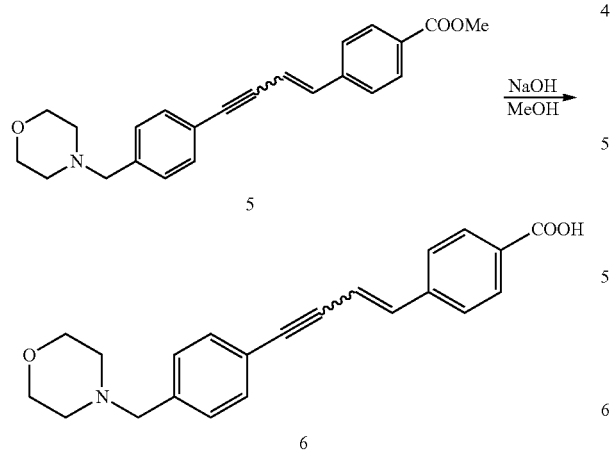

To a solution of compound (5) (188 mg, 0.521 mmol) in MeOH (5 mL) was added NaOH (84 mg, 1.08 mmol). The reaction mixture was heated at reflux for 4 hrs and cooled to rt, the reaction mixture was neutralized to pH=7 with HCl solution (4 N in dioxane). Removal of solvent under reduced pressure, the solid residue was washed with CH$_2$Cl$_2$. The combined CH$_2$Cl$_2$ was evaporated to give crude compound (6) (259 mg, 70% purity, 100% yield, MS$^+$=348.0).

Step 7

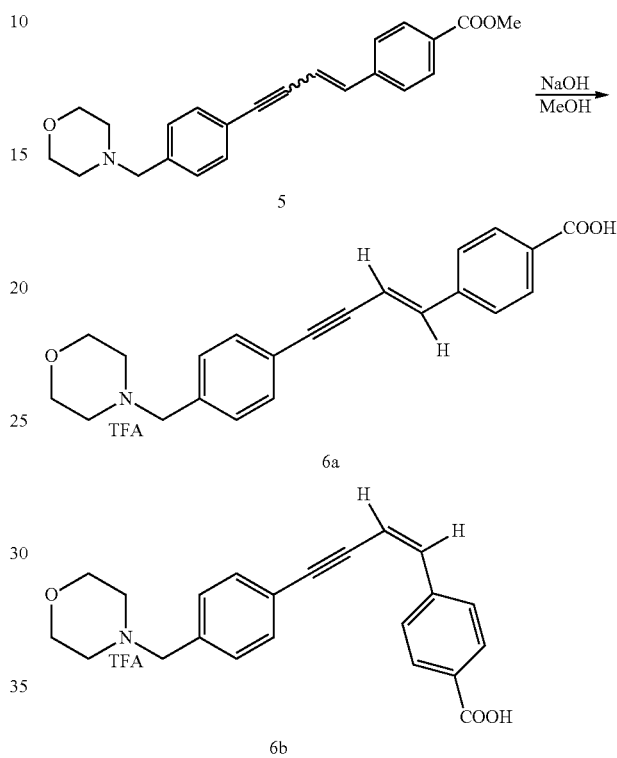

To a solution of compound (5) (320 mg, 0.886 mmol) in MeOH (5 mL) was added NaOH (142 mg, 3.54 mmol). The reaction mixture was heated at reflux for 4 hrs and cooled to rt. The reaction mixture was concentrated under reduced pressure. The crude product was purified by prep. HPLC to give compound (6a) (105.5 mg, 25.8% yield, MS$^+$=348.0) and (6b) (30.9 mg, 7.4%, MS$^+$=348.0) as TFA salt.

Step 8

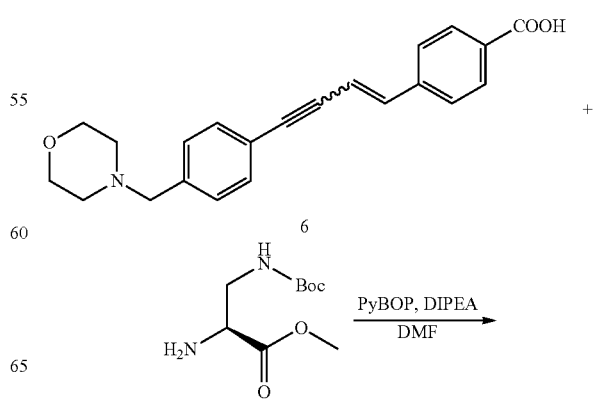

To a solution of compound (6) (44 mg, 0.126 mmol) and methyl 3-Boc-2,3-diaminopropanoade (64 mg, 0.253 mmol) and PyBOP (131 mg, 0.253 mmol) in DMF (2 mL) was added DIPEA (81 mg, 0.65 mmol). The reaction mixture was stirred at rt. overnight and diluted with water (50 ml), extracted with EtOAc (50 ml×2). The combined organic layers were washed with water (50 ml×2), brine (50 ml), dried (NaSO₄) and concentrated under reduced pressure. The crude product was purified by chromatography on silica gel eluting with MeOH/CH₂Cl₂ (0-5%) to give product 7 (47 mg, 68.1%, MS⁺=548.1).

Step 9

To a solution of compound (7) (48 mg, 0.08 mmol) in CH₂Cl₂ (1 mL)/MeOH (2 mL) was added NH₂OH.HCl (61 mg, 0.88 mmol) and NaOH (58 mg, 1.05 mmol). The reaction mixture was stirred at rt for 3 days, and then diluted with CH₂Cl₂ (20 mL), then treated with NH₄Cl (saturated) solution to adjust pH=7. The organic layer was separated, and the aq. layer was extracted with CH₂Cl₂ (20 mL×2). The combined CH₂Cl₂ layers were washed with brine (20 ml), dried (NaSO₄) and concentrated under reduced pressure. The crude product was purified by chromatography on silica gel eluting with CH₂Cl₂/MeOH (0-10%) to give product (8) (10 mg, 22.8%. MS⁺=549.1)

Step 10

The desired product (9a) (90 mg, 89.7%, MS⁺=463.1) was prepared by the reaction of compound (6a) (100 mg, 0.217 mmol), L-Threonine ethyl ester (75 mg, 0.434 mmol), HATU (165 mg, 0.434 mmol) and DIPEA (138 mg, 1.07 mmol) in DMF (3 mL) according to the synthetic procedure for the preparation of compound (7).

The desired product (9b) (26 mg, 90%, MS⁺=463.1) was prepared by the reaction of compound (6a) (30 mg, 0.065 mmol), L-Threonine ethyl ester (22 mg, 0.13 mmol), HATU (49 mg, 0.138 mmol) and DIPEA (42 mg, 0.325 mmol) in DMF (1 mL) according to the synthetic procedure for the preparation of compound (7).

Step 11

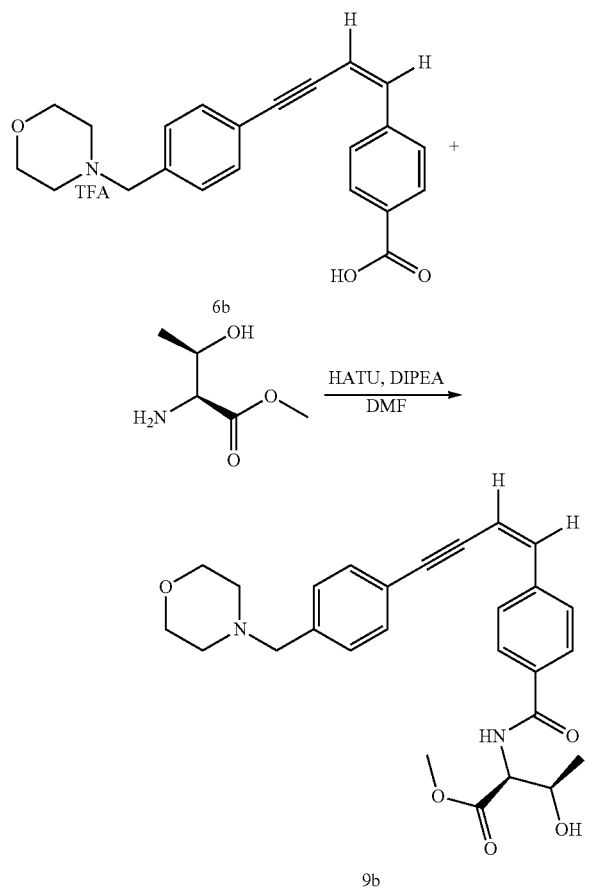

Step 12

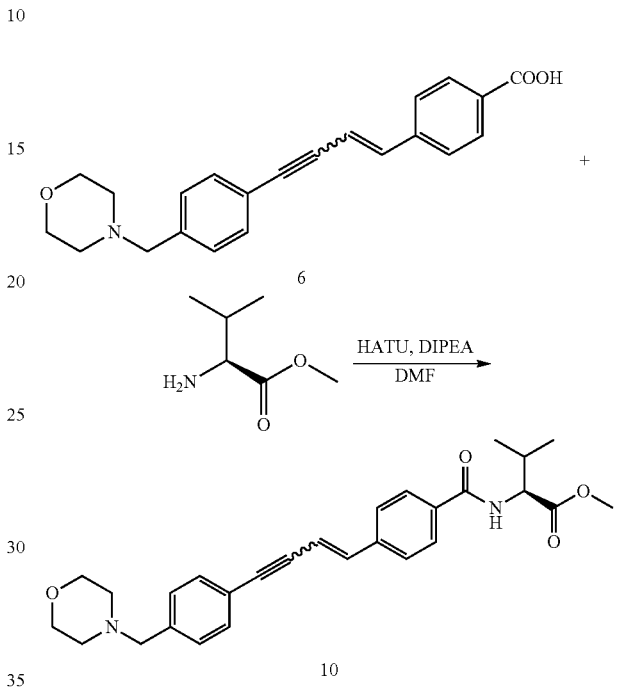

The desired product (10) (36 mg, 46.0%, MS⁺=461.1) was prepared by the reaction of compound (6) (60 mg, 0.17 mmol), valine methyl ester (54 mg, 0.323 mmol), HATU (128 mg, 0.338 mmol) and DIPEA (104 mg, 0.81 mmol) in DMF (3 mL) according to the synthetic procedure for the preparation of compound (7).

Step 13

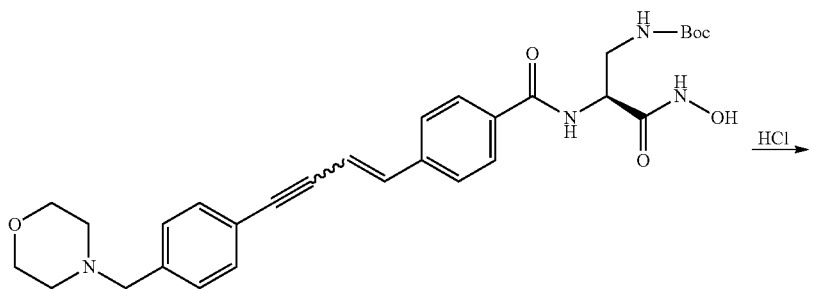

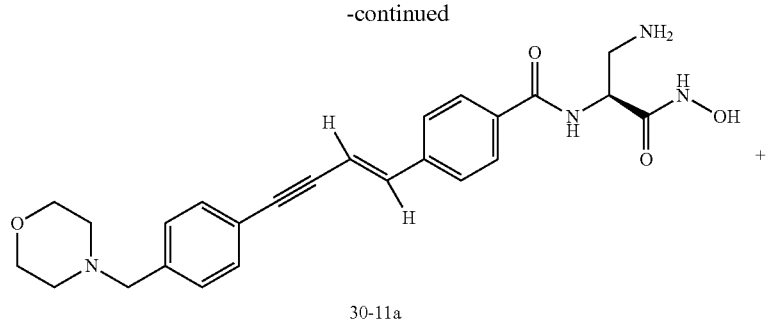
30-11a
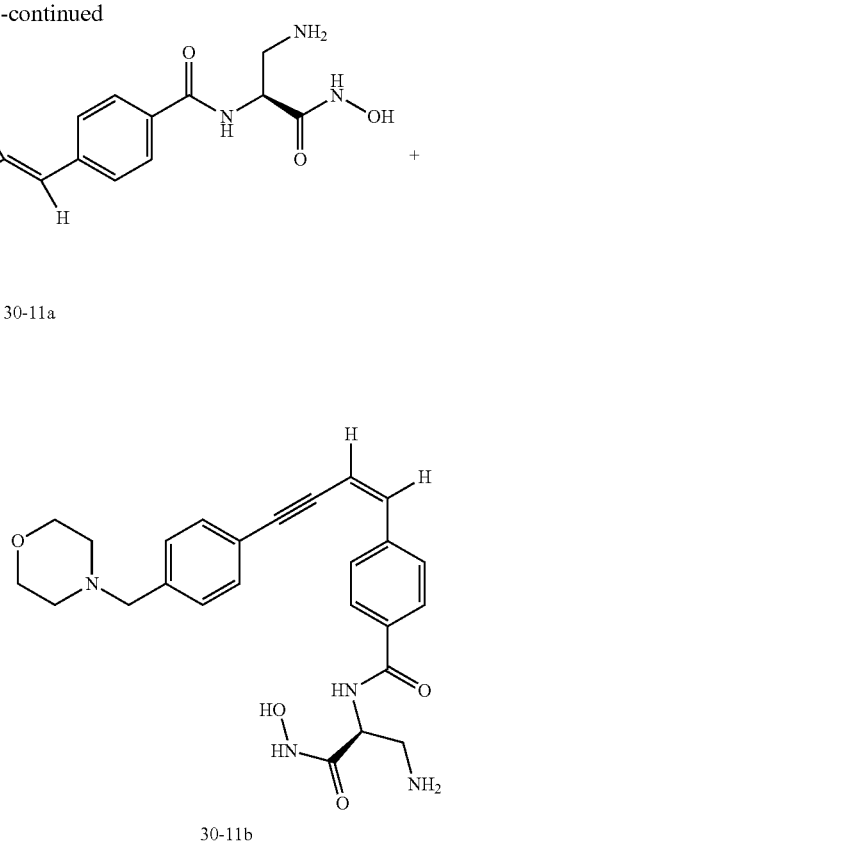
30-11b
To a solution of compound (8) (48 mg, 0.088 mmol) in CH$_2$Cl$_2$ (1 ml) was added HCl (1 ml, 4 N in dioxane). The reaction mixture was stirred at rt. for 2 hrs. and concentrated under reduced pressure. The solid residue was purified by prep. HPLC to give compound (30-11a) (53 mg, 90% yield) and (30-11b) (0.3 mg, 0.5% yield) as double TFA salt.
Step 14
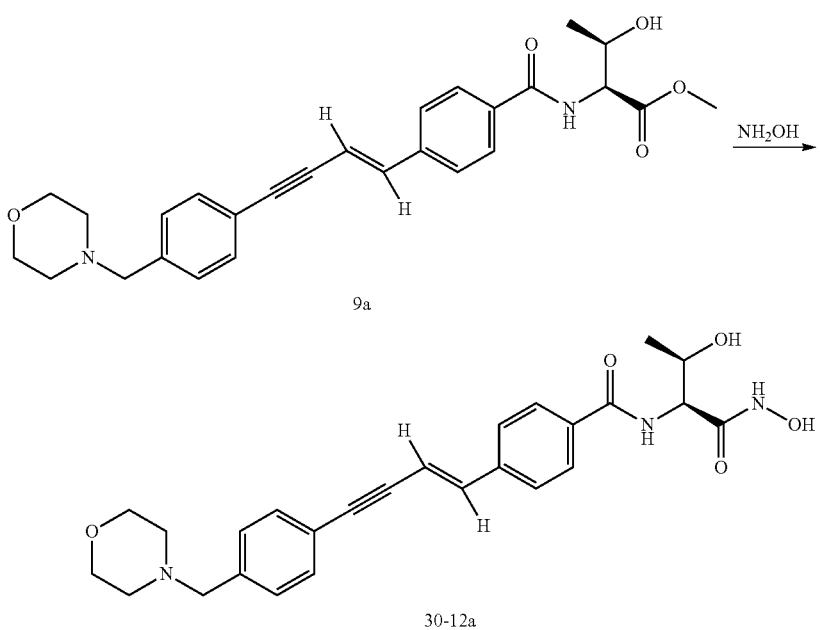
9a
30-12a The desired product (30-12a) (53.8 mg, 14.9%, MS+=464.1) was prepared by the reaction of compound (9a) (90 mg, 0.195 mmol) and NH$_2$OH.HCl (134 mg, 1.95 mmol) and NaOMe (128.7 mg, 2.34 mmol) in MeOH (5 ml) according to the synthetic procedure for the preparation of compound (8).

Step 15

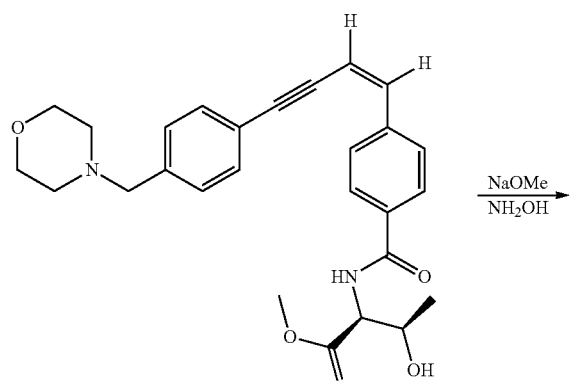

9b

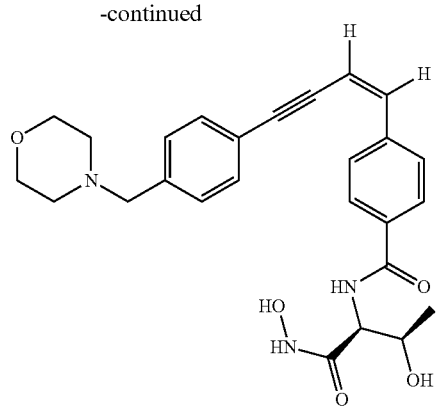

30-12b

Compound (30-12b) (6.2 mg, 24% yield) was prepared by the reaction of compound (9b) (26 mg, 0.056 mmol) and NH$_2$OH.HCl (38.7 mg, 0.56 mmol) and NaOMe (37 mg, 0.672 mmol) in MeOH (3 ml) according to the synthetic procedure for the preparation of compound (8).

Step 16

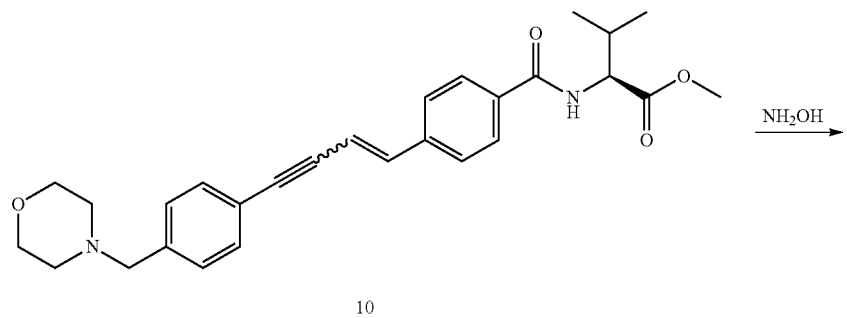

10

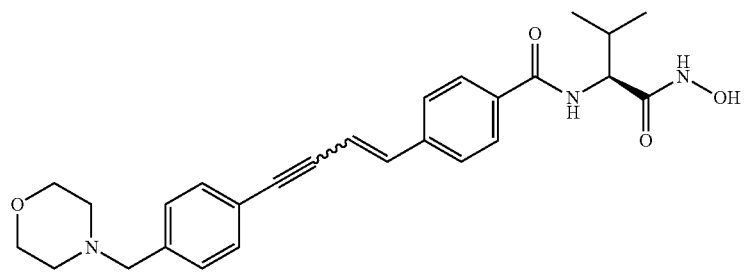

13

The desired product (13) is prepared by the reaction of compound (10), NH₂OH.HCl and NaOH in CH₂Cl₂/MeOH according to the synthetic procedure for the preparation of compound (8).

Step 17

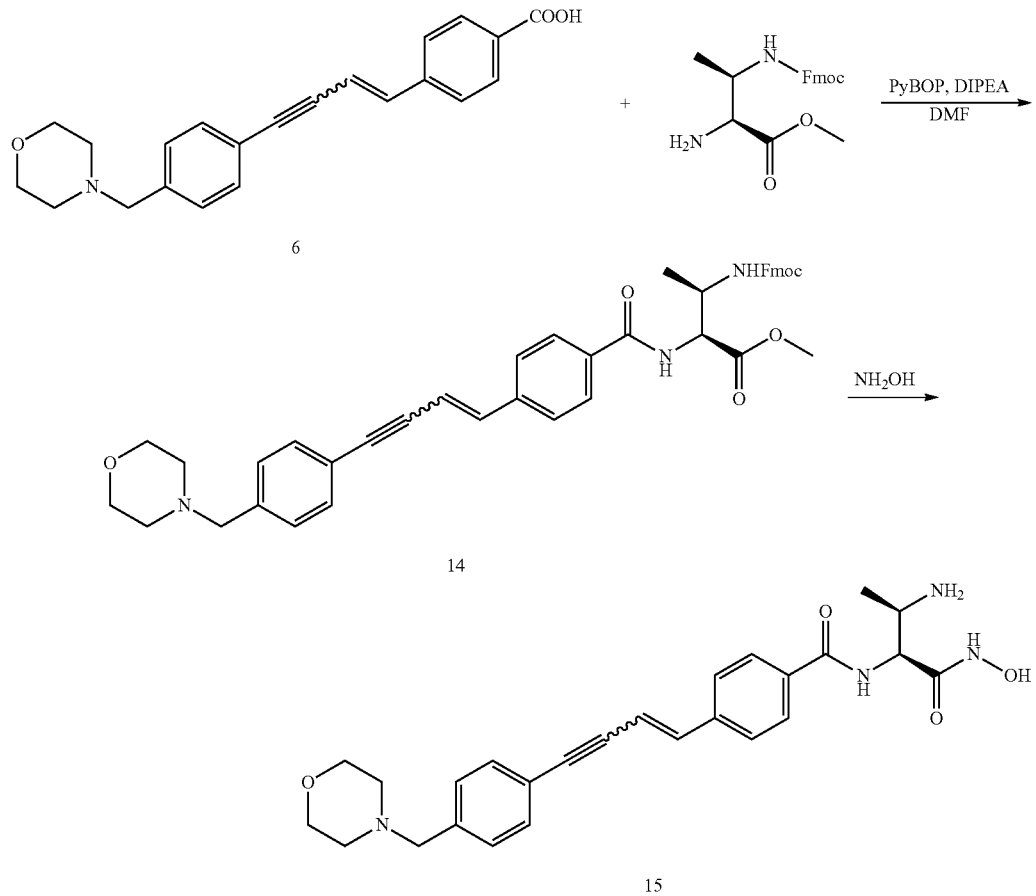

The desired product (14) is prepared by the reaction of compound (6) and (2S,3R)-2-amino-3-Fmoc-butyric acid methyl ester hydrochloride according to the synthetic procedure for the preparation of compound (7). The desired product (15) is prepared by the reaction of compound (14), NH₂OH.HCl and NaOMe in CH₂Cl₂/MeOH according to the synthetic procedures for the preparation of compound (8).

Synthesis of (2S,3R)-2-amino-3-Fmoc-butyric acid methyl ester hydrochloride

-continued

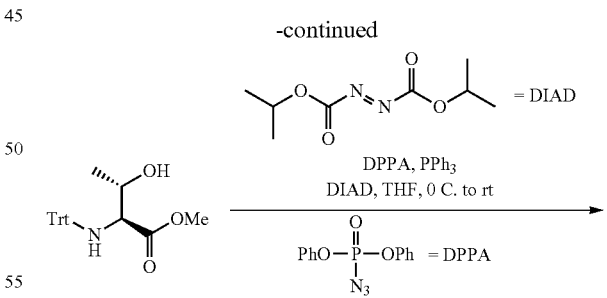

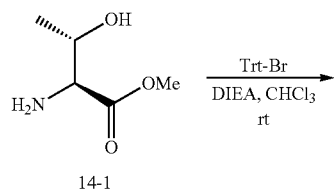

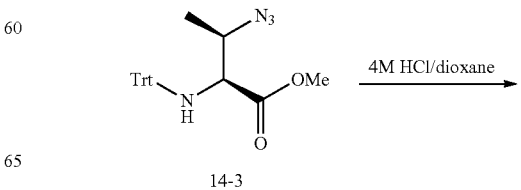

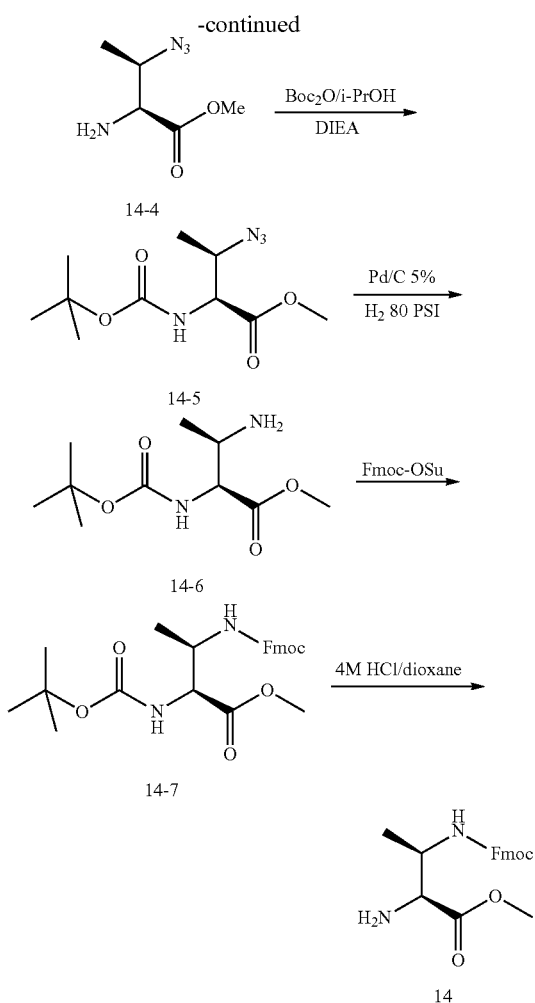

(2S,3S)-methyl-3-hydroxy-2-(tritylamino)butanoate (14-2)

To a solution of H-allo-Thr-OMe.HCl (compound 14-1) (CAS 79617-27-9, Chem-Impex, 5 g, 29.5 mmoL) in CH₂Cl₂ (30 mL) and DIEA (15 mL, 88.5 mmol) was added trityl bromide (10 g, 32.4 mmol) in CHCl₃ (30 mL) dropwise through an addition funnel at 0° C. The reaction mixture was warmed to rt slowly and stirred overnight, and washed with water (2×10 mL) and brine, dried (Na₂SO₄), filtered and concentrated to give the desired product as a thick oil, which was solidified to a white crystalline material in vacuo. The solid was treated with ethyl ether and sonicated for 30 min, filtered and washed with ethyl ether to give the pure product (14-2) (8 g, 21.3 mmol, 72% yield, mw 375.5) as a white solid.

(2S,3R)-methyl 3-azido-2-(tritylamino)butanoate (14-3)

To a mixture of compound (14-2) (6 g, 16 mmol), PPh₃ (4.2 g, 16 mmol) in CH₂Cl₂ (30 mL) at 0° C. with stirring under nitrogen was added diethyl azodicarboxylate (DIAD) (5.2 g, 25.6 mmol) in CH₂Cl₂ (5 mL) slowly, followed by diphenylphosphonic azide (DPPA) in CH₂Cl₂ (5 mL). The reaction mixture was allowed to warm to rt. After stirring at rt overnight, the reaction was concentrated under reduced pressure. The residue was purified by chromatography on silica gel on an ISCO system eluting with hexane/EtOAc to give the desired product (14-3) (2.9 g, ~7.2 mmol, 45% mw 400.5) as a yellow oil (NMR shows there is DIAD in the product).

(2S,3R)-methyl 2-amino-3-azidobutanoate (14-4)

A mixture of compound (14-3) (2.9 g) in CH₂Cl₂ (10 mL) and HCl (5 mL, 4 M in dioxane) was stirred overnight. The reaction mixture was concentrated and the residue was treated with hexane. The suspension formed was filtered to give the desired product (14-4) (600 mg, 52%) as a white solid. (Alternately, compound (14-3) can be dissolved in THF (1 g:8 mL), HCl2M (3 eq.) in ether can be added at 0° C. The reaction is allowed to warm and is complete after ~3 h. The reaction mixture can be diluted with ether to precipitate the product as an HCl salt which is filtered and washed with ether. The resulting white powder, after drying in vacuo, is highly pure and gives about 86% yield, mw 158.2 free base and 194.2 with 1HCl salt. No further purification is needed.)

(2S,3R)-3-Azido-2-Boc-amino-butyric acid methyl ester (14-5)

A solution of di-tert-butyl dicarbonate (810 mg, 3.7 mmol), (2S,3R)-2-amino-3-azido-butyric acid methylester hydrochloride (compound 14-4) (660 mg, 3.38 mmol) and DIEA (645 µl, 3.7 mmol) in i-PrOH (10 ml) was maintained at ambient temperature for 10 h. The reaction mixture was evaporated in vacuum. The residue was dissolved in water (4 mL) and extracted with hexane/ether (1:1) (4×10 mL). The combined organic layers were dried (Na₂SO₄) and concentrated under reduced pressure. The residue was subjected to flash chromatography on CombiFlash® Companion unit equipped with RediSep® flash column (normal phase, 35-60 micron average particle size silicagel, 40 g, Teledyne Isco); flow rate=35 ml/min; injection volume 2 ml (EtOAc); mobile phase A: hexane; mobile phase B: EtOAc; gradient 0-50% B in 1 h. Fractions containing the desired product were combined and concentrated under reduced pressure to provide compound (14-5) (564 mg, 2.2 mmol, 65% yield, mw 258.3) as colorless oil. (Alternately, the reaction can be run using 1.2 eq Boc₂O and 2.5 eq DIEA in ACN (1 g (14-5) in 30 mL ACN). After stirring overnight, the reaction was concentrated and purified by silica chromatography eluting with 10-15% EtOAc/Hexane. The product fractions were collected to give 98% yield, >98% purity as a clear oil.

(2S,3R)-3-Amino-2-tert-butoxycarbonylamino-butyric acid methyl ester (14-6)

Compound (14-5) (786 mg, 3.05 mmol) was dissolved in methanol (20 ml) followed by the addition of Pd/C (5% wt, 200 mg). The reaction mixture was subjected to hydrogenation (Parr apparatus, 80 psi) at ambient temperature for 40 min. The solid catalyst was filtered and washed with methanol. The filtrate was evaporated under reduced pressure to provide compound (14-6) (682 mg, 96% yield, mw 232.3) as colorless oil.

(2S,3R)-2-Boc-amino-3-Fmoc-aminobutyric acid methyl ester (14-7)

A mixture of compound (14-6) (682 mg, 2.94 mmol) and Fmoc-OSu (1.04 g, 3.08 mmol) in acetone (5 ml) was stirred at rt for 2 h. The solvent was evaporated under reduced pressure. The residue was dissolved in EtOAc (50 ml) and washed with 5% NaHCO$_3$ (10 ml) and brine (10 ml). Organic layer was dried (Na$_2$SO$_4$) and evaporated under reduced pressure. The residue was subjected to flash chromatography on CombiFlash® Companion unit equipped with RediSep® flash column (normal phase, 35-60 micron average particle size silicagel, 40 g, Teledyne Isco); flow rate=35 ml/min; injection volume 2 ml (EtOAc); mobile phase A: hexane; mobile phase B: EtOAc; gradient 0-45% B in 1 h. Fractions containing the desired product were combined and concentrated in vacuum to provide compound (14-7) (1.10 g, 2.4 mmol, 82% yield, mw 454.5) as colorless oil. The oil solidified while under vacuum. (Alternatively, THF may be used as the solvent instead of acetone. It is also recommended to use 1 eq. of DIEA to accelerate the reaction. Add the DIEA to the reaction after the Fmoc reagent. The reaction can be concentrated, dissolved in EtOAc, washed with 1 M citrate or 5% NaHSO$_4$, water, 5% NaHCO$_3$, water, brine, dried (Na$_2$SO$_4$) and evaporated under reduced pressure. A standard silica column purification can be accomplished eluting with 25% EtOAc in Hexane to give 99% purity and 91% yield.)

(2S,3R)-2-Amino-3-Fmoc-aminobutyric acid methyl ester hydrochloride (14)

Compound (14-7) (1.10 g, 2.42 mmol) was dissolved in 4 NHCl/dioxane (8 ml) at ambient temperature for 20 min. with stirring under nitrogen. The resulting suspension was diluted with ether and the precipitate was filtered and washed with ether (3×10 mL). The compound (14) was dried in vacuo to provide the hydrochloric salt (840 mg, 2.15 mmol, 89%, mw 354.4 free base, HCl salt 390.4) as white solid. [M+H]=355.0. Retention time: 4.11 min [Chromolith SpeedRod RP-18e C18 column (4.6×50 mm); flow rate 1.5 ml/min; mobile phase A: 0.1% TFA/water; mobile phase B 0.1% TFA/ACN; gradient elution from 5% B to 100% B over 12 min, detection 254 nm]

Synthesis of Alternate Intermediate 009

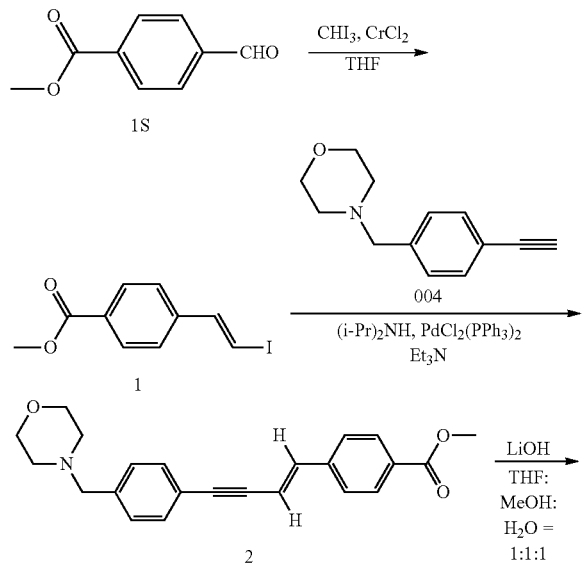

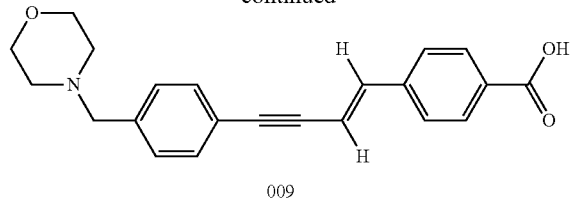

(E)-methyl 4-(2-iodovinyl)benzoate (1)

Chromium chloride anhydrous (8.9 g, 73 mmol, 8 equiv) was dissolved in 100 mL THF under nitrogen at 0° C. Triiodomethane (14.4 g, 37 mmol, 4 equiv) in 150 mL THF was added dropwise in 10 min. Then compound (1S) (1.5 g, 9.1 mmol, 1 equiv) in 20 mL THF was added dropwise. The mixture was stirred at 0° C. for 2 hours and then at room temperature for 1 more hour. The mixture was poured into iced water then extracted with EtOAc (100 mL×2). The organic phase was washed with 20% aq. Na$_2$S$_2$O$_3$ (100 mL), brine (100 mL) and dried (Na$_2$SO$_4$). The crude product was purified by chromatography on silica gel eluting with EtOAc/petroleum ether (0-2%) to give the title compound (1) (2.2 g, 85%). MS (m/z): [M+H]$^+$=289.7. $^1$H NMR (300 MHz, d$_6$-DMSO): 3.92 (s, 3H), 7.01~7.05 (d, 1H), 7.33~7.34 (d, 1H), 7.35~7.36 (d, 1H), 7.44~7.49 (d. 1H), 7.97~7.98 (d, 1H), 7.99~8.00 (d, 1H).

(E)-methyl 4-(4-(4-(morpholinomethyl)phenyl)but-1-en-3-ynyl)benzoate (2)

Compound (1) (2 g, 6.9 mmol, 1 equiv), diisopropylamine (0.7 g, 6.9 mmol, 1 equiv) and PdCl$_2$(PPh$_3$)$_2$ (0.24 g, 0.34 mmol, 0.05 equiv) was dissolved in 20 mL triethylamine at room temperature under nitrogen. The mixture was stirred for 15 min followed by addition of compound (004) (1.4 g, 6.9 mmol, 1 equiv). The mixture was stirred at room temperature for 12 hours. The reaction mixture was diluted with 50 mL EtOAc, filtered and concentrated. Then, the residue was diluted with 100 ml EtOAc and washed with water (100 mL) and brine (100 mL), dried (Na$_2$SO$_4$) and concentrated under reduced pressure. The crude product was purified by chromatography on silica gel eluting with EtOAc/petroleum ether (0-10%) to give the title compound (2) (1.5 g, 60%). MS (m/z): [M+H]$^+$=362. $^1$H NMR (300 MHz, d$_6$-DMSO): 2.32~2.34 (d, 4H), 3.46 (s, 1H), 3.54~3.57 (t, 4H), 3.83 (s, 3H), 6.77~6.82 (d. 1H), 7.13~7.18 (d, 1H), 7.32~7.34 (d, 2H), 7.43~7.45 (d, 2H), 7.68~7.71 (d, 2H), 7.90~7.93 (d, 2H).

(E)-4-(4-(4-(morpholinomethyl)phenyl)but-1-en-3-ynyl)benzoic acid (009)

Compound (2) (1.5 g, 4.2 mmol, 1 equiv) was dissolved in a solvent of (THF:MeOH:H$_2$O=1:1:1, 20 mL) at room temperature. Then, lithium hydroxide (0.35 g, 6.4 mmol, 2 equiv) was added. The mixture was stirred for 12 hours at room temperature. The pH was adjusted to 7 by acetic acid. The mixture was stirred for 1 hour. The solid was filtered and washed with water (20 mL), ether 20 mL and dried in vacuo to give the target product (009) (0.9 g, 62%). MS (m/z): [M+H]$^+$=348. NMR (300 MHz, d$_6$-DMSO): 2.32~2.35 (t, 4H), 3.47 (s, 2H), 3.54~3.57 (t, 4H), 6.75~6.80 (d. 1H), 7.12~7.18 (d, 1H), 7.32~7.35 (d, 2H), 7.43~7.45 (d, 2H), 7.66~7.68 (d, 2H), 7.88~7.91 (d, 2H).

Synthesis of Alternate Intermediate (011)

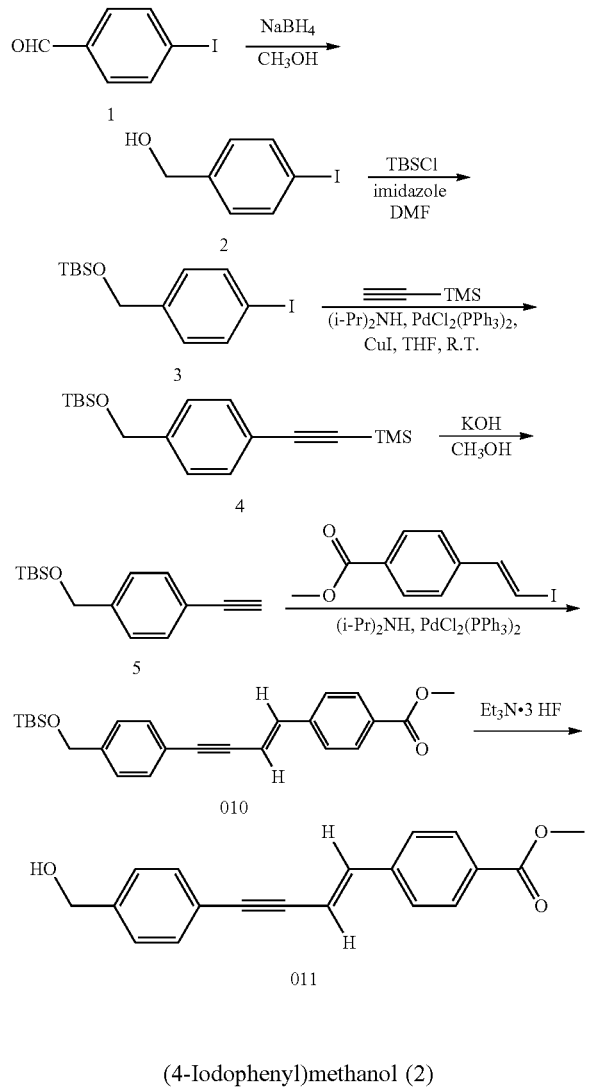

(4-Iodophenyl)methanol (2)

To a solution of compound (1) (50 g, 0.21 mol, 1.0 equiv) in methanol (500 mL) was added with NaBH$_4$ (20.5 g, 0.5 mol, 2.5 equiv) slowly under 10° C. for 1 h and stirred for 2 h. The reaction mixture was concentrated under reduced pressure, quenched with water (300 mL), and extracted with EtOAc (300 mL×3). The organic layer was dried over Na$_2$SO$_4$, filtered and concentrated under reduced pressure. The residue was dried in vacuo overnight to provide the title compound (2) (49 g, 97%).

Tert-butyl(4-iodobenzyloxy)dimethylsilane (3)

To a solution of compound (2) (9 g, 38.5 mmol, 1.0 equiv), TBSCl (5.8 g, 38.5 mmol, 1.0 equiv) and imidazole (5.3 g, 77 mmol, 2.0 equiv) in DMF (18 mL) was stirred for 2 h at 45° C. The reaction mixture was diluted with CH$_2$Cl$_2$ (200 mL) and washed with water (200 mL×3). The organic layer was dried over Na$_2$SO$_4$, filtered and concentrated under reduced pressure. The residue was dried under high vacuum overnight to produce the title compound (3) (11.6 g, 87%). $^1$H NMR (300 MHz, d$_6$-DMSO): 0.05 (s, 6H), 0.88 (s, 9H), 4.64 (s, 2H), 7.09~7.11 (d. 2H), 7.66~7.69 (d, 2H).

Tert-butyldimethyl(4-((trimethylsilyl)ethynyl)benzyloxy)silane (4)

Under nitrogen, ethynyltrimethylsilane (3.929 g, 37 mmol, 1.1 equiv) was added to a solution of compound (3) (11.6 g, 33.4 mmol 1.0 equiv), PdCl$_2$(PPh$_3$)$_2$ (2.345 g, 3.34 mmol, 0.1 equiv), CuI (0.636 g, 3.34 mmol, 0.1 equiv) and i-Pr$_2$NH (10.05 mL) in THF (anhydrous, 200 ml) at room temperature. The mixture was allowed to reaction at ambient temperature for 3 h. Then, the precipitate was isolated. The filter cake was washed with EtOAc (50 mL). The filtrate was concentrated under reduced pressure. The residue was dissolved in EtOAc (300 mL) and washed with water (50 ml), 1M HCl aq. (50 ml), water (50 ml×2) and brine (50 ml). The organic layer was separated, dried (Na$_2$SO$_4$) and the filtrate was concentrated under reduced pressure. The residue was purified by chromatography (EtOAc/petroleum ether 0-2%) on silica gel to give the title compound (4) (9.2 g, 87%). $^1$H NMR (300 MHz, d$_6$-DMSO): 0.10 (s, 6H), 0.26 (s, 9H), 0.93 (s, 9H), 4.73 (s, 2H), 7.23~7.26 (d. 2H), 7.42~7.44 (d, 2H).

Tert-butyl(4-ethynylbenzyloxy)dimethylsilane (5)

To a solution of compound (4) (5.2 g, 16.4 mmol, 1.0 equiv) in methanol (100 mL) was treated with KOH/methanol (0.457 g/5 mL) slowly below 10° C., then the mixture was allowed to react at ambient temperature for 5 min. The reaction mixture was neutralized with acetic acid and concentrated under reduced pressure. The residue was dissolved in EtOAc (100 mL). The organic layer was washed with 5% aq. Na$_2$CO$_3$ (50 ml×2), dried over Na$_2$SO$_4$, filtered and concentrated under reduced pressure. The residue was dried in vacuo overnight to provide the title compound (5) (4 g, 99%). $^1$H NMR (300 MHz, d$_6$-DMSO): 0.04 (s, 6H), 0.87 (s, 9H), 4.09 (s, 1H), 4.68 (s, 2H), 7.26~7.29 (d. 2H), 7.41~7.43 (d, 2H).

(E)-methyl 4-(4-(4-((tert-butyldimethylsilyloxy)methyl)phenyl)but-1-en-3-ynyl)benzoate (010)

Under nitrogen, (E)-methyl 4-(2-iodovinyl)benzoate (1 g, 3.47 mmol, 1.0 equiv) was added to a solution of compound (5) (0.855 g, 3.47 mmol, 1.0 equiv), PdCl$_2$(PPh$_3$)$_2$ (0.244 g, 0.347 mmol, 0.1 equiv), CuI (0.066 g, 0.347 mmol, 0.1 equiv) and i-Pr$_2$NH (2 mL) in THF (anhydrous, 10 mL) at room temperature. The mixture was allowed to reaction at ambient temperature for 3 h. Then, the precipitate was filtered. The filter cake was washed with EtOAc. The filtrate and wash liquid were combined and concentrated under reduced pressure. The residue was dissolved in EtOAc (30 ml) and washed with water (10 ml), 1M HCl aq. (10 ml), water (10 ml×2) and brine (10 ml). The organic layer was separated, dried (Na$_2$SO$_4$), filtered and concentrated under reduced pressure. The residue was purified by chromatography (EtOAc/petroleum ether 0-3%) on silica gel to give the target compound (010) (9.2 g, 86.6%). $^1$H NMR (300 MHz, d$_6$-CDCl$_3$): 0.10 (s, 6H), 0.94 (s, 9H), 3.91 (s, 3H), 4.74 (s, 2H), 6.46~6.52 (d, 1H), 7.01~7.07 (d, 1H), 7.26~7.31 (t, 2H), 7.43~7.49 (m, 4H), 7.99~8.02 (t, 2H).

Example 31

Step 1

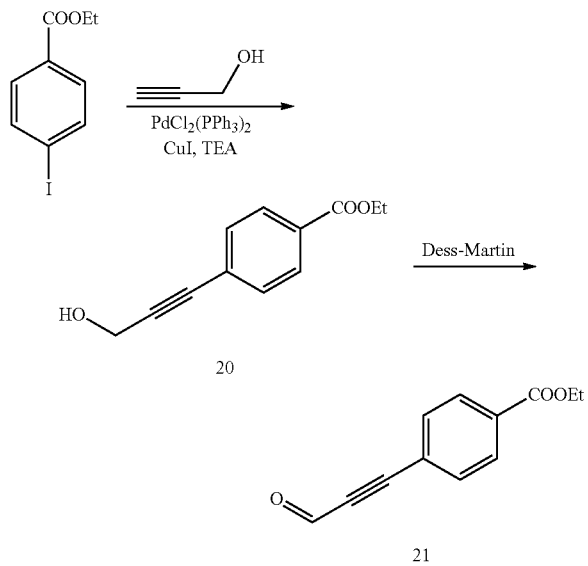

A solution of ethyl 4-iodo-benzoate (2.43 g, 8.81 mmol) and propargyl alcohol (543.3 mg, 9.69 mmol) in THF (35 mL) was purged by nitrogen for 30 min, followed by addition of $PdCl_2(PPh_3)_2$ (74 mg, 0.106 mmol) and CuI (40 mg, 0.212 mmol). The reaction mixture was cooled to 0° C. and triethyl amine (1.34 g, 13.22 mmol) was added. The reaction mixture was warmed to rt and stirred overnight under $N_2$. The reaction mixture was filtered through a plug of celite and the filtrate was concentrated. The residue was treated with water (200 mL) and extracted with EtOAc (200 mL×2). The combined organic layers were washed with water (200 mL×2), brine (200 mL) and dried ($NaSO_4$). The crude product was purified by chromatography on silica gel eluting with EtOAc/Hexane (0-50%) to give 1.53 g, 85% yield) of the product (20).

Dess-Martin reagent (4.78 g, 11.25 mmol) was added to a solution of compound (20) (1.53 g, 7.5 mmol) in $CH_2Cl_2$ (20 mL) at 0° C. The reaction mixture was warmed to rt and stirred overnight. The reaction mixture was diluted with $CH_2Cl_2$ (200 mL), basified with $NaHCO_3$ (saturated) to pH=7 and then washed with water (200 mL) and brine (200 mL), dried ($NaSO_4$) and concentrated under reduced pressure. The crude product was purified by chromatography on silica gel eluting with EtOAc/Hexane (0-40%) to give the desired product (21) (1.24 g, 81.8%).

Step 2

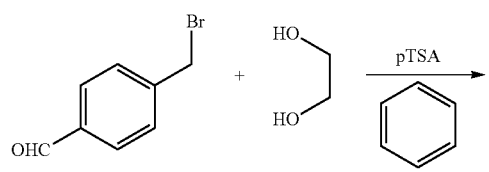

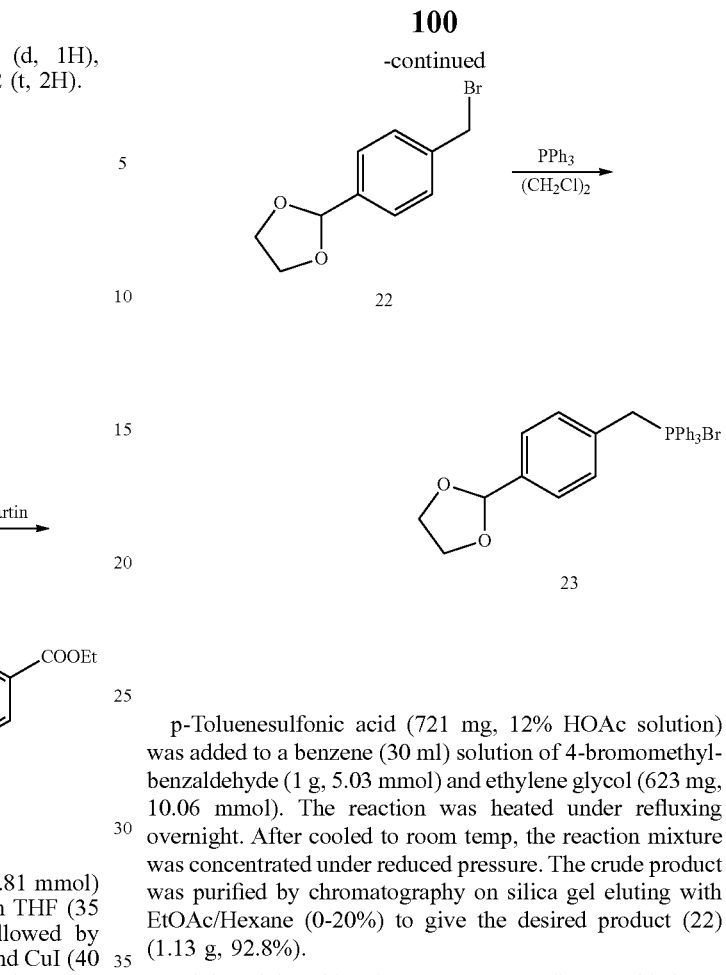

p-Toluenesulfonic acid (721 mg, 12% HOAc solution) was added to a benzene (30 ml) solution of 4-bromomethyl-benzaldehyde (1 g, 5.03 mmol) and ethylene glycol (623 mg, 10.06 mmol). The reaction was heated under refluxing overnight. After cooled to room temp, the reaction mixture was concentrated under reduced pressure. The crude product was purified by chromatography on silica gel eluting with EtOAc/Hexane (0-20%) to give the desired product (22) (1.13 g, 92.8%).

Triphenylphosphine (1.34 g, 5.11 mmol) was added to a 1,2-dichloroethane (10 ml) solution of compound (22) (1.13 g, 4.65 mmol). The reaction was heated to 70° C. for 4 hours. After cooling to room temp., the organic solution was concentrated with rotavap. Diethyl ether (50 ml) was added to the residue with vigorous stirring to precipitated the wittig salt. After filtration, the collected solid was washed with ether (3×50 ml) and dried under high vacuum to give compound (23) (2 g, 85% yield).

Step 3

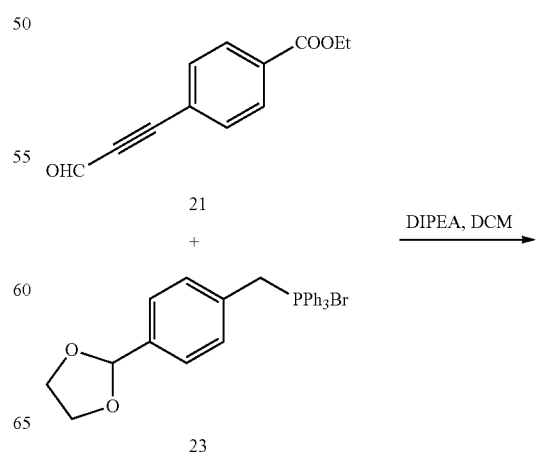

-continued

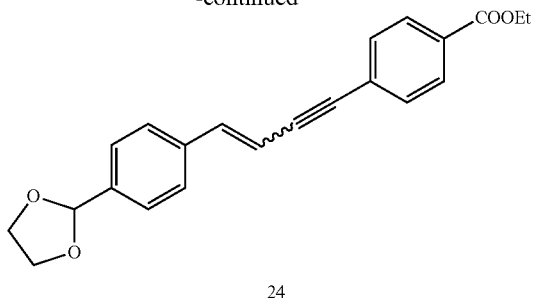

24

To a solution of compound (23) (1.36 g, 2.69 mmol) in DCM (10 ml) was added DIPEA (694 mg, 5.38 mmol). The reaction mixture was stirred at rt for 10 min., followed by addition of compound (21) (544 mg, 2.69 mmol) in DCM (10 ml) solution. The resulting mixture was stirred at rt overnight and concentrated under reduced pressure. The residue was treated with EtOAc (100 ml), washed with water (2×100 ml) and brine (100 ml), dried (NaSO₄) and concentrated under reduced pressure. The crude product was purified by chromatography on silica gel (0-20% EtOAc/Hexane) to give compound (24) (600 mg, 63.9%).

Step 4

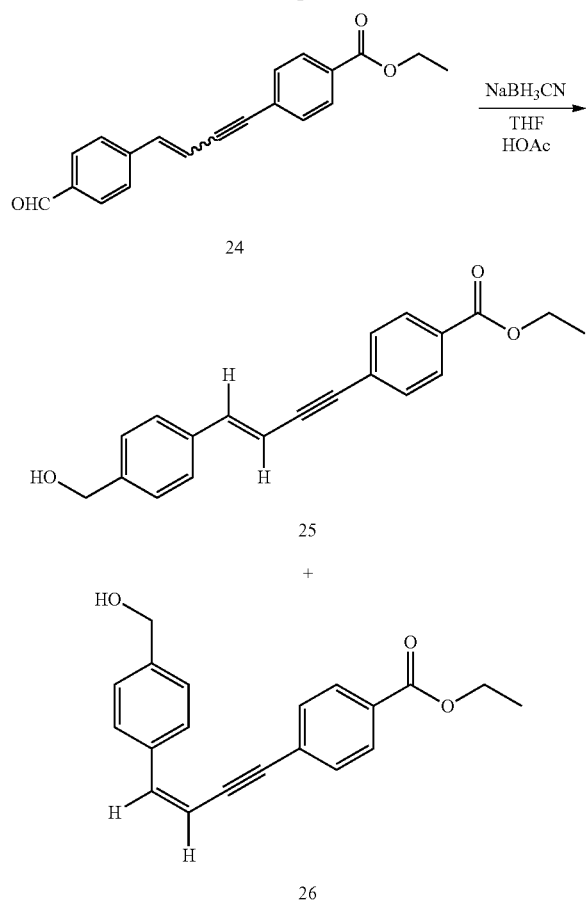

To a solution of compound (24) (718 mg, 2.35 mmol) in THF (6 ml) and HOAc (6 ml) was added NaBH₃CN (211 mg, 3.55 mmol). The reaction was stirred at room temp. for 30 min. The reaction mixture was then concentrated under reduced pressure. The residue was diluted with EtOAc (200 ml) and treated with NaHCO₃ (sat'd) to pH=8. After separation, the aqueous layer was extracted with EtOAc (2×200 ml). The combined organic layers was washed with H₂O (2×100 ml), brine (100 ml) and dried with Na₂SO₄. Concentrated by ratovap, the residue was purified by chromatography on silica gel (0-50% EtOAc/Hexane) to give compound (25a) (300 mg) and (25b) (187.5 mg) with 67% total yield.

Step 5

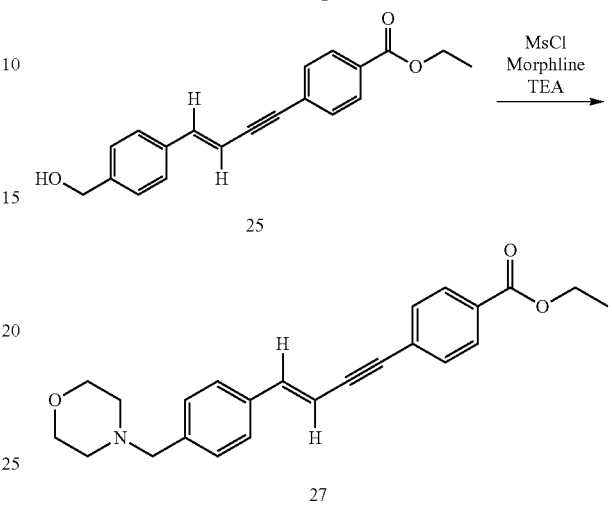

A DCM solution (5 ml) of compound 25 (300 mg, 0.98 mmol) and DIPEA (158 mg, 1.23 mmol) was cooled to 0° C., followed by the addition MsCl (124 mg, 1.08 mmol). The reaction was warmed to rt and stirred for 30 min. Morphline (171 mg, 1.96 mmol) was added to reaction and stirred for 2 hours at rt. Diluted with EtOAc (200 ml), reaction mixture was washed with H₂O (2×100 ml), brine (100 ml) and dried with Na₂SO₄. Concentrated under reduced pressure, the crude product was purified by chromatography on silica gel (0-50% EtOAc/Hexane) to give compound (27) (345 mg) in 94% yield.

Step 6

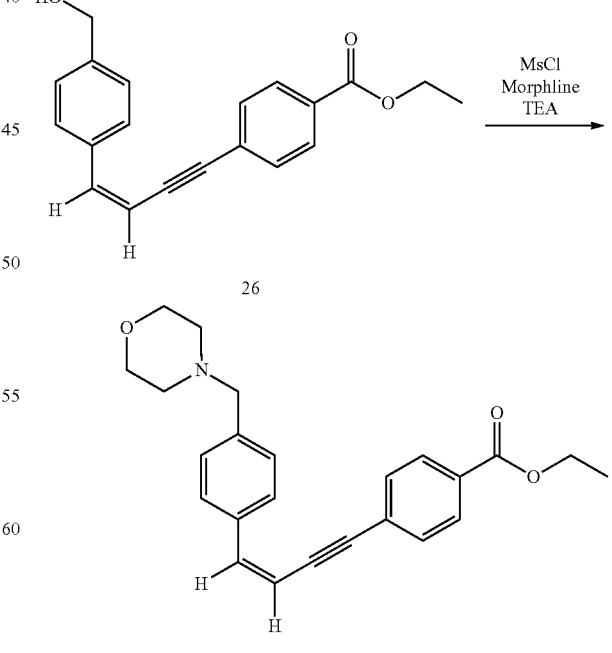

The desired product (28) (284 mg, 95%) was prepared with compound (26) (244 mg, 0.8 mmol), MsCl (80.5 mg, 0.88 mmol), morphline (106 mg, 1.22 mmol) and DIPEA (100 mg, 0.88 mmol) according to the synthetic procedure for the preparation of compound (27).

Step 7

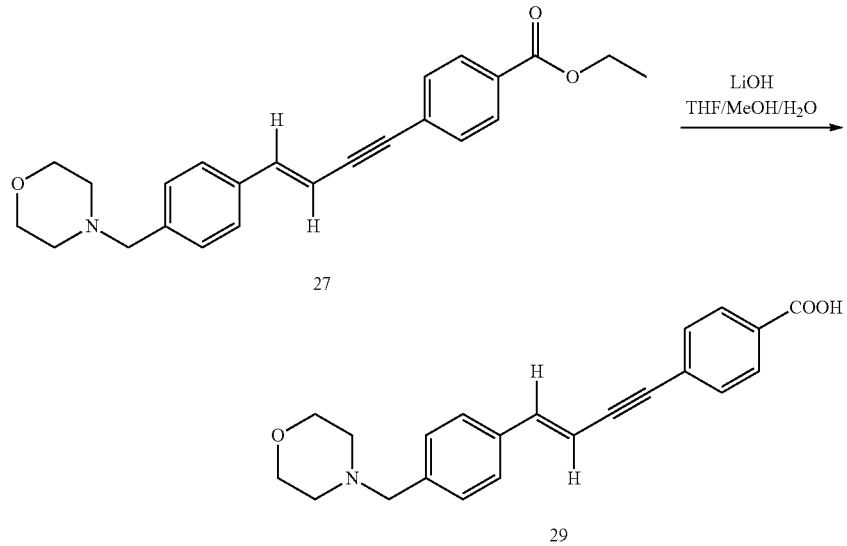

To a mix solution (6 ml) of THF/MeOH/H₂O (1:1:1) of compound (27) (345 mg, 0.92 mmol) was added LiOH (44 mg, 1.84 mmol). Reaction was stirred over at rt. HOAc was added to the reaction to pH=7. The reaction was concentrated under reduced pressure. The residue was re-dissolved in CH₃CN (1 ml) and H₂O (2 ml) and dried with lyophlizer to give crude product (29) (482 mg, 66% pure, 100% yield).

Step 8

The desired product (30) (374 mg, 76% pure, 100% yield) was prepared with compound (28) (284 mg, 0.76 mmol), LiOH (36 mg, 1.52 mmol) according to the synthetic procedure for the preparation of compound (29).

Step 9

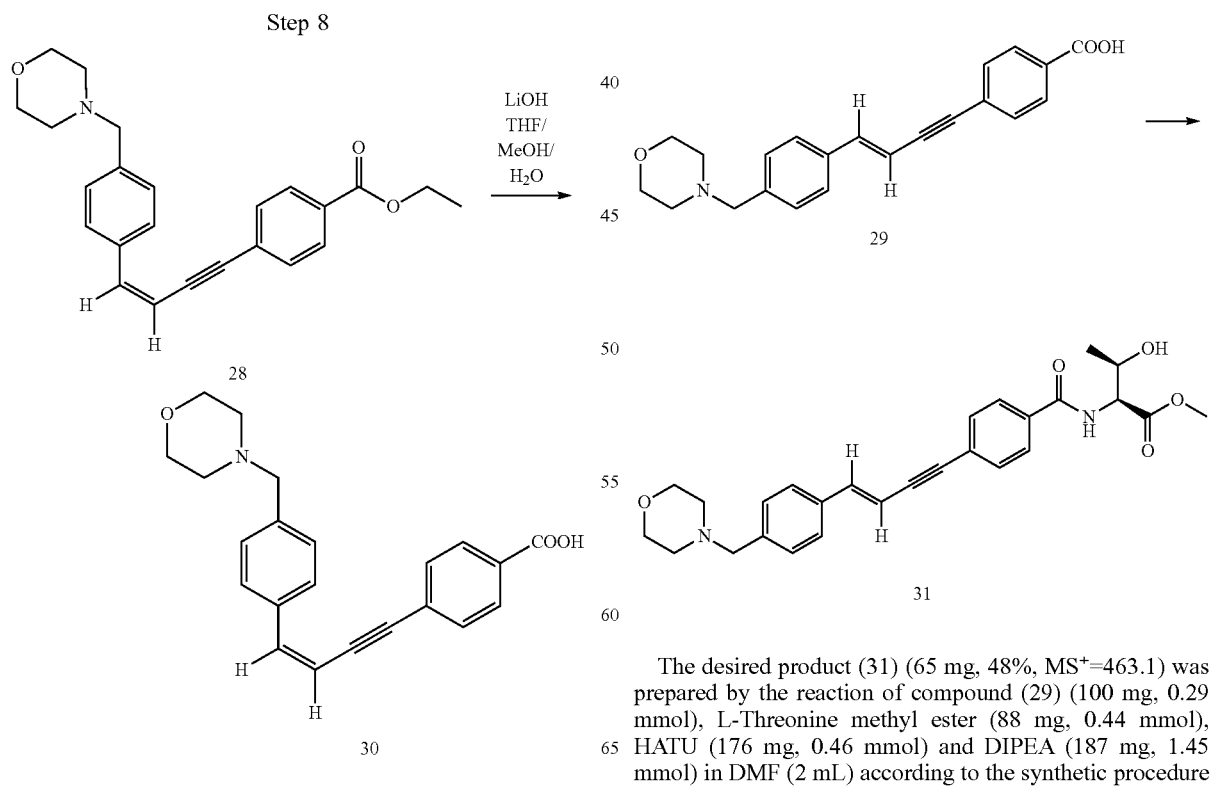

The desired product (31) (65 mg, 48%, MS⁺=463.1) was prepared by the reaction of compound (29) (100 mg, 0.29 mmol), L-Threonine methyl ester (88 mg, 0.44 mmol), HATU (176 mg, 0.46 mmol) and DIPEA (187 mg, 1.45 mmol) in DMF (2 mL) according to the synthetic procedure for the preparation of compound (7).

Step 10

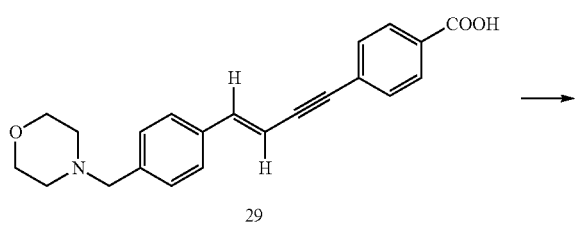

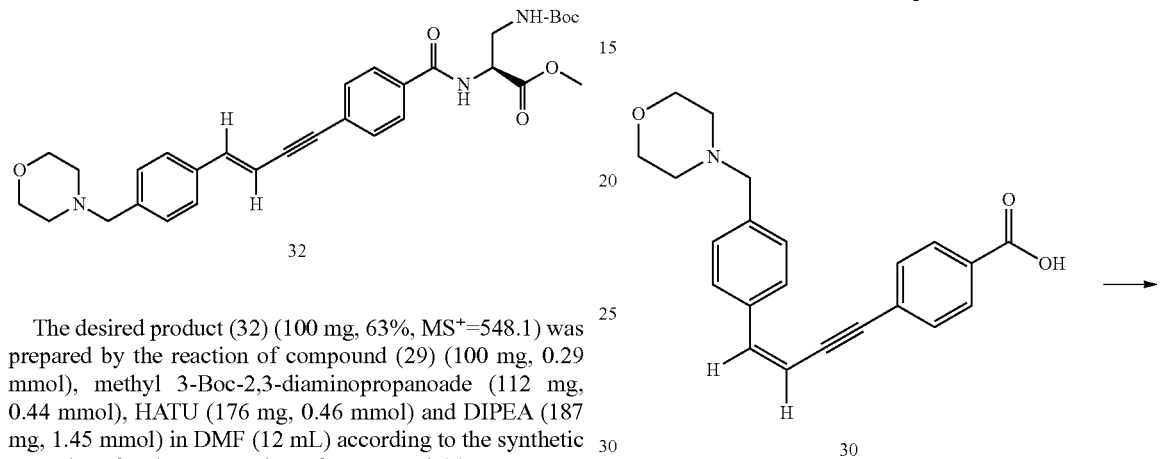

The desired product (32) (100 mg, 63%, MS$^+$=548.1) was prepared by the reaction of compound (29) (100 mg, 0.29 mmol), methyl 3-Boc-2,3-diaminopropanoade (112 mg, 0.44 mmol), HATU (176 mg, 0.46 mmol) and DIPEA (187 mg, 1.45 mmol) in DMF (12 mL) according to the synthetic procedure for the preparation of compound (7).

Step 11

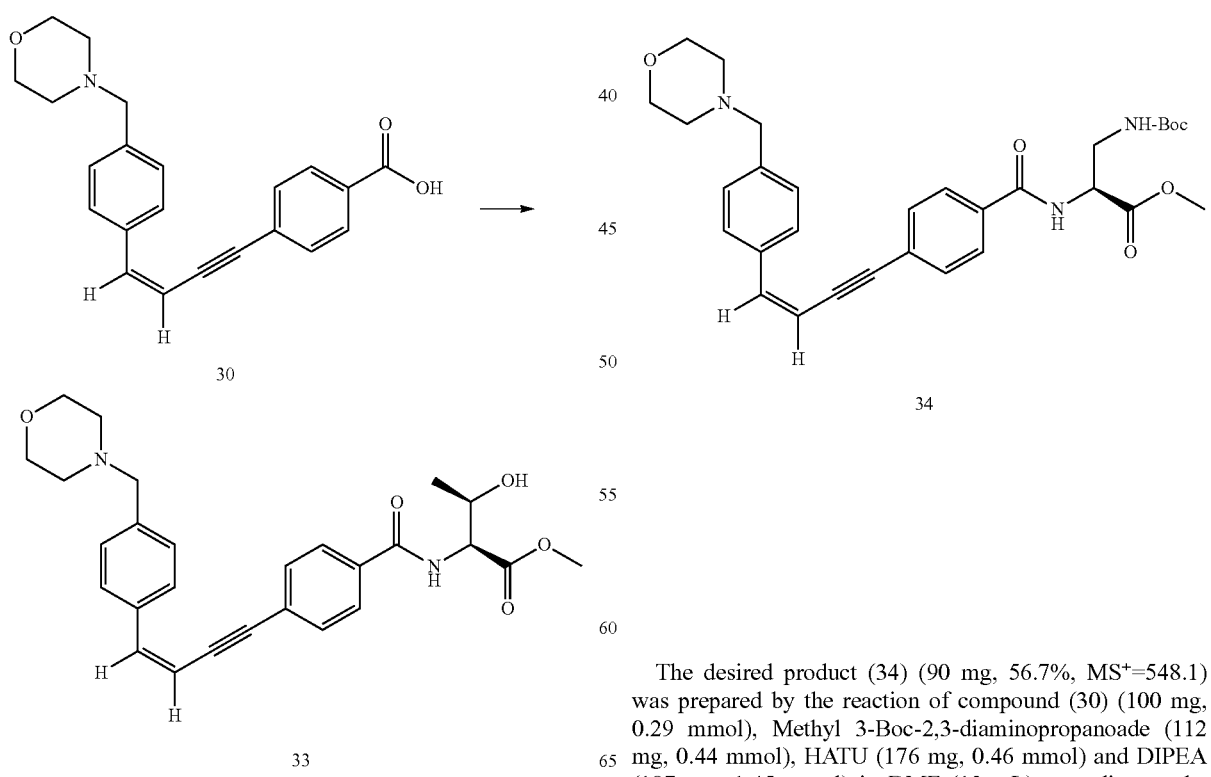

The desired product (33) (70 mg, 52%, MS$^+$=463.1) was prepared by the reaction of compound (30) (100 mg, 0.29 mmol), L-Threonine methyl ester (88 mg, 0.44 mmol), HATU (176 mg, 0.46 mmol) and DIPEA (187 mg, 1.45 mmol) in DMF (2 mL) according to the synthetic procedure for the preparation of compound (7).

Step 12

The desired product (34) (90 mg, 56.7%, MS$^+$=548.1) was prepared by the reaction of compound (30) (100 mg, 0.29 mmol), Methyl 3-Boc-2,3-diaminopropanoade (112 mg, 0.44 mmol), HATU (176 mg, 0.46 mmol) and DIPEA (187 mg, 1.45 mmol) in DMF (12 mL) according to the synthetic procedure for the preparation of compound (7).

Step 13
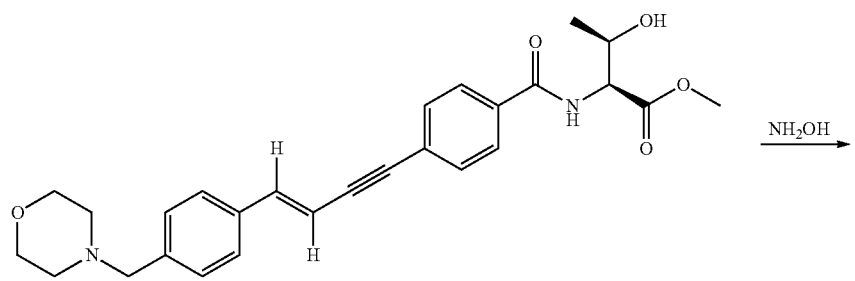
The desired product (35) (20 mg, 14.9%, MS$^+$=464.1) was prepared by the reaction of compound (31) (65 mg, 0.14 mmol) and NH$_2$OH.HCl (96.6 mg, 1.4 mmol) and NaOMe (115 mg, 2.1 mmol) in MeOH (5 ml) according to the synthetic procedure for the preparation of compound (8).
Step 14
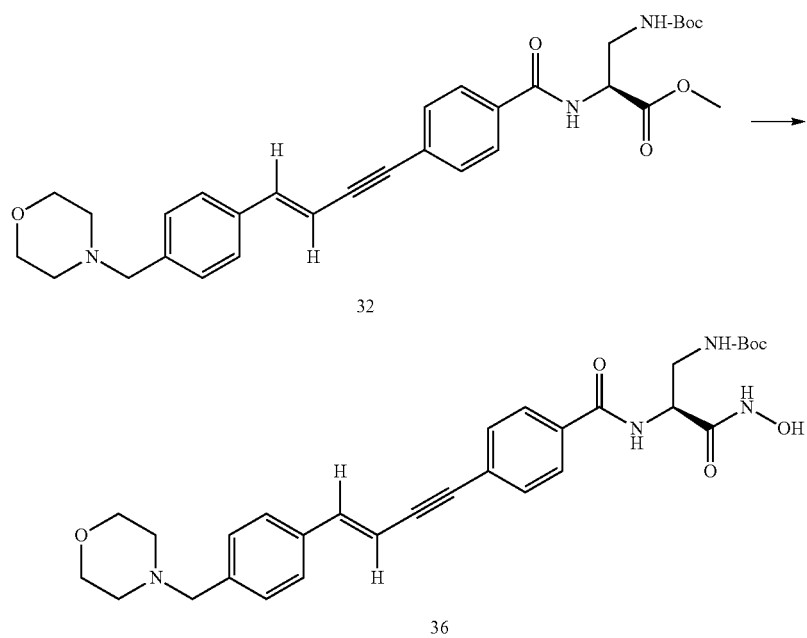

The desired product (36) (30 mg, 30%, MS⁺=464.1) was prepared by the reaction of compound (32) (100 mg, 0.182 mmol) and NH$_2$OH.HCl (126 mg, 1.8 mmol) and NaOMe (148.5 mg, 2.7 mmol) in MeOH (5 ml) according to the synthetic procedure for the preparation of compound (8).

Step 15

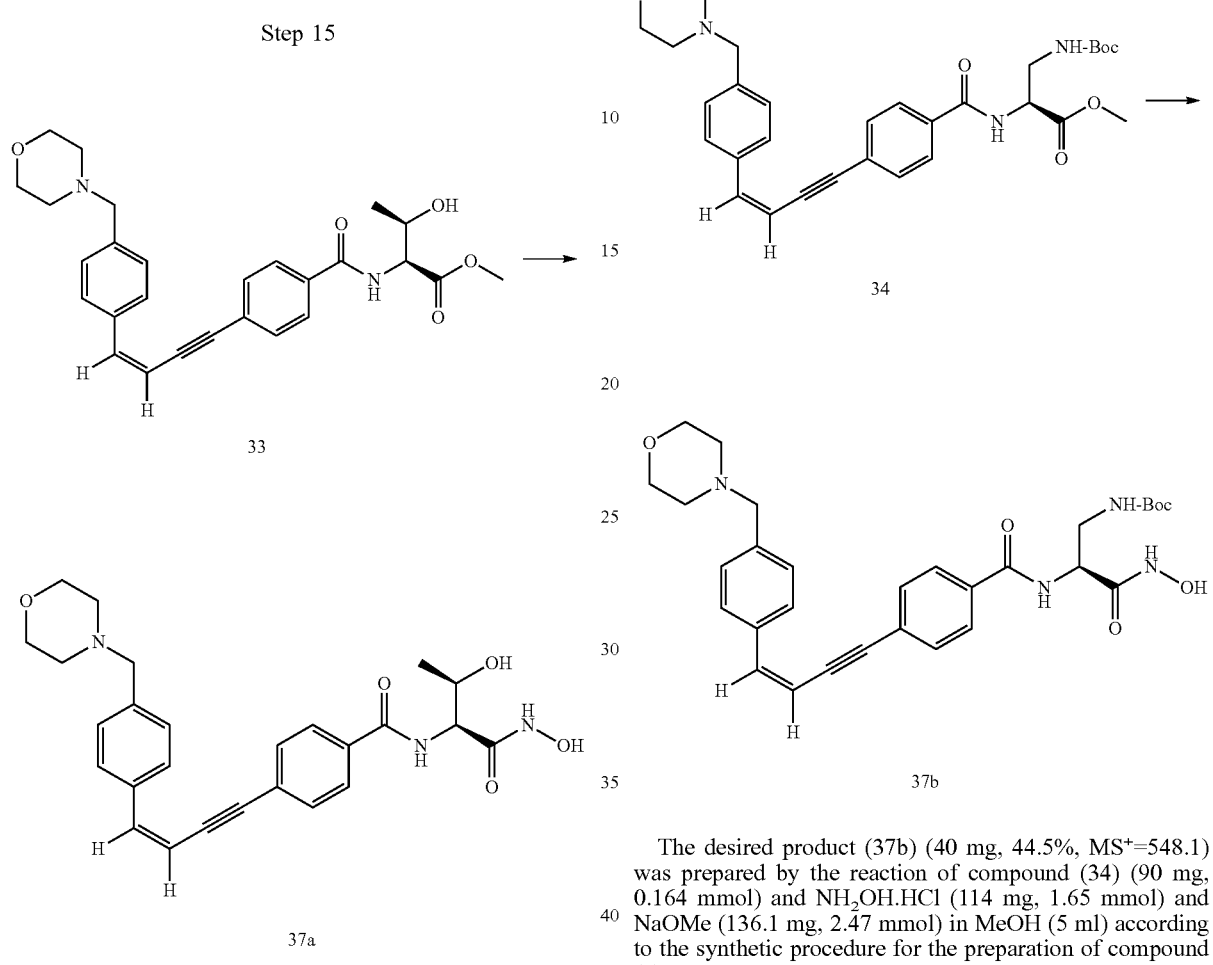

The desired product (37a) (20 mg, 28.4%, MS⁺=464.1) was prepared by the reaction of compound (33) (70 mg, 0.152 mmol) and NH$_2$OH.HCl (104 mg, 1.52 mmol) and NaOMe (125 mg, 2.28 mmol) in MeOH (5 ml) according to the synthetic procedure for the preparation of compound (8).

Step 16

The desired product (37b) (40 mg, 44.5%, MS⁺=548.1) was prepared by the reaction of compound (34) (90 mg, 0.164 mmol) and NH$_2$OH.HCl (114 mg, 1.65 mmol) and NaOMe (136.1 mg, 2.47 mmol) in MeOH (5 ml) according to the synthetic procedure for the preparation of compound (8).

Step 17

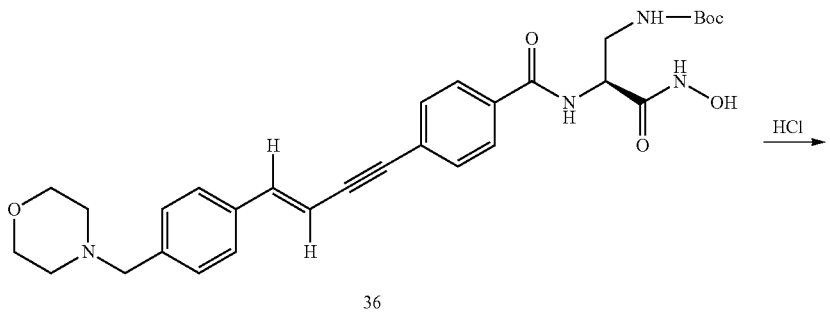

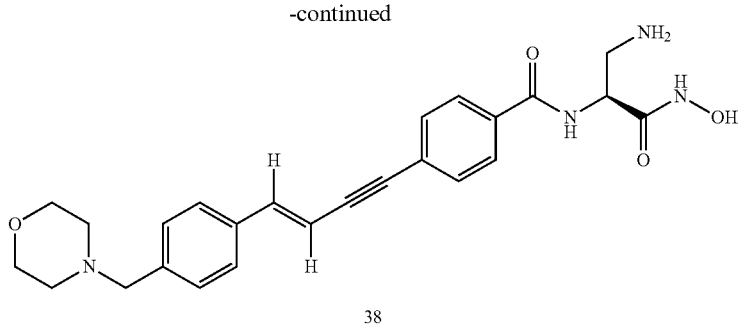

38

To a solution of compound (36) (30 mg, 0.055 mmol) in CH$_2$Cl$_2$ (1 ml) was added HCl (1 ml, 4 N in dioxane). The reaction mixture was stirred at rt. for 2 hrs. and concentrated under reduced pressure. The solid residue was purified by prep. HPLC to give compound (38) (10 mg, 40% yield, MS$^+$=449.1) as double TFA salt.

Step 18

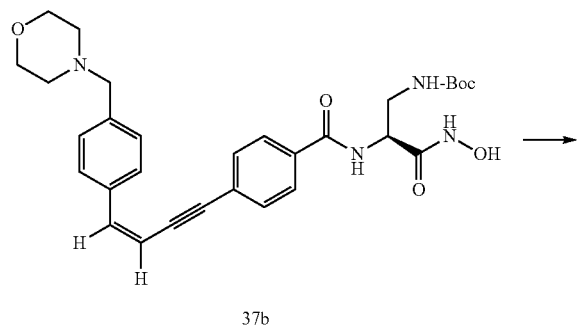

37b

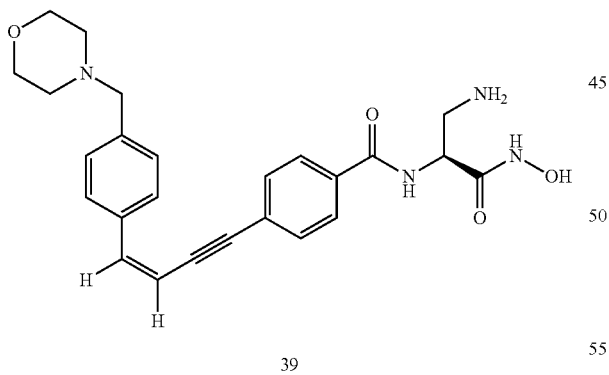

39

To a solution of compound (37b) (40 mg, 0.073 mmol) in CH$_2$Cl$_2$ (1 ml) was added HCl (1 ml, 4 N in dioxane). The reaction mixture was stirred at rt. for 2 hrs. and concentrated under reduced pressure. The solid residue was purified by prep. HPLC to give compound (39) (15 mg, 45.8% yield, MS$^+$=449.1) as double TFA salt.

Step 19

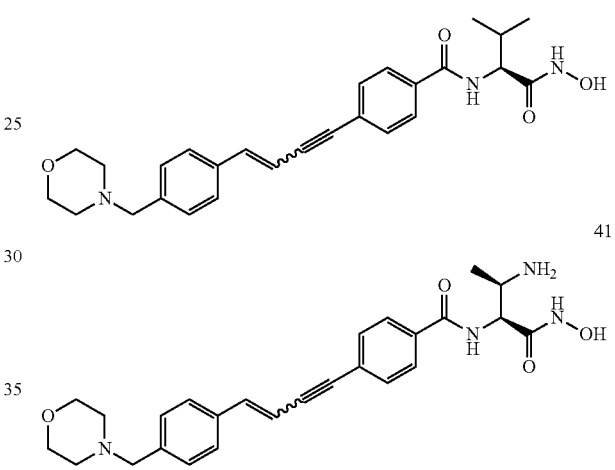

The desired products (40) and (41) may be prepared according to the foregoing synthetic procedures.

Example 32

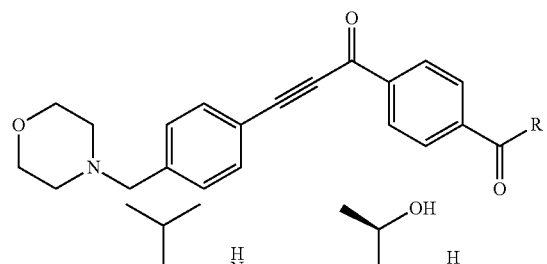

R =

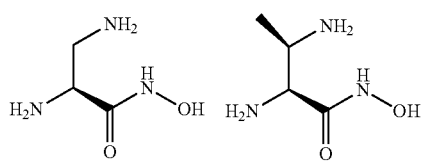

Step 1

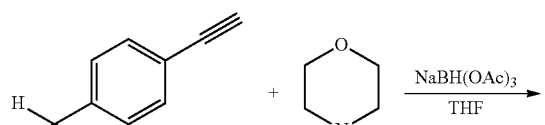

NaBH(OAc)₃ (2.28 g, 0.76 mmol) was added at 0° C. to a solution of 4-ethylnyl-benzylaldehyde (1.0 g, 7.69 mmol) and morpholine (462 mg, 5.37 mmol) in THF (20 mL). The reaction mixture was then warmed to rt and stirred overnight. The solvent was removed (RV) and the residue was extracted with EtOAc (2×) from aqueous NaHCO₃ (pH=8~9). The combined organic extracts were dried (Na₂SO₄) and concentrated to dryness (RV). Column chromatography (silica gel, EtOAc/DCM 0-50%) yielded compound (40) (1.31 g, 84.8% yield, M+H⁺=202.0).

Step 2

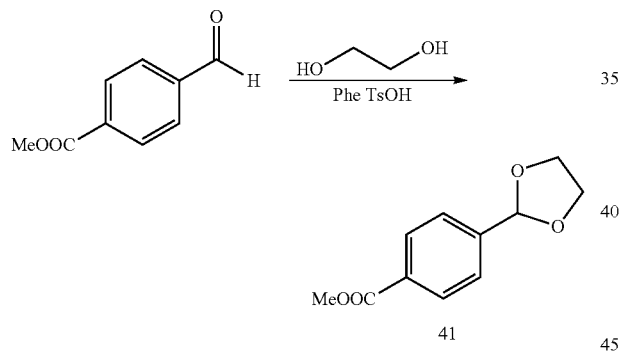

A solution of methyl 4-formylbenzoate (1 g, 6.09 mmol) and p-TSA (12% in AcOH, 104 mg, 0.609 mmol) in benzene solution (50 mL) was heated at reflux for 3 hours. The reaction mixture was cooled to rt, diluted with EtOAc (200 ml) and washed with water (200 mL×2) and brine (200 mL). The crude product was purified by chromatography on silica gel eluting with EtOAc/Hexane (0-50%) to give compound (41) (1.1 g, 87%)

Step 3

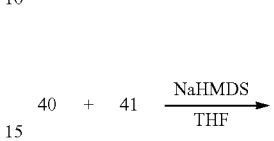

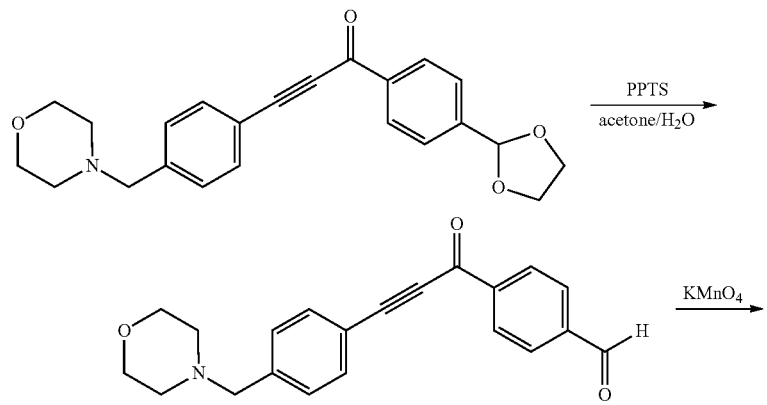

NaHMDS was added to a solution of compound (40) in THF at 0° C. The reaction was stirred for 1 hour, followed by addition of compound (41) in THF at 0° C. The reaction mixture was warmed to rt and stirred overnight. The reaction mixture was treated with NH₄Cl (saturated) and extracted with EtOAc. The combined organic layers were washed with brine (20 ml), dried (NaSO₄) and concentrated under reduced pressure. The crude product was purified by chromatography on silica gel.

Further Steps

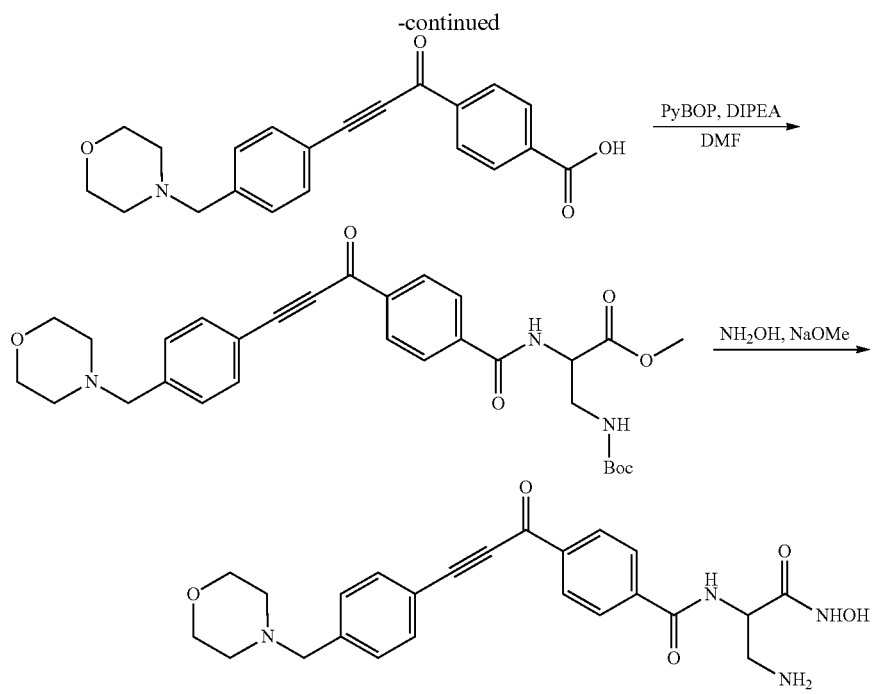
Example 33
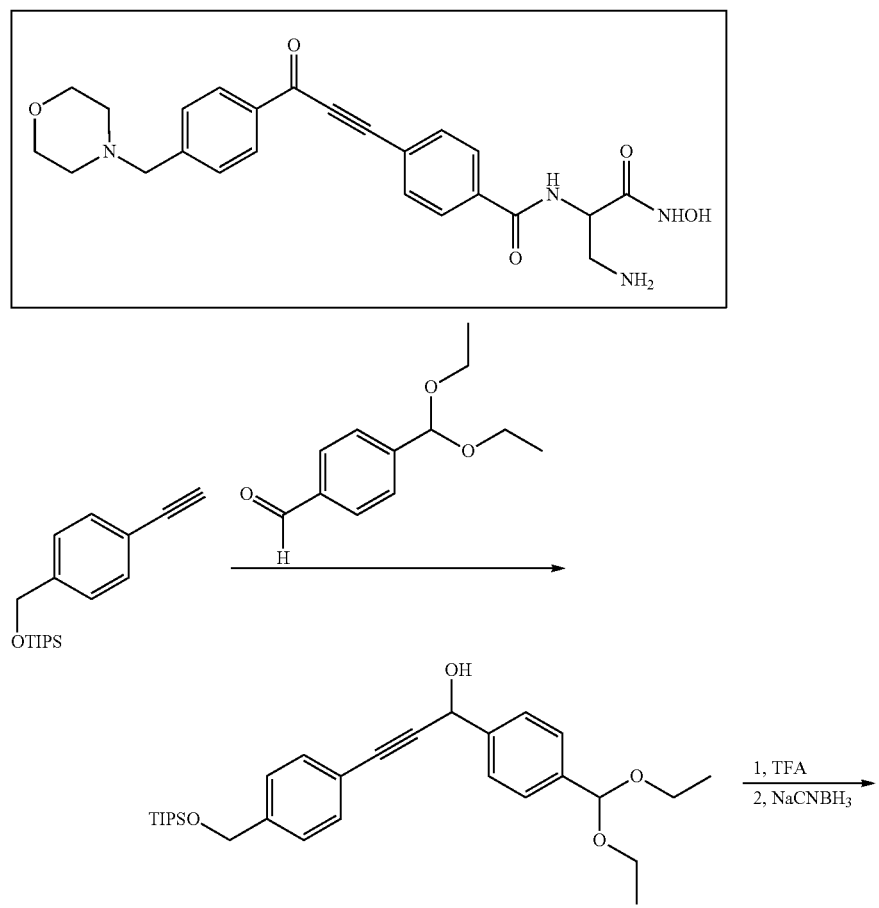

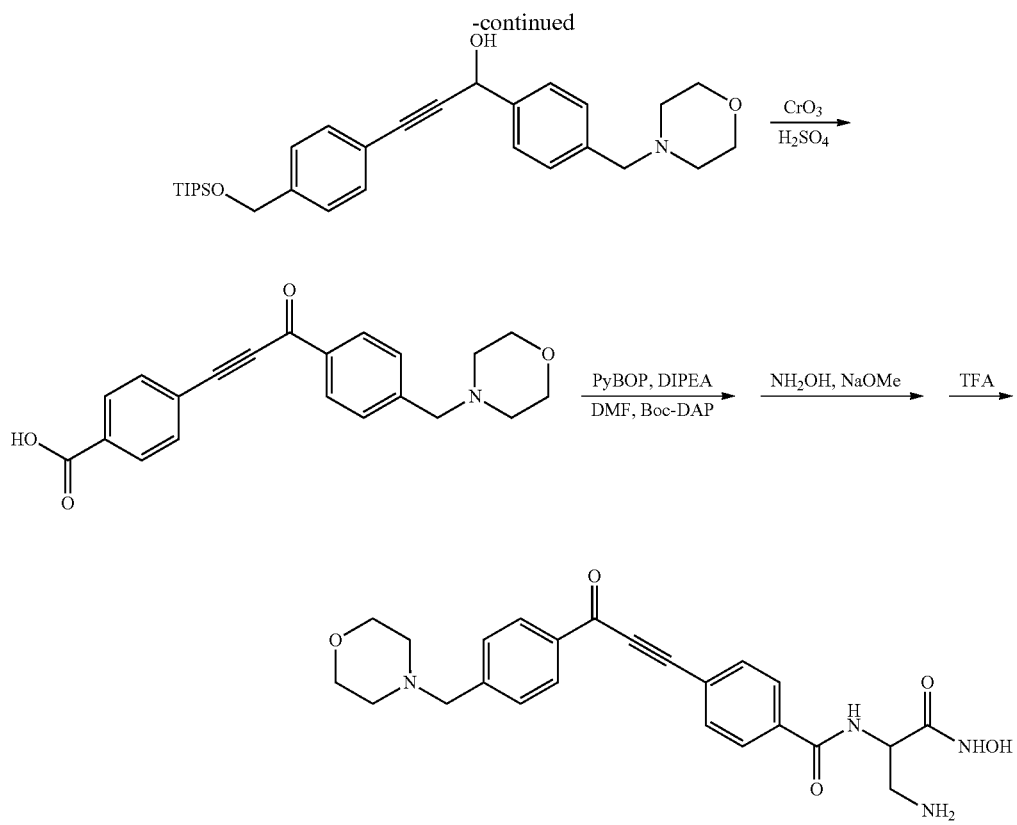
Example 34
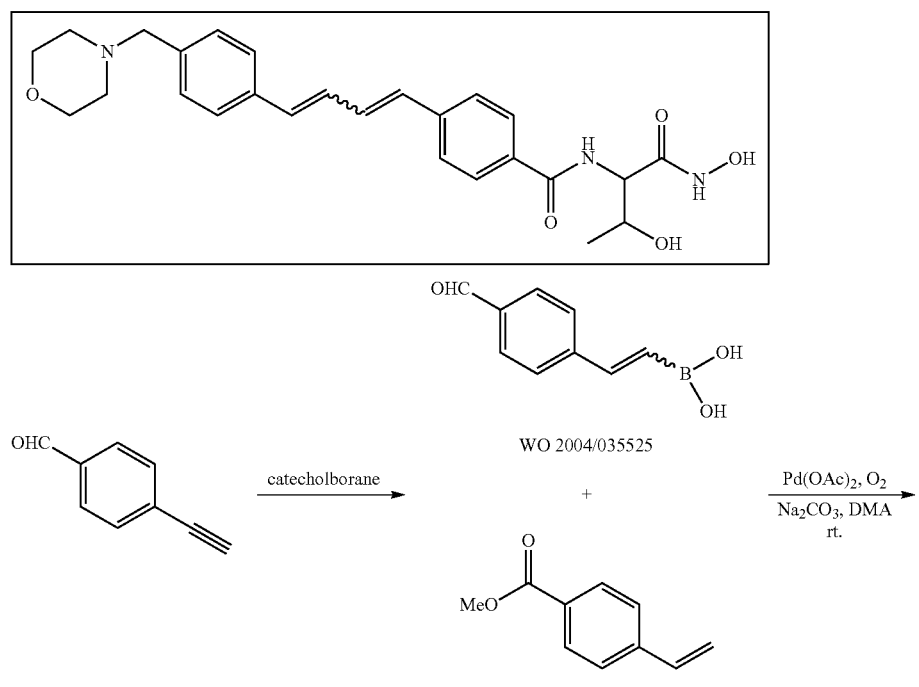

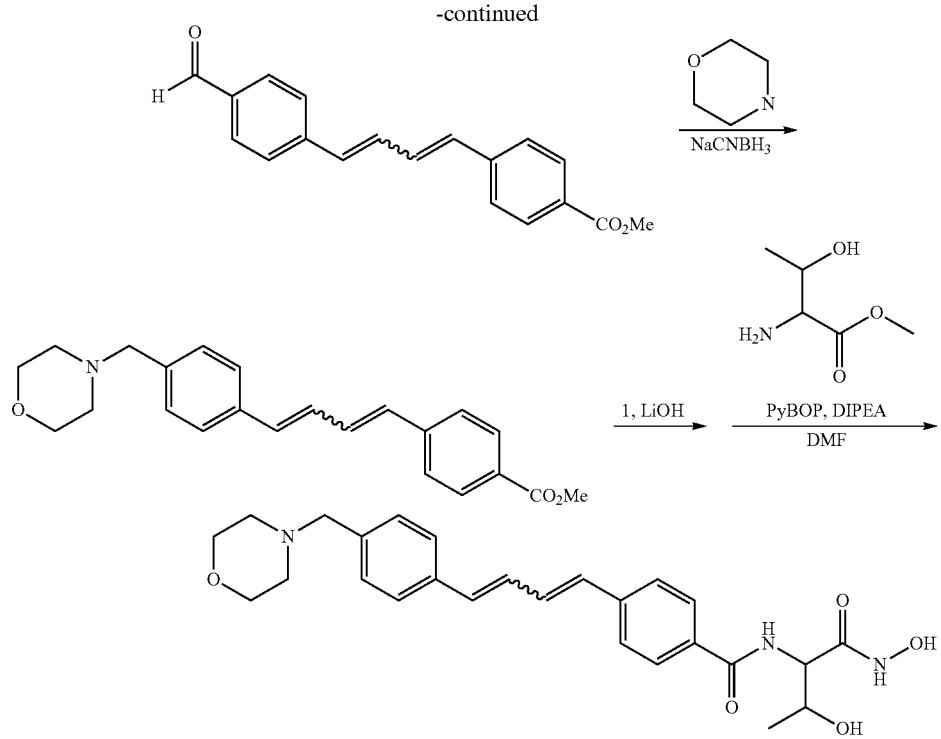
30
Example 35
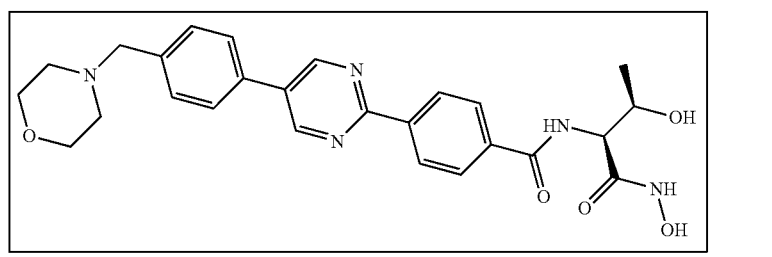
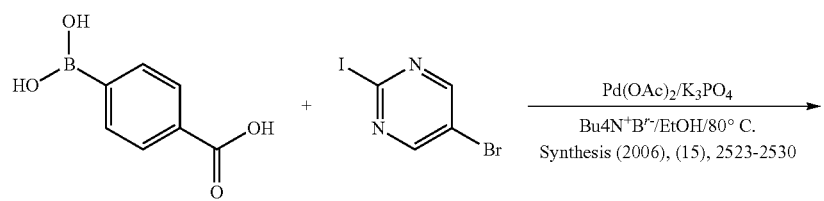
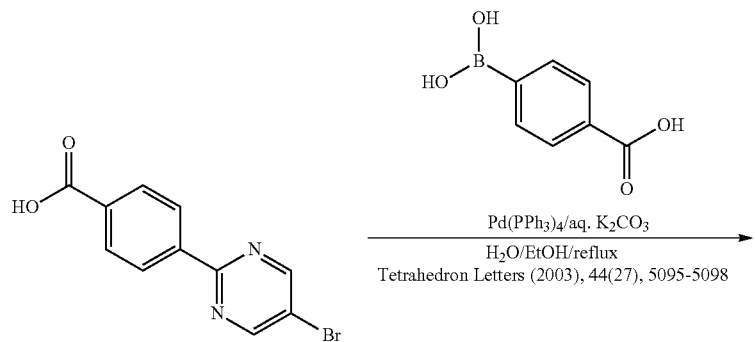

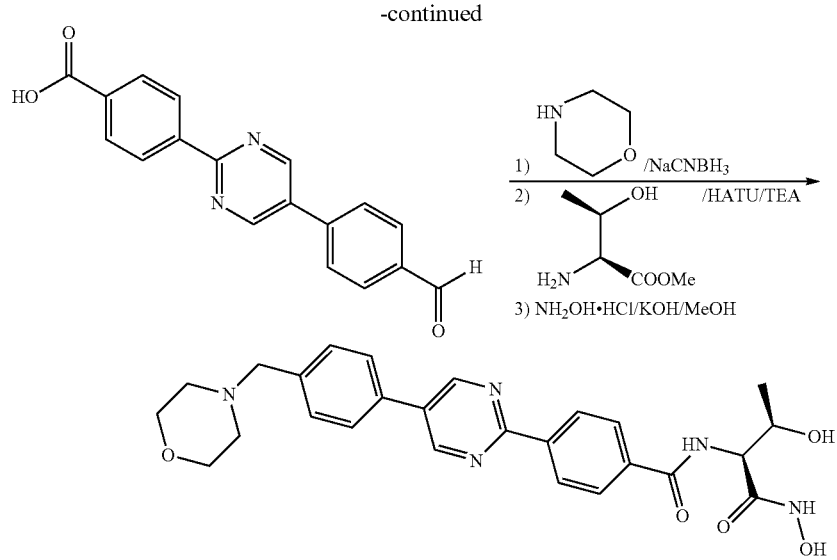
Example 36
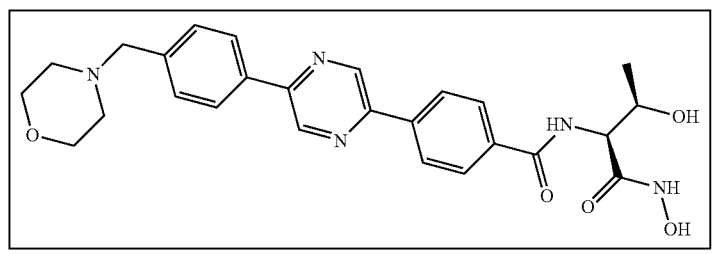
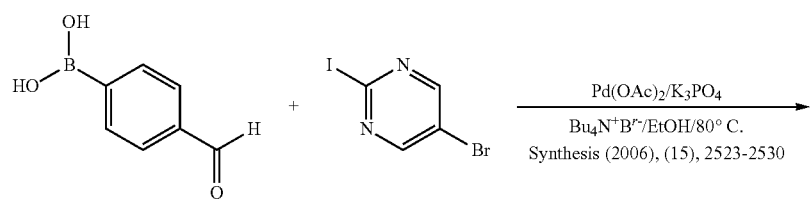
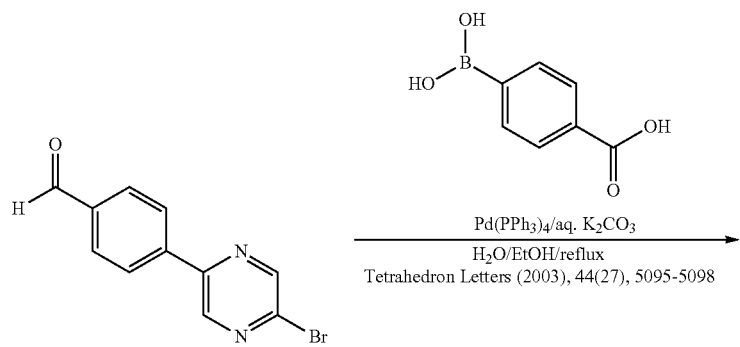

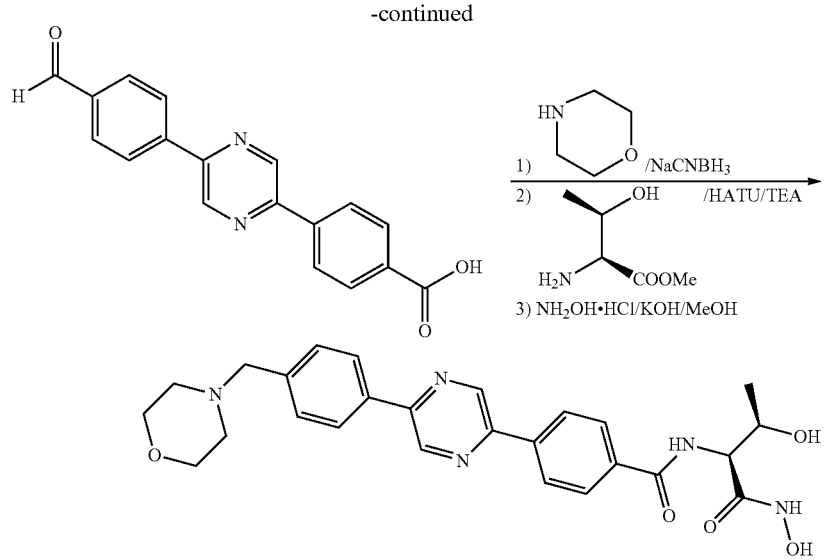
The following compounds may be synthesized as described in this, and the foregoing, Example.
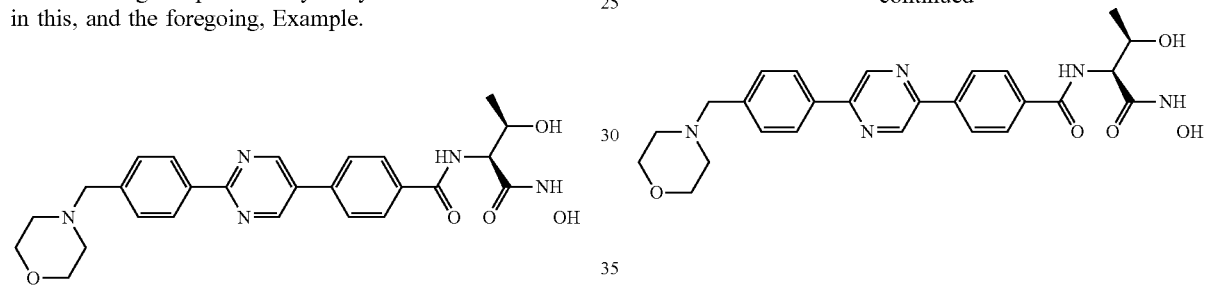
Examples 37A and 37B
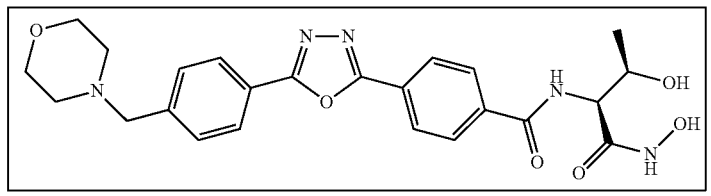
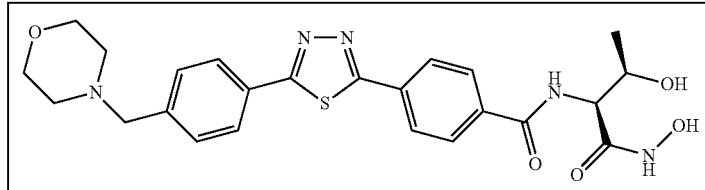
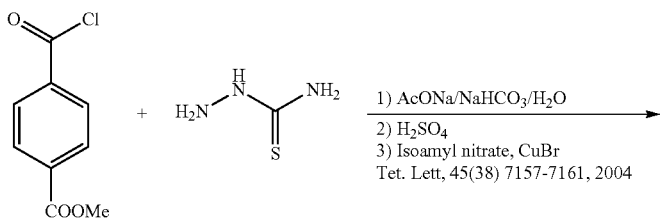

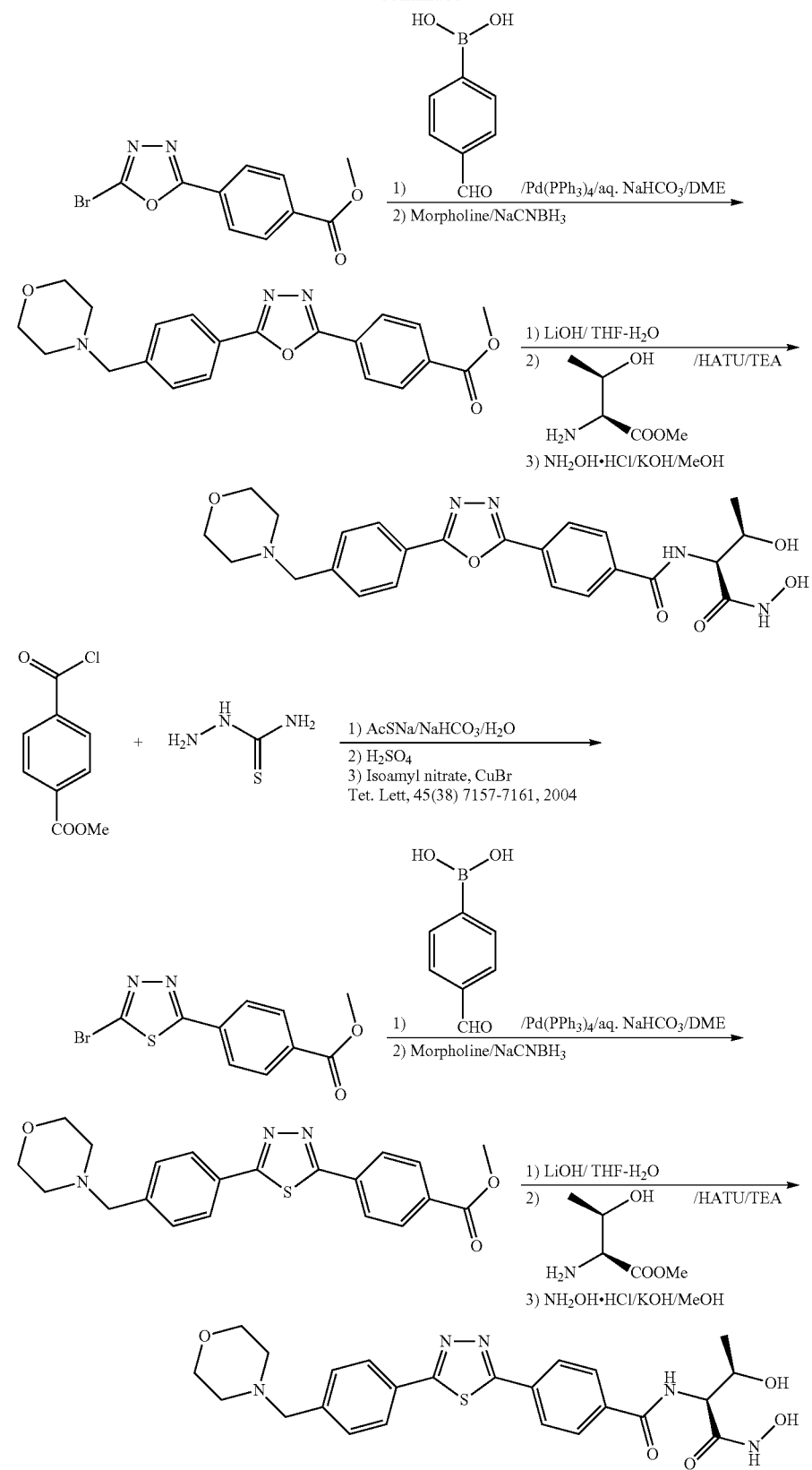

Example 38
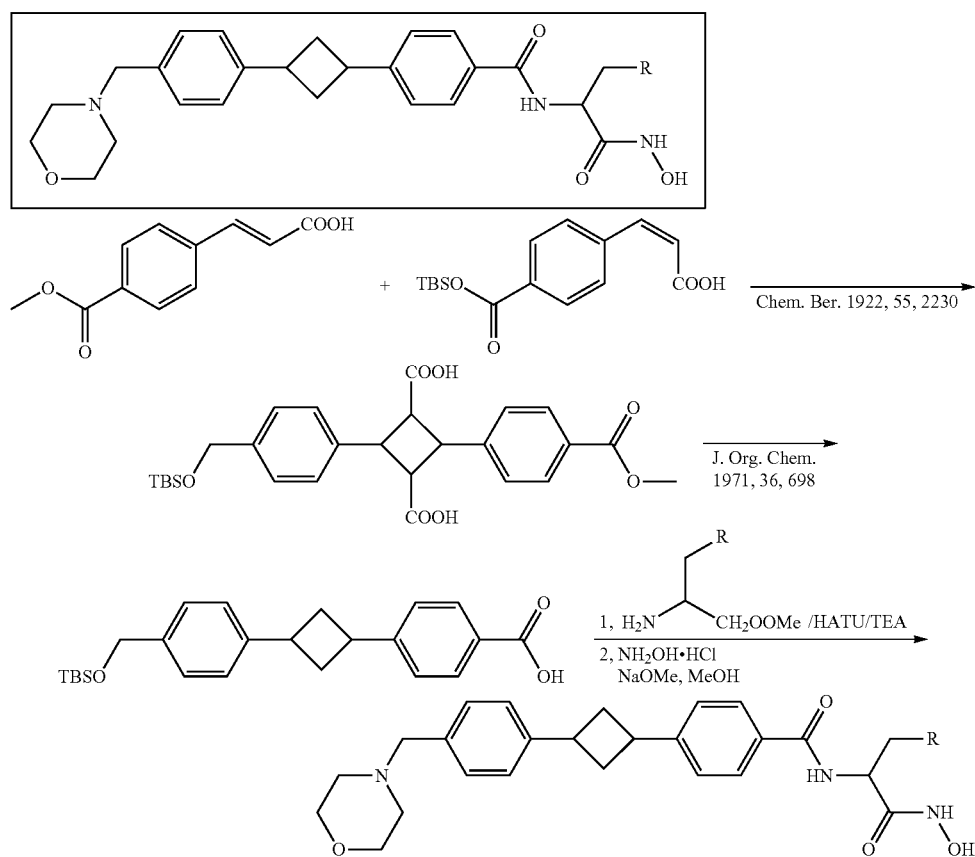
Example 39
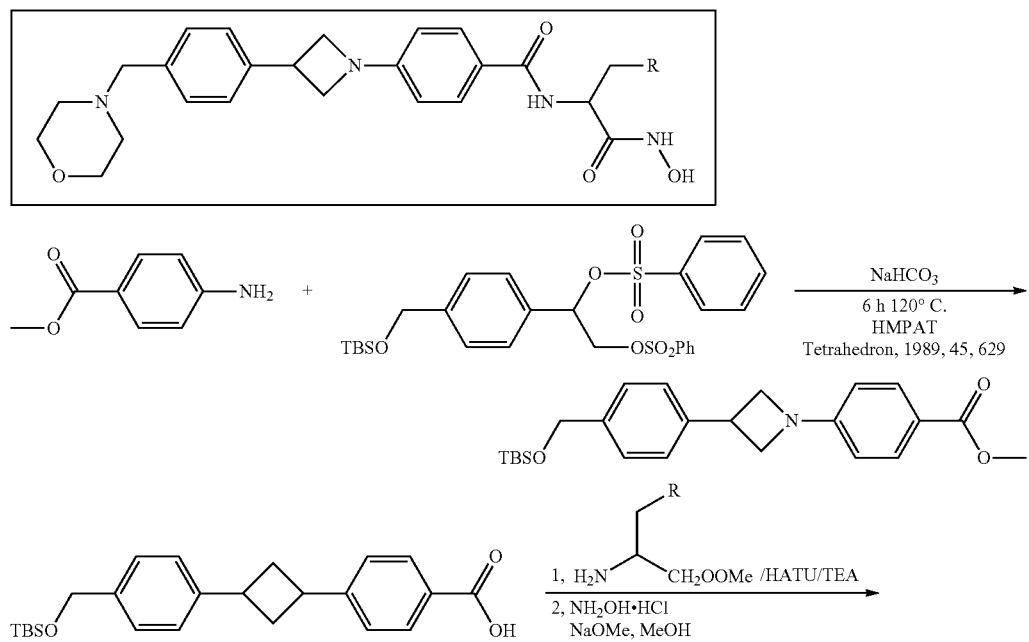

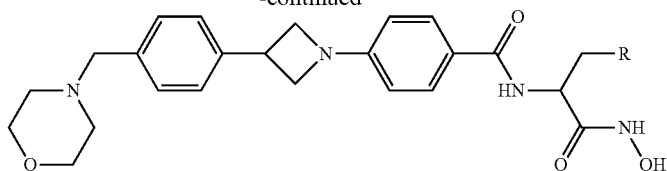
The following compound may be synthesized as described in this Example.
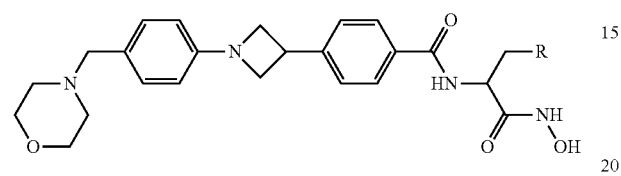
Example 40
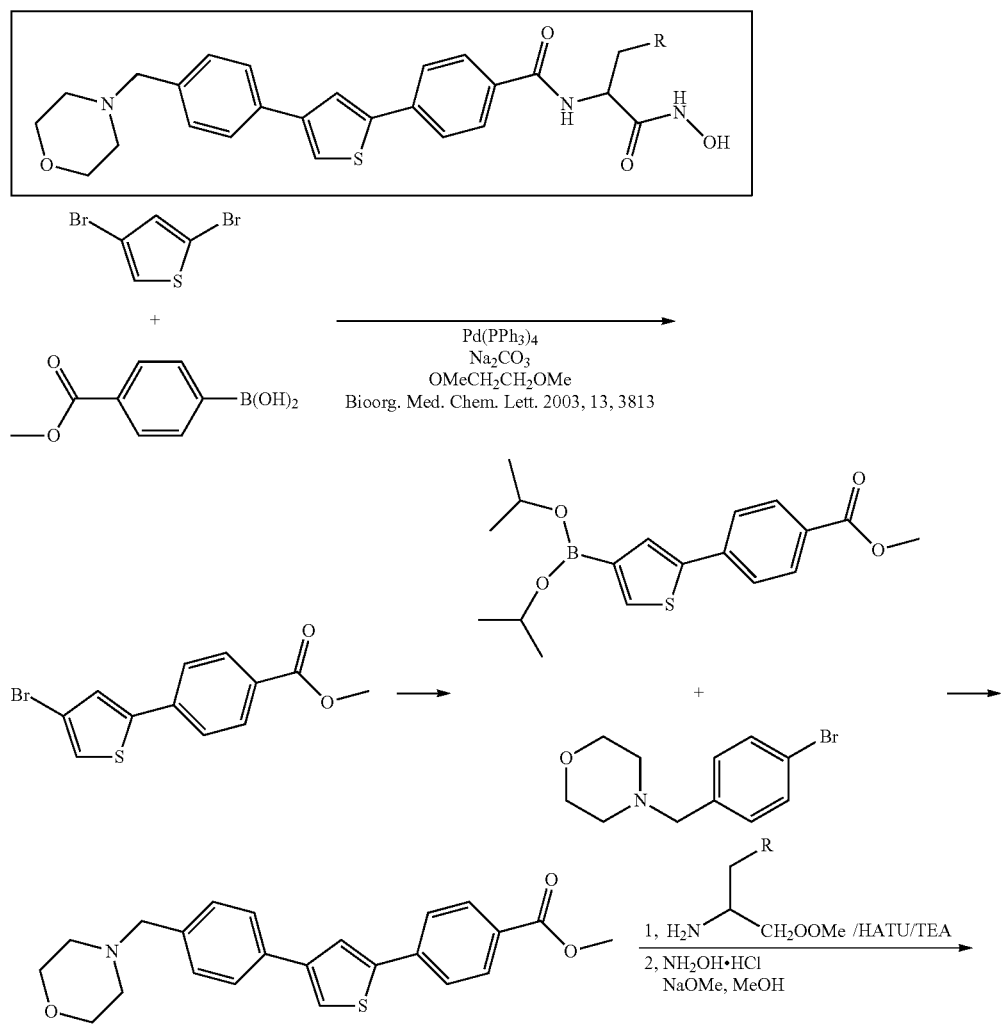

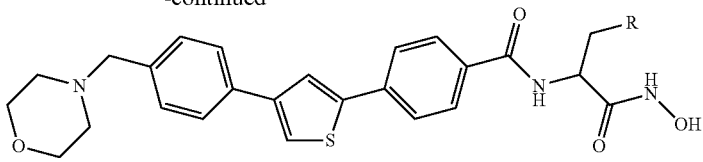
Example 41
N-((1S,2R)-2-Hydroxy-1-hydroxycarbamoyl-propyl)-4-[1-(4-morpholin-4-ylmethyl-phenyl)-piperidin-4-yl]-benzamide
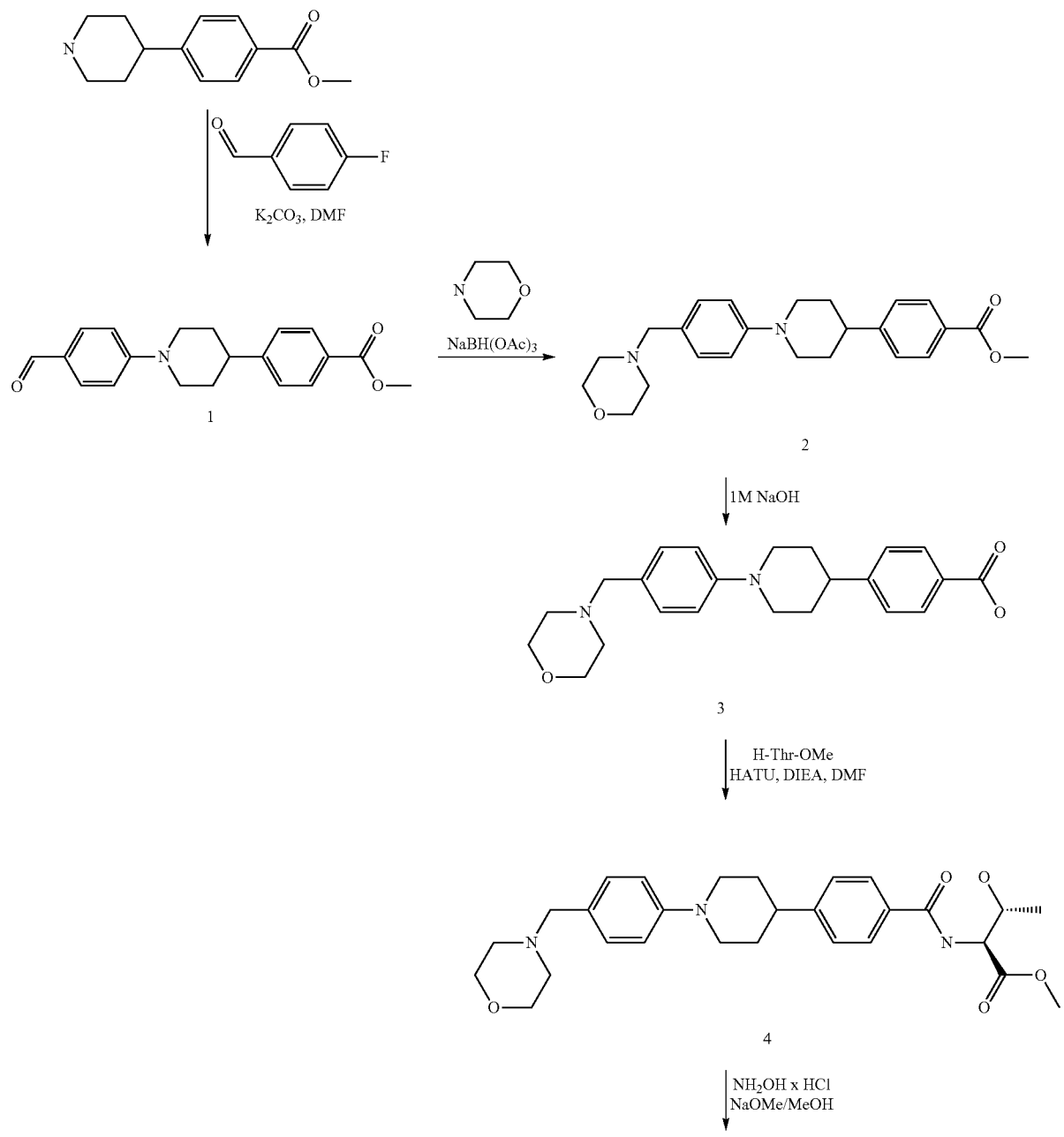

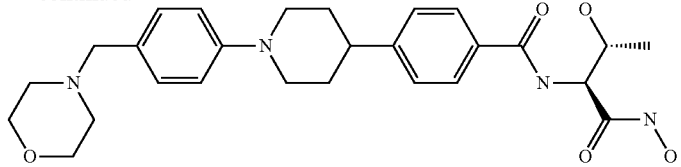

41-5

Synthesis of 4-[1-(4-formyl-phenyl)-piperidin-4-yl]-benzoic acid methyl ester (1)

A mixture of 4-(4-methoxycarboxyphenyl)piperidine HCl (256 mg, 1.0 mmol), 4-fluoro-benzaldehyde (105 μl, 1.0 mmol) and K$_2$CO$_3$ (250 mg, 1.8 mmol) in DMF (5 ml) was stirred at ambient temperature overnight. Reaction was diluted with water (30 ml). Formed precipitate was filtrated, washed with water (20 ml) and ether (20 ml), and dried in vacuum overnight to provide target compound (1) (203 mg, 63%) as white solid. LC-MS [M+H] 324.3 (C$_{20}$H$_{21}$NO$_3$+H, requires 324.41).

Synthesis of 4-[1-(4-morpholin-4-ylmethyl-phenyl)-piperidin-4-yl]-benzoic acid methyl ester (2)

A mixture of compound (1) (200 mg, 0.62 mmol), NaBH(OAc)$_3$ (158 mg, 0.75 mmol) and morpholine (60 μl, 0.68 mmol) in DCM (5 ml) was stirred at ambient temperature overnight. Reaction was quenched with 5% aq. NaHCO$_3$ (15 ml) and extracted with EtOAc (30 ml×2). Organic layer was washed with brine (20 ml) and dried over MgSO$_4$ (anh.). Solvent was evaporated in vacuum. Residue was dried in vacuum overnight to provide target compound (2) (225 mg, 92%) as yellowish solid. LC-MS [M+H] 308.1 (C$_{24}$H$_{30}$N$_2$O$_3$+H, requires 395.53).

Synthesis of 4-[1-(4-morpholin-4-ylmethyl-phenyl)-piperidin-4-yl]-benzoic acid (3)

A solution of compound (2) (225 mg, 0.57 mmol) and 1 M aq. NaOH (10 ml, 10 mmol) in dioxane (6 ml) was stirred at ambient temperature overnight. Reaction mixture was acidified with 1 M aq. HCl to pH~6. Volatile solvent was evaporated in vacuum. Formed precipitate was filtrated and washed with water (10 ml) and cold ether (5 ml) and dried in vacuum overnight to provide di-hydrochloric salt of target material (3) (211 mg, 89%) as off-white solid. LC-MS [M+H] 381.4 (C$_{23}$H$_{28}$N$_2$O$_3$+H, requires 381.50).

Synthesis of (2S,3R)-3-hydroxy-2-{4-[1-(4-morpholin-4-ylmethyl-phenyl)-piperidin-4-yl]-benzoylamino}-butyric acid methyl ester (4)

A solution of compound (3) (70 mg, 0.15 mmol), HATU (63 g, 0.17 mmol) and DIEA (131 μl, 0.75 mmol) in DMF (800 μl) was maintained at ambient temperature for 10 min followed by the addition of H-Thr-OMe hydrochloride (37 mg, 0.22 mmol). Reaction mixture was stirred at ambient temperature overnight followed by the dilution with EtOAc (100 ml). Solution was extracted with water (20 ml×2) and brine (20 ml). Organic layer was dried over MgSO$_4$ and evaporated. Residue was dried in vacuum to provide target compound (4) (73 mg, 99%) as yellow solid. LC-MS [M+H] 496.3 (C$_{28}$H$_{37}$N$_3$O$_5$+H, requires 496.63).

Synthesis of N-((1S,2R)-2-hydroxy-1-hydroxycarbamoyl-propyl)-4-[1-(4-morpholin-4-ylmethyl-phenyl)-piperidin-4-yl]-benzamide (41-5)

A solution of hydroxylamine hydrochloride (63 mg, 0.9 mmol) in MeOH (2 ml) was cooled to −5° C. followed by the addition of 25% NaOMe/MeOH (308 μl, 4.5 mmol) under nitrogen. Reaction mixture was stirred at −5° C. for additional 5 min, cooled to −20° C., and solution of compound 4 (73 mg, 0.15 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide di-trifluoroacetic salt of target product (41-5) as white solid. LC-MS [M+H] 497.7 (C$_{27}$H$_{36}$N$_4$O$_5$+H, requires 497.62).

| Compound | Scale (mmol) | Yield (mg) | Yield (%) | Purity (%) | [M + H] | Retention time (min)* |
|---|---|---|---|---|---|---|
| (41-5) | 0.15 | 76 | 70 | 100 | 497.7 | 1.97 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 42

N-((1S,2R)-2-Hydroxy-1-hydroxycarbamoyl-propyl)-4-[4-(4-morpholin-4-ylmethyl-phenyl)-piperidin-1-yl]-benzamide

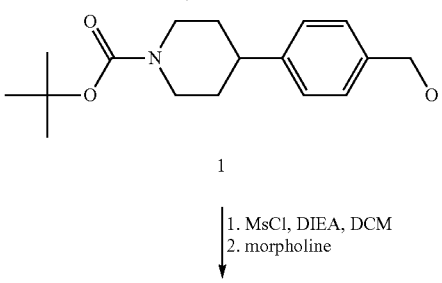

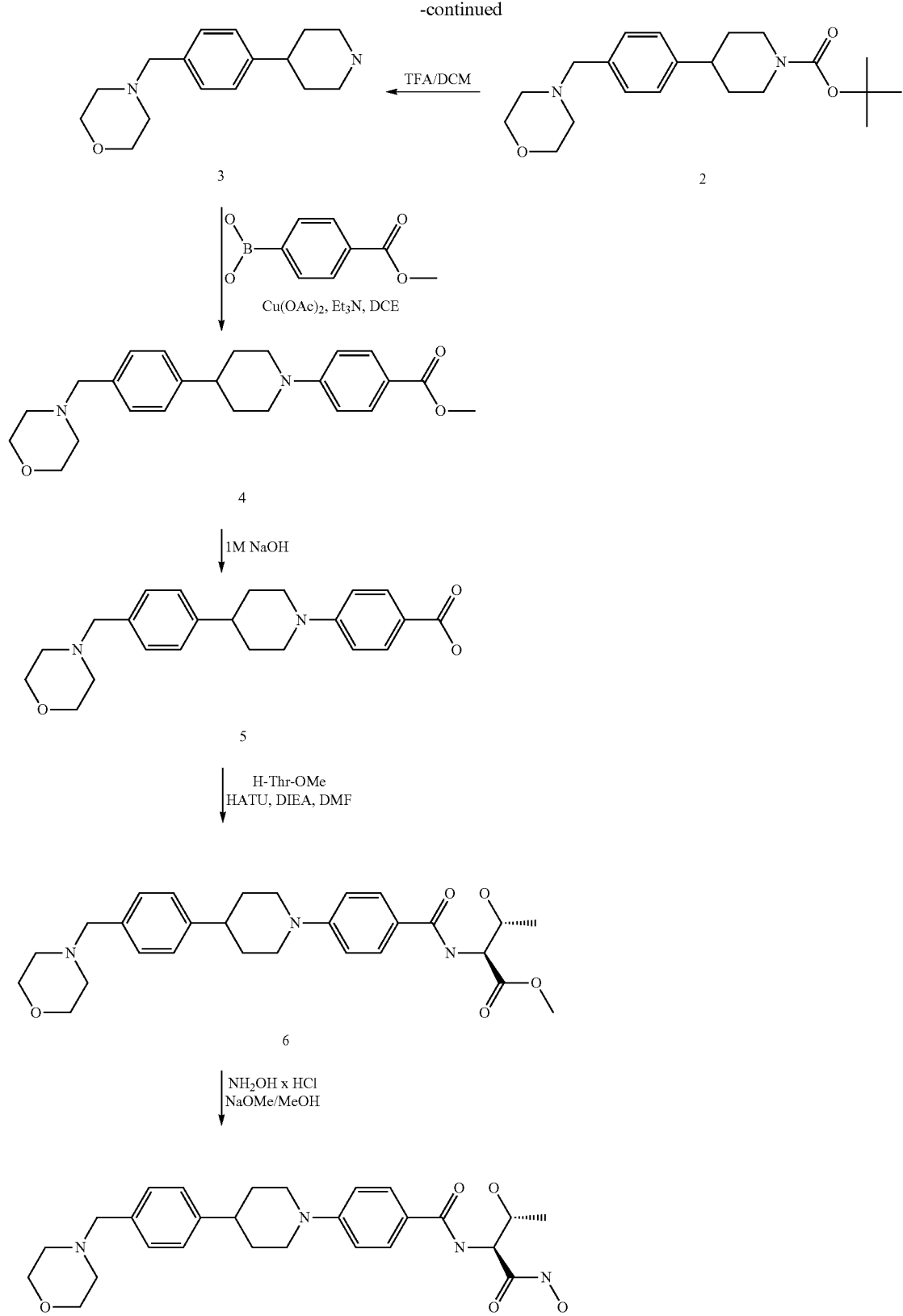

Synthesis of 4-(4-hydroxymethyl-phenyl)-piperidine-1-carboxylicacid tert-butyl ester (1)

A solution of N-Boc-4-(4-carboxyphenyl)piperidine (305 mg, 1.0 mmol) and 1 M BH$_3$ THF (3.1 ml, 3.1 mmol) in THF (3 ml) was maintained under nitrogen at ambient temperature overnight. Reaction was quenched with 5% aq. NH$_4$Cl (5 ml) and extracted with EtOAc (30 ml×2). Organic layer was washed with 5% NaHCO$_3$ (20 ml) and brine (20 ml) and dried over MgSO$_4$. Solvent was evaporated in vacuum. Residue was dried in vacuum overnight to provide target compound (1) (272 mg, 93%) as white solid. LC-MS [M+H] 292.3 (C$_{17}$H$_{25}$NO$_3$+H, requires 292.40).

Synthesis of 4-(4-Morpholin-4-ylmethyl-phenyl)-piperidine-1-carboxylic acid tert-butyl ester (2)

A solution of compound (1) (272 mg, 0.93 mmol) and DIEA (198 μA, 1.14 mmol) in DCM (5 ml) was cooled to 0° C. followed by the addition of MsCl (87 μl, 1.12 mmol). Reaction mixture was maintained at 0° C. for 10 min followed by the addition of mixture of DIEA (179 μl, 1.1 mmol) and morpholine (90 μl, 1.1 mmol). Temperature of the reaction mixture was allowed to rise to ambient. Reaction mixture was maintained at ambient temperature overnight and diluted with EtOAc (80 ml). Organic layer was washed with 5% NaHCO$_3$ (20 ml) and brine (20 ml) and dried over MgSO$_4$ (anh.). Solvent was evaporated in vacuum. Residue was dried in vacuum overnight to provide target compound (2) (315 mg, 94%) as brownish oil. LC-MS [M+H] 361.4 (C$_{21}$H$_{32}$N$_2$O$_3$+H, requires 361.51).

Synthesis of 4-(4-piperidin-4-yl-benzyl)-morpholine (3)

A solution of compound (2) (315 mg, 1.13 mmol), TFA (3 ml, 40 mmol) in DCM (3 ml) was maintained at ambient temperature for 3 h. Solvents were evaporated in vacuum. Residue was dissolved in DCM (1 ml) and 1 M HCl/ether (50 ml) was added. Formed precipitate was filtrated, washed with ether and dried in vacuum overnight to provide di-hydrochloric salt of target compound (3) (281 mg, 91%) as off-white solid. LC-MS [M+H] 261.1 (C$_{16}$H$_{24}$N$_2$O+H, requires 261.39).

Synthesis of 4-[4-(4-morpholin-4-ylmethyl-phenyl)-piperidin-1-yl]-benzoic acid methyl ester (4)

A mixture of compound (3) (261 mg, 0.78 mmol), 4-methoxycarbonylphenyl) boronic acid (388 mg, 2.16 mmol), Cu(OAc)$_2$ (216 mg, 1.19 mmol), molecular sieves (4A, 200 mg) and Et$_3$N (750 μl, 5.6 mmol) in DCE (5 ml) was stirred at ambient temperature overnight under nitrogen. Formed precipitate was filtrated. Filtrate was diluted with EtOAc (100 ml) and extracted with water (20 ml×2) and brine (20 ml). Solvent was evaporated in vacuum. Residue was dissolved in DMSO (1 ml) and subjected to HPLC purification. [YMC-Pack ODS-A C-18 column (30×100 mm); flow rate=10 ml/min; injection volume 1.0 ml; mobile phase A: 100% water, 0.1% TFA; mobile phase B: 100% ACN, 0.1% TFA; gradient elution from 10% B to 60% B in 70 min., detection 254 nm]. Fractions containing the desired product were combined and concentrated in vacuum. The residue was dissolved in EtOAc (25 ml), extracted with 5% aq. NaHCO$_3$ (20 ml) and brine (20 ml) and dried over MgSO$_4$ (anh.). Solvent was evaporated in vacuum. Residue was dried in vacuum overnight to provide target product (4) (24 mg, 6%) as white solid. LC-MS [M+H] 394.8 (C$_{24}$H$_{30}$N$_2$O$_3$+H, requires 395.53).

Synthesis of 4-[4-(4-morpholin-4-ylmethyl-phenyl)-piperidin-1-yl]-benzoic acid (5)

A solution of compound (4) (24 mg, 0.06 mmol) and 1 M aq. NaOH (500 μl, 0.5 mmol) in dioxane (500 μl) was stirred at ambient temperature overnight. Reaction mixture was acidified with 1 M aq. HCl to pH~2. Formed precipitate was filtrated and washed with water (10 ml) and dried in vacuum overnight to provide di-hydrochloric salt of target material (5) (24 mg, 88%) as off-white solid. LC-MS [M+H] 381.4 (C$_{23}$H$_{28}$N$_2$O$_3$+H, requires 381.50).

Synthesis of (2S,3R)-3-hydroxy-2-{4-[4-(4-morpholin-4-ylmethyl-phenyl)-piperidin-1-yl]-benzoylamino}-butyric acid methyl ester (6)

A solution of compound (5) (24 mg, 0.053 mmol), HATU (25 g, 0.066 mmol) and DIEA (52 μl, 0.3 mmol) in DMF (600 μl was maintained at ambient temperature for 10 min followed by the addition of H-Thr-OMe hydrochloride (14 mg, 0.08 mmol). Reaction mixture was stirred at ambient temperature overnight followed by the dilution with EtOAc (100 ml). Solution was extracted with water (20 ml×2) and brine (20 ml). Organic layer was dried over MgSO$_4$ and evaporated. Residue was dried in vacuum to provide target compound (6) (26 mg, 99%) as yellow solid. LC-MS [M+H] 496.4 (C$_{28}$H$_{37}$N$_3$O$_5$+H, requires 496.63).

Synthesis of N-((1S,2R)-2-Hydroxy-1-hydroxycarbamoyl-propyl)-4-[4-(4-morpholin-4-ylmethyl-phenyl)-piperidin-1-yl]-benzamide (42-7)

A solution of hydroxylamine hydrochloride (24 mg, 0.34 mmol) in MeOH (2 ml) was cooled to −5° C. followed by the addition of 25% NaOMe/MeOH (117 μl, 0.51 mmol) under nitrogen. Reaction mixture was stirred at −5° C. for additional 5 min, cooled to −20° C., and solution of compound (6) (26 mg, 0.053 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide di-trifluoroacetic salt of target product 42-7 as white solid. LC-MS [M+H] 497.5 (C$_{27}$H$_{36}$N$_4$O$_5$+H, requires 497.62).

| Compound | Scale (mmol) | Yield (mg) | Yield (%) | Purity (%) | [M + H] | Retention time (min)* |
|---|---|---|---|---|---|---|
| (42-7) | 0.053 | 17.5 | 46 | 99.8 | 497.5 | 2.22 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 43
N-((1S,2R)-2-Hydroxy-1-hydroxycarbamoyl-propyl)-4-[4-(4-morpholin-4-ylmethyl-phenyl)-piperazin-1-yl]-benzamide
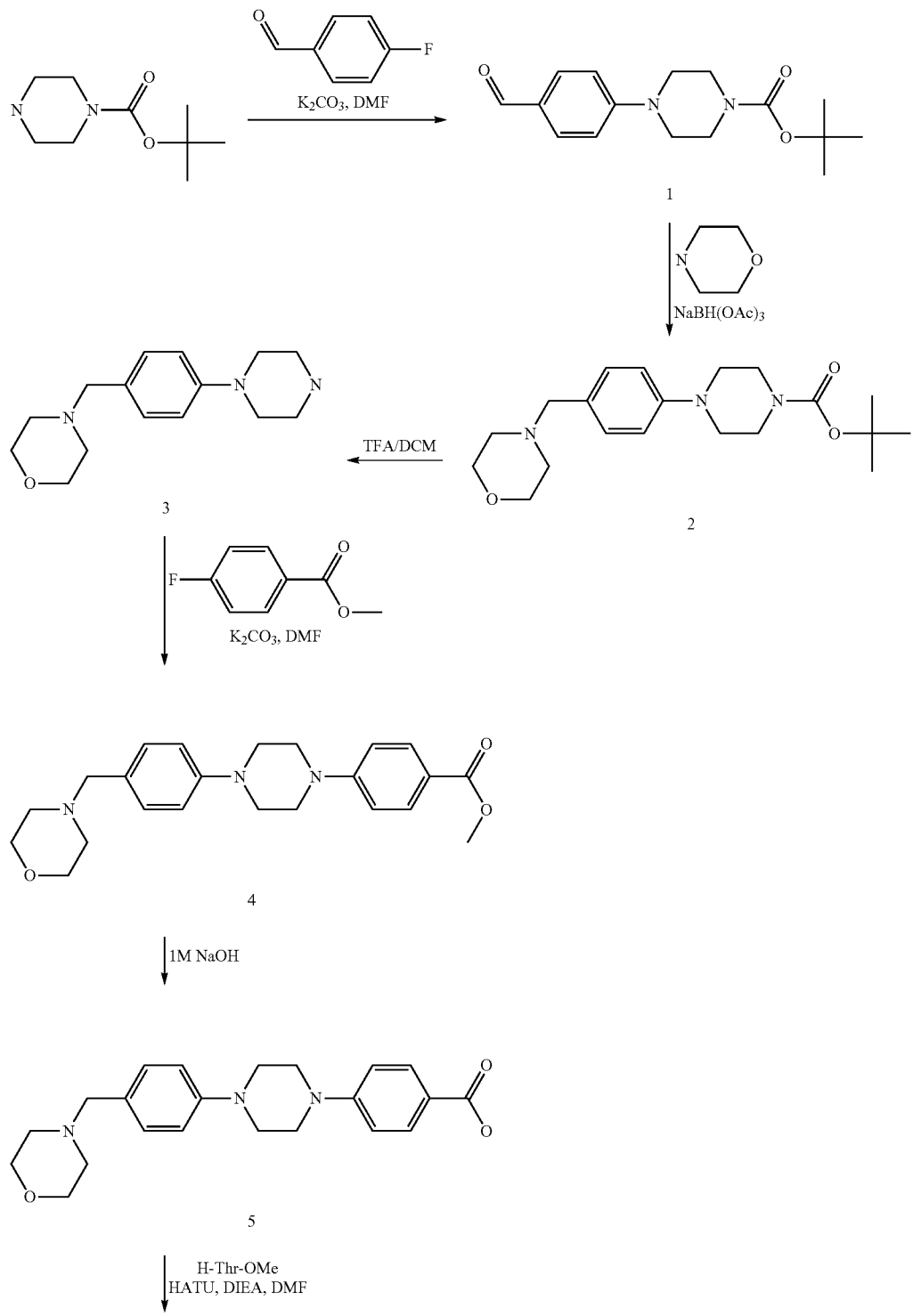

-continued

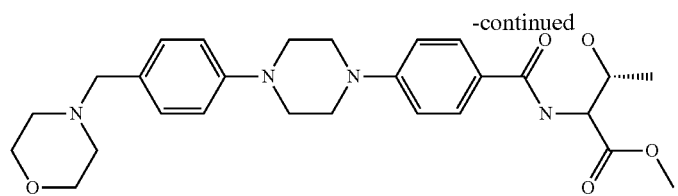
6

| NH₂OH x HCl
| MaOMe/MeOH
↓

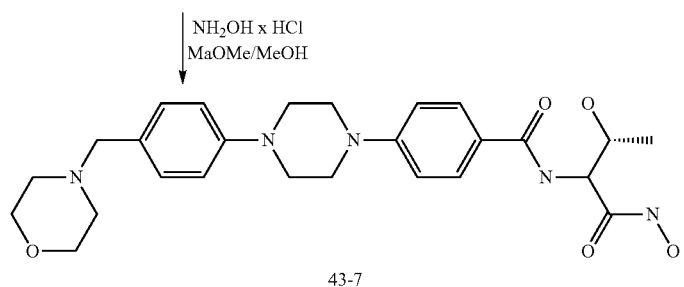
43-7

Synthesis of 4-(4-formyl-phenyl)-piperazine-1-carboxylic acid tert-butyl ester (1)

A mixture of 4-(tert-butyl-1-piperazinecarboxylate (556 mg, 3.0 mmol), 4-fluoro-benzaldehyde (315 μl, 3.0 mmol) and K₂CO₃ (514 mg, 3.7 mmol) in DMF (5 ml) was stirred at ambient temperature overnight. Reaction was diluted with water (30 ml) and extracted with EtOAc (50 ml×2). Organic layer was washed with water (20 ml), 1 M aq. HCl (20 ml), water (20 ml×2) and brine (20 ml) and dried over MgSO₄ (anh.). Solvent was evaporated in vacuum. Residue was triturated with hexane. Formed precipitate was filtrated and dried in vacuum overnight to provide target compound (1) (342 mg, 39%) as off-white solid. LC-MS [M+H] 291.2 (C₁₆H₂₂N₂O₃+H, requires 291.38).

Synthesis of 4-(4-morpholin-4-ylmethyl-phenyl)-piperazine-1-carboxylic acid tert-butyl ester (2)

A mixture of compound (1) (342 mg, 1.18 mmol), NaBH(OAc)₃ (300 mg, 1.42 mmol) and morpholine (113 μl, 1.3 mmol) in DCM (5 ml) was stirred at ambient temperature overnight. Reaction was quenched with 5% aq. NaHCO₃ (15 ml) and extracted with EtOAc (30 ml×2). Organic layer was washed with brine (20 ml) and dried over MgSO₄ (anh.). Solvent was evaporated in vacuum. Residue was dried in vacuum overnight to provide target compound (2) (408 mg, 96%) as white solid. LC-MS [M+H] 361.9 (C₂₀H₃₁N₃O₃+H, requires 362.50).

Synthesis of 4-(4-piperazin-1-yl-benzyl)-morpholine (3)

A solution of compound (2) (408 mg, 1.13 mmol), TFA (5 ml, 68 mmol) in DCM (5 ml) was maintained at ambient temperature for 40 min. Solvents were evaporated in vacuum. Residue was dissolved in 1 M aq. NaOH (10 ml) and extracted with EtOAc (30 ml×2). Organic layer was washed with brine (20 ml) and dried over MgSO₄ (anh.). Solvent was evaporated in vacuum. Residue was dried in vacuum overnight to provide target compound (3) (212 mg, 72%) as yellowish solid. LC-MS [M+H] 262.3 (C₁₅H₂₃N₃O+H, requires 262.38).

Synthesis of 4-[4-(4-morpholin-4-ylmethyl-phenyl)-piperazin-1-yl]-benzoic acid methyl ester (4)

A mixture of compound (3) (140 mg, 0.54 mmol), methyl 4-fluorobenzoate (76 μl, 0.59 mmol) and DIEA (141 μl, 0.81 mmol) in DMSO (2 ml) was irradiated in microwave oven (max. power 250 W, 160° C.) for 2 h and cooled to ambient temperature. Reaction mixture was diluted with water (30 ml). Formed precipitate was filtrated and dissolved in EtOAc (100 ml). Solution was washed with 5% aq. NaHCO₃ (20 ml) and brine (20 ml) and dried over MgSO₄ (anh.). Solvent was evaporated in vacuum. Residue was dried in vacuum overnight to provide target compound (4) (98 mg, 46%) as yellowish solid. LC-MS [M+H] 396.2 (C₂₃H₂₉N₃O₃+H, requires 396.52).

Synthesis of 4-[4-(4-morpholin-4-ylmethyl-phenyl)-piperazin-1-yl]-benzoic acid (5)

A solution of compound (4) (98 mg, 0.57 mmol) and 1 M aq. NaOH (2 ml, 2 mmol) in dioxane (2 ml) was stirred at ambient temperature overnight. Reaction mixture was acidified with 1 M aq. HCl to pH~6 and evaporated in vacuum. Residue was dissolved in DMSO (1 ml) and subjected to HPLC purification. [YMC-Pack ODS-A C-18 column (30× 100 mm); flow rate=10 ml/min; injection volume 1.0 ml; mobile phase A: 100% water, 0.1% TFA; mobile phase B: 100% ACN, 0.1% TFA; gradient elution from 0% B to 45% B in 72 min., detection 254 nm]. Fractions containing the desired product were combined and concentrated in vacuum. The residue was dissolved in i-PrOH (15 ml) and evaporated in vacuum. Obtained residue was dissolved in i-PrOH (5 ml) and 1 M HCl/ether (50 ml) was added. Precipitate was filtrated and dried in vacuum to provide tri-hydrochloric salt of target product (5) (30 mg, 24%) as off-white solid. LC-MS [M+H] 382.6 (C₂₂H₂₇N₃O₃+H, requires 382.49).

Synthesis of (2S,3R)-3-hydroxy-2-{4-[4-(4-morpholin-4-ylmethyl-phenyl)-piperazin-1-yl]-benzoylamino}-butyric acid methyl ester (6)

A solution of compound (5) (30 mg, 0.06 mmol), HATU (25 g, 0.066 mmol) and DIEA (63 μl, 0.36 mmol) in DMF (500 μl) was maintained at ambient temperature for 10 min followed by the addition of H-Thr-OMe hydrochloride (14 mg, 0.084 mmol). Reaction mixture was stirred at ambient temperature overnight followed by the dilution with EtOAc (100 ml). Solution was extracted with water (20 ml×2) and brine (20 ml). Organic layer was dried over $MgSO_4$ and evaporated. Residue was dried in vacuum to provide target compound (6) (30 mg, 99%) as yellow solid. LC-MS [M+H] 479.0 ($C_{27}H_{36}N_4O_5$+H, requires 497.62).

Synthesis of N-((1S,2R)-2-hydroxy-1-hydroxycarbamoyl-propyl)-4-[4-(4-morpholin-4-ylmethyl-phenyl)-piperazin-1-yl]-benzamide (43-7)

A solution of hydroxylamine hydrochloride (63 mg, 0.36 mmol) in MeOH (2 ml) was cooled to −5° C. followed by the addition of 25% NaOMe/MeOH (123 μl, 0.36 mmol) under nitrogen. Reaction mixture was stirred at −5° C. for additional 5 min, cooled to −20° C., and solution of compound (6) (30 mg, 0.06 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide tri-trifluoroacetic salt of target product (43-7) as white solid. LC-MS [M+H] 498.3 ($C_{26}H_{35}N_5O_5$+H, requires 498.61).

| Compound | Scale (mmol) | Yield (mg) | Yield (%) | Purity (%) | [M + H] | Retention time (min)* |
|---|---|---|---|---|---|---|
| (43-7) | 0.06 | 15.3 | 31 | 100 | 498.61 | 2.64 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

The following compounds may be synthesized as described in this Example.

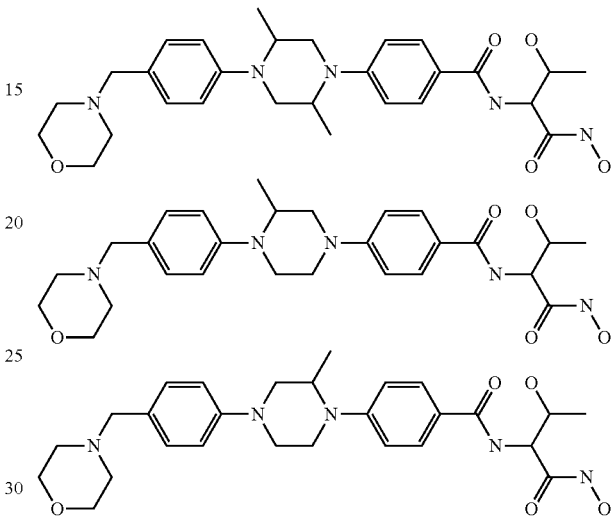

Example 44

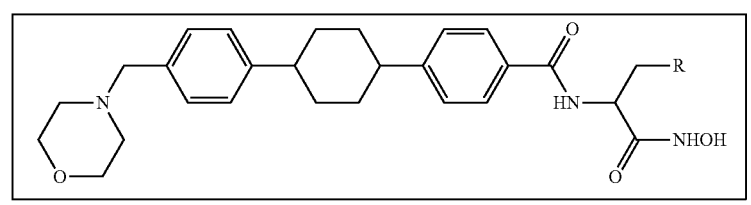

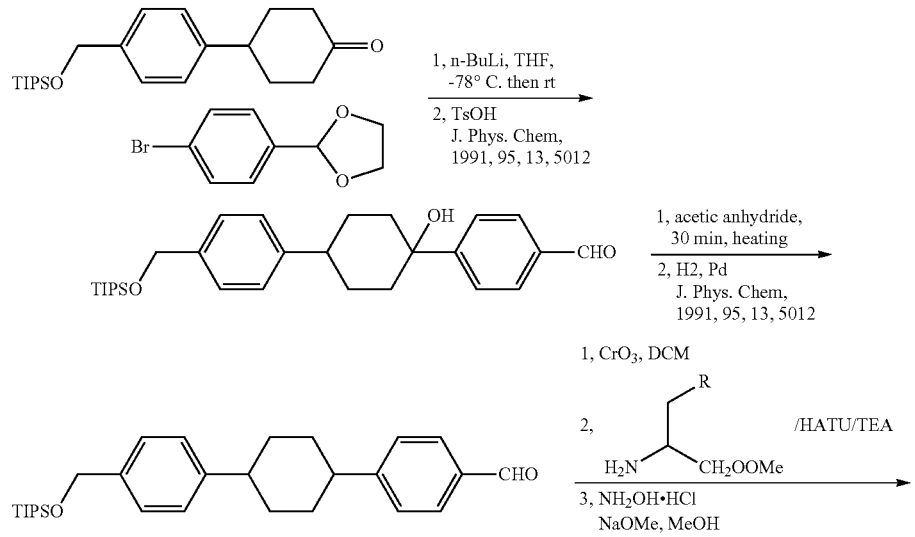

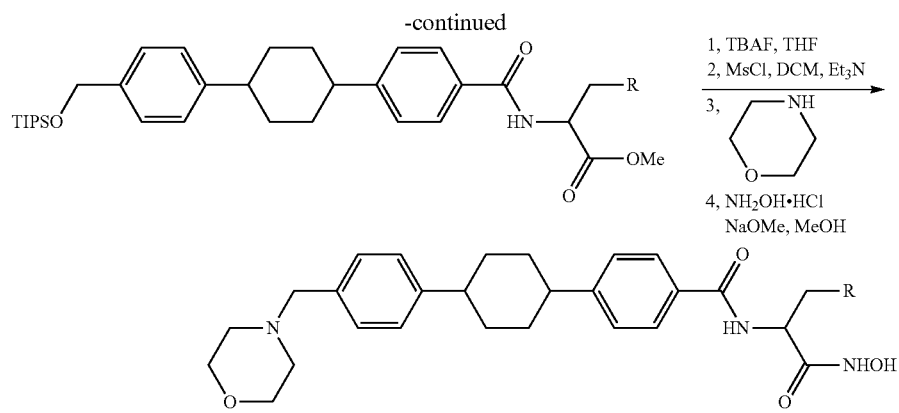
Example 45
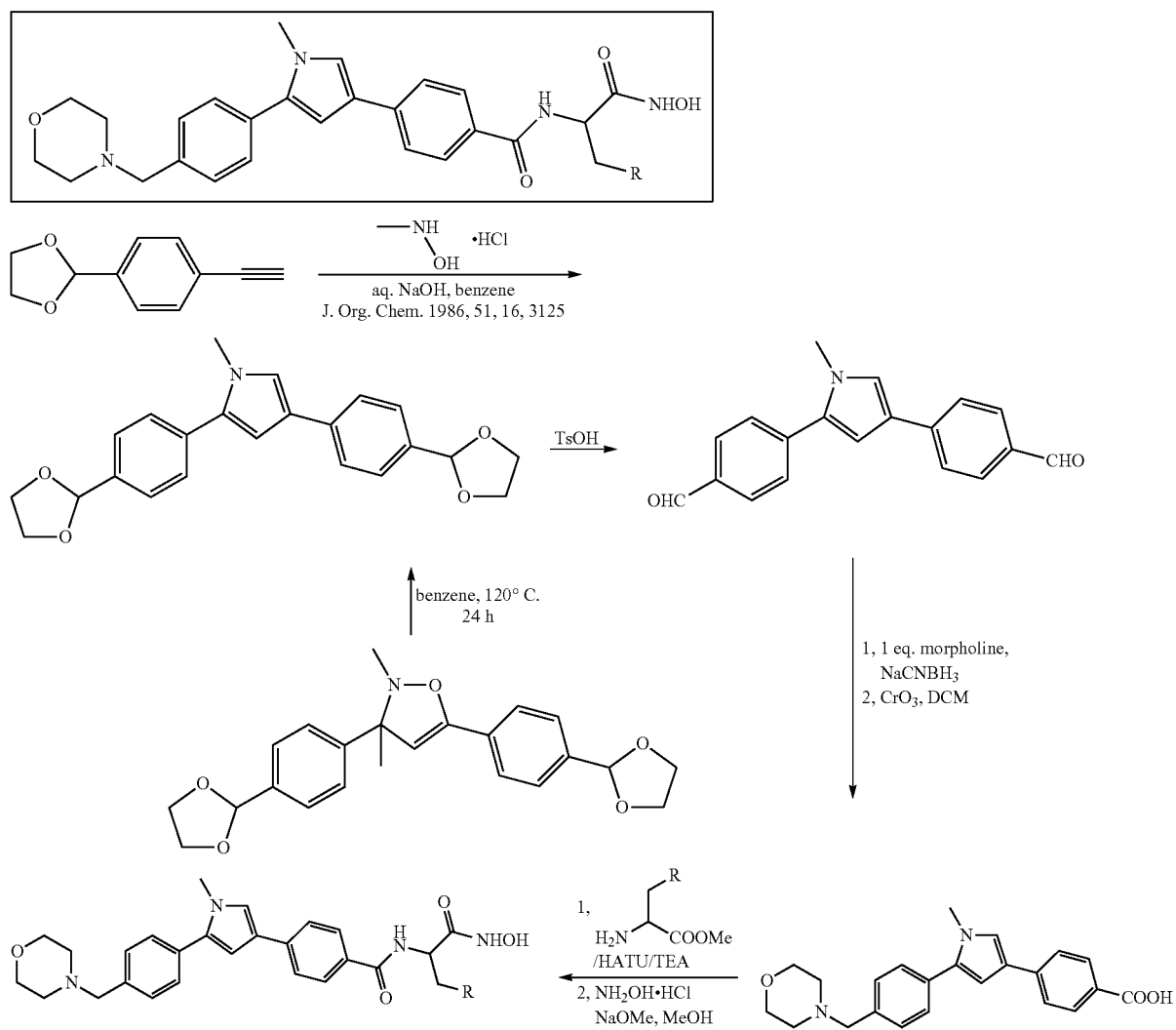

Example 46
N-((1S,2R)-2-Hydroxy-1-hydroxycarbamoyl-propyl)-4-(4-morpholin-4-ylmethyl-benzylsulfanyl)-benzamide
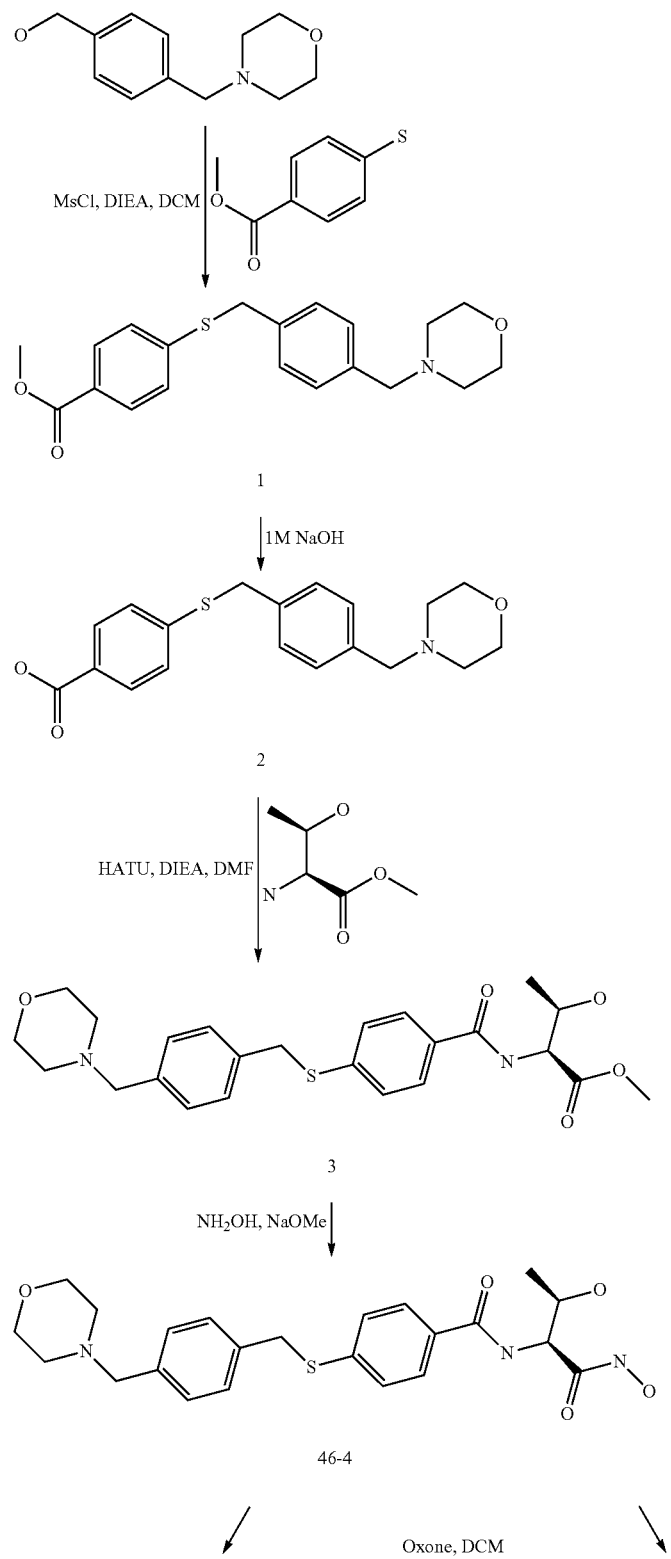

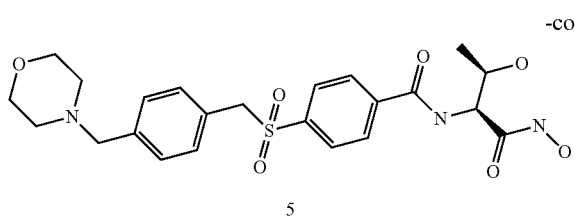

5

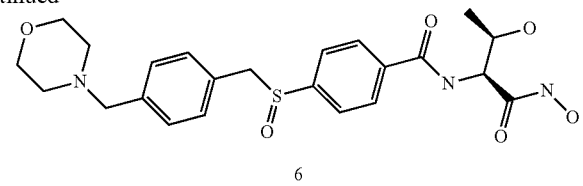

6

Synthesis of 4-(4-morpholin-4-ylmethyl-benzylsulfanyl)-benzoic acid methyl ester (1)

A solution of (4-(morpholinomethyl)phenyl)methanol (207 mg, 1.0 mmol) and DIEA (192 μl, 1.1 mmol) in DCM (3 ml) was cooled to 0° C. followed by the addition of MsCl (94 μl, 1.2 mmol). Reaction mixture was maintained at 0° C. for 1 h followed by the addition of mixture of DIEA (192 μl, 1.1 mmol) and methyl-4-mercaptobenzoate (185 mg, 1.1 mmol). Temperature of the reaction mixture was allowed to rise to ambient. Reaction mixture was maintained at ambient temperature 40 min and diluted with EtOAc (80 ml). Organic layer was washed with 5% NaHCO₃ (20 ml) and brine (20 ml) and dried over MgSO₄ (anh.). Solvent was evaporated in vacuum. Residue (1) was used as is for the next transformation. LC-MS [M+H] 358.1 ($C_{20}H_{23}NO_3S$+H, requires 358.49).

Synthesis of 4-(4-morpholin-4-ylmethyl-benzylsulfanyl)-benzoic acid (2)

To a solution of compound (1) (1.0 mmol) in dioxane (1 ml) 1 M aq. NaOH (1.5 ml, 1.5 mmol) was added. Reaction mixture was maintained at ambient temperature overnight and acidified with 1 M aq. HCl to pH~5. Solvents were evaporated. Residue was dissolved in DMSO (1 ml) and subjected to HPLC purification. [YMC-Pack ODS-A C-18 column (30×100 mm); flow rate=10 ml/min; injection volume 1.5 ml; mobile phase A: 100% water, 0.1% TFA; mobile phase B: 100% ACN, 0.1% TFA; gradient elution from 5% B to 50% B in 70 min., detection 254 nm]. Fractions containing the desired product were combined and concentrated in vacuum. The residue was dissolved in i-PrOH (15 ml) and evaporated. Obtained residue was dissolved in i-PrOH (5 ml) and 1 M HCl/ether (50 ml) was added. Precipitate was filtrated and dried in vacuum to provide hydrochloric salt of target product (2) (161 mg, 54%) as white solid. LC-MS [M+H] 344.1 ($C_{19}H_{21}NO_3S$+H, requires 344.46).

Synthesis of (2S,3R)-3-hydroxy-2-[4-(4-morpholin-4-ylmethyl-benzylsulfanyl)-benzoyl amino]-butyric acid methyl ester (3)

A solution of compound (2) (34 mg, 0.09 mmol), HATU (34 g, 0.09 mmol) and DIEA (63 μl, 0.36 mmol) in DMF (800 μl) was maintained at ambient temperature for 10 min followed by the addition of H-Thr-OMe hydrochloride (18 mg, 0.11 mmol). Reaction mixture was stirred at ambient temperature overnight followed by the dilution with EtOAc (100 ml). Solution was extracted with water (20 ml×2) and brine (20 ml). Organic layer was dried over MgSO₄ and evaporated. Residue was dried in vacuum to provide target compound (3) (40 mg, 98%) as yellow solid. LC-MS [M+H] 459.2 ($C_{24}H_{30}N_2O_5S$+H, requires 459.59).

Synthesis of N-((1S,2R)-2-hydroxy-1-hydroxycarbamoyl-propyl)-4-(4-morpholin-4-ylmethyl-benzylsulfanyl)-benzamide (46-4)

A solution of hydroxylamine hydrochloride (19 mg, 0.27 mmol) in MeOH (2 ml) was cooled to −5° C. followed by the addition of 25% NaOMe/MeOH (94 μl, 0.41 mmol) under nitrogen. Reaction mixture was stirred at −5° C. for additional 5 min, cooled to −20° C., and solution of compound (3) (40 mg, 0.09 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (46-4) (25.8 mg, 50%) as white solid. LC-MS [M+H] 460.2 ($C_{23}H_{29}N_3O_5S$+H, requires 460.58).

| Compound | Scale (mmol) | Yield (mg) | Yield (%) | Purity (%) | [M + H] | Retention time (min)* |
|---|---|---|---|---|---|---|
| (46-4) | 0.09 | 25.8 | 50 | 98.7 | 460.2 | 3.11 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Compounds (5) and (6)

Compounds (5) and (6) may be synthesized from compound 4 using OXONE oxidation in dichloromethane.

Example 47
N-((1S,2R)-2-Hydroxy-1-hydroxycarbamoyl-propyl)-4-(4-morpholin-4-ylmethyl-phenylsulfanyl)-benzamide-4-ylmethyl-phenylethynyl)-benzamide
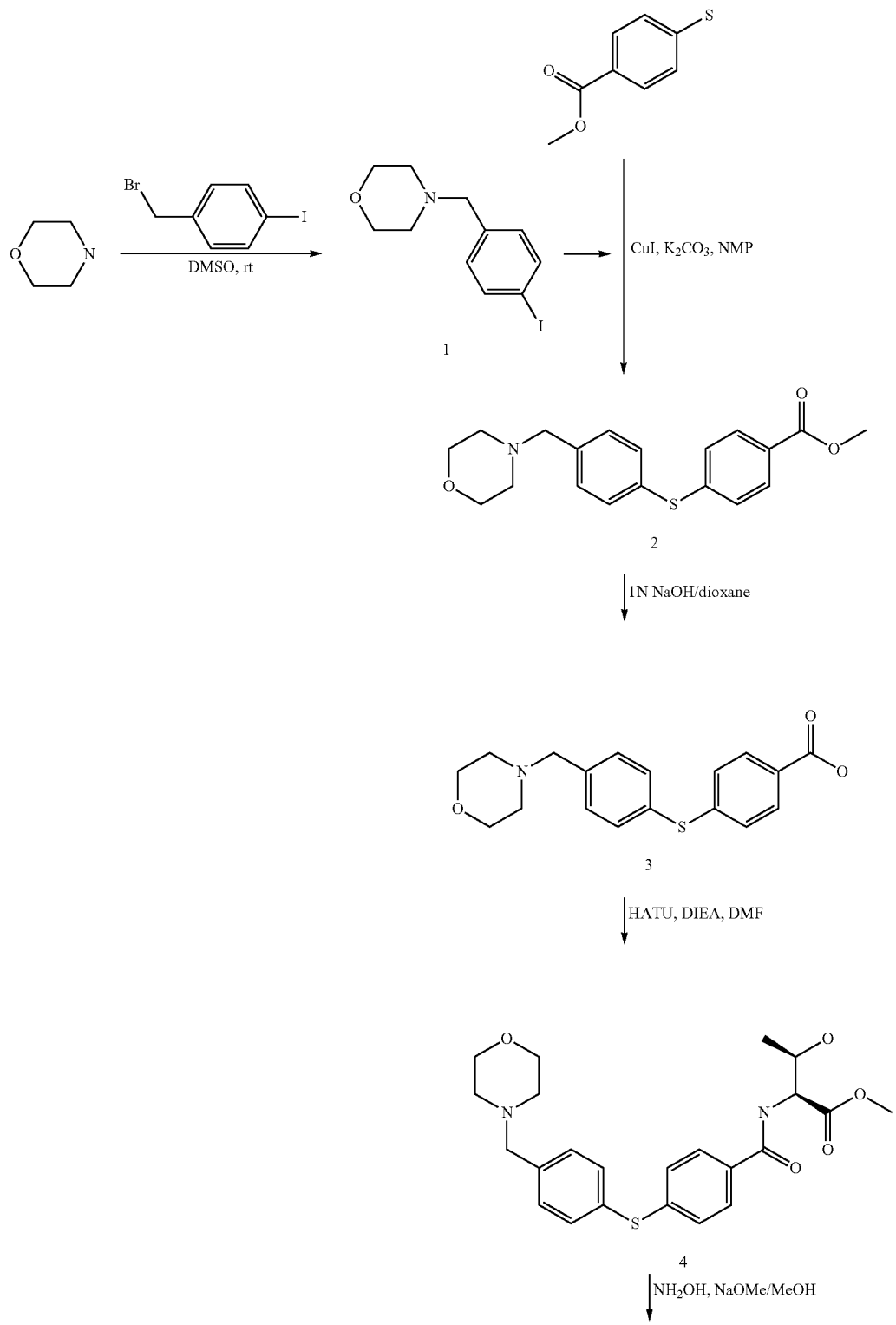

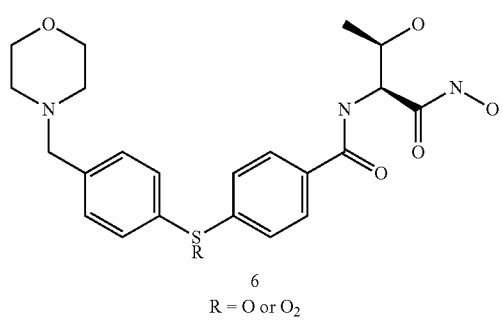

6
R = O or O₂

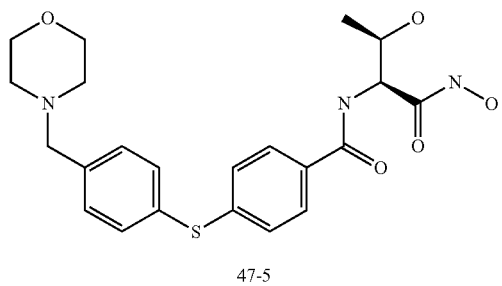

47-5

Synthesis of 4-(4-iodo-benzyl)-morpholine (1)

To a solution of morpholine (353 μl, 4.06 mmol) in DMSO (5 ml) was added 4-iodobenzylbromide (402 mg, 1.35 mmol). Reaction mixture was stirred at ambient temperature overnight. Reaction mixture was diluted with 5% NaHCO₃ (100 ml) and extracted with EtOAc (50 ml×2). Organic layer was washed with brine (30 ml), dried over MgSO₄ (anh.) and evaporated in vacuum. Residue was dried in vacuum overnight at ambient temperature to provide target material (1) (344 g, 84%) as white solid. LC-MS [M+H] 304.1 ($C_{11}H_{14}INO+H$, requires 304.15).

Synthesis of 4-(4-morpholin-4-ylmethyl-phenylsulfanyl)-benzoic acid methyl ester (2)

A mixture of compound (1) (260 mg, 0.86 mmol), methyl-4-mercaptobenzoate (159 mg, 0.94 mmol), CuI (16.3 mg, 0.086 mmol and K₂CO₃ (237 mg, 1.72 mmol) in NMP (2 ml) was stirred was irradiated in microwave oven (max. power 250 W, 160° C.) for 40 min and cooled to ambient temperature. Reaction mixture was diluted with EtOAc (80 ml) and extracted with 5% aq. NaHCO₃ (20 ml) and brine (20 ml) and dried over MgSO₄ (anh.). Solvent was evaporated in vacuum. Residue was dried in vacuum overnight to provide target compound (2) (289 mg, 98%) as yellowish solid. LC-MS [M+H] 344.3 ($C_{19}H_{21}NO_3S+H$, requires 344.46).

Synthesis of 4-(4-morpholin-4-ylmethyl-phenylsulfanyl)-benzoic acid (3)

To a solution of compound (2) (289 mg, 0.84 mmol) in dioxane (500 μl) 1 M aq. NaOH (1 ml) was added. Reaction mixture was maintained at ambient temperature for 1.5 h, acidified with 1 M aq. HCl to pH~5 and evaporated in vacuum. Residue was dissolved in DMSO (1 ml) and subjected to HPLC purification. [YMC-Pack ODS-A C-18 column (30×100 mm); flow rate=10 ml/min; injection volume 1.0 ml; mobile phase A: 100% water, 0.1% TFA; mobile phase B: 100% ACN, 0.1% TFA; gradient elution from 5% B to 50% B in 72 min., detection 254 nm]. Fractions containing the desired product were combined and concentrated in vacuum. The residue was dissolved in i-PrOH (15 ml) and evaporated in vacuum. Obtained residue was dissolved in i-PrOH (5 ml) and 1 M HCl/ether (50 ml) was added. Precipitate was filtrated and dried in vacuum to provide hydrochloric salt of target product (3) (77 mg, 25%) as yellowish solid. LC-MS [M+H] 330.1 ($C_{18}H_{19}NO_3S+H$, requires 330.43).

Synthesis of (2S,3R)-3-hydroxy-2-[4-(4-morpholin-4-ylmethyl-phenylsulfanyl)-benzoyl amino]-butyric acid methyl ester (4)

A solution of compound (3) (33 mg, 0.09 mmol), HATU (34 g, 0.09 mmol) and DIEA (63 μl, 0.36 mmol) in DMF (800 μl) was maintained at ambient temperature for 10 min followed by the addition of compound H-Thr-OMe hydrochloride (18 mg, 0.11 mmol). Reaction mixture was stirred at ambient temperature overnight followed by the dilution with EtOAc (80 ml). Solution was extracted with water (20 ml×2) and brine (20 ml). Organic layer was dried over MgSO₄ and evaporated. Residue was dried in vacuum to provide target compound (4) (39 mg, 98%) as brown solid. LC-MS [M+H] 445.3 ($C_{23}H_{28}N_2O_5S+H$, requires 445.56).

Synthesis of N-((1S,2R)-2-hydroxy-1-hydroxycarbamoyl-propyl)-4-(4-morpholin-4-ylmethyl-phenylsulfanyl)-benzamide (47-5)

A solution of hydroxylamine hydrochloride (39 mg, 0.54 mmol) in MeOH (anh, 2 ml) was cooled to −5° C. followed by the addition of 25% NaOMe/MeOH (188 μl, 0.81 mmol) under nitrogen. Reaction mixture was stirred at −5° C. for additional 5 min, cooled to −20° C., and solution of compound (4) (0.09 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (47-5) (25.8 mg, 52%) as white solid. LC-MS [M+H] 446.2 ($C_{22}H_{27}N_3O_5S+H$, requires 446.55).

| Compound | Scale (mmol) | Yield (mg) | Yield (%) | Purity (%) | [M + H] | Retention time (min)* |
|---|---|---|---|---|---|---|
| (47-5) | 0.09 | 25.8 | 52 | 98.7 | 446.2 | 3.11 |

*[Chromolith SpeedRod RP-18e C18 column (4.6 x 50 mm); flow rate 1.5 ml/min; mobile phase A: 0.1% TFA/water; mobile phase B 0.1% TFA/ACN; gradient elution from 5% B to 100% B over 9.6 min, detection 254 nm Compound (6)

Compound (6) may be synthesized from compound (5) using OXONE oxidation in dichloromethane.

Example 48

N-((1S,2R)-2-Hydroxy-1-hydroxycarbamoyl-propyl)-4-(4-morpholin-4-ylmethyl-benzyl)-benzamide

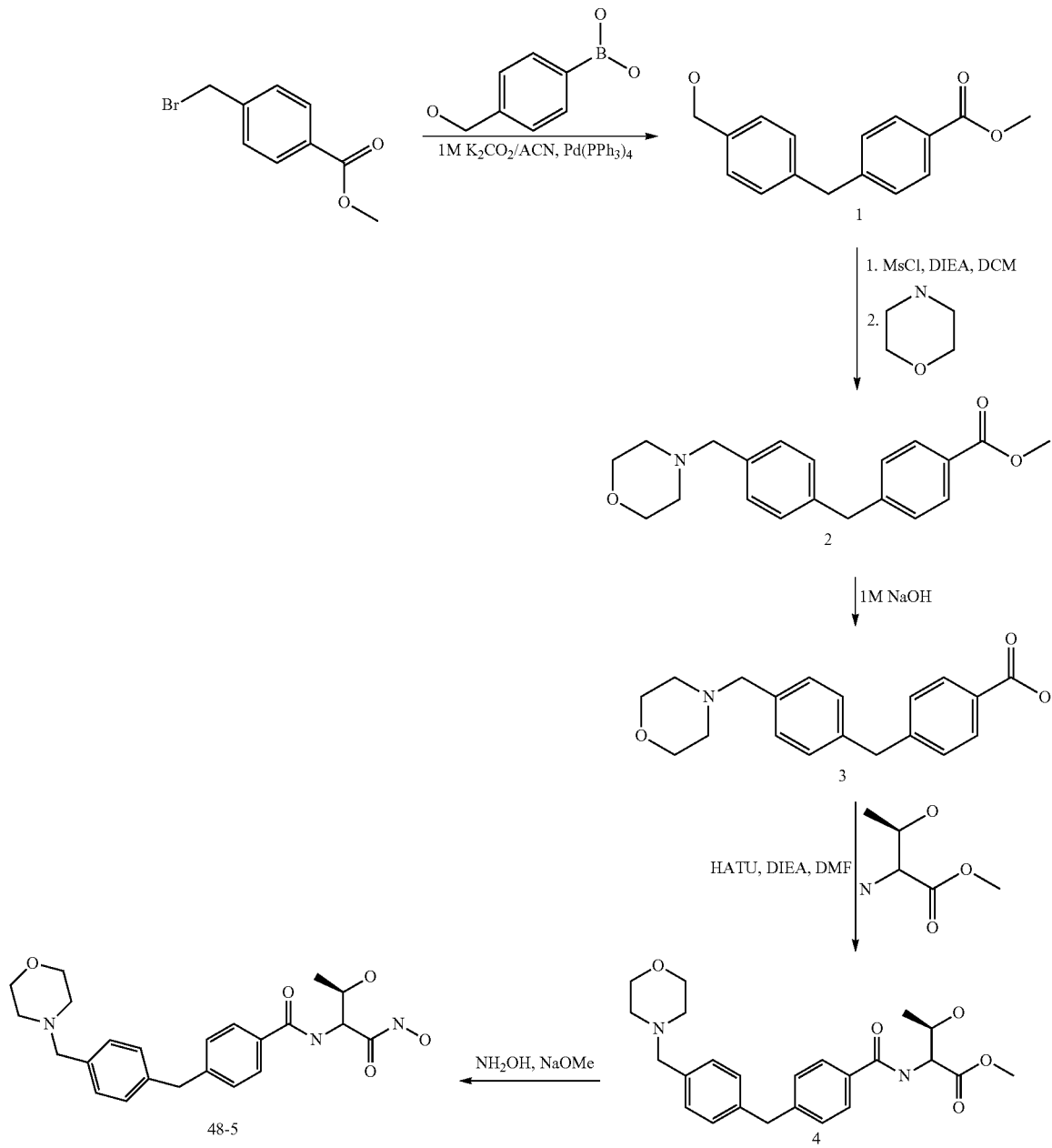

Synthesis of 4-(4-hydroxymethyl-benzyl)-benzoic acid methyl ester (1)

A mixture of 4-(hydroxymethyl)phenylboronic acid (304 mg, 2.0 mmol), methyl 4-(bromomethyl)-benzoate (229 mg, 1.0 mmol), Pd(PPh$_3$)$_4$ (12 mg, 0.01 mmol) and 1 M aq. K$_2$CO$_3$ (400 µl) in ACN (800 µl) was irradiated in microwave oven (max. power 250 W, 160° C.) for 7 min and cooled to ambient temperature. Reaction mixture was diluted with EtOAc (100 ml) and extracted with 5% aq. NaHCO$_3$ (30 ml) and brine (30 ml). Organic layer was dried over MgSO$_4$ (anh.). Solvent was evaporated in vacuum. Residue was dried in vacuum overnight to provide target product (1) (224 mg, 88%) as yellow oil.

Synthesis of 4-(4-morpholin-4-ylmethyl-benzyl)-benzoic acid methyl ester (2)

A solution of compound (1) (204 mg, 0.8 mmol) and DIEA (191 µl, 1.1 mmol) in DCM (2 ml) was cooled to 0° C. followed by the addition of MsCl (86 µl, 1.1 mmol).

Reaction mixture was maintained at 0° C. for 1 h followed by the addition of mixture of DIEA (191 μl, 1.1 mmol) and morpholine (131 μl, 1.5 mmol). Temperature of the reaction mixture was allowed to rise to ambient. Reaction mixture was maintained at ambient temperature overnight and diluted with EtOAc (80 ml). Organic layer was washed with 5% NaHCO$_3$ (20 ml) and brine (20 ml) and dried over MgSO$_4$ (anh.). Solvent was evaporated in vacuum. Residue was dissolved in DMSO (1 ml) and subjected to HPLC purification. [YMC-Pack ODS-A C-18 column (30×100 mm); flow rate=15 ml/min; injection volume 1.0 ml; mobile phase A: 100% water, 0.1% TFA; mobile phase B: 100% ACN, 0.1% TFA; gradient elution from 15% B to 70% B in 70 min., detection 254 nm]. Fractions containing the desired product were combined and concentrated in vacuum. The residue was dissolved in EtOAc (25 ml), extracted with 5% aq. NaHCO$_3$ (20 ml) and brine (20 ml) and dried over MgSO$_4$ (anh.). Solvent was evaporated in vacuum. Residue was dried in vacuum overnight to provide target product (2) (73 mg, 28%) as white solid. LC-MS [M+H] 326.3 (C$_{20}$H$_{23}$NO$_3$+H, requires 326.42).

Synthesis of
4-(4-morpholin-4-ylmethyl-benzyl)-benzoic acid (3)

To a solution of compound (2) (73 mg, 0.22 mmol) in dioxane (500 μl) 1 M aq. NaOH (1.5 ml, 1.5 mmol) was added. Reaction mixture was maintained at ambient temperature overnight and acidified with 1 M aq. HCl to pH~5. Solvents were evaporated. Residue was dissolved in DMSO (1 ml) and subjected to HPLC purification. [YMC-Pack ODS-A C-18 column (30×100 mm); flow rate=15 ml/min; injection volume 1 ml; mobile phase A: 100% water, 0.1% TFA; mobile phase B: 100% ACN, 0.1% TFA; gradient elution from 5% B to 50% B in 70 min., detection 254 nm]. Fractions containing the desired product were combined and concentrated in vacuum. The residue was dissolved in i-PrOH (15 ml) and evaporated in vacuum. Obtained residue was dissolved in i-PrOH (5 ml) and 1 M HCl/ether (50 ml) was added. Precipitate was filtrated and dried in vacuum to provide hydrochloric salt of target product (3) (38 mg, 50%) as white solid. LC-MS [M+H] 312.4 (C$_{19}$H$_{21}$NO$_3$+H, requires 312.39).

Synthesis of (2S,3R)-3-hydroxy-2-[4-(4-morpholin-4-ylmethyl-benzyl)-benzoylamino]-butyric acid methyl ester (4)

A solution of compound (3) (31 mg, 0.09 mmol), HATU (34 g, 0.09 mmol) and DIEA (63 μl, 0.36 mmol) in DMF (800 μl) was maintained at ambient temperature for 10 min followed by the addition of H-Thr-OMe hydrochloride (18 mg, 0.11 mmol). Reaction mixture was stirred at ambient temperature overnight followed by the dilution with EtOAc (100 ml). Solution was extracted with water (20 ml×2) and brine (20 ml). Organic layer was dried over MgSO$_4$ and evaporated. Residue was dried in vacuum to provide target compound (4) (31 mg, 82%) as yellow solid. LC-MS [M+H] 427.1 (C$_{24}$H$_{30}$N$_2$O$_5$+H, requires 427.53).

Synthesis of N-((1S,2R)-2-Hydroxy-1-hydroxycarbamoyl-propyl)-4-(4-morpholin-4-ylmethyl-benzyl)-benzamide (48-5)

A solution of hydroxylamine hydrochloride (15 mg, 0.22 mmol) in MeOH (2 ml) was cooled to −5° C. followed by the addition of 25% NaOMe/MeOH (75 μl, 0.33 mmol) under nitrogen. Reaction mixture was stirred at −5° C. for additional 5 min, cooled to −20° C., and solution of compound 4 (31 mg, 0.07 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (48-5) (18.8 mg, 50%) as white solid. LC-MS [M+H] 428.1 (C$_{23}$H$_{29}$N$_3$O$_5$+H, requires 428.51).

| Compound | Scale (mmol) | Yield (mg) | Yield (%) | Purity (%) | [M + H] | Retention time (min)* |
|---|---|---|---|---|---|---|
| (48-5) | 0.07 | 18.8 | 50 | 99.3 | 428.1 | 2.73 |

*[Chromolith SpeedRod RP-18e C18 column (4.6 x 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 49

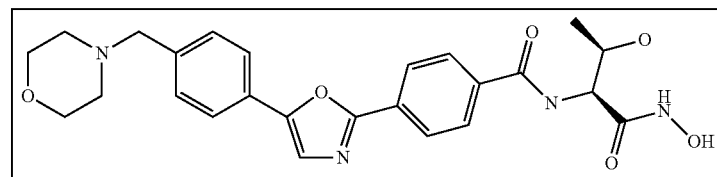

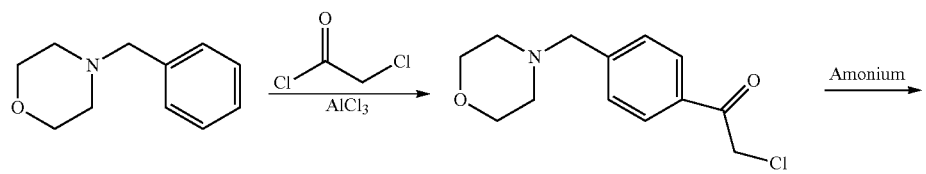

-continued
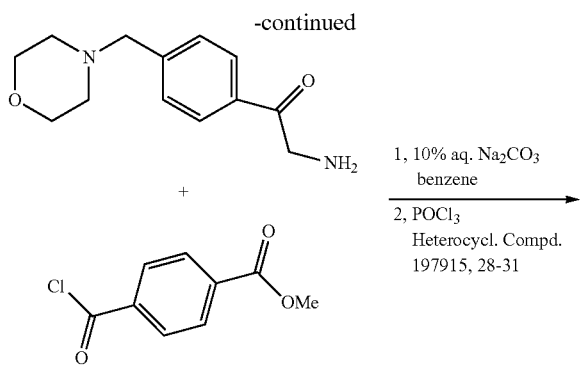
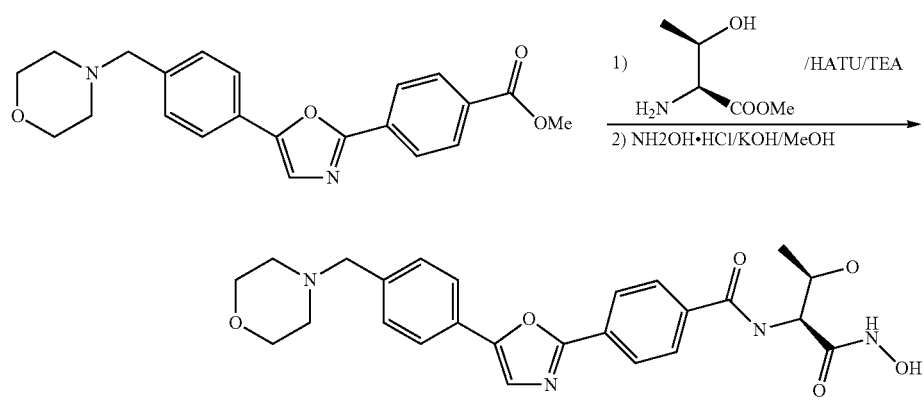
Examples 50A and 50B
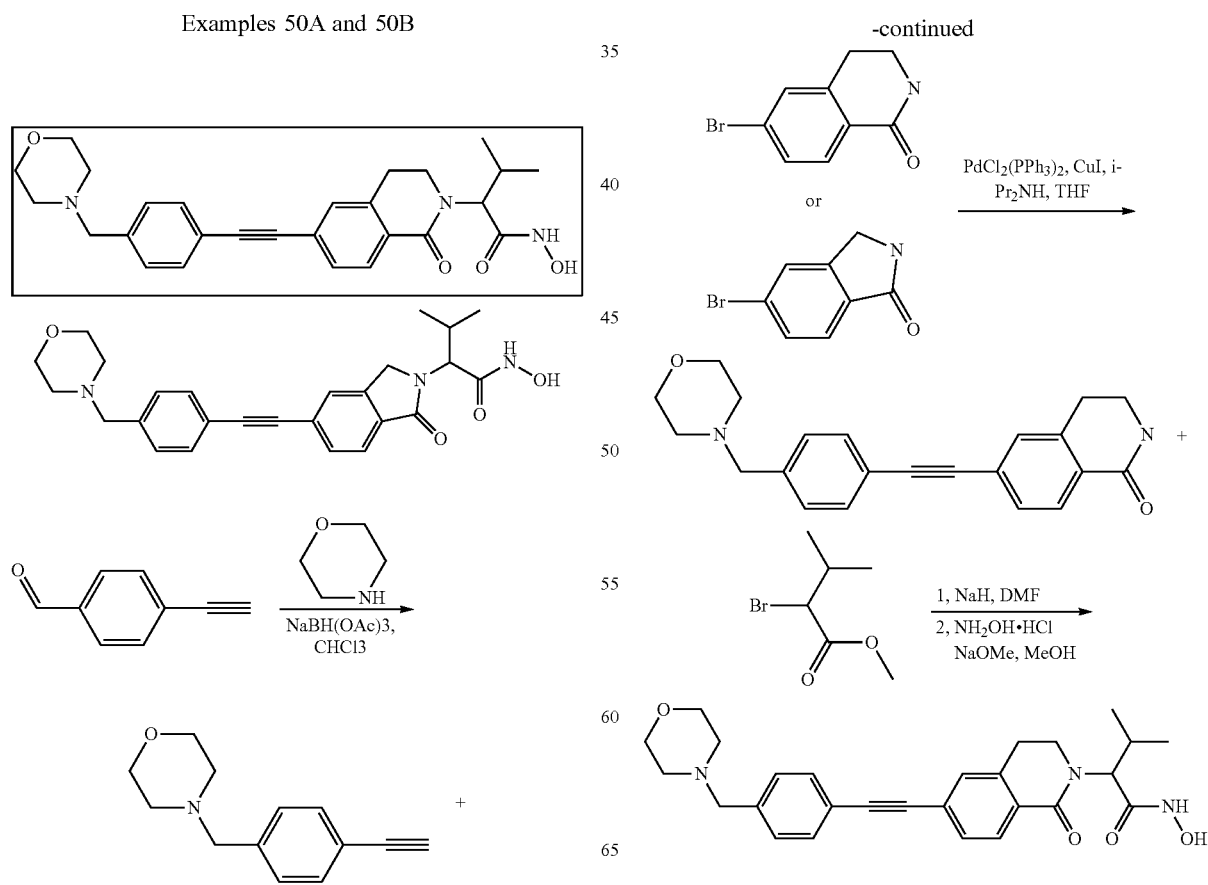

Example 51
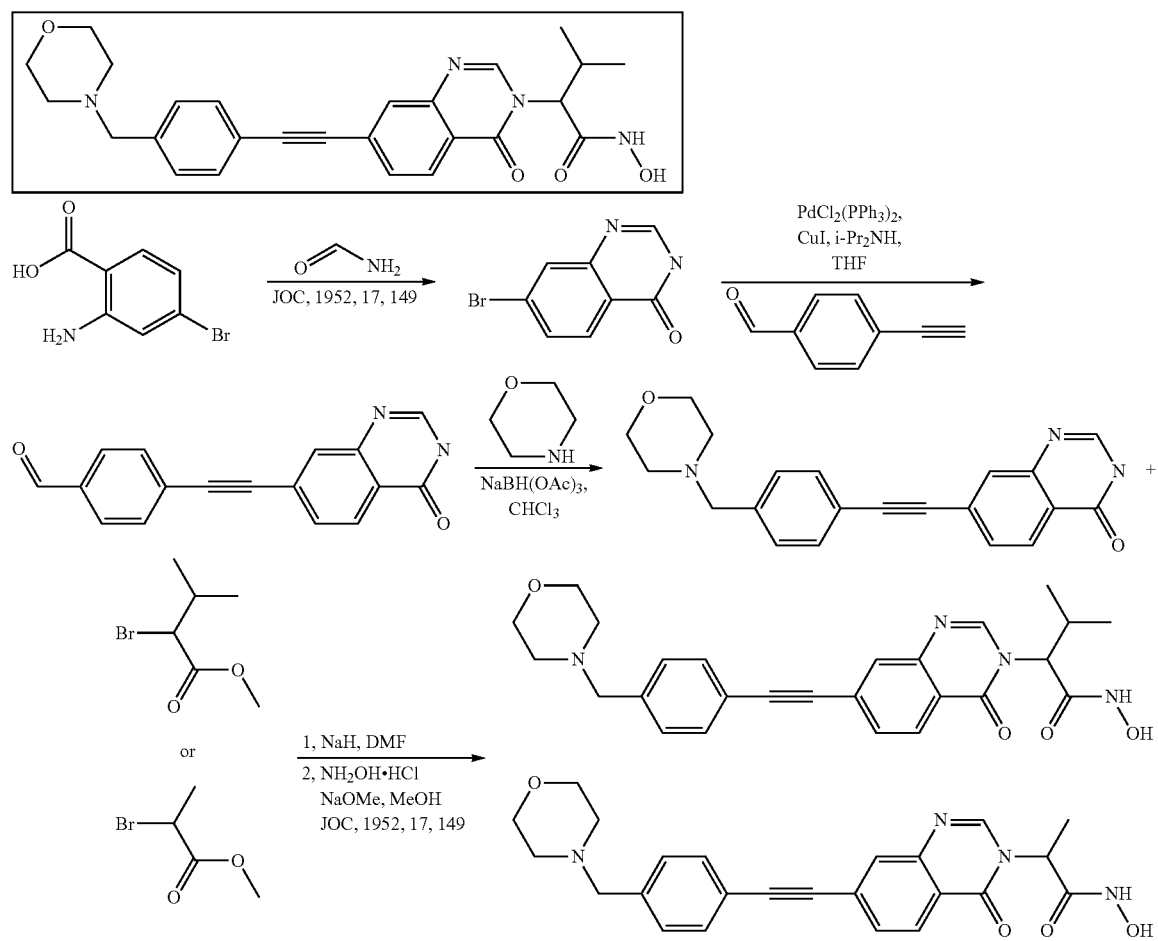
Example 52
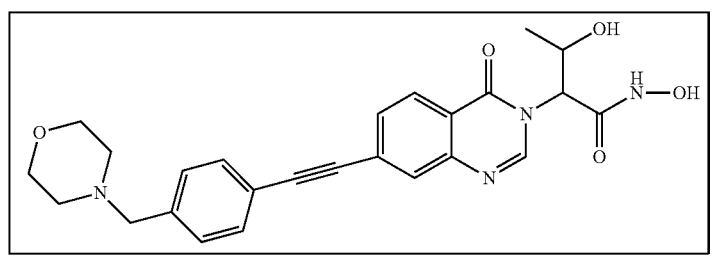
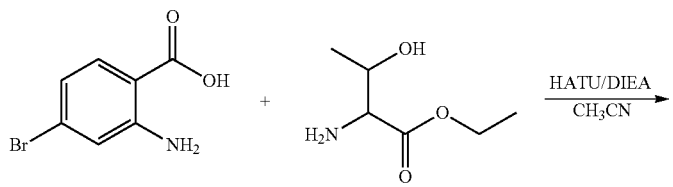

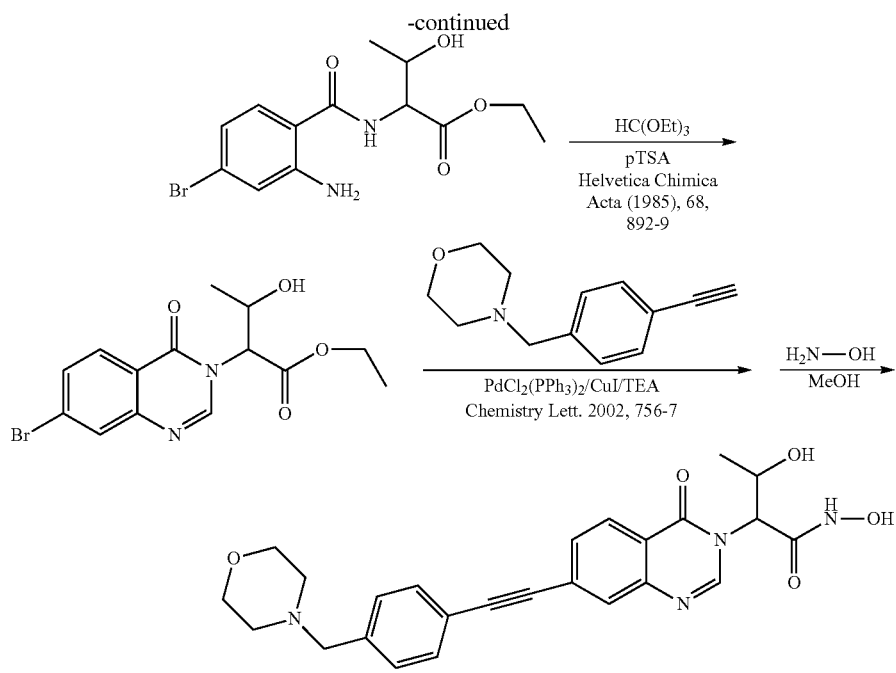
Example 53
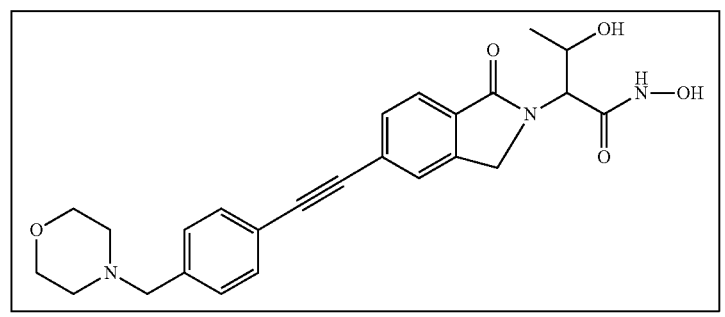
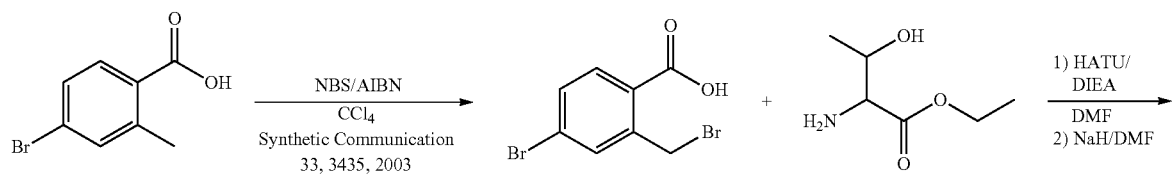
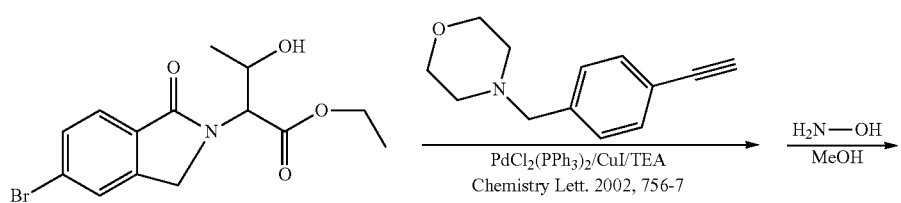

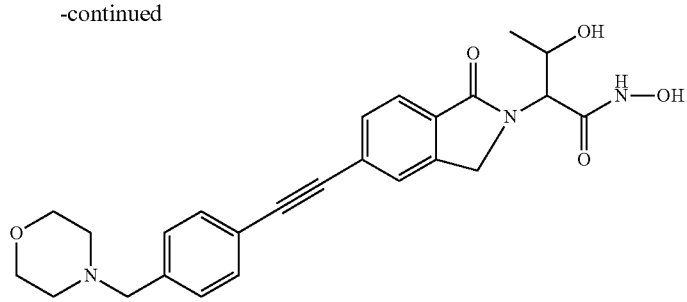
Example 54
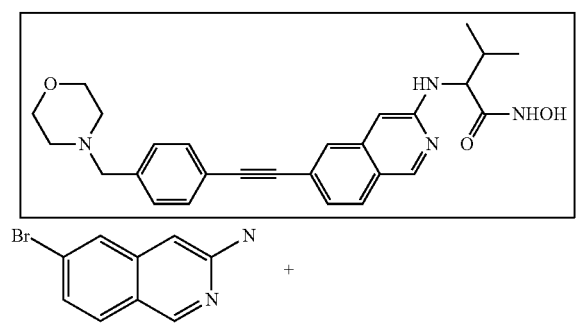
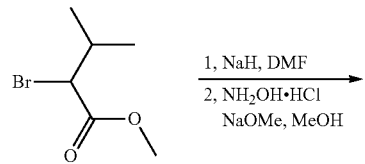
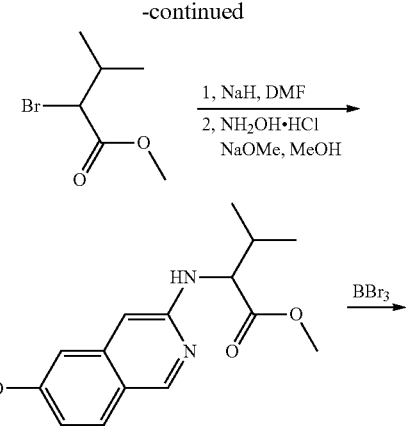
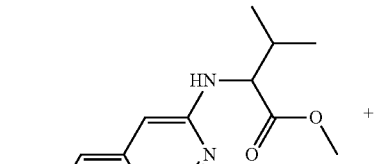
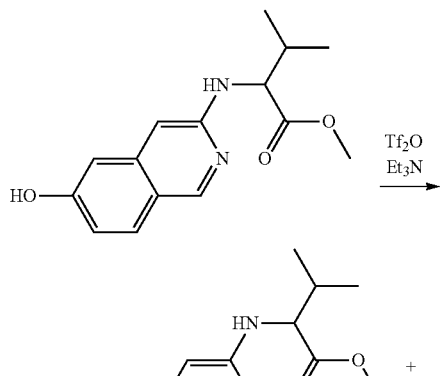
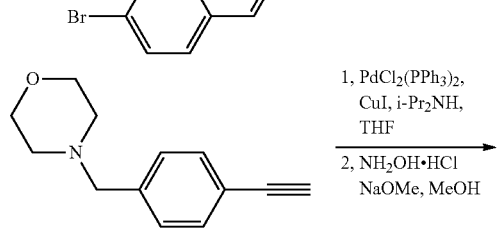
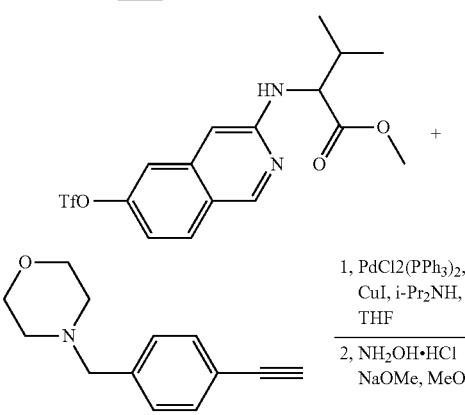
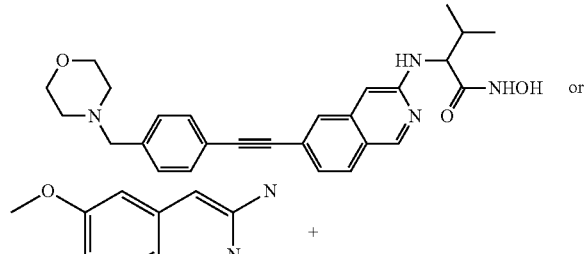
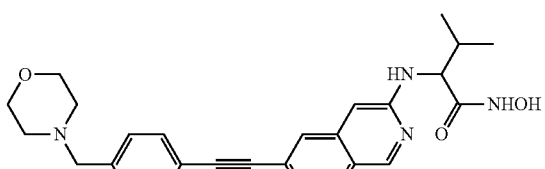

Example 55
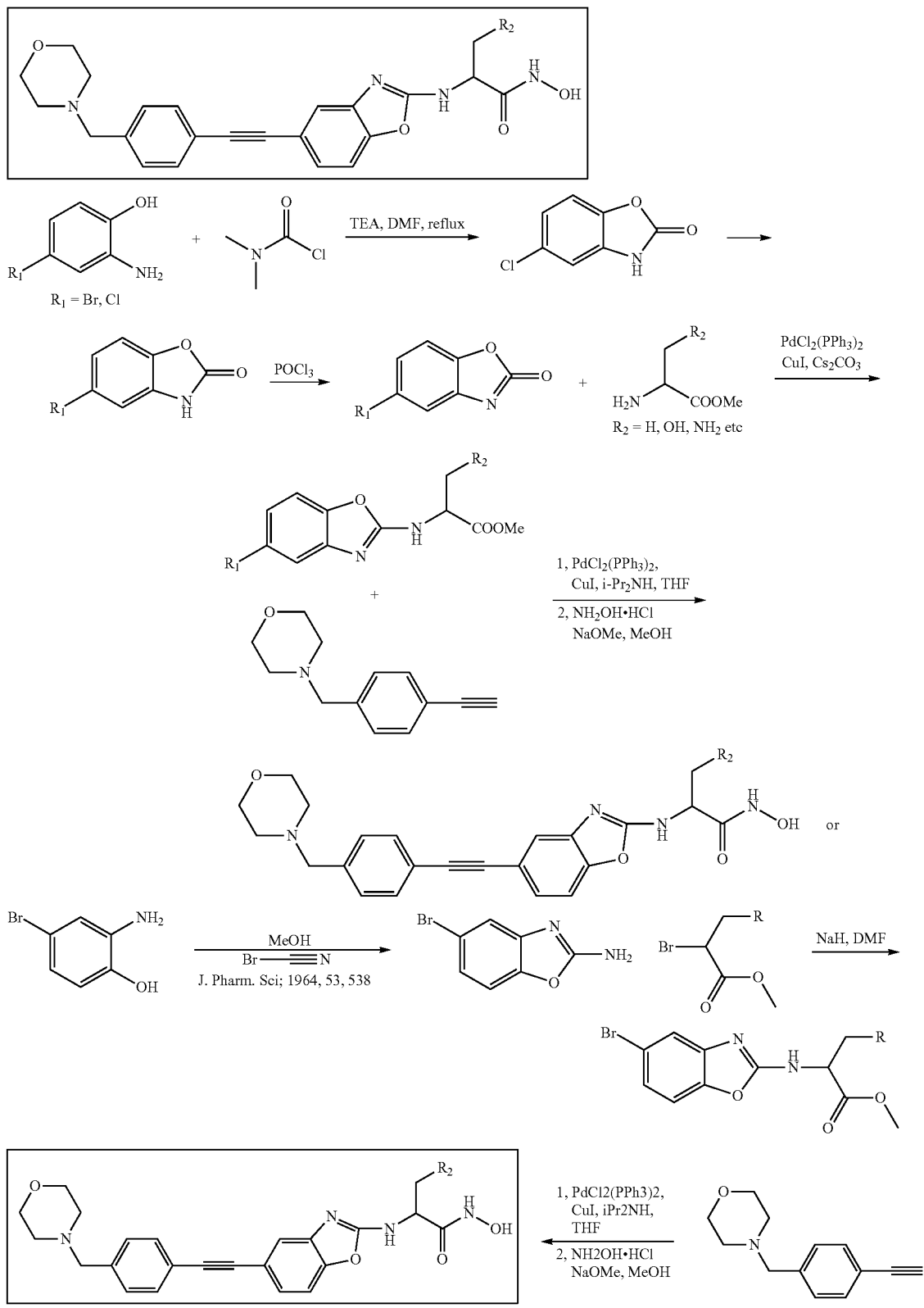

Example 56
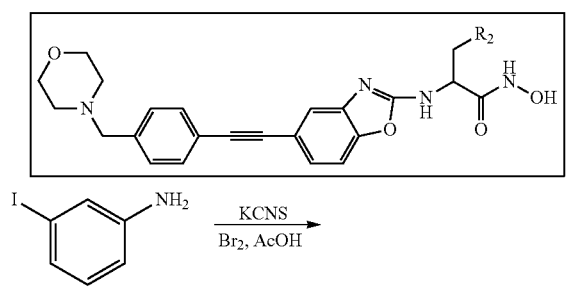
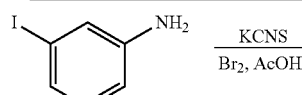
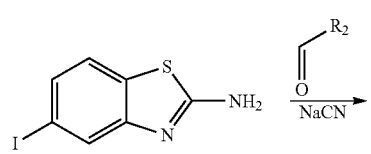
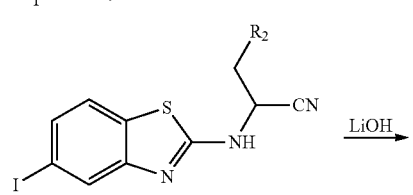
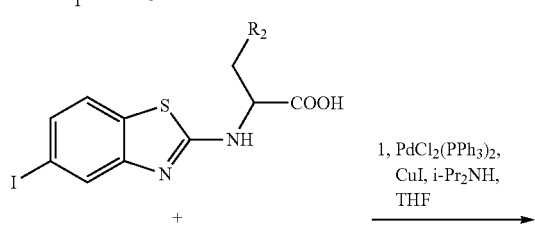
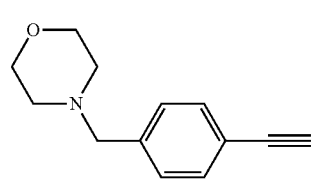
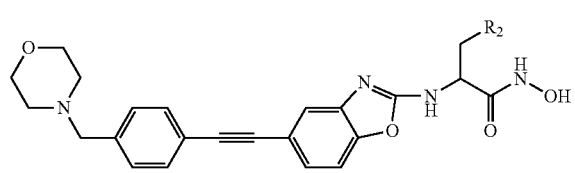
Example 57
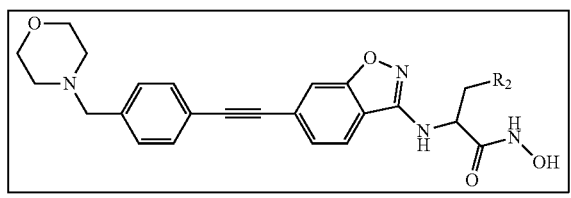
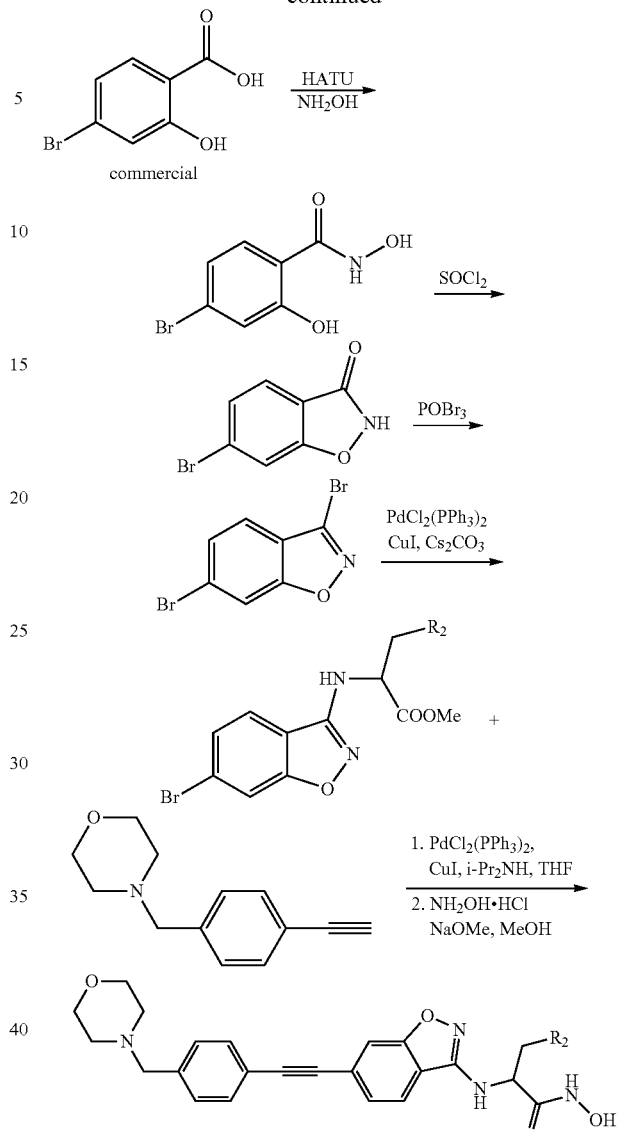
Example 58
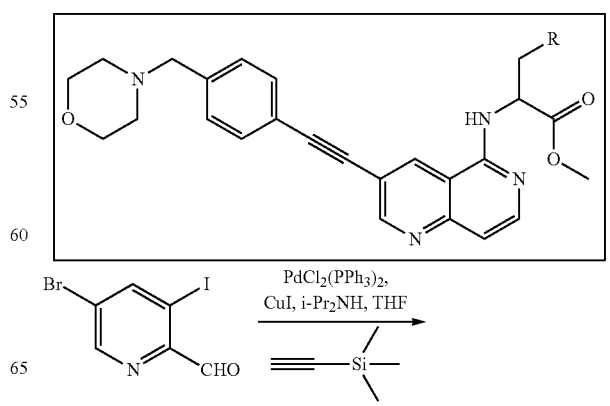

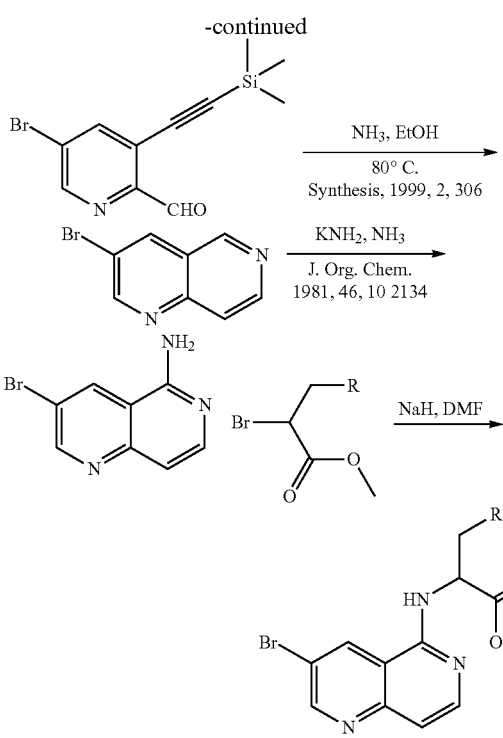
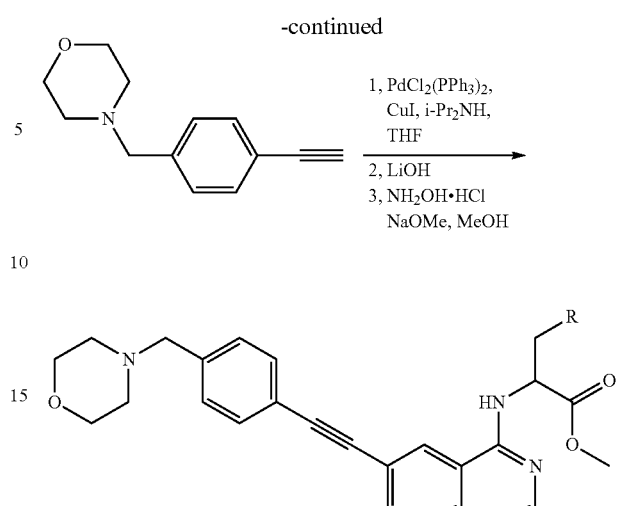
Example 59
(S)-3-amino-N-hydroxy-2-(7-((4-(morpholinomethyl)phenyl)ethynyl)-4-oxoquinazolin-3(4H)-yl)propanamide (59-8)
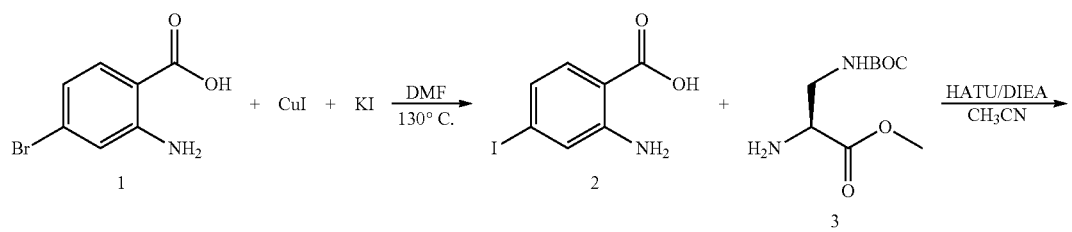
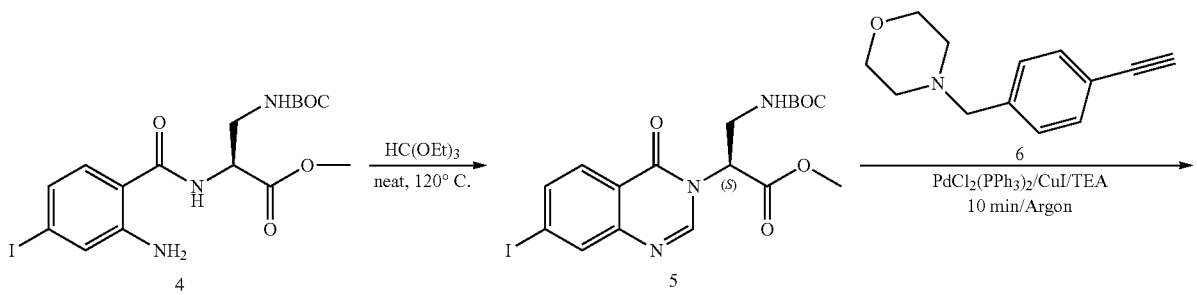
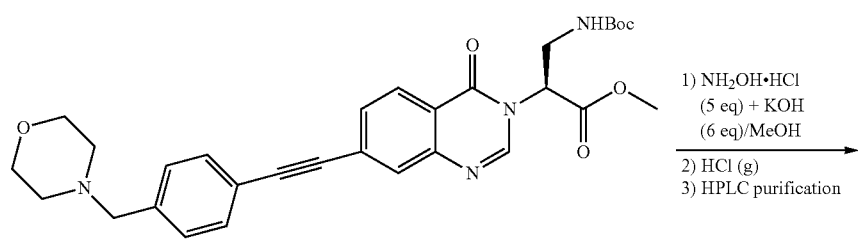

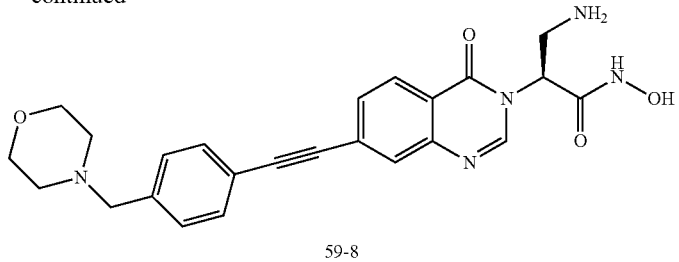

59-8

2-amino-4-iodobenzoic acid (2)

A solution of 2-amino-4-bromobenzoic acid (1) (2.15 g, 10 mmol) in degassed DMF (25 ml), CuI (3.80 g, 20 mmol) and KI (8.8 g, 50 mmol) was heated in a sealed tube at 130° C. for 18 h. The reaction mixture was cooled to room temperature and solid was filtered off. The filtrate was concentrated to dryness and the residue was stirred in ethyl acetate (400 ml) and water (100 ml) and the organic layer was separated and concentrated. The crude product was then purified over a silica gel column to give (2) (0.98 g).

(S)-methyl 2-(2-amino-4-iodobenzamido)-3-(tert-butoxycarbonylamino)propanoate (4)

To a solution of 2-amino-4-iodobenzoic acid (2) (0.98 g, 3.37 mmol), DAP hydrochloride methyl ester (compound 3) (0.952 g, 3.74 mmol), DIEA (2 mL, excess) in acetonitrile (26 mL) was added HATU (1.42 g, 3.74 mmol). The reaction mixture was stirred for 30 min and concentrated. The crude product extracted with ethyl acetate (200 mL) and concentrated to give (4) and used as such in the next step.

(S)-methyl-3-(tert-butoxycarbonylamino)-2-(7-iodo-4-oxoquinazolin-3(4H)-yl)propanoate (5)

Compound (4) (1.42 g) was heated in neat triethyl orthoformate (18 mL) at 120° C. for 24 h. Excess triethyl orthoformate was removed under reduced pressure and crude product was purified on silica gel column to give compound (5) (0.48 g).

(S)-methyl-3-(tert-butoxycarbonylamino)-2-(7-((4-(morpholinomethyl)phenyl)ethynyl)-4-oxoquinazolin-3(4H)-yl)propanoate (7)

CuI (15 mg) and PdCl$_2$(PPh$_3$)$_2$ (21 mg) was added to a degassed THF (10 ml) solution of (S)-methyl-3-(tert-butoxycarbonylamino)-2-(7-iodo-4-oxoquinazolin-3(4H)-yl)propanoate (5) (0.48 g, 1.01 mmol), diisopropyl amine (2 mL) and 4-(4-ethynylbenzyl)morpholine (6) (0.21 g, 1.05 mmol) and stirred for 1 h. The solvent was removed and extracted with ethyl acetate (2×100 ml), dried over Na$_2$SO$_4$, and concentrated to give compound (7) (0.521 g).

(S)-3-amino-N-hydroxy-2-(7-((4-(morpholinomethyl)phenyl) ethynyl)-4-oxoquinazolin-3(4H)-yl) propanamide (59-8)

To a stirred solution of compound (7) (0.18 g, 0.338 mmol) and hydroxylamine hydrochloride (118 mg, 1.69 mmol) in methanol (10 ml), KOH (113 mg, 2 mmol) was added and stirred for 30 min. Excess solvent was removed and crude product was acidified with dilute AcOH (10%) and extracted with ethyl acetate (2×50 ml), dried and concentrated. After deprotection of BOC group using HCl gas in ethyl acetate, crude product was purified using HPLC to give compound (59-8). [M+H$^+$]=448

Example 60

N-Hydroxy-2-isopropyl-N'-[4-(4-morpholin-4-ylmethyl-phenylethynyl)-phenyl]-malonamide

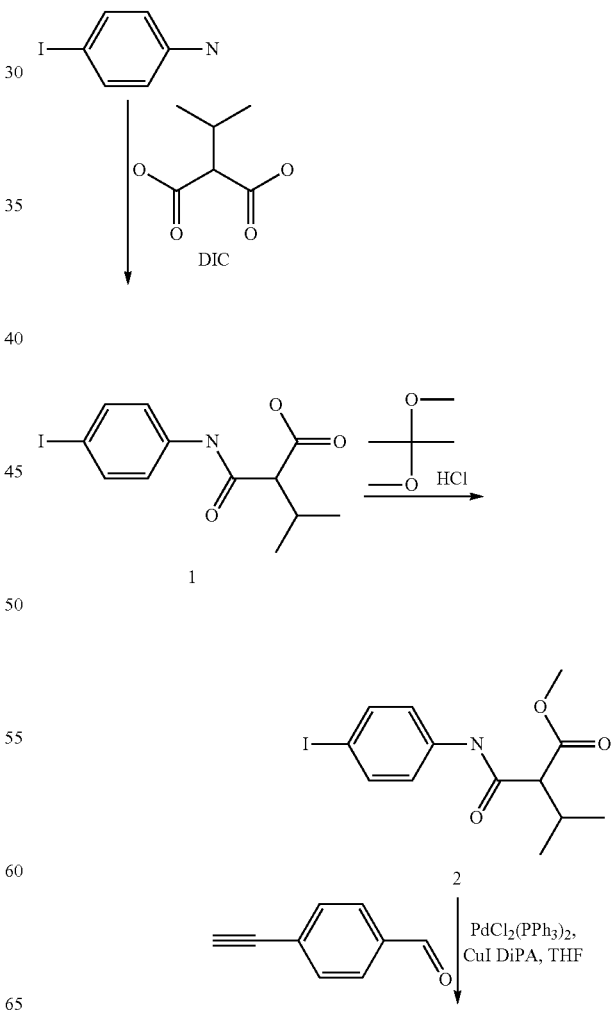

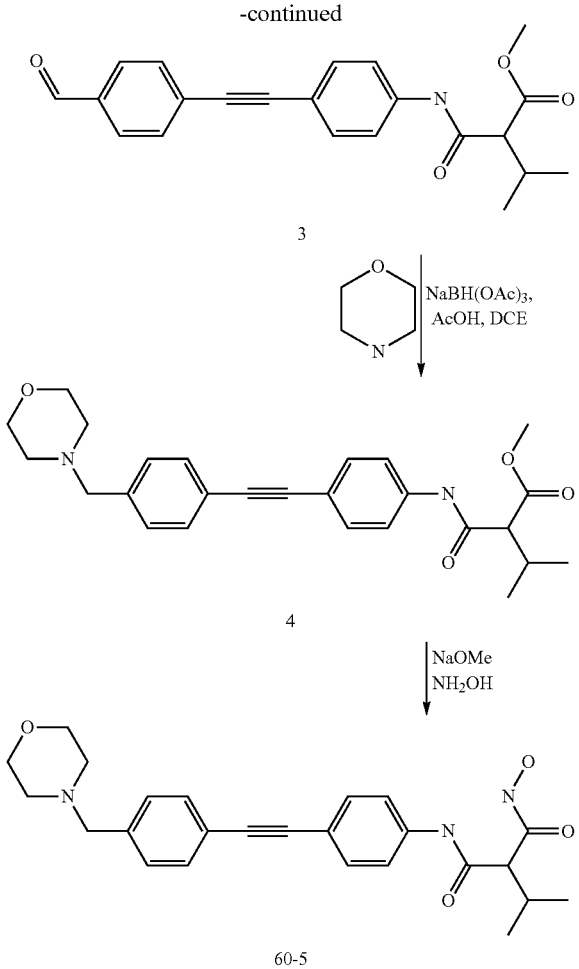

Synthesis of 2-(4-Iodo-phenylcarbamoyl)-3-methyl-butyric acid (1)

A solution of isopropylmalonic acid (613 mg, 4.2 mmol) and DIC (330 μl, 2.1 mmol) in chloroform (2 ml) was maintained at ambient temperature for 10 min followed by the addition of 4-iodoaniline (438 mg, 2.0 mmol). Reaction mixture was stirred at ambient temperature for additional 2 h and diluted with EtOAc (150 ml). Solution was extracted with water (30 ml×2) and brine (30 ml), and dried over MgSO$_4$ (anh). Solvent was evaporated in vacuum. Residue was dissolved in DCM (2 ml) and subjected to flash chromatography on CombiFlash® Companion unit equipped with RediSep® flash column (normal phase, 35-60 micron average particle size silicagel, 80 g, Teledyne Isco); flow rate=60 ml/min; injection volume 2.5 ml; mobile phase A: DCM; mobile phase B: MeOH; gradient 0-60% B in 60 min. Fractions containing the desired product were combined and concentrated in vacuum. Residue was dried in vacuum overnight to obtain target product (1) (89 mg, 13%) as white solid. LC-MS [M+H] 348.1 (C$_{12}$H$_{14}$INO$_3$+H, requires 348.16).

Synthesis of 2-(4-iodo-phenylcarbamoyl)-3-methyl-butyric acid methyl ester (2)

A solution of compound (1) (89 g, 0.26 mmol) and HCl (conc., 500 μl) in 2,2-dimethoxypropane (2.0 ml, 16 mmol) was maintained at ambient temperature overnight. Reaction mixture was evaporated in vacuum. Residue was dissolved in i-PrOH (10 ml) and evaporated in vacuum. The aforementioned procedure was repeated twice. Residue was triturated with ether, filtrated, washed with ether and dried in vacuum overnight to obtained hydrochloric salt of target product (2) (84 mg, 99%) as white amorphous solid. LC-MS [M+H] 361.9 (C$_{13}$H$_{16}$INO$_3$+H, requires 362.19).

Synthesis of 2-[4-(4-formyl-phenylethynyl)-phenylcarbamoyl]-3-methyl-butyric acid methyl ester (3)

A solution of compound (2) (84 mg, 0.23 mmol), 4-ethynylbenzaldehyde (36 mg, 0.28), Ph$_3$P (6 mg, 0.23 mmol) and di-isopropylamine (400 in THF (anh., 800 μl was purged with dry nitrogen for 2 min followed by the addition of mixture of PdCl$_2$(PPh$_3$)$_2$ (5 mg, 0.007 mmol) and CuI (3 mg, 0.014 mmol). Reaction mixture was irradiated in microwave oven (max. power 250 W, 120° C.) for 10 min and cooled to ambient temperature. Solvents were evaporated in vacuum. Residue was dissolved in EtOAc (80 ml) and extracted with 5% aq. NaHCO$_3$ (20 ml×2) and brine (20 ml). The organic layer was dried over anh. MgSO$_4$ and evaporated in vacuum. Residue was dried in vacuum overnight at ambient temperature to provide target material (3) (82 mg, 99%) as brown solid. LC-MS [M+H] 364.2 (C$_{22}$H$_{21}$NO$_4$+H, requires 364.43).

Synthesis of 3-methyl-2-[4-(4-morpholin-4-ylmethyl-phenylethynyl)-phenylcarbamoyl]-butyric acid methyl ester (4)

A solution of compound (3) (82 mg, 0.23 mmol), AcOH (52 μl, 0.92 mmol) and morpholine (30 μl, 0.35 mmol) in DCE (1 ml) was maintained at ambient temperature for 10 min followed by the addition of sodium triacetoxyborohydride (98 mg, 0.46 mmol). Reaction mixture was stirred for 2 h at ambient temperature. Reaction was quenched with 5% aq. NaHCO$_3$ (20 ml) and extracted with EtOAc (50 ml×2). Organic layer was washed with brine (20 ml), dried over anh. MgSO$_4$ and evaporated in vacuum. Residue was dried in vacuum overnight to provide target material (4) (98 g, 98%) as yellowish solid. LC-MS [M+H] 435.0 (C$_{26}$H$_{30}$N$_2$O$_4$+H, requires 435.55).

Synthesis of N-hydroxy-2-isopropyl-N'-[4-(4-morpholin-4-ylmethyl-phenylethynyl)-phenyl]-malonamide (60-5)

A solution of hydroxylamine hydrochloride (97 mg, 1.38 mmol) in MeOH (anh, 2 ml) was cooled to −5° C. followed by the addition of 25% NaOMe/MeOH (473 μl, 1.8 mmol) under nitrogen. Reaction mixture was stirred at −5° C. for additional 5 min, cooled to −20° C., and solution of compound (4) (98 mg, 0.23 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (60-5) (12 mg, 9.4%) as white solid. LC-MS [M+H] 436.0 ($C_{25}H_{29}N_3O_4$+H, requires 436.54).

| Com-pound | Scale (mmol) | Yield (mg) | Yield (%) | Purity (%) | [M + H] | Retention time (min)* |
|---|---|---|---|---|---|---|
| (60-5) | 0.23 | 12 | 9.4 | 99.8 | 436.0 | 3.31 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 61

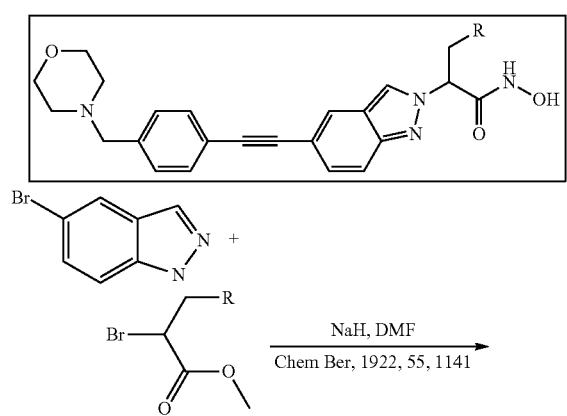

Example 62

Synthesis of (R)—N-Hydroxy-2-[4-(4-morpholin-4-yl-methyl-phenylethynyl)-benzenesulfonylamino]-3-phenylpropionamide

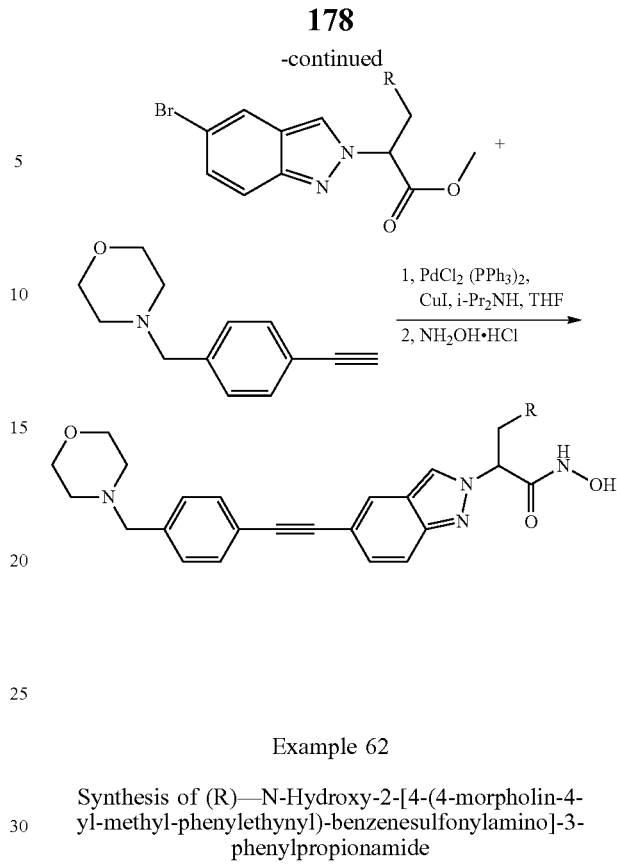

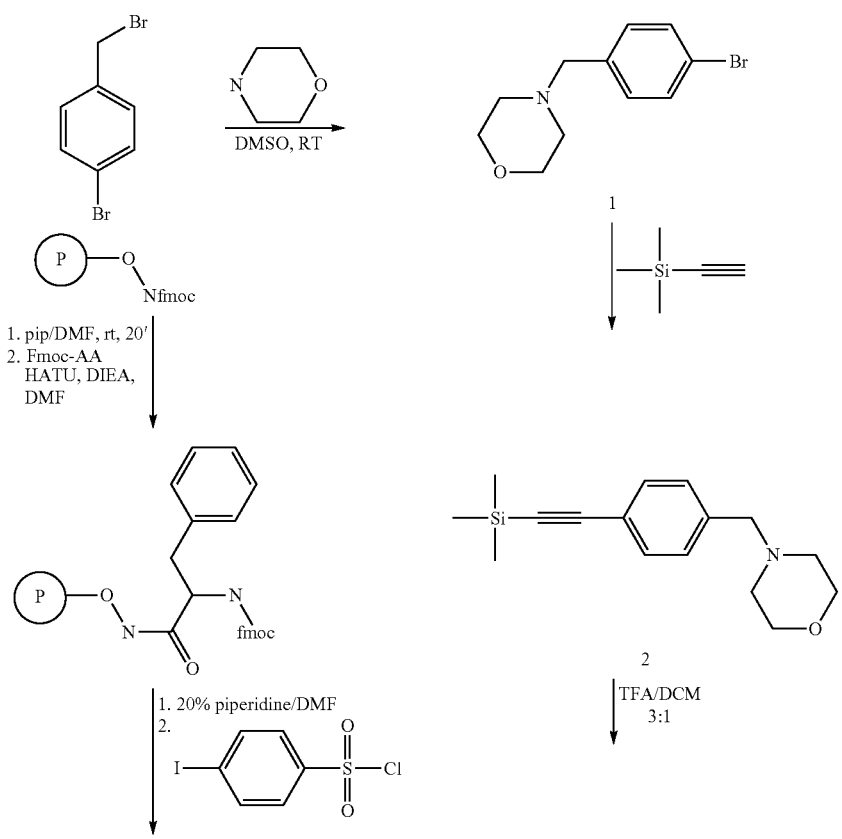

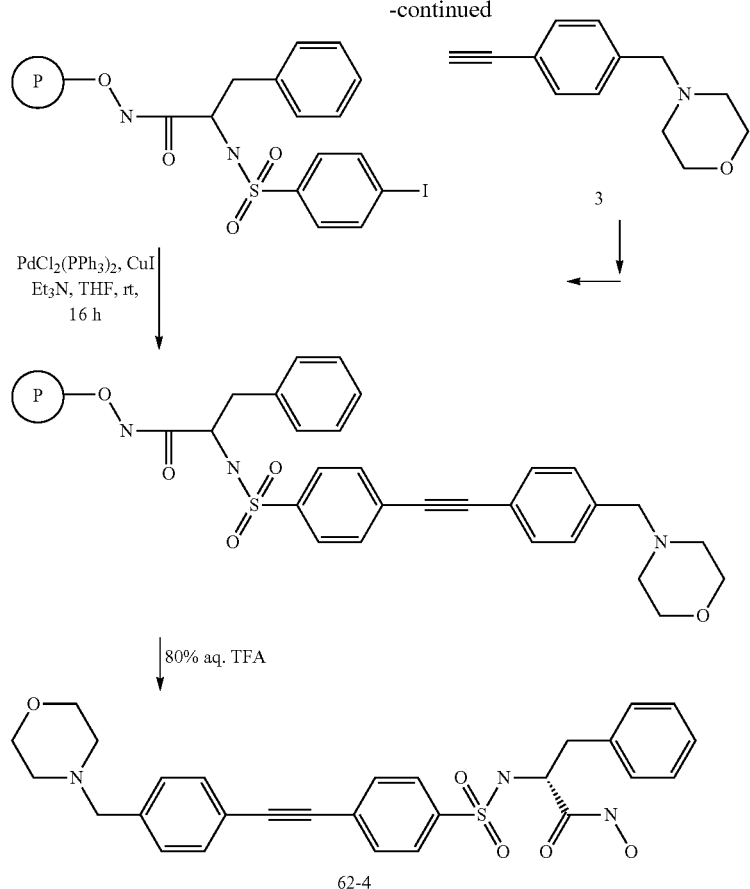

Synthesis of 4-(4-bromo-benzyl)-morpholine (1)

To a solution of morpholine (2.61 ml, 30 mmol) in DMSO (25 ml) was added 4-bromobenzylbromide (2.5 g, 10 mmol). Reaction mixture was stirred at ambient temperature for 30 min. Solvents were evaporated in vacuum. Residue was dissolved in EtOAc (150 ml) and extracted with 5% aq. NaHCO$_3$ (50 ml×2) and brine (50 ml). The organic layer was dried over anh. MgSO$_4$ and evaporated in vacuum. Residue was dried in vacuum overnight at ambient temperature to provide target material (1) (2.27 g, 87%) as a white solid.

Synthesis of 4-(4-trimethylsilanylethynyl-benzyl)-morpholine (2)

To a solution of compound (1) (2.27 g, 8.9 mmol), ethynyltrimethylsilane (1.0 g, 10 mmol), PPh$_3$ (262 mg, 1 mmol) and dipropylamine (5 ml, 36.5 mmol) in DMF (10 ml) was added a mixture of PdCl$_2$(PPh$_3$)$_2$ (130 mg, 0.18 mmol) and CuI (100 mg, 0.5 mmol). Reaction mixture was irradiated in microwave oven (max. power 250 W, 120° C.) for 25 min and cooled to ambient temperature. Reaction mixture was diluted with water (100 ml) and extracted with EtOAc (50 ml×2). Organic layer was washed with 5% aq. NaHCO$_3$ (50 ml) and brine (50 ml), and dried over MgSO$_4$ (anh). Solvent was evaporated in vacuum. Residue was dried in vacuum overnight to produce target material (2) (2.36 g, 97%) as brown oil. LC-MS [M+H] 274.1 (C$_{16}$H$_{23}$NOSi+H, requires 274.46).

4-(4-Ethynyl-benzyl)-morpholine (3)

To a solution of compound (2) (2.36 g, 8.6 mmol) in DCM (3 ml) was added TFA (10 ml, 135 mmol). Reaction mixture was maintained at ambient temperature for 1.5 h. Solvent was evaporated in vacuum. Residue was dissolved in DMSO (15 ml) and subjected to HPLC purification. [Nanosyn-Pack Microsorb 100-10 C-18 column (50×300 mm); flow rate=50 ml/min; injection volume 18 ml; mobile phase A: 100% water, 0.1% TFA; mobile phase B: 100% ACN, 0.1% TFA; gradient elution from 5% B to 20% B in 60 min., detection 254 nm]. Fractions containing the desired product were combined and concentrated in vacuum. Residue was dissolved in ether (100 ml) and washed with 1 M aq. NaOH (50 ml), and brine (50 ml). Organic layer was dried over MgSO$_4$ (anh). Solvent was evaporated in vacuum. Residue was dried in vacuum overnight to produce target material (3) (687 mg, 40%) as off-white solid. LC-MS [M+H] 202.4 (C$_{13}$H$_{15}$NO+H, requires 202.28).

Synthesis of (R)—N-Hydroxy-2-[4-(4-morpholin-4-ylmethyl-phenylethynyl)-benzenesulfonyl amino]-3-phenyl-propionamide (62-4)

2-Chlorotrityl-N-Fmoc-hydroxylamine resin (50 mg, 0.03 mmol) was placed in 3 cc plastic syringe equipped with plunger and plastic frit. Resin was swelled in DCM (2 ml) at ambient temperature for 10 min. DCM was discharged followed by the treatment with 20% piperidine/DMF (2 ml×2×10 min). Solvents were discharged and resin was washed with DCM (2 ml×6×5 min) followed by the addition of mixture of Fmoc-D-Phe-OH (47 mg, 0.12 mmol), HATU (46 mg, 0.12 mmol) and DIEA (42 µl, 0.24 mmol) in DMF (500 µl). Syringe was agitating at 85 rpm on orbital shaker at ambient temperature overnight. Solution was discharged and resin was washed with DMF (2 ml×6×5 min) followed by the treatment with 20% piperidine/DMF (2 ml×2×10 min). Solvents were discharged and resin was washed with DCM (2 ml×6×5 min) followed by the addition of mixture of compound (3) (48 mg, 0.24 mmol), PdCl$_2$(PPh$_3$)$_2$ (20 mg, 0.03 mmol), CuI (10 mg, 0.05 mmol) and di-propylamine (200 µl) in DMF (400 µl). Syringe was agitating at 85 rpm on orbital shaker at ambient temperature overnight. Solution was discharged and resin was washed with DMF (3 ml×4×5 min) and DCM (3 ml×4×5 min) followed by the addition of 80% aq. TFA (2 ml). Syringe was agitating at 85 rpm on orbital shaker at ambient temperature for 3 min. Solution was collected and evaporated in vacuum. Residue was dissolved in DMSO (500 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (62-4) as white solid. LC-MS [M+H] 520.5 (C$_{28}$H$_{29}$N$_3$O$_5$S+H requires 520.63).

| Compound | Scale (mmol) | Yield (mg) | Yield (%) | Purity (%) | [M + H] | Retention time (min)* |
|---|---|---|---|---|---|---|
| (62-4) | 0.03 | 4.04 | 21 | 100 | 520.5 | 3.70 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.5 min, detection 254 nm]

The following compounds were synthesized as described in this Example.

| Compound # | Structure | [M + H] |
|---|---|---|
| (62-5) | 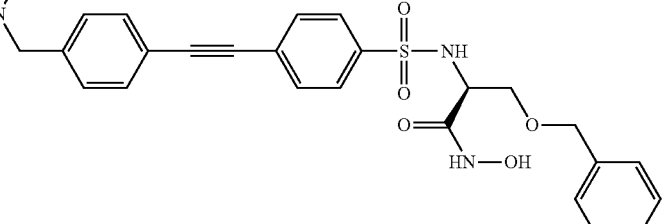 | 550 |
| (62-6) | 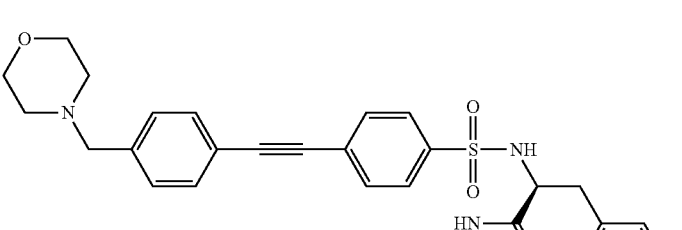 | 520 |
| (62-7) | 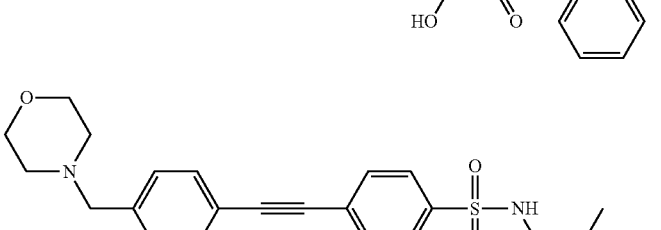 | 474 |
| (62-8) | 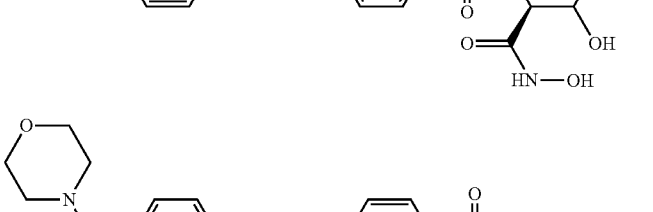 | 484 |

| Compound # | Structure | [M + H] |
|---|---|---|
| (62-9) | ![structure] | 490 |
| (62-10) | ![structure] | 470 |
| (62-11) | ![structure] | 456 |
Example 63
(2S,3R)-3,N-Dihydroxy-2-[4-(4-morpholin-4-ylmethyl-phenylethynyl)-benzenesulfinylamino]-butyramide
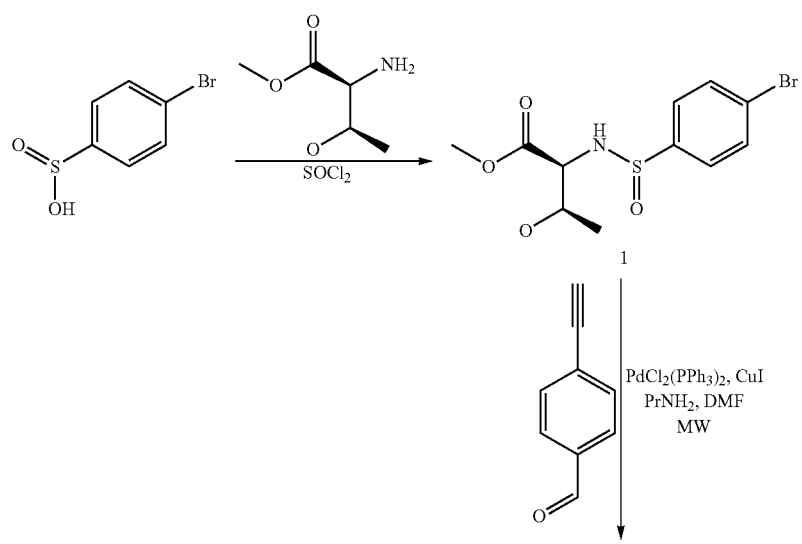

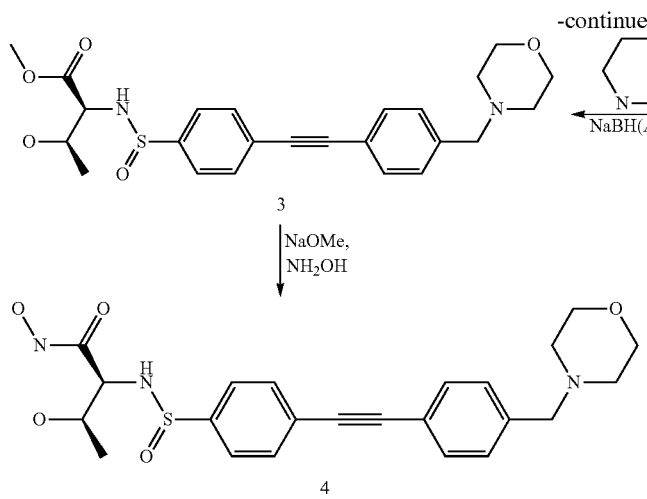
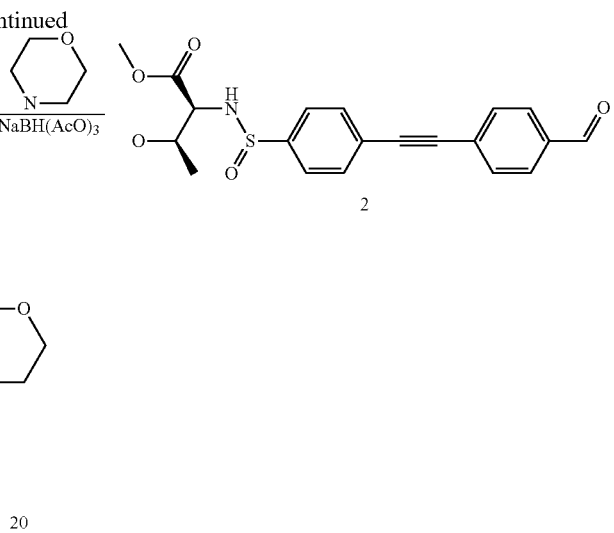

Synthesis of (2S,3R)-2-(4-bromo-benzenesulfinylamino)-3-hydroxy-butyric acid methyl ester (1)

A solution of 4-Bromobenzenesulfinic acid sodium salt dihydrate (250 mg, 0.9 mmol) in SOCl$_2$ (3 ml, 41.1 mmol) was maintained at ambient temperature for 3 h. Solvent was evaporated. Residue was dissolved in DCM (8 ml) and combined with H-Thr-OMe hydrochloride (253 mg, 1.5 mmol) followed by the dropwise addition of DIEA (500 µl, 3.0 mmol) over the period of 5 min. After stirring at ambient temperature for additional hour reaction mixture was subjected to flash chromatography on CombiFlash® Companion unit equipped with RediSep® flash column (normal phase, 35-60 micron average particle size silicagel, 4 g, Teledyne Isco); flow rate=18 ml/min; injection volume 10 ml; mobile phase A: hexane; mobile phase B: EtOAc; gradient 0-100% B in 40 min. Fractions containing the desired product were combined and concentrated in vacuum. Residue was dried in vacuum overnight to provide target product (1) (100 mg, 33%) as white solid. LC-MS [M+H] 337.8 ($C_{11}H_{14}BrNO_4S+H$, requires 337.22).

Synthesis of (2S,3R)-2-[4-(4-Formyl-phenylethynyl)-benzenesulfinylamino]-3-hydroxy-butyric acid methyl ester (2)

A solution of compound (1) (100 mg, 0.30 mmol), 4-ethynylbenzaldehyde (43 mg, 0.32 mmol), Ph$_3$P (123 mg, 0.34) and di-propylamine (1 ml) in DMF (2 ml) was purged for 5 min with dry nitrogen. Catalysts PdCl$_2$(PPh$_3$)$_2$ (30 mg, 0.043 mmol), and CuI (15 mg, 0.079 mmol) were added and reaction mixture was subjected to microwave irradiation (max. power 250 W, 120° C.) for 15 min. Reaction mixture was cooled to ambient temperature, diluted with EtOAc (100 ml) and extracted with water (30 ml), 2% aq. H$_2$SO$_4$ (30 ml), water (30 ml×2) and brine (30 ml). Organic layer was dried over Na$_2$SO$_4$ and evaporated. Residue was dried in vacuum to provide target compound (2) as brownish amorphous solid. LC-MS [M+H] 385.6 ($C_{20}H_{19}NO_5S+H$, requires 386.45). Compound (2) was used as is for the next transformation.

Synthesis of (2S,3R)-3-Hydroxy-2-[4-(4-morpholin-4-ylmethyl-phenylethynyl)-benzenesulfinylamino]-butyric acid methyl ester (3)

A solution of compound (2) (0.30 mmol) and morpholine (52 µl, 0.6 mmol) in chloroform (10 ml) was treated with NaBH(OAc)$_3$ (100 mg, 0.47 mmol) for 5 h at ambient temperature under nitrogen. Reaction was quenched with 5% aq. NaHCO$_3$ (20 ml) and extracted with EtOAc (50 ml×2). Organic layer was dried over anhydrous Na$_2$SO$_4$ and evaporated in vacuum. Residue was dissolved in DCM (2 ml) and subjected to flash chromatography on CombiFlash® Companion unit equipped with RediSep® flash column (normal phase, 35-60 micron average particle size silicagel, 12 g, Teledyne Isco); flow rate=30 ml/min; injection volume 3 ml; mobile phase A: DCM; mobile phase B: MeOH; gradient 0-5% B in 15 min. Fractions containing the desired product were combined and concentrated in vacuum. Residue was dried in vacuum overnight to provide target product (3) (92 mg, 33%) as colorless oil. LC-MS [M+H] 457.3 ($C_{24}H_{28}N_2O_5S+H$, requires 457.58).

Synthesis of (2S,3R)-3,N-dihydroxy-2-[4-(4-morpholin-4-ylmethyl-phenylethynyl)-benzenesulfinylamino]-butyramide (4)

A solution of hydroxylamine hydrochloride (84 mg, 1.2 mmol) in MeOH (anh., 2 ml) was cooled to −5° C. followed by the addition of 25% NaOMe/MeOH (411 µl, 3.15 mmol) under nitrogen. Reaction mixture was stirred at −5° C. for additional 5 min, cooled to −20° C., and solution of compound (3) (92 mg, 0.20 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (800 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and neutralized with 1 N aq. NaOH. Organics were evaporated in vacuum. Water layer was extracted with EtOAc (10 ml), dried over Na$_2$SO$_4$ and evaporated in vacuum. Residue was dried in vacuum overnight to provide free base of target product (4) (4 mg, 4.4%) as white solid. LC-MS [M+H] 458.1 ($C_{23}H_{27}N_3O_5S+H$, requires 458.56).

| Compound | Scale (mmol) | Yield (mg) | Yield (%) | Purity (%) | [M + H] | Retention time (min)* |
|---|---|---|---|---|---|---|
| (4) | 0.2 | 4 | 4.4 | 98.5 | 475.1 | 2.96 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.5 min, detection 254 nm

Example 64
N-(Hydroxycarbamoyl-pyrrolidin-3-yl-methyl)-4-(4-morpholin-4-ylmethyl-phenylethynyl)-benzamide
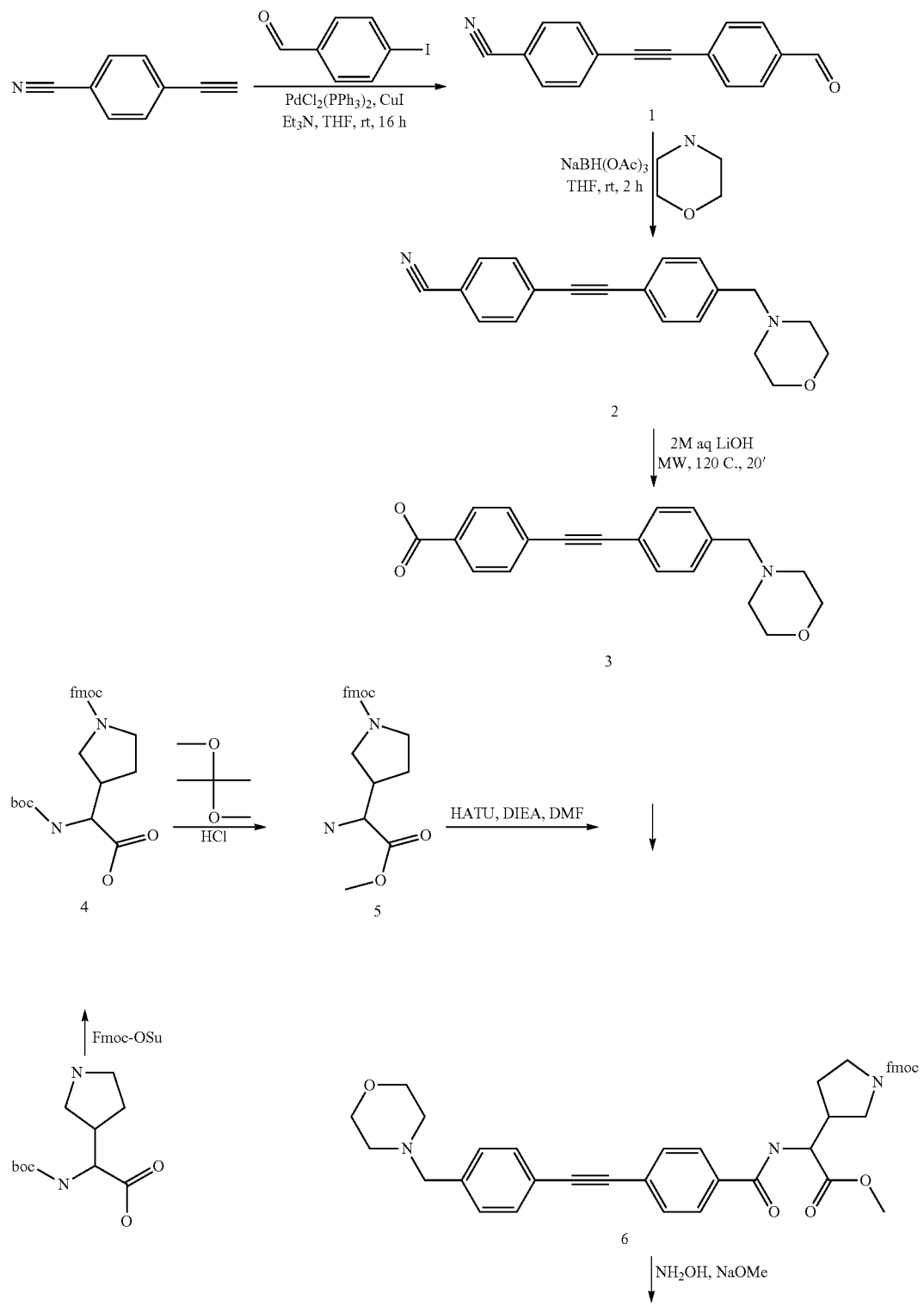

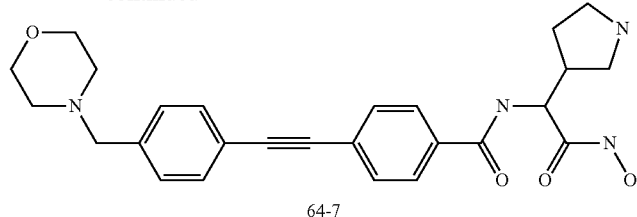

64-7

Synthesis of 4-(4-formyl-phenylethynyl)-benzonitrile (1)

To a solution of 4-ethynylbenzonitrile (2.27 g, 17.9 mmol), 4-iodobenzaldehyde (5.40 g, 23.3) and triethylamine (7.0 ml, 2.3 mmol) in THF (anh., 360 ml) was added mixture of PdCl$_2$(PPh$_3$)$_2$ (400 mg, 0.6 mmol) and CuI (216 mg, 1.1 mmol). Reaction mixture was stirred at ambient temperature overnight. Solvents were evaporated in vacuum. Residue was dissolved in EtOAc (150 ml) and extracted with 5% aq. NaHCO$_3$ (50 ml×2) and brine (50 ml). The organic layer was dried over anh. Na$_2$SO$_4$ and evaporated in vacuum. Residue was dried in vacuum overnight at ambient temperature to provide target material (1) (3.75 g, 90%) as yellow solid.

Synthesis of 4-(4-morpholin-4-ylmethylphenylethynyl)-benzonitrile (2)

To a solution of compound (1) (2.0 g, 8.6 mmol) and morpholine (1.08 ml, 12.4 mmol) in chloroform (30 ml) was added sodium triacetoxyborohydride (2.80 g, 13.2 mmol). Reaction mixture was stirred for 4 h at ambient temperature. Reaction was quenched with 5% aq. NaHCO$_3$ (50 ml) and extracted with EtOAc (150 ml×2). Organic layer was washed with brine (50 ml), dried over anh. Na$_2$SO$_4$ and evaporated in vacuum. Residue was dried in vacuum overnight to provide target material (2)(2.65 g, 97%) as off-white solid. LC-MS [M+H] 303.2 (C$_{20}$H$_{18}$N$_2$O+H, requires 303.39).

Synthesis of 4-(4-morpholin-4-ylmethyl-phenylethynyl)-benzoic acid (3)

A mixture of compound (2) (2.65 g, 8.8 mmol) and 2M aq. LiOH (22 ml, 44 mmol) in dioxane (20 ml) was irradiated in microwave oven (max. power 250 W, 130° C.) for 45 min and cooled to ambient temperature. Reaction mixture was diluted with water (300 ml) and extracted with EtOAc (100 ml×2). Water layer was acidified with 1 M HCl to pH~3 and extracted with EtOAc (300 ml×3). Organic layer was washed with water (50 ml×2) and brine (50 ml), and dried over MgSO$_4$ (anh). Solvent was evaporated in vacuum. Residue was dried in vacuum overnight to produce hydrochloric salt of target material (3) (2.23 g, 71%) as yellowish solid. LC-MS [M+H] 322.1 (C$_{20}$H$_{19}$NO$_3$+H, requires 322.39).

Synthesis of 3-(tert-butoxycarbonylamino-carboxymethyl)-pyrrolidine-1-carboxylic acid 9H-fluoren-9-ylmethyl ester (4)

To a solution of Boc-DL-pyrrolidin-3-yl-acetic acid (2.0 g, 8.6 mmol) in water (2 ml) was added solution of Fmoc-OSu (621 mg, 1.84 mmol) in ACN (5 ml). Reaction mixture was stirred for 2 h at ambient temperature. Reaction was diluted with EtOAc (50 ml). Organic layer was washed with water (30 ml×2) and brine (30 ml), dried over anh. Na$_2$SO$_4$ and evaporated in vacuum. Residue was dried in vacuum overnight to provide target material (4) (500 mg, 58%) as white solid. LC-MS [M+H] 467.2 (C$_{26}$H$_{30}$N$_2$O$_6$+H, requires 467.55).

Synthesis of 3-(amino-methoxycarbonyl-methyl)-pyrrolidine-1-carboxylic acid 9H-fluoren-9-ylmethyl ester (5)

A solution of compound (4) (500 mg, 1.07 mmol) and HCl (conc., 100 µl) in 2,2-dimethoxypropane (3 ml, 24 mmol) was maintained at ambient temperature overnight. Reaction mixture was evaporated in vacuum. Residue was dissolved in DCM (1 ml) and subjected to flash chromatography on CombiFlash® Companion unit equipped with RediSep® flash column (normal phase, 35-60 micron average particle size silicagel, 12 g, Teledyne Isco); flow rate=30 ml/min; injection volume 1.5 ml; mobile phase A: DCM; mobile phase B: MeOH; gradient 0-30% B in 43 min. Fractions containing the desired product were combined and concentrated in vacuum. Residue was triturated with ether, filtrated, washed with ether and dried in vacuum overnight to obtained hydrochloric salt of target product (5) (300 mg, 67%) as off-white powder. LC-MS [M+H] 381.1 (C$_{22}$H$_{24}$N$_2$O$_4$+H, requires 381.46).

Synthesis of 3-{methoxycarbonyl-[4-(4-morpholin-4-ylmethyl-phenylethynyl)benzoylamino]-methyl}-pyrrolidine-1-carboxylic acid 9H-fluoren-9-ylmethyl ester (6)

A solution of compound (3) hydrochloride (110 mg, 0.34 mmol), HATU (136 mg, 0.36 mmol) and DIEA (330 µl, 1.9 mmol) in DMF (1.5 ml) was maintained at ambient temperature for 10 min followed by the addition of compound 5 hydrochloride (150 mg, 0.36 mmol). Reaction mixture was stirred at ambient temperature overnight, diluted with EtOAc (80 ml) and extracted with water (20 ml×2) and brine (20 ml). Organic layer was dried over anh. MgSO$_4$, evaporated in vacuum and dried in vacuum overnight to provide target product (6) (228 mg, 99%) as brown solid. LC-MS [M+H] 684.6 (C$_{42}$H$_{41}$N$_3$O$_6$+H, requires 684.82).

Synthesis of N-(hydroxycarbamoyl-pyrrolidin-3-ylmethyl)-4-(4-morpholin-4-ylmethyl-phenylethynyl)-benzamide (64-7)

A solution of hydroxylamine hydrochloride (140 mg, 0.33 mmol) in MeOH (anh, 2 ml) was cooled to −5° C. followed by the addition of 25% NaOMe/MeOH (678 µl, 2.0 mmol) under nitrogen. Reaction mixture was stirred at −5° C. for additional 5 min, cooled to −20° C., and solution of compound (6) (228 mg, 0.33 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide di-trifluoroacetic salt of target product (64-7) (4.8 mg, 2.1%) as white solid. LC-MS [M+H] 463.2 ($C_{26}H_{30}N_4O_4$+H, requires 463.56).

| Compound | Scale (mmol) | Yield (mg) | Yield (%) | Purity (%) | [M + H] | Retention time (min)* |
|---|---|---|---|---|---|---|
| (64-7) | 0.33 | 4.8 | 2.1 | 97.4 | 463.2 | 2.31 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 65

N—((S)-Hydroxycarbamoyl-piperidin-4-yl-methyl)-4-(4-morpholin-4-ylmethyl-phenylethynyl)-benzamide

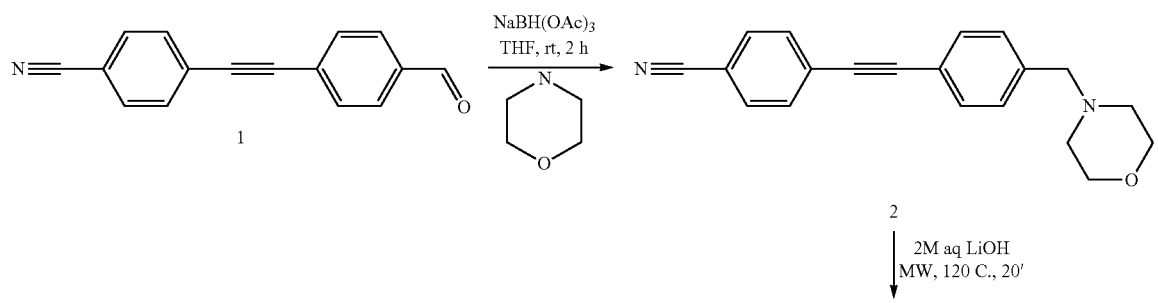

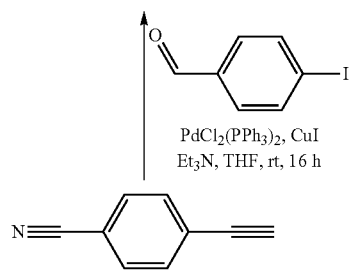

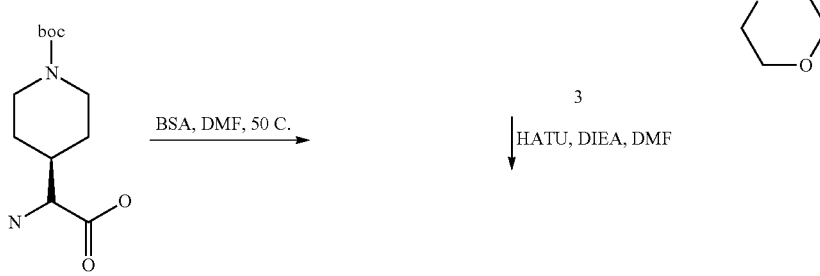

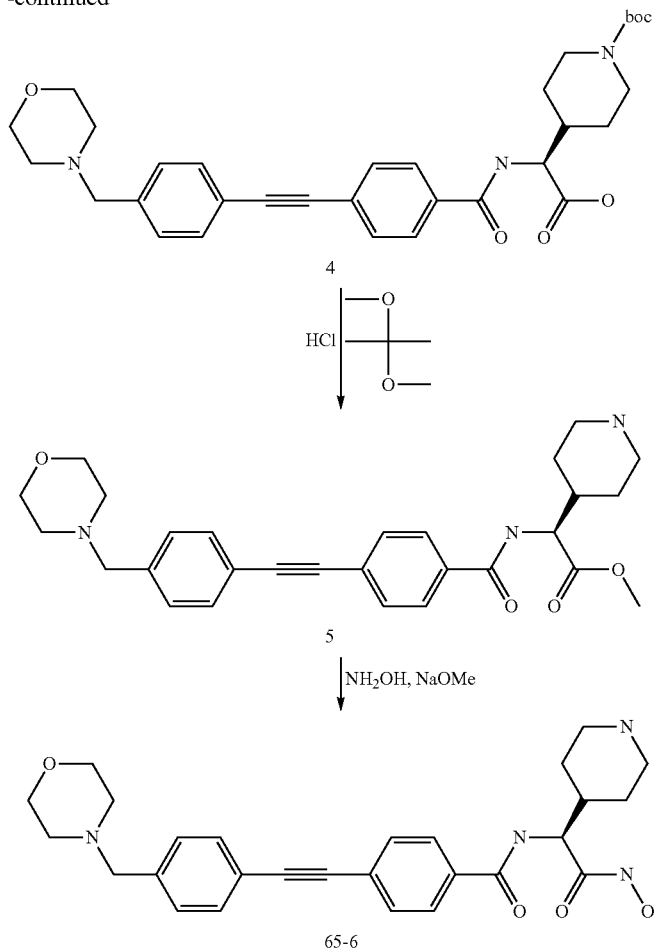

Synthesis of 4-(4-formyl-phenylethynyl)-benzonitrile (1)

To a solution of 4-ethynylbenzonitrile (2.27 g, 17.9 mmol), 4-iodobenzaldehyde (5.40 g, 23.3) and triethylamine (7.0 ml, 2.3 mmol) in THF (anh., 360 ml) was added mixture of $PdCl_2(PPh_3)_2$ (400 mg, 0.6 mmol) and CuI (216 mg, 1.1 mmol). Reaction mixture was stirred at ambient temperature overnight. Solvents were evaporated in vacuum. Residue was dissolved in EtOAc (150 ml) and extracted with 5% aq. $NaHCO_3$ (50 ml×2) and brine (50 ml). The organic layer was dried over anh. $Na_2SO_4$ and evaporated in vacuum. Residue was dried in vacuum overnight at ambient temperature to provide target material (1) (3.75 g, 90%) as yellow solid.

Synthesis of 4-(4-morpholin-4-ylmethylphenylethynyl)-benzonitrile (2)

To a solution of compound (1) (2.0 g, 8.6 mmol) and morpholine (1.08 ml, 12.4 mmol) in chloroform (30 ml) was added sodium triacetoxyborohydride (2.80 g, 13.2 mmol). Reaction mixture was stirred for 4 h at ambient temperature. Reaction was quenched with 5% aq. $NaHCO_3$ (50 ml) and extracted with EtOAc (150 ml×2). Organic layer was washed with brine (50 ml), dried over anh. $Na_2SO_4$ and evaporated in vacuum. Residue was dried in vacuum overnight to provide target material (2) (2.65 g, 97%) as off-white solid. LC-MS [M+H] 303.2 ($C_{20}H_{18}N_2O$+H, requires 303.39).

Synthesis of 4-(4-morpholin-4-ylmethyl-phenylethynyl)-benzoic acid (3)

A mixture of compound (2) (2.65 g, 8.8 mmol) and 2M aq. LiOH (22 ml, 44 mmol) in dioxane (20 ml) was irradiated in microwave oven (max. power 250 W, 130° C.) for 45 min and cooled to ambient temperature. Reaction mixture was diluted with water (300 ml) and extracted with EtOAc (100 ml×2). Water layer was acidified with 1 M HCl to pH~3 and extracted with EtOAc (300 ml×3). Organic layer was washed with water (50 ml×2) and brine (50 ml), and dried over $MgSO_4$ (anh). Solvent was evaporated in vacuum. Residue was dried in vacuum overnight to produce hydrochloric salt of target material (3) (2.23 g, 71%) as yellowish solid. LC-MS [M+H] 322.1 ($C_{20}H_{19}NO_3$+H, requires 322.39).

Synthesis of 4-{(S)-carboxy-[4-(4-morpholin-4-ylmethyl-phenylethynyl)-benzoylamino]-methyl}-piperidine-1-carboxylic acid tert-butyl ester (4)

A solution of compound (3) (110 mg, 0.31 mmol), HATU (136 mg, 0.36 mmol) and DIEA (330 μl, 1.9 mmol) in DMF (1.5 ml) was maintained at ambient temperature for 30 min. A mixture of H-Gly[4-Pip(Boc)]-OH (150 mg, 0.36 mmol) and BSA (170 µl, 0.7 mmol) in dioxane (1.5 ml) was stirred at 100° C. for 10 min and cooled to the ambient temperature. Reaction mixtures were combined and stirred at ambient temperature overnight followed by the dilution with EtOAc (100 ml). Solution was extracted with water (20 ml), 2% aq. $H_2SO_4$ (20 ml), water (20 ml×2) and brine (20 ml). Organic layer was dried over $MgSO_4$ and evaporated. Residue was dried in vacuum to provide target compound (4) (172 mg, 99%) as yellow solid. LC-MS [M+H] 562.2 ($C_{32}H_{39}N_3O_6$+H, requires 562.69).

Synthesis of (S)-[4-(4-morpholin-4-ylmethyl-phenylethynyl)-benzoylamino]-piperidin-4-yl-acetic acid methyl ester (5)

A solution of compound (4) (172 mg, 0.31 mmol) and HCl (conc., 1 ml) in 2,2-dimethoxypropane (5 ml, 40 mmol) was maintained at 60° C. for 3 h. Reaction mixture was cooled to ambient temperature and evaporated in vacuum. Residue was dissolved in DCM (1 ml) and subjected to flash chromatography on CombiFlash® Companion unit equipped with RediSep® flash column (normal phase, 35-60 micron average particle size silicagel, 4 g, Teledyne Isco); flow rate=18 ml/min; injection volume 1.5 ml; mobile phase A: hexane; mobile phase B: EtOAc; gradient 0-20% B in 30 min. Fractions containing the desired product were combined and concentrated in vacuum. Residue was dried in vacuum overnight to obtained hydrochloric salt of target product (5) (44 mg, 91%) as off-white powder. LC-MS [M+H] 476.4 ($C_{28}H_{33}N_3O_4$+H, requires 476.60).

Synthesis of N—((S)-hydroxycarbamoyl-piperidin-4-yl-methyl)-4-(4-morpholin-4-ylmethyl-phenylethynyl)-benzamide (65-6)

A solution of hydroxylamine hydrochloride (118 mg, 0.28 mmol) in MeOH (anh, 2 ml) was cooled to −5° C. followed by the addition of 25% NaOMe/MeOH (575 µl, 2.52 mmol) under nitrogen. Reaction mixture was stirred at −5° C. for additional 5 min, cooled to −20° C., and solution of compound (5) (144 mg, 0.28 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide di-trifluoroacetic salt of target product (65-6) (11.1 mg, 5.6%) as white solid. LC-MS [M+H] 477.5 ($C_{26}H_{30}N_4O_4$+H, requires 463.56).

| Compound | Scale (mmol) | Yield (mg) | Yield (%) | Purity (%) | [M + H] | Retention time (min)* |
|---|---|---|---|---|---|---|
| (65-6) | 0.28 | 11.1 | 5.6 | 99.5 | 477.5 | 2.36 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 66

N—((S)-Hydroxycarbamoyl-phenyl-methyl)-4-(4-morpholin-4-ylmethyl-phenylethynyl)-benzamide

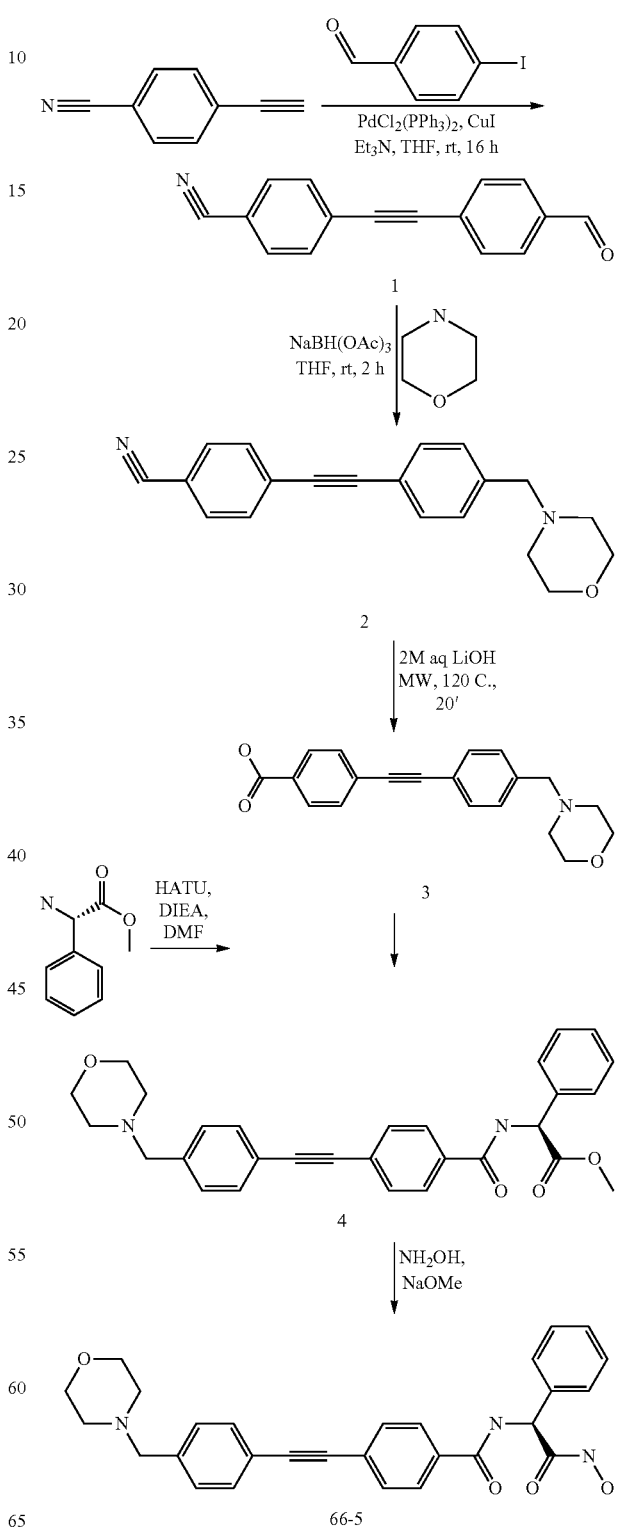

Synthesis of 4-(4-formyl-phenylethynyl)-benzonitrile (1)

To a solution of 4-ethynylbenzonitrile (2.27 g, 17.9 mmol), 4-iodobenzaldehyde (5.40 g, 23.3) and triethylamine (7.0 ml, 2.3 mmol) in THF (anh., 360 ml) was added mixture of $PdCl_2(PPh_3)_2$ (400 mg, 0.6 mmol) and CuI (216 mg, 1.1 mmol). Reaction mixture was stirred at ambient temperature overnight. Solvents were evaporated in vacuum. Residue was dissolved in EtOAc (150 ml) and extracted with 5% aq. $NaHCO_3$ (50 ml×2) and brine (50 ml). The organic layer was dried over anh. $Na_2SO_4$ and evaporated in vacuum. Residue was dried in vacuum overnight at ambient temperature to provide target material (1) (3.75 g, 90%) as yellow solid.

Synthesis of 4-(4-morpholin-4-ylmethylphenylethynyl)-benzonitrile (2)

To a solution of compound (1) (2.0 g, 8.6 mmol) and morpholine (1.08 ml, 12.4 mmol) in chloroform (30 ml) was added sodium triacetoxyborohydride (2.80 g, 13.2 mmol). Reaction mixture was stirred for 4 h at ambient temperature. Reaction was quenched with 5% aq. $NaHCO_3$ (50 ml) and extracted with EtOAc (150 ml×2). Organic layer was washed with brine (50 ml), dried over anh. $Na_2SO_4$ and evaporated in vacuum. Residue was dried in vacuum overnight to provide target material (2) (2.65 g, 97%) as off-white solid. LC-MS [M+H] 303.2 ($C_{20}H_{18}N_2O$+H, requires 303.39).

Synthesis of 4-(4-morpholin-4-ylmethyl-phenylethynyl)-benzoic acid (3)

A mixture of compound (2) (2.65 g, 8.8 mmol) and 2M aq. LiOH (22 ml, 44 mmol) in dioxane (20 ml) was irradiated in microwave oven (max. power 250 W, 130° C.) for 45 min and cooled to ambient temperature. Reaction mixture was diluted with water (300 ml) and extracted with EtOAc (100 ml×2). Water layer was acidified with 1 M HCl to pH~3 and extracted with EtOAc (300 ml×3). Organic layer was washed with water (50 ml×2) and brine (50 ml), and dried over $MgSO_4$ (anh). Solvent was evaporated in vacuum. Residue was dried in vacuum overnight to produce hydrochloric salt of target material (3) (2.23 g, 71%) as yellowish solid. LC-MS [M+H] 322.1 ($C_{20}H_{19}NO_3$+H, requires 322.39).

Synthesis of S)-[4-(4-morpholin-4-ylmethyl-phenylethynyl)-benzoylamino]-phenyl-acetic acid methyl ester (4)

A solution of compound (3) hydrochloride (143 mg, 0.4 mmol), HATU (152 mg, 0.4 mmol) and DIEA (278 μl, 1.6 mmol) in DMF (1.5 ml) was maintained at ambient temperature for 10 min followed by the addition of H-Phg-OMe hydrochloride (89 mg, 0.44 mmol). Reaction mixture was stirred at ambient temperature overnight, diluted with EtOAc (80 ml) and extracted with water (20 ml×2) and brine (20 ml). Organic layer was dried over anh. $MgSO_4$, evaporated in vacuum and dried in vacuum overnight to provide target product (4) (181 mg, 97%) as brown amorphous solid. LC-MS [M+H] 469.2 ($C_{29}H_{28}N_2O_4$+H, requires 469.57).

Synthesis of N—((S)-hydroxycarbamoyl-phenyl-methyl)-4-(4-morpholin-4-ylmethyl-phenylethynyl)-benzamide (66-5)

A solution of hydroxylamine hydrochloride (168 mg, 2.4 mmol) in MeOH (anh, 2 ml) was cooled to −5° C. followed by the addition of 25% NaOMe/MeOH (832 μl, 3.78 mmol) under nitrogen. Reaction mixture was stirred at −5° C. for additional 5 min, cooled to −20° C., and solution of compound (4) (181 mg, 0.4 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilised to provide trifluoroacetic salt of target product (66-5) (143 mg, 8.3%) as white solid. LC-MS [M+H] 470.2 ($C_{28}H_{27}N_3O_4$+H, requires 470.56).

| Compound | Scale (mmol) | Yield (mg) | Yield (%) | Purity (%) | [M + H] | Retention time (min)* |
|---|---|---|---|---|---|---|
| (66-5) | 0.4 | 143 | 61 | 99.4 | 470.2 | 3.46 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min, detection 254 nm]

The following compounds were synthesized as described in this Example.

| Compound # | Structure | [M + H] |
|---|---|---|
| (66-6) | 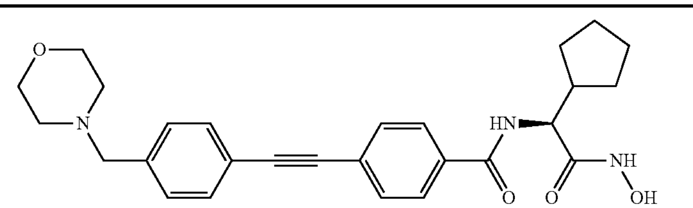 | |

Example 67

N—[Hydroxycarbamoyl-(tetrahydro-pyran-4-yl)-methyl]-4-(4-morpholin-4-ylmethyl-phenylethynyl)-benzamide

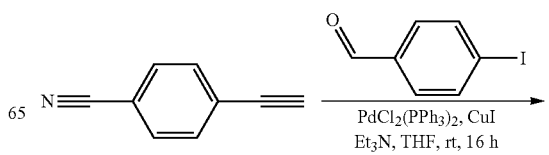

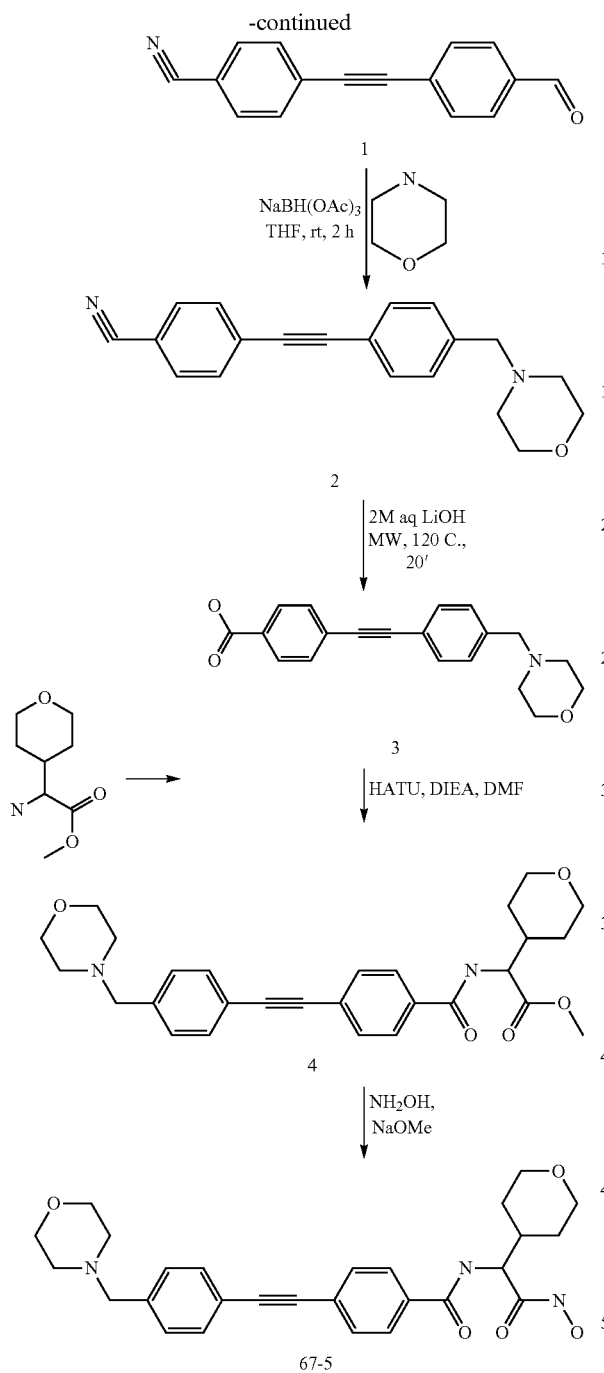

Synthesis of 4-(4-formyl-phenylethynyl)-benzonitrile (1)

To a solution of 4-ethynylbenzonitrile (2.27 g, 17.9 mmol), 4-iodobenzaldehyde (5.40 g, 23.3) and triethylamine (7.0 ml, 2.3 mmol) in THF (anh., 360 ml) was added mixture of $PdCl_2(PPh_3)_2$ (400 mg, 0.6 mmol) and CuI (216 mg, 1.1 mmol). Reaction mixture was stirred at ambient temperature overnight. Solvents were evaporated in vacuum. Residue was dissolved in EtOAc (150 ml) and extracted with 5% aq. $NaHCO_3$ (50 ml×2) and brine (50 ml). The organic layer was dried over anh. $Na_2SO_4$ and evaporated in vacuum. Residue was dried in vacuum overnight at ambient temperature to provide target material (1) (3.75 g, 90%) as yellow solid.

Synthesis of 4-(4-morpholin-4-ylmethylphenylethynyl)-benzonitrile (2)

To a solution of compound (1) (2.0 g, 8.6 mmol) and morpholine (1.08 ml, 12.4 mmol) in chloroform (30 ml) was added sodium triacetoxyborohydride (2.80 g, 13.2 mmol). Reaction mixture was stirred for 4 h at ambient temperature. Reaction was quenched with 5% aq. $NaHCO_3$ (50 ml) and extracted with EtOAc (150 ml×2). Organic layer was washed with brine (50 ml), dried over anh. $Na_2SO_4$ and evaporated in vacuum. Residue was dried in vacuum overnight to provide target material (2) (2.65 g, 97%) as off-white solid. LC-MS [M+H] 303.2 ($C_{20}H_{18}N_2O$+H, requires 303.39).

Synthesis of 4-(4-morpholin-4-ylmethyl-phenylethynyl)-benzoic acid (3)

A mixture of compound (2) (2.65 g, 8.8 mmol) and 2M aq. LiOH (22 ml, 44 mmol) in dioxane (20 ml) was irradiated in microwave oven (max. power 250 W, 130° C.) for 45 min and cooled to ambient temperature. Reaction mixture was diluted with water (300 ml) and extracted with EtOAc (100 ml×2). Water layer was acidified with 1 M HCl to pH~3 and extracted with EtOAc (300 ml×3). Organic layer was washed with water (50 ml×2) and brine (50 ml), and dried over $MgSO_4$ (anh). Solvent was evaporated in vacuum. Residue was dried in vacuum overnight to produce hydrochloric salt of target material (3) (2.23 g, 71%) as yellowish solid. LC-MS [M+H] 322.1 ($C_{20}H_{19}NO_3$+H, requires 322.39).

Synthesis of [4-(4-morpholin-4-ylmethyl-phenylethynyl)-benzoylamino]-(tetrahydro-pyran-4-yl)-acetic acid methyl ester (4)

A solution of compound (3) hydrochloride (110 mg, 0.31 mmol), HATU (167 mg, 0.44 mmol) and DIEA (330 µl, 2.0 mmol) in DMF (3 ml) was maintained at ambient temperature for 10 min followed by the addition of DL-(4-tetrahydropyranyl)Ala-OMe hydrochloride (84 mg, 0.4 mmol). Reaction mixture was stirred at ambient temperature overnight, diluted with EtOAc (100 ml) and extracted with water (30 ml×2) and brine (30 ml). Organic layer was dried over anh. $MgSO_4$, evaporated in vacuum and dried in vacuum overnight to provide target product (4) (144 mg, 98%) as brown solid. LC-MS [M+H] 477.2 ($C_{28}H_{32}N_2O_5$+H, requires 477.59).

Synthesis of N-[hydroxycarbamoyl-(tetrahydro-pyran-4-yl)-methyl]-4-(4-morpholin-4-ylmethyl-phenylethynyl)-benzamide (67-5)

A solution of hydroxylamine hydrochloride (126 mg, 1.8 mmol) in MeOH (anh, 2 ml) was cooled to −5° C. followed by the addition of 25% NaOMe/MeOH (616 µl, 2.7 mmol) under nitrogen. Reaction mixture was stirred at −5° C. for additional 5 min, cooled to −20° C., and solution of compound (4) (144 mg, 0.30 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (67-5) (65.7 mg, 37%) as white solid. LC-MS [M+H] 408.2 ($C_{27}H_{31}N_3O_5$+H, requires 478.58).

| Compound | Scale (mmol) | Yield (mg) | Yield (%) | Purity (%) | [M + H] | Retention time (min)* |
|---|---|---|---|---|---|---|
| (67-5) | 0.30 | 65.7 | 37 | 99.9 | 478.3 | 2.85 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.6 min. detection 254 nm]

The following compounds were synthesized as described in this Example.

| Compound # | Structure | [M + H] |
|---|---|---|
| (67-7) | 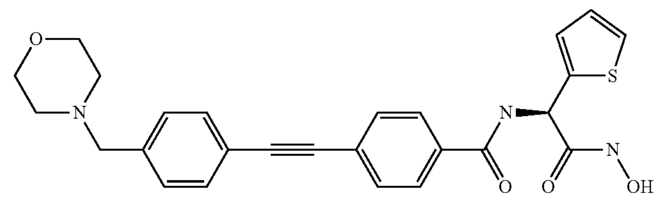 [SMILES: O=C(N[C@H](C(=O)NO)c1cccs1)c1ccc(C#Cc2ccc(CN3CCOCC3)cc2)cc1] | 476.3 |
| (67-8) | 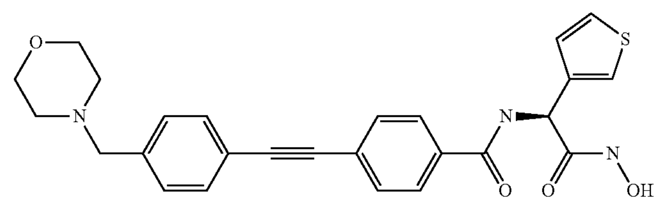 [SMILES: O=C(N[C@H](C(=O)NO)c1ccsc1)c1ccc(C#Cc2ccc(CN3CCOCC3)cc2)cc1] | 476.2 |
| (67-9) | 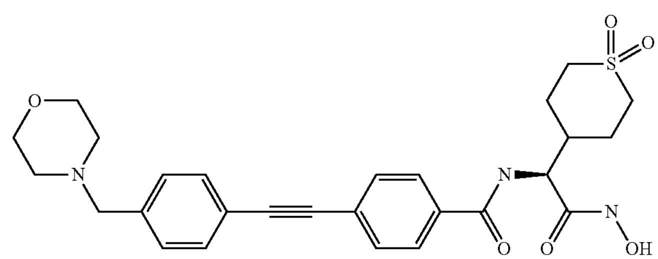 [SMILES: O=C(N[C@H](C(=O)NO)C1CCS(=O)(=O)CC1)c1ccc(C#Cc2ccc(CN3CCOCC3)cc2)cc1] | 526.2 |

Example 68

N—((S)-Cyclopropyl-hydroxycarbamoyl-methyl)-4-(4-morpholin-4-ylmethyl-phenylethynyl)-benzamide

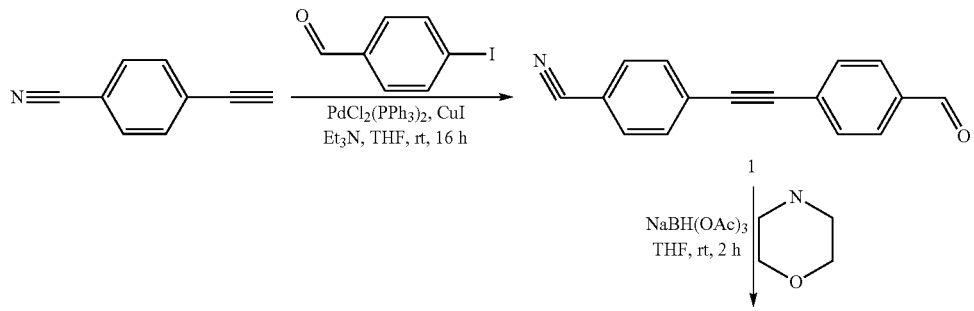

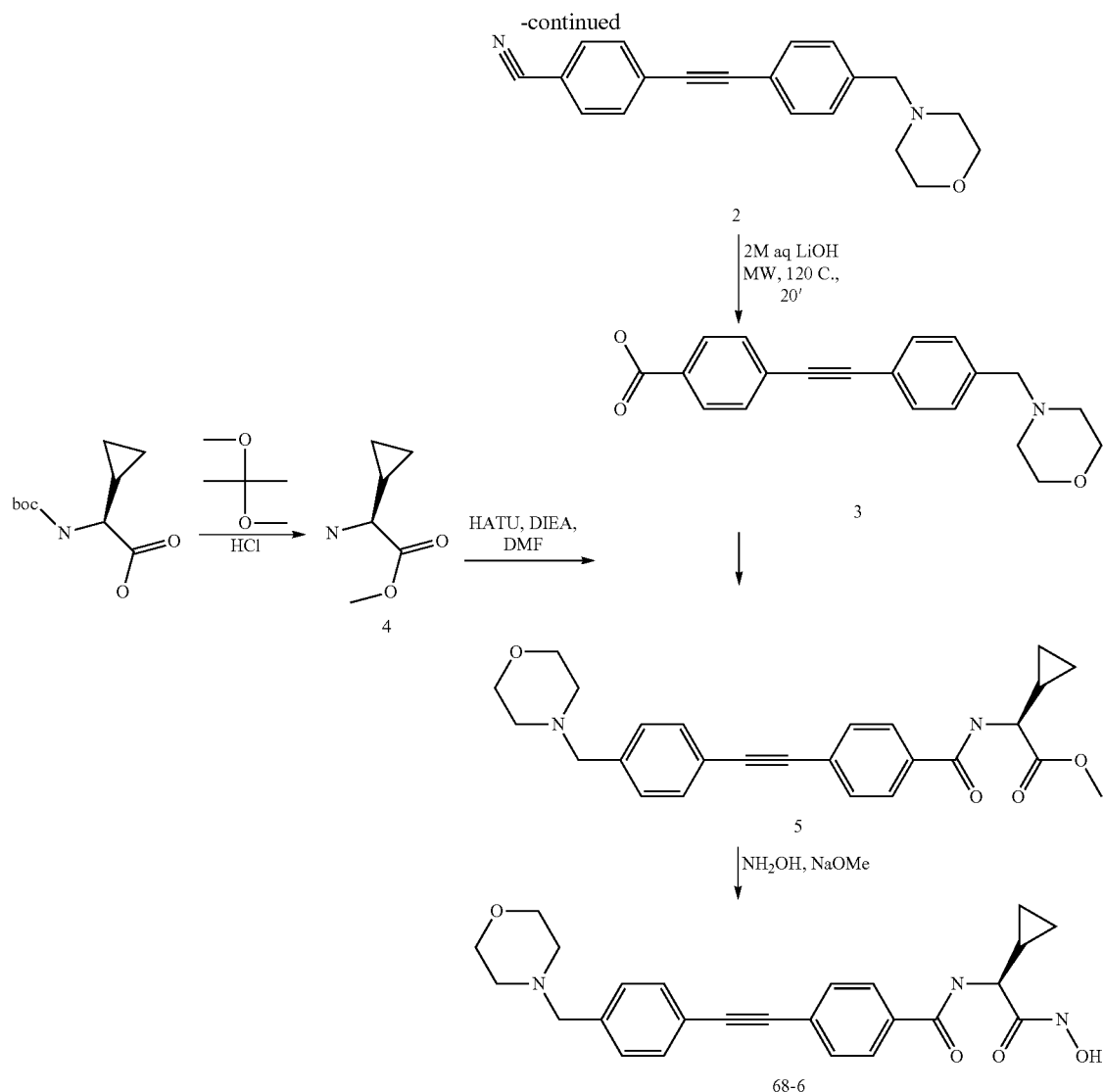

Synthesis of 4-(4-formyl-phenylethynyl)-benzonitrile (1)

To a solution of 4-ethynylbenzonitrile (2.27 g, 17.9 mmol), 4-iodobenzaldehyde (5.40 g, 23.3) and triethylamine (7.0 ml, 2.3 mmol) in THF (anh., 360 ml) was added mixture of PdCl$_2$(PPh$_3$)$_2$ (400 mg, 0.6 mmol) and CuI (216 mg, 1.1 mmol). Reaction mixture was stirred at ambient temperature overnight. Solvents were evaporated in vacuum. Residue was dissolved in EtOAc (150 ml) and extracted with 5% aq. NaHCO$_3$ (50 ml×2) and brine (50 ml). The organic layer was dried over anh. Na$_2$SO$_4$ and evaporated in vacuum. Residue was dried in vacuum overnight at ambient temperature to provide target material (1) (3.75 g, 90%) as yellow solid.

Synthesis of 4-(4-morpholin-4-ylmethylphenylethynyl)-benzonitrile (2)

To a solution of compound (1) (2.0 g, 8.6 mmol) and morpholine (1.08 ml, 12.4 mmol) in chloroform (30 ml) was added sodium triacetoxyborohydride (2.80 g, 13.2 mmol). Reaction mixture was stirred for 4 h at ambient temperature. Reaction was quenched with 5% aq. NaHCO$_3$ (50 ml) and extracted with EtOAc (150 ml×2). Organic layer was washed with brine (50 ml), dried over anh. Na$_2$SO$_4$ and evaporated in vacuum. Residue was dried in vacuum overnight to provide target material (2) (2.65 g, 97%) as off-white solid. LC-MS [M+H] 303.2 (C$_{20}$H$_{18}$N$_2$O+H, requires 303.39).

Synthesis of 4-(4-morpholin-4-ylmethyl-phenylethynyl)-benzoic acid (3)

A mixture of compound (2) (2.65 g, 8.8 mmol) and 2M aq. LiOH (22 ml, 44 mmol) in dioxane (20 ml) was irradiated in microwave oven (max. power 250 W, 130° C.) for 45 min and cooled to ambient temperature. Reaction mixture was diluted with water (300 ml) and extracted with EtOAc (100 ml×2). Water layer was acidified with 1 M HCl to pH~3 and extracted with EtOAc (300 ml×3). Organic layer was washed with water (50 ml×2) and brine (50 ml), and dried over MgSO$_4$ (anh). Solvent was evaporated in vacuum. Residue was dried in vacuum overnight to produce hydrochloric salt of target material (3) (2.23 g, 71%) as yellowish solid. LC-MS [M+H] 322.1 ($C_{20}H_{19}NO_3$+H, requires 322.39).

Synthesis of (S)-amino-cyclopropyl-acetic acid methyl ester (4)

A solution of Boc-L-cyclopropylglycine (97 mg, 0.45 mmol) and HCl (conc., 500 µl) in 2,2-dimethoxypropane (5 ml, 40 mmol) was maintained at 40° C. overnight. Reaction mixture was evaporated in vacuum. Residue was dissolved in i-PrOH (10 ml) and evaporated in vacuum. The aforementioned procedure was repeated twice. Residue was triturated with ether, filtrated, washed with ether and dried in vacuum overnight to obtained hydrochloric salt of target product (4) (73 mg, 98%) as off-white powder. LC-MS [M+H] 130.0 ($C_6H_{11}NO_2$+H, requires 130.17).

Synthesis of (S)-cyclopropyl-[4-(4-morpholin-4-ylmethyl-phenylethynyl)-benzoylamino]-acetic acid methyl ester (5)

A solution of compound (3) hydrochloride (143 mg, 0.4 mmol), HATU (176 mg, 0.44 mmol) and DIEA (313 µA 1.8 mmol) in DMF (1 ml) was maintained at ambient temperature for 10 min followed by the addition of compound (4) hydrochloride (73 mg, 0.44 mmol). Reaction mixture was stirred at ambient temperature overnight, diluted with EtOAc (80 ml) and extracted with water (20 ml×2) and brine (20 ml). Organic layer was dried over anh. $MgSO_4$ and evaporated in vacuum. Residue was dissolved in DCM (1 ml) and subjected to flash chromatography on CombiFlash® Companion unit equipped with RediSep® flash column (normal phase, 35-60 micron average particle size silicagel, 4 g, Teledyne Isco); flow rate=18 ml/min; injection volume 1.5 ml; mobile phase A: DCM; mobile phase B: MeOH; gradient 0-30% B in 38 min. Fractions containing the desired product were combined and concentrated in vacuum.

Residue was dried in vacuum overnight to obtain target product 5 (112 mg, 65%) as off-white powder. LC-MS [M+H] 433.2 ($C_{26}H_{28}N_2O_4$+H, requires 433.53).

Synthesis of N—((S)-cyclopropyl-hydroxycarbamoyl-methyl)-4-(4-morpholin-4-ylmethyl-phenylethynyl)-benzamide (68-6)

A solution of hydroxylamine hydrochloride (107 mg, 1.6 mmol) in MeOH (anh, 2 ml) was cooled to −5° C. followed by the addition of 25% NaOMe/MeOH (534 µl, 2.34 mmol) under nitrogen. Reaction mixture was stirred at −5° C. for additional 5 min, cooled to −20° C., and solution of compound (5) (122 mg, 0.26 mmol) in THF/MeOH (1:1, 2 ml) was added dropwise over the period of 5 min. Temperature of reaction mixture was raised to ambient. Completion of the reaction was monitored by LC-MS. After completion reaction mixture was acidified with 1 N aq. HCl to pH~7 and evaporated in vacuum. Residue was dissolved in DMSO (600 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide trifluoroacetic salt of target product (68-6) (39.5 mg, 28%) as white solid. LC-MS [M+H] 434.3 ($C_{25}H_{27}N_3O_4$+H, requires 434.52).

| Compound | Scale (mmol) | Yield (mg) | Yield (%) | Purity (%) | [M + H] | Retention time (min)* |
|---|---|---|---|---|---|---|
| (68-6) | 0.26 | 39.5 | 28 | 100 | 434.3 | 2.98 |

*[Chromolith SpeedRod RP-18e C18 column (4.6 x 50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 69

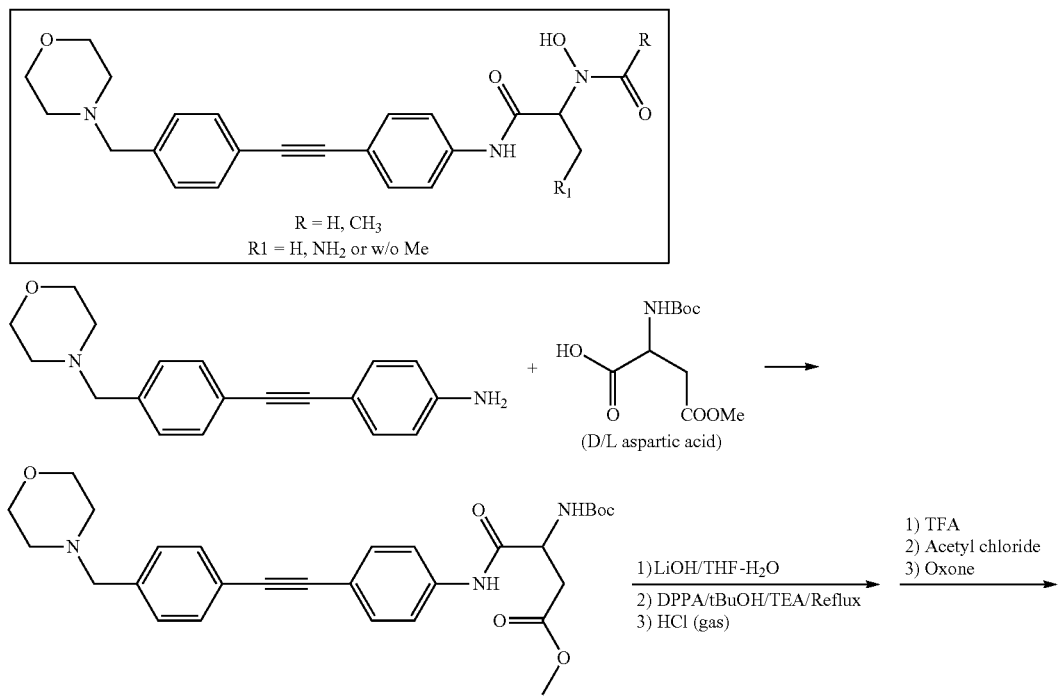

-continued
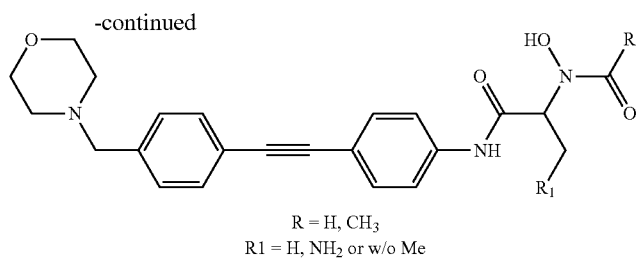
R = H, CH₃
R1 = H, NH₂ or w/o Me
Example 70
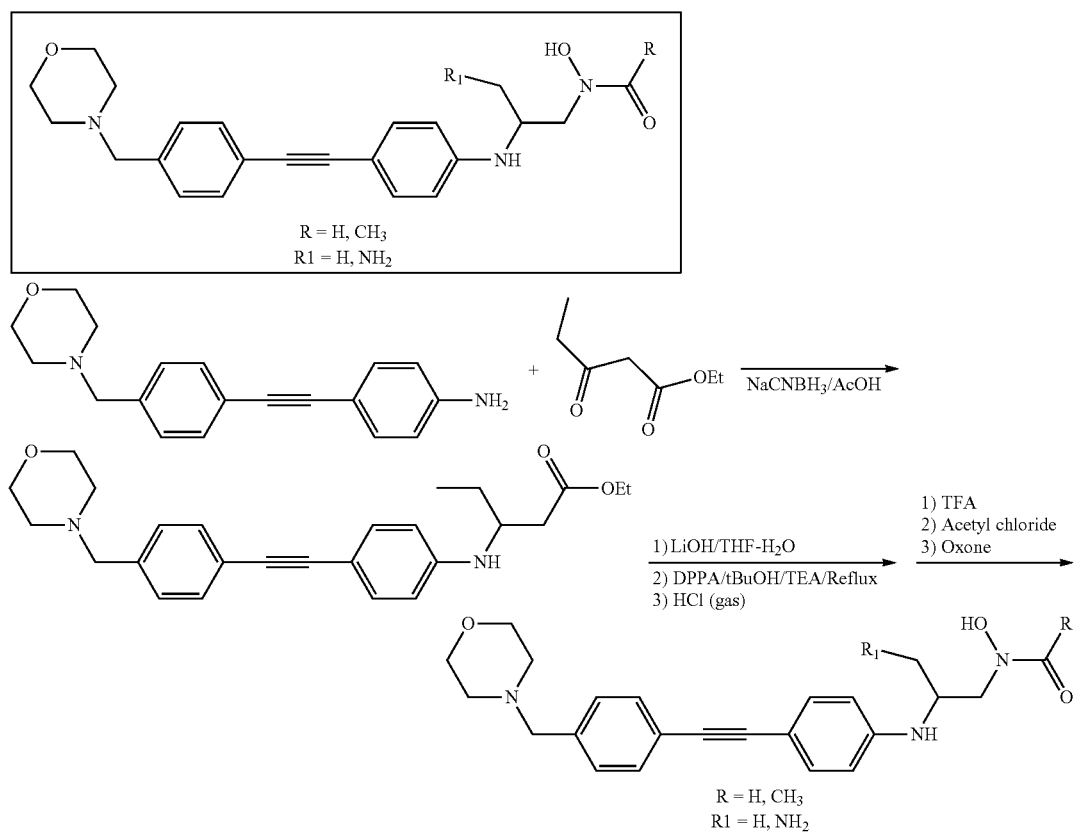
Example 71
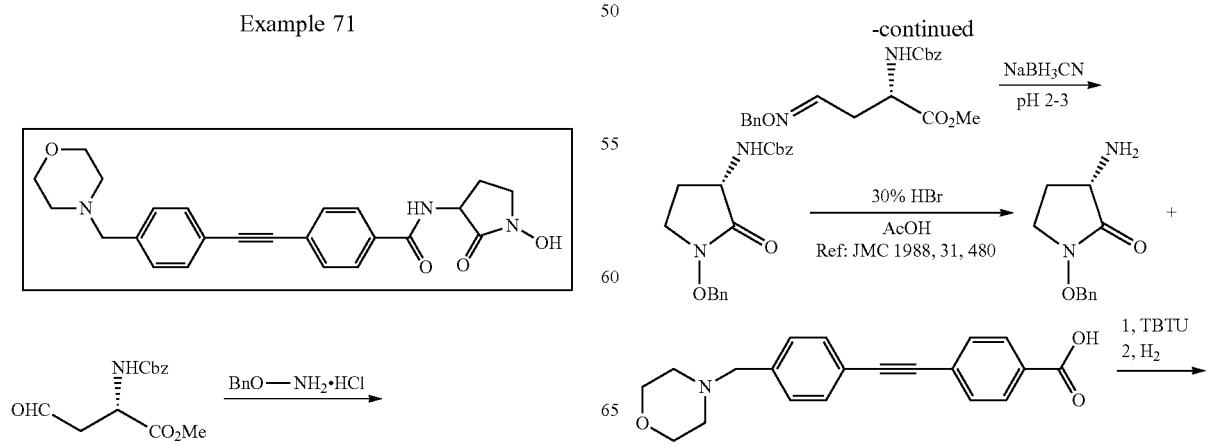

209
-continued
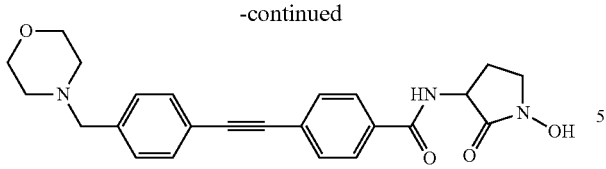
Example 72
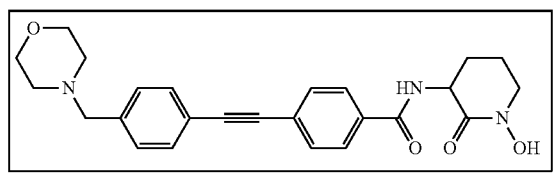
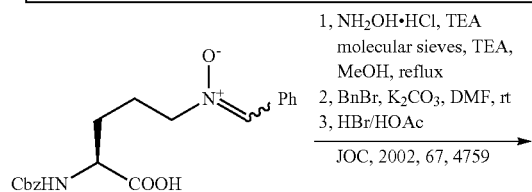
1, NH₂OH·HCl, TEA
molecular sieves, TEA,
MeOH, reflux
2, BnBr, K₂CO₃, DMF, rt
3, HBr/HOAc
JOC, 2002, 67, 4759
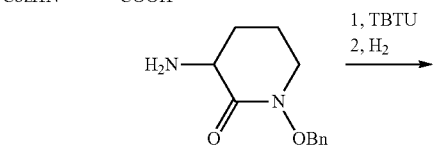
1, TBTU
2, H₂
⟶
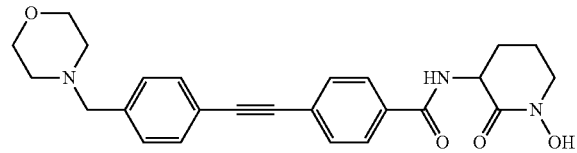
Example 73
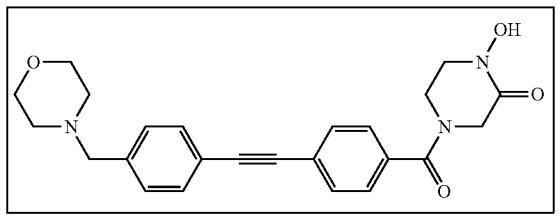
Org. Lett. 2004, 4069
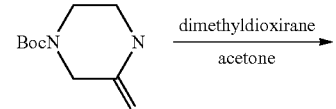
Acta Chem. Scand,
1993, 47, 11, 1141
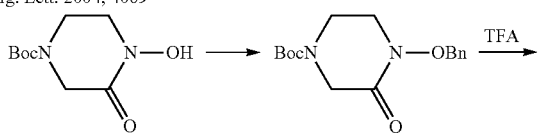
210
-continued
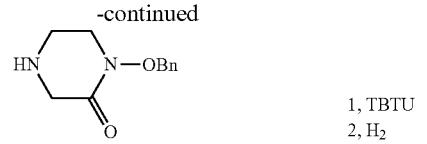
1, TBTU
2, H₂
⟶
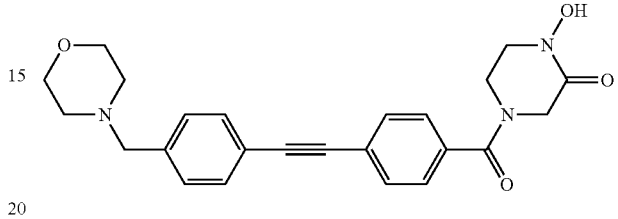
Example 74
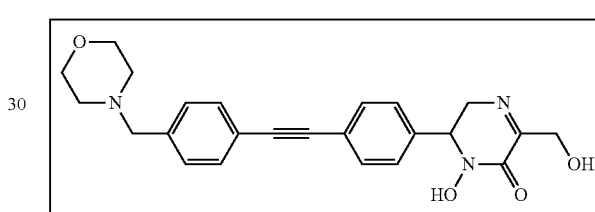
Ref. J. Med. Chem. (1973), 16, 901-8
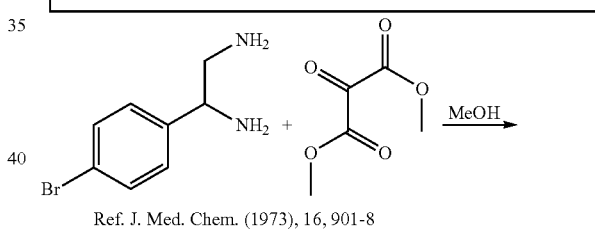
LiBH₄/MeOH
⟶
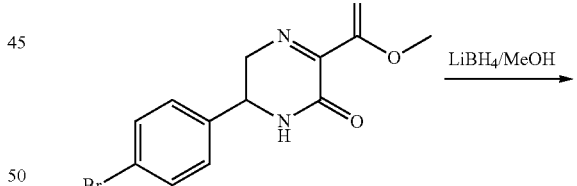
Oxarine
Acetone
⟶
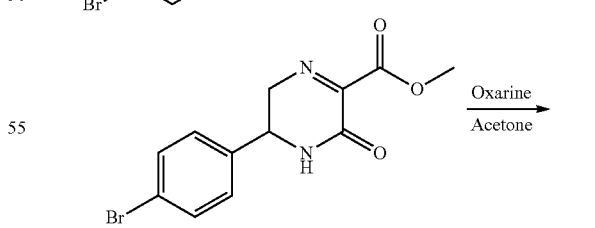
PdCl₂(PPh₃)₂/CuI/TEA
Ref. Chemistry Lett. 2002, 756-7
⟶
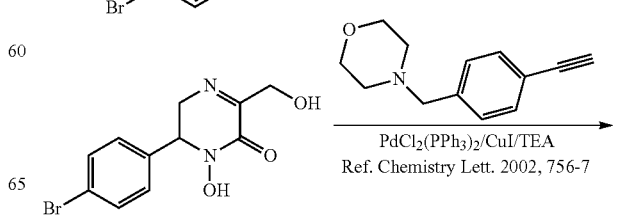

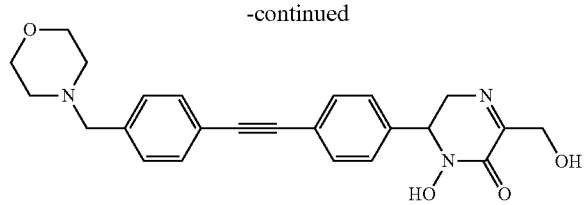
Example 75
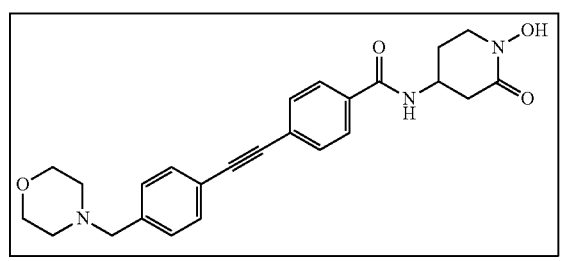
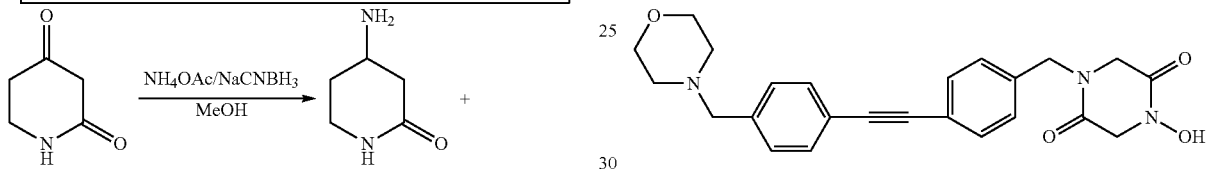
Example 76
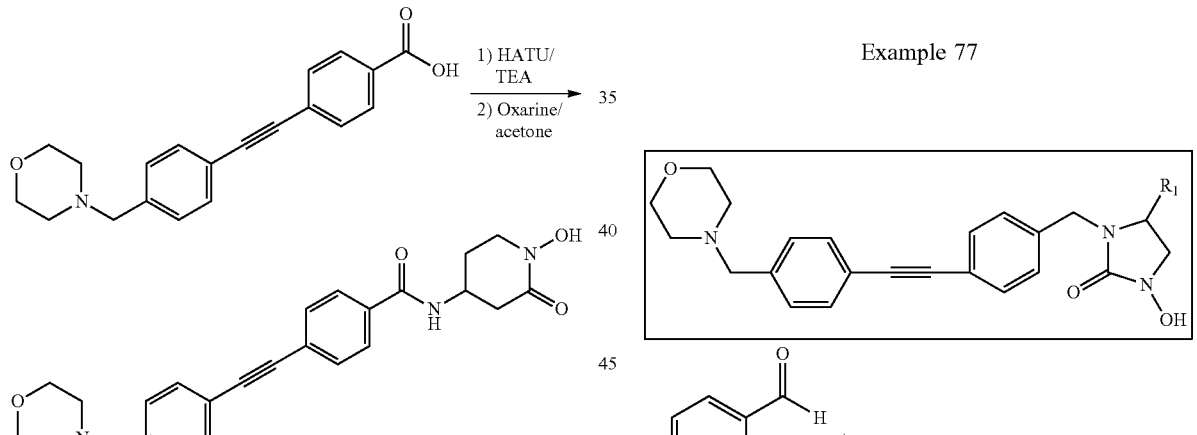
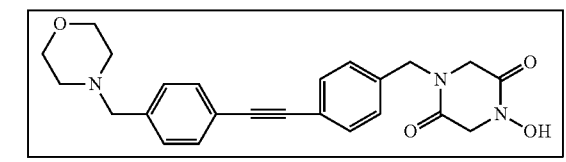
Example 77
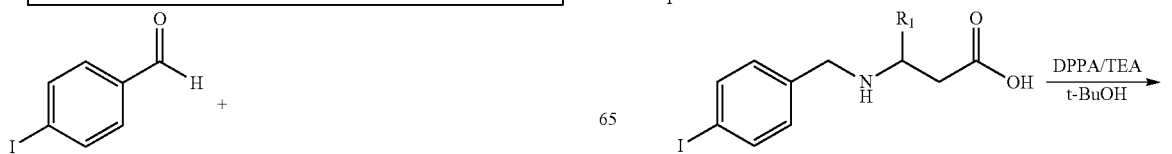

213
-continued
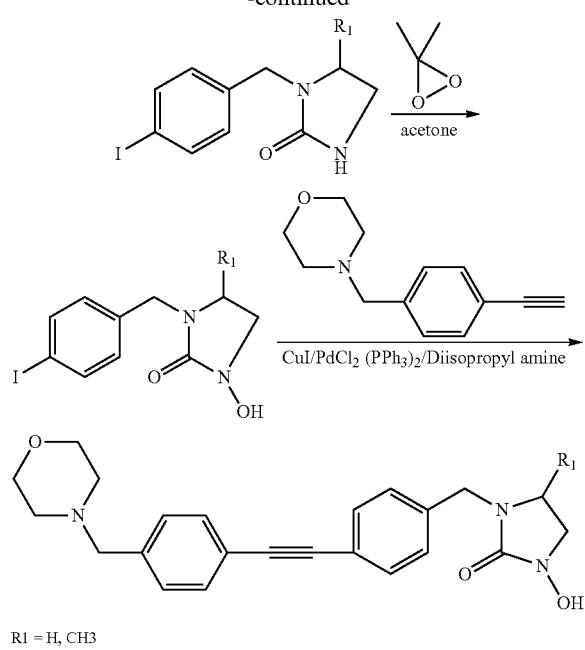
R1 = H, CH3
Example 78
214
-continued
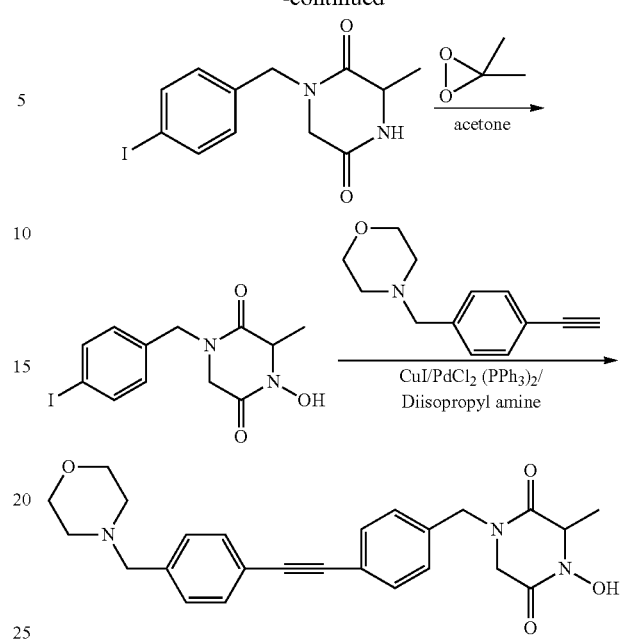
Example 79
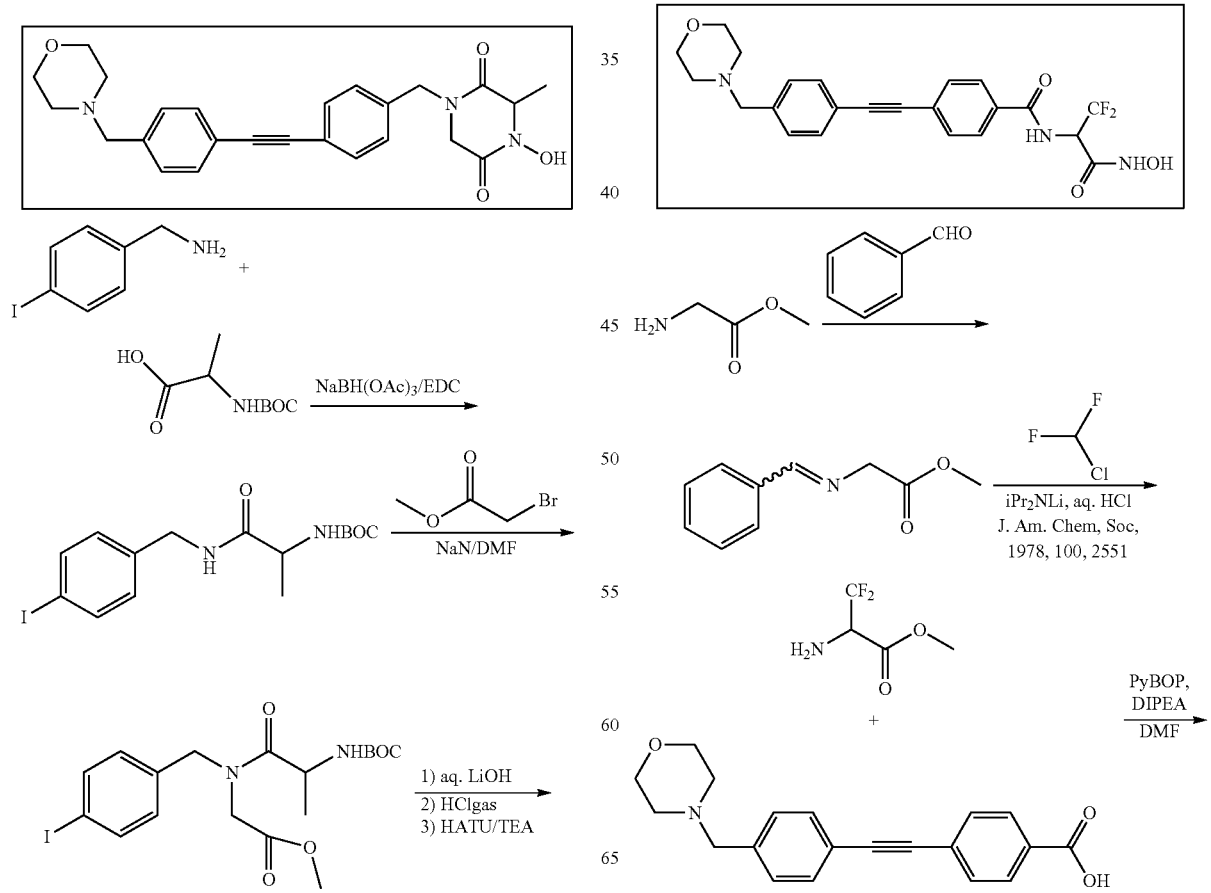

215
-continued
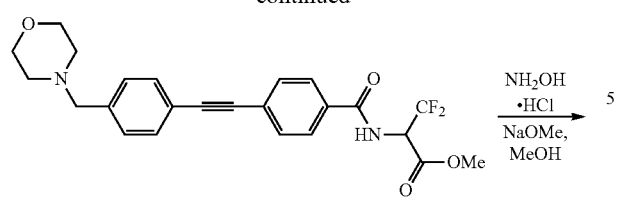
216
-continued
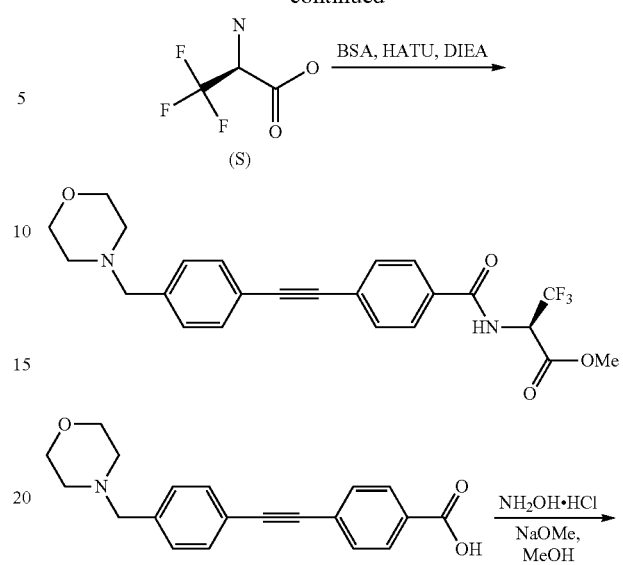
Example 80
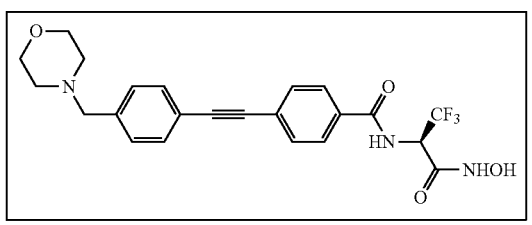
Example 81
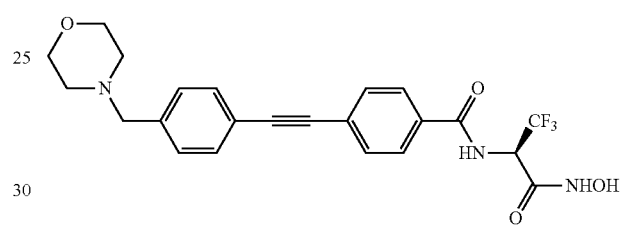
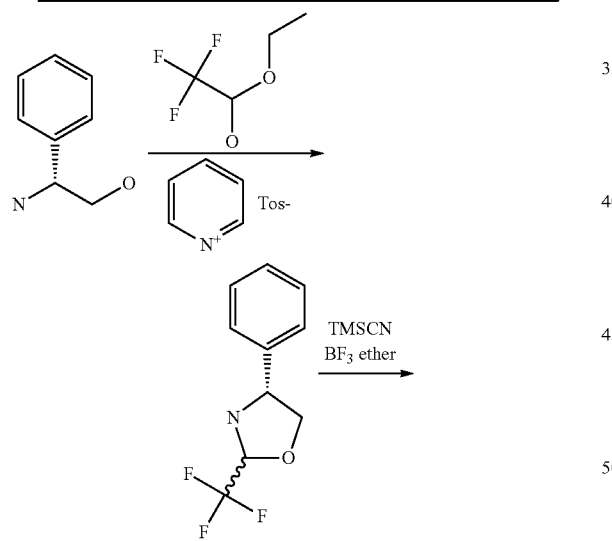
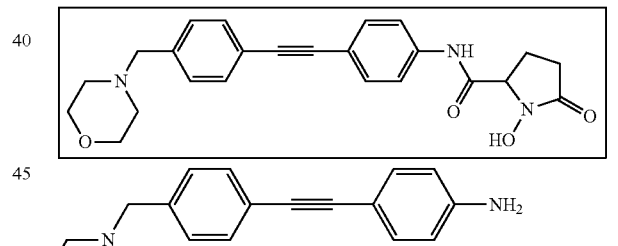
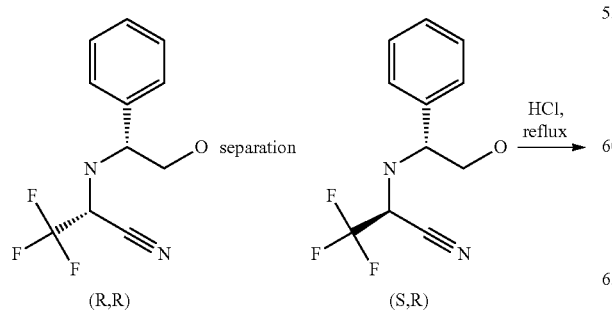
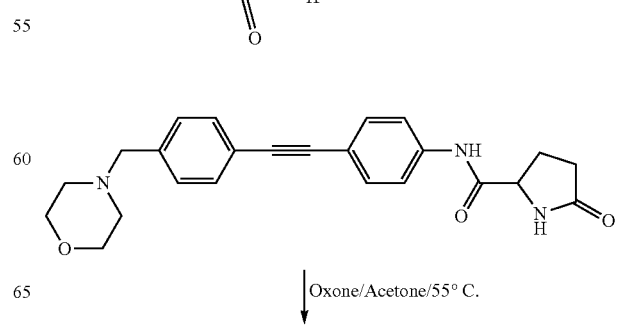

-continued

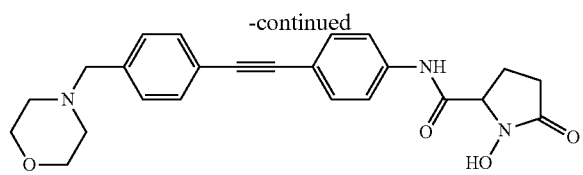

General Procedures for Following Examples

Method 1-A (1-Bromo-1-alkyne/Alkyne Coupling)

A solution of the 1-bromo-1-alkyne (0.35 mmol, 1.0 equiv), alkyne (0.35 mmol, 1.0 equiv), $PdCl_2(PPh_3)_2$ (0.0035 mmol, 0.01 equiv), $P(tBu)_3$ $HBF_4$ (0.007 mmol, 0.02 equiv), Cu(I)I (0.0018 mmol, 0.005 equiv) and $Et_3N$ (1.05 mmol, 3.0 equiv) in deoxygenated THF (5 mL) was allowed to stir at ambient temperature under $N_2$ until the starting material was consumed as determined by TLC or LC-MS analysis. The solution was concentrated in vacuo and purified by normal phase flash chromatography to provide the desired compound.

Method 1-B (Vinyldibromide/Alkyne Coupling)

A solution of vinyldibromide (2.0 mmol, 1.0 equiv), alkyne* (2.8 mmol, 1.4 equiv), $Pd_2(dba)_3$ (0.02 mmol, 0.01 equiv), tri(4-methoxyphenyl)phosphine (0.08 mmol, 0.04 equiv) and $Et_3N$ (6.0 mmol, 3.0 equiv) in deoxygenated DMF (5 mL) was heated at 80° C. for 2-6 h under nitrogen. The reaction was monitored by LC-MS until disappearance of the vinyldibromide. The reaction mixture was diluted with EtOAc (120-150 mL), washed with water (2×50 mL), brine (1×50 mL) dried ($Na_2SO_4$) and concentrated in vacuo. The crude material was purified by normal phase flash chromatography to provide the desired compound.

*In the case of a volatile alkyl- or cycloalkyl acetylene, amount of the acetylene was increased to 2-3 equivalents, and the reaction vessel was sealed before heating.

Method 1-C (Cadiot-Chodkiewicz Coupling)

To a solution of the alkyne (8.37 mmol, 1.0 equiv) in MeOH (25 mL) at 0° C. was added aqueous $EtNH_2$ (70%, 35 mL) and Cu(I)Cl (0.419 mmol, 0.05 equiv). The this solution at 0° C. was then added a solution of the 1-bromo-1-alkyne (8.37 mmol, 1.0 equiv) in THF (25 mL). Solid $NH_2OH$ HCl (8.37 mmol, 1.0 equiv) was then added in one portion and the solution was allowed to stir at 0° C. until starting material was consumed as determined by TLC or LC-MS analysis. The solution was then diluted with EtOAc (50 mL) and deionized water (50 mL). The layers were separated and the organic layer was washed with aqueous HCl (0.1 N, 2×25 mL) and brine (1×25 mL). The organics were then dried ($Na_2SO_4$), filtered and concentrated in vacuo. Crude material was then purified by flash chromatography to provide the desired compound.

Method 2-A (Basic Hydrolysis)

To a solution of the methyl ester (1.0-1.5 mmol, 1.0 equiv) in 1,4-dioxane* (2-4 mL) was added 1.5 N NaOH (aq) (4-6 mL, 6.0 equiv) and the mixture was heated at 70-90° C. for 1-4 h, monitored by LC-MS until starting material was consumed. After cooling to ambient temperature, the reaction mixture was acidified with 2 N HCl (aq)**, and the solid was collected by filtration, washed with water (2×) and dried under high vacuum to give the desired compound. The product was used without further purification in the next synthetic step.

* Alternatively, THF or EtOH can be used.
** Alternatively, 10% $H_3PO_4$ (aq) or AcOH can be used.

Method 2-B (Acidic Hydrolysis)

A solution of the methyl ester (1-2 mmol, 1.0 equiv) in 2 N HCl (aq) (8 mL, 8-16 equiv) was heated at 80° C. for 6-10 min, monitored by LC-MS until starting material was consumed. The reaction mixture was cooled to 5° C. and the solid was collected by filtration, washed with water and dried under high vacuum to give the desired compound. The product was used without further purification in the next synthetic step.

Method 3-A (HATU Coupling)

To a solution of the acid (0.50 mmol, 1.0 equiv) and DIEA (1.5 mmol, 3.0 equiv) in DMF (0.1-0.5 M) was added HATU (0.60 mmol, 1.2 equiv), and the mixture was stirred at ambient temperature* for 5 min. The amine (0.55 mmol, 1.1 eq) was then added and the mixture was stirred at ambient temperature for 18 h or until the starting material was consumed as determined by TLC or LC-MS analysis. The mixture was then added to aqueous HCl (0.1 N, 50 mL) and extracted with EtOAc (3×25 mL). Combined organic layers were washed with water (1×25 mL) and brine (1×25 mL), dried ($Na_2SO_4$), filtered and concentrated in vacuo to give the desired compound. Crude product may be used in next synthetic step without additional purification or purified by normal phase flash chromatography.

*An ice/water bath should be used if scale more 2 mmol.

Method 3-B (EDC/HOBT Coupling)

The carboxylic acid (1.15 mmol, 1.0 equiv), amine (1.27 mmol, 1.1 equiv), EDC (2.30 mmol, 2.0 equiv) and HOBT (2.30 mmol, 2.0 equiv) were slurried in anhydrous $CH_2Cl_2$ (12 mL). To this slurry was added N,N-diisopropylethylamine (5.40 mmol, 4.0 equiv) in one portion. The solution was then allowed to stir at ambient temperature until complete conversion is observed by LCMS analysis. The solution was then concentrated in vacuo and the crude solid was purified by normal phase flash chromatography to provide the desired compound.

Method 4-A (Boc Deprotection)

To the Boc protected amine (0.5 mmol, 1.0 equiv) was added 4 M HCl/dioxane (3-6 mL), and the mixture was stirred at ambient temperature for 0.5-2 h, or until complete as determined by TLC or LC-MS analysis. Volatiles were removed in vacuo or under a stream of nitrogen to give the desired compound as the hydrochloride salt.

Method 4-B (Boc Deprotection)

To Boc protected amine (0.50 mmol, 1.0 equiv) in $CH_2Cl_2$ (10 mL) was added TFA (2 mL) and the mixture was stirred at ambient temperature until complete as determined by TLC or LC-MS analysis. Volatiles were removed in vacuo or under a stream of nitrogen to give the desired compound as the TFA salt.

Method 4-C (Fmoc Deprotection)

To Fmoc protected amine (13.5 mmol, 1.0 equiv) in DMF (135 mL) at 0° C. was added morpholine (25 mL). The solution was allowed to stir at 0° C. until complete as determined by TLC or LC-MS analysis. The solution was then vacuum filtered through a pad of Celite and diluted with EtOAc (400 mL). The organics were then washed with deionized water (3×100 mL), dried (MgSO$_4$), filtered and concentrated in vacuo. The crude material was then purified by normal phase flash chromatography.

Method 5-a (Hydroxamate Formation, Aqueous)

Isopropyl alcohol (1-4 mL) was added to a corresponding methyl ester (~0.5 mmol, 1.0 eq) and the mixture was optionally cooled in an ice/water bath for 5 min. NH$_2$OH (50% aq) (1-4 mL) was added to the mixture, dropwise for the first ½ vol. After 5 min, the ice bath was removed and the reaction mixture was stirred for 6-24 h, or until complete as determined by LC-MS analysis of the reaction mixture. Solvent volume was reduced by half using a nitrogen stream and water (10-15 mL) was added. The suspension was thoroughly agitated (vibro mixer and sonication), centrifuged and the supernatant was discarded. Water (10-15 mL) was added to the solid and the suspension was thoroughly agitated, centrifuged and the supernatant was discarded. Wet solid was optionally dried by lyophilization to give the crude corresponding hydroxamate.

Method 5-B (Hydroxamate Formation and Fmoc Deprotection, Anhydrous)

To a stirred suspension of a corresponding methyl ester (~0.5 mmol, 1.0 eq) and hydroxylamine hydrochloride (5 mmol, 10 eq) in anhydrous MeOH (2 mL) and optionally anhyd THF (2 mL) cooled at −5° C. in a ice/salt/water bath, was added dropwise 25% NaOMe/MeOH (1.2 mL, 10 mmol) under nitrogen. The reaction mixture was stirred at −5° C. for an additional 5 min then stirred for 0.5-2 h or until complete as determined by LC-MS analysis$^2$ of the reaction mixture. Reaction mixture was cooled, acidified to pH~6 with 1 M HCl, and concentrated in vacuo or under a stream of nitrogen to give the crude corresponding hydroxamate.

Method 6 (DAST Fluorination)

To a stirred solution of the corresponding alcohol (2.8 mmol, 1.0 equiv) in anhydrous CH$_2$Cl$_2$ (50 mL) was slowly added diethylamino sulfur trifluoride (2.8 mmol, 1.0 equiv) at 0° C. The solution was allowed to stir at 0° C. for 1 h or until complete as determined by TLC or LC-MS analysis. Solution was then diluted with aqueous, saturated NaHCO$_3$ (50 mL) and the layers were separated. The aqueous layer was extracted with CH$_2$Cl$_2$ (1×25 mL) and the combined organics were dried (Na$_2$SO$_4$), filtered and concentrated in vacuo. Crude material was used as is or purified by normal phase flash chromatography.

Purification A (1-200 Mg Scale)

Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 0% B to 100% B, UV (254 nm) and MS detection). Fractions containing the desired product were combined and lyophilized to provide the trifluoroacetate salt of target compound as a white solid.

Purification B (200-2500 Mg Scale).

[Varian L/L 4002-2 column (5×50 cm.; Microsorb 100-10 C-18), flow rate=50 ml/min; mobile phase A: 100% water, 0.1% TFA; mobile phase B: 100% ACN, 0.1% TFA; gradient elution from 20% B to 95% B in 90 min., detection 254 nm].

Synthesis of (2S,3R)-2-amino-3-(Fmoc-amino)-butyric acid methyl ester hydrochloride (6)

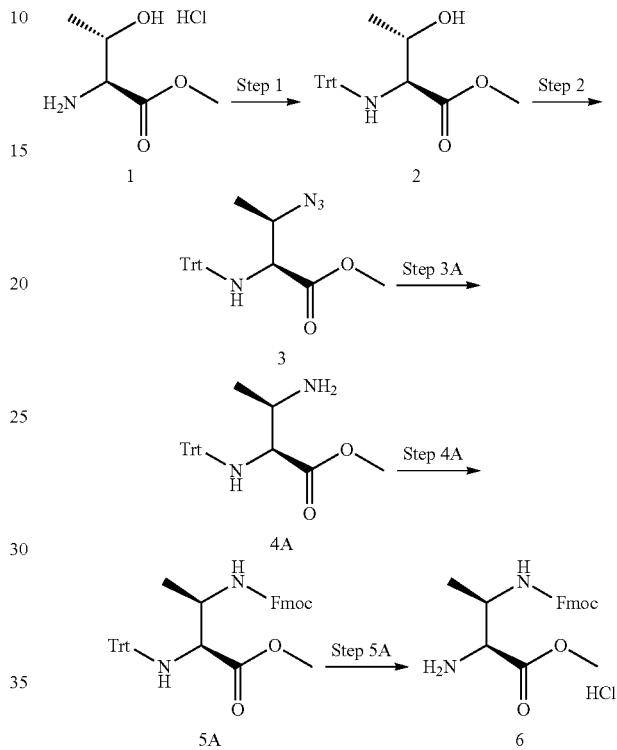

Step 1: (2S,3S)-3-hydroxy-2-(trityl-amino)-butyric acid methyl ester (2)

A suspension of H-allo-Thr-OMe.HCl (1, 45.8 g, 270 mmol) in anhydrous CH$_2$Cl$_2$ (225 ml) was ice cooled. Anhydrous NEt$_3$ (85 ml, 610 mmol) was added, followed by a solution of trityl chloride (79 g, 284 mmol) in anhydrous CH$_2$Cl$_2$ (225 ml) (dropwise over 30 min). The reaction mixture was allowed to warm to room temperature and stirred overnight. The resulting suspension was filtered and the white solid was washed with CH$_2$Cl$_2$ (2×450 ml). The filtrate was combined with the first CH$_2$Cl$_2$ washing and was washed with sat. NaHCO$_3$ (225 ml) and brine (225 ml). The second CH$_2$Cl$_2$ washing was used to back extract the aqueous extracts. The combined CH$_2$Cl$_2$ solutions were dried (Na$_2$SO$_4$), filtered, and concentrated. Hexane (450 ml) was added and the resulting mixture was concentrated. The resulting solid was triturated with hexane (600 ml), filtered, and washed with hexane to provide 2 (102.5 g, 100% yield, 98% pure by NMR) as a white solid.

Step 2: (2S,3R)-3-azido-2-(trityl-amino)-butyric acid methyl ester (3)

A solution of 2 (98.4 g, 262 mmol) and PPh$_3$ (68.7 g, 262 mmol) in anhydrous CH$_2$Cl$_2$ (1.7 l) was ice cooled. Diisopropyl azodicarboxylate (DIAD, 78 ml, 396 mmol) was added dropwise over 20 min, followed by diphenylphosphoric azide (DPPA, 93 ml, 432 mmol) added dropwise over 20 min. The resulting solution was allowed to warm to room temperature and stirred for two days. Solvent was evaporated and the residue was purified twice by flash chromatography (2 kg of SiO₂ each, eluting with 30% CH₂Cl₂ in hexanes, containing 1% NEt₃) to provide 3 (46.7 g, 45% yield) as a clear oil.

Step 3A: (2S,3R)-3-amino-2-(trityl-amino)-butyric acid methyl ester (4A)

To a solution of 3 (10 g, 25 mmol) in EtOAc (200 ml) was added Pd/C (5% wt, 2.5 g) and the resulting mixture was stirred under an H₂ ballon at room temperature for two days. The reaction mixture was filtered through Celite and the filtrate was concentrated to provide the desired compound 4A (9.2 g, 99% yield) which was used directly in the next step.

Step 4A: (2S,3R)-3-(Fmoc-amino)-2-(trityl-amino)-butyric acid methyl ester (5A)

A solution of 4A (0.94 g, 2.5 mmol) and Fmoc-OSu (0.89 g, 2.63 mmol) in anhydrous THF (5 ml) was stirred at room temperature for 3.5 h. Solvent was evaporated and the resulting residue was purified by flash chromatography (CombiFlash, 40 g silica gel column, 35 ml/min, 10-30% EtOAc in hexane) to provide 5A (1.2 g, 81% yield) as a white solid.

Step 5A: (2S,3R)-2-amino-3-(Fmoc-amino)-butyric acid methyl ester (6)

To a solution of 5A (1.2 g, 2 mmol) in anhydrous THF (6 ml) was added 2 M HCl/ether (3 ml, 6 mmol) and the resulting solution was stirred at room temperature. A precipitate slowly begun forming. Anhydrous ether (9 ml) was added after 3.5 h and the resulting mixture was stirred at room temperature overnight. The solid was collected by filtration and was washed with ether (15 ml) to provide 6 (0.7 g, ca. 90% yield). NMR showed that this material contains about 4% of trityl alcohol. Trituration in ether is in progress.

Synthesis of (2S,3R)-2-amino-3-(Boc-amino)-butyric acid methyl ester hydrochloride (6A-HCl)

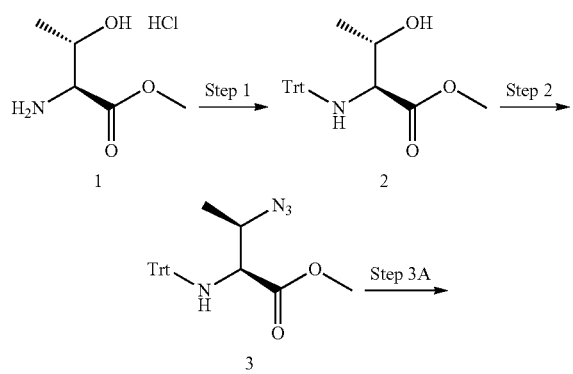

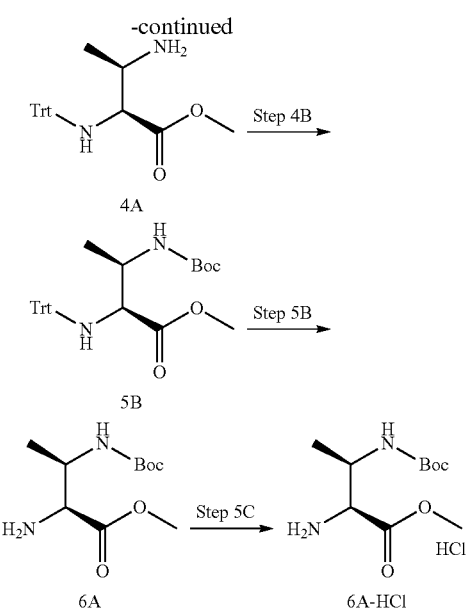

Note:
Steps 1, 2 and 3A were described in the experimentals for (6) above.

Step 4B: (2S,3R)-3-(Boc-amino)-2-(trityl-amino)-butyric acid methyl ester (5B)

A solution of 4A (137 g, 366 mmol) and Boc anhydride (96 g, 438 mmol) in anhydrous CH₂Cl₂ (350 ml) was stirred at room temperature overnight. Solvent was evaporated and the resulting residue was purified by flash chromatography (SiO₂, 10-30% EtOAc/hexane) to provide 5B (111.8 g, 64% yield) as a white solid.
¹H-NMR (300 MHz, DMSO-d₆) δ 7.42 (bd, J=7.2 Hz, 6H), 7.26 (bt, J=7.2 Hz, 6H), 7.18 (bt, J=7.2 Hz, 3H), 6.98 (bd, J=8.8 Hz, 1H), 3.9-3.75 (m, 1H), 3.24 (dd, J=11.3, 5.8 Hz, 1H), 3.01 (s, 3H), 2.66 (d, J=11.3 Hz, 1H), 1.37 (s, 9H), 1.09 (d, J=6.9 Hz, 3H).

Step 5B: (2S,3R)-2-amino-3-(Boc-amino)-butyric acid methyl ester (6A)

To a solution of 5B (126.8 g, 267 mmol) in anhydrous MeOH (1.4 l) was added Pd/C (10%, wet, 19.5 g) and the resulting mixture was hydrogenated in a Parr apparatus (50 psi pressure) over two days. The reaction mixture was filtered through Celite and solvent was evaporated. The residue was purified by flash chromatography (SiO₂, 50-100% EtOAc/hexane, then 0-10% MeOH/EtOAc) to provide 6A (57.6 g, 92% yield) as an oil. ¹H-NMR (300 MHz, DMSO-d₆) δ 6.62 (bd, J=9.1 Hz, 1H), 3.9-3.75 (m, 1H), 3.57 (s, 3H), 3.28 (d, J=4.1 Hz, 1H), 1.69 (bs, 2H), 1.36 (s, 9H), 1.03 (d, J=6.9 Hz, 3H)

Step 5C: (2S,3R)-2-amino-3-(Boc-amino)-butyric acid methyl ester HCl salt (6A-HCl)

A solution of 6A (57.6 g, 248 mmol) in anhydrous ether (300 ml) was ice cooled. A solution of HCl in ether (2 M, 124 ml, 248 mmol) was added dropwise over 15 minutes. The resulting solution was stirred for 5 minutes, hexane (900 ml) was added, and the resulting solid was collected by filtration. The solid was washed with hexane and was dried under high vacuum to provide 6A-HCl (63.3 g, 95% yield)

as a white solid. $^1$H-NMR (300 MHz, DMSO-$d_6$) δ 8.53 (bs, 3H), 6.96 (d, J=8.3 Hz, 1H), 4.15-4.05 (m, 2H), 3.70 (s, 3H), 1.38 (s, 9H), 1.13 (d, J=6.9 Hz, 3H). MS (APCI, pos): 233 (M+1, 20%), 177 (233-CH$_2$=CMe$_2$, 100%), 133 (177-CO$_2$). Elemental Analysis: Found: C, 44.16; H, 7.90; N, 10.06; Cl, 13.03. Calc.: C, 44.10; H, 7.92; N, 10.29; Cl, 13.02; (C$_{10}$H$_{21}$N$_2$O$_4$Cl.0.2H$_2$O). LC purity: 100% (MS, TIC).

(2S,3S)-methyl 3-(((9H-fluoren-9-yl)methoxy)carbonylamino)-2-aminobutanoate hydrochloride (7)

(2R,3S)-methyl 3-(((9H-fluoren-9-yl)methoxy)carbonylamino)-2-aminobutanoate hydrochloride (8)

(2R,3R)-methyl 3-(((9H-fluoren-9-yl)methoxy)carbonylamino)-2-aminobutanoate hydrochloride (9)

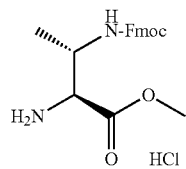

7

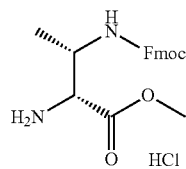

8

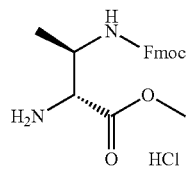

9

(7), (8) and (9) were prepared using the same method as described in the synthesis of compound (6).

Synthesis of 2-amino-3-(Boc-amino)-3-methyl-butyric acid methyl ester (C001)

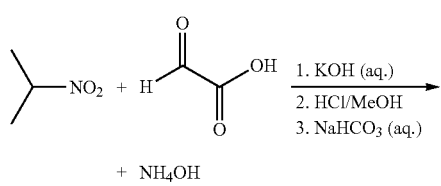

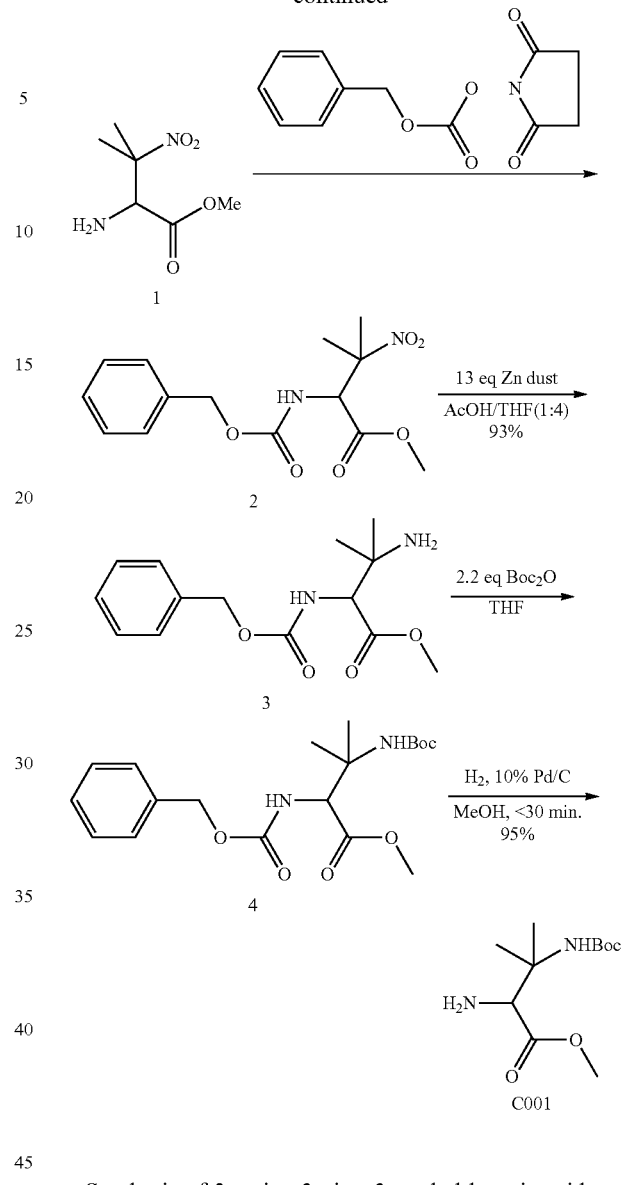

Synthesis of 2-amino-3-nitro-3-methyl-butyric acid methyl ester (1)

Reference: *J. Chem. Soc. Perkin Trans.* 1, 2659-2660 (1999).

2-Nitropropane (4.1 mL, 46 mmol, 2 eq) was taken up in 60 mL water containing KOH (3 g, 54 mmol, 2.3 eq). A solution of glyoxylic acid hydrate (2.15 g, 23 mmol, 1 eq) was treated with 30 mL of ammonia water (28-30%, ca. 10 eq), and this was added to the mixture containing the nitropropane. The clear, colorless reaction mixture was stirred vigorously for three hours at room temperature. The reaction mixture was cooled in ice water and treated with conc. HCl (aq) to pH=1-2. The reaction mixture attained a blue color at ca. pH 4 but remained homogeneous. The blue color was removed by washing sequentially with 2×50 mL and 1×25 mL chloroform, then the aqueous layer was stripped to yield a white solid. The solid was then taken up in one liter of absolute ethanol. Insoluble material was removed by filtration and discarded, and the filtrate was stripped to give 2-amino-3-methyl-3-nitrobutanoic acid (1) as a white solid, which was used without further purification.

This material was taken up in methanol and cooled in ice. HCl gas was bubbled through for ca. one hour, and the reaction mixture was stirred at room temperature overnight. A white solid formed, which was removed by filtration and deemed not to be product by $^1$H NMR. The methanol was removed in vacuo and the resulting slightly greasy off-white solid taken up in 750 mL of chloroform and stirred with 500 mL of sat. NaHCO$_3$ (aq.) to remove HCl. The layers were separated and the chloroform layer dried over Na$_2$SO$_4$, then stripped to an oil. Pure product was obtained via chromatography on silica gel using 5% ethyl acetate/hexanes. After removal of solvent, the resulting yellow oil was dried under vacuum for no more than one hour to avoid loss of material. No solvents were detected in the $^1$H NMR. Yield: 24 g (50%). TLC R$_f$=0.31 (40% ethyl acetate/hexanes). APCI(+) m/z=177, 130 amu (the latter peak is the most prominent, and is due to loss of HNO$_2$ occurring in the mass spectrometer). $^1$H NMR (CDCl$_3$, 300 MHz) δ 4.15 (s, 1H), 3.74 (s, 3H), 1.59 (s, 1H), 1.58 (s, 1H). C$_6$H$_{12}$N$_2$O$_4$ requires C, 40.91; H, 6.87; N, 15.90. Found C, 41.50; H, 6.99; N, 15.34.

2-(Z-amino)-3-methyl-3-nitro-butyric acid methyl ester (2)

To a solution of 2-Amino-3-nitro-3-methyl-butyric acid methyl ester 1 (5.37 g, 30.5 mmol) in 60 mL of THF and DIEA (6.6 mL, 40 mmol) Z—OSu (7.23 g, 29 mmol) was added and the reaction mixture was stirred 4 h at r.t. THF was removed under reduced pressure, the residue was taken in EtOAc (200 mL). Organics was washed with water (50 mL×2), brine (50 mL) and dried over Na$_2$SO$_4$. The solvent was removed by rotary evaporation and colorless oil 2 (5.9 g, 62%), which was used on next step without purification.

2-(Z-amino)-3-amino-3-methyl-butyric acid methyl ester (3)

To a cold (ice bath) solution of compound 2 (5.9 g, 19 mmol) in 10 mL of AcOH and 40 ml of THF, Zn dust (16.5 g, 250 mmol, 13 eq) was added over 2 min. After adding of zinc dust, the temperature of the reaction mixture was allowed to rise to ambient. Reaction was monitored by LCMS. After 2-3 hrs, LCMS showed the major peak of amine along with a small peak of acid (~5%). The reaction mixture was filtered through Celite using THF to rinse, and the filtrate was concentrated by rotary evaporation to give thick syrup. (Note: this syrup contained some amount of Zn(OAc)$_2$, but it would not affect next reaction).

2-(Z-amino)-3-(Boc-amino)-3-methyl-butyric acid methyl ester (4)

The above syrup was re-dissolved in 40 ml THF. Boc$_2$O (9.1 g, 41.8 mmol, 2.2 eq) was added, followed by addition of DIEA (10 ml, 57 mmol, 3 eq). The reaction mixture was stirred for 3 hr at ambient temperature. When LC-MS indicated the completion of reaction, solvent was evaporated and the resulting residue was purified by flash chromatography (Combiflash™, 80 g Si gel column, 40 ml/min, 0-30% EtOAc in Hexanes) to provide the desired compound (5.3 g, 74% on two steps) as white crystal.

2-Amino-3-(Boc-amino)-3-methyl-butyric acid methyl ester (C001)

To a solution of compound 4 (5.2 g, 14 mmol) in 70 ml of MeOH was added Pd/C (5% wt, 800 mg) and the resulting mixture was hydrogenated using a Parr shaker (50 psi H$_2$) for 30 min. Catalyst was removed by filtration and the filtrate was concentrated to give target compound C001 (3.3 g, as white crystal, 97.3%).

(2S)-2-Amino-3-(tert-butoxycarbonylamino)-3-methyl-butyric acid methyl ester HCl salt Via S-alpha-Methylbenzylamine (E-(S)—HCl)

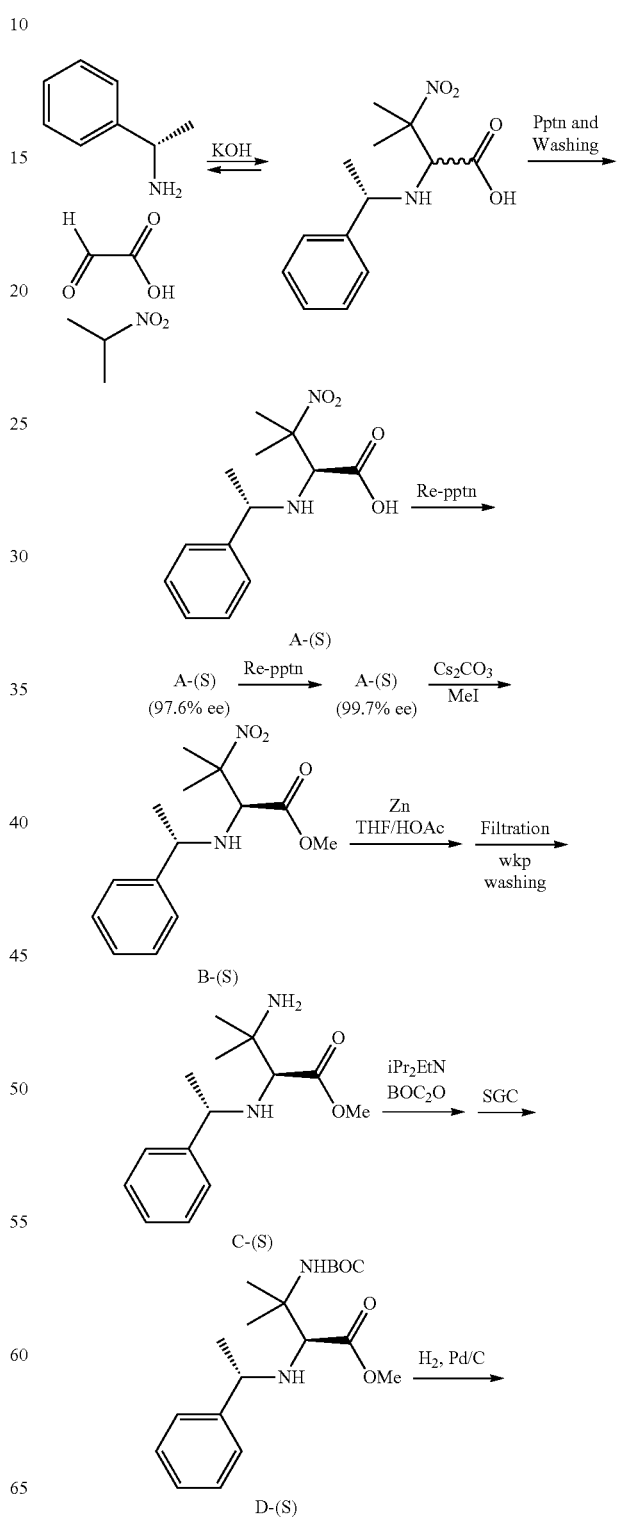

-continued

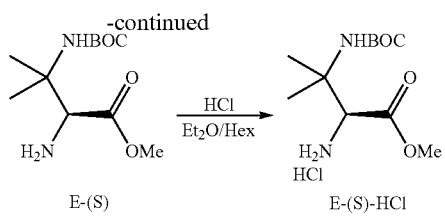

Synthesis of 3-Methyl-3-nitro-(2(S)-(1(S)-phenylethyl-amino))-butyric acid (A-(S))

The 2-nitropropane (90.87 g, 1.02 mol, 1.02 eq) and water (1.0 L) were placed under nitrogen in a 2 L Erlenmeyer flask with a large stirbar (2"×⅜"). With good stirring, the potassium hydroxide (~90%; 74.81 g, 1.20 mol, 1.2 eq) was added all at once (solution warms to ~40° C.). The flask was placed in a regulated water or oil bath heated to 45° C. The (S)-alpha-methylbenzylamine (130 mL, 1.02 mol, 1.02 eq) was measured and added very quickly (very fast $CO_2$ absorption). The reaction mixture was maintained at ~44-46° C. and stirred swiftly as the glyoxylic acid (50% aq, 112 mL, 1.00 mol, 1.00 eq) was added slowly dropwise (60 min, slowest for the last one-third) via a dropping funnel. The reaction mixture becomes cloudy, then clear, and when the solids begin forming again the addition was slowed down. After complete addition, the reaction was stirred for an additional 2-4 h under nitrogen as the temperature cools to 25-30° C. Additional water (200 mL) was added and the reaction mixture warmed to 34° C. (internal) and stirred swiftly as the 3.00 M aq hydrochloric acid (610 mL, 1.83 mol, 1.83 eq) was warmed in a dropping funnel and added as a stream over 20-30 min. The thick slightly off-white suspension was stirred for 0-16 h at room temperature (and if necessary, then placed in a −10° C. bath to cool to ~18-20° C. internally). The cooled suspension was then filtered with suction through paper and rinsed with dilute aq hydrochloric acid (0.2 M, 2 L), water (2 L) and ethyl ether (500 mL). The filtercake was then suctioned to compact "dryness" over 30-60 min. The filtercake was then transferred to a 20° C. desiccator or vacuum oven and dried under full vacuum for 2-6 h. The solids were then ground and placed in the vacuum oven for 2-4 h at 50-60° C., and 2-4 h at 90° C. to yield A-(S) as a slightly off-white powder (127.0 g, 47.7% yield). Check of a sample by HPLC-MS* showed a 4.5:95.5 ratio of diastereomers (2.13 min (minor), 2.30 min (major)) of the product with an overall purity of 94%. Both peaks show the same molecular weight ($MH^+$=266.7). LC-MS [M+H] 267.7 (C13H18N2O4+H, requires 267.30).

*[Common HPLC method: Onyx monolithic C18 column, 50×4.6 mm; 1.5 mL/min; 9.10 min gradient of 5%-60% MeCN in $H_2O$ with 0.1% TFA; UV (254 nm); MS; ELSD. Retention times are reported for UV (254 nm) unless otherwise noted.]

Purification of 3-Methyl-3-nitro-(2(S)-(1(S)-phenylethyl-amino))-butyric acid (A-(S))

A solution of dilute aq hydrochloric acid (3.0 M, 250 mL), water (3.0 L) and acetic acid (350 mL) was placed in a 4 L Erlenmeyer flask and stirred well as it was immersed in a 45-60° C. bath and warmed to 40° C. (internal). Once the solution was up to temperature, dissolve the amino-acid A-(S) (~10:90 d.r., 33.03 g) in stirred warm DMSO (50° C., dry, 150 mL) and add 100 mL of acetic acid to form a clear solution. Pour the solution into a separatory (dropping) funnel that was warmed and contains 150 mL of warm acetic acid and 100 mL of warm DMSO and mix. Suspend the dropping funnel over a fast vortex in the Erlenmeyer flask and add the warm DMSO solution to the Erlenmeyer flask at an even dropwise rate (~5-10 mL/min, ~45-60 min addition). The suspension was then filtered through paper by suction and rinsed with dilute aq hydrochloric acid (0.2 M, 2 L), water (4 L), isopropanol (150 mL) and ethyl ether (500 mL). The filtercake was then suctioned to compact "dryness" over 20-40 min. The filtercake was then transferred to a 20° C. vacuum oven and dried under full vacuum for 3-12 h. The solids are then ground and placed in the vacuum oven for 2 h at 50-60° C., and 2-4 h at 90-95° C. to yield A-(S) as a pale tan-white powder (29.66 g, 89.8% yield). Check of a sample by HPLC-MS showed a 1.2:98.8 ratio of diastereomers (HPLC-MS: 2.12 min (minor), 2.29 min (major); both $MH^+$=267.6) of the product with an overall purity>99%.

Second Purification of 3-Methyl-3-nitro-(2(S)-(1(S)-phenylethyl-amino))-butyric acid (A-(S))

(Procedure was similar to the first precipitation above.) A solution of dilute aq hydrochloric acid (3.0 M, 250 mL), water (3.0 L) and acetic acid (450 mL) was placed in a 4 L Erlenmeyer flask and stirred well as it was immersed in a 45-60° C. bath and warmed to 40° C. (internal). Once the solution was up to temperature, dissolve the amino-acid A-(S) (1.2:98.8 d.r., 31.05 g) in stirred warm DMSO (50° C., dry, 175 mL) and add 100 mL of acetic acid to form a clear solution. Pour the solution into a separatory (dropping) funnel that was warmed and contains 100 mL of warm acetic acid and 75 mL of warm DMSO and mix. Suspend the dropping funnel over a fast vortex in the Erlenmeyer flask and add the warm DMSO solution to the Erlenmeyer flask at an even dropwise rate (~5-10 mL/min, ~45-60 min addition). Upon complete addition, the suspension was stirred and placed in a −10° C. bath to cool to ~20-22° C. internally. The suspension was then filtered through paper by suction and rinsed with dilute aq hydrochloric acid (0.2 M, 2 L), water (4 L), isopropanol (150 mL) and ethyl ether (500 mL). The filtercake was then suctioned to compact "dryness" over 20-40 min. The filtercake was then transferred to a 20° C. vacuum oven and dried under full vacuum for 3-12 h. The solids are then ground and placed in the vacuum oven for 2 h at 50-60° C., and 2-4 h at 90-95° C. to yield A-(S) as a slightly off-white powder (29.6 g, 95% yield). Check of a sample by HPLC-MS showed a 0.15:99.85 ratio of diastereomers (2.12 min (minor), 2.31 min (major)) of the product with an overall purity>99%.

Synthesis of 3-Methyl-3-nitro-2(S)-(1(S)-phenylethyl-amino)-butyric acid methyl ester (B—(S))

Into a dry 100 mL flask with a stirbar was placed the amino-acid A-(S) (9.77 g, 36.7 mmol) and cesium carbonate (12.55 g, 38.05 mmol, 1.05 eq.) under nitrogen. With rapid stirring the dimethylformamide (37 mL) was added rapidly and stirred for 10 min, with sonication for 1 min. The reaction mixture was then cooled in a 10-15° C. water bath as the first portion of iodomethane (1.75 mL, two-thirds of the 2.63 mL) was added dropwise over 15 min. The bath was removed and the reaction was brought to room temperature over 20 min. The second portion of iodomethane (0.88 mL, one-third of the 2.63 mL) was added dropwise more slowly over 30 min. After the reaction was stirred for an additional 20 min, check of a sample by HPLC-MS showed a major product peak (5.89 min, $MH^+$=281.7; 99.2% convn) with of a small amount of the SM (2.64 min, ~0.75%). After the reaction was stirred for an additional 60 min, check of a sample by HPLC-MS showed complete conversion to the product peak. The reaction was then washed with EtOAc and water into a separatory funnel containing EtOAc (250 mL), water (70 mL) and 3 M aq HCl (12.8 mL, 38.4 mmol). The phases were shaken and the aqueous layer was adjusted to pH~7-8 and separated. The organic phase was washed with 3% aq $Li_2SO_4$ (3×100 mL), half-saturated aq $NaHCO_3$ (50 mL) and satd aq NaCl (2×100 mL), dried ($Na_2SO_4$), filtered and evaporated under reduced pressure with a heptane chaser to an amber oil. After placing under full vacuum for >4 h, the amino-ester B—(S) (9.88 g, 96% yield) was obtained. Check of a sample by HPLC-MS showed a major product peak (3.32 min, $MH^+$=281.7). LC-MS [M+H] 281.7 (C14H20N2O4+H, requires 281.33).

Synthesis of 3-Amino-3-methyl-(2(S)-(1(S)-phenylethyl-amino))-butyric acid methyl ester (C—(S))

The amino-ester B—(S) (9.88 g, 35.24 mmol) was dissolved in dry THF (100 mL) and glacial acetic acid (150 mL) along with activated powdered molecular sieves (4 A, 12 g) and stirred mildly for 2-4 h under nitrogen. The flask was then immersed in a 0° C. bath and stirred well for 20 min. To the cooled reaction mixture was then added the zinc dust (20.74 g, 317 mmol, 9 eq) portionwise: 1 eq of zinc dust (2.30 g) was added and the flask removed from the bath and stirred for 10 min, and then immersed in a 20° C. bath, stirred for 20 min. Another 2 eq portion of zinc dust (4.61 g) was added and the mixture stirred ~20-30 min until slight venting through a bubbler ceased. The last sequence was repeated 3 more times to finish the addition of zinc dust (9 eq total). After stirring a total of 18 h, a check of a sample by HPLC-MS showed a major product peak (3.36 min, $MH^+$=251.7) with a minor diamino-acid peak (1.38 min, $MH^+$=237.6). This mixture was then diluted with THF (~150 mL) and filtered through a celite pad with additional THF (~-300 mL) washing. This slightly cloudy solution was rotary evaporated under full vacuum to yield a slightly yellow oily solid (32.6 g). This material was dissolved in 3:1 chloroform/isopropanol (200 mL) and poured into a separatory funnel containing 3:1 chloroform/isopropanol (500 mL) and 0.25 M EDTA solution at pH 10.5-11 (275 mL). Aqueous 4 M NaOH soln (18 mL) was added and the mixture was shaken and the pH of the aqueous checked. Additional 4 M NaOH soln was added in portions to reach pH 10.5-11.0. The funnel contents were thoroughly shaken, and the aqueous phase separated. The organic phase was then thoroughly shaken with 0.25 M EDTA solution at pH 10.5-11 (1×200 mL, 1×50 mL), and separated. The organic phase was then washed with satd aq NaCl (3×150 mL), dried ($Na_2SO_4$), filtered and evaporated under reduced pressure, followed with addition of heptane (3×100 mL) and evaporation to yield a light-amber oil. After placing under full vacuum for ~1-2 h, the diamino-ester C—(S) (7.62 g, 86.4% yield) was obtained. Check of a sample by HPLC-MS showed a major product peak (3.32 min, $MH^+$=251.7). LC-MS [M+H] 251.7 (C14H22N2O2+H, requires 251.34).

Synthesis of 3-(tert-Butoxycarbonylamino)-3-methyl-(2(S)-(1(S)-phenylethyl-amino))-butyric acid methyl ester (D-(S))

The diamino-ester C—(S) (7.62 g, 30.44 mmol, 1.0 eq) was dissolved in THF (150 mL) under nitrogen and diisopropylethylamine (5.8 mL, 33.5 mmol, 1.10 eq) was added to this solution. The tert-butylpyrocarbonate (9.96 g, 45.66 mmol, 1.50 eq) was added in two portions: the first portion (7.97 g, 1.20 eq) was followed by the second portion (1.99 g, 0.30 eq) 1 h later. After stirring for 10 h, a check of a sample by HPLC-MS showed a major product peak (4.94 min, $MH^+$=351.7) with a minor SM peak (3.59 min, ~2%). After stirring for 16 h, a check of a sample by HPLC-MS showed complete reaction. The reaction mixture was then dissolved in EtOAc (~300 mL) and washed with water containing 1 eq HCl (0.3 M HCl, 100 mL), half saturated $NaHCO_3$ soln (100 mL), ~14% aq $NH_4OH$ (2×75 mL), satd aq NaCl (2×70 mL), dried ($Na_2SO_4$), filtered and concentrated under reduced pressure to yield the BOC-diamino-ester D-(S) (10.5 g) as an oily part crystalline residue. This material was dissolved in a minimum of DCM and loaded onto a Combiflash column (silica gel, 230-400 mesh, 400 g) and chromatographed using DCM (85 mL/min) as eluant for 10 min, followed with a gradient of EtOAc (0-10% over 40 min) in DCM. The pure fractions eluted between 0.6% and 5% EtOAc in DCM. Evaporation gave 6.30 g of pure BOC-diamino-ester D-(S) as a slightly crystalline viscous oil. Check of a sample by HPLC-MS showed a major product peak (4.85 min, $MH^+$=351.7). LC-MS [M+H] 351.7 (C19H30N2O4+H, requires 351.46).

Synthesis of (2S)-2-Amino-3-(tert-butoxycarbonylamino)-3-methyl-butyric acid methyl ester (E-(S))

The combined BOC-diamino-ester D-(S) (6.30 g, 17.98 mmol) was dissolved in THF (5% soln, 125 mL) in Parr shaker bottle and placed under nitrogen. The palladium hydroxide catalyst (2.27 g, 18 wt %) was rapidly weighed and added to the shaker flask with a following flush with nitrogen. The shaker flask was then connected to hydrogen and evacuated and refilled 3 times. The flask was then filled with hydrogen (70 psi) and shaking was commenced. The pressure was kept above 60 psi as the hydrogen was consumed. After 1 h, check of a sample by HPLC-MS showed incomplete deprotection. After 11 h, check of a sample by HPLC-MS showed a major product peak (2.55 min (MS-TIC), 2.59 (ELSD), $MH^+$=247.5) with no other peaks visible by UV (254 nm), MS, or ELSD. This mixture was then carefully flushed with nitrogen and filtered through a celite pad with additional MeOH (~250 mL) washing. This clear solution was rotary evaporated under reduced pressure (to 35° C.) followed with addition of heptane (50 mL) and evaporation to yield a "water" clear oil (4.2 g) that was kept under vacuum. LC-MS [M+H] 247.5 (C11H22N2O4+H, requires 247.31).

Synthesis of (2S)-2-Amino-3-(tert-butoxycarbonylamino)-3-methyl-butyric acid methyl ester HCl salt (E-(S)—HCl)

The BOC-Me₂DAP methyl ester (E-(S)) (506 mg, 2.05 mmol) under nitrogen was dissolved in diethyl ether (3 mL), cooled in a 0° C. bath and rapidly stirred as a 2 M in $Et_2O$ hydrochloric acid soln (1.05 mL, 2.10 mmol, 1.02 eq) was added over 1 min. After stirring an additional 4 min, hexanes (25 mL) was added, and the suspension shaken, centrifuged and decanted. Additional hexanes (~20 mL) was added and the suspension shaken, cooled in a 0° C. bath, centrifuged and decanted. The white precipitate was dried under full vacuum to yield the BOC-diamino-ester hydrochloride salt (E-(S)—HCl) (592 mg, 101.9% yield). Check of the sample by HPLC-MS showed the major product peak (2.89 min (MS-TIC), 2.92 (ELSD), MH+=247.5) with no other peaks visible by UV (254 nm), MS, or ELSD. LC-MS [M+H] 247.5 (C11H22N2O4+H, requires 247.31).

| Compound | Scale (mmol) | Yield (mg) | Yield (%) | Purity (%) | [M + H] | Retention time (min)* |
|---|---|---|---|---|---|---|
| E-(S)-HCl | 2.05 | 592 | 100 | 100 | 247.5 | 2.89 |

*[HPLC method: Onyx monolithic C18 column, 50 × 4.6 mm; 1.5 mL/min; 9.10 min gradient of 5%-60% MeCN in H2O with 0.1% TFA; UV (254 nm); MS; ELSD. Retention times reported for UV (254 nm).]

Synthesis of (2R)-2-Amino-3-(Boc-amino)-3-methyl-butyric acid methyl ester (C002)

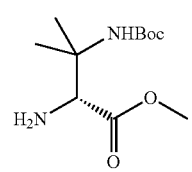

C002

(C002) was prepared using the same method described in the synthesis of compound (E-(S)—HCl) by R-alpha-Methylbenzylamine instead.

Synthesis of di-Me-(S)-Ser methyl ester

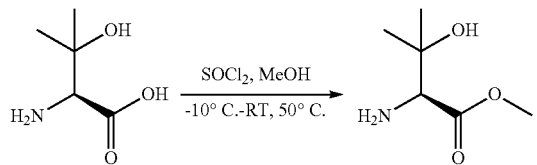

Thionyl chloride (0.34 ml, 4.7 mmol) was added dropwise to a suspension of H—(S)-di-Me-Ser-OH (250 mg, 1.88 mmol) in MeOH (4 ml) at −10° C. Reaction mixture was stirred at low temperature for 30 min and then temperature of reaction was raised to ambient. After the reaction mixture was heated at 50° C. for 2 days. Then, additional amount of thionyl chloride (0.34 ml, 4.7 mmol) was added to the reaction mixture at low temperature. Stirring was continued at 50° C. for 3 days. Completion of the reaction was monitored by TLC (in order to check a starting amino acid) and LCMS. After completion (5-6 days) solvent was evaporated in vacuum and residue was dried in vacuum overnight to provide target compound hydrochloride (343 mg, 100%) as white solid. Compound was used as is for the next step transformation with no additional purification.

Example 82

N-((1S,2R)-2-Amino-1-hydroxycarbamoyl-propyl)-4-[4-(4-methoxy-phenyl)-buta-1,3-diynyl]-benzamide (82-1)

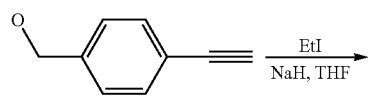

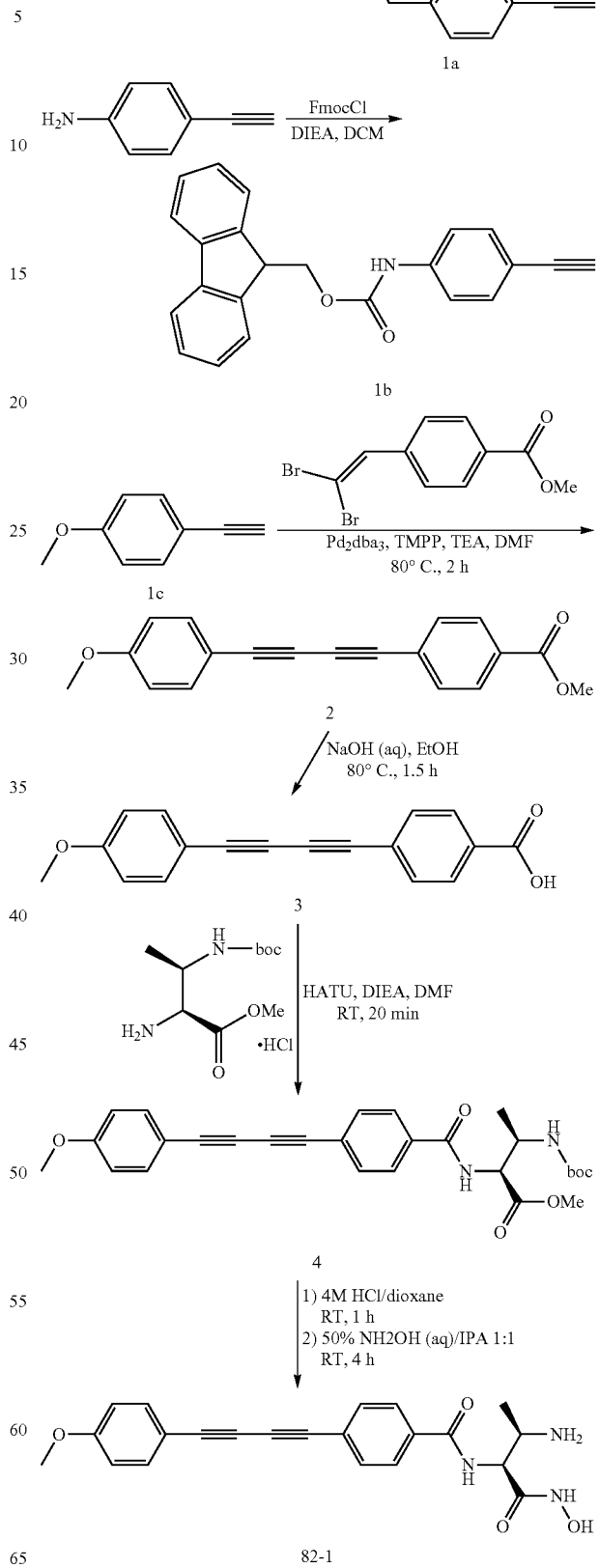

Synthesis of 1-ethoxymethyl-4-ethynyl-benzene (1a)

To a cold solution of 4-ethynyl benzyl alcohol (500 mg, 3.8 mmol) and iodoethane (336 mL, 4.2 mmol) in anhydrous THF (3 mL) at 0° C. was added NaH (212 mg, 5.3 mmol). The reaction mixture was stirred at 25° C. for 30-60 min, monitored by LC-MS until there was no starting material remained. The solution was quenched with MeOH (1 mL) and volatiles were removed in vacuo. The crude mixture was partitioned in aqueous HCl (1 N, 10 mL) and EtOAc (10 mL), the aqueous layer was extracted with ethyl acetate and the combined organics were washed with brine, dried ($Na_2SO_4$), filtered and concentrated in vacuo. Crude material was purified by flash chromatography (20 g $SiO_2$, EtOAc/Hex) to give the desired compound (300 mg, 61%) as light yellow oil.

Synthesis of 1-(Fmoc-amino)-4-ethynyl-benzene (1b)

To a cold solution of 4-ethynyl aniline (1.4 g, 11.9 mmol) and DIEA (33 mL, 20 mmol) in $CH_2Cl_2$ (20 mL) at 0° C. was added Fmoc-Cl (3.25 g, 5.3 mmol) over 2 min. The solution was stirred at ambient temperature overnight. Solution was concentrated in vacuo and the crude material was redissolved in EtOAc (200 mL) and washed with water (2×70 mL) and brine (1×100 mL), dried ($Na_2SO_4$), filtered and concentrated in vacuo to provide the desired compound as a brown solid (3.35 g, 83%). $[M+H]^+$=439.1; Ret. Time (Method A)=6.78 min.

Synthesis of 4-[4-(4-Methoxy-phenyl)-buta-1,3-diynyl]-benzoic acid methyl ester (2)

Prepared as described in Method 1-B using 1c (2.0 g, 15.1 mmol) and methyl 4-(2,2-dibromovinyl)benzoate (4.00 g, 12.5 mmol). Purified by normal phase flash chromatography (80 g $SiO_2$, 0-50% EtOAc/Hex) to provide the desired compound 2 (940 mg, 26%) as an off-white solid. LC-MS: $[M+H]^+$=Not observed; Ret. Time (Method A) 7.76 min; $^1H$ NMR (250 MHz, $CDCl_3$) δ 3.8 (3H, s), 3.9 (3H, s), 6.8 (2H, d), 7.45 (2H, d), 7.6 (2H, d), 8.0 (2H, d).

Synthesis of 4-[4-(4-Methoxy-phenyl)-buta-1,3-diynyl]-benzoic acid (3)

Prepared as described in Method 2-A using compound 2 (470 mg, 1.62 mmol) to provide the desired compound 3 (412 mg, 92%) as an off-white solid. LC-MS: $[M+H]^+$=Not observed; Ret. Time (Method A) 6.34 min.

Synthesis of (2S,3R)-3-tert-Butoxycarbonylamino-2-{4-[4-(4-methoxy-phenyl)-buta-1,3-diynyl]-benzoylamino}-butyric acid methyl ester (4)

Prepared as described in Method 3-A using compound 3 (150 mg, 0.543 mmol) and (2S,3R)-3-methyl Dap.HCl (160 mg, 0.598 mmol) to provide the desired compound 4 (448 mg, 168%) as a viscous amber oil. LC-MS: $[M+H]^+$=491.2; Ret. Time (Method A) 6.99 min.

Synthesis of N-((1S,2R)-2-Amino-1-hydroxycarbamoyl-propyl)-4-[4-(4-methoxy-phenyl)-buta-1,3-diynyl]-benzamide (82-1)

Prepared as described in Method 5-A using compound 4 (266 mg, 0.543 mmol) to provide the crude product (119 mg, 56%) as an off-white solid. Crude product was purified by Purification Method A to provide the TFA salt of desired compound 82-1 (9 mg, 3%) as a white solid. LC-MS: $[M+H]^+$=392.4; Ret. Time (Method A) 4.34 min.

| Compound | Scale (mmol)[1] | Yield (mg) | Yield (%)[1] | Purity (%)[2] | [M + H] | Retention time (min)[2] |
|---|---|---|---|---|---|---|
| 82-1 | 0.543 | 8.5 | 3.1 | 99.1 | 392.4 | 4.34 |

[1]Based on the amount of carboxylic acid used in the coupling reaction.
[2]Using LC-MS Analytical Method A.

Each of the following compounds was synthesized as described above using the appropriate phenyl acetylene (all commercially available with the exception of 1a and 1b), amino acid and deprotection.

| Compound # | Structure | MH+ (m/z) | Ret. Time (min) | HPLC-MS Method |
|---|---|---|---|---|
| 82-2 | 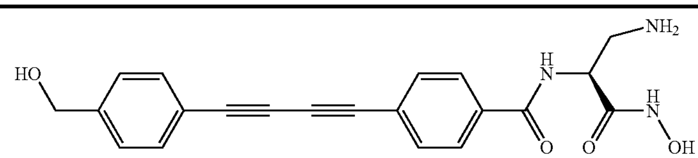 | 4.79 | 378.3 | A |
| 82-3 | 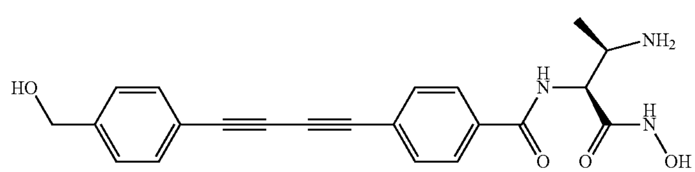 [SMILES: C[C@@H](N)[C@H](NC(=O)c1ccc(C#CC#Cc2ccc(CO)cc2)cc1)C(=O)NO] | 4.95 | 392.3 | A |
| 82-4 | 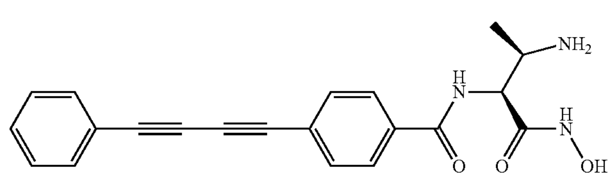 [SMILES: C[C@@H](N)[C@H](NC(=O)c1ccc(C#CC#Cc2ccccc2)cc1)C(=O)NO] | 6.67 | 362.3 | A |

-continued

| Compound # | Structure | MH+ (m/z) | Ret. Time (min) | HPLC-MS Method |
|---|---|---|---|---|
| 82-5 | 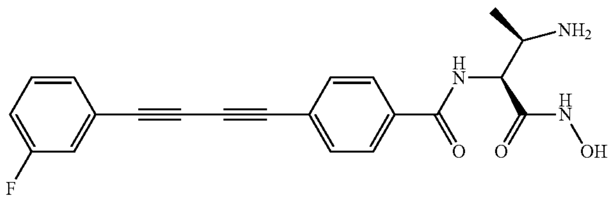 [SMILES: C[C@@H](N)[C@H](NC(=O)c1ccc(C#CC#Cc2cccc(F)c2)cc1)C(=O)NO] | 6.87 | 380.3 | A |
| 82-6 | 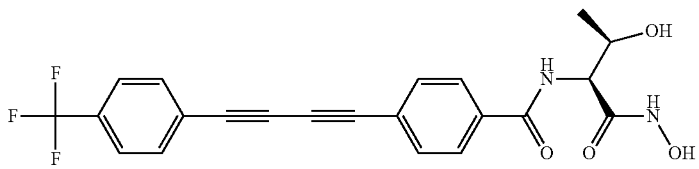 [SMILES: C[C@@H](O)[C@H](NC(=O)c1ccc(C#CC#Cc2ccc(C(F)(F)F)cc2)cc1)C(=O)NO] | 7.78 | 430.3 | A |
| 82-7 | 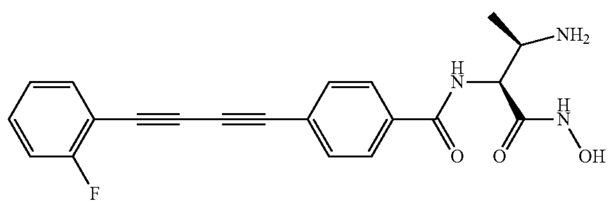 [SMILES: C[C@@H](N)[C@H](NC(=O)c1ccc(C#CC#Cc2ccccc2F)cc1)C(=O)NO] | 6.58 | 380.3 | A |
| 82-8 | 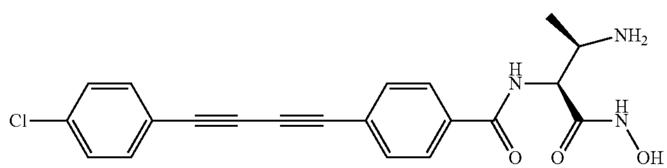 [SMILES: C[C@@H](N)[C@H](NC(=O)c1ccc(C#CC#Cc2ccc(Cl)cc2)cc1)C(=O)NO] | 7.47 | 395.9 | A |
| 82-9 | 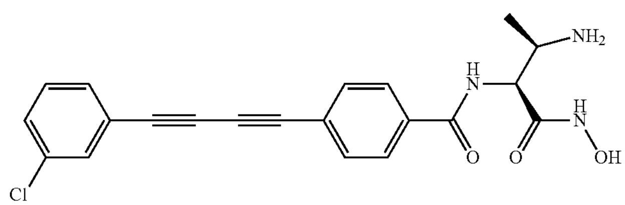 [SMILES: C[C@@H](N)[C@H](NC(=O)c1ccc(C#CC#Cc2cccc(Cl)c2)cc1)C(=O)NO] | 7.36 | 395.9 | A |
| 82-10 | 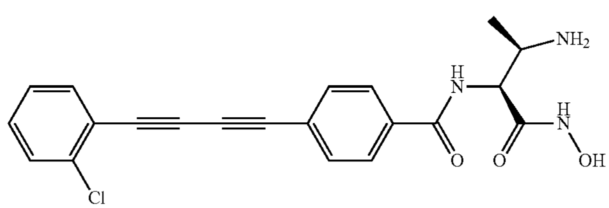 | 6.97 | 396.3 | A |
| 82-11 | 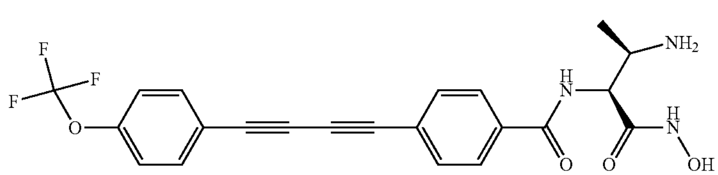 [SMILES: C[C@@H](N)[C@H](NC(=O)c1ccc(C#CC#Cc2ccc(OC(F)(F)F)cc2)cc1)C(=O)NO] | 7.90 | 446.3 | A |
| 82-12 | 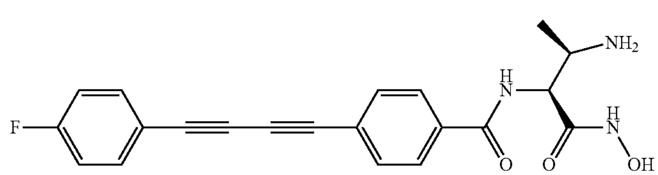 [SMILES: C[C@@H](N)[C@H](NC(=O)c1ccc(C#CC#Cc2ccc(F)cc2)cc1)C(=O)NO] | 6.79 | 380.3 | A |

-continued

| Compound # | Structure | MH+ (m/z) | Ret. Time (min) | HPLC-MS Method |
|---|---|---|---|---|
| 82-13 | 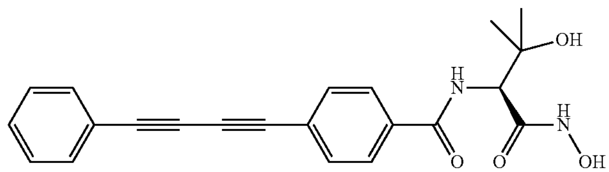 [SMILES: CC(C)(O)[C@H](NC(=O)c1ccc(C#CC#Cc2ccccc2)cc1)C(=O)NO] | 6.48 | 377.1 | A |
| 82-14 | 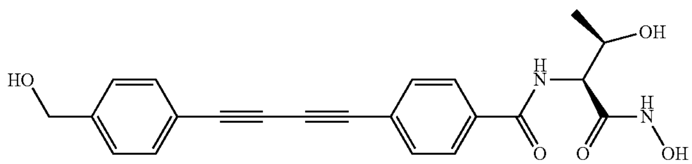 [SMILES: C[C@@H](O)[C@H](NC(=O)c1ccc(C#CC#Cc2ccc(CO)cc2)cc1)C(=O)NO] | 5.60 | 393.1 | A |
| 82-15 | 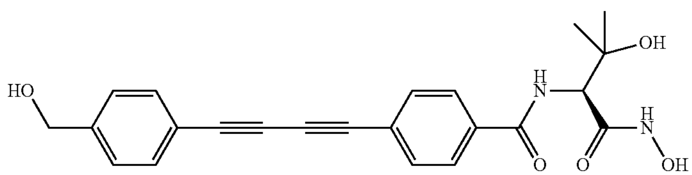 [SMILES: CC(C)(O)[C@H](NC(=O)c1ccc(C#CC#Cc2ccc(CO)cc2)cc1)C(=O)NO] | 5.89 | 407.1 | A |
| 82-16 | 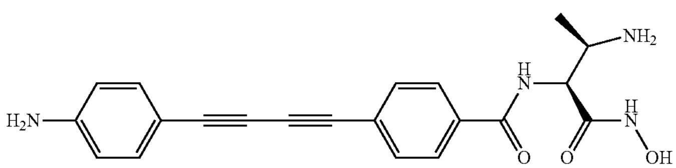 [SMILES: C[C@@H](N)[C@H](NC(=O)c1ccc(C#CC#Cc2ccc(N)cc2)cc1)C(=O)NO] | 4.10 | 377.1 | A |
| 82-17 | 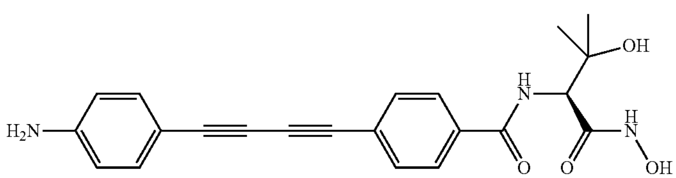 [SMILES: CC(C)(O)[C@H](NC(=O)c1ccc(C#CC#Cc2ccc(N)cc2)cc1)C(=O)NO] | 4.90 | 392.3 | A |
| 82-18 | 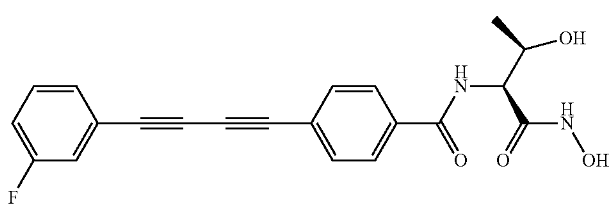 [SMILES: C[C@@H](O)[C@H](NC(=O)c1ccc(C#CC#Cc2cccc(F)c2)cc1)C(=O)NO] | 7.55 | 381.1 | A |
| 82-19 | 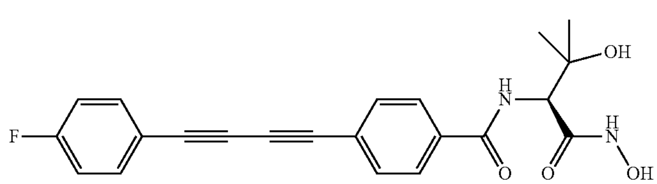 [SMILES: CC(C)(O)[C@H](NC(=O)c1ccc(C#CC#Cc2ccc(F)cc2)cc1)C(=O)NO] | 7.78 | 395.1 | A |
| 82-20 | 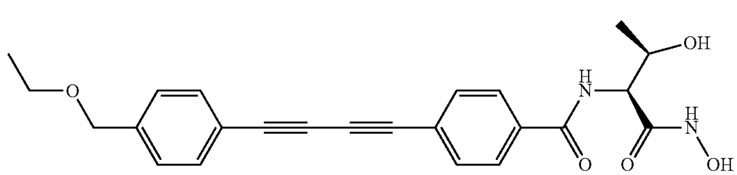 [SMILES: CCOCc1ccc(C#CC#Cc2ccc(C(=O)N[C@H](C(=O)NO)[C@@H](C)O)cc2)cc1] | 7.71 | 421.1 | A |

-continued

| Compound # | Structure | MH+ (m/z) | Ret. Time (min) | HPLC-MS Method |
|---|---|---|---|---|
| 82-21 | 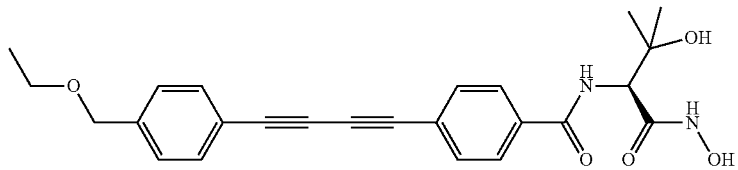 [SMILES: CCOCc1ccc(C#CC#Cc2ccc(C(=O)N[C@H](C(=O)NO)C(C)(C)O)cc2)cc1] | 8.03 | 435.1 | A |
| 82-22 | 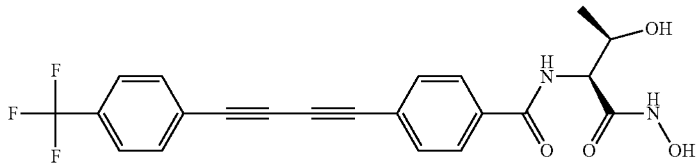 [SMILES: C[C@@H](O)[C@H](NC(=O)c1ccc(C#CC#Cc2ccc(C(F)(F)F)cc2)cc1)C(=O)NO] | 5.70 | 431.1 | A |
| 82-23 | 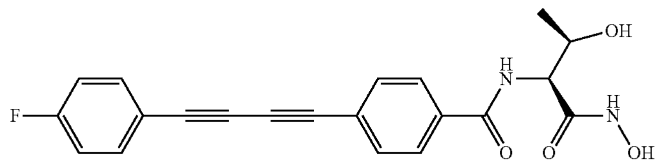 [SMILES: C[C@@H](O)[C@H](NC(=O)c1ccc(C#CC#Cc2ccc(F)cc2)cc1)C(=O)NO] | 5.13 | 381.1 | A |
| 82-24 | 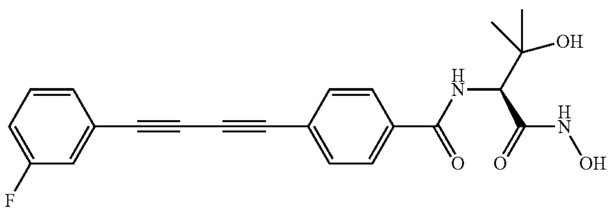 [SMILES: CC(C)(O)[C@H](NC(=O)c1ccc(C#CC#Cc2cccc(F)c2)cc1)C(=O)NO] | | | A |
| 82-25 | 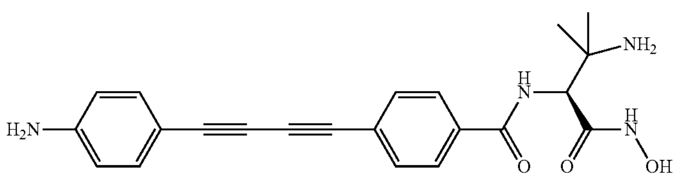 [SMILES: CC(C)(N)[C@H](NC(=O)c1ccc(C#CC#Cc2ccc(N)cc2)cc1)C(=O)NO] | | | A |
| 82-26 | 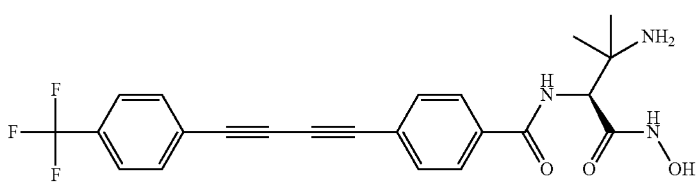 [SMILES: CC(C)(N)[C@H](NC(=O)c1ccc(C#CC#Cc2ccc(C(F)(F)F)cc2)cc1)C(=O)NO] | | | A |
| 82-27 | 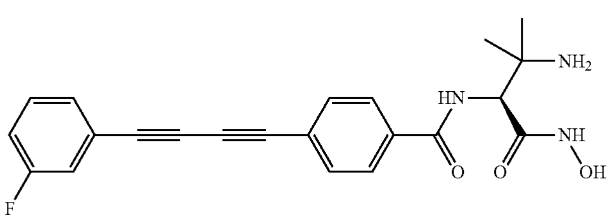 [SMILES: CC(C)(N)[C@H](NC(=O)c1ccc(C#CC#Cc2cccc(F)c2)cc1)C(=O)NO] | 7.05 | 394.3 | A |
| 82-28 | 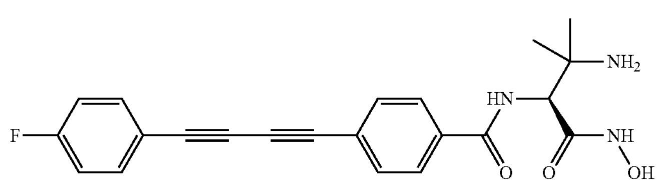 [SMILES: CC(C)(N)[C@H](NC(=O)c1ccc(C#CC#Cc2ccc(F)cc2)cc1)C(=O)NO] | 7.01 | 394.3 | A |

| Compound # | Structure | MH+ (m/z) | Ret. Time (min) | HPLC-MS Method |
|---|---|---|---|---|
| 82-29 | 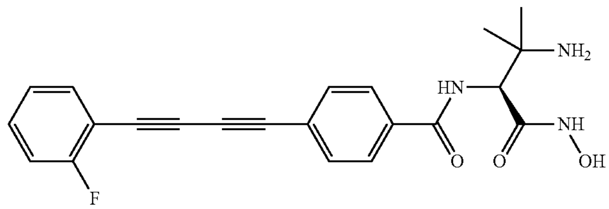 [SMILES: CC(C)(N)[C@H](NC(=O)c1ccc(C#CC#Cc2ccccc2F)cc1)C(=O)NO] | 394.3 | 6.83 | A |
Example 83
N—((S)-2-Amino-1-hydroxycarbamoyl-2-methyl-propyl)-4-[4-(4-hydroxy-phenyl)-buta-1,3-diynyl]-benzamide (83-1)
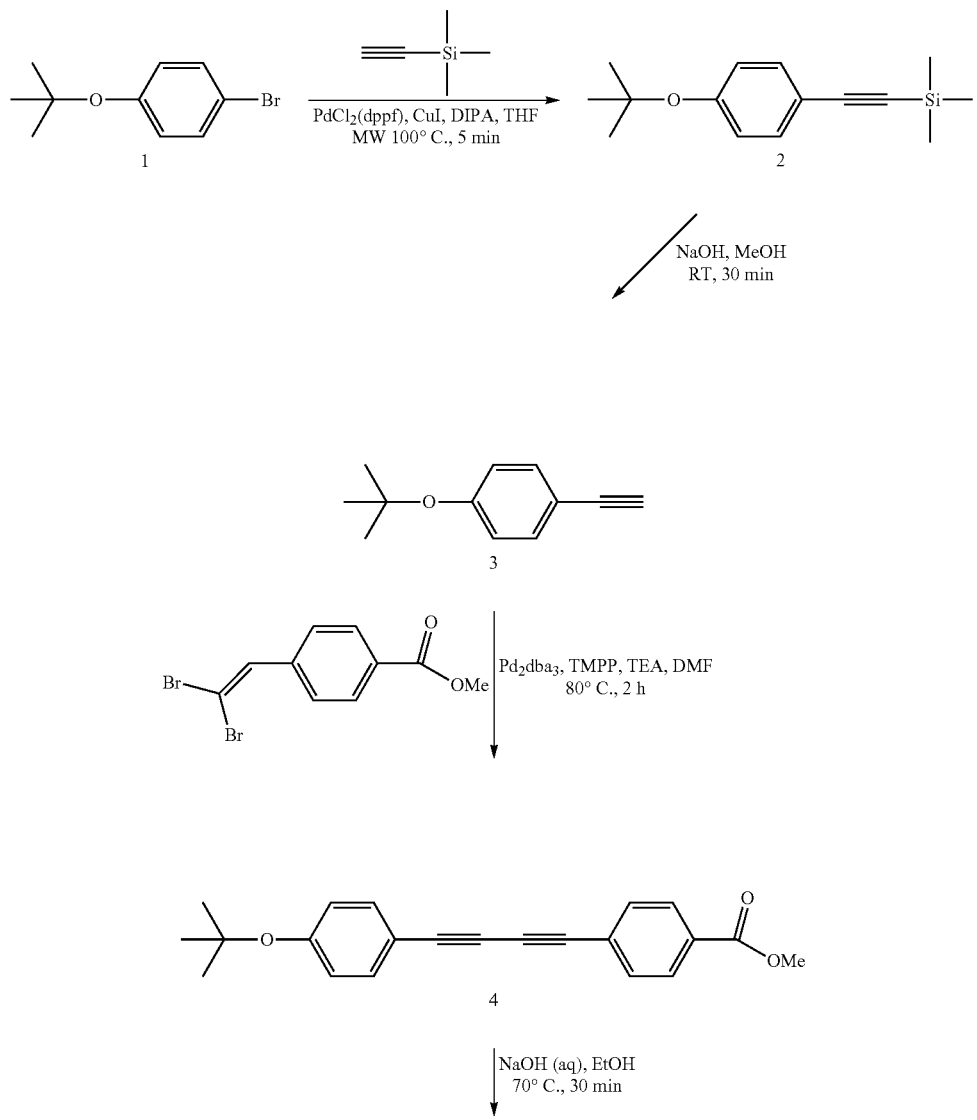

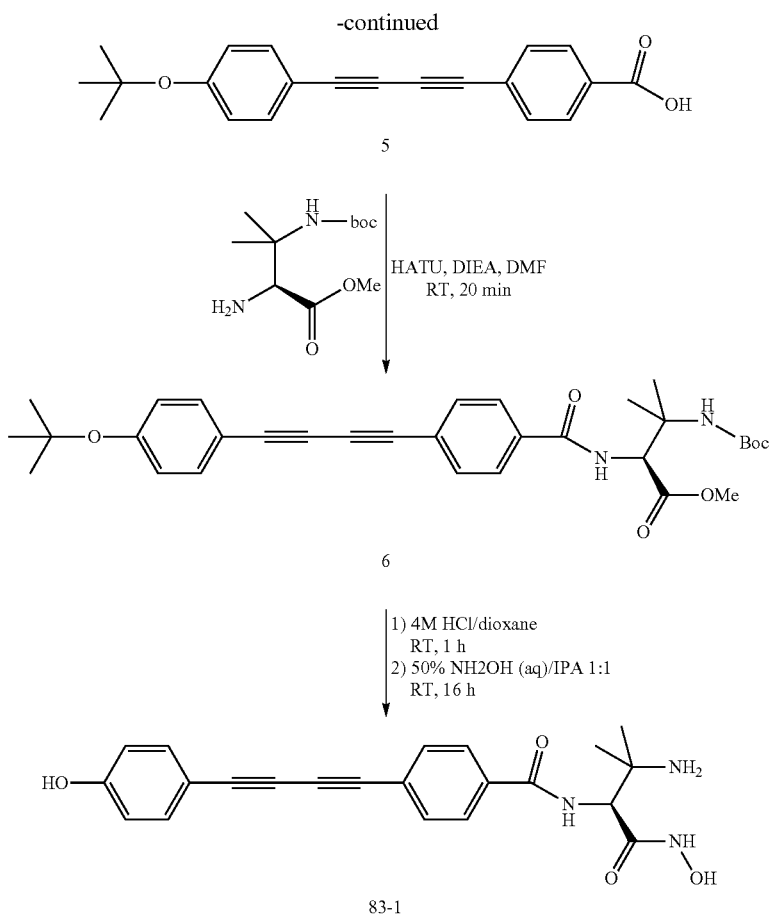

Synthesis of (4-tert-butoxy-phenylethynyl)-trimethyl-silane (2)

A 20 mL microwave tube was charged with a mixture of 1-bromo-4-tert-butoxybenzene 1 (1.0 g, 4.36 mmol), $PdCl_2$(dppf) (71 mg, 0.087 mmol), CuI (33 mg, 0.174 mmol), DIPA (0.924 mL, 6.55 mmol), and THF (15 mL). Tube was backfilled with nitrogen, sealed, and irradiated in a microwave reactor (max. power 250 W) at 100° C. for 5 min. Solution was diluted with water (200 mL) and extracted with EtOAc (3×80 mL). Combined organic layers were washed with water (1×100 mL) and brine (1×80 mL), dried ($Na_2SO_4$), filtered and concentrated in vacuo. Crude product was purified by normal phase flash chromatography (40 g $SiO_2$, O-30% EtOAc/Hex) to provide the desired compound 2 (488 mg, 45%) as a clear colorless oil. LC-MS: $[M+H]^+$=Not observed; Ret. Time (Method A) 7.87 min; $^1$H NMR (250 MHz, $CDCl_3$) δ 0.2 (s, 9H), 1.3 (s, 9H), 6.9 (d, 2H), 7.4 (d, 2H).

Synthesis of 1-tert-Butoxy-4-ethynyl-benzene (3)

Prepared as described in Method 3-A using compound 2 (488 mg, 1.98 mmol) to provide the desired compound 3 (373 mg, 108%) as a clear colorless oil. LC-MS: $[M+H]^+$=Not observed; Ret. Time (Method A) 5.87 min; $^1$H NMR (250 MHz, $CDCl_3$) δ 1.3 (s, 9H), 3.0 (s, 1H), 6.9 (d, 2H), 7.4 (d, 2H).

Synthesis of 4-[4-(4-t-Butoxy-phenyl)-buta-1,3-diynyl]-benzoic acid methyl ester (4)

Prepared as described in Method 1-B using compound 3 (373 mg, 2.14 mmol) and methyl 4-(2,2-dibromovinyl)benzoate (822 mg, 2.57 mmol) to provide the desired compound 4 (160 mg, 23%) as an off-white solid. LC-MS: $[M+H]^+$=Not observed; Ret. Time (Method A) 8.28 min; $^1$H NMR (250 MHz, $CDCl_3$) δ 1.35 (s, 9H), 3.9 (s, 3H), 6.9 (d, 2H), 7.45 (d, 2H), 7.6 (d, 2H), 8.0 (d, 2H).

Synthesis of 4-[4-(4-tert-Butoxy-phenyl)-buta-1,3-diynyl]-benzoic acid (5)

Prepared as described in Method 2-A using compound 4 (160 mg, 0.482 mmol) to provide the desired compound 5 (130 mg, 85%) as a slightly off-white solid. LC-MS: $[M+H]^+$=Not observed; Ret. Time (Method A) 7.10 min.

Synthesis of (S)-3-tert-Butoxycarbonylamino-2-{4-[4-(4-tert-butoxy-phenyl)-buta-1,3-diynyl]-benzoylamino}-3-methyl-butyric acid methyl ester (6)

Prepared as described in Method 3-A using compound 5 (65 mg, 0.205 mmol) and (2S,3R)-3-methyl Dap (56 mg, 0.227 mmol) to provide the desired compound 6 (117 mg, 104%) as a light amber solid. LC-MS: $[M+H]^+$=547.2; Ret. Time (Method A) 8.23 min.

Synthesis of N—((S)-2-Amino-1-hydroxycarbamoyl-2-methyl-propyl)-4-[4-(4-hydroxy-phenyl)-buta-1,3-diynyl]-benzamide (83-1)

Prepared as described in Method 5-A using compound 6 (112 mg, 0.205 mmol) to provide the desired compound 83-1. Crude material was purified by Purification Method A to provide the TFA salt of the desired compound 83-1 (36 mg, 35%) as a white solid. LC-MS: [M+H]$^+$=391.8; Ret. Time (Method A) 3.65 min.

| Compound | Scale (mmol)[1] | Yield (mg) | Yield (%)[1] | Purity (%)[2] | [M + H] | Retention time (min)[2] |
|---|---|---|---|---|---|---|
| 83-1 | 0.205 | 36.2 | 34.9 | 99.2 | 391.8 | 3.65 |

[1]Based on the amount of carboxylic acid used in the coupling reaction.
[2]Using LC-MS Analytical Method A.

The following compound was synthesized as described above.

| Compound # | Structure | RT[1] (min) | [M + H] |
|---|---|---|---|
| 83-2 | 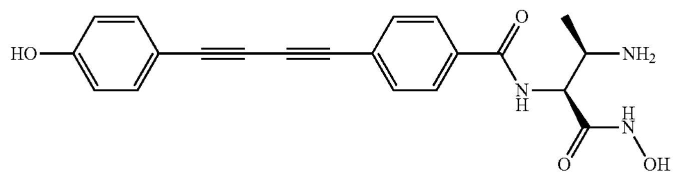 [SMILES: C[C@@H](N)[C@H](NC(=O)c1ccc(C#CC#Cc2ccc(O)cc2)cc1)C(=O)NO] | 3.53 | 378.4 |

[1]Using LC-MS Analytical Method A.

Example 84

N-((1S,2R)-2-Amino-1-hydroxycarbamoyl-propyl)-4-[4-(4-cyclopropoxy-phenyl)-buta-1,3-diynyl]-benzamide (84-1)

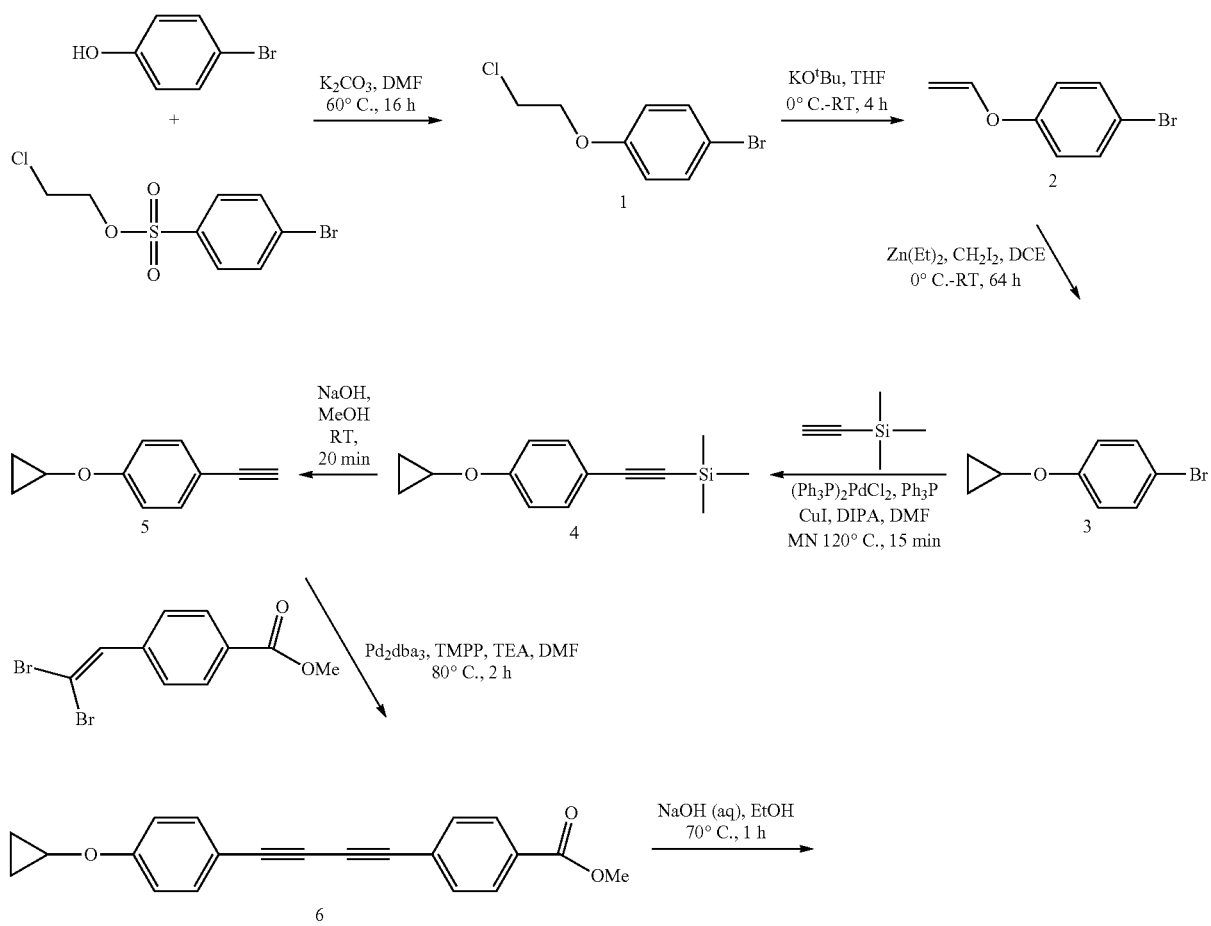

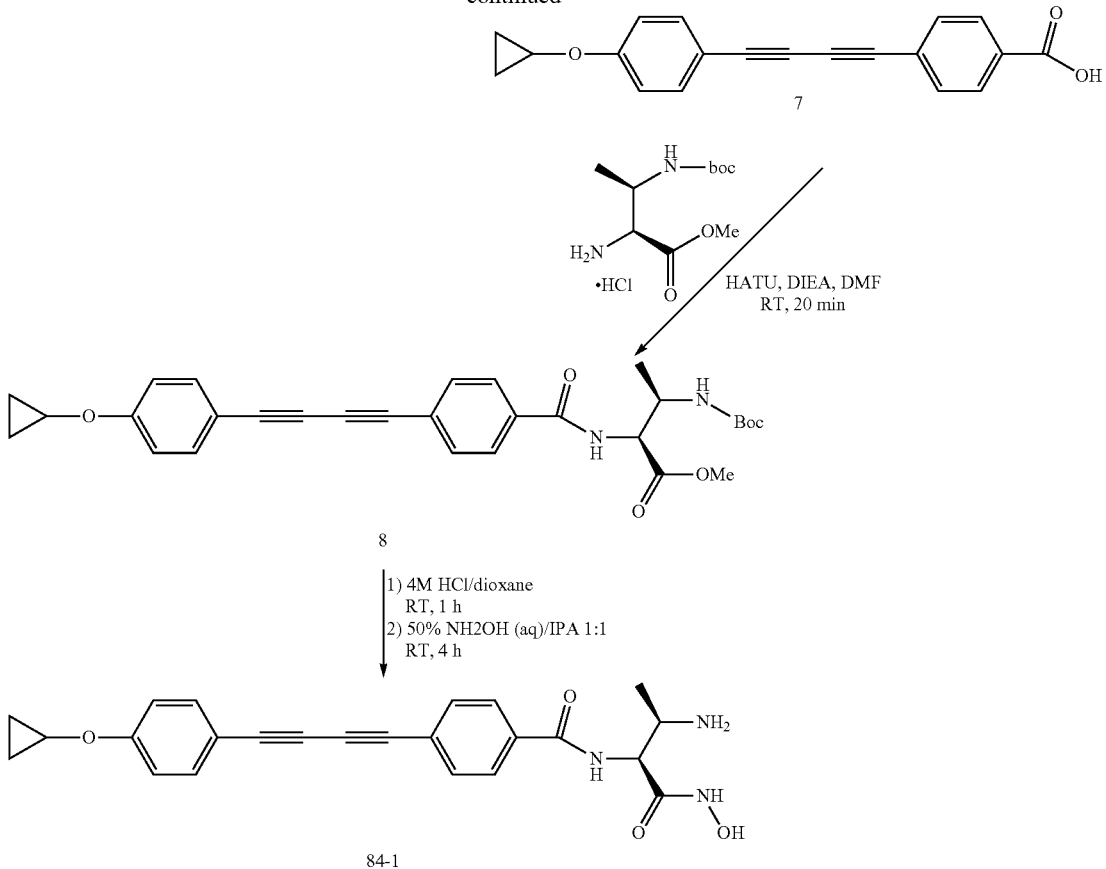

Synthesis of 1-Bromo-4-(2-chloro-ethoxy)-benzene (1)

To a mixture of 4-bromophenol (2.0 g, 11.6 mmol) and $K_2CO_3$ (3.20 g, 23.2 mmol) in DMF (50 mL) was added 3-chloroethyl p-toluenesulfonate (2.52 mL, 13.9 mmol) and the mixture was stirred at 60° C. for 16 h. Reaction mixture was concentrated in vacuo, and the residue was partitioned between water (200 mL) and $CH_2Cl_2$ (50 mL). Aqueous layer was further extracted with $CH_2Cl_2$ (3×20 mL). Combined organic layers were washed with water (30 mL) and brine (30 mL), dried ($Na_2SO_4$), filtered and concentrated in vacuo to provide the desired compound 1 (3.12 g, 115%) as a light amber oil. LC-MS: [M+H]$^+$=Not observed; Ret. Time (Method A) 5.83 min; $^1$H NMR (250 MHz, CDCl$_3$) δ 3.8 (t, 2H), 4.2 (t, 2H), 6.8 (d, 2H), 7.4 (d, 2H).

Synthesis of 1-Bromo-4-vinyloxy-benzene (2)

To a stirred solution of compound 1 (2.7 g, 11.6 mmol) in THF (30 mL), at 0° C., was added potassium tert-butoxide (1.95 g, 17.3 mmol) in three portions. After 10 min the solution was allowed to warm to ambient temperature and stirred for 16 h. The solution was then concentrated in vacuo and partitioned between water (150 mL) and $CH_2Cl_2$ (50 mL). Aqueous layer was further extracted with $CH_2Cl_2$ (3×30 mL). Combined organic layers were washed with water (40 mL) and brine (40 mL), dried ($Na_2SO_4$), filtered and concentrated in vacuo. Crude material was purified by normal phase flash chromatography (40 g SiO$_2$, 100% Hex) to provide the desired compound 2 (1.70 g, 74%) as a clear oil. LC-MS: [M+H]$^+$=Not observed; Ret. Time (Method A) 5.95 min; $^1$H NMR (250 MHz, CDCl$_3$) δ 4.45 (dd, 1H), 4.75 (dd, 1H), 6.6 (dd, 1H), 6.85 (d, 2H), 7.4 (d, 2H).

Synthesis of 1-Bromo-4-cyclopropoxy-benzene (3)

To a stirred solution of compound 2 (1.70 g, 8.55 mmol) and $CH_2I_2$ (5.52 mL, 68.4 mmol) in anhydrous 1,2-dichloroethane (75 mL), under $N_2$ at 0° C. was cautiously added a solution of diethylzinc (1.0 M, 68.4 mL) in hexanes. After 30 min the solution was allowed to warm to ambient temperature and stirred for 64 h. Solution was then added cautiously to saturated, aqueous NH$_4$Cl (200 mL). The mixture was shaken and layers separated, and aqueous layer was extracted with $CH_2Cl_2$ (3×30 mL). Combined organic layers were washed with aqueous HCl (1.0 N, 1×100 mL), water (1×100 mL), saturated NaHCO$_3$ (aq) (1×100 mL) and brine (1×80 mL), dried (Na$_2$SO$_4$), filtered and concentrated in vacuo to. Crude product was purified by normal phase flash chromatography (40 g SiO$_2$, 100% Hex) to provide the desired compound 3 (1.31 g, 72%) as a clear oil. LC-MS: [M+H]$^+$=Not observed; Ret. Time (Method A) 5.87 min; $^1$H NMR (250 MHz, CDCl$_3$) δ 0.75 (m, 4H), 3.7 (m, 1H), 6.9 (d, 2H), 7.4 (d, 2H).

Synthesis of (4-Cyclopropoxy-phenylethynyl)-trimethyl-silane (4)

To a mixture of compound 3 (900 mg, 4.22 mmol), PdCl$_2$(Ph$_3$P)$_2$ (150 mg, 0.211 mmol), CuI (80 mg, 0.420 mmol), Ph₃P (1.44 g, 5.49 mmol), and DIPA (5 mL, 35.4 mmol) in DMF (10 mL), in a 20 mL microwave tube, was added ethynyltrimethylsilane (0.716 mL, 5.07 mmol). Tube was backfilled with N₂, sealed, and irradiated in a microwave reactor (max. power 250 W) at 120° C. for 15 min. Solution was diluted with water (200 mL) and extracted with EtOAc (3×60 mL). Combined organic layers were washed with water (1×100 mL) and brine (1×60 mL), dried (Na₂SO₄), filtered and concentrated in vacuo. Crude product was purified by normal phase flash chromatography (40 g silica gel, 0-10% EtOAc/Hex) to provide a mixture of target compound 4 (840 mg) and triphenylphosphine. LC-MS: [M+H]⁺=Not observed; Ret. Time (Method A) 7.52 min.

Synthesis of 1-Cyclopropoxy-4-ethynyl-benzene (5)

To a solution of compound 4 (972 mg, 4.22 mmol) in MeOH (15 mL) was added NaOH (400 mg, 10 mmol) and the mixture was stirred at ambient temperature for 20 min. Solution was diluted with water (150 mL), cooled to 0° C., neutralized with aqueous HCl (1.0 N), and extracted with CH₂Cl₂ (4×40 mL). Combined organic layers were washed with water (1×80 mL) and brine (1×80 mL), dried (Na₂SO₄), filtered and concentrated in vacuo. Crude material was purified by preparative scale reverse-phase HPLC (Varian Microsorb 100-10 C-18 column (50×300 mm), flow rate: 50 mL/min, mobile phase A: 0.1% TFA/water, mobile phase B: 0.1% TFA/ACN, gradient elution from 10% B to 80% B over 90 min, UV 254 nm monitor). Fractions containing the desired product were combined and neutralized with NaHCO₃ (aq). Acetonitrile was removed by evaporation in vacuo, and the residual aqueous solution was extracted with EtOAc (3×40 mL). The combined organic layers were washed with water (1×60 mL) and brine (1×60 mL), dried (Na₂SO₄), filtered and concentrated in vacuo to provide the desired compound 5 (34 mg, 5%) as a clear oil. LC-MS: [M+H]⁺=Not observed; Ret. Time (Method A) 5.55 min; ¹H NMR (250 MHz, CDCl₃) δ 0.75 (m, 4H), 3.0 (s, 1H), 3.7 (m, 1H), 7.0 (d, 2H), 7.4 (d, 2H).

Synthesis of 4-[4-(4-Cyclopropoxy-phenyl)-buta-1,3-diynyl]-benzoic acid methyl ester (6)

Prepared as described in Method 1-B using compound 5 (34 mg, 0.216 mmol) and methyl 4-(2,2-dibromovinyl) benzoate (83 mg, 0.259 mmol) to provide the desired compound 6 (40 mg, 59%) as an off-white solid. LC-MS: [M+H]⁺=Not observed; Ret. Time (Method A) 8.03 min.

Synthesis of 4-[4-(4-Cyclopropoxy-phenyl)-buta-1,3-diynyl]-benzoic acid (7)

Prepared as described in Method 2-A using compound 6 (40 mg, 0.127 mmol) to provide the desired compound 7 (33 mg, 86%) as an off-white solid. LC-MS: [M+H]⁺=Not observed; Ret. Time (Method A) 6.81 min.

Synthesis of (2S,3R)-3-tert-Butoxycarbonylamino-2-{4-[4-(4-cyclopropoxy-phenyl)-buta-1,3-diynyl]-benzoylamino}-butyric acid methyl ester (8)

Prepared as described in Method 3-A using compound 7 (33 mg, 0.109 mmol) and (2S,3R)-3-methyl Dap (32 mg, 0.120 mmol) to provide the desired compound 8 (89 mg, 158%) as a viscous amber oil. LC-MS: [M+H]⁺=517.4; Ret. Time (Method A) 7.55 min.

Synthesis of N-((1S,2R)-2-Amino-1-hydroxycarbamoyl-propyl)-4-[4-(4-cyclopropoxy-phenyl)-buta-1,3-diynyl]-benzamide (84-1)

Prepared as described in Method 4-A followed by Method 5-A using compound 8 (56 mg, 0.109 mmol) to provide the desired compound 84-1. Crude material was purified by Purification Method A to provide the TFA salt of the desired compound 84-1 (25 mg, 44%) as a white solid. LC-MS: [M+H]⁺=418.4; Ret. Time (Method A) 4.84 min.

| Compound | Scale (mmol)[1] | Yield (mg)[1] | Yield (%)[1] | Purity (%)[2] | [M + H] | Retention time (min)[2] |
|---|---|---|---|---|---|---|
| 84-1 | 0.109 | 25.3 | 43.6 | 95.1 | 418.4 | 4.84 |

[1]Based on the amount of carboxylic acid used in the coupling reaction.
[2]Using LC-MS Analytical Method A.

Example 85

Synthesis of N—[(S)-2-(2-Cyclopropylamino-acetylamino)-1-hydroxycarbamoyl-ethyl]-4-(4-phenyl-buta-1,3-diynyl)-benzamide (85-1)

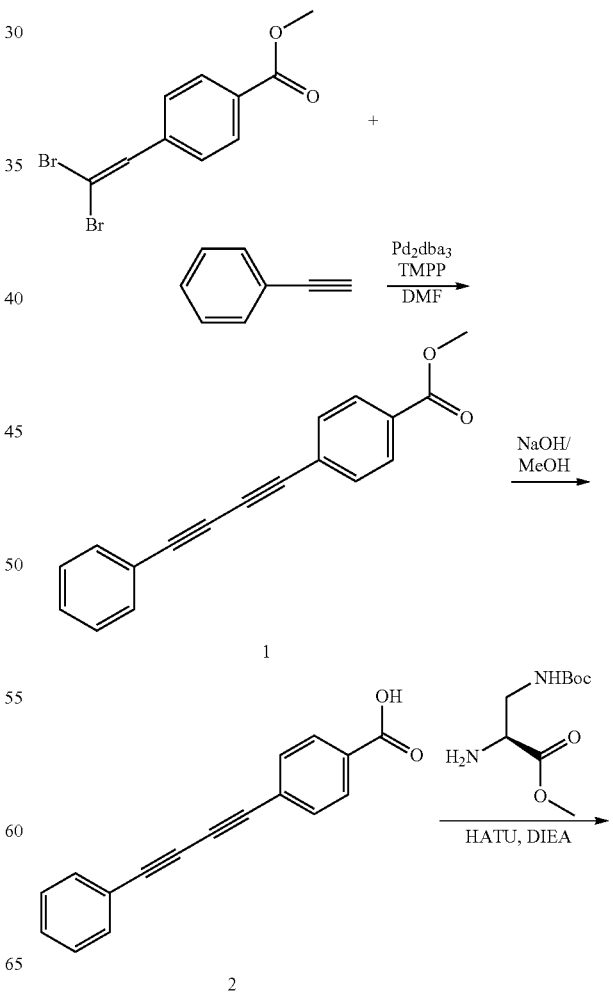

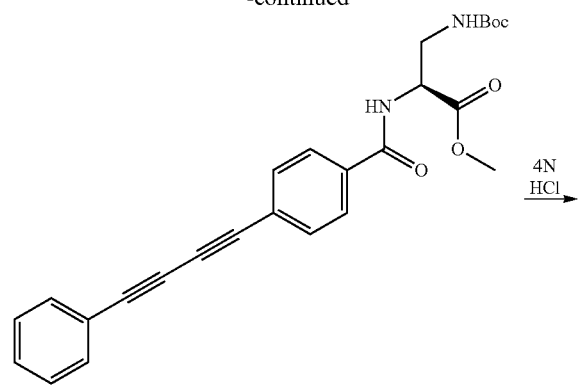

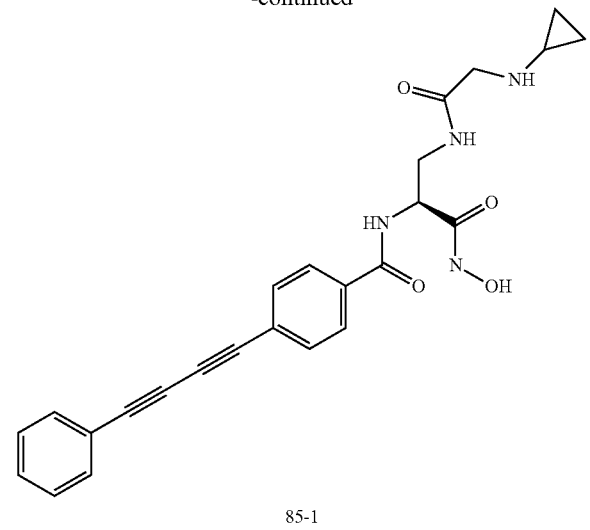

85-1

Synthesis of 4-(4-Phenyl-buta-1,3-diynyl)-benzoic acid methyl ester (1)

Prepared as described in Method 1-B using phenylacetylene (760 mg, 7.44 mmol) and methyl 4-(2,2-dibromovinyl)benzoate (1.70 g, 5.31 mmol) to provide the desired compound 1 (1.14 g, 82%) as an off-white solid.

Synthesis of 4-(4-Phenyl-buta-1,3-diynyl)-benzoic acid (2)

Prepared as described in Method 2-A using compound 1 (1.14 g, 4.37 mmol) to provide the desired compound 2 (995 mg, 92%) as a white solid.

Synthesis of (S)-3-tert-Butoxycarbonylamino-2-[4-(4-phenyl-buta-1,3-diynyl)-benzoyl amino]-propionic acid methyl ester (3)

Prepared as described in Method 3-A using compound 2 (100 mg, 0.40 mmol) and (2S) (Boc)Dap.HCl (111 mg, 0.42 mmol) to provide the desired compound 3 (127 mg, 70%) as a white solid. LC-MS: [M+H]$^+$=447.3; Ret. Time (Method A) 6.87 min.

Synthesis of (S)-3-Amino-2-[4-(4-phenyl-buta-1,3-diynyl)-benzoylamino]-propionic acid methyl ester (4)

Prepared as described in Method 4-A using compound 3 (127 mg, 0.28 mmol) to provide the desired compound 4 (100 mg, 95%). LC-MS: [M+H]$^+$=347.4; Ret. Time (Method A) 4.82 min.

Synthesis of (S)-3-[2-(tert-Butoxycarbonyl-cyclopropyl-amino)-acetylamino]-2-[4-(4-phenyl-buta-1,3-diynyl)-benzoylamino]-propionic acid methyl ester (5)

Prepared as described in Method 3-A using compound 4 (100 mg, 0.40 mmol) and N-cyclopropyl-N-Boc-glycine.HCl (111 mg, 0.42 mmol) to provide the desired compound 3 (127 mg, 70%). LC-MS: Ret. Time (Method A) 5.34 min.

Synthesis of (S)-3-(2-Cyclopropylamino-acetylamino)-2-[4-(4-phenyl-buta-1,3-diynyl)-benzoylamino]-propionic acid methyl ester (6)

Prepared as described in Method 4-A using compound 5 (127 mg, 0.23 mmol) to provide the desired compound 6. LC-MS: [M+H]⁺=444.5; Ret. Time (Method A) 4.99 min.

Synthesis of N—[(S)-2-(2-Cyclopropylamino-acetylamino)-1-hydroxycarbamoyl-ethyl]-4-(4-phenyl-buta-1,3-diynyl)-benzamide (85-1)

Prepared as described in Method 5-B using compound 6 (235 mg, 0.40 mmol) to provide the desired compound 85-1. Crude material was purified by Purification Method A to provide the TFA salt of the desired compound 85-1 (16 mg, 7% yield) as a white solid. LC-MS: [M+H]⁺=445.1; Ret. Time (Method A) 6.75 min.

| Compound | Scale (mmol)[1] | Yield (mg) | Yield (%)[1] | Purity (%)[2] | [M + H] | Retention time (min)[2] |
|---|---|---|---|---|---|---|
| 85-1 | 0.4 | 15.5 | 6.9 | 98.4 | 445.1 | 6.75 |

[1]Based on the amount of carboxylic acid used in the coupling reaction.
[2]Using LC-MS Analytical Method A.

The following compound was synthesized as described above using the appropriate amino acid and deprotection.

| Compound # | Structure | MH⁺ (m/z) | Ret. Time (min) | HPLC-MS Method |
|---|---|---|---|---|
| 85-2 | 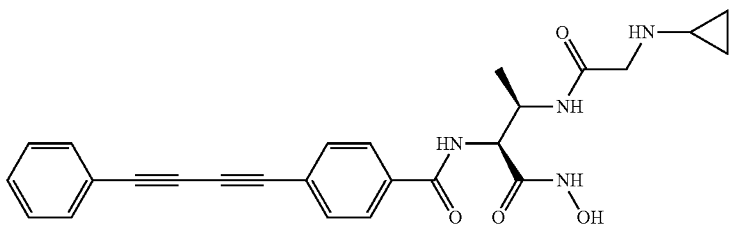 [SMILES: C[C@@H](NC(=O)CNC1CC1)[C@H](NC(=O)c1ccc(C#CC#Cc2ccccc2)cc1)C(=O)NO] | 459.1 | 6.84 | A |

Example 86

Synthesis of N-((1S,2R)-2-Amino-1-hydroxycarbamoyl-propyl)-4-(4-{4-[(2,2-difluoro-ethylamino)-methyl]-phenyl}-buta-1,3-diynyl)-benzamide (86-1)

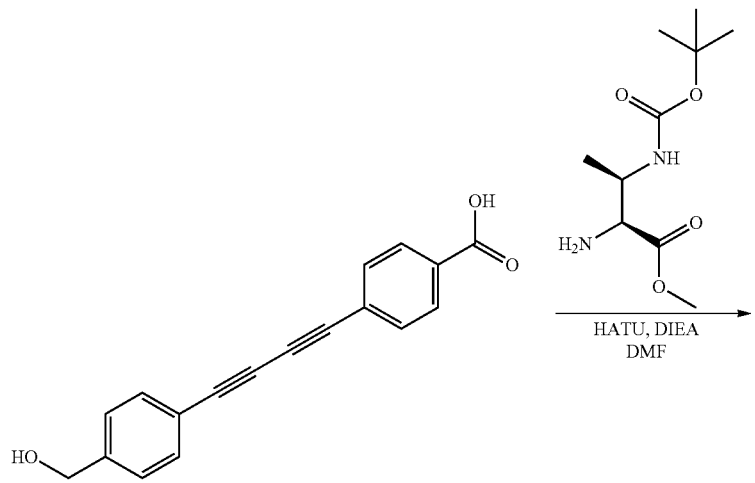

-continued
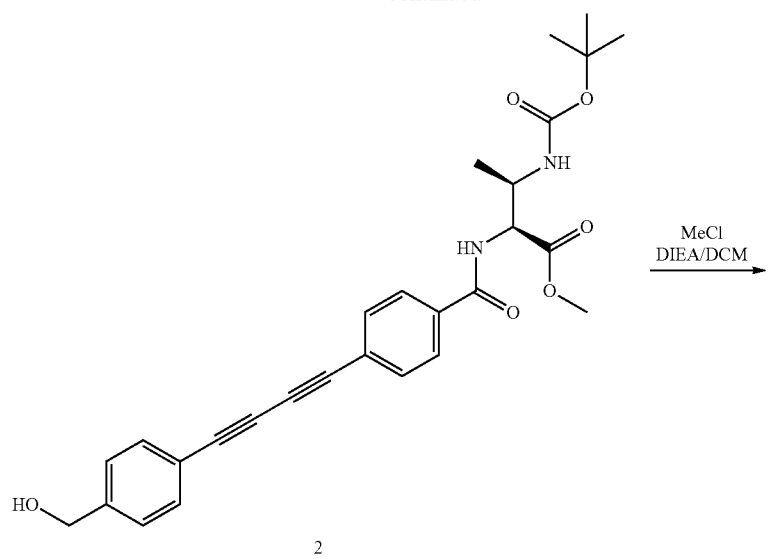
2
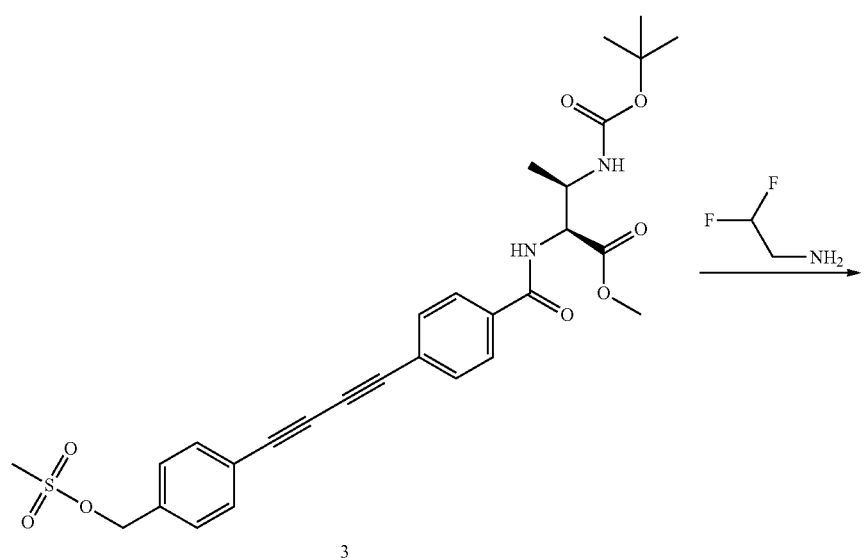
3
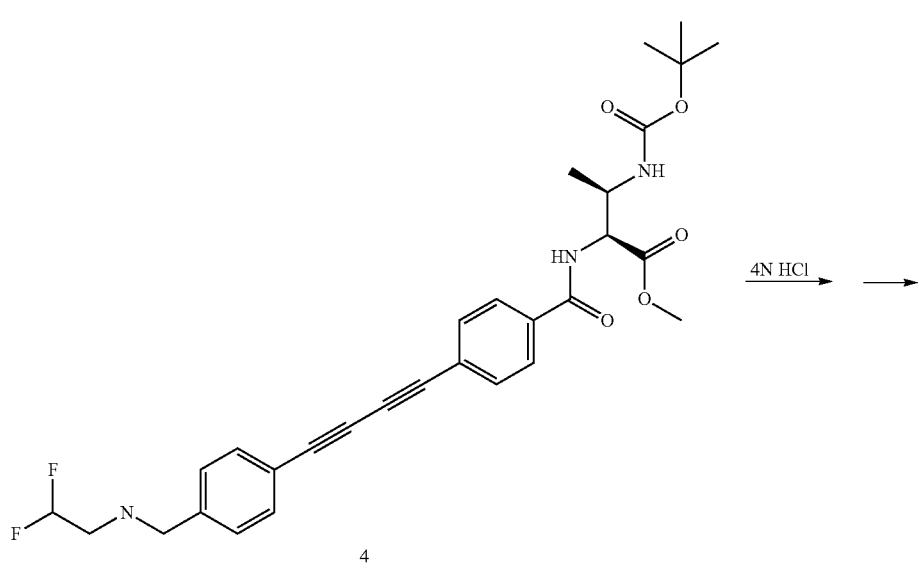
4

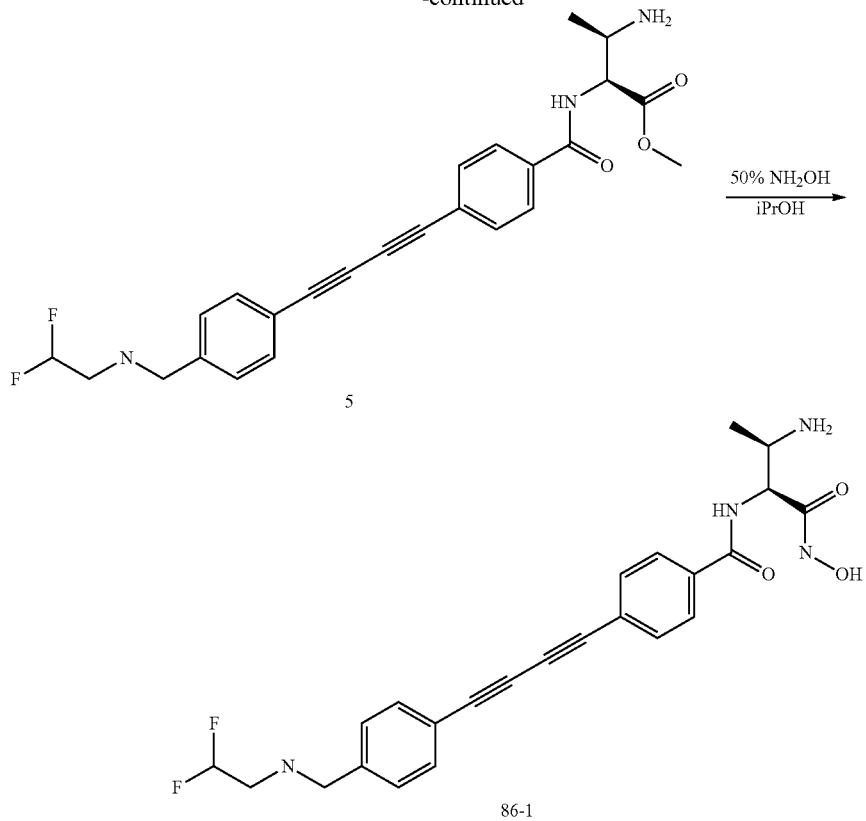

Synthesis of (2S,3R)-3-tert-Butoxycarbonylamino-2-{4-[4-(4-hydroxymethyl-phenyl)-buta-1,3-diynyl]-benzoylamino}-butyric acid methyl ester (2)

Prepared as described in Method 3-A using compound 1 (390 mg, 1.4 mmol) and (S)-Boc-Me-Dap-OMe.HCl (403 mg, 1.5 mmol) to provide the desired compound 2 (660 mg, 96%). LC-MS: [M+H]$^+$=491.2; Ret. Time (Method A) 5.98 min.

Synthesis of (2S,3R)-3-tert-Butoxycarbonylamino-2-[4-(4-{4-[(2,2-difluoro-ethylamino)-methyl]-henyl}-buta-1,3-diynyl)-benzoylamino]-butyric acid methyl ester (4)

To a solution of compound 2 (660 mg, 1.35 mmol) and TEA (0.42 mL, 3.0 mmol) in CH$_2$Cl$_2$ (6 mL) at 0° C., methanesulfonyl chloride (113 mg, 1.45 mmol) was added. The solution was then allowed to warm to ambient temperature and stirred for 1 h. To this solution containing compound 3 was added 2,2-difluoroethylamine (273 mg, 3.37 mmol) dropwise and stirred overnight at 50° C. All volatiles were removed in vacuo and the crude material was diluted with EtOAc (100 mL) and washed with water (2×40 mL), brine (1×40 mL), dried (Na$_2$SO$_4$), filtered and concentrated in vacuo to provide the desired compound 4. LC-MS: [M+H]$^+$=554.5; Ret. Time (Method A) 4.81 min.

Synthesis of (2S,3R)-3-Amino-2-[4-(4-{4-[(2,2-difluoro-ethylamino)-methyl]-phenyl}-buta-1,3-diynyl)-benzoylamino]-butyric acid methyl ester (5)

Prepared as described in Method 4-A using compound 4 (374 mg, 0.68 mmol) to provide the desired compound 5. LC-MS: [M+H]$^+$=454.8; Ret. Time (Method A) 3.07 min.

Synthesis of N-((1S,2R)-2-Amino-1-hydroxycarbamoyl-propyl)-4-(4-{4-[(2,2-difluoro-ethylamino)-methyl]-phenyl}-buta-1,3-diynyl)-benzamide (86-1)

Prepared as described in Method 5-A using compound 5 (355 mg, 0.675 mmol) to provide the desired compound 86-1. Crude material was purified by Purification Method A to provide the TFA salt of the desired compound 86-1 (76 mg, 16%) as a white solid. LC-MS: [M+H]$^+$=455.8; Ret. Time (Method A) 3.79 min.

| Compound | Scale (mmol)[1] | Yield (mg) | Yield (%)[1] | Purity (%)[2] | [M + H] | Retention time (min)[2] |
|---|---|---|---|---|---|---|
| 86-1 | 0.7 | 75.7 | 18 | 98.6 | 455.8 | 3.79 |

[1]Based on the amount of carboxylic acid used in the coupling reaction.
[2]Using LC-MS Analytical Method A.

Each of the following compounds was synthesized as described above using the appropriate amine and amino acid.

| Compound # | Structure | MH+ (m/z) | Ret. Time (min) | HPLC-MS Method |
| --- | --- | --- | --- | --- |
| 86-2 | 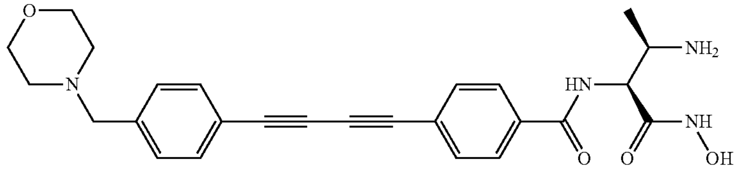 [SMILES: C[C@@H](N)[C@H](NC(=O)c1ccc(C#CC#Cc2ccc(CN3CCOCC3)cc2)cc1)C(=O)NO] | 3.71 | 461.1 | A |
| 86-3 | 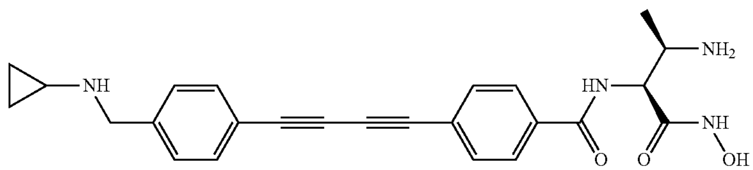 [SMILES: C[C@@H](N)[C@H](NC(=O)c1ccc(C#CC#Cc2ccc(CNC3CC3)cc2)cc1)C(=O)NO] | 4.01 | 431.5 | A |
| 86-4 | 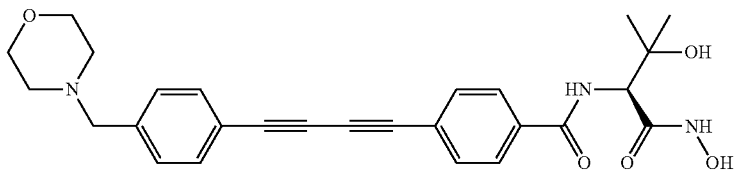 [SMILES: CC(C)(O)[C@H](NC(=O)c1ccc(C#CC#Cc2ccc(CN3CCOCC3)cc2)cc1)C(=O)NO] | 3.38 | 475.9 | A |
| 86-5 | 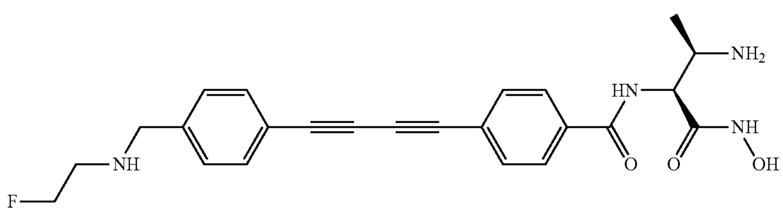 [SMILES: C[C@@H](N)[C@H](NC(=O)c1ccc(C#CC#Cc2ccc(CNCCF)cc2)cc1)C(=O)NO] | 3.75 | 437.1 | A |
| 86-6 | 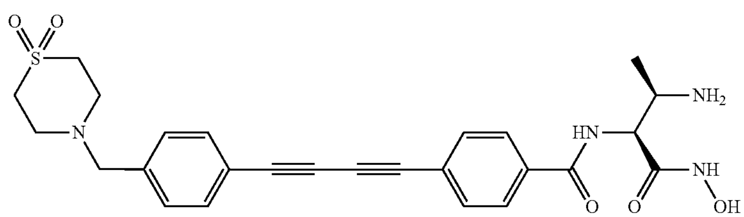 [SMILES: C[C@@H](N)[C@H](NC(=O)c1ccc(C#CC#Cc2ccc(CN3CCS(=O)(=O)CC3)cc2)cc1)C(=O)NO] | 4.22 | 509.1 | A |
| 86-7 | 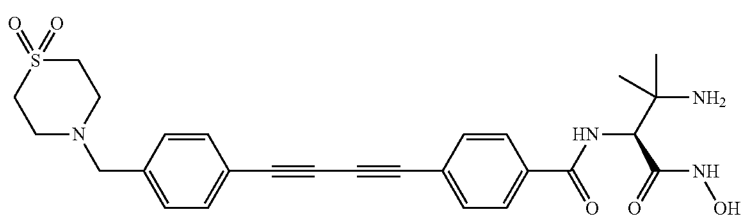 [SMILES: CC(C)(N)[C@H](NC(=O)c1ccc(C#CC#Cc2ccc(CN3CCS(=O)(=O)CC3)cc2)cc1)C(=O)NO] | 4.42 | 523.5 | A |
Example 87
Synthesis of N-(2-Amino-1-hydroxycarbamoyl-2-methyl-propyl)-4-[4-(4-cyclopropylaminomethyl-phenyl)-buta-1,3-diynyl]-benzamide (87-1)
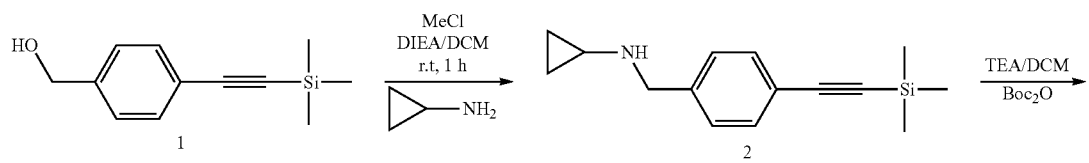

261
262
-continued
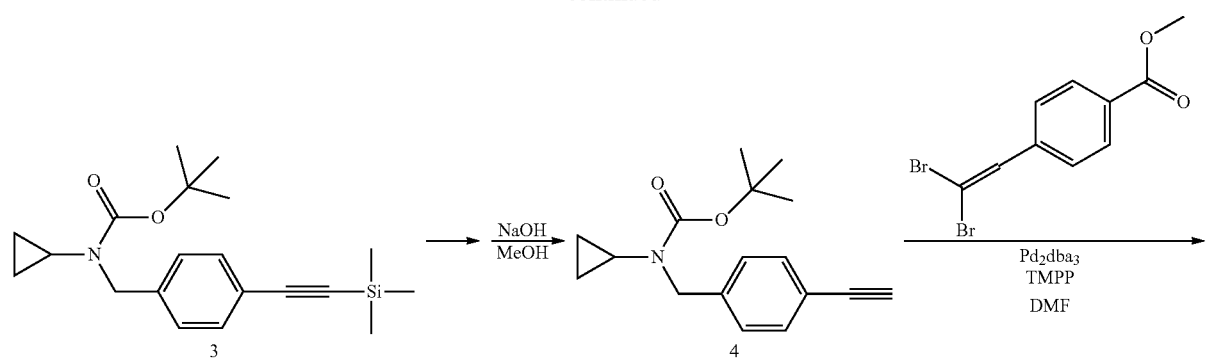
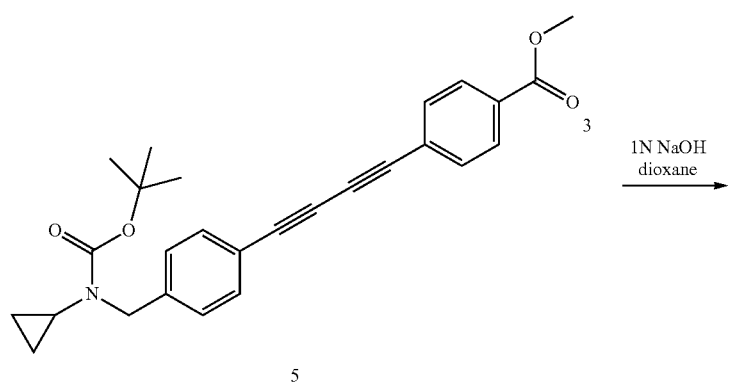
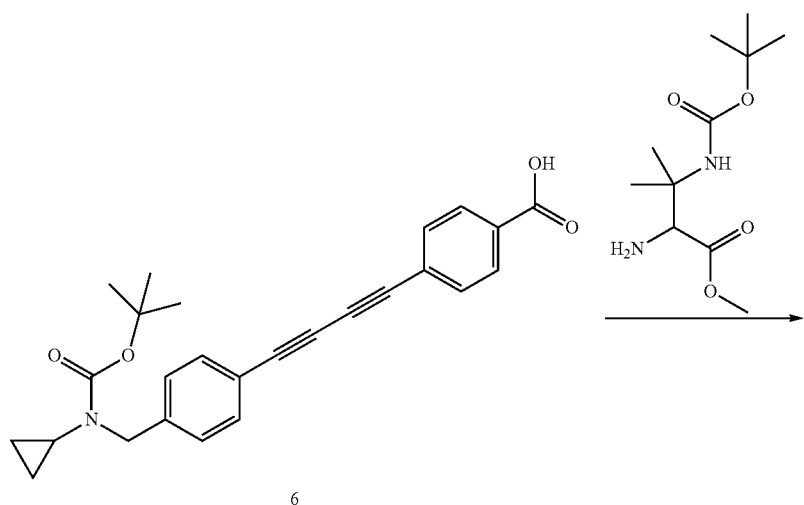

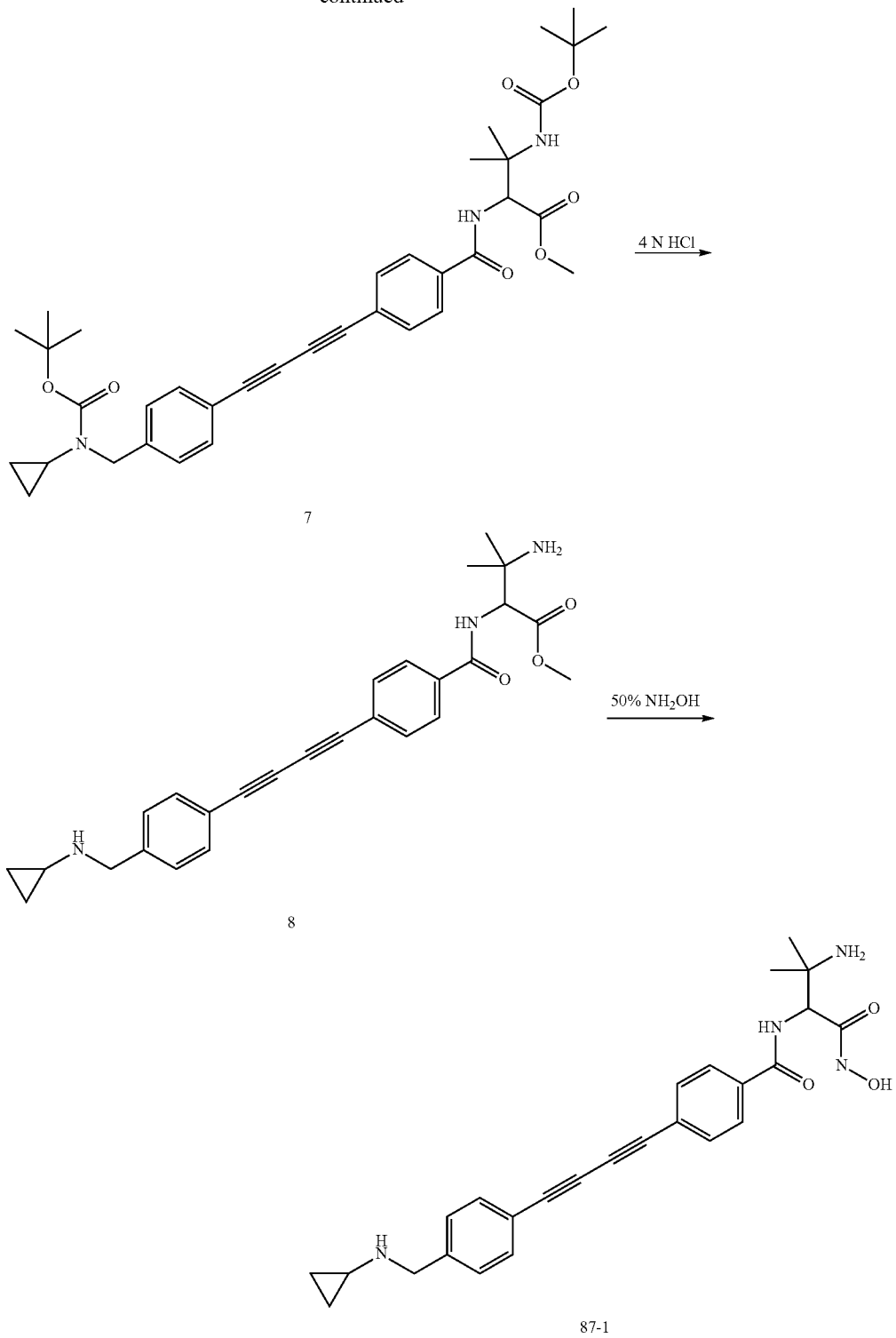

Synthesis of Cyclopropyl-(4-trimethylsilanylethynyl-benzyl)-amine (2)

To a solution of compound 1 (10 g, 48.9 mmol) and DIEA (16 mL, 96.5 mmol) in CH$_2$Cl$_2$ (25 mL) at 0° C., was added methanesulfonyl chloride (4.56 mL, 58.7 mmol) dropwise. The solution was allowed to warm to ambient temperature and stirred for 1 h. Cyclopropyl amine (25.69 g, 450 mmol) was added dropwise and resulting solution was stirred overnight at ambient temperature. The solution was concentrated in vacuo and the crude material was diluted with EtOAc (200 mL), washed with water (2×70 mL), brine (1×100 mL) and dried (Na$_2$SO$_4$), filtered and concentrated in vacuo. The crude material was purified by normal phase chromatography (120 g SiO$_2$, CHCl$_3$/MeOH) to provide the desired compound 2 (3.6 g, 30%) as brown liquid. LC-MS: [M+H]$^+$=244.2; Ret. Time (Method A) 4.86 min.

Synthesis of Cyclopropyl-(4-trimethylsilanylethynyl-benzyl)-carbamic acid tert-butyl ester (3)

To a solution of compound 2 (3.6 g, 14.8 mmol) and Et$_3$N (4.17 mL, 30 mmol) in CH$_2$Cl$_2$ (15 mL), was added Boc$_2$O (3.55 g, 16.26 mmol) and the resulting mixture was stirred for 2 h at ambient temperature. The solution was concentrated in vacuo and the crude material was diluted with EtOAc (150 mL), washed with water (2×70 mL), brine (1×80 mL) and dried (Na$_2$SO$_4$), filtered and concentrated in vacuo to provide the desired compound 3 (4.32 g) as a brown oil. LC-MS: [M+H]$^+$=Not observed; Ret. Time (Method A) 8.31 min.

Synthesis of Cyclopropyl-(4-ethynyl-benzyl)-carbamic acid tert-butyl ester (4)

To a solution of NaOH (0.20 g, 5.0 mmol) in MeOH (75 mL), was added compound 3 (4.32 g, 12.6 mmol) and resulting mixture was stirred for 1 h at ambient temperature. The solution was concentrated in vacuo. and the crude material was diluted with EtOAc (120 mL), washed with water (2×30 mL), brine (1×50 mL), dried (Na$_2$SO$_4$), filtered and concentrated in vacuo. The crude material was purified by normal phase flash chromatography (40 g SiO$_2$, EtOAc/Hex) to provide the desired compound 4 (1.58 g, 47%) as white solid. LC-MS: [M+H]$^+$=Not observed; Ret. Time (Method A) 6.38 min.

Synthesis of 4-(4-{4-[(tert-Butoxycarbonyl-cyclopropyl-amino)-methyl]-phenyl}-buta-1,3-diynyl)-benzoic acid methyl ester (5)

Prepared as described in Method 1-B using 4 (1.07 g, 3.94 mmol) and methyl 4-(2,2-dibromovinyl)benzoate (1.38 g, 4.33 mmol) to provide the desired compound 5 (615 mg, 36%) as a white solid. LC-MS: [M+H]$^+$=430.4; Ret. Time (Method A) 8.73 min.

Synthesis of 4-(4-{4-[(tert-Butoxycarbonyl-cyclopropyl-amino)-methyl]-phenyl}-buta-1,3-diynyl)-benzoic acid (6)

Prepared as described in Method 2-A using compound 5 (615 mg, 1.4 mmol) to provide the desired compound 6 (509 mg, 88%) as a white solid. LC-MS: [M+H]$^+$=416.5; Ret. Time (Method A) 7.44 min.

Synthesis of 3-tert-Butoxycarbonylamino-2-[4-(4-{4-[(tert-butoxycarbonyl-cyclopropyl-amino)-methyl]-phenyl}-buta-1,3-diynyl)-benzoylamino]-3-methyl-butyric acid methyl ester (7)

Prepared as described in Method 3-A using compound 6 (400 mg, 0.96 mmol) and (2S)-3-dimethylDap-(OMe) (249 mg, 1.01 mmol) to provide the desired compound 6 (585 mg, 96%) as a white solid. LC-MS: [M+H]$^+$=644.5; Ret. Time (Method A) 8.47 min.

Synthesis of 3-Amino-2-[4-{4-(4-cyclopropylaminomethyl-phenyl)-buta-1,3-diynyl]-benzoylamino}-3-methyl-butyric acid methyl ester (8)

Prepared as described in Method 4-A using compound 7 (585 mg, 0.91 mmol) to provide the desired compound 8 (407 mg). LC-MS: [M+H]$^+$=444.5; Ret. Time (Method A) 3.42 min.

Synthesis of N-(2-Amino-1-hydroxycarbamoyl-2-methyl-propyl)-4-[4-(4-cyclopropylaminomethyl-phenyl)-buta-1,3-diynyl]-benzamide (87-1)

Prepared as described in Method 5-A using compound 8 (407 mg, 0.91 mmol) to provide the crude compound 87-1. Crude product was purified by Purification Method A to provide the TFA salt of desired compound 87-1 (266 mg, 18%) as a white solid. LC-MS: [M+H]$^+$=445.5; Ret. Time (Method A) 3.10 min.

| Compound | Scale (mmol)[1] | Yield (mg) | Yield (%)[1] | Purity (%)[2] | [M + H] | Retention time (min)[2] |
|---|---|---|---|---|---|---|
| 87-1 | 0.96 | 266 | 53.3 | 99.6 | 445.1 | 3.10 |

[1]Based on the amount of carboxylic acid used in the coupling reaction.
[2]Using LC-MS Analytical Method A.

Each of the following compounds was synthesized as described above using the appropriate amino acid.

| Compound # | Structure | [MH$^+$] (m/z) | Ret. Time (min) | HPLC-Ms Method |
|---|---|---|---|---|
| 87-2 | 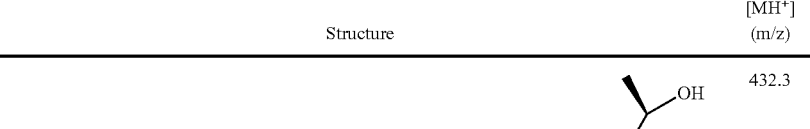 | 432.3 | 4.64 | A |
| 87-3 | 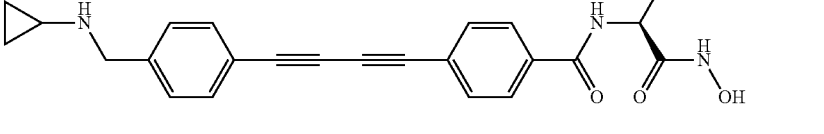 | 446.3 | 4.90 | A |

| Compound # | Structure | [MH+] (m/z) | Ret. Time (min) | HPLC-Ms Method |
|---|---|---|---|---|
| 87-4 | 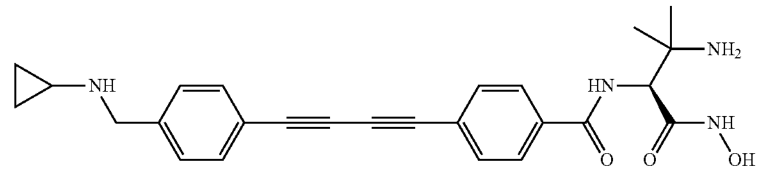 [SMILES: CC(C)(N)[C@H](NC(=O)c1ccc(C#CC#Cc2ccc(CNC3CC3)cc2)cc1)C(=O)NO] | 445.5 | 4.07 | A |

Example 88

Synthesis of N-((1S,2R)-2-Amino-1-hydroxycarbamoyl-propyl)-4-[4-(3-methyl-3H-imidazol-4-yl)-buta-1,3-diynyl]-benzamide (88-1)

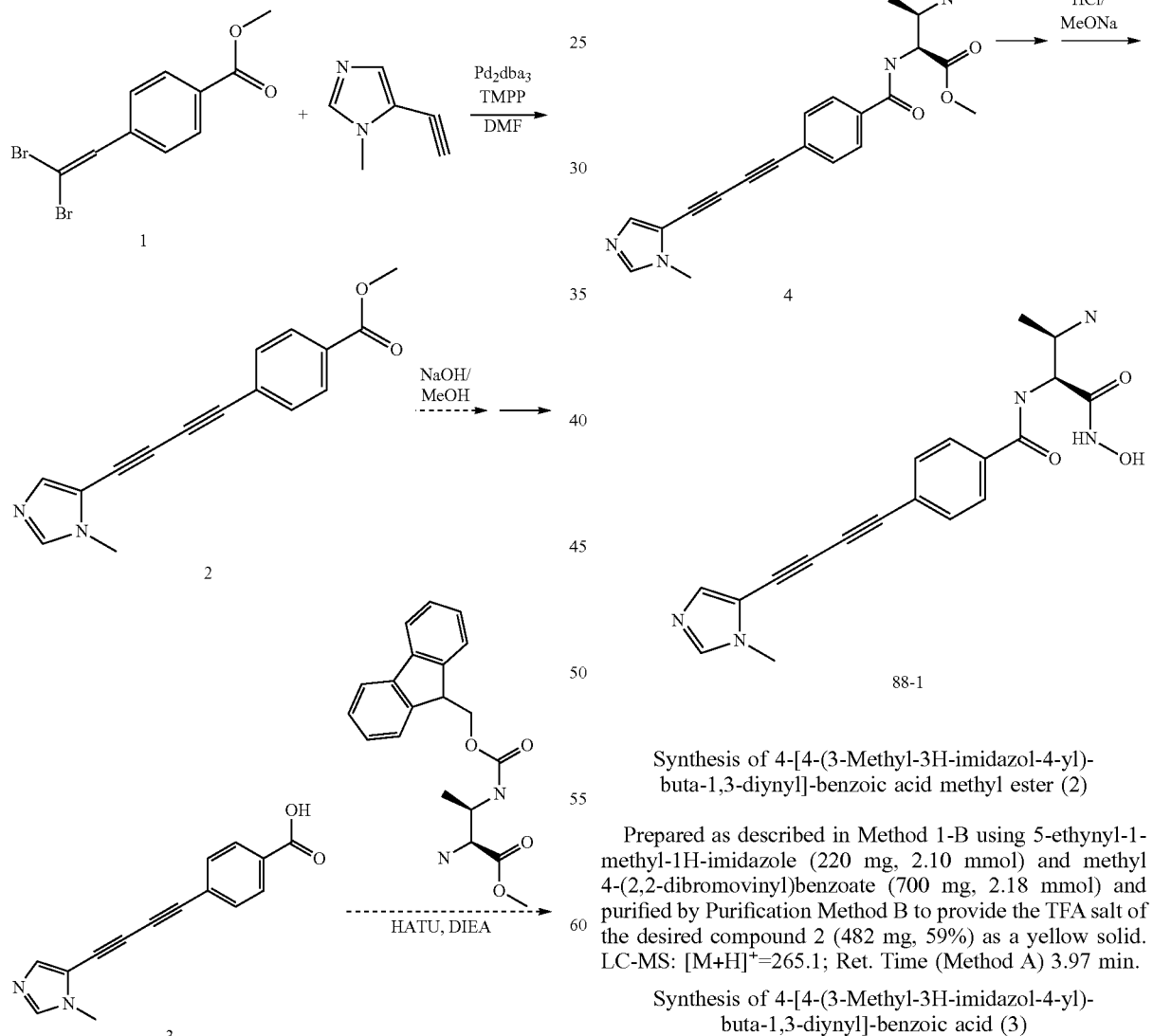

Synthesis of 4-[4-(3-Methyl-3H-imidazol-4-yl)-buta-1,3-diynyl]-benzoic acid methyl ester (2)

Prepared as described in Method 1-B using 5-ethynyl-1-methyl-1H-imidazole (220 mg, 2.10 mmol) and methyl 4-(2,2-dibromovinyl)benzoate (700 mg, 2.18 mmol) and purified by Purification Method B to provide the TFA salt of the desired compound 2 (482 mg, 59%) as a yellow solid. LC-MS: [M+H]+=265.1; Ret. Time (Method A) 3.97 min.

Synthesis of 4-[4-(3-Methyl-3H-imidazol-4-yl)-buta-1,3-diynyl]-benzoic acid (3)

Prepared as described in Method 2-A (Method 2-B for pyridyl derivatives) using compound 2 (482 mg, 1.83 mmol)

to provide the desired compound 3 (334 mg, 73%) as an off-white solid. LC-MS: [M+H]$^+$=250.9; Ret. Time (Method A) 3.13 min.

Synthesis of (2S,3R)-3-(9H-Fluoren-9-ylmethoxycarbonylamino)-2-{4-[4-(3-methyl-3H-imidazol-4-yl)-buta-1,3-diynyl]-benzoylamino}-butyric acid methyl ester (4)

Prepared as described in Method 3-A using compound 3 (100 mg, 0.40 mmol) and (2S,3R)Fmoc-3-Me-Dap(OMe) HCl (164 mg, 0.67 mmol) to provide the desired compound 4 (235 mg). LC-MS: [M+H]$^+$=586.7; Ret. Time (Method A) 5.21 min.

Synthesis of N-((1S,2R)-2-Amino-1-hydroxycarbamoyl-propyl)-4-[4-(3-methyl-3H-imidazol-4-yl)-buta-1,3-diynyl]-benzamide (88-1)

| Reagent | MW, d | Eq. | mmol | mg, ml |
| --- | --- | --- | --- | --- |
| Compound 4 | 586.65 | 1.0 | 0.4 | 235 mg |
| NH2OH × HCl | 69.49 | 6.14 | 1.72 | 120 mg |
| 25% MeONa in MeOH | | | | 0.5 mL |
| THF | | | | 1 mL |
| MeOH | | | | 2.5 mL |

The Compound 88-1 was made using the General Method for hydroxamate formation. Check of a sample by HPLC-MS showed a major product peak (Ret. time (Method A) 2.03 min, MH$^+$=366.2). Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 15% B to 40% B over 60 min, MS detection). Fractions containing the desired product were combined and lyophilized to provide the trifluoroacetate salt of target compound 88-1 (112.4 mg, 47.3% yield) as a white solid. LC-MS: RT (Method A) 2.13 min; [M+H] 366.3 (C$_{19}$H$_{19}$N$_5$O$_3$+H, requires 366.4).

| Compound | Scale (mmol)[1] | Yield (mg) | Yield (%)[1] | Purity (%)[2] | [M + H] | Retention time (min)[2] |
| --- | --- | --- | --- | --- | --- | --- |
| 88-1 | 0.4 | 112.4 | 47.3 | 98.8 | 366.2 | 2.13 |

[1]Based on the amount of carboxylic acid used in the coupling reaction.
[2]Using LC-MS Analytical Method A.

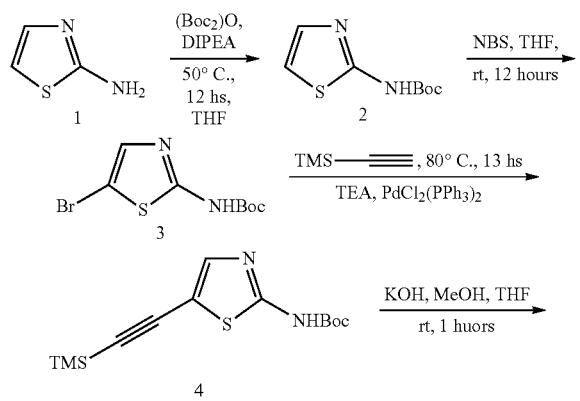

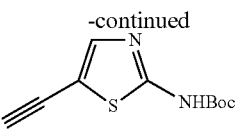

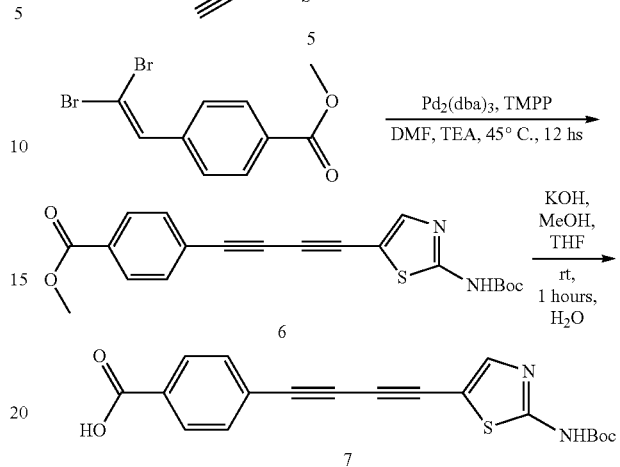

tert-Butyl thiazol-2-ylcarbamate 2

A solution of thiazol-2-amine (10.0 g, 0.10 mol, 1.0 equiv), (Boc$_2$)O (26.2 g, 0.12 mol, 1.2 equiv), and DIPEA (25.8 g, 0.20 mol, 2.0 equiv) in THF (150 mL) was stirred at 50° C. for 12 hours. The reaction mixture was concentrated in vacuum and EtOAc (300 mL) was added. Then, the organic layer was washed by water (250 mL×2) and brine (250 mL×2), dried (MgSO$_4$), filtrated, concentrated in vacuum to give target product (6.3 g, 31.5%). [M+1]: 201.1 tert-Butyl 5-bromothiazol-2-ylcarbamate 3

A suspension of NBS (6.2 g, 34.6 mmol, 1.1 equiv) and tert-butyl thiazol-2-ylcarbamate (6.3 g, 31.5 mmol, 1.0 equiv) in THF (100 mL) was stirred at room temperature for 12 hours. Then, the reaction mixture was filtrated and purified by column chromatography to give target compound (6.5 g, 73.9%)

tert-Butyl 5-((trimethylsilyl)ethynyl)thiazol-2-ylcarbamate 4

A mixture of tert-butyl 5-bromothiazol-2-ylcarbamate (6.5 g, 23.3 mmol, 1.0 equiv), ethynyltrimethylsilane (3.4 g, 34.9 mmol, 1.5 equiv), PdCl$_2$(PPh$_3$)$_2$ (0.16 g, 0.23 mmol, 0.01 equiv), CuI (0.14 mg, 0.84 mmol, 0.03 equiv) in TEA (50 mL) was stirred at 80° C. for 4 hours under nitrogen. The reaction mixture was extracted with EtOAc (500 ml) and organics was washed with water (200 mL×2) and brine (200 mL) Organic layer was dried over Na$_2$SO$_4$ and evaporated. The residue was purified by column chromatography to give target compound (1.5 g, 30%).

tert-Butyl 5-ethynylthiazol-2-ylcarbamate 5

To a solution of tert-butyl 5-((trimethylsilyl)ethynyl)thiazol-2-ylcarbamate (1.50 g, 5.1 mmol, 1.0 equiv) in THF (50 mL) was treated with KOH/methanol (10.2 mmol, 0.57 g/10 mL, 2 equiv) slowly below 10° C., then the mixture was allowed to react at ambient temperature for 1 hours. Then, the reaction mixture concentrated in vacuum. The residue was dissolved in EtOAc (100 mL). The organic layer was washed with water (50 mL×2) and brine (50 mL), dried over Na₂SO₄, filtered and concentrated in vacuum. The residue was dried in vacuum overnight to provide the title compound (1.1 g, 96%)

Methyl 4-((2-(tert-butoxycarbonylamino)thiazol-5-yl)buta-1,3-diynyl)benzoate 6

A mixture of methyl 4-(2,2-dibromovinyl)benzoate (1.10 g, 5.4 mmol, 1.1 equiv), tert-butyl 5-ethynylthiazol-2-ylcarbamate (1.70 g, 4.9 mmol, 1.0 equiv), Pd$_2$(dba)$_3$ (9 mg, 0.01 mmol, 0.02 equiv), TMPP (14 mg, 0.02 mmol, 0.04 equiv) and TEA (97 mg, 9.8 mmol, 2 equiv) in DMF (20 ml) was stirred at 45° C. for 12 hours under nitrogen. The reaction mixture was extracted with EtOAc (100 ml) and organics was washed with water (100 ml×2) and brine (50 ml). Organic layer was dried over Na₂SO₄ and evaporated. The residue was purified by column chromatography to give target compound (0.9 g, 46%). ¹H-NMR: (400 MHz, DMSO-d₆): δ 1.50 (s, 9H), 3.87 (s, 3H), 7.74 (dd, J=2.4 Hz, 6.4 Hz), 7.93 (s, 1H), 7.99 (dd, J=2.0 Hz, 6.0 Hz), 12.09 (s, 1H).

4-((2-(tert-Butoxycarbonylamino)thiazol-5-yl)buta-1,3-diynyl)benzoic acid 7

To a solution of methyl-4-((2-(tert-butoxycarbonylamino) thiazol-5-yl)buta-1,3-diynyl)benzoate (0.9 g, 2.4 mmol, 1 equiv) in THF (10 mL) and MeOH (10 mL), 2 M NaOH aq. (2.0 ml) was added and the reaction was stirred at room temperature for 1 h. After cooling the reaction mixture was acidified to a pH of 1-2 with 10% HCl. The formed solid was collected by filtration, washed with water (2×10 ml) and ice-cold MeOH (10 ml). The filtration was dried in vacuum overnight to give the final product (650 mg, 71%). [M+1]: 369.0; ¹H-NMR: (400 MHz, DMSO-d₆): δ 1.50 (s, 9H), 7.68 (d, J=6.0 Hz), 7.91 (s, 1H), 7.97 (d, J=6.4 Hz). Compound 7 was used for synthesis of compound 88-17 and 88-18 using the appropriate amino acids.

Each of the following compounds was synthesized as described above using the appropriate amino acid and deprotection.

| Compound # | Structure | Ret. Time (min) | MH⁺ (m/z) | HPLC-MS Method |
|---|---|---|---|---|
| 88-2 | 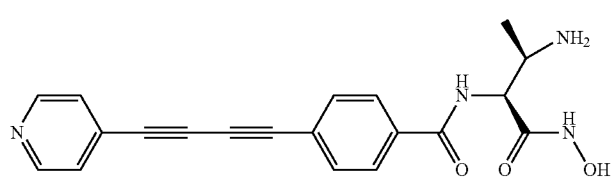 [SMILES: C[C@@H](N)[C@H](NC(=O)c1ccc(C#CC#Cc2ccncc2)cc1)C(=O)NO] | 2.67 | 363.5 | A |
| 88-3 | 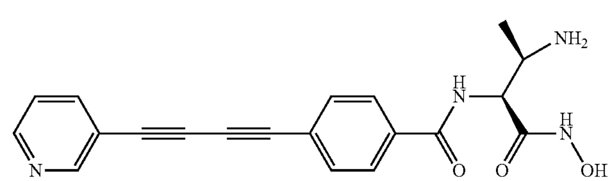 [SMILES: C[C@@H](N)[C@H](NC(=O)c1ccc(C#CC#Cc2cccnc2)cc1)C(=O)NO] | 3.44 | 363.5 | A |
| 88-4 | 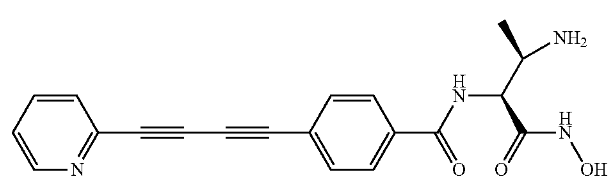 [SMILES: C[C@@H](N)[C@H](NC(=O)c1ccc(C#CC#Cc2ccccn2)cc1)C(=O)NO] | 3.77 | 363.5 | A |
| 88-5 | 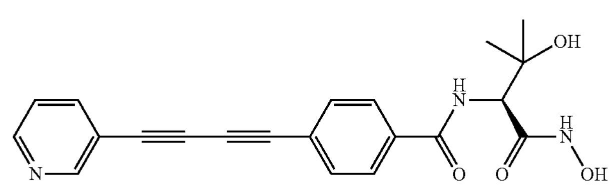 [SMILES: CC(C)(O)[C@H](NC(=O)c1ccc(C#CC#Cc2cccnc2)cc1)C(=O)NO] | 4.30 | 378.3 | A |
| 88-6 | 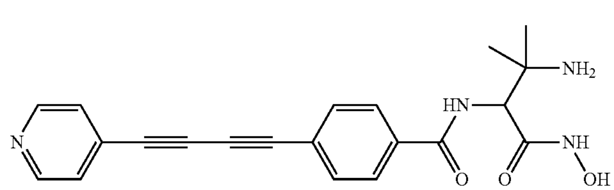 [SMILES: CC(C)(N)C(NC(=O)c1ccc(C#CC#Cc2ccncc2)cc1)C(=O)NO] | 2.36 | 377.1 | A |

-continued

| Compound # | Structure | Ret. Time (min) | MH+ (m/z) | HPLC-MS Method |
|---|---|---|---|---|
| 88-7 | 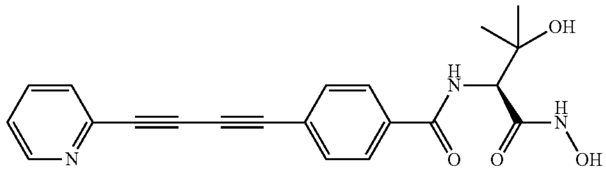 [SMILES: CC(C)(O)[C@H](NC(=O)c1ccc(C#CC#Cc2ccccn2)cc1)C(=O)NO] | 3.41 | 378.3 | A |
| 88-8 | 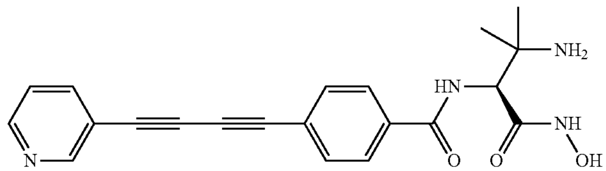 [SMILES: CC(C)(N)[C@H](NC(=O)c1ccc(C#CC#Cc2cccnc2)cc1)C(=O)NO] | 3.71 | 377.8 | A |
| 88-9 | 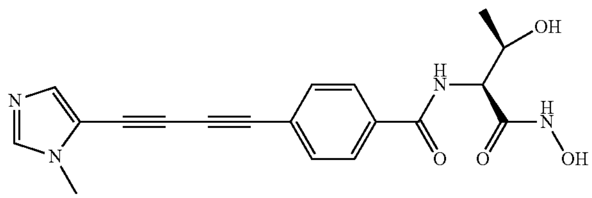 [SMILES: C[C@@H](O)[C@H](NC(=O)c1ccc(C#CC#Cc2cncn2C)cc1)C(=O)NO] | 2.84 | 367.1 | A |
| 88-10 | 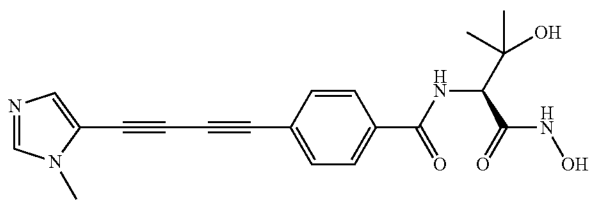 [SMILES: Cn1cncc1C#CC#Cc1ccc(C(=O)N[C@H](C(=O)NO)C(C)(C)O)cc1] | 3.13 | 381.1 | A |
| 88-11 | 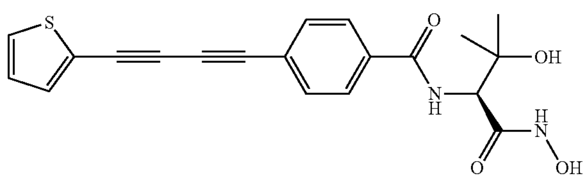 [SMILES: CC(C)(O)[C@H](NC(=O)c1ccc(C#CC#Cc2cccs2)cc1)C(=O)NO] | 4.82[1] | 383.3 | A |
| 88-12 | 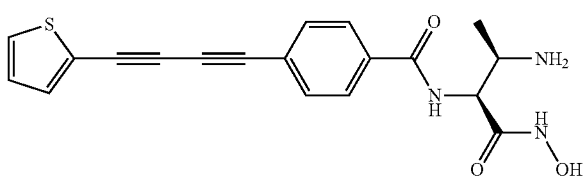 | 6.22[2] | 367.9 | B |
| 88-13 | 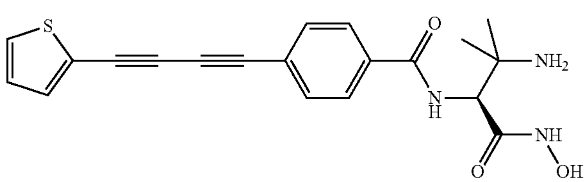 [SMILES: CC(C)(N)[C@H](NC(=O)c1ccc(C#CC#Cc2cccs2)cc1)C(=O)NO] | 4.36[2] | 382.0 | B |
| 88-14 | 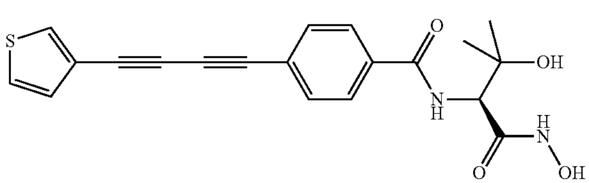 [SMILES: CC(C)(O)[C@H](NC(=O)c1ccc(C#CC#Cc2ccsc2)cc1)C(=O)NO] | 4.77 | 383.2 | A |

-continued

| Compound # | Structure | Ret. Time (min) | MH+ (m/z) | HPLC-MS Method |
|---|---|---|---|---|
| 88-15 | 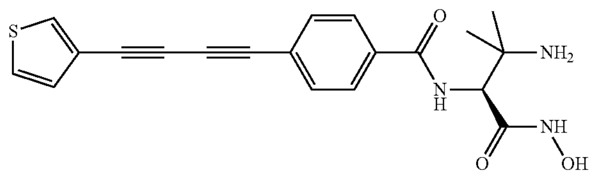 [SMILES: CC(C)(N)[C@H](NC(=O)c1ccc(C#CC#Cc2ccsc2)cc1)C(=O)NO] | 4.31 | 382.0 | B |
| 88-16 | 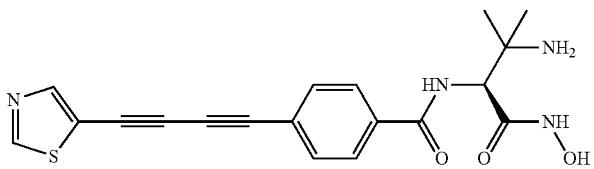 [SMILES: CC(C)(N)[C@H](NC(=O)c1ccc(C#CC#Cc2cncs2)cc1)C(=O)NO] | 4.95 | 383.1 | A |
| 88-17 | 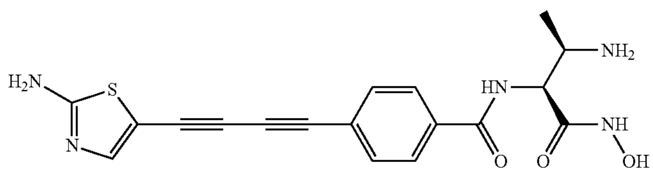 [SMILES: C[C@@H](N)[C@H](NC(=O)c1ccc(C#CC#Cc2cnc(N)s2)cc1)C(=O)NO] | 3.08 | 383.9 | A |
| 88-18 | 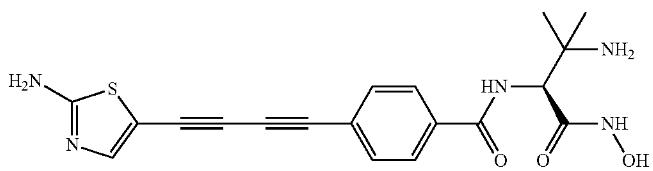 [SMILES: CC(C)(N)[C@H](NC(=O)c1ccc(C#CC#Cc2cnc(N)s2)cc1)C(=O)NO] | 3.08 | 383.9 | A |
| 88-19 | 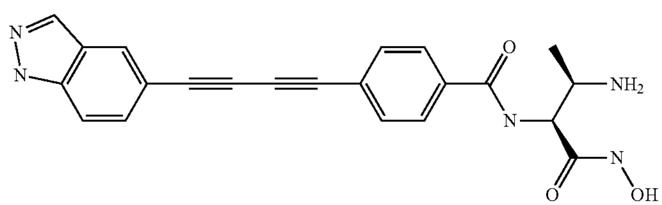 [SMILES: C[C@@H](N)[C@H](NC(=O)c1ccc(C#CC#Cc2ccc3[nH]ncc3c2)cc1)C(=O)NO] | | 401.4 | |
| 88-20 | 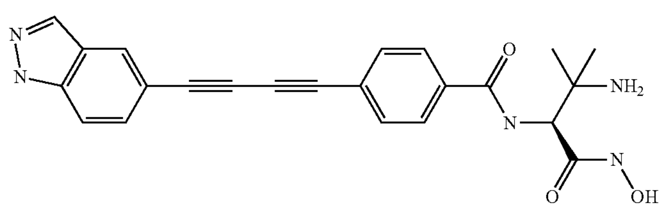 [SMILES: CC(C)(N)[C@H](NC(=O)c1ccc(C#CC#Cc2ccc3[nH]ncc3c2)cc1)C(=O)NO] | | 405 expted | |
| 88-21 | 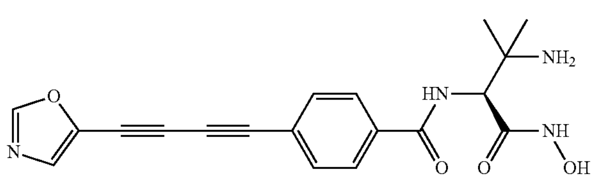 | | 366.1 expted | A |
| 88-22 | 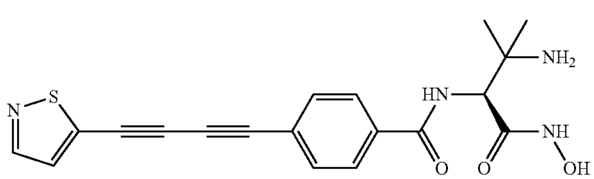 [SMILES: CC(C)(N)[C@H](NC(=O)c1ccc(C#CC#Cc2ccns2)cc1)C(=O)NO] | | 382 expted | A |

| Compound # | Structure | Ret. Time (min) | MH+ (m/z) | HPLC-MS Method |
|---|---|---|---|---|
| 88-23 | 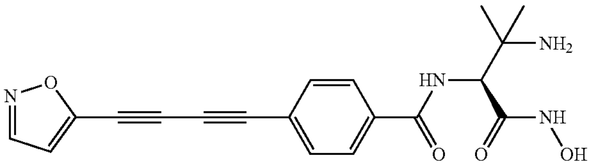 | | 366.1 expted | |
| 88-24 | 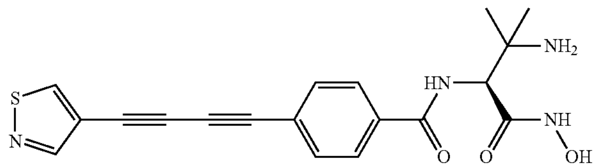 [SMILES: CC(C)(N)[C@H](NC(=O)c1ccc(C#CC#Cc2cnsc2)cc1)C(=O)NO] | | 382 expted | |
Example 89
N-((2S,3R)-3-amino-1-(hydroxyamino)-1-oxobutan-2-yl)-4-(1-methyl-1H-pyrazol-4-yl)buta-1,3-diynyl)benzamide
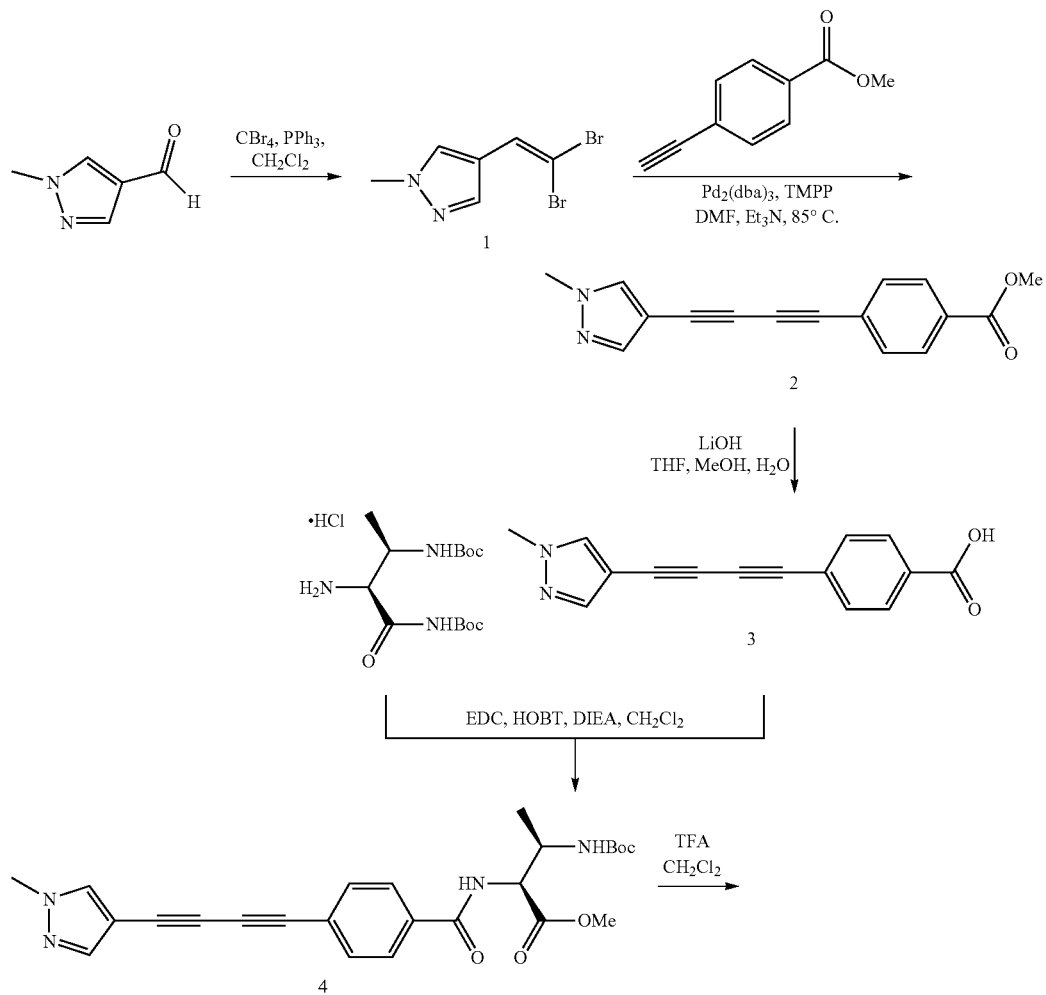

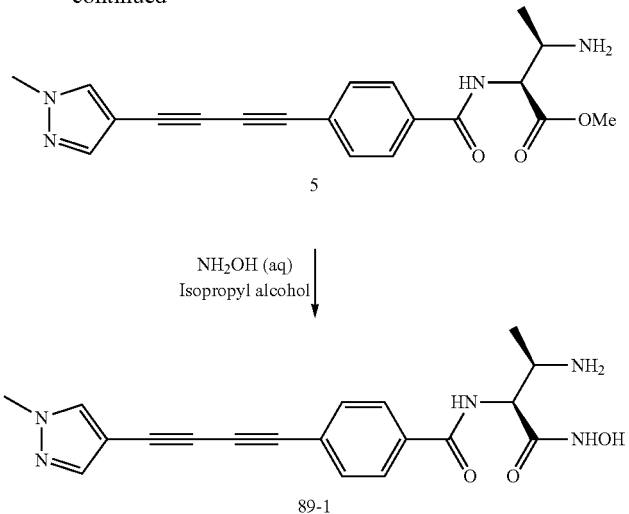

Synthesis of 4-(2,2-dibromovinyl)-1-methyl-1H-pyrazole (1)

The 1-methyl-1H-pyrazole-4-carbaldehyde (1.00 g, 9.08 mmol) and carbon tetrabromide (3.16 g, 9.54 mmol) were dissolved in CH$_2$Cl$_2$ (27 mL) and the solution was cooled to 0° C. To this chilled solution was then added PPh$_3$ (5.01 g, 19.1 mmol) in four portions over 5 min. The solution was then allowed to warm to ambient temperature for 18 h. The solution was diluted with hexanes (30 mL) and stirred for 15 min. The slurry was filtered and the filtrate was concentrated in vacuo and was purified by flash chromatography (50% EtOAc/Hex) to provide the desired product 1 as a white solid (1.72 g, 71%). LC-MS [M+H]$^+$=266.8 (Theoretical, C$_6$H$_7$Br$_2$N$_2$$^+$=266.9).

Synthesis of methyl 4-((1-methyl-1H-pyrazol-4-yl)buta-1,3-diynyl)benzoate (2)

The methyl 4-ethynylbenzoate (1.09 g, 6.79 mmol) and compound 1 (1.72 g, 6.47 mmol) were dissolved in DMF (65 mL) and this solution was deoxygenated by bubbling N$_2$ through for 10 min. To this deoxygenated solution was then added Et$_3$N (1.3 mL, 9.39 mmol). N$_2$ was then bubbled through for an additional 5 min followed by addition of Pd$_2$(dba)$_3$ (0.060 g, 0.065 mmol) and tri(4-methoxyphenyl)phosphine (0.091 g, 0.259 mmol). The dark brown solution was then allowed to stir at 80° C. for 18 h then cooled to ambient temperature. The solution was diluted with EtOAc (100 mL), washed with deionized water (3×50 mL) and brine (1×50 mL), dried (MgSO$_4$), filtered and concentrated in vacuo. The crude oil was purified by flash chromatography (0-50% EtOAc/CH$_2$Cl$_2$) to provide the desired product 2 as a yellow solid (1.03 g, 60%). LC-MS [M+H]$^+$=265.0 (Theoretical, C$_{16}$H$_{13}$N$_2$O$_2$$^+$=265.1).

Synthesis of 4-((1-methyl-1H-pyrazol-4-yl)buta-1,3-diynyl)benzoic acid (3)

To a solution of compound 2 (1.03 g, 3.90 mmol) in a mixture of THF (13 mL), MeOH (13 mL), and water (13 mL) was added LiOH monohydrate (0.491 g, 11.7 mmol) in one portion. The solution was allowed to stir at ambient temperature for 18 h. The pH of the solution was adjusted with aqueous HCl (1.0 N) and aqueous NaHCO$_3$ (sat.) to pH~7.5. The resulting solution was then extracted with EtOAc (3×100 mL), dried (MgSO$_4$), filtered and concentrated in vacuo to provide the desired product 3 (0.400 g, 41%) as an off white solid. LC-MS [M+H]$^+$=251.0 (Theoretical, C$_{15}$H$_{11}$N$_2$O$_2$$^+$=251.1).

Synthesis of (2S,3R)-methyl 3-(tert-butoxycarbonylamino)-2-(4-((1-methyl-1H-pyrazol-4-yl)buta-1,3-diynyl)benzamido)butanoate (4)

Compound 3 (0.400 g, 1.60 mmol), (2S,3R)-methyl 3-(Boc)-2-aminobutanoate HCl (0.473 g, 1.76 mmol), EDC (0.613 g, 3.20 mmol) and HOBT (0.432 g, 3.20 mmol) were slurried in anhydrous CH$_2$Cl$_2$ (16 mL). To this slurry was added N,N-diisopropylethylamine (1.04 mL, 6.40 mmol) in one portion. The solution was then allowed to stir at ambient temperature for 18 h. The solution was then concentrated in vacuo and the crude solid was purified by flash chromatography (0-50% EtOAc/CH$_2$Cl$_2$) to provide the desired product 4 (0.785 g, 81%) as an off white solid. $^1$H NMR (DMSO) δ 8.43 (d, J=8.4, 1H), 8.22 (s, 1H), 7.91 (d, J=7.9, 2H) 7.80 (s, 1H), 7.72 (d, J=7.3, 2H) 7.00 (d, J=9.7, 1H), 4.62 (dd, J=4.2, 8.2, 1H) 4.22-4.27 (m, 1H) 3.86 (s, 3H), 3.61 (s, 3H), 1.36 (s, 9H), 1.11 (d, J=7.0, 3H).

Synthesis of (2S,3R)-methyl 3-amino-2-(4-((1-methyl-1H-pyrazol-4-yl)buta-1,3-diynyl)benzamido)butanoate (5)

To a solution of compound 4 (0.286 g, 0.616 mmol) in of CH$_2$Cl$_2$ (10 mL) was added TFA (2 mL) slowly. The solution was allowed to stir at ambient temperature for 1 h then concentrated in vacuo. The thick oil was then azeotroped with CH$_2$Cl$_2$ (3×) to provide the TFA salt of the desired product 5 (0.284 g, 100%) as an off white solid. LC-MS [M+H]$^+$=365.1 (Theoretical, C$_{20}$H$_{21}$N$_4$O$_3$$^+$=365.2).

Synthesis of N-((2S,3R)-3-amino-1-(hydroxyamino)-1-oxobutan-2-yl)-4-((1-methyl-1H-pyrazol-4-yl)buta-1,3-diynyl)benzamide (89-1)

The TFA salt of 5 (0.284 g, 0.616 mmol) was dissolved in isopropyl alcohol (6 mL) and the hydroxylamine solution (0.81 mL, 12.3 mmol) was added in one portion at ambient temperature and the solution was allowed to stir for 18 h at ambient temperature. The volatiles were removed in vacuo and the resulting crude material was purified by reverse phase HPLC (5-30% MeCN/H$_2$O, w/0.1% TFA) then lyophilized to dryness to provide the desired product (89-1) (0.090 g, 40%) as a white solid; LC-MS [M+H]$^+$=366.1 (Theoretical, C$_{19}$H$_{20}$N$_5$O$_3$$^+$=366.2).

Each of the following compounds was synthesized as described above.

| Compound # | Structure | Ret. Time (min) | MH$^+$ (m/z) | HPLC-MS Method |
|---|---|---|---|---|
| 89-2 | 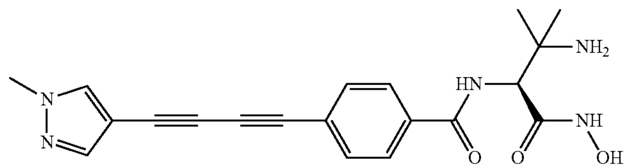 | 4.71 | 380.3 | A |
| 89-3 | 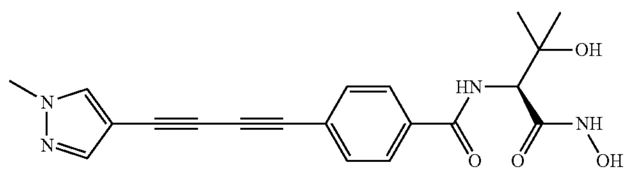 [SMILES: Cn1cc(C#CC#Cc2ccc(C(=O)N[C@H](C(=O)NO)C(C)(C)N)cc2)cn1] | 5.43 | 381.1 | A |
| 89-4 | 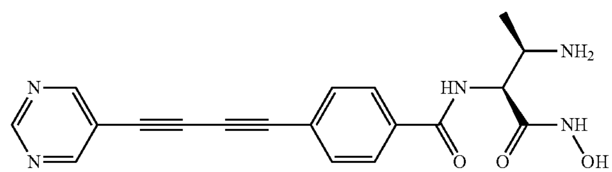 [SMILES: C[C@@H](N)[C@H](NC(=O)c1ccc(C#CC#Cc2cncnc2)cc1)C(=O)NO] | 3.99 | 364.3 | A |
| 89-5 | 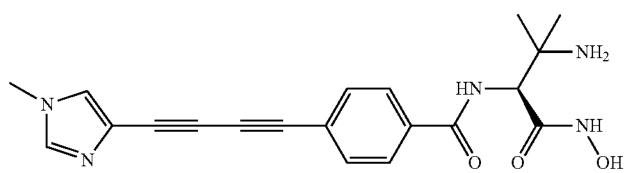 [SMILES: Cn1cnc(C#CC#Cc2ccc(C(=O)N[C@H](C(=O)NO)C(C)(C)N)cc2)c1] | 2.46 | 380.3 | A |
| 89-6 | 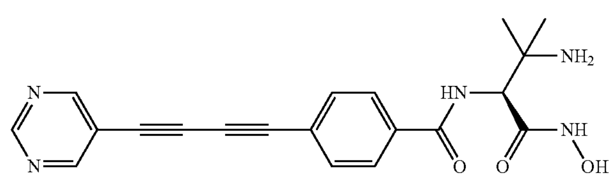 [SMILES: CC(C)(N)[C@H](NC(=O)c1ccc(C#CC#Cc2cncnc2)cc1)C(=O)NO] | 4.26 | 378.3 | A |
| 89-7 | 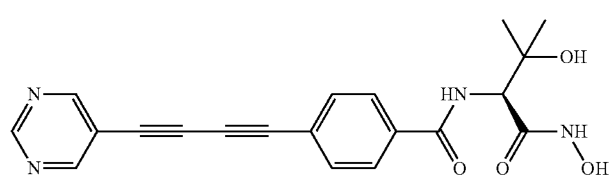 [SMILES: CC(C)(O)[C@H](NC(=O)c1ccc(C#CC#Cc2cncnc2)cc1)C(=O)NO] | 4.96 | 379.1 | A |

Example 90
Synthesis of (S)-4-((1H-pyrazol-4-yl)buta-1,3-diynyl)-N-(3-amino-1-(hydroxyamino)-3-methyl-1-oxobutan-2-yl)benzamide (90-1)
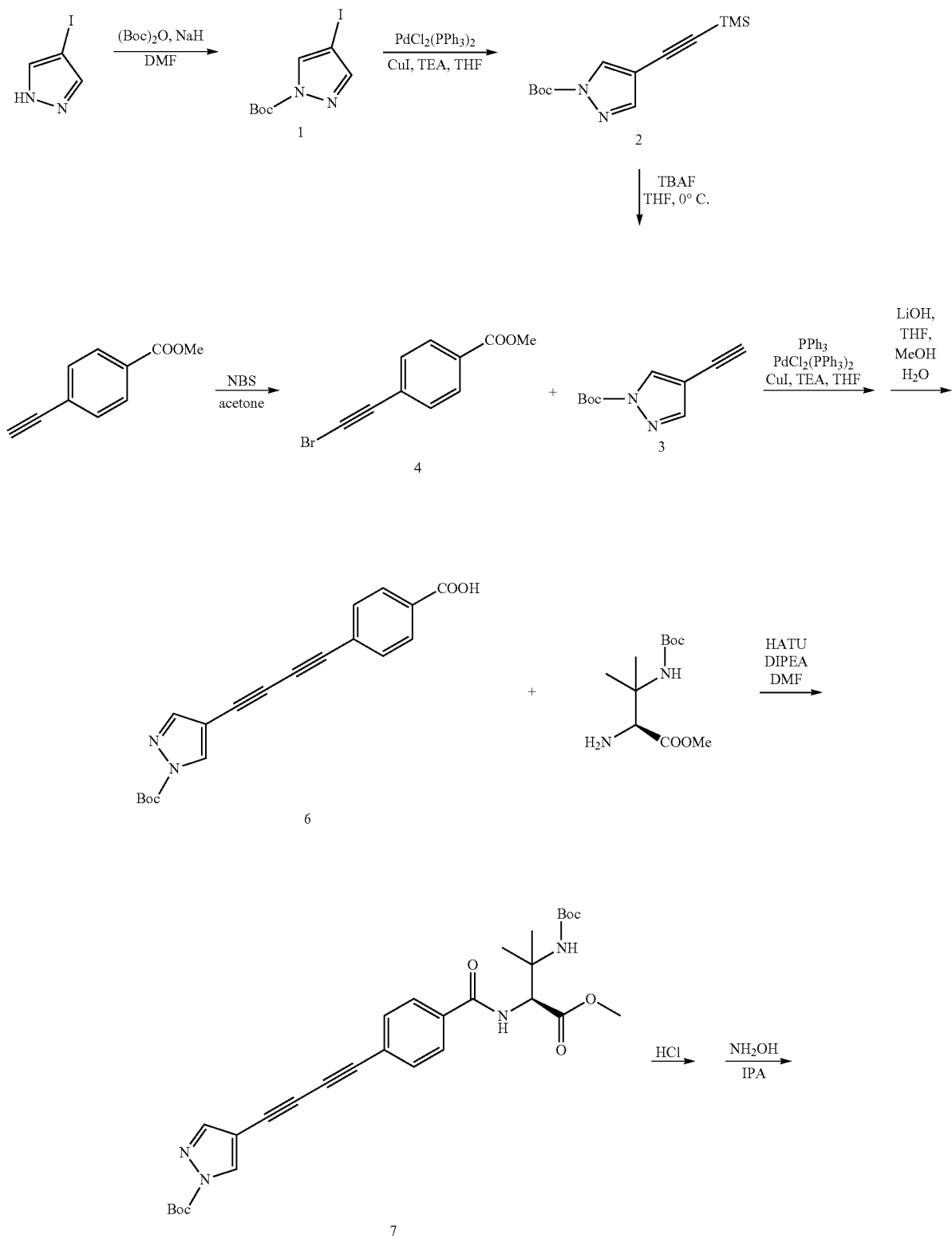

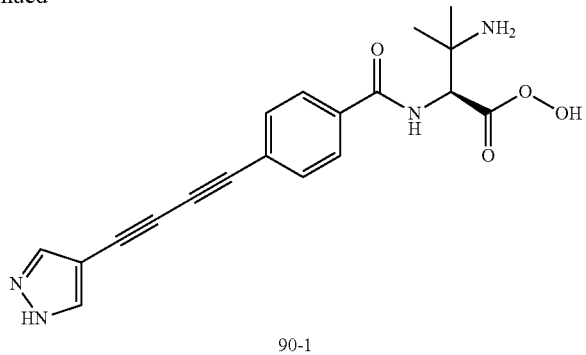

90-1

Synthesis of tert-butyl 4-iodo-1H-pyrazole-1-carboxylate (1)

NaH (247 mg, 6.18 mmol) was added to the DMF (50 ml) solution of 4-iodo-1H-pyrazole (1.0 g, 5.15 mmol) at 0° C. The reaction was stirred at 0° C. in 30 min. (Boc)$_2$O (1.68 g, 7.76 mmol) was added to the reaction at 0° C. The reaction was warmed to r.t. and stirred overnight. H$_2$O (200 ml) was added to quench the reaction. The mixture was extracted with EtOAc (3×200 ml). The combined EtOAc extracts was washed with H$_2$O (2×200 ml), brine (200 ml) and dried with Na$_2$SO$_4$ the crude product was purified with ISCO normal phase column (0-20% EtOAc/DCM). Compound 20 (1.3 g) was obtained in the yield of 86%.

Synthesis of tert-butyl 4-((trimethylsilyl)ethynyl)-1H-pyrazole-1-carboxylate (2)

THF was degassed by passing through N$_2$ gas for 30 min. TEA (6.0 ml, 11.5 mmol) was added to the THF solution (20 ml) of Compound 1 (1.69 g, 5.75 mmol), Trimethylsilyl-ethyne (845 mg, 8.63 mml), PdCl$_2$(PPh$_3$)$_2$ (404 mg, 0575 mmol) and CuI (109 mg, 0.575 mmol). The reaction was stirred overnight. The reaction was diluted with EtOAc and filtered through celite. The organic solution was washed with H$_2$O, brine and dried with Na$_2$SO$_4$. The crude product was purified with ISCO normal phase column The crude product was purified with ISCO normal phase column (0-2% EtOAc/DCM). Compound 21 (1.02 g, 67.2%) was obtained

Synthesis of tert-butyl 4-ethynyl-1H-pyrazole-1-carboxylate (3)

TBAF (5.2 ml, 1.0M in THF) was added to the THF solution (10 ml) of Compound 2 (1.02 g, 3.46 mmol) at 0° C. The reaction was stirred at 0° C. for 10 min. The THF was removed and the residue was dissolved in EtOAc. The EtOAc solution was washed with H$_2$O, brine and dried with Na$_2$SO$_2$. The crude produce was purified with ISCO normal phase column. The crude product was purified with ISCO normal phase column (0-30% EtOAc/hexane). Compound 3 (362.3 mg, 54.5%) was obtained.

Synthesis of methyl 4-(bromoethynyl)benzoate (4)

NBS (13.4 g, 75 mmol) was added to the acetone solution (250 ml) of 4-ethynyl-benzoic methyl ester (8 g, 50 mmol) and CF$_3$COOAg (850 mg, 5 mmol). The reaction was stirred at r.t for 2 hrs. The reaction was poured into ice-water (500 ml) and stirred for 30 min. After separation, the H$_2$O layer was extracted with EtOAc (300 ml×3). The combined EtOAc layers was washed with H$_2$O (2×200 ml) and brine (200 ml) and dried with Na$_2$SO$_4$. The crude product was purified with ISCO normal phase column (0-50% EtOAc/hexane). Compound 27 (12.0 g, 100%) was obtained.

Synthesis of methyl 4-((1-methyl-1H-pyrazol-4-yl)buta-1,3-diynyl)benzoate (5)

THF was degassed by passing through N$_2$ gas for 30 min. TEA was added to the THF solution (10 ml) of Compound 3 (362 mg, 1.89 mmol), Compound 4 (666 mg, 2.27 mmol), PdCl$_2$(PPh$_2$)$_2$ (133 mg, 0.189 mmol), PPh$_3$ (25 mg, 0.095 mmol) and CuI (36 mg, 0.189 mmol). The reaction was stirred at r.t. for 30 min followed by the addition of CuI. The reaction was heated to 45° C. overnight. The reaction was diluted with EtOAc and filtered through celite. The organic solution was washed with H$_2$O, brine and dried with Na$_2$SO$_4$. The crude product was purified with ISCO normal phase column. The crude product was purified with ISCO normal phase column (0-50% EtOAc/hexane). Compound 28 (150 mg, 19.7%) was obtained

Synthesis of 4-((1-(tert-butoxycarbonyl)-1H-pyrazol-4-yl)buta-1,3-diynyl)benzoic acid (6)

Compound 6 (120 mg, 94%) was made using the General Method for basic hydrolysis used to the next step without further purification.

Synthesis of methyl 3-(tert-butoxycarbonylamino)-2-(4-(imidazo[1,2-a]pyridin-6-ylbuta-1,3-diynyl)benzamido)-3-methylbutanoate (7)

Compound 7 (100 mg, 48%) was coupled to BocDAP-OMe using the General Method for HATU coupling used in the next step without purification.

Synthesis of (S)-methyl 2-(4-((1H-pyrazol-4-yl)buta-1,3-diynyl)benzamido)-3-amino-3-methylbutanoate (8)

The Compound 8 was made using the General Method for Boc deprotection and used on next step without purification. Compound 8 (65 mg, 100%)

Synthesis of (S)-4-((1H-pyrazol-4-yl)buta-1,3-diynyl)-N-(3-amino-1-(hydroxyamino)-3-methyl-1-oxobutan-2-yl)benzamide (90-1)

The target product (33 mg, 50%, m+z=366.66) was prepared by following General Method 3-A for hydroxamate Method (Hydroxyamide formation, aqueous).
The following compounds were synthesized by using above procedure with corresponding acid and amine.

| Compound # | Structure | Ret. Time (min) | MH+ (m/z) | HPLC-MS Method |
|---|---|---|---|---|
| 90-2 | 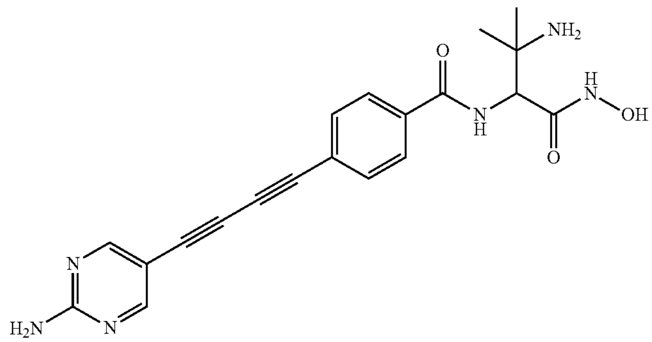 [SMILES: CC(C)(N)C(NC(=O)c1ccc(C#CC#Cc2cnc(N)nc2)cc1)C(=O)NO] | | 393.7 | A |
| 90-3 | 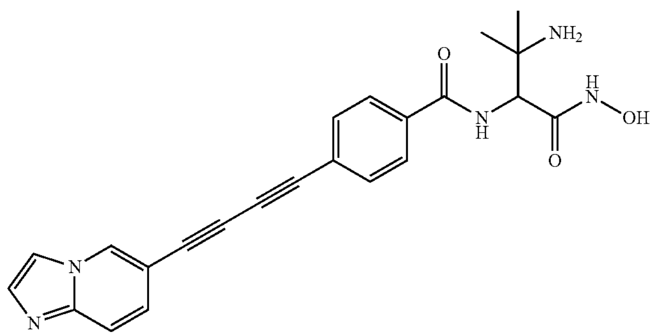 [SMILES: CC(C)(N)C(NC(=O)c1ccc(C#CC#Cc2ccc3nccn3c2)cc1)C(=O)NO] | | 416.6 | A |

Example 91

N—((S)-2-Amino-1-hydroxycarbamoyl-2-methyl-propyl)-4-hexa-1,3-diynyl-benzamide (91-1)

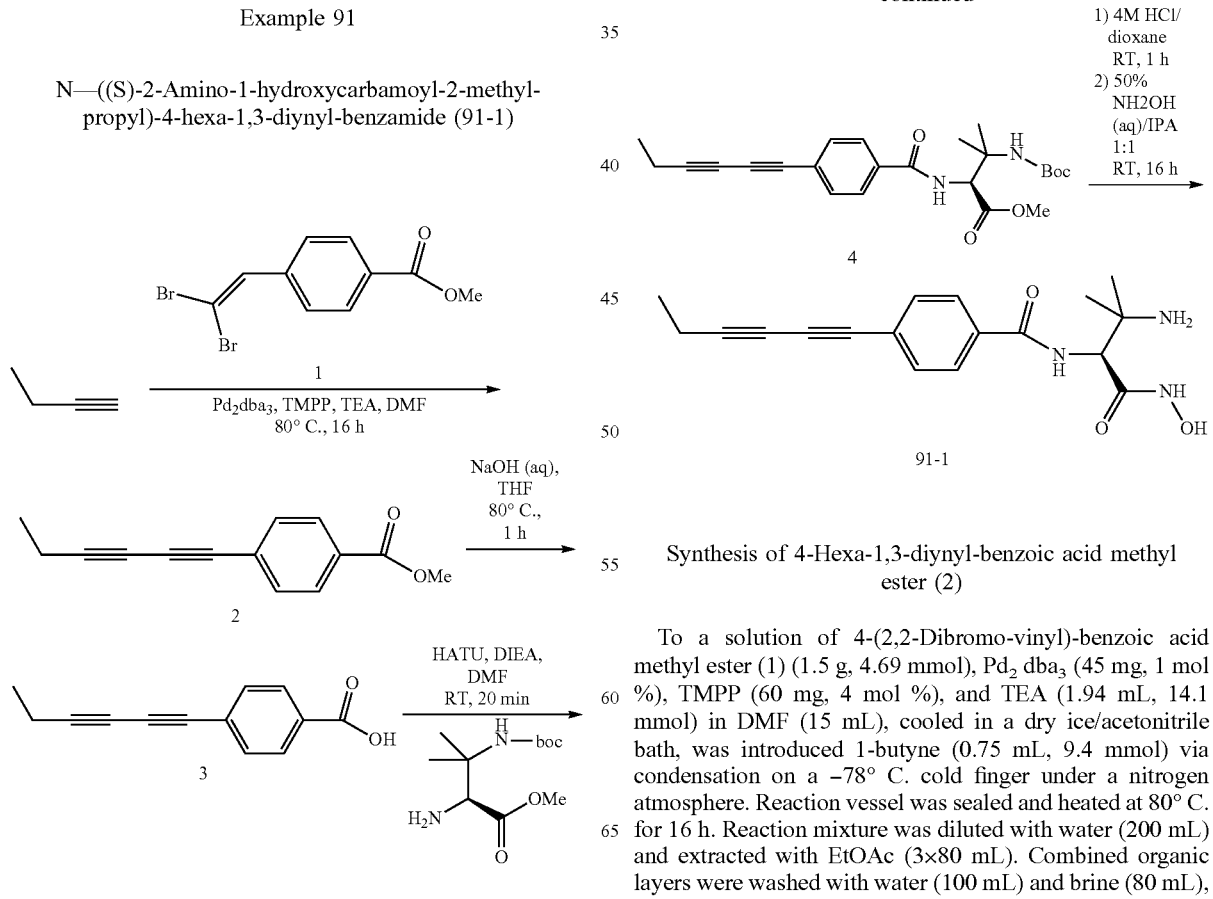

Synthesis of 4-Hexa-1,3-diynyl-benzoic acid methyl ester (2)

To a solution of 4-(2,2-Dibromo-vinyl)-benzoic acid methyl ester (1) (1.5 g, 4.69 mmol), Pd$_2$dba$_3$ (45 mg, 1 mol %), TMPP (60 mg, 4 mol %), and TEA (1.94 mL, 14.1 mmol) in DMF (15 mL), cooled in a dry ice/acetonitrile bath, was introduced 1-butyne (0.75 mL, 9.4 mmol) via condensation on a −78° C. cold finger under a nitrogen atmosphere. Reaction vessel was sealed and heated at 80° C. for 16 h. Reaction mixture was diluted with water (200 mL) and extracted with EtOAc (3×80 mL). Combined organic layers were washed with water (100 mL) and brine (80 mL), dried over anhydrous $Na_2SO_4$, and concentrated in vacuo to give a sticky brown solid. Crude product was purified by normal phase flash chromatography on a CombiFlash® Companion™ unit equipped with Luknova flash column (40 g silica gel, 40-60 μm average particle size, 60 Å pore size); flow rate: 40 mL/min; mobile phase A: hexane; mobile phase B: EtOAc; gradient elution from 0% B to 30% B over 70 min. Fractions containing the desired product were combined and concentrated in vacuo to give target compound 2 (1.093 mg, 110%) as a slightly sticky light brown solid. LC-MS: RT (Method A) 6.67 min; compound not significantly ionizable. $^1$H NMR (250 MHz, $CDCl_3$) δ 1.15 (3H, t), 2.35 (2H, q), 3.9 (3H, s), 7.6 (2H, d), 8.0 (2H, d).

Synthesis of 4-Hexa-1,3-diynyl-benzoic acid (3)

To compound 2 (4.69 mmol) were added THF (8 mL) and 3 M NaOH (aq) (12 mL, 36 mmol). Reaction mixture was heated at 80° C. for 1 h. Reaction mixture was diluted with water (150 mL), cooled in ice/water bath, acidified to pH 3 with 10% $H_3PO_4$ (aq), and filtered. Solids were washed with water (3×50 mL) and dried by lyophilization to give target compound 3 (766.9 mg, 83.4% from 1) as an off-white solid. LC-MS: RT (Method A) 5.38 min; compound not significantly ionizable.

Synthesis of (S)-3-tert-Butoxycarbonylamino-2-(4-hexa-1,3-diynyl-benzoylamino)-3-methyl-butyric acid methyl ester (4)

| Reagent | MW | Eq. | mg/mL | mmol |
|---|---|---|---|---|
| Compound 3 | 198.22 | 1.0 | 96.1 mg | 0.485 |
| Chiral dimethyl DAP | 246.31 | 1.1 | 133 mg | 0.540 |
| HATU | 380.2 | 1.2 | 224 mg | 0.589 |
| DIEA | 129.25 | 3.0 | 0.256 mL | 1.47 |
| DMF | | | 4 mL | |

Compound 4 (231.6 mg, 112%) as a sticky amber solid prepared using the General Method for HATU coupling and used on next step without purification. LC-MS: RT (Method A) 6.90 min; [M+H] 427.1 ($C_{24}H_{30}N_2O_5$+H, requires 427.53).

Synthesis of N—((S)-2-Amino-1-hydroxycarbamoyl-2-methyl-propyl)-4-hexa-1,3-diynyl-benzamide (91-1)

To compound 4 (~0.485 mmol) was added 4 M HCl/dioxane (4 mL), and the mixture was stirred at ambient temperature for 1 h. Volatiles were removed in vacuo to give a sticky amber solid. LC-MS: RT (Method A) 4.31 min; [M+H] 327.1 ($C_{19}H_{22}N_2O_3$+H, requires 327.41). Isopropyl alcohol (4 mL) was added to the solid and the mixture was cooled in an ice/water bath for 5 min. $NH_2OH$ (50%, aq) (4 mL) was added to the mixture, dropwise for the first 2 mL. Reaction mixture was allowed to stir in ice bath for 5 min, and then allowed to stir at ambient temperature for 16 h. Solvent volume was reduced approximately by half under a stream of nitrogen, and water (10 mL) was added. The suspension was thoroughly agitated (vibro mixer and sonication), centrifuged and the supernatant was discarded. Water (10 mL) was added to the solid and the suspension was thoroughly agitated, centrifuged and the supernatant was discarded. Wet solid was dried by lyophilization to give crude product (127 mg, 80.3% crude yield from 3) as an off-white solid. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 15% B to 40% B over 60 min, MS detection). Fractions containing the desired product were combined and lyophilized to provide the trifluoroacetate salt of target compound 91-1 (64.8 mg, 30.3% yield from 3, 37.8% recovery from crude product) as a white solid. LC-MS: RT (Method A) 3.77 min; [M+H] 328.3 ($C_{18}H_{21}N_3O_3$+H, requires 328.40).

| Compound | Scale (mmol)[1] | Yield (mg) | Yield (%)[1] | Purity (%)[2] | [M + H] | Retention time (min)[2] |
|---|---|---|---|---|---|---|
| 91-1 | 0.485 | 64.8 | 30.3 | 98.5 | 328.3 | 3.77 |

[1]Based on the amount of carboxylic acid used in the coupling reaction.
[2]Using LC-MS Analytical Method A.

Intermediate Acid IC-1

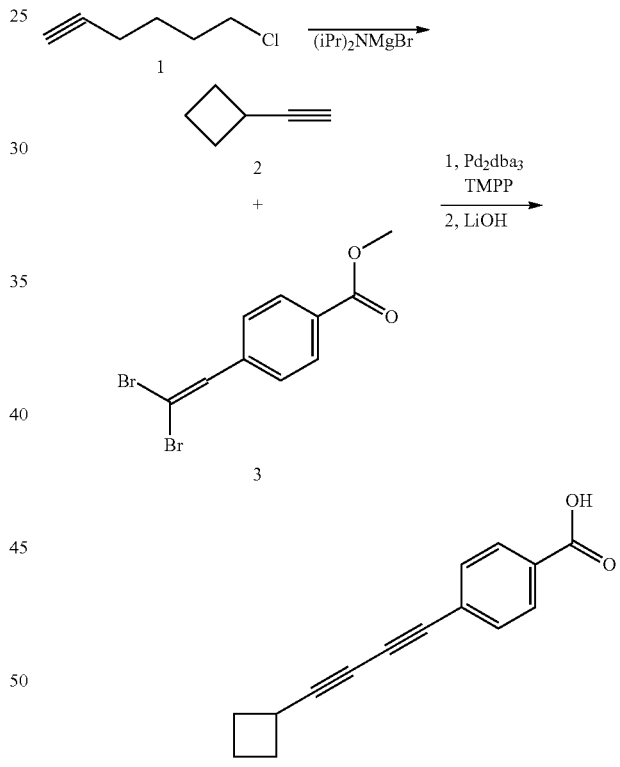

IC-1

Synthesis of cyclobutylacetylene (2)

The synthesis was done according to U.S. Pat. No. 6,303,057 entitled "Preparation of cycloalkylacetylene compounds".

Into a 0.5 liter round bottom flask equipped with an addition funnel and a reflux condenser were placed), diisopropylamine (10.1 g, 0.1 mol) and THF (250 ml). Bromoethane (59.9 g, 0.55 mol) was added dropwise to this mixture via the addition funnel at such a rate as to maintain a refluxing solution. Ethane was evolved during the addition.

The reaction was determined to be complete once all of the magnesium was consumed. This process produced a solution containing EtMgBr and (iPr)$_2$NMgBr. 6-Chlorohexyne (23.32 g, 0.2 mol) was added dropwise and the resulting reaction mixture was stirred at 65° C. for 36 h. The cooled reaction mixture was poured onto crashed ice. Organic upper layer was separated, washed 3 times with water (3×100 mL) and dried over Na$_2$SO$_4$. Na$_2$SO$_4$ was separated by filtration to give 21.7 g of yellow liquid, which was used on next step without purification.

Synthesis of 4-(4-Cyclobutyl-buta-1,3-diynyl)-benzoic acid (IC-1)

| Reagent | MW | Eq. | mmol | g, ml |
|---|---|---|---|---|
| Methyl 4-(2,2-dibromovinyl)-benzoate | 319.98 | 1.0 | 7.8 | 2.5 g |

-continued

| Reagent | MW | Eq. | mmol | g, ml |
|---|---|---|---|---|
| Cyclobutylacetylene (2) | 80.13 | 1.4 | 10.93 | 0.88 g |
| Tris(dibenzyllidene-acetone)dipalladium(0) | 915.72 | 0.08 | 0.065 | 60 mg |
| Tris(4-methoxyphenyl)phosphine | 352.36 | 0.03 | 0.24 | 85 mg |
| TEA | 101.19 | 3.2 | 25 | 3.47 mL |
| DMF(anhydrous) | | | | 10 mL |

The 4-(4-Cyclobutyl-buta-1,3-diynyl)-benzoic acid methyl ester (4) was made and separated using the General Method for Sonogashira coupling*. Yield: 11.3%. (Yellow solid). Check of a sample by HPLC-MS showed a major product peak (Ret. time (Method A) 7.58 min, [MH+]=239.2). This product was subject to basic hydrolysis to give the desired acid IC-1, used to prepare compound 10-16 and 10-17.

For syntheses of the following alkyl- and cycloalkyl diacetylenes, commercially available acetylenes were used.

| Compound # | Structure | Ret. Time (min) | MH+ (m/z) | HPLC-MS Method |
|---|---|---|---|---|
| 91-2 | 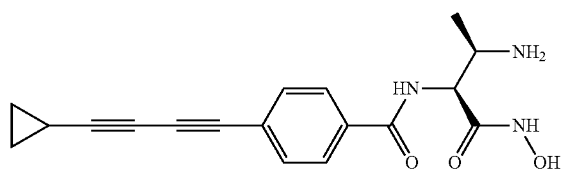 | 5.46 | 326.3 | A |
| 91-3 | 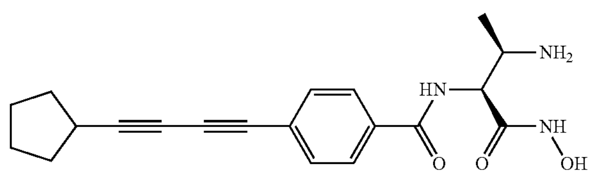 [SMILES: C[C@@H](N)[C@H](NC(=O)c1ccc(C#CC#CC2CCCC2)cc1)C(=O)NO] | 6.79 | 354.3 | A |
| 91-4 | 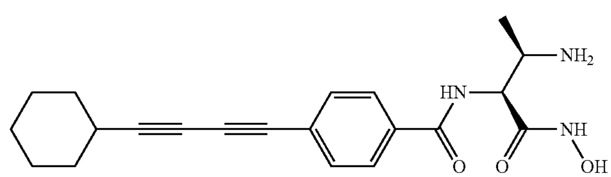 [SMILES: C[C@@H](N)[C@H](NC(=O)c1ccc(C#CC#CC2CCCCC2)cc1)C(=O)NO] | 7.35 | 368.3 | A |
| 91-5 | 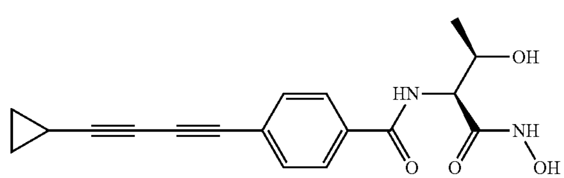 | 6.12 | 327.1 | A |
| 91-6 | 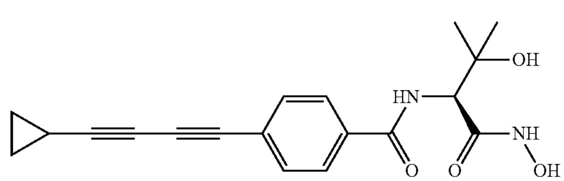 [SMILES: CC(C)(O)[C@H](NC(=O)c1ccc(C#CC#CC2CC2)cc1)C(=O)NO] | 6.50 | 341.1 | A |
| 91-7 | 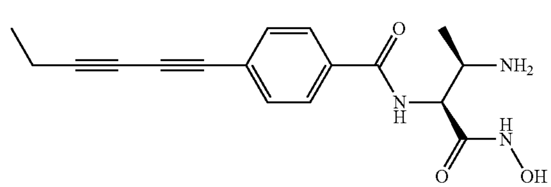 [SMILES: CCC#CC#Cc1ccc(C(=O)N[C@H](C(=O)NO)[C@@H](C)N)cc1] | 3.64 | 314.1 | A |

-continued
| Compound # | Structure | Ret. Time (min) | MH+ (m/z) | HPLC-MS Method |
|---|---|---|---|---|
| 91-8 | 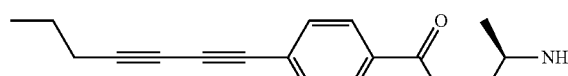 | 4.04 | 328.3 | A |
| 91-9 | 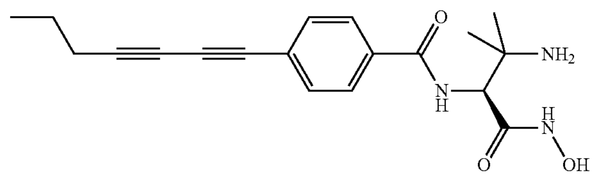 [SMILES: CCCC#CC#Cc1ccc(C(=O)N[C@H](C(=O)NO)C(C)(C)N)cc1] | 4.14 | 342.2 | A |
Each of the following compounds was synthesized as described above using the Boc protected amino acid and HCl deprotection.
| Compound # | Structure | Ret. Time (min) | MH+ (m/z) | HPLC-MS Method |
|---|---|---|---|---|
| 91-10 | 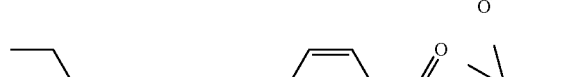 | 4.01 | 340.3 | A |
| 91-11 | 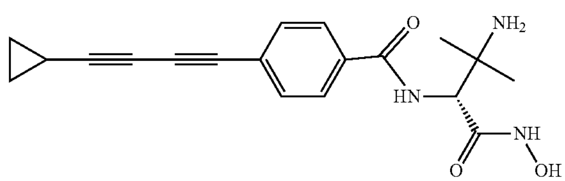 [SMILES: CC(C)(N)[C@@H](NC(=O)c1ccc(C#CC#CC2CC2)cc1)C(=O)NO] | 3.97 | 339.9 | A |
| 91-12 | 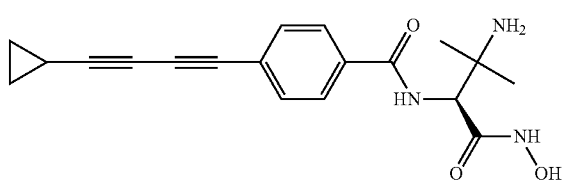 [SMILES: CC(C)(N)[C@H](NC(=O)c1ccc(C#CC#CC2CC2)cc1)C(=O)NO] | 3.95 | 340.3 | A |
| 91-13 | 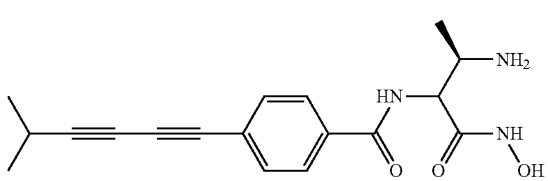 [SMILES: CC(C)C#CC#Cc1ccc(C(=O)NC(C(=O)NO)[C@@H](C)N)cc1] | 4.16 | 328.3 | A |
| 91-14 | 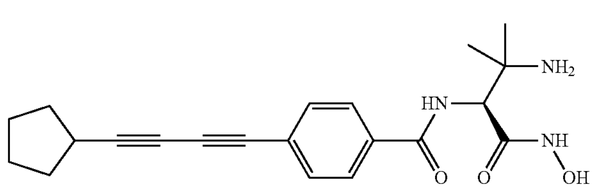 [SMILES: CC(C)(N)[C@H](NC(=O)c1ccc(C#CC#CC2CCCC2)cc1)C(=O)NO] | 6.95 | 368.3 | A |

-continued

| Compound # | Structure | Ret. Time (min) | MH+ (m/z) | HPLC-MS Method |
|---|---|---|---|---|
| 91-15 | 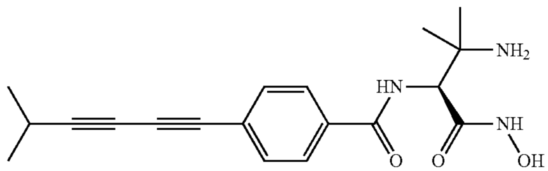 [SMILES: CC(C)C#CC#Cc1ccc(C(=O)N[C@H](C(=O)NO)C(C)(C)N)cc1] | 6.08 | 342.6 | A |
| 91-16 | 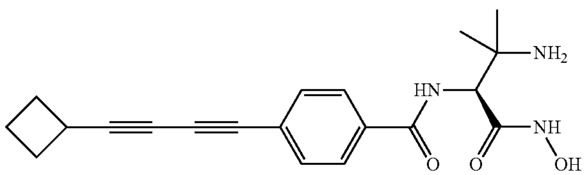 [SMILES: CC(C)(N)[C@H](NC(=O)c1ccc(C#CC#CC2CCC2)cc1)C(=O)NO] | 6.32 | 354.3 | A |
| 91-17 | 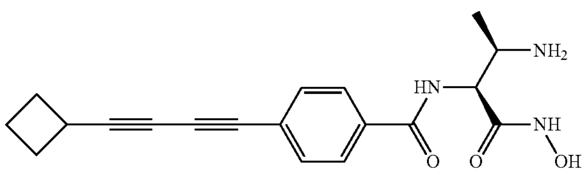 [SMILES: C[C@@H](N)[C@H](NC(=O)c1ccc(C#CC#CC2CCC2)cc1)C(=O)NO] | 3.18 | 340.2 | A |

Intermediate Acid IC-2

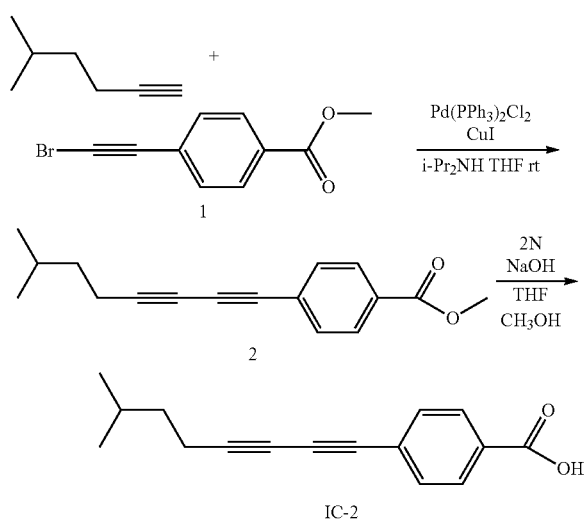

Methyl 4-(7-methylocta-1,3-diynyl)benzoate (2)

To a degassed solution of compound 1 (2.8 g, 11 mmol), Pd(PPh₃)₂Cl₂ (0.411 g, 0.58 mmol) and CuI (0.11 g, 0.58 mmol) in dried THF (50 mL) was added 5-methylhex-1-yne (1.35 g, 1.86 mL, 14 mmol), followed by diisopropylamine (3.56 g, 4.9 ml, 35.1 mmol) dropwise. After the addition of diisopropylamine, the reaction mixture was stirred overnight at room temperature. The suspension was filtered and washed the cake with $CH_2Cl_2$. The filtrate was concentrated in vacuo. The residue was purified by silica-gel column chromatography (PE: EA=100:1) to give compound 2 (2.25 g, 75%) as a brown solid.

4-(7-Methylocta-1,3-diynyl)benzoic acid (3)

| Reagent | MW | Eq. | mmol | g, mL |
|---|---|---|---|---|
| Compound 2 | 254.32 | 1 | 8.6 | 2.15 g |
| 2N NaOH | 40 | 2.3 | 20 | 10 mL |
| THF | | | | 30 mL |
| MeOH | | | | 10 mL |

Compound 3 (1.5 g, 70%) as a white solid made and separated using the General Method for basic hydrolysis. ¹H-NMR (400 MHz, DMSO-d₆): 0.89 (d, J=6.4, 6H), 1.39-1.45 (m, 2H), 1.61-1.70 (m, 1H), 2.44-2.51 (m, 2H), 7.65 (d, J=8.4 Hz, 2H), 7.93 (d, J=8.8 Hz, 2H), 13.24 (s, 1H).

The intermediate acids for making the following analogues were synthesized by using the same synthetic method for compound 10-18. Each of the following compounds of was synthesized as described above using the Boc protected amino acid and HCl deprotection.

| Compound # | Structure | Ret. Time (min) | MH+ (m/z) | HPLC-MS Method |
|---|---|---|---|---|
| 91-18 | 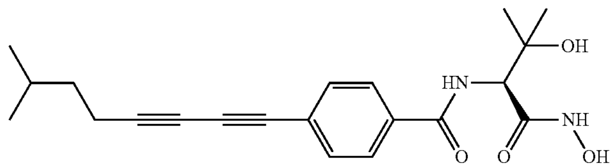 [SMILES: CC(C)CCC#CC#Cc1ccc(C(=O)N[C@H](C(=O)NO)C(C)(C)O)cc1] | 8.55 | 371.1 | A |
| 91-19 | 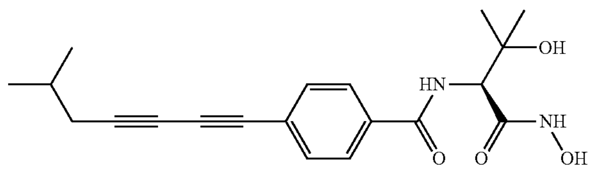 [SMILES: CC(C)CC#CC#Cc1ccc(C(=O)N[C@H](C(=O)NO)C(C)(C)O)cc1] | 7.84 | 357.1 | A |
| 91-20 | 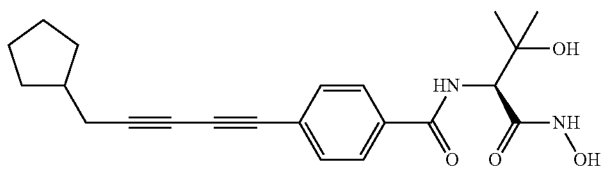 [SMILES: CC(C)(O)[C@H](NC(=O)c1ccc(C#CC#CCC2CCCC2)cc1)C(=O)NO] | 8.73 | 383.1 | A |
| 91-21 | 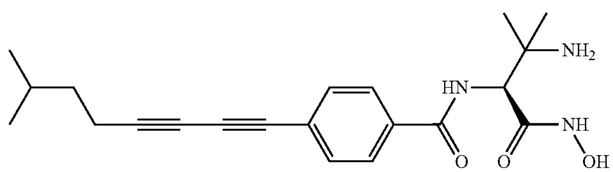 [SMILES: CC(C)CCC#CC#Cc1ccc(C(=O)N[C@H](C(=O)NO)C(C)(C)N)cc1] | 7.50 | 370.3 | A |
| 91-22 | 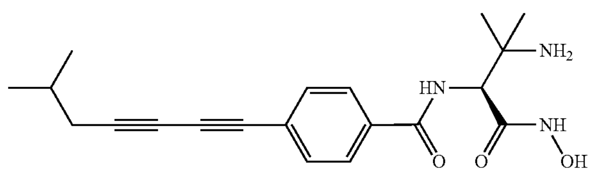 [SMILES: CC(C)CC#CC#Cc1ccc(C(=O)N[C@H](C(=O)NO)C(C)(C)N)cc1] | 6.90 | 356.3 | A |
| 91-23 | 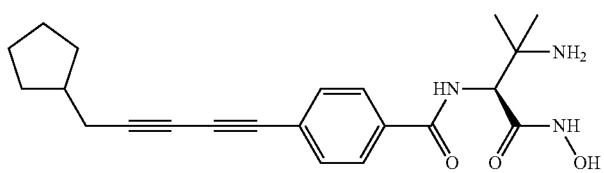 | 7.69 | 382.3 | A |
| 91-24 | 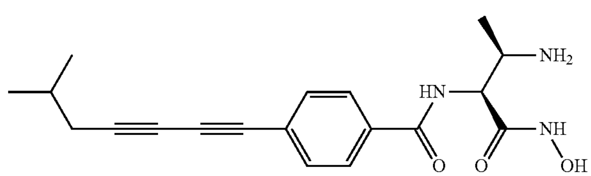 [SMILES: CC(C)CC#CC#Cc1ccc(C(=O)N[C@H](C(=O)NO)[C@@H](C)N)cc1] | 6.67 | 342.3 | A |
| 91-25 | 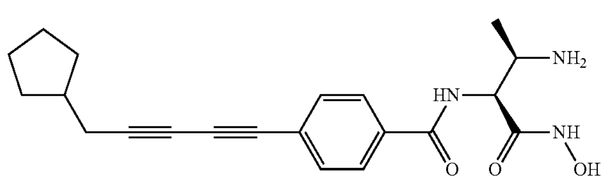 [SMILES: C[C@@H](N)[C@H](NC(=O)c1ccc(C#CC#CCC2CCCC2)cc1)C(=O)NO] | 7.64 | 368.3 | A |
| 91-26 | 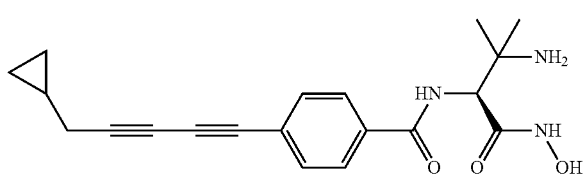 [SMILES: CC(C)(N)[C@H](NC(=O)c1ccc(C#CC#CCC2CC2)cc1)C(=O)NO] | 6.43 | 354.3 | A |

| Compound # | Structure | Ret. Time (min) | MH+ (m/z) | HPLC-MS Method |
|---|---|---|---|---|
| 91-27 | 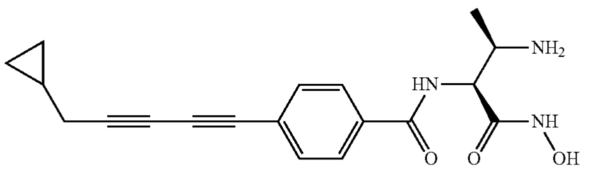 [SMILES: C[C@@H](N)[C@H](NC(=O)c1ccc(C#CC#CCC2CC2)cc1)C(=O)NO] | 6.22 | 340.3 | A |
| 91-28 | 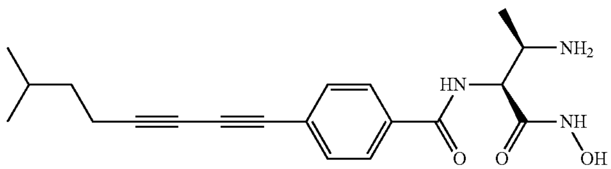 [SMILES: CC(C)CCC#CC#Cc1ccc(C(=O)N[C@H](C(=O)NO)[C@@H](C)N)cc1] | 7.31 | 356.3 | A |
| 91-29 | 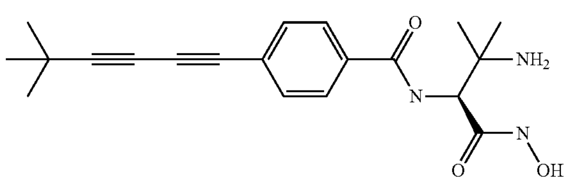 [SMILES: CC(C)(C)C#CC#Cc1ccc(C(=O)N[C@H](C(=O)NO)C(C)(C)N)cc1] | | 355.2 | |
| 91-30 | 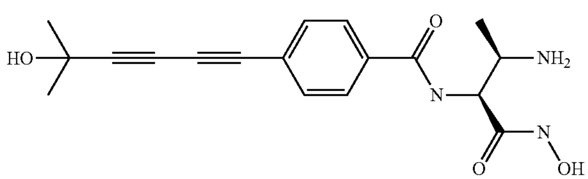 [SMILES: C[C@@H](N)[C@H](NC(=O)c1ccc(C#CC#CC(C)(C)O)cc1)C(=O)NO] | | 344.1 | |
Example 92
N-((2S,3R)-3-amino-1-(hydroxyamino)-1-oxobutan-2-yl)-4-(R)-5-morpholinohexa-1,3-diynyl)benzamide AND N-((2S,3R)-3-amino-1-(hydroxyamino)-1-oxobutan-2-yl)-4-((S)-5-morpholinohexa-1,3-diynyl)benzamide (92-1 and 92-2)
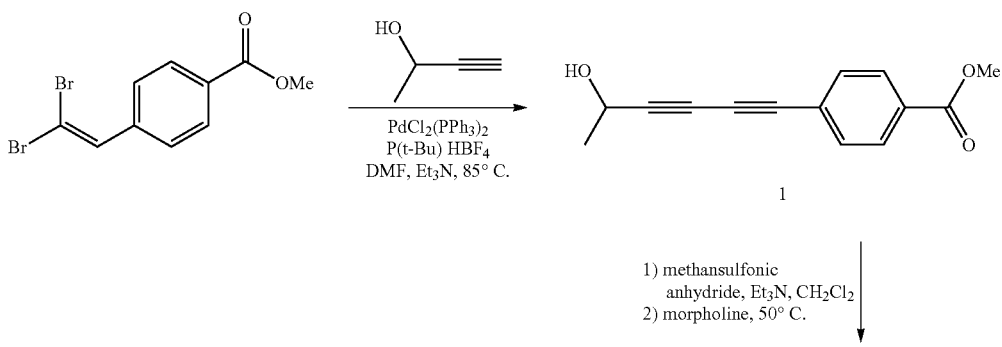

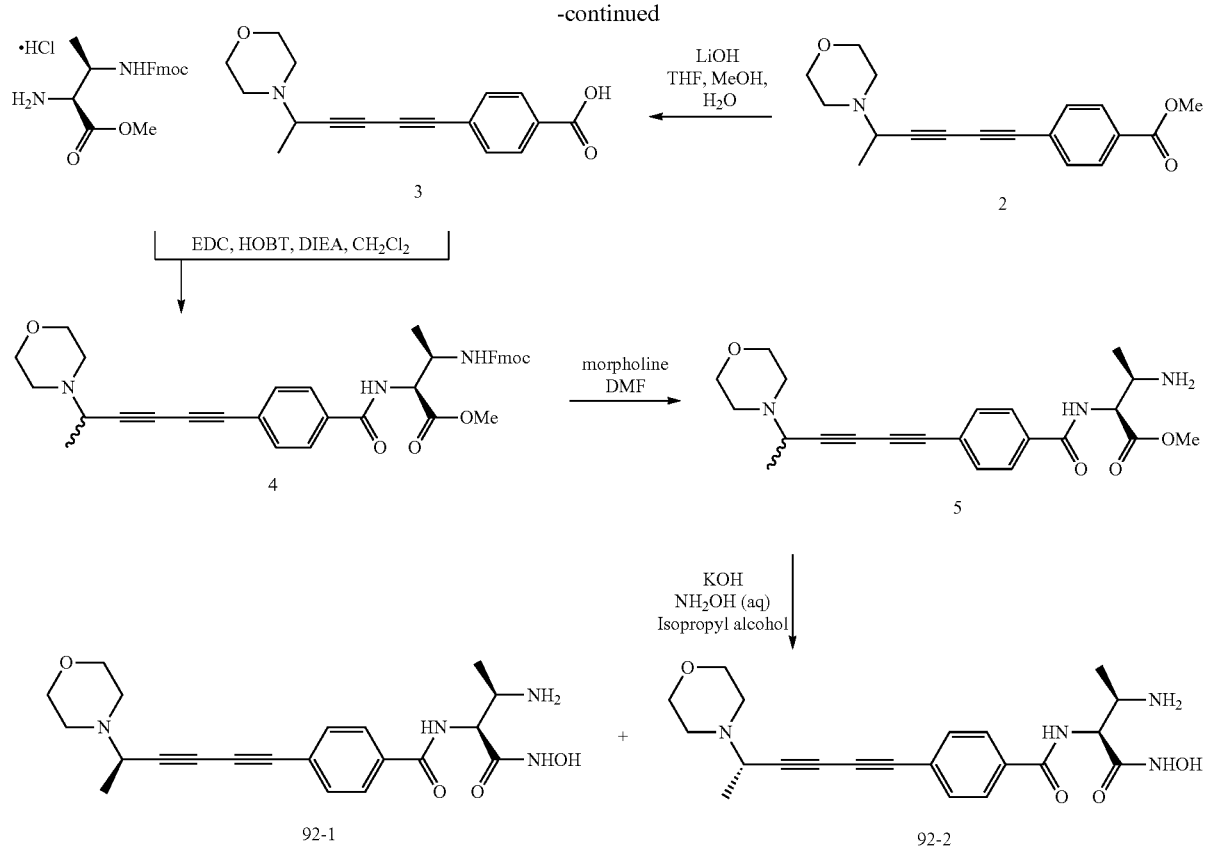

Synthesis of (rac)-methyl 4-(5-hydroxyhexa-1,3-diynyl)benzoate (1)

The methyl 4-(2,2-dibromovinyl)benzoate (3.00 g, 9.38 mmol) was dissolved in DMF (50 mL) and this solution was deoxygenated by bubbling $N_2$ through for 10 min. To this deoxygenated solution was then added $Et_3N$ (1.3 mL, 9.39 mmol) and 2-methyl-3-butyn-2-ol (0.342 g, 4.07 mmol). $N_2$ was then bubbled through for an additional 5 min followed by addition of $PdCl_2(PPh_3)_2$ (0.022 g, 0.031 mmol) and $P(tBu)_3HBF_4$ (0.036 g, 0.125 mmol). The dark brown solution was then allowed to stir at 85° C. for 3 h then cooled to ambient temperature. The solution was diluted with EtOAc (100 mL), washed with deionized water (3×50 mL) and brine (1×50 mL), dried ($MgSO_4$), filtered and concentrated in vacuo. The crude oil was purified by flash chromatography (0-50% EtOAc/Hex) to provide the desired product 1 as a brown solid (1.10 g, 71%). LC-MS $[M+H]^+=229.1$ (Theoretical, $C_{15}H_{13}O_2^+=229.1$).

Synthesis of (rac)-methyl 4-(5-morpholinohexa-1,3-diynyl)benzoate (2)

Compound 1 (0.400 g, 1.75 mmol) was dissolved in anhydrous $CH_2Cl_2$ (20 mL) under $N_2$ and cooled to 0° C. To this chilled solution was added methanesulfonic anhydride (0.336 g, 1.93 mmol) in one portion followed by slow addition of $Et_3N$ (0.37 mL, 2.63 mmol). The solution was allowed to stir at 0° C. for 30 min then morpholine (5 mL) was added and the solution was heated to 50° C. for 30 min. The solution was then removed from heat and allowed to stir at ambient temperature for 18 h. The solution was concentrated in vacuo and the crude oil was purified by flash chromatography (0-50% EtOAc/$CH_2Cl_2$) to provide the desired product 2 (0.468 g, 90%) as a solid. LC-MS $[M+H]^+=298.1$ (Theoretical, $C_{18}H_{20}NO_3^+=298.1$).

Synthesis of (racy-4-(5-morpholinohexa-1,3-diynyl)benzoic acid (3)

To a solution of compound 2 (0.468 g, 1.57 mmol) in a mixture of THF (5 mL), MeOH (5 mL), and water (5 mL) was added LiOH monohydrate (0.198 g, 4.71 mmol) in one portion. The solution was allowed to stir at ambient temperature for 4 h. The volatile organics were then carefully removed and the pH of the resulting aqueous solution was adjusted with $NaHSO_4$ (1.0 N) to ~2. The resulting slurry was vacuum filtered and the solid was washed with deionized water (1×20 mL) to provide the desired product 3 (0.445 g, 99%) as an offwhite solid. LC-MS $[M+H]^+=284.1$ (Theoretical, $C_{17}H_{18}NO_3^+=284.1$).

Synthesis of (2S,3R)-methyl 3-(((9H-fluoren-9-yl)methoxy)carbonylamino)-2-(4-((R)-5-morpholinohexa-1,3-diynyl)benzamido)butanoate and (2S,3R)-methyl 3-(((9H-fluoren-9-yl)methoxy)carbonylamino)-2-(4-((S)-5-morpholinohexa-1,3-diynyl)benzamido) butanoate (4)

Compound 3 (0.445 g, 1.57 mmol), (2S,3R)-methyl 3-(Fmoc)-2-aminobutanoate (0.676 g, 1.73 mmol), EDC (0.602 g, 3.14 mmol) and HOBT (0.424 g, 3.14 mmol) were slurried in anhydrous $CH_2Cl_2$ (15 mL). To this slurry was added N,N-diisopropylethylamine (1.02 mL, 6.28 mmol) in one portion. The solution was then allowed to stir at ambient temperature for 18 h. The solution was then diluted with water (20 mL) and $CH_2Cl_2$ (15 mL), then the layers were separated. The aqueous layer was extracted with $CH_2Cl_2$ (3×10 mL) and the combined organics were dried ($MgSO_4$), filtered and concentrated in vacuo. The crude solid was purified by flash chromatography (0-10% MeOH/$CH_2Cl_2$) to provide the desired mixture of diastereomers 4 (0.785 g, 81%) as an oil. LC-MS $[M+H]^+$=620.3 (Theoretical, $C_{37}H_{38}N_3O_6^+$=620.2).

Synthesis of (2S,3R)-methyl 3-amino-2-(4-((R)-5-morpholinohexa-1,3-diynyl)benzamido)butanoate and (2S,3R)-methyl 3-amino-2-(4-((S)-5-morpholinohexa-1,3-diynyl)benzamido)butanoate (5)

The mixture of diastereomers 4 (0.785 g, 1.27 mmol) was dissolved in DMF (13 mL) and morpholine (2.2 mL, 25.4 mmol) was added in one portion at ambient temperature and allowed to stir for 18 h. The resultant slurry was vacuum filtered and the filtrate was concentrated in vacuo. The crude solid was purified by flash chromatography (0-10% MeOH/$CH_2Cl_2$) to provide the desired mixture of diastereomers 5 (0.307 g, 61%) as a pale yellow oil. LC-MS $[M+H]^+$=398.2 (Theoretical, $C_{22}H_{28}N_3O_4^+$=398.2).

Synthesis of N-((2S,3R)-3-amino-1-(hydroxyamino)-1-oxobutan-2-yl)-4-((R)-5-morpholinohexa-1,3-diynyl)benzamide (92-1) and N-((2S,3R)-3-amino-1-(hydroxyamino)-1-oxobutan-2-yl)-4-((S)-5-morpholinohexa-1,3-diynyl)benzamide (92-2)

The mixture of diastereomers 5 (0.307 g, 0.722 mmol) was dissolved in isopropyl alcohol (8 mL) and the hydroxylamine solution (1.02 mL, 15.4 mmol) was added in one portion at ambient temperature. To this was then added solid potassium hydroxide (0.130 g, 2.31 mmol) in one portion and the solution was allowed to stir for 18 h at ambient temperature. The volatiles were removed in vacuo and the resulting crude material was purified by reverse phase HPLC (5-40% MeCN/$H_2O$, w/0.1% TFA) then lyophilized to dryness to provide both of the desired products 92-1 (0.0xx g, xx %) as a white solid; LC-MS $[M+H]^+$=399.1 (Theoretical, $C_{21}H_{27}N_4O_4^+$=399.2). $^1$H NMR (DMSO) δ 11.31 (s, 1H), 9.42 (br s, 1H), 8.60 (d, J=8.3, 1H), 8.36 (br s, 3H), 7.91 (d, J=8.2, 2H), 7.71 (d, J=8.0, 2H), 4.33 (q, J=6.6, 1H), 3.60-3.70 (m, 6H), 2.55-2.65 (m, 4H), 1.37 (d, J=6.7, 3H), 1.15 (d, J=8.3, 3H) and 92-2 (0.0xx g, xx %) as a white solid; LC-MS $[M+H]^+$=399.0 (Theoretical, $C_{21}H_{27}N_4O_4^+$=399.2). $^1$H NMR (DMSO) δ 11.15 (s, 1H), 8.87 (d, J=8.6, 1H), 8.05 (br s, 3H), 7.96 (d, J=8.3, 2H) 7.72 (d, J=8.0, 2H) 4.39-5.41 (m, 2H), 3.78 (br s, 4H), 3.56-3.59 (m, 1H) 2.97-3.09 (m, 4H), 1.49 (d, J=5.9, 3H), 1.20 (d, 6.4, 3H).

Example 93

N-((2S,3R)-3-amino-1-(hydroxyamino)-1-oxobutan-2-yl)-4-((4-(methylsulfonamido)phenyl)buta-1,3-diynyl)benzamide (93-1)

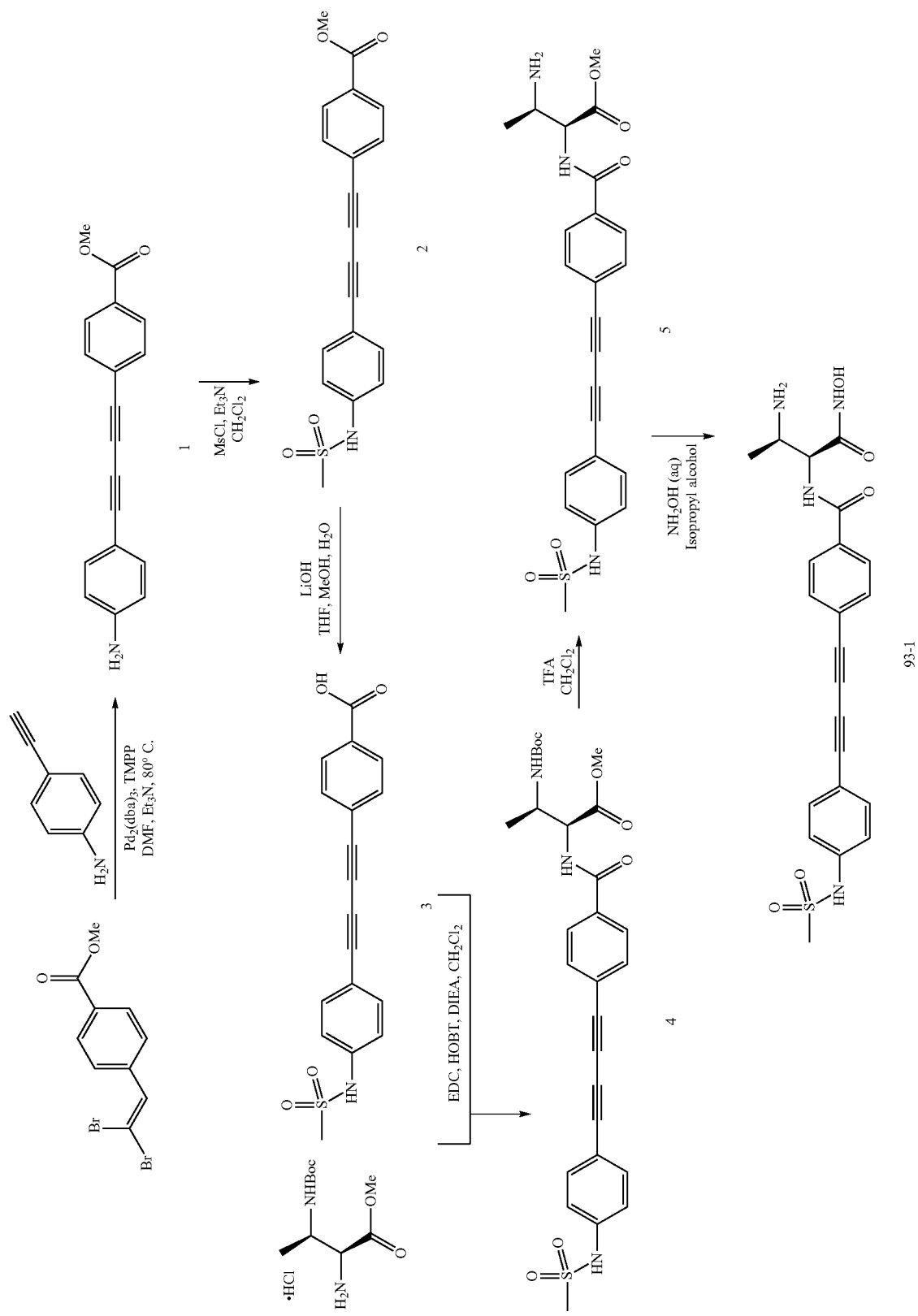

Synthesis of methyl 4-((4-aminophenyl)buta-1,3-diynyl)benzoate (1)

The methyl 4-(2,2-dibromovinyl)benzoate (2.73 g, 8.54 mmol) and 4-ethynylaniline (1.00 g, 8.54 mmol) were dissolved in DMF (40 mL) and this solution was deoxygenated by bubbling $N_2$ through for 10 min. To this deoxygenated solution was then added $Et_3N$ (3.6 mL, 25.6 mmol). $N_2$ was then bubbled through for an additional 5 min followed by addition of $Pd_2(dba)_3$ (0.078 g, 0.085 mmol) and tri(4-methoxyphenyl)phosphine (0.121 g, 0.342 mmol). The dark brown solution was then allowed to stir at 80° C. for 18 h then cooled to ambient temperature. The solution was diluted with EtOAc (100 mL), washed with deionized water (3×50 mL) and brine (1×50 mL), dried ($MgSO_4$), filtered and concentrated in vacuo. The crude oil was purified by flash chromatography (0-50% EtOAc/$CH_2Cl_2$) to provide the desired product 1 as a yellow solid (0.671 g, 29%). LC-MS $[M+H]^+$=276.0 (Theoretical, $C_{18}H_{14}NO_2^+$=276.1).

Synthesis of methyl 4-((4-(methylsulfonamido)phenyl)buta-1,3-diynyl)benzoate (2)

To a solution of compound 2 (0.370 g, 1.34 mmol) in $CH_2Cl_2$ (13 mL) was added methanesulfonyl chloride (0.11 mL, 1.47 mmol) slowly, followed by dropwise addition of $Et_3N$ (0.21 mL, 1.47 mmol). The solution was allowed to stir at ambient temperature for 3 h. The solution was diluted with EtOAc (50 mL) and washed with aqueous HCl (1.0 N, 1×25 mL), aqueous $NaHCO_3$ (sat., 1×25 mL) and brine (1×25 mL). The organics were then dried ($MgSO_4$), filtered and concentrated in vacuo to provide the desired product 2 (0.345 g, 73%) as an orange solid. $^1H$ NMR (DMSO) δ 7.99 (d, J=7.3, 2H), 7.72-7.80 (m, 4H), 7.62 (d, J=7.5, 2H), 3.87 (s, 3H), 2.40 (s, 3H).

Synthesis of 4-((4-(methylsulfonamido)phenyl)buta-1,3-diynyl)benzoic acid (3)

To a solution of compound 2 (0.345 g, 0.976 mmol) in a mixture of THF (3 mL), MeOH (3 mL), and water (3 mL) was added LiOH monohydrate (0.123 g, 2.93 mmol) in one portion. The solution was allowed to stir at ambient temperature for 90 min. The pH of the solution was adjusted with aqueous HCl (1.0 N) to pH~1. The resulting solution was then extracted with EtOAc (3×20 mL), dried ($MgSO_4$), filtered and concentrated in vacuo the desired product 3 (0.176 g, 53%) as a yellow solid. $^1H$ NMR (DMSO) δ 10.24 (s, 1H), 7.96 (d, J=7.9, 2H), 7.71 (d, J=8.0, 2H), 7.60 (d, J=8.4, 2H), 7.23 (d, J=8.5, 2H), 3.09 (s, 3H).

Synthesis of (2S,3R)-methyl 3-(tert-butoxycarbonylamino)-2-(4-((4-(methylsulfonamido) phenyl)buta-1,3-diynyl)benzamido)butanoate (4)

| Reagent | MW | Eq. | g/mL | mmol |
|---|---|---|---|---|
| Compound 3 | 339.37 | 1.0 | 0.176 g | 0.518 |
| (2S,3R)-methyl 3-(Boc)-2-aminobutanoate | 268.74 | 1.1 | 0.153 g | 0.570 |
| EDC | 191.70 | 2.0 | 0.199 g | 1.04 |
| HOBT | 135.12 | 2.0 | 0.141 g | 1.04 |
| N,N-Diisopropylethylamine | 129.24 | 4.0 | 0.34 mL | 2.08 |
| $CH_2Cl_2$ | | | 5 mL | |

Compound 4 (0.285 g, 99%) as a yellow solid was prepared using General EDC coupling. $^1H$ NMR (DMSO) δ 10.23 (s, 1H), 8.44 (d, J=8.2, 1H), 7.92 (d, J=8.4, 2H) 7.74 (d, J=8.4, 2H), 7.60 (d, J=8.6, 2H), 7.23 (d, J=8.6, 2H) 7.00 (d, J=9.7, 1H), 4.62 (dd, J=4.1, 8.5, 1H) 4.22-4.25 (m, 1H) 3.61 (s, 3H), 3.09 (s, 3H), 1.19 (s, 9H), 1.11 (d, J=6.8, 3H).

Synthesis of (2S,3R)-methyl 3-amino-2-(4-((4-(methylsulfonamido)phenyl)buta-1,3-diynyl)benzamido)butanoate (5)

To a solution of compound 4 (0.285 g, 0.515 mmol) in of $CH_2Cl_2$ (10 mL) was added TFA (2 mL) slowly. The solution was allowed to stir at ambient temperature for 1 h then concentrated in vacuo. The thick oil was then azeotroped with $CH_2Cl_2$ (3×) to provide the TFA salt of the desired product 5 (0.284 g, 100%) as an off white solid. LC-MS $[M+H]^+$=454.1 (Theoretical, $C_{23}H_{24}N_3O_5S^+$=454.1).

Synthesis of N-((2S,3R)-3-amino-1-(hydroxyamino)-1-oxobutan-2-yl)-4-((4-(methyl sulfonamido)phenyl)buta-1,3-diynyl)benzamide 93-1

The TFA salt of 5 (0.284 g, 0.515 mmol) was dissolved in isopropyl alcohol (6 mL) and the hydroxylamine solution (0.68 mL, 10.3 mmol) was added in one portion at ambient temperature and the solution was allowed to stir for 18 h at ambient temperature. The volatiles were removed in vacuo and the resulting crude material was purified by reverse phase HPLC (5-40% MeCN/$H_2O$, w/0.1% TFA) then lyophilized to dryness to provide the desired product (93-1) (0.067 g, 29%) as a white solid; LC-MS $[M+H]^+$=455.1 (Theoretical, $C_{22}H_{23}N_4O_5S^+$=455.1).

Example 94

Synthesis of 4-(cyclopropylbuta-1,3-diynyl)-N-(2-(hydroxyamino)-1-(1-hydroxycyclopropyl)-2-oxoethyl)benzamide 94-1

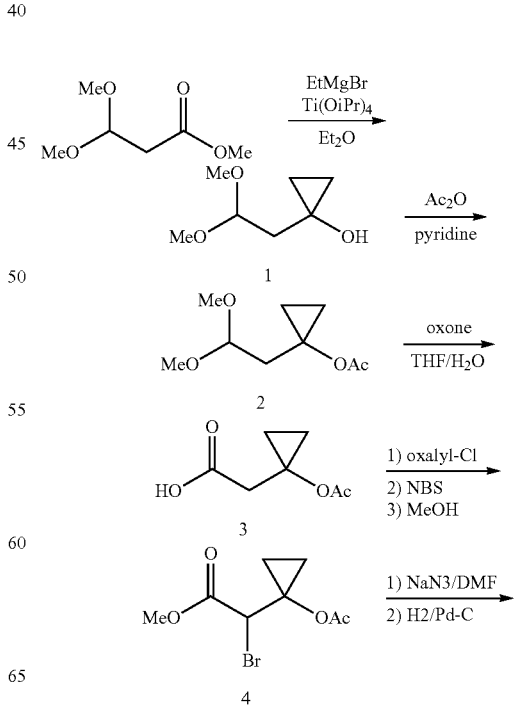

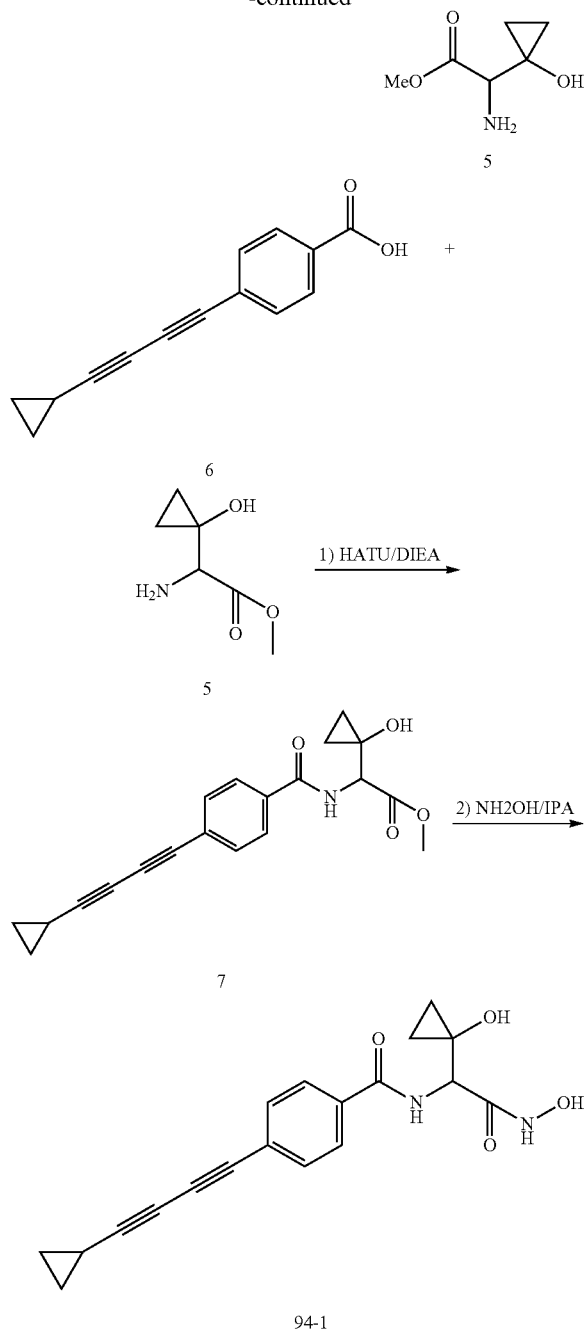

Synthesis of 1-(2,2-dimethoxyethyl)cyclopropanol (1)

A solution of methyl 3,3-dimethoxypropanoate (28.2 g, 190 mmol) in a three-neck flask equipped with a overhead stirrer was cooled to 0° C. under N$_2$. The Ti(OiPr)$_4$ (11.3 mL, 38.1 mmol) was then slowly added and the solution was allowed to stir for 10 min at 0° C. To this cooled solution with vigorous stirring was then added the EtMgBr solution (158 mL, 475 mmol) via syringe pump at ~3 mL/min. After the addition was complete, the solution was allowed to slowly warm to ambient temperature and stirred for an additional 18 h. The solution was then cooled to 0° C. and deionized water (45 mL) was slowly added with vigorous stirring. After stirring for 20 min at 0° C. the mixture vacuum filtered through a pad of anhydrous MgSO$_4$. The clear, colorless solution was the concentrated in vacuo and purified by flash chromatography (0-50% EtOAc/Hex) to provide the desired product (1) as a clear, colorless oil (8.60 g, 31%). $^1$H NMR (DMSO) δ 5.04 (s, 1H), 4.62 (t, J=5.3, 1H), 3.22 (s, 6H), 1.69 (d, J=5.3, 2H) 0.50 (dd, J=4.9, 6.9, 2H), 0.37 (dd, J=4.2, 6.2, 2H).

Synthesis of 1-(2,2-dimethoxyethyl)cyclopropyl acetate (2)

To a solution of compound 1 (8.60 g, 58.8 mmol) in CH$_2$Cl$_2$ was added DMAP (0.718 g, 5.88 mmol) and pyridine (7.13 mL, 88.2 mmol) sequentially. The solution was then cooled to 0° C. and acetic anhydride was added dropwise. After the addition was complete, the solution was stirred at 0° C. for 10 min then allowed to warm to ambient temperature and stirred for 18 h. The solution was then washed with aqueous NaHSO$_4$ (1.0 N, 2×100 mL), aqueous NaHCO$_3$ (sat., 2×100 mL), dried (MgSO$_4$), filtered and concentrated in vacuo. Isolated the desired product, (2) as a clear, colorless oil (11.1 g, 99%). $^1$H NMR (DMSO) δ 4.50 (t, J=5.5, 1H), 3.21 (2, 6H), 1.95 (d, J 5.3, 2H), 1.92 (s, 3H), 0.73-0.78 (m, 2H), 0.66-0.71 (m, 2H).

Synthesis of 2-(1-acetoxycyclopropyl)acetic acid (3)

Compound 2 (11.1 g, 58.8 mmol) was dissolved in THF (50 mL) and water (100 mL) and cooled to 0° C. To this cooled solution was added Oxone® in portions. After complete addition the slurry was allowed to stir at 0° C. for 10 min the warmed to ambient temperature. After 8 h at ambient temperature the slurry was diluted with deionized H2O (100 mL) and extracted with EtOAc (3×150 mL). The combined organics were dried (MgSO$_4$), filtered and concentrated in vacuo. The product (3) was isolated as a thick, colorless oil (9.1 g, 98%). $^1$H NMR (DMSO) δ 2.66 (s, 2H), 1.92 (s, 3H), 0.77-0.85 (m, 4H).

Synthesis of methyl 2-(1-acetoxycyclopropyl)-2-bromoacetate (4)

Compound 3 (3.35 g, 21.2 mmol) was dissolved in anhydrous DCE (60 ml) under N$_2$ and cooled to 0° C. Thionyl chloride (3.5 g, 30 mmol) was then added slowly and the solution was refluxed for 30 min. At ambient temperature, were added NBS (4.78 g, 26 mmol) and 4 drops of concentrated HBr and the solution was heated under reflux for 4 h. MeOH (50 ml) was added at room temperature and the solution was stirred at rt for 3 h. The solvent were removed under reduced pressure, water (100 ml) was added and product was extracted with ethyl acetate, dried (Na2SO4), and concentrated to give 3.8 g of 4.

Synthesis of methyl 2-amino-2-(1-hydroxycyclopropyl)acetate (5)

The bromide product 4 was redessolved in dry DMF (20 ml), NaN$_3$ (2.05 g, 30 mmol) was added and heated at 85° C. for 4 h. The reaction mixture was diluted with ethyl acetate (100 ml) and water 5 ml was added. The organic layer was separated, dried and concentrated. The product (2.6 g) was the hydrogenated Pd—C (1.2 g) (40 psi) for 2 h.

The catalyst was filtered off and ethanol solution were concentrated to give 5 (2.42 g)

Synthesis of methyl 2-(4-(cyclopropylbuta-1,3-diynyl)benzamido)-2-(1-hydroxycyclopropyl)acetate (7)

| Reagent | MW | Eq. | g/ml | mmol |
|---|---|---|---|---|
| 4-(cyclopropylbuta-1,3-diynyl)benzoic acid | 201 | 1 | 210 mg | 1 |
| methyl 2-amino-2-(1-hydroxycyclopropyl)acetate | 145 | 2 | 300 mg | 2.06 |
| HATU | 380.23 | 1.0 | 395 mg | 1.05 |
| DIEA | 129.24 | 4 | 1.2 mL | excess |
| CH3CN | | | 10 ml | |

Compound (7) (172 mg) was prepared using the General Method for HATU coupling and used on next step without purification. LC-Ms (M+1) 338.

Synthesis of 4-(cyclopropylbuta-1,3-diynyl)-N-(2-(hydroxyamino)-1-(1-hydroxycyclopropyl)-2-oxo-ethyl)benzamide (94-1)

Aq. Hydroxylamine (2 ml, 50% aq.) was added to a stirred solution of ester 7, (0.17 g, 0.51 mmol) in isopropanol (15 ml), stirred for 18 h. Excess solvent was removed and the product was purified on a reverse phase HPLC to give compound (94-1) (42 mg) LC-MS (M+1) 339: Chemical Formula: C19H18N2O4, MW: 338.36.

Example 95

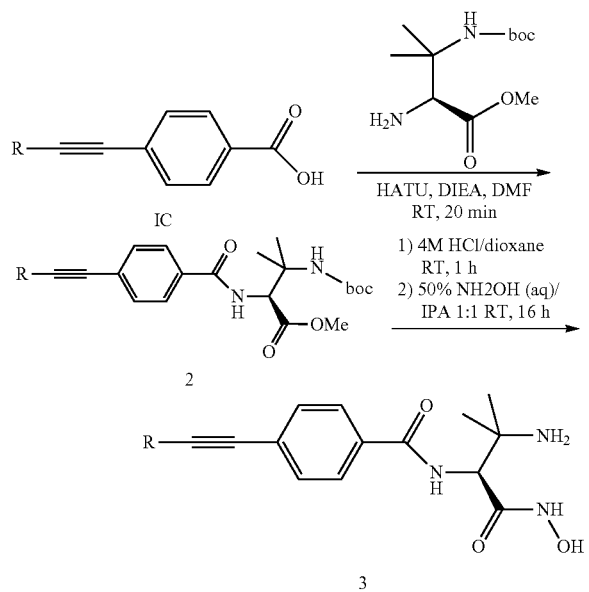

Example 95 was prepared by using the General Method for HATU coupling, General Method for Boc deprotection and General Method for hydroxamate formation

Synthesis of Intermediate Acid IC-3

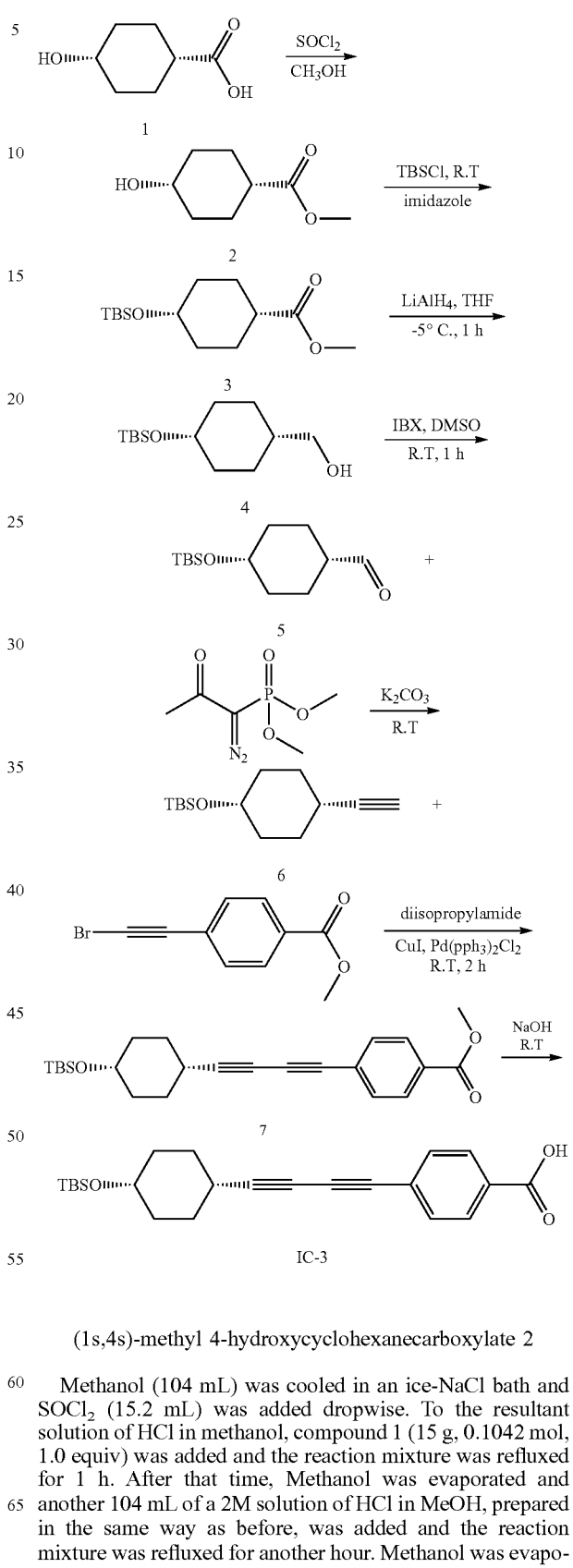

(1s,4s)-methyl 4-hydroxycyclohexanecarboxylate 2

Methanol (104 mL) was cooled in an ice-NaCl bath and SOCl$_2$ (15.2 mL) was added dropwise. To the resultant solution of HCl in methanol, compound 1 (15 g, 0.1042 mol, 1.0 equiv) was added and the reaction mixture was refluxed for 1 h. After that time, Methanol was evaporated and another 104 mL of a 2M solution of HCl in MeOH, prepared in the same way as before, was added and the reaction mixture was refluxed for another hour. Methanol was evaporated again to give compound 2 (16.3 g, 99%) as a light yellow liquid. $^1$H NMR (400 MHz, DMSO-d$_6$): 1.47-1.83 (m, 9H), 2.36-2.51 (m, 1H), 3.63 (s, 3H), 4.26 (s, 1H)

(1s,4s)-Methyl 4-(tert-butyldimethylsilyloxy)cyclohexanecarboxylate (3)

To a solution of compound 2 (16.3 g, 0.1032 mol, 1.0 equiv) and imidazole (14.03 g, 0.206 mol, 2.0 equiv) in dried DMF (100 mL) was added TBSCl (17.1 g, 0.114 mol, 1.1 equiv) in eight portions at 0° C., then the reaction mixture was warmed to 30° C. and reacted at this temperature for 2 h. DMF was evaporated, DCM (150 mL) was added, washed with water (80 mL×2) and brine (100 mL), dried over anhydrous sodium sulfate, evaporated the DCM and purified by silica-gel column (EA:PE, 1:50) to give compound 3 (17 g, 61%) as a colorless liquid. $^1$H NMR (400 MHz, CDCl$_3$): δ 0.032 (s, 6H), 0.88 (s, 9H), 1.45-1.51 (m, 2H), 1.61-1.68 (m, 4H), 1.90-1.98 (m, 2H), 2.29-2.34 (m, 1H), 3.67 (s, 3H), 3.89 (s, 1H)

(1s, 4s)-4-(tert-butyldimethylsilyloxy)cyclohexyl) methanol (4)

To a stirred suspension of LiAlH$_4$ (1.9 g, 0.05 mol) in dried THF (50 mL), under N$_2$, cooled to 0° C., a solution of compound 3 (17 g, 0.0625 mol) in dried THF (20 mL) was added dropwise. The reaction mixture was stirred for 1.5 h at 0° C., then quenched by the addition of Na$_2$SO$_4$.10H$_2$O (5 g), filtered and evaporated the solvent, purified by silica-gel column (EA: PE, 1:20) to give compound 4 (10.5 g, 69%) as a thick oil. $^1$H NMR (400 MHz, DMSO-d$_6$): δ 0.02 (s, 6H), 0.86 (s, 9H), 1.14-1.41 (m, 7H), 1.51-1.55 (m, 2H), 3.17 (t, J=10.8 Hz, 2H), 3.94 (s, 1H), 4.36 (t, J=10.8 Hz, 1H)

(1s, 4s)-4-(tert-butyldimethylsilyloxy)cyclohexanecarbaldehyde (5)

IBX (14.45 g, 0.052 mol) was dissolved in DMSO (50 mL) completely, then compound 4 (10.5 g. 0.043 mol) was added in one portion and reacted at 30° C. for 3 h. Water (60 mL) was added to quench the reaction, filtered, EA (100 mL) was added, washed with water (80 mL×2), brine (100 mL), dried over anhydrous sodium sulfate, evaporated EA and the residue was purified by silica-gel column (EA:PE, 1:50) to give compound 5 (6.29 g, 50%) as a colorless liquid. $^1$H NMR (400 MHz, DMSO-d$_6$): 0.021 (s, 6H), 0.84 (s, 9H), 1.43-1.48 (m, 2H), 1.51-1.60 (M, 4H), 1.67-1.76 (m, 2H), 2.27-2.33 (m, 1H), 3.86 (s, 1H), 9.56 (s, 1H)

Tert-butyl ((1s,4s)-4-ethynylcyclohexyloxy)dimethylsilane (6)

To a solution of compound 5 (6.29 g, 0.026 mol) and K$_2$CO$_3$ (7.18 g, 0.052 mol) in methanol (50 mL) was added dimethyl-1-diazo-2-oxopropylphosphonate (5.99 g, 0.031 mol) and stirred overnight. The reaction mixture was diluted with Et$_2$O (50 mL), washed with an aqueous solution (5%) of NaHCO$_3$ (30 mL) and dried over anhydrous sodium sulfate, after filtration and evaporation of the solvent in cacuo to give compound 6 (3.09 g, 50%) as a light yellow liquid. $^1$H NMR (400 MHz, DMSO-d$_6$): 0.025 (s, 6H), 0.85 (s, 9H), 1.16-1.36 (m, 3H), 1.51 (d, J=4.8 Hz, 2H), 1.74-1.87 (m, 3H), 2.26-2.30 (m, 1H), 2.83-2.86 (m, 1H), 3.6-3.74 (m, 1H)

Methyl 4-(((1s,4s)-4-(tert-butyldimethylsilyloxy) cyclohexyl)buta-1,3-diynyl)benzoate (7)

| Reagent | MW | Eq. | mmol | g, mL |
|---|---|---|---|---|
| Compound 6 | 238.44 | 1.3 | 13 | 3.09 g |
| Methyl 4-(bromoethynyl)benzoate | 239.07 | 1.0 | 10 | 2.58 g |
| Pd(PPh$_3$)$_2$Cl$_2$ | 701.9 | 0.05 | 0.5 | 0.38 g |
| CuI | 190.45 | 0.05 | 0.5 | 0.1 g |
| Diisopropylamine | 101.19 | 3 | 30 | 4.54 mL |
| THF | | | | 50 mL |

Compound 7 (2.9 g, 58%) as a light yellow solid was prepared using the same method for making IC-2. $^1$H NMR (400 MHz, DMSO-d$_6$): 0.032 (s, 6H), 0.85 (s, 9H), 1.23-1.95 (m, 8H), 2.57-2.73 (m, 1H), 3.59-3.77 (m, 1H), 3.86 (s, 3H), 7.67 (d, J=8 Hz, 2H), 7.95 (d, J=8.4 Hz, 2H).

4-(((1s,4s)-4-(tert-butyldimethylsilyloxy)cyclohexyl) buta-1,3-diynyl)benzoic acid (8)

| Reagent | MW | Eq. | mmol | g, mL |
|---|---|---|---|---|
| Compound 7 | 396.59 | 1.0 | 7.32 | 2.9 g |
| NaOH (2N solution) | | | | 7 mL |
| THF | | | | 7 mL |
| Methanol | | | | 7 mL |

Compound 8 (2.0 g, 71%) as a white solid made and separated using the General Method for basic hydrolysis. $^1$H NMR (400 MHz, DMSO-d$_6$): 0.036 (s, 6H), 0.85 (s, 9H), 1.28-1.95 (m, 8H), 2.57-2.77 (m, 1H), 3.65-3.78 (m, 1H), 7.64 (d, J=8 Hz, 2H), 7.93 (d, J=8.4 Hz, 2H), 13.23 (s, 1H)

Synthesis of Intermediate Acid IC-4

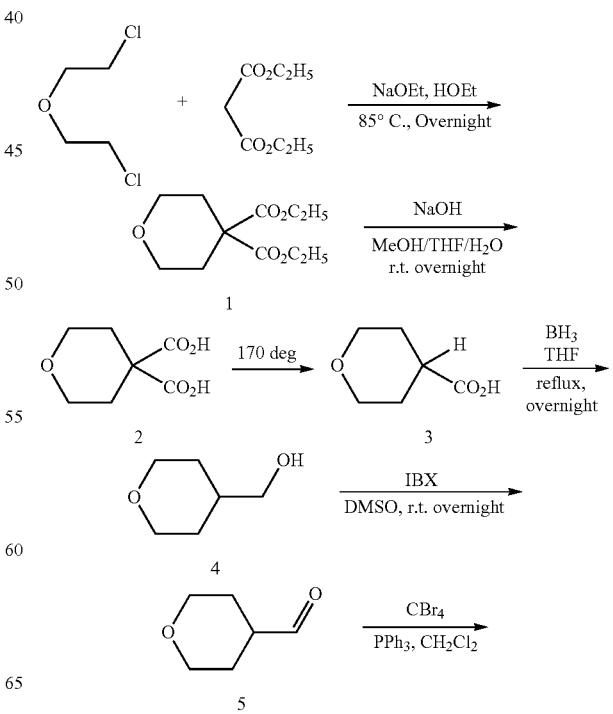

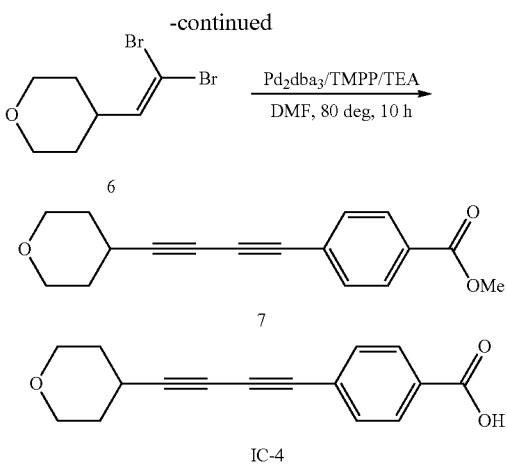

Diethyl tetrahydropyran-4,4-dicarboxylate (1)

Under ice bath, a three-necked flask was added 600 mL EtOH, then 23 g (1 mmol) Na was added. After Na was almost dissolved, diethyl malonate 160 ml (1 mol) and 1-chloro-2-(2-chloroethoxy)ethane (118 ml, 1.2 mol) were added dropwise sequentially to the solution at R.T. and stirred for another half hour. Then the mixture was heated to reflux for 1 h and cooled to r.t., then the other part of NaOEt (25 g Na dissolved in 600 mL EtOH) solution (1.2 mol) was poured into the mixture and refluxed overnight. The next day, the solvent was evaporated. The residue was dissolved in water and extracted the product with EtOAc three times. The organic layer was washed with brine, dried on $Na_2SO_4$ and evaporated to give the crude product, which gave the pure product (120 g, Y=52%) by distillation. $^1$H NMR (400 MHz, $CDCl_3$): δ ppm 4.2 (q, 4H), 3.68 (m, 4H), 2.12 (m, 4H), 1.26 (t, 6H).

Tetrahydropyran-4,4-dicarboxylic acid (2)

To a solution of compound 1 (40.0 g, 1.0 equiv) in $CH_3OH/THF/H_2O$=5/5/1 (600 mL) was added NaOH (27.8 g, 4.0 equiv) and the mixture reacted at 25° C. overnight. Then, the reaction solvents was removed and neutralized with 1 N HCl to PH=3-5. The product was extracted with EtOAc and concentrated under reduced pressure to give the desired product 2 (27.3 g 91%). $^1$H NMR (400 MHz, DMSO-$d_6$): δ ppm 12.84 (S, 2H), 3.53 (M, 4H), 1.89 (m, 4H).

Tetrahydro-2H-pyran-4-carboxylic acid (3)

2 (27.3 g) was placed in a bottle and gradually heated to 170° C. over a period of 1 h until gas was ceased. The left solid was the desired product 3 (20.4 g, Y=100%). $^1$H NMR (400 MHz, DMSO-$d_6$): δ ppm 12.19 (s, 1H), 3.80 (m, 2H), 3.28 (m, 2H), 2.47 (m, 1H), 1.69 (m, 2H), 1.53 (m, 2H).

(Tetrahydro-2H-pyran-4-yl)methanol (4)

3 (6.5 g, 50 mmol. 1 eq.) was dissolved in dry THF (150 mL) and added $BF_3.Et_2O$ (7.0 mL, 50 mmol, 1.0 eq.) dropwise. The mixture was heated to reflux. While at this temperature 1M/L $BH_3.THF$ (55 mL, 55 mmol, 1.1 eq.) was added dropwise. When the addition finished, the mixture was left refluxing overnight. The next day 3M/L NaOH solution □970 mL. 4.0 eq.) was added while the mixture was cooled to r.t. and reheated to reflux for 1.5 h. Later, solvents were removed and the product was extracted with EtOAc three times. The organic layer was washed with brine dried and evaporated to give the crude product which purified by column chromatography (PE/EA=6:1-2:1) to obtain the pure desired product 14 (4.8 g, Y=83%). $^1$H NMR (400 MHz, DMSO-$d_6$): δ ppm 4.31 (m, 1H), 3.71 (m, 2H), 3.09 (m, 4H), 1.40 (m, 3H), 0.98 (m, 2H).

Tetrahydro-2H-pyran-4-carbaldehyde (5)

IBX (5.8 g, 1.2 eq.) were dissolved in 30 mL DMSO at 40° C. and 4 (2.0 g, 1.0 eq.) was added to the mixture and left stirring overnight. The next day, filtrated the solid, the filtrate was diluted with 80 mL water, and extracted the product with ether four times. The ether layer was washed with brine dried and evaporated the solvents under ice bath to give the crude product 1.3 g (the product was broken up under the air). $^1$H NMR (400 MHz, DMSO-$d_6$): δ ppm 9.62 (s, 1H), 3.81 (m, 2H), 3.34 (m, 2H), 2.56 (m, 1H), 1.75 (m, 2H), 1.50 (m, 2H).

4-(2,2-Dibromovinyl)-tetrahydro-2H-pyran (6)

To a 0° C. solution of compound 18-5 (1.3 g, 11.4 mmol, 1.0 eq.) and carbon tetrabromide (4.2 g, 12.5 mol, 1.1 eq.) in dry $CH_2Cl_2$ (30 ml) was added triphenylphosphine (6.27 g, 24.0 mmol, 2.1 equiv.) in 4 portions at 3 min intervals. The reaction was then stirred for 1 h at 25° C. Hexane was added to the reaction mixture with good stirring, and the resulting slurry was filtered through silica gel and evaporated to give the crude product, which purified by column chromatography (PE/EA=0-10%) to obtain the pure product 6 (2.0 g, 65%). $^1$H NMR (400 MHz, DMSO-$d_6$): δ ppm 6.20 (d, J=8.8 Hz), 3.87 (m, 2H), 3.37 (m, 2H), 2.47 (m, 1H), 1.57 (m, 2H), 1.42 (m, 2H).

Methyl 4-((tetrahydro-2H-pyran-4-yl)buta-1,3-diynyl)benzoate (7)

A solution of 6 (2.0 g 7.4 mmol, 1 equiv), methyl 4-ethynylbenzoate (1.80 g 11.1 mmol, 1.5 equiv), $Pd_2$ $dba_3$ (68 mg, 0.08 mmol, 0.01 equiv), TMPP (106 mg, 0.32 mmol, 0.04 equiv) and TEA (3 mL, 22.2 mmol, 3 equiv) in anhydrous DMF (30 ml) was flushed with $N_2$ and heated at 80° C. for 10 hours. Then, most DMF was evaporated under reduced pressure, the residue was dissolved in EtOAc (500 ml) and washed with semi-saturated NaCl solution (300 ml×4), dried on $Na_2SO_4$ and evaporated to give a crude product, which was purified by chromatography (EA/PE=1/20-1/5) to give the desired product 7 (360 mg, 30%). MS: [M+1]$^+$269

4-((Tetrahydro-2H-pyran-4-yl)buta-1,3-diynyl)benzoic acid (IC-4)

| Reagent | MW | Eq. | mmol | g, mL |
| --- | --- | --- | --- | --- |
| Compound 7 | 268 | 1.0 | 1.3 | 360 mg |
| NaOH | 40 | 4.0 | 5.4 | 300 m |
| $CH_3OH/THF/H_2O$ = 5/5/1 | | | | 50 mL |

Compound IC-4 (310 mg, 98%) was made and separated using the General Method for basic hydrolysis. MS: [M+1]$^+$ 255. $^1$H NMR (400 MHz, DMSO-$d_6$): δ ppm 13.21 (s, 1H), 7.94 (d, J=8.4 Hz, 2H), 7.66 (d, J=8.4 Hz, 2H), 3.77 (m, 2H), 3.44 (m, 2H0, 2.93 (m, 1H), 1.83 (m, 2H), 1.62 (m, 2H).

Synthesis of Intermediate Acid IC-5

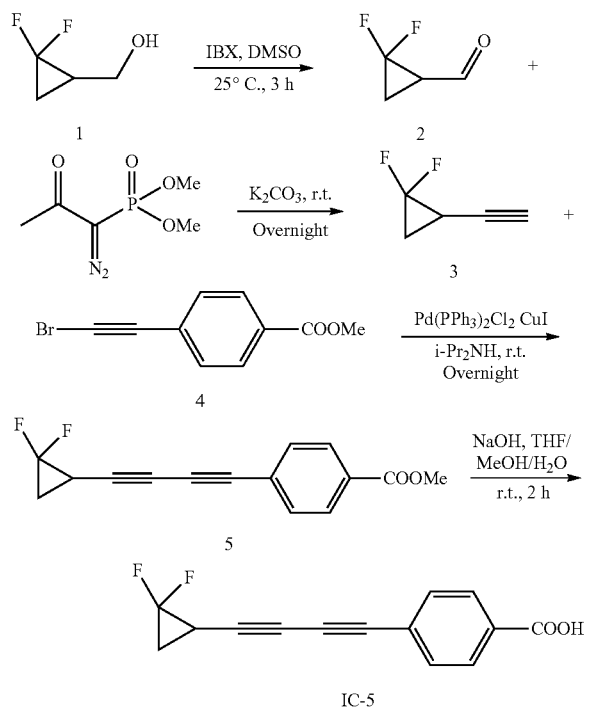

Methyl 4-(2,2-difluorocyclopropyl buta-1,3-diynyl)benzoate (5)

IBX (2.8 g, 10 mmol) was added to DMSO (20 mL) in one portion. After IBX was totally dissolved, compound 1 was added in one portion and the mixture was stirred for 3 h at 25° C. Then, 80 mL water was added and the white precipitate was filtered off without suction. The filtrate was extracted with toluene (3×15 mL). Then the organic layer was washed with water (5×10 mL), dried overnight with anhydrous $MgSO_4$. $MgSO_4$ was filtered off and the solid was washed twice with toluene. A 3-neck flask charged with $K_2CO_3$ (2.61 g, 18 mmol) was flushed with nitrogen 3 times. Then, MeOH (30 mL), the toluene solution from the former step and dimethyl-1-diazo-2-oxopropyl phosphonate (1.728 g, 9 mmol) were added sequentially. The reaction mixture was stirred at r.t. overnight and washed with distilled water (3×10 mL). Then, the organic layer was dried over anhydrous $MgSO_4$ for 4 hours. Filtration without suction gave the toluene solution of compound 3 for the next step. Another 3-neck flask with methyl 4-ethynyl benzoate (480 mg, 3 mmol), $Pd(PPh_3)_2Cl_2$ (105 mg, 0.15 mmol), CuI (57 mg, 0.3 mmol) was charged with $N_2$. The dried toluene solution with compound 3 in it was put into the flask by a syringe. Diisopropylamine (909 mg, 9 mmol) was added dropwise. The reaction mixture was stirred overnight and filtered. The solid was washed with EtOAc (3×20 mL). The filtrate was concentrated in vacuo and purified by flash chromatography (PE:EA=50:1) to give compound 5 (262 mg, yield 11% from 3 steps) as a yellow solid. $^1H$ NMR (500 MHz, $CDCl_3$): δ ppm, 7.98 (d, J=8.0 Hz, 2H), 7.54 (d, J=8.0 Hz, 2H), 3.92 (s, 3H), 2.25-2.32 (m, 1H), 1.79-1.83 (m, 1H), 1.63-1.68 (m, 1H).

4-(2,2-Difluorocyclopropyl buta-1,3-diynyl)benzoic acid (IC-5)

To a solution of compound 5 (260 mg, 1 mmol) in THF (5 mL), MeOH (5 mL) and a solution of NaOH (160 mg, 4 mmol) in water (2 mL) was added at 0° C. Then, the mixture was stirred at r.t. for 2 h as monitored by TLC. The solvent was evaporated and 20 mL water was added. Then, the mixture PH value was adjusted to 2-3 and extracted with EtOAc (3×15 mL). The organic layer was dried over $MgSO_4$, filtered and concentrated to give compound IC-5 (200 mg, 81%) as a light pink solid. $^1H$ NMR (500 MHz, DMSO-$d_6$): δ ppm, 7.94 (d, J=6.5 Hz, 2H), 7.69 (d, J=6.5 Hz, 2H), 2.90-2.94 (m, 1H), 2.15-2.19 (m, 1H), 1.90-1.97 (m, 1H).

Synthesis of Intermediate Acid IC-6

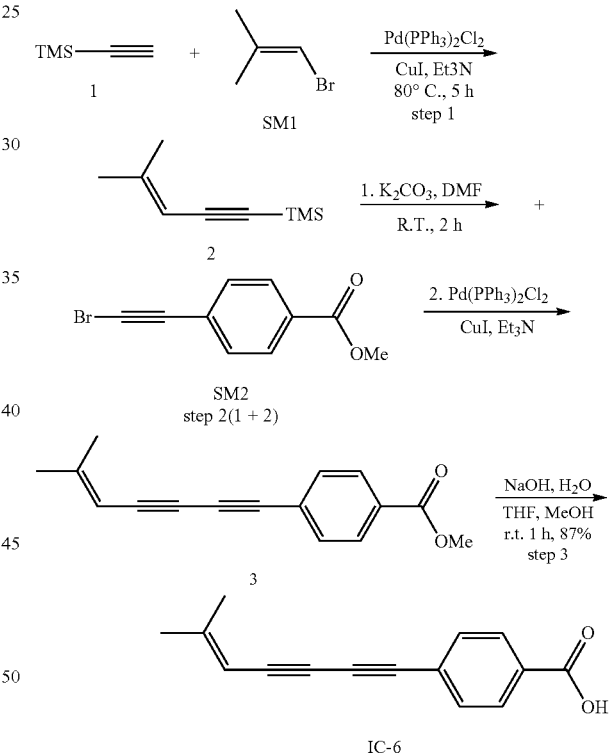

Step 1: Trimethyl(4-methylpent-3-en-1-ynyl)silane 2

Under nitrogen, ethynyltrimethylsilane 1 (3.5 g, 0.036 mol, 1.2 equiv) was added to a solution of compound SM1 (4 g, 0.03 mol, 1.0 equiv), $PdCl_2(PPh_3)_2$ (1.05 g, 1.5 mmol, 0.05 equiv) and CuI (0.6 g, 0.003 mmol, 0.1 equiv) in TEA (50 mL) at 90° C. The mixture was allowed to react overnight. Then, the precipitate was isolated. The filter cake was washed with $Et_2O$ (100 mL). The filtrate was concentrated under reduced pressure. The residue was dissolved in $Et_2O$ (100 mL) and washed 1 M HCl aq. (200 mL), water (200 mL×2) and brine (200 mL). The organic layer was separated, dried (Na₂SO₄) and the filtered. The filtrate was concentrated under reduced pressure to give the crude product of title compound 2 as liquid (3 g, 65% yield). The purity was about 70% from LCMS.

Step 2: Methyl 4-(6-methylhepta-5-en-1,3-diynyl)benzoate 3

To a solution of compound 2 (2 g, 0.02 mol, 1.0 equiv) in DMF (50 mL) was treated with K₂CO₃ (16 g, 0.12 mol, 4 equiv) at r.t. Then, the mixture was stirred at room temperature for 1 h. Then, the reactant methyl 4-(bromoethynyl) benzoate SM2 (5 g, 0.02 mol, 1.0 equiv), PdCl₂(PPh₃)₂ (0.7 g, 0.001 mol, 0.05 equiv) and CuI (0.38 g, 0.002 mmol, 0.1 equiv) and diisopropylamine HN(i-Pr)₂ (4 g, 0.04 mol, 2.0 equiv) was added in to the reaction mixture quickly under N₂ protection. The mixture was stirred for overnight. Then, the reaction mixture was added EtOAc (200 mL) and washed with dilute HCl aqueous (150×2), H₂O (200×2). The organic layer was washed, dried (Na₂SO₄), filtered and concentrated under reduced pressure. The residue was purified by chromatography on silica gel to give the desired product 3 (0.4 g, 10%). LCMS (m/z): [M+H]⁺=239.0. ¹H NMR (300 MHz, CDCl₃): δ 7.97-7.99 (m, 2H), 7.57-7.49 (m, 2H), 5.40 (s, 1H), 3.92 (s, 3H), 1.98 (s, 3H), 1.87 (s, 3H).

Step 3: 4-(6-Methylhepta-5-en-1,3-diynyl)benzoic acid 4

To a solution of compound 3 (0.25 g, 1.7 mmol, 1.0 equiv) in methanol (5 mL) was treated with KOH/H₂O (0.3 g/3 mL) at r.t. The reaction mixture was neutralized with acetic acid and EtOAc (100 mL). The organic layer was washed with 5% aq. Na₂CO₃ (50 mL×2), dried over Na₂SO₄, filtered and concentrated under reduced pressure. The residue was dried in vacuo overnight to provide the title compound IC-6 (0.2 g, 87%). LCMS (m/z): [M+H]⁺=225.0. ¹H NMR (300 MHz, DMSO): δ 7.93-7.95 (d, 2H), 7.66-7.68 (d, 2H), 5.58 (m, 1H), 1.93 (s, 3H), 1.87 (s, 3H).

Synthesis of Intermediate Acid IC-7

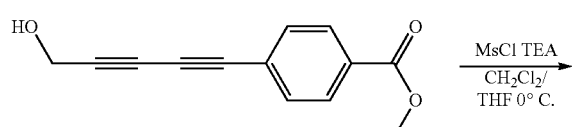

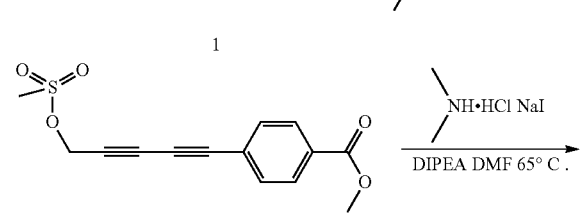

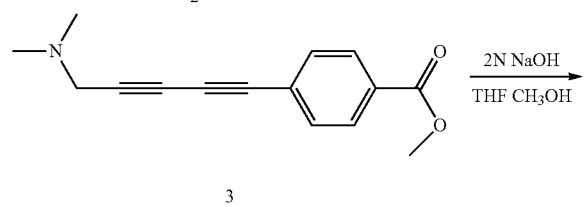

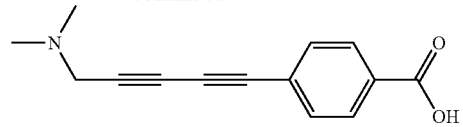

IC-7

Methyl 4-(5-(methylsulfonyloxy)penta-1,3-diynyl)benzoate (2)

To a stirred solution of compound 1 (0.7 g, 3.27 mmol), TEA (0.55 mL, 3.92 mmol) in dichloromethane (30 mL) and THF (10 mL) was added methanesulfonyl chloride (0.56 g, 0.38 mL, 4.9 mmol) dropwise under ice cooling. After addition cooling-bath was removed and stirred continued for 2 hours. The mixture was diluted with dichloromethane (100 mL) and washed successively with water (30 mL), saturated NH₄Cl (20 mL), brine (50 mL), dried (Na₂SO₄) and filtered. The residue was evaporated to give the crude product as a dark brown solid. MS (m/z): [M+H]⁺=293

Methyl 4-(5-(dimethylamino)penta-1,3-diynyl)benzoate (3)

To a solution of compound 2 (0.533 g, 3.27 mmol) in DMF (20 mL), was added dimethylamine hydrochloride (3.2 g, 39 mmol), followed by DIPEA (5.9 g, 7.9 mL, 45.8 mmol). After being stirred at 65° C. for 2 hours, cooled down to room temperature, diluted with saturated NaHCO₃ aqueous and extracted with dichloromethane (3×100 mL). The combined organic layers was washed (water, brine), dried (Na₂SO₄), filtered and evaporated to dry. The crude product was purified by silica gel column chromatography (PE/EA=20:1) to give the desired product (0.2 g, 25%). MS (m/z): [M+H]⁺=242. ¹H-NMR (400 MHz, DMSO-d₆): 2.22 (s, 6H), 3.50 (s, 2H), 3.59 (s, 3H), 7.72 (d, J=8.4 Hz, 2H), 7.96 (d, J=8.8 Hz, 2H).

4-(5-(Dimethylamino)penta-1,3-diynyl)benzoic acid (IC-7)

To a solution of compound 3 (0.2 g, 0.83 mmol) in a mixture solution of THF (20 mL) and CH₃OH (10 mL) was added 2N NaOH (5 mL) dropwise at ambient temperature. The mixture was allowed to react at room temperature for 3 hours, distilled the solvent, extracted with ether. The aqueous layer was adjusted the PH at 7 with 2 N HCl aqueous and filtered to give compound 4 (129 mg, 68%) as a yellow solid. MS (m/z): [M+H]⁺=228. ¹H-NMR (400 MHz, DMSO-d₆): 2.23 (s, 6H), 3.51 (s, 2H), 3.59 (s, 3H), 7.69 (d, J=8 Hz, 2H), 7.94 (d, J=7.6 Hz, 2H).

Synthesis of Intermediate Acid IC-8

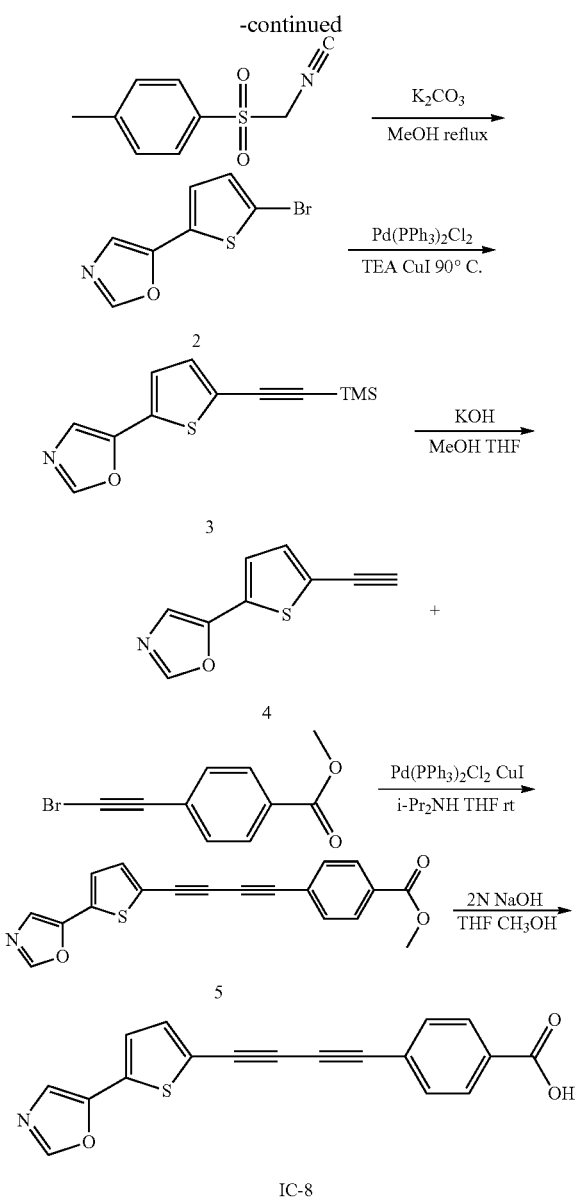

5-(5-Bromothiophen-2-yl)oxazole (2)

To a degassed solution of tosylmethyl isocyanide (0.56 g, 2.88 mmol), $K_2CO_3$ (0.4 g, 2.88 mmol) in dried $CH_3OH$ (15 mL) was added compound 1 (0.5 g, 2.9 mL, 2.6 mmol). The reaction mixture refluxed under nitrogen for 2 hours. Volatiles were removed in vacuo and the residue was purified by silica gel column (PE:EA=50:1) to give compound 2 (0.45 g, 75%) as a light yellow solid. $^1$H-NMR (400 MHz, $CDCl_3$): 7.04 (d, J=4 Hz, 1H), 7.07 (d, J=4 Hz, 1H), 7.19 (s, 1H), 7.86 (s, 1H).

5-(5-((Trimethylsilyl)ethynyl)thiophen-2-yl)oxazole (3)

Under nitrogen ethynyltrimethylsilane (85 mg, 0.13 mL, 0.87 mmol) was added to a solution of compound 2 (0.1 g, 0.43 mmol), $Pd(PPh_3)_2Cl_2$ (10 mg, 0.014 mmol), CuI (8 mg, 0.04 mmol) in TEA (5 mL) at 60° C. The solution was heated to 90° C. for 2 hours. The reaction was treated with EA (100 mL), washed with water (100 mL), brine (100 mL), dried ($Na_2SO_4$), evaporated in vacuo. The residue product was purified by silica gel column (PE: EA=50:1) to give desired product (73 mg, 68%) as a light yellow solid.

5-(5-Ethynylthiophen-2-yl)oxazole (4)

To a solution of compound 3 (4.3 g, 17.4 mmol) in a mixture solution of methanol (40 mL) and THF (50 mL) was treated with $KOH/CH_3OH$ (0.49 g/10 mL) dropwise below 10° C. The reaction mixture was allowed to react at ambient temperature for 0.5 h. The reaction solution was neutralized with acetic acid to PH=7 and concentrated under reduced pressure. The residue was purified by silica gel column (PE: EA=50:1) to give desired product (2.0 g, 67%) as a yellow solid. $^1$H-NMR (400 MHz, $CDCl_3$): 3.44 (s, 1H), 7.23 (d, J=2, 1H), 7.26 (d, J=1.6, 1H), 7.18 (s, 1H), 7.87 (s, 1H),

Methyl 4-((5-(oxazol-5-yl)thiophen-2-yl)buta-1,3-diynyl)benzoate (5)

To a degassed solution of compound 4 (1.9 g, 10.8 mmol), methyl 4-(bromoethynyl)benzoate (2.7 g, 11.4 mmol), $Pd(PPh_3)_2Cl_2$ (0.38 g, 0.54 mmol), CuI (0.10 g, 0.54 mmol) in THF (90 mL) was added i-$Pr_2NH$ (3.29 g, 4.6 mL, 32.5 mmol) at room temperature. The mixture was allowed to react at this temperature for 3 h. The mixture was treated with EA (300 mL), washed with water (200 mL), saturated $NH_4Cl$ (100 mL), brine (300 mL), dried ($Na_2SO_4$), concentrated in vacuo. The residue was purified by silica gel column (PE/EA=1:1) to give desired product (1.45 g, 40%) as a yellow solid.

4-((5-(Oxazol-5-yl)thiophen-2-yl)buta-1,3-diynyl) benzoic acid (IC-8)

To a solution of compound 5 (1.43 g, 4.3 mmol) in a mixture solution of THF (300 mL) and $CH_3OH$ (50 mL) was added 2 N NaOH (10 mL) at ambient temperature. The reaction solution was allowed to react for 3 hours. Then evaporated the organic solvent, adjusted the PH at 6 with 2 N HCl. Filtration gave crude product, which was triturated in THF. The precipitate was collected by filtration to give desired product (0.262 g, 20%) as a yellow solid. $^1$H-NMR (400 MHz, DMSO-$d_6$): 7.52 (d, J=4, 1H), 7.66 (d, J=3.6, 1H), 7.72-7.74 (m, 3H), 7.98 (d, J=8, 2H), 8.51 (s, 1H).

Synthesis of Intermediate Acid IC-9

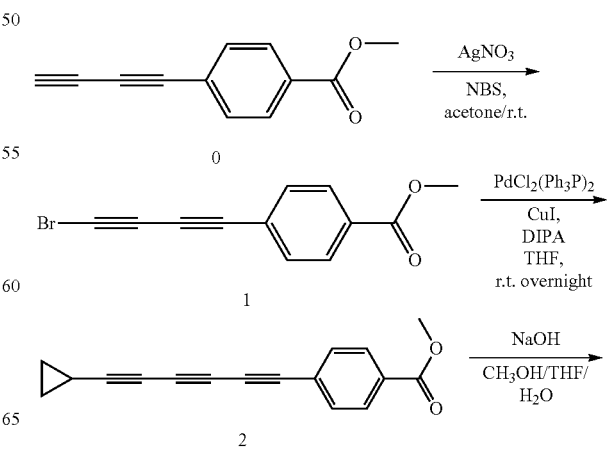

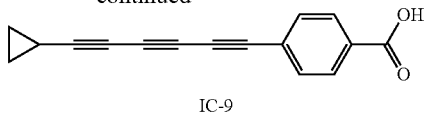

IC-9

Methyl 4-(bromobuta-1,3-diynyl)benzoate (1)

0 (368 mg, 2 mmol, 1.0 eq.) and AgNO$_3$ (40 mg, 0.1 eq.) were dissolved in 50 mL acetone and stirring for 2 h at r.t. Then, NBS (4 mmol, 2.0 eq.) was added to the mixture and stirred for 2 h. TLC monitored the reaction. When the reaction was complete, filtered the solid and the filtrate was evaporated and dissolved in EtOAc. The organic layer was washed with sat. NaHCO$_3$, H$_2$O and brine, dried, filtered and evaporated to give the desired product 1 without purification (526 mg, Y=100%). $^1$H NMR (400 MHz, CDCl$_3$): δ ppm 8.00 (d, J=8.4 Hz, 2H), 7.56 (d, J=8.4 Hz, 2H), 3.92 (s, 3H).

Methyl 4-(cyclopropylhexa-1,3,5-triynyl)benzoate (2)

Under nitrogen, diisopropylethylamine (DIPEA) (1 mL, 3.0 equiv) and ethynylcyclopropane (4 mmol, 2.0 equiv.) were added to a solution of compound 1 (526 mg, 2 mmol 1.0 equiv), PdCl$_2$(PPh$_3$)$_2$ (0.181 g, 0.05 mmol, 0.025 equiv) and CuI (0.191 g, 0.1 mmol, 0.1 equiv) in dry THF (50 mL) in ice bath. The mixture was allowed to react at r.t. overnight. Then, the solvents were evaporated and the residue was purified by column chromatography to get the pure desired product 2 (380 mg, 76.6%). MS: [M+1]$^+$=249

4-(Cyclopropylhexa-1,3,5-triynyl)benzoic acid (IC-9)

To a solution of compound 2 (380 mg, 1.0 equiv) in CH$_3$OH/THF/H$_2$O=5/5/1 (50 mL) was added NaOH (300 mg, 4.0 equiv). Then, the mixture was stirred at 25° C. overnight. Then, the solvent was removed and neutralized with 1 N HCl to PH=3-5. The product was extracted with EtOAc and concentrated under reduced pressure to give the desired product IC-9 (310 mg, 86.6%). LC-MS: [M−H]$^+$=233. $^1$H NMR (400 MHz, DMSO-d$_6$): δ ppm 13.32 (s, 1H), 7.95 (d, J=8.4 Hz, 2H), 7.73 (d, J=8.4 Hz, 2H), 1.61 (m, 1H), 0.95 (m, 2H), 0.85 (m, 2H).

Synthesis of Intermediate Acid IC-10

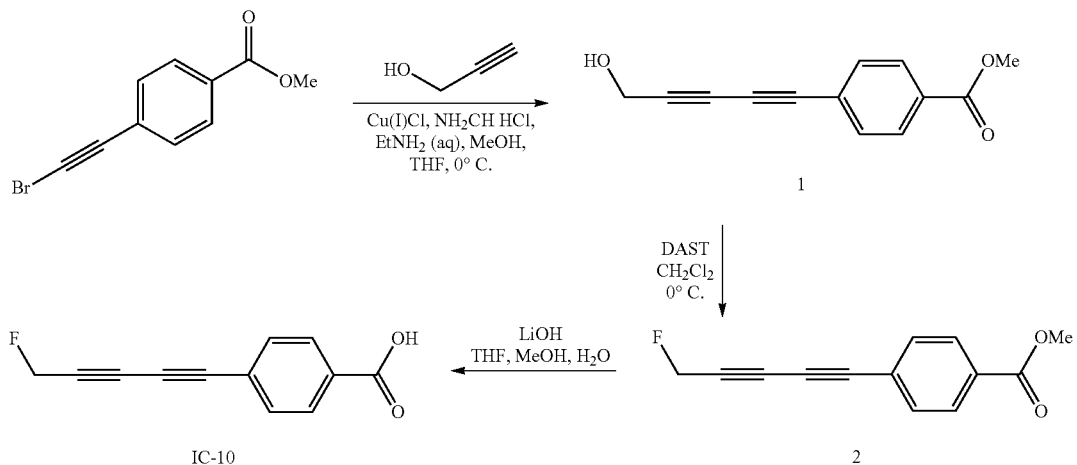

The target product was prepared by following the General procedure for Method 1-C (Cadiot-Chodkiewicz Coupling), Method 6 (DAST Fluorination) and Method 2-A (Basic hydrolysis)

The following compounds were synthesized as described above.

| Compound # | Structure | MH$^+$ (m/z) theo | Ret. Time (min) | HPLC-MS Method |
|---|---|---|---|---|
| 95-1 | 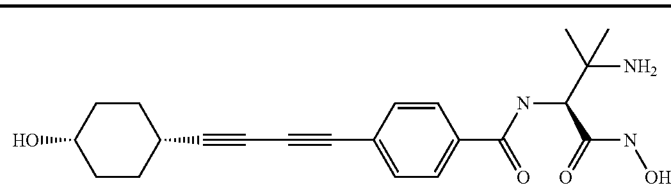 | 397 | | |

-continued

| Compound # | Structure | MH+ (m/z) theo | Ret. Time (min) | HPLC-MS Method |
|---|---|---|---|---|
| 95-2 | 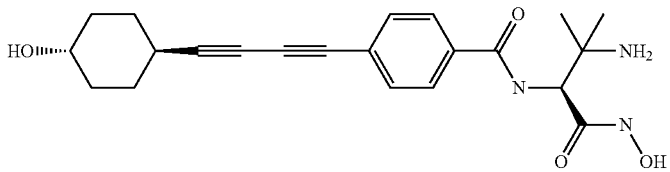 [SMILES: CC(C)(N)[C@H](NC(=O)c1ccc(C#CC#C[C@H]2CC[C@H](O)CC2)cc1)C(=O)NO] | 397 | | |
| 95-3 | 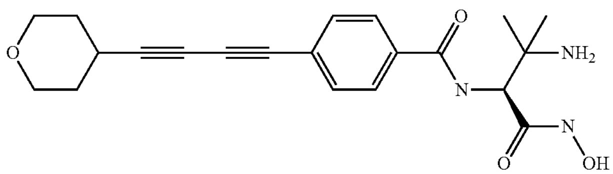 [SMILES: CC(C)(N)[C@H](NC(=O)c1ccc(C#CC#CC2CCOCC2)cc1)C(=O)NO] | 383 | | |
| 95-4 | 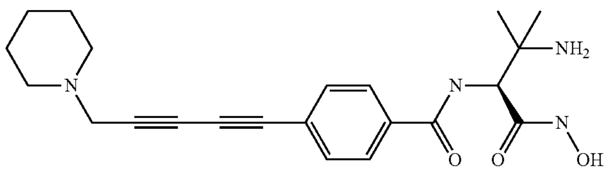 [SMILES: CC(C)(N)[C@H](NC(=O)c1ccc(C#CC#CCN2CCCCC2)cc1)C(=O)NO] | 396 | | |
| 95-5 | 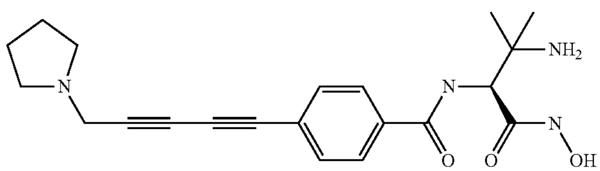 [SMILES: CC(C)(N)[C@H](NC(=O)c1ccc(C#CC#CCN2CCCC2)cc1)C(=O)NO] | 382 | | |
| 95-6 | 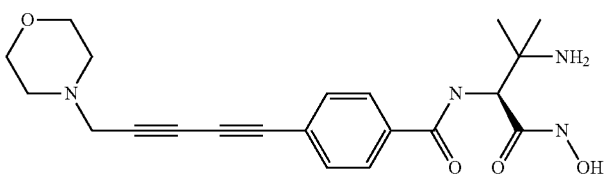 [SMILES: CC(C)(N)[C@H](NC(=O)c1ccc(C#CC#CCN2CCOCC2)cc1)C(=O)NO] | 398 | | |
| 95-7 | 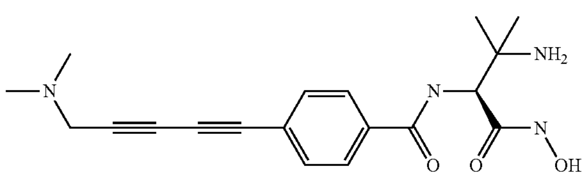 | 356 | | |
| 95-8 | 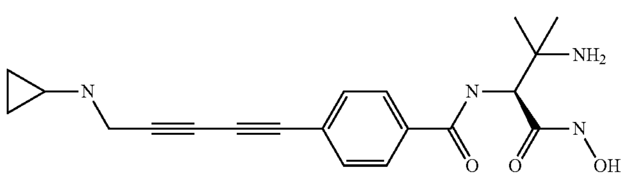 [SMILES: CC(C)(N)[C@H](NC(=O)c1ccc(C#CC#CCNC2CC2)cc1)C(=O)NO] | 368 | | |
| 95-9 | 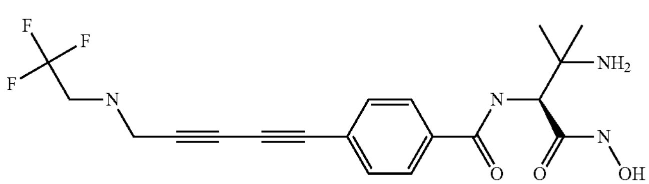 [SMILES: CC(C)(N)[C@H](NC(=O)c1ccc(C#CC#CCNCC(F)(F)F)cc1)C(=O)NO] | 410 | | |

-continued

| Compound # | Structure | MH+ (m/z) theo | Ret. Time (min) | HPLC-MS Method |
|---|---|---|---|---|
| 95-10 | 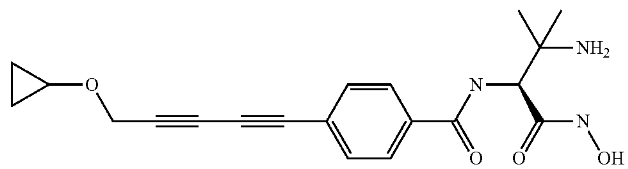 [SMILES: CC(C)(N)[C@H](NC(=O)c1ccc(C#CC#CCOC2CC2)cc1)C(=O)NO] | 369 | | |
| 95-11 | 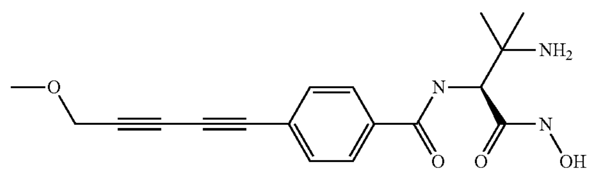 | 343 | | |
| 95-12 | 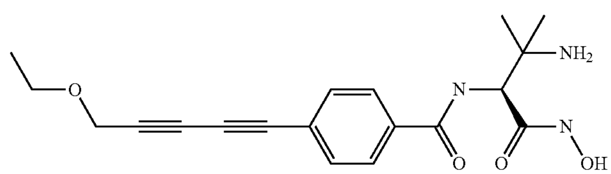 [SMILES: CCOCC#CC#Cc1ccc(C(=O)N[C@H](C(=O)NO)C(C)(C)N)cc1] | 357 | | |
| 95-13 | 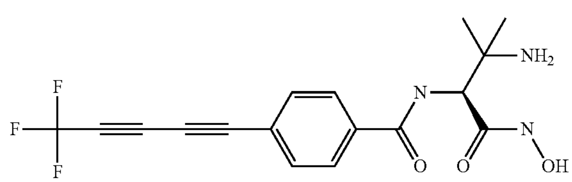 [SMILES: CC(C)(N)[C@H](NC(=O)c1ccc(C#CC#CC(F)(F)F)cc1)C(=O)NO] | 367 | | |
| 95-14 | 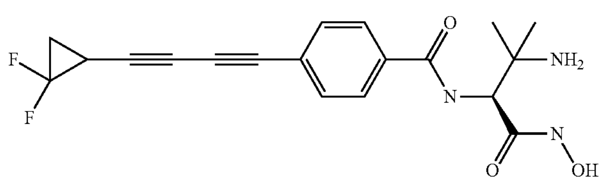 [SMILES: CC(C)(N)[C@H](NC(=O)c1ccc(C#CC#CC2CC2(F)F)cc1)C(=O)NO] | 375 | | |
| 95-15 | 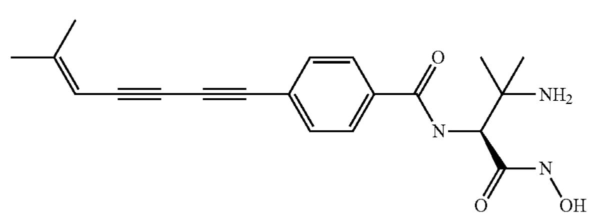 [SMILES: CC(C)=CC#CC#Cc1ccc(C(=O)N[C@H](C(=O)NO)C(C)(C)N)cc1] | 353 | | |
| 95-16 | 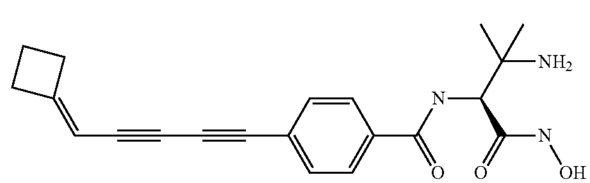 [SMILES: CC(C)(N)[C@H](NC(=O)c1ccc(C#CC#CC=C2CCC2)cc1)C(=O)NO] | 365 | | |
| 95-17 | 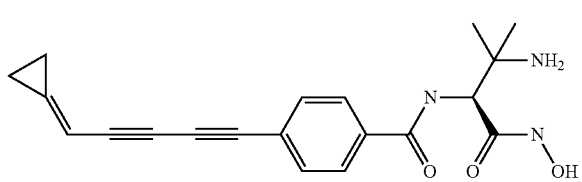 [SMILES: CC(C)(N)[C@H](NC(=O)c1ccc(C#CC#CC=C2CC2)cc1)C(=O)NO] | 351 | | |

| Compound # | Structure | MH+ (m/z) theo | Ret. Time (min) | HPLC-MS Method |
|---|---|---|---|---|
| 95-18 | 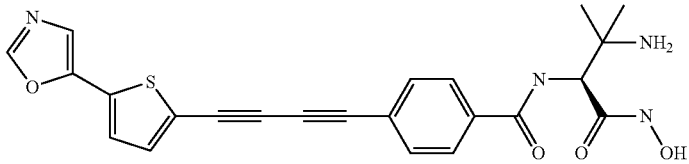 [SMILES: CC(C)(N)[C@H](NC(=O)c1ccc(C#CC#Cc2ccc(-c3cnco3)s2)cc1)C(=O)NO] | 448 | | |
| 95-19 | 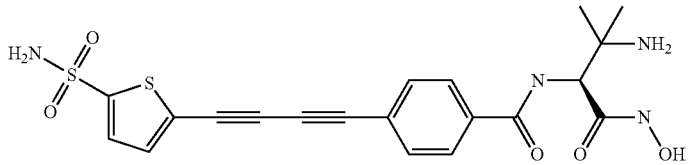 | 460 | | |
| 95-20 | 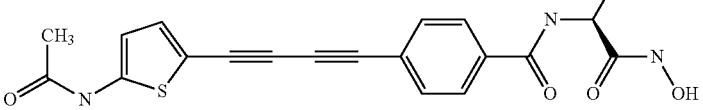 | 438 | | |
| 95-21 | 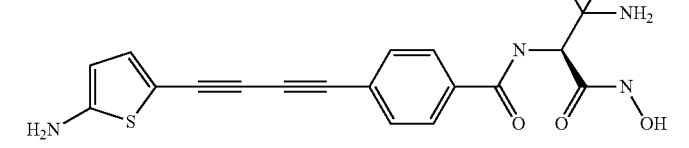 | 396 | | |
| 95-22 | 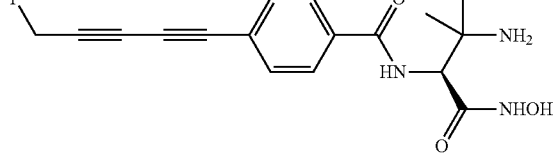 | 332 | | |
| 95-23 | 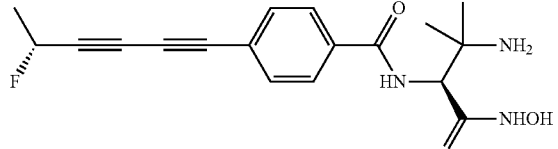 | 346 | | |
| 95-24 | 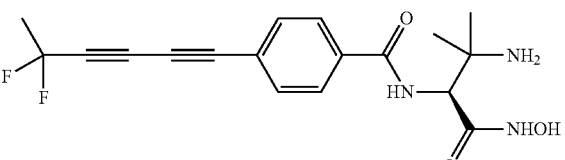 | 364 | | |
| 95-25 | 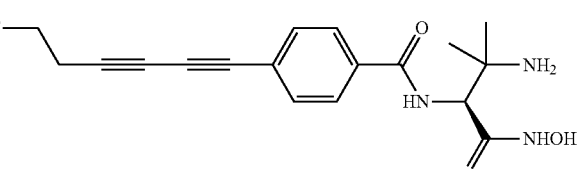 | 346 | | |

Example 96

Synthesis of (E)-4-[4-(4-morpholin-4-ylmethylphenyl)-but-3-en-1-ynyl]benzoic acid (1)

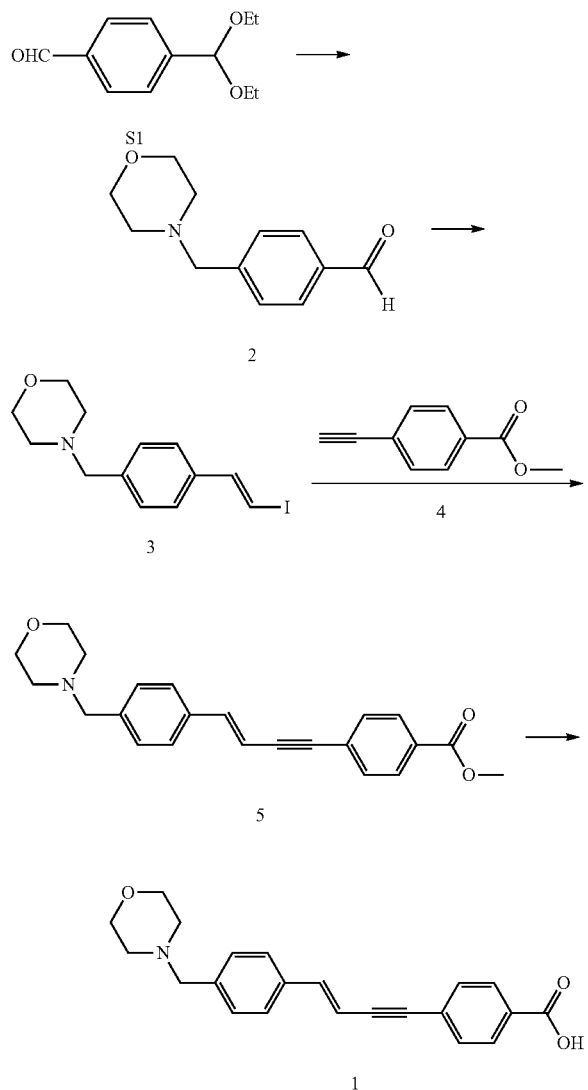

4-Morpholin-4-ylmethylbenzaldehyde (2)

To a solution containing morpholine (5.25 mL, 60 mmol) in dichloromethane (50 mL) was added HCl (5 mL, 20 mmol, 4 M in dioxane) dropwise following by 4-diethoxymethylbenzaldehyde (1, 2.08 g, 10 mmol), NaBH$_3$CN (0.44 g, 7 mmol) and Aliquat 336 (2.93 g, 7 mmol). Then 1 g of 4A molecular sieves was added. The mixture was stirred at room temperature overnight, filtered, and the solvent removed in vacuo. Then 200 mL water was added to the residue and the pH was adjusted to 4 by 0.5 M citric acid. The mixture was stirred for 1 hour and then extracted with ether (2×100 mL). The pH of the aqueous layer was adjusted to 9 by 1.0 M sodium hydroxide. It was extracted with ether (3×100 mL). The combined organic layers were washed with water (150 mL), brine (50 mL) dried (MgSO$_4$), filtered and concentrated under reduced pressure to give the title compound 2 (1.0 g, 48%). MS (m/z): [M+H]$^+$=206. $^1$H NMR (300 MHz, CDCl$_3$): in ppm, 2.48 (br s, 4H), 3.59 (s, 2H), 3.70-3.78 (m, 4H), 7.54 (d, J=8.0 Hz, 2H), 7.85 (d, J=8.3 Hz, 2H), 10.0 (s, 1H).

(E)-4-[4-(2-Iodovinyl)benzyl]morpholine (3)

Chromium chloride anhydrous (19.1 g, 155 mmol, 8 eq) was added to THF (400 mL) under nitrogen. A solution of triiodomethane (30.7 g, 78 mmol, 4 eq) in THF (500 mL) was added dropwise at 0° C. under nitrogen. Then a solution of 2 (4.0 g, 19.5 mmol, 1 eq) in THF (100 mL) was added dropwise. The mixture was stirred at 0° C. for 2 h and then at room temperature for 2 h. The mixture was poured into iced water and extracted with EtOAc (2×800 mL). The combined organic phase was washed with 20% aq. Na$_2$S$_2$O$_3$ (300 mL), brine (300 mL), dried (MgSO$_4$), filtered and concentrated under reduced pressure. The residue was purified by chromatography on silica gel (0 to 5% EtOAc/Hexanes) to give the title compound 3 (3.55 g, 55%). MS (m/z): [M+H]$^+$=330. $^1$H NMR (300 MHz, CDCl$_3$): in ppm, 2.44 (t, J=4.6 Hz, 4H), 3.47 (s, 2H), 3.70 (t, J=4.6 Hz, 4H), 6.80 (d, J=15 Hz, 1H), 7.22-7.27 (m, 4H), 7.41 (d, J=15 Hz, 1H).

(E)-4-[4-(4-morpholin-4-yl-methyl-phenyl)-but-3-en-1-ynyl]-benzoic acid methyl ester (5)

To a mixture of 3 (290 mg, 0.88 mmol, 1.0 eq), 4 (141 mg, 0.88 mmol, 1.0 eq.), diisopropylamine (0.125 mL, 0.88 mmol) and PdCl$_2$(PPh$_3$)$_2$ (32 mg, 0.044 mmol, 0.05 eq) in Et$_3$N (15 mL) was added CuI (18 mg, 0.09 mmol, 0.1 eq) under nitrogen at room temperature. The mixture was stirred at room temperature for 12 h, diluted with EtOAc (40 mL), filtered and concentrated. The residue was dissolved into EtOAc (50 mL) and washed with water (50 mL) and brine (50 mL), and dried (MgSO$_4$). After filtration and concentration, the residue was purified by chromatography on silica gel (0 to 30% EtOAc/Hexanes) to give the title compound 5 (209 mg, 66%). MS (m/z): [M+H]$^+$=362. $^1$H NMR (300 MHz, CDCl$_3$): in ppm, 2.44 (t, J=4.6 Hz, 4H), 3.48 (s, 2H), 3.70 (t, J=4.6 Hz, 4H), 3.90 (s, 3H), 6.36 (d, J=16.2 Hz, 1H), 7.06 (d, J=16.2 Hz, 1H), 7.30 (d, J=8.4 Hz, 2H), 7.37 (d, J=8.4 Hz, 2H), 7.50 (d, J=8.9 Hz, 2H), 7.99 (d, J=8.9 Hz, 2H).

(E)-4-[4-(4-Morpholin-4-ylmethylphenyl)-but-3-en-1-ynyl]benzoic acid (1)

To a solution of 5 (4.3 g, 11.9 mmol, 1.0 eq) in THF/MeOH/H$_2$O (80 mL, 1/1/1) was added LiOH.H$_2$O (1.0 g, 23.8 mmol, 2.0 eq). The mixture was stirred at room temperature for 24 h. The pH was adjusted to 7 by 1 M HCl. The mixture was stirred for 1 h. The solid was filtered and washed with water (40 mL) and ether (40 mL) and dried in vacuo. To a suspension of above solid in ether (40 mL) was added HCl (24 mL, 48 mmol, 2 M in ether). The mixture was stirred at room temperature for 1 h. The solid was filtered and washed with ether (40 mL), and dried in vacuo at 45° C. overnight to give the target product 1-HCl (3.0 g, 71%). MS (m/z): [M+H]F=348. $^1$H NMR (300 MHz, CDCl$_3$): in ppm, 2.95-3.20 (m, 4H), 3.75-4.00 (m, 4H), 4.29 (s, 2H), 6.78 (d, J=16.2 Hz, 1H), 7.22 (d, J=16.2 Hz, 1H), 7.61 (d, J=8.4 Hz, 2H), 7.67 (br, s, 4H), 7.96 (d, J=8.4 Hz, 2H), 11.7 (br s, 1H).

N-((1S,2R)-2-Hydroxy-1-hydroxycarbamoyl-propyl)-4-[(E)-4-(4-morpholin-4-ylmethyl-phenyl)-but-3-en-1-ynyl]-benzamide (96-1)

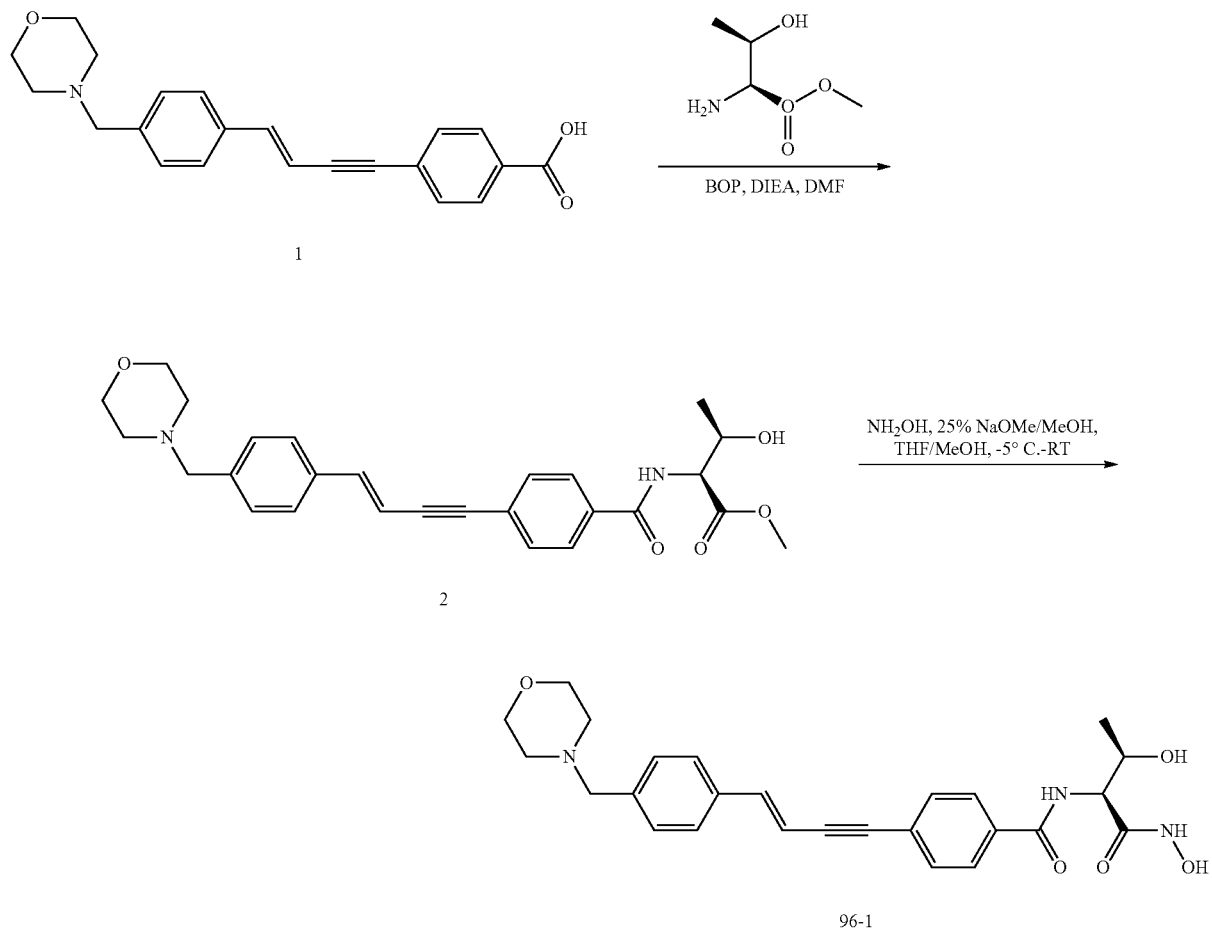

Synthesis of (2S,3R)-3-hydroxy-2-{4-[(E)-4-(4-morpholin-4-ylmethyl-phenyl)-but-3-en-1-ynyl]-benzoylamino}-butyric acid methyl ester (2)

To the mixture of compound 1 (70 mg, 0.20 mmol) and H—(S)-Thr-OMe hydrochloride (41 mg, 0.24 mmol) in DMF (1.5 mL) was added BOP (115 mg, 0.26 mmol) followed by DIEA (104 µl, 0.6 mmol). Reaction mixture was stirred at ambient temperature for 20 min, diluted with EtOAc (50 mL), extracted with water (30 mL×2) and brine (30 mL). Organic layer was dried over anh. $Na_2SO_4$, evaporated in vacuo and dried in vacuo overnight to provide target product 2 (92 mg, 100%) as white solid. LC-MS [M+H] 463.3 (C27H30N2O5+H, requires 463.55). Compound was used in next synthetic step without additional purification.

Synthesis of N-((1S,2R)-2-hydroxy-1-hydroxycarbamoyl-propyl)-4-[(E)-4-(4-morpholin-4-ylmethyl-phenyl)-but-3-en-1-ynyl]-benzamide (96-1)

To a stirred suspension of compound 2 (92 mg, 0.2 mmol) and hydroxylamine hydrochloride (84 mg, 1.2 mmol) in MeOH (anh, 2 mL) and THF (anh, 2 mL) was added NaOtBu (154 mg, 1.6 mmom) powder in one portion at −5° C. under nitrogen. Reaction mixture was stirred at −5° C. for additional 5 min. Temperature of reaction mixture was raised to ambient. Completion of the reaction was monitored by LC-MS. After completion (in 20 min) reaction mixture was acidified with 1 N HCl in MeOH to pH~6 at low temperature and evaporated in vacuo. Residue was dissolved in DMSO (600 µl) and subjected to HPLC purification. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide trifluoroacetate salt of target product (15-1) (20.5 mg) as white solid. LC-MS [M+H] 464.3 (C26H29N3O5+H, requires 464.54).

| Compound | Scale (mmol)* | Yield (mg) | Yield (%)* | Purity (%) | [M + H] | Retention time (min)** |
|---|---|---|---|---|---|---|
| 96-1 | 0.2 | 20.5 | 17.8 | 97.7 | 464.3 | 4.06 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 96-2 | 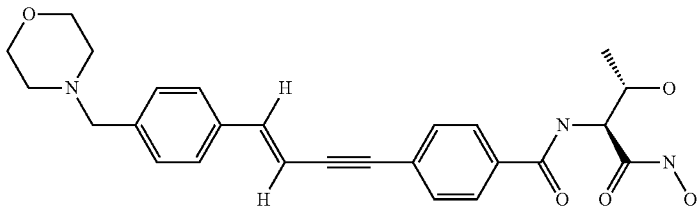 [SMILES: C[C@H](O)[C@H](NC(=O)c1ccc(C#C/C=C/c2ccc(CN3CCOCC3)cc2)cc1)C(=O)NO] | 464.4 | 4.08 | B |
| 96-3 | 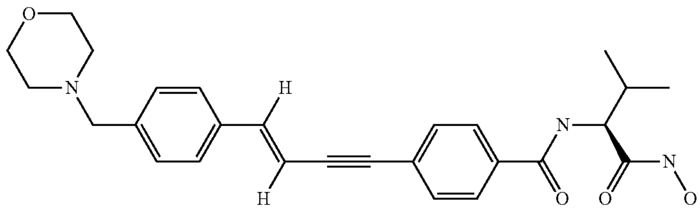 | 462.4 | 5.01 | B |
| 96-4 | 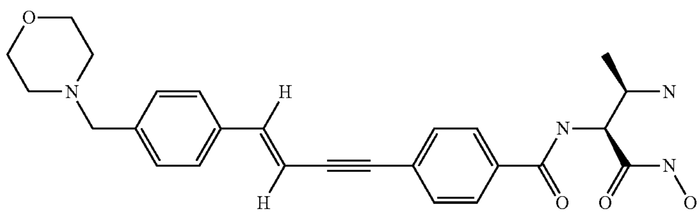 [SMILES: C[C@@H](N)[C@H](NC(=O)c1ccc(C#C/C=C/c2ccc(CN3CCOCC3)cc2)cc1)C(=O)NO] | 463.3 | 3.57 | B |

Example 97

N-((1S,2R)-1-Hydroxycarbamoyl-2-methoxy-propyl)-4-[(E)-4-(4-morpholin-4-ylmethyl-phenyl)-but-3-en-1-ynyl]-benzamide (97-1)

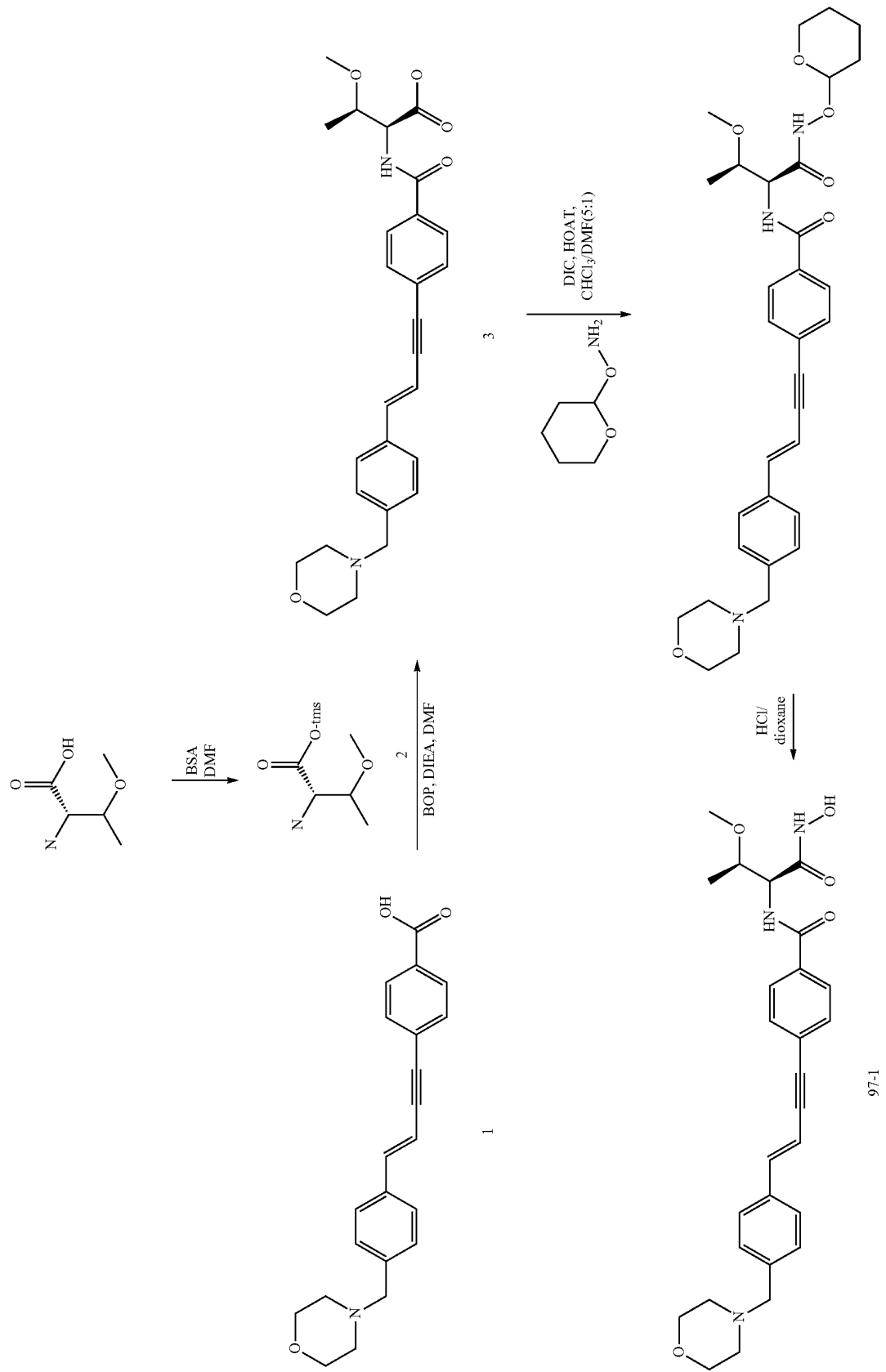

Synthesis of (2S,3R)-3-methoxy-2-{4-[(E)-4-(4-morpholin-4-ylmethyl-phenyl)-but-3-en-1-ynyl]-benzoylamino}-butyric acid methyl ester (3)

| Reagent | MW | Eq. | mg/mL | mmol |
|---|---|---|---|---|
| Compound 1 (Ach-Tr-Db-(Morpholine)-OH | 347.41 | 1.0 | 80 mg | 0.23 |
| H-(S)-Thr(Me)-OTMS | 133.15 | 1.2 | 37 mg | 0.28 |
| BSA | 203.43 | 2.9 | 160 µl | 0.67 |
| BOP | 442.28 | 1.26 | 127 mg | 0.29 |
| DIEA | 129.24 | 4.0 | 160 µl | 0.92 |
| DMF | | | 2 mL | |

Compound 3 (100 mg, 95%) as light yellow oil was prepared using the BOP coupling described in Example 96 for compound 2. LC-MS [M+H] 463.2 (C27H30N2O5+H, requires 463.5).

Synthesis of N N-[(1S,2R)-2-methoxy-1-(tetra-hydro-pyran-2-yloxycarbamoyl)-propyl]-4-[(E)-4-(4-morpholin-4-ylmethyl-phenyl)-but-3-en-1-ynyl]-benzamide (4)

A solution of compound 3 (100 mg, 0.22 mmol), DIC (51 µl, 0.33 mmol) and HOAT (45 mg) in CHCl3 (1.67 mL) and DMF (0.33 mL) was stirred at 0° C. for 10 min followed by addition of THP—O—NH2 (52 mg, 0.44 mmol). Reaction mixture was stirred at 0° C. for additional 30 min. Then reaction mixture was allowed to warm to ambient temperature, diluted with water (50 mL), extracted with CHCl3 (50 mL×2). Combined organic phase was washed with brine (30 mL), dried over anh. Na2SO4 and concentrated in vacuo. Flash chromatography on silica gel of the residue gave target product 4 (63 mg, 51%) as white solid. LC-MS [M+H] 562.4 (C32H39N3O6+H, requires 562.7).

Synthesis of N-((1S,2R)-1-hydroxycarbamoyl-2-methoxy-propyl)-4-[(E)-4-(4-morpholin-4-ylmethyl-phenyl)-but-3-en-1-ynyl]-benzamide (97-1)

A solution of compound 4 (63 mg, 0.11 mmol) in 0.5 mL of dioxane was cooled to 0° C. followed by 4 N HCl/dioxane (0.5 mL, 2 mmol). Reaction mixture was allowed to warm to ambient temperature and stirred for 30 min. Solvent was evaporated in vacuo. Residue was dissolved in DMSO (400 µl) and subjected to HPLC purification. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide trifluoroacetate salt of target product 97-1 (12.8 mg) as white solid. LC-MS [M+H] 478.2 (C27H31N3O5+H, requires 478.7).

| Compound # | Scale (mmol)* | Yield (mg) | Yield (%)* | Purity (%) | [M + H] | Retention time (min)** |
|---|---|---|---|---|---|---|
| 97-1 | 0.23 | 12.8 | 9.4 | 95 | 478.2 | 4.8 |

*Based on the amount of carboxylic acid used in the coupling reaction
**HPLC-MS Method B The following compound was synthesized as described above.

| Compound # | Structure | MH+ (m/z) | Ret. Time (min) | HPLC-MS Method |
|---|---|---|---|---|
| 97-2 | (structure) | 478.2 | 4.43 | B |

Example 98
Synthesis of N—((S)-2-amino-1-hydroxycarbamoyl-ethyl)-4-[(E)-4-(4-morpholin-4-ylmethyl-phenyl)-but-3-en-1-ynyl]-benzamide (98-1)
N—[(S)-2-(2-dimethylamino-acetylamino)-1-hydroxycarbamoyl-ethyl]-4-[(E)-4-(4-morpholin-4-ylmethyl-phenyl)-but-3-en-1-ynyl]-benzamide (98-2)
N—((S)-2-acetylamino-1-hydroxycarbamoyl-ethyl)-4-[(E)-4-(4-morpholin-4-ylmethyl-phenyl)-but-3-en-1-ynyl]-benzamide (98-3)
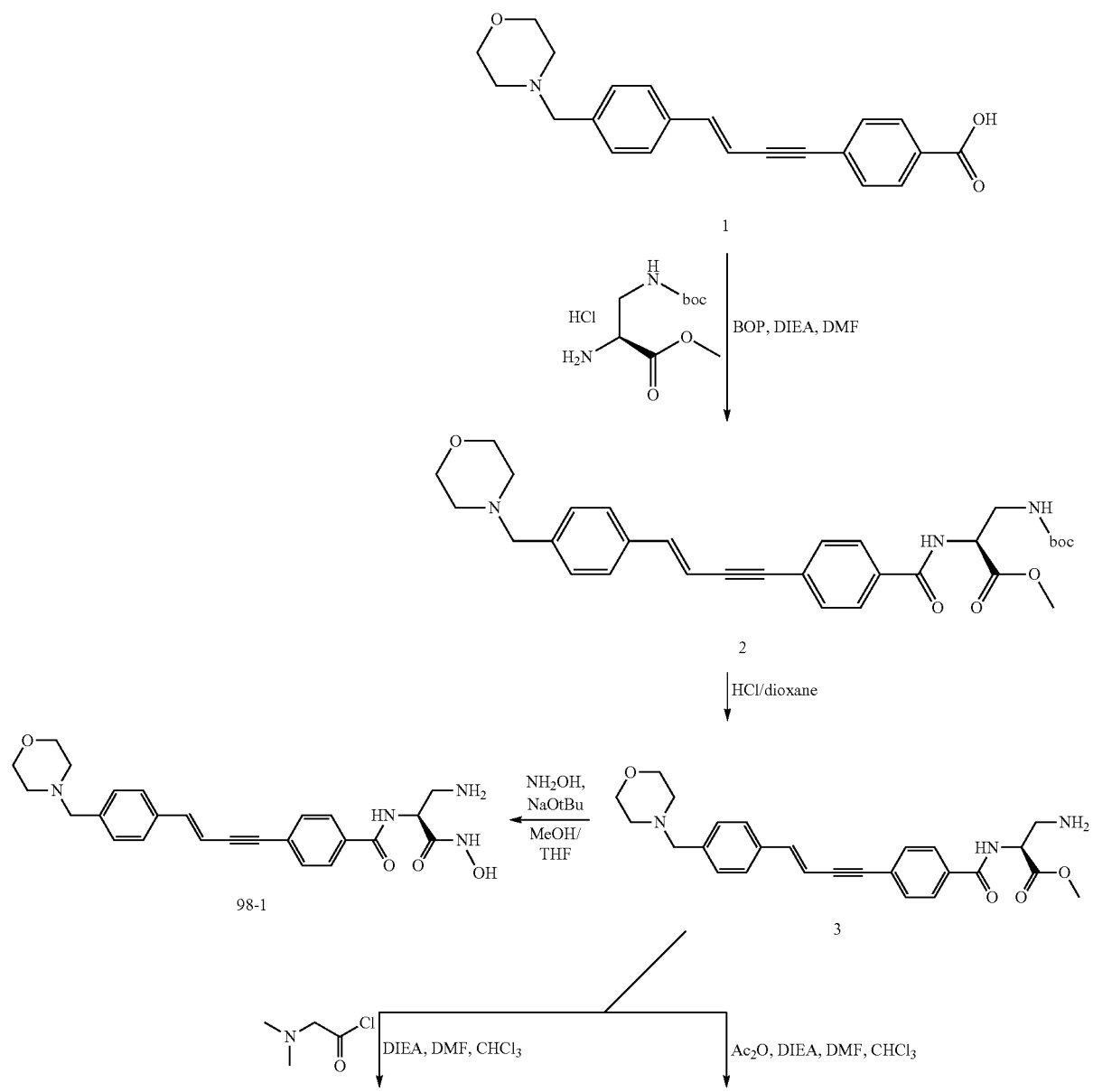

343

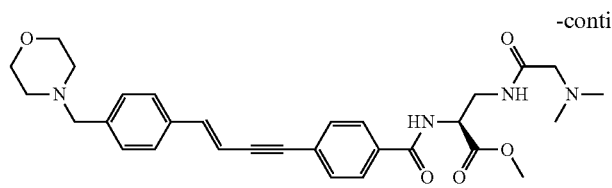

5

↓ NH₂OH, NaOtBu, MeOH/THF

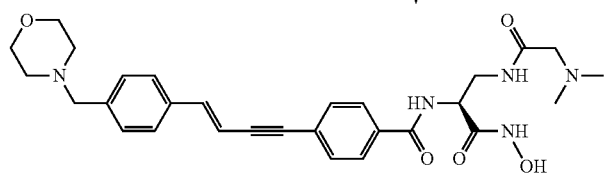

98-2

Synthesis of (S)-3-tert-butoxycarbonylamino-2-{4-[(E)-4-(4-morpholin-4-ylmethyl-phenyl)-but-3-en-1-ynyl]-benzoylamino}propionic acid methyl ester (2)

| Reagent | MW | Eq. | mg/mL | mmol |
|---|---|---|---|---|
| Compound 1 (Ach-Tr-Db-(Morpholine)-OH | 347.41 | 1.0 | 280 mg | 0.80 |
| N-Boc-(S)-DAP-OMe × HCl | 254.71 | 1.2 | 245 mg | 0.96 |
| BOP | 442.28 | 1.25 | 442.3 mg | 1.0 |
| DIEA | 129.24 | 3.0 | 418 µl | 2.4 |
| DMF | | | 5 mL | |

The product 2 (338 mg, 77%) as yellow solid was prepared using the BOP coupling described in Example 96 for compound 2. LC-MS [M+H] 548.4 (C31H37N3O6+H, requires 548.6). Compound was used in next synthetic step without additional purification.

Synthesis of (S)-3-amino-2-{4-[(E)-4-(4-morpholin-4-ylmethyl-phenyl)-but-3-en-1-ynyl]-benzoylamino}-propionic acid methyl ester 3

| Reagent | MW | Eq. | mg/mL | mmol |
|---|---|---|---|---|
| Compound 2 | 547.64 | 1.0 | 338 mg | 0.62 |
| 4N HCl/dioxane | | 13 | 2 mL | 8 |
| Dioxane/MeOH (1:1) | | | 2 mL | |

The product 3 (321 mg, 100%) as white solid was made using the General Method for Boc deprotection. LC-MS [M+H] 448.4 (C26H29N3O4+H, requires 448.5).

Synthesis of N—((S)-2-amino-1-hydroxycarbamoyl-ethyl)-4-[(E)-4-(4-morpholin-4-ylmethyl-phenyl)-but-3-en-1-ynyl]-benzamide (98-1)

| Reagent | MW | Eq. | mg/mL | mmol |
|---|---|---|---|---|
| Compound 3 × 2 HCl | 518.5 | 1.0 | 104 mg | 0.2 |
| NH₂OH × HCl | 69.49 | 6.0 | 84 mg | 1.2 |

344

-continued

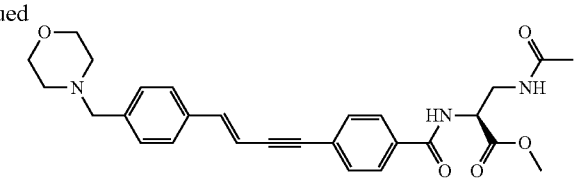

7

↓ NH₂OH, NaOtBu, MeOH/THF

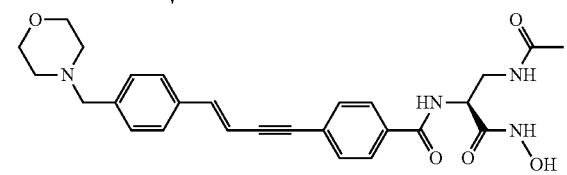

98-3

-continued

| Reagent | MW | Eq. | mg/mL | mmol |
|---|---|---|---|---|
| NaOtBu | 96.11 | 8.0 | 154 mg | 1.6 |
| MeOH | | | 2 mL | |
| THF | | | 2 mL | |

The product 4 (20.5 mg) as white solid was prepared using the Hydroxyamide formation described in Example 96 for compound 96-1. LC-MS [M+H] 449.2 (C25H28N4O4+H, requires 449.5).

| Compound | Scale (mmol)* | Yield (mg) | Yield (%)* | Purity (%) | [M + H] | Retention time (min)* |
|---|---|---|---|---|---|---|
| 98-1 | 0.2 | 20.5 | 18.3 | 97.5 | 449.2 | 3.48 |

*Based on the amount of compound 3.
**HPLC-MS Method B

Synthesis of (S)-3-(2-dimethylamino-acetylamino)-2-{4-[(E)-4-(4-morpholin-4-ylmethyl-phenyl)-but-3-en-1-ynyl]-benzoylamino}-propionic acid methyl ester (5)

To the mixture of compound 3 di-hydrochloride (104 mg, 0.20 mmol) and dimethylaminoacetyl chloride hydrochloride (41 mg, 0.26 mmol) in DMF (0.5 mL) and CHCl₃ (1.5 mL) was added DIEA (210 µl, 1.2 mmol). Reaction mixture was stirred at ambient temperature overnight. Solvent was concentrated in vacuo. Residue was dissolved in EtOAc (50 mL), washed with 5% solution of NaHCO₃ (50 mL) and brine (30 mL) Organic phase was dried over anh. Na₂SO₄, evaporated in vacuo and dried in vacuo overnight to provide target product 5 (75 mg, 71%) as white solid. LC-MS [M+H] 533.5 (C30H36N4O5+H, requires 533.6). Compound was used in next synthetic step without additional purification.

Synthesis of N—[(S)-2-(2-dimethylamino-acetylamino)-1-hydroxycarbamoyl-ethyl]-4-[(E)-4-(4-morpholin-4-ylmethyl-phenyl)-but-3-en-1-ynyl]-benzamide (98-2)

| Reagent | MW | Eq. | mg/mL | mmol |
|---|---|---|---|---|
| Compound 5 | 532.6 | 1.0 | 75 mg | 0.14 |
| NH$_2$OH × HCl | 69.49 | 6.0 | 58 mg | 0.84 |
| NaOtBu | 96.11 | 8.0 | 108 mg | 1.12 |
| MeOH | | | 1.5 mL | |
| THF | | | 1.5 mL | |

Compound was prepared using the same procedure as for synthesis of compound (98-1). LC-MS [M+H] 534.4 (C29H35N5O5+H, requires 534.6).

| Compound | Scale (mmol)* | Yield (mg) | Yield (%)* | Purity (%) | [M + H] | Retention time (min)* |
|---|---|---|---|---|---|---|
| 98-2 | 0.2 | 25.8 | 20% | 100 | 534.4 | 3.51 |

*Based on the amount of compound 3.
**HPLC-MS Method B

Synthesis of (S)-3-acetylamino-2-{4-[(E)-4-(4-morpholin-4-ylmethyl-phenyl)-but-3-en-1-ynyl]-benzoylamino}-propionic acid methyl esterster (7)

To the mixture of compound 3 di-hydrochloride (104 mg, 0.20 mmol) and acetic anhydride (36 μl, 0.38 mmol) in DMF (0.5 mL) and CHCl$_3$ (1.5 mL) was added DIEA (210 μl, 1.2 mmol). Reaction mixture was stirred at ambient temperature overnight. Solvent was concentrated in vacuo. Residue was dissolved in EtOAc (50 mL), washed with 5% solution of NaHCO$_3$ (30 mL) and brine (30 mL). Organic phase was dried over anh. Na$_2$SO$_4$, evaporated in vacuo and dried in vacuo overnight to provide target product 7 (70 mg, 71%) as white solid. LC-MS [M+H] 490.3 (C28H31N3O5+H, requires 490.5). Compound was used in next synthetic step without additional purification.

Synthesis of N—((S)-2-acetylamino-1-hydroxycarbamoyl-ethyl)-4-[(E)-4-(4-morpholin-4-ylmethyl-phenyl)-but-3-en-1-ynyl]-benzamide (98-3)

| Reagent | MW | Eq. | mg/mL | mmol |
|---|---|---|---|---|
| Compound 7 | 489.6.6 | 1.0 | 70 mg | 0.14 |
| NH$_2$OH × HCl | 69.49 | 6.0 | 58 mg | 0.84 |
| NaOtBu | 96.11 | 8.0 | 108 mg | 1.12 |
| MeOH | | | 1.5 mL | |
| THF | | | 1.5 mL | |

Compound was prepared using the same procedure as for synthesis of compound (98-1). LC-MS [M+H] 491.2 (C27H30N4O5+H, requires 491.5).

| Compound | Scale (mmol)* | Yield (mg) | Yield (%)* | Purity (%) | [M + H] | Retention time (min)** |
|---|---|---|---|---|---|---|
| 98-3 | 0.2 | 22.4 | 18.6% | 100 | 491.2 | 3.41 |

*Based on the amount of compound 3.
**HPLC-MS Method B

Example 99

4-[(E)-4-(4-{[Ethyl-(2-methoxy-ethyl)-amino]-methyl}-phenyl)-but-3-en-1-ynyl]-N—((S)-1-hydroxycarbamoyl-2-methylamino-ethyl)-benzamide (99-1)

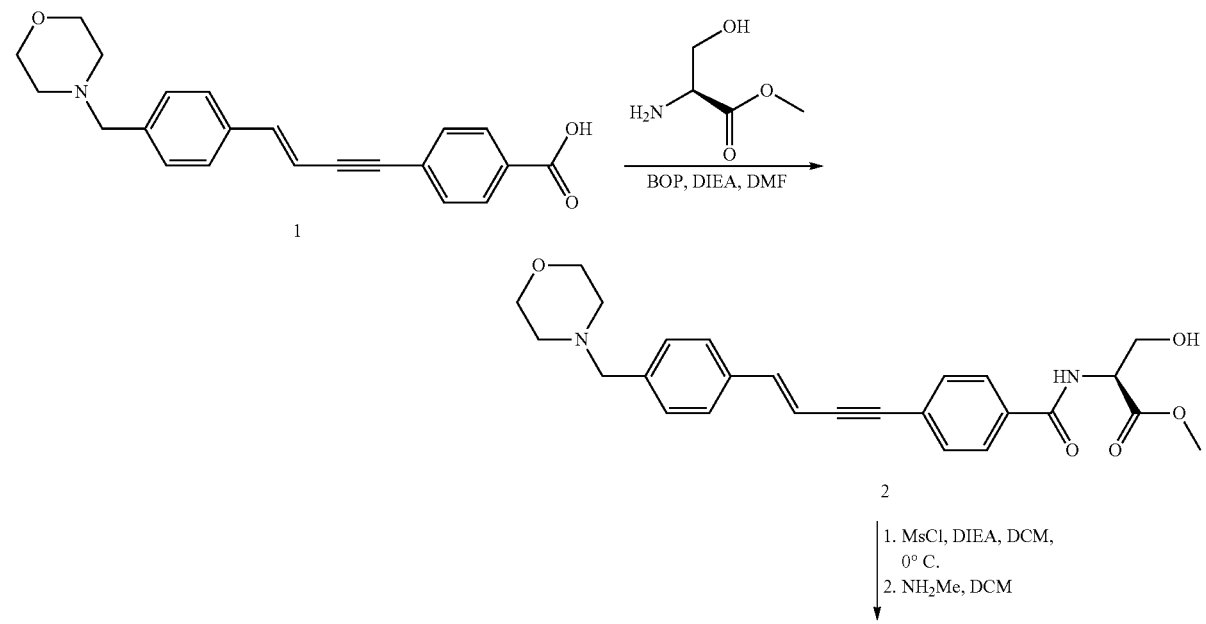

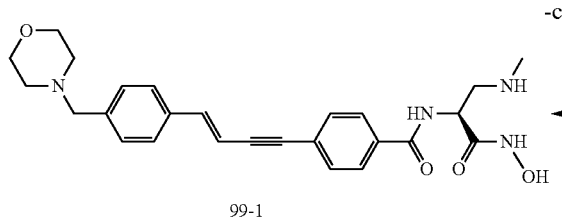 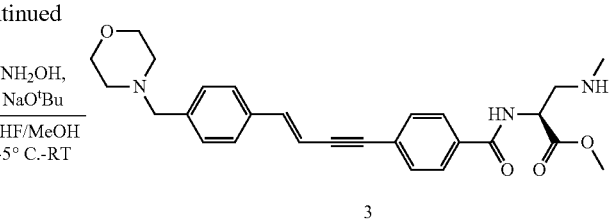

Synthesis of (S)-3-hydroxy-2-{4-[(E)-4-(4-morpholin-4-ylmethyl-phenyl)-but-3-en-1-ynyl]-benzoylamino}-propionic acid methyl ester (2)

Synthesis of 4-[(E)-4-(4-{[ethyl-(2-methoxy-ethyl)-amino]-methyl}-phenyl)-but-3-en-1-ynyl]-N—((S)-1-hydroxycarbamoyl-2-methylamino-ethyl)-benzamide (99-1)

| Reagent | MW | Eq. | mg/mL | mmol |
|---|---|---|---|---|
| Compound 1 (Ach-Tr-Db-(Morpholine)-OH) | 347.41 | 1.0 | 139 mg | 0.40 |
| H-(S)-Ser-OMe × HCl | 155.58 | 1.2 | 75 mg | 0.48 |
| BOP | 442.28 | 1.25 | 223 mg | 0.50 |
| DIEA | 129.24 | 3.0 | 210 µl | 1.20 |
| DMF | | | 4 ml | |

The product 2 (179 mg, 100%) as white solid was prepared using the BOP coupling described in Example 96 for compound 2. LC-MS [M+H] 449.4 (C26H28N2O5+H, requires 449.51). Compound was used in next synthetic step without additional purification.

Synthesis of (S)-3-methylamino-2-{4-[(E)-4-(4-morpholin-4-ylmethyl-phenyl)-but-3-en-1-ynyl]-benzoylamino}-propionic acid methyl ester (3)

A solution of compound 2 (179 mg, 0.4 mmol) and DIEA (140 µl, 0.8 mmol) in CH2Cl2 (5 ml) was cooled to 0° C. followed by the addition of MsCl (37 µl, 0.48 mmol). Reaction mixture was maintained at 0° C. for 30 min followed by the addition of 2 M solution of methylamine in THF (2 ml, 4 mmol). Temperature of the reaction mixture was raised to ambient. Reaction mixture was maintained at ambient temperature. After completion (in 30 min) solvent was removed in vacuo. Residue was dissolved in EtOAc (50 ml), washed with water (30 ml×2), brine (50 ml) and dried over anh. Na2SO4. Solvent was evaporated in vacuo and dried in vacuo overnight to provide compound 3 (120 mg, 65%) as light yellow solid. LC-MS [M+H] 462.4 (C27H31N3O4+H, requires 462.5).

| Reagent | MW | Eq. | mg/ml | mmol |
|---|---|---|---|---|
| Compound 3 | 461.55 | 1.0 | 120 mg | 0.26 |
| NH2OH × HCl | 69.49 | 6.0 | 110 mg | 1.56 |
| NaOtBu | 96.11 | 8.0 | 200 mg | 2.1 |
| MeOH | | | 2 ml | |
| THF | | | 2 ml | |

The product 99-1 (11.2 mg) as white solid was prepared by using the same procedure as for synthesis of compound (98-1). LC-MS [M+H] 463.3 (C26H30N4O4+H, requires 463.5).

| Compound | Scale (mmol)* | Yield (mg) | Yield (%)* | Purity (%) | [M + H] | Retention time (min)** |
|---|---|---|---|---|---|---|
| 99-1 | 0.4 | 11.2 | 4.1 | 92.2 | 463.3 | 3.48 |

*Based on the amount of carboxylic acid used in the coupling reaction
**HPLC-MS Method B

Example 100

N—[(S)-2-(2-Cyclopropylamino-acetylamino)-1-hydroxycarbamoyl-ethyl]-4-[(E)-4-(4-morpholin-4-ylmethyl-phenyl)-but-3-en-1-ynyl]-benzamide (100-1)

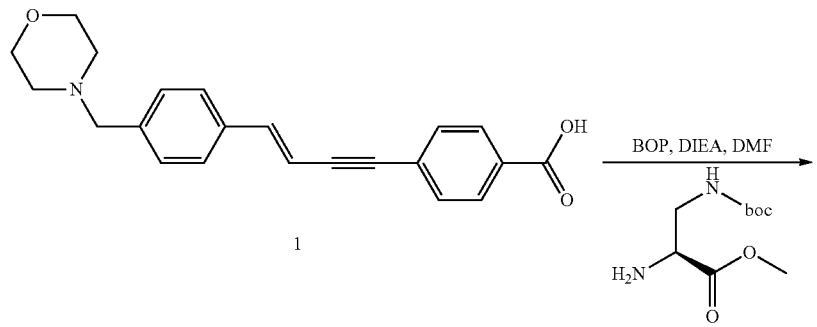

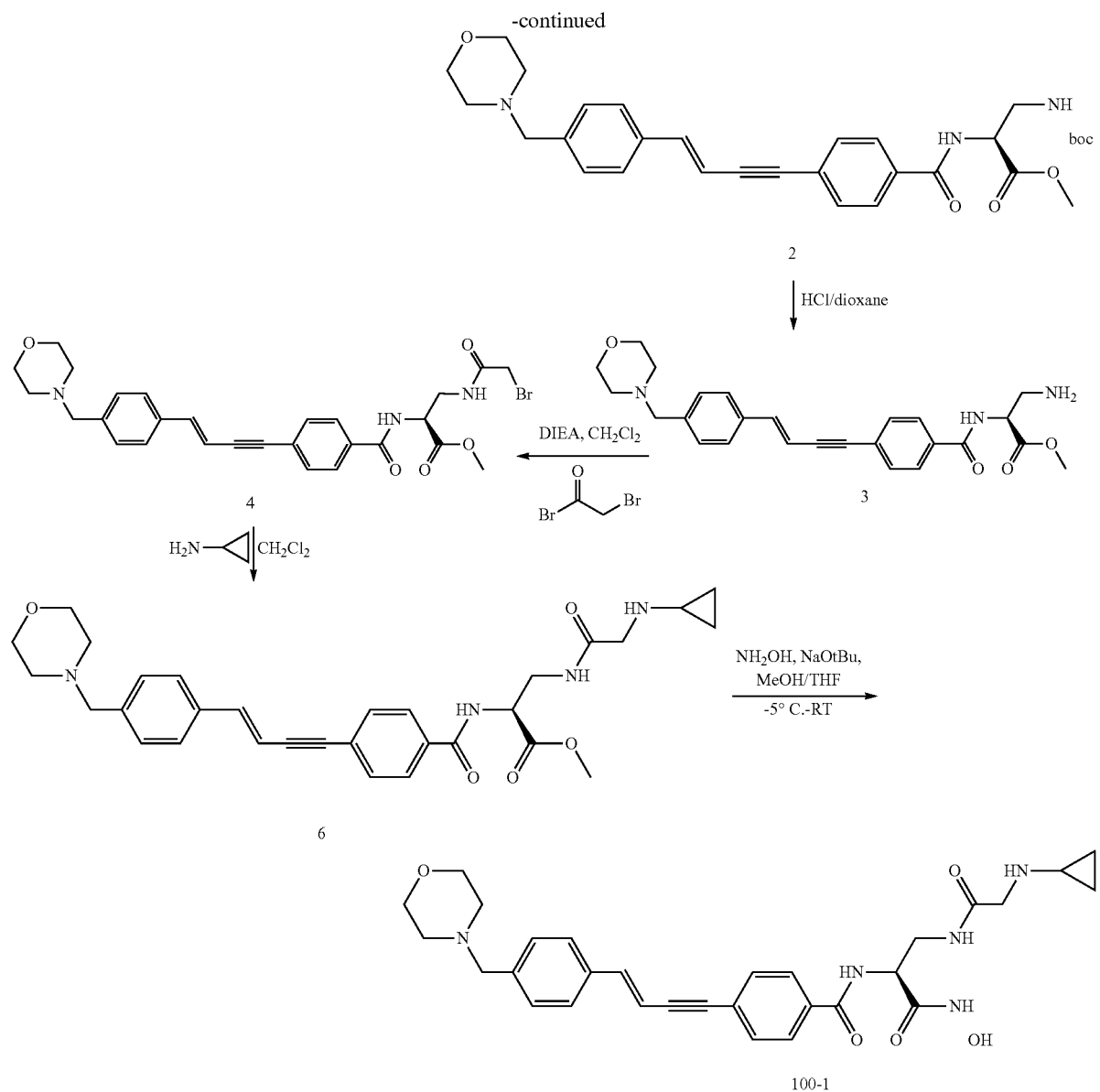

Synthesis of (S)-3-tert-butoxycarbonylamino-2-{4-[(E)-4-(4-morpholin-4-ylmethyl-phenyl)-but-3-en-1-ynyl]-benzoylamino}-propionic acid methyl ester (2)

| Reagent | MW | Eq. | mg/mL | mmol |
|---|---|---|---|---|
| Compound 1 (Ach-Tr-Db-(Morpholine)-OH | 347.41 | 1.0 | 139 mg | 0.40 |
| N-Boc-(S)-DAP-OMe × HCl | 254.71 | 1.2 | 122 mg | 0.48 |
| BOP | 442.28 | 1.25 | 223 mg | 0.50 |
| DIEA | 129.24 | 3.0 | 210 µl | 1.2 |
| DMF | | | 4 mL | |

The product 2 (207 mg, 94%) as yellow solid was prepared using the BOP coupling described in Example 96 as for the synthesis of the compound 2. LC-MS [M+H] 548.4 (C31H37N3O6+H, requires 548.6). Compound was used in next synthetic step without additional purification.

Synthesis of (S)-3-amino-2-{4-[(E)-4-(4-morpholin-4-ylmethyl-phenyl)-but-3-en-1-ynyl]-benzoylamino}-propionic acid methyl ester (3)

| Reagent | MW | Eq. | mg/mL | mmol |
|---|---|---|---|---|
| Compound 2 | 547.64 | 1.0 | 207 mg | 0.38 |
| 4N HCl/dioxane | | 21 | 2 mL | 8 |
| Dioxane/MeOH (1:1) | | | 2 mL | |

The product 3 (208 mg, 100%) as white solid was made using the General Method for Boc deprotection. LC-MS [M+H] 448.4 (C26H29N3O4+H, requires 448.5). Compound was used in next synthetic step without additional purification.

Synthesis of (S)-3-(2-bromo-acetylamino)-2-[4-((3E,5E,7E)-5,8-dimethyl-9-morpholin-4-yl-nona-3,5,7-trien-1-ynyl)-benzoylamino]-propionic acid methyl ester (4)

To the mixture of compound 3 di-hydrochloride (207 mg, 0.40 mmol) and DIEA (180 μl) in CH$_2$Cl$_2$ (4 mL) was added bromoacetyl bromide (35 μl, 0.4 mmol) at 0° C. Reaction mixture was allowed to warm to ambient temperature and stirred for 30 min. Solvent was evaporated in vacuo. Residue was dissolved in EtOAc (50 mL), washed with 5% solution of NaHCO$_3$ (50 mL) and brine (50 mL×2). Organic phase was dried over anh. Na$_2$SO$_4$, evaporated in vacuo and dried in vacuo overnight to provide target product 4 (146 mg, 64%) as white solid. LC-MS [M+H] 570.1 (C28H30BrN3O5+H, requires 569.5). Compound was used in next synthetic step without additional purification.

Synthesis of (S)-3-(2-cyclopropylamino-acetylamino)-2-{4-[(E)-4-(4-morpholin-4-ylmethyl-phenyl)-but-3-en-1-ynyl]-benzoylamino}-propionic acid methyl ester (5)

To a solution of compound 4 (146 mg, 0.26 mmol) in CH$_2$Cl$_2$ (4 mL) was added cyclopropylamine (36 μl, 0.52 mmol) at 0° C. Reaction mixture was maintained at 0° C. for 10 min, then mixture was allowed to warm to ambient temperature and stirred overnight. After completion the solvent was removed in vacuo. Residue was dissolved in EtOAc (60 mL), washed with water (50 mL×2), brine (50 mL), dried over anh. Na$_2$SO$_4$ and concentrated in vacuum. Residue was dissolved in DMSO (800 μl) and subjected to HPLC purification. [YMC-Pack ODS-AC-18 column (30× 100 mm); flow rate=40 mL/min; mobile phase A: 100% water, 0.1% TFA; mobile phase B: 100% ACN, 0.1% TFA; gradient elution from 10% B to 50% B in 50 min., detection 254 nm]. Fractions containing the desired product were combined and evaporated in vacuo. Residue was dissolved in i-PrOH (10 mL), evaporated in vacuum and dried in vacuo overnight to provide di-trifluoroacetate salt of the target product 5 (70 mg, 36%) as white solid. LC-MS [M+H] 545.0 (C31H36N4O5+H, requires 545.6).

Synthesis of N—[(S)-2-(2-cyclopropylamino-acetylamino)-1-hydroxycarbamoyl-ethyl]-4-[(E)-4-(4-morpholin-4-ylmethyl-phenyl)-but-3-en-1-ynyl]-benzamide (100-1)

| Reagent | MW | Eq. | mg/mL | mmol |
|---|---|---|---|---|
| Compound 5 × 2 TFA | 738.6 | 1.0 | 70 mg | 0.095 |
| NH$_2$OH × HCl | 69.49 | 6.0 | 40 mg | 0.57 |
| NaOtBu | 96.11 | 8.0 | 73 mg | 0.76 |
| MeOH |  |  | 1 mL |  |
| THF |  |  | 1 mL |  |

The product 100-1 (18.4 mg) as white solid was prepared using the same procedure as for synthesis of compound (98-1). LC-MS [M+H] 546.6 (C30H35N5O5+H, requires 546.6).

| Compound | Scale (mmol*) | Yield (mg) | Yield (%)* | Purity (%) | [M + H] | Retention time (min)** |
|---|---|---|---|---|---|---|
| 100-1 | 0.4 | 18.4 | 6.0% | 95 | 546.6 | 3.68 |

*Based on the amount of carboxylic acid used in the coupling reaction
**HPLC-MS Method B

Example 101

Synthesis of (E)-4-[4-(4-Hydroxymethylphenyl)but-3-en-1-ynyl]benzoic acid methyl ester (I-2)

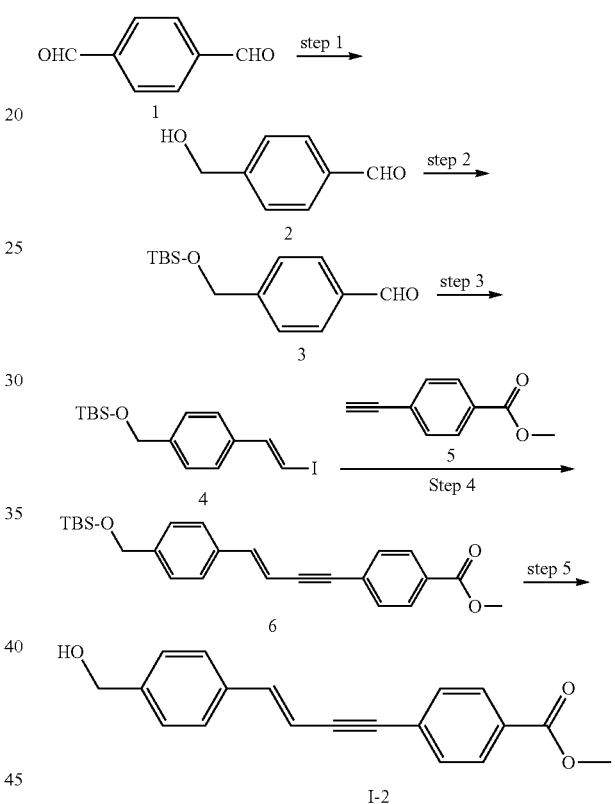

Step 1: 4-Hydroxymethylbenzaldehyde (2)

A suspension of terephthaldehyde (200 g, 1.492 mol, 1.0 eq.) in THF (1500 mL) was cooled to 0° C. NaBH$_4$ (16.94 g, 0.448 mol, 0.3 eq.) was added in one portion. The mixture was stirred at 10~20° C. overnight. 800 mL 1 N HCl was added and the mixture was stirred for 20 min and turned clear. Most THF was removed in vacuum. Then, the residue was extracted by EtOAc (500 mL×3). The combined organic layer was washed with water (2×400 mL), brine (400 mL) and dried (MgSO$_4$), filtered and concentrated to give the compound 2 (200 g, 98%) which was used directly in next step without purification.

Step 2: 4-(tert-Butyldimethylsilanyloxymethyl)benzaldehyde (3)

A solution of compound 2 (200 g, 1.47 mol, 1.0 eq.), TBSCl (220 g, 1.47 mol, 1.0 eq.) and imidazole (200 g, 2.94 mol, 2.0 eq.) in DMF (1000 mL) was heated at 45° C. for 2 hrs. The mixture was concentrated to remove most DMF and DCM (2000 mL) was added. The mixture was washed with water (500 mL×2), brine (500 mL) and dried (MgSO$_4$), filtered and concentrated under reduced pressure. The residue was purified by chromatography on silica gel (0 to 5% EtOAc/PE) to give the compound 3 (130 g, 35.4%). $^1$H-NMR (300 MHz, CDCl$_3$): in ppm, 0.10 (s, 6H), 0.94 (s, 9H), 4.80 (s, 2H), 7.47 (d, J=8.7 Hz, 2H), 7.84 (d, J=8.1 Hz, 2H), 9.98 (s, 1H).

Step 3: (E)-tert-Butyl-[4-(2-iodo-vinyl)benzyloxy]dimethylsilane (4)

Chromium chloride anhydrous (29.3 g, 240 mmol, 6 eq) was added to THF (500 mL) under nitrogen. A solution of triiodomethane (31.4 g, 80 mmol, 2 eq) in THF (200 mL) was added dropwise at 0-10° C. under nitrogen. Then, a solution of compound 3 (10.0 g, 40 mmol, 1 eq) in THF (100 mL) was added dropwise. The mixture was stirred at 0~10° C. for 2 hrs and then at 10-20° C. for 2 more hours. 400 mL iced water was added and the mixture was stirred for 20 min, extracted with EtOAc (500 mL×3). The combined organic phase was washed with 20% aq. Na$_2$S$_2$O$_3$ aqueous (500 mL), water (500 mL), brine (500 mL) and dried (MgSO$_4$), filtered and concentrated under reduced pressure. The residue was purified by chromatography on silica gel (0 to 2% EtOAc/PE) to give the title compound 4 (9 g, 60%). $^1$H-NMR (300 MHz, CDCl$_3$): in ppm, 0.09 (s, 6H), 0.93 (s, 9H), 4.72 (s, 2H), 6.79 (d, J=15 Hz, 1H), 7.26 (s, 4H), 7.41 (d, J=15 Hz, 1H).

Step 4: (E)-4-{4-[4-(tert-Butyldimethylsilanyloxymethyl)phenyl]but-3-en-1-ynyl}benzoic acid methyl ester (6)

To a mixture of compound 4 (1.02 g, 2.7 mmol, 1.0 eq), 5 (0.43 g, 2.7 mmol, 1.0 eq), PdCl$_2$(PPh$_3$)$_2$ (190 mg, 0.27 mmol, 0.1 eq) and Et$_3$N (5 mL) in THF (50 mL) was added CuI (51 mg, 0.27 mmol, 0.1 eq) under nitrogen. The mixture was stirred at 10~20° C. for 12 hrs. The reaction mixture was diluted with EtOAc (50 mL), filtered and concentrated. The residue was dissolved into EtOAc (100 mL) and washed with water (100 mL) and brine (50 mL), and dried (MgSO$_4$). After filtration and concentration, the residue was purified by chromatography on silica gel (0 to 2% EtOAc/PE) to give the title compound 6 (0.625 g, 57%). $^1$H-NMR (300 MHz, CDCl$_3$): in ppm, 0.10 (s, 6H), 0.94 (s, 9H), 3.92 (s, 3H), 4.76 (s, 2H), 6.36 (d, J=18 Hz, 1H), 7.08 (d, J=18 Hz, 1H), 7.31 (d, J=9.0 Hz, 2H), 7.40 (d, J=9.0 Hz, 2H), 7.52 (d, J=8.5 Hz, 2H), 7.99 (d, J=8.5 Hz, 2H).

Step 5: (E)-4-[4-(4-Hydroxymethylphenyl)but-3-en-1-ynyl]benzoic acid methyl ester (I-2)

To a solution of compound 6 (5.65 g, 13.9 mmol, 1 eq) in THF (50 mL) was added Et$_3$N·3HF (6.72 g, 21.7 mmol, 3 eq) at room temperature. The mixture was stirred at 10~20° C. for 10 hrs. The mixture was concentrated to remove solvent and EtOAc (100 mL), NaHCO$_3$ (50 mL) was added. The mixture was filtered and the organic of filtrate was separated, washed with brine (2×100 mL) and dried by MgSO$_4$, filtered. The filtrate was concentrated to 10 mL and filtered. The combined filter cake was dried in vacuum to give the target compound I-2 (3.25 g, 80%). $^1$H-NMR (300 MHz, DMSO-d$_6$): in ppm, 3.86 (s, 3H), 4.51 (d, J=5.76 Hz, 2H), 5.25 (t, J=5.76 Hz, 1H) 6.65 (d, J=16.5 Hz, 1H), 7.17 (d, J=16.2 Hz, 1H), 7.33 (d, J=8.0 Hz, 2H), 7.55 (d, J=8.2 Hz, 2H), 7.61 (d, J=8.25 Hz, 2H), 7.97 (d, J=8.52 Hz, 2H).

N-((1S,2R)-2-Hydroxy-1-hydroxycarbamoyl-propyl)-4-[(E)-4-(4-hydroxymethyl-phenyl)-but-3-en-1-ynyl]-benzamide (101-1)

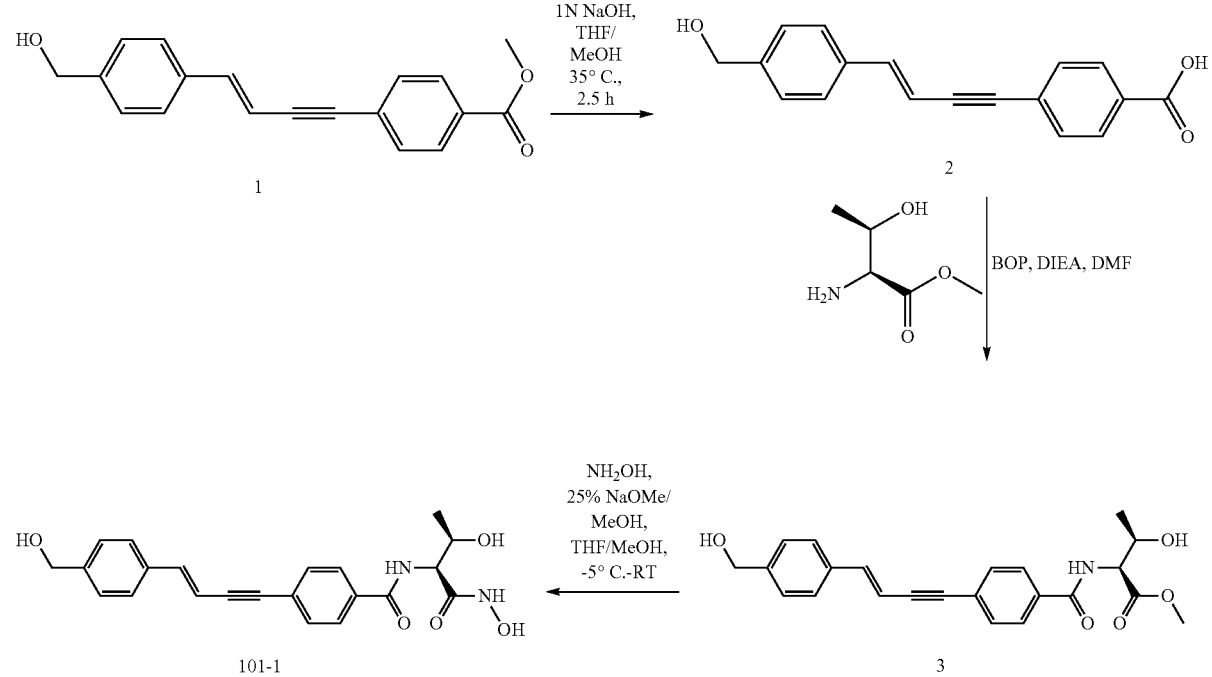

Synthesis of 4-[(E)-4-(4-hydroxymethyl-phenyl)-but-3-en-1-ynyl]-benzoic acid (2)

| Reagent | MW | Eq. | g/mL | mmol |
|---|---|---|---|---|
| Compound 1 (Ach-Triple-Double (OH)-OMe) | 293.33 | 1.0 | 780 mg | 2.63 |
| 1N NaOH | | 2.5 | 6.5 mL | 6.57 |
| THF | | | 4 mL | |
| MeOH | | | 4 mL | |

The compound 2 (710 mg, 90%) as white solid was made and separated using the General Method for basic hydrolysis.

Synthesis of (2S,3R)-3-hydroxy-2-{4-[(E)-4-(4-hydroxymethyl-phenyl)-but-3-en-1-ynyl]-benzoylamino}-butyric acid methyl ester (3)

| Reagent | MW | Eq. | mg/mL | mmol |
|---|---|---|---|---|
| Compound 2 × sodium salt | 300.28 | 1.0 | 99 mg | 0.33 |
| H-(S)-Thr-OMe × HCl | 169.6 | 1.2 | 66 mg | 0.39 |
| BOP | 442.28 | 1.3 | 184 mg | 0.42 |
| DIEA | 129.24 | 3.0 | 172 µl | 0.99 |
| DMF | | | 2 mL | |

The compound 3 (120 mg, 92%) as off-white solid was prepared using the BOP coupling described in Example 96 as for the synthesis of the compound 2. LC-MS [M+H] 394.3 (C23H23NO5+H, requires 394.4). Compound was used in next synthetic step without additional purification.

Synthesis of 4 N-((1S,2R)-2-hydroxy-1-hydroxycarbamoyl-propyl)-4-[(E)-4-(4-hydroxymethyl-phenyl)-but-3-en-1-ynyl]-benzamide (101-1)

| Reagent | MW | Eq. | mg/mL | mmol |
|---|---|---|---|---|
| Compound 3 | 393.4 | 1.0 | 120 mg | 0.30 |
| NH$_2$OH × HCl | 69.49 | 6.5 | 135 mg | 1.94 |
| 25% NaOMe/MeOH | | 8.8 | 600 µl | 2.64 |
| MeOH | | | 4 mL | |
| THF | | | 1.5 mL | |

The target product 101-1 (20.7 mg) as white solid made using the General Method for hydroxamate formation. LC-MS [M+H] 395.2 (C22H22N2O5+H, requires 395.4).

| Compound | Scale (mmol)* | Yield (mg) | Yield (%)* | Purity (%) | [M + H] | Retention time (min)** |
|---|---|---|---|---|---|---|
| 101-1 | 0.33 | 20.7 | 16.0 | 90.0 | 395.2 | 5.31 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 101-2* | 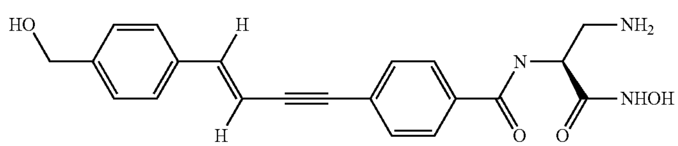 | 380.5 | 4.56 | B |
| 101-3 | 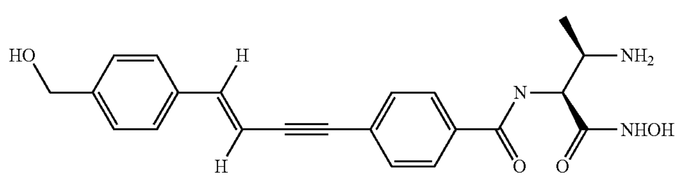 | 394.2 | 4.65 | B |
| 101-4 | 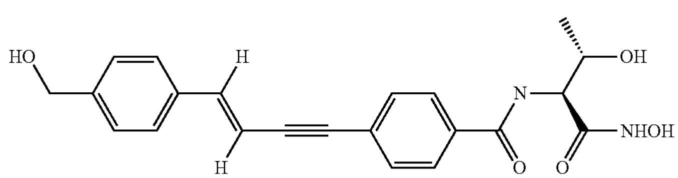 | 395.3 | 5.36 | B |
| 101-5** | 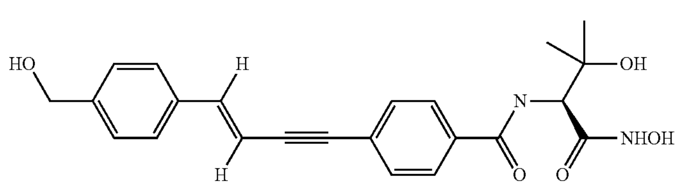 | 409.2 | 5.61 | B |

-continued
| Compound # | Structure | MH+ (m/z) | Ret. Time (min) | HPLC-MS Method |
|---|---|---|---|---|
| 101-6* | 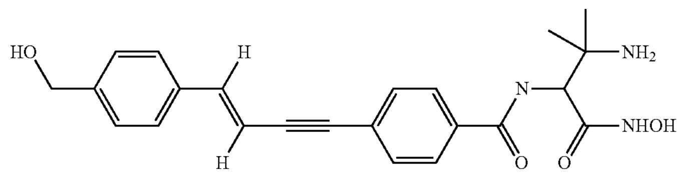 | 421.1 | 2.52 | A |
*Boc-protecting group from intermediate was removed by 4M HCl/dioxane.
**Methyl ester of diMeSer was prepared according to general procedure.
Example 102
4-[(E)-4-(4-Cyclopropylaminomethyl-phenyl)-but-3-en-1-ynyl]-N-((1S,2R)-2-hydroxy-1-hydroxycarbamoyl-propyl)-benzamide (102-1)
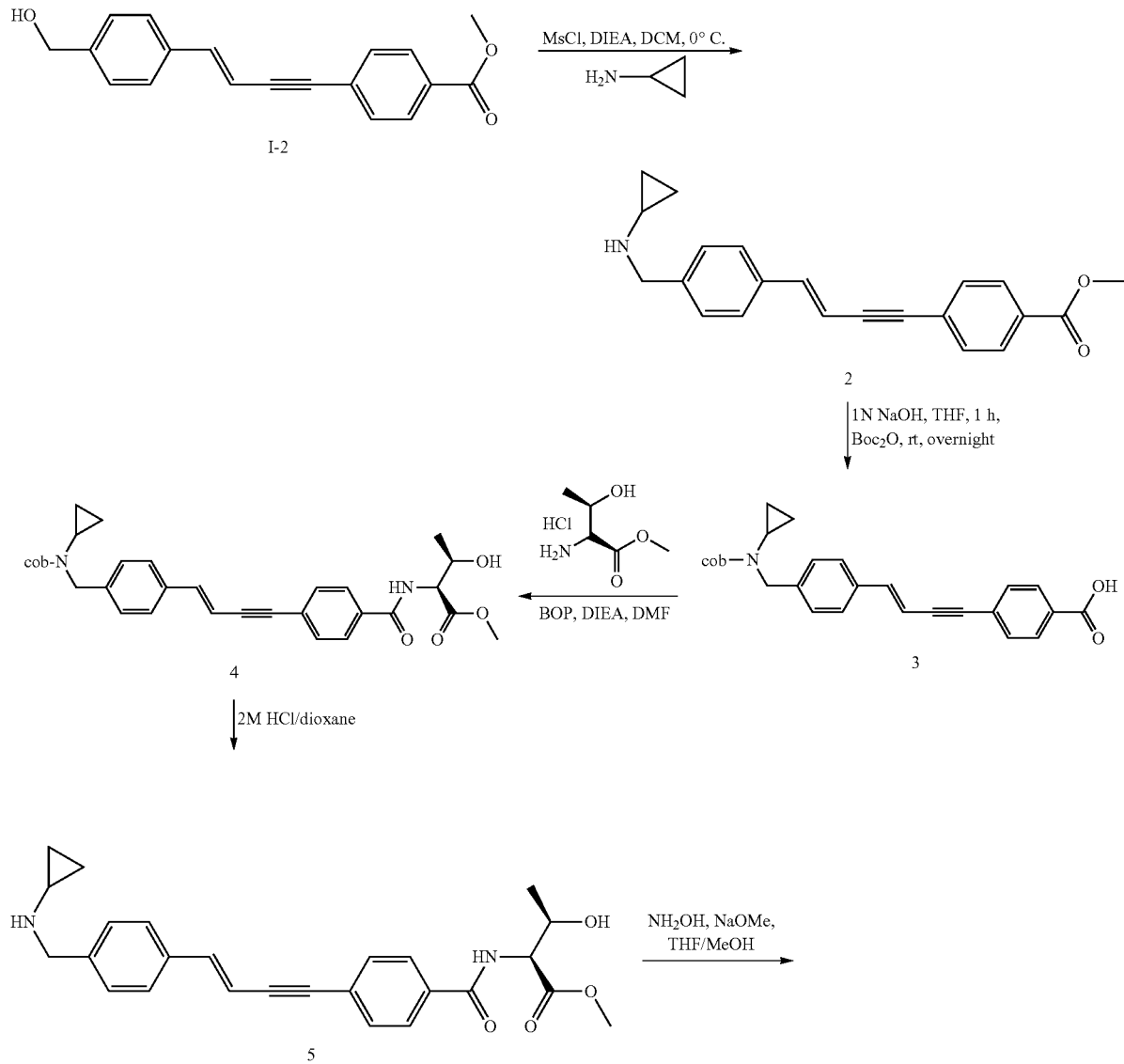

-continued

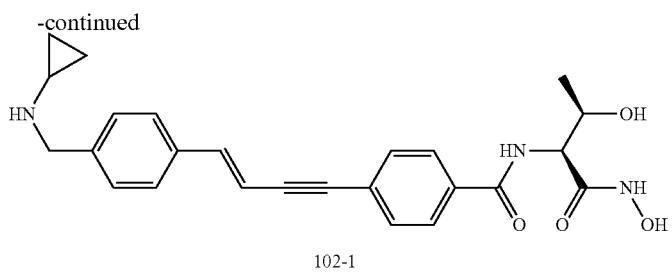

102-1

Synthesis of 4-[(E)-4-(4-cyclopropylaminomethyl-phenyl)-but-3-en-1-ynyl]-benzoic acid methyl ester (2)

A solution of compound 1 (750 mg, 2.56 mmol) and DIEA (1.1 mL, 6.40 mmol) in $CH_2Cl_2$ (15 mL) was cooled to 0° C. followed by the addition of MSCl (0.22 mL, 2.82 mmol) dropwise over the period of 5 min. Reaction mixture was maintained at 0° C. for 10 min followed by the addition of cyclopropylamine (0.89 mL, 12.8 mmol). Temperature of the reaction mixture was allowed to rise to ambient. Reaction mixture was maintained at ambient temperature overnight. After completion solvent was removed in vacuo. Residue was dissolved in EtOAc (150 mL), washed with water (150 mL×2), brine (150 mL) and dried over anh. $Na_2SO_4$. Solvent was evaporated in vacuo to provide compound 2 (848 mg, 100%) as light yellow oil. LC-MS [M+H] 332.2 (C22H21NO2+H, requires 332.41). Compound was used in next synthetic step without additional purification.

Synthesis of 4-((E)-4-{4-[(tert-butoxycarbonyl-cyclopropyl-amino)-methyl]-phenyl}-but-3-en-1-ynyl)-benzoic acid (3)

| Reagent | MW | Eq. | g/mL | mmol |
|---|---|---|---|---|
| Compound 2 | 331.41 | 1.0 | 848 mg | 2.56 |
| 1N aq NaOH | | 3.1 | 8 mL | 8.0 |
| Di-tert-butyl dicarbonate | 218.2 | 1.1 | 615 mg | 2.82 |
| THF | | | 8 mL | |
| dioxane | | | 5 mL | |

The compound 3 (795 mg, 75%) as white solid was made and separated using the General Method for Boc protection. LC-MS [M+H] 418.3 (C26H27NO4+H, requires 418.5).

Synthesis of (2S,3R)-2-[4-((E)-4-{4-[(tert-butoxycarbonyl-cyclopropyl-amino)-methyl]-phenyl}-but-3-en-1-ynyl)-benzoylamino]-3-hydroxy-butyric acid methyl ester (4)

| Reagent | MW | Eq. | mg/mL | mmol |
|---|---|---|---|---|
| Compound 3 | 417.5 | 1.0 | 155 mg | 0.37 |
| H-(S)-Thr-OMe × HCl | 169.6 | 1.2 | 75 mg | 0.44 |
| BOP | 442.28 | 1.3 | 212 mg | 0.48 |
| DIEA | 129.24 | 3.0 | 190 µl | 1.10 |
| DMF | | | 2.5 mL | |

The product 4 (140 mg, 71%) as light yellow oil was prepared using the BOP coupling described in Example 96 as for the synthesis of the compound 2. LC-MS [M+H] 533.4 (C31H36N2O6+H, requires 533.6). Compound was used in next synthetic step without additional purification.

Synthesis of (2S,3R)-2-{4-[(E)-4-(4-cyclopropylaminomethyl-phenyl)-but-3-en-1-ynyl]-benzoylamino}-3-hydroxy-butyric acid methyl ester (5)

| Reagent | MW | Eq. | mg/mL | mmol |
|---|---|---|---|---|
| Compound 4 | 532.6 | 1.0 | 140 mg | 0.26 |
| 4N HCl/dioxane | | 23.0 | 1.5 mL | 6.0 |
| dioxane | | | 1.5 mL | |

The product 5 (121 mg, 100%) as white solid was made using the General Method for Boc deprotection. LC-MS [M+H] 433.4 (C26H28N2O4+H, requires 433.5). Compound was used in next synthetic step without additional purification.

Synthesis of 4-[(E)-4-(4-cyclopropylaminomethyl-phenyl)-but-3-en-1-ynyl]-N-((1S,2R)-2-hydroxy-1-hydroxycarbamoyl-propyl)-benzamide (102-1)

| Reagent | MW | Eq. | mg/mL | mmol |
|---|---|---|---|---|
| Compound 5 × HCl | 468.97 | 1.0 | 121 mg | 0.26 |
| $NH_2OH$ × HCl | 69.49 | 7.4 | 135 mg | 1.94 |
| 25% NaOMe/MeOH | | 10.0 | 600 µl | 2.64 |
| MeOH | | | 4 mL | |
| THF | | | 1.5 mL | |

The product 102-1 (57.6 mg) as white solid was made using the General Method for hydroxamate formation. LC-MS [M+H] 434.4 (C25H27N3O4+H, requires 434.5).

| Compound | Scale (mmol)* | Yield (mg) | Yield (%)* | Purity (%) | [M + H] | Retention time (min)** |
|---|---|---|---|---|---|---|
| 102-1 | 0.37 | 57.6 | 28.5 | 90.1 | 434.3 | 4.41 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 102-2 | 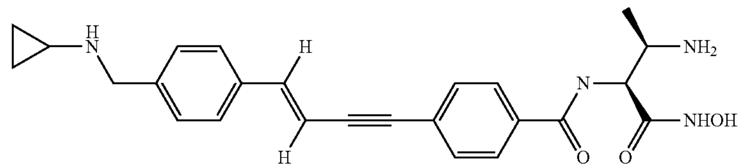 | 433.2 | 3.86 | B |
| 102-3 | 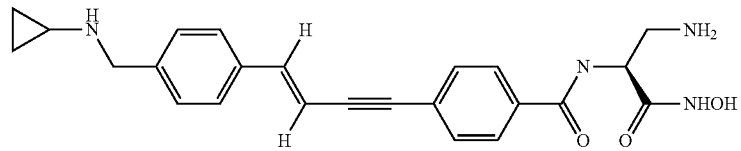 | 419.6 | 3.69 | B |
| 102-4 | 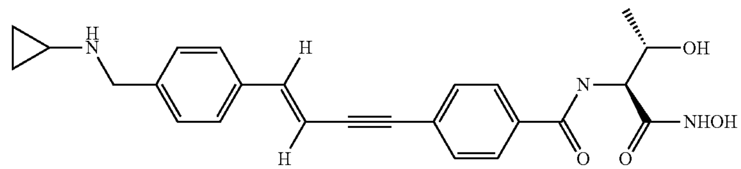 | 434.3 | 4.44 | B |
| 102-5* | 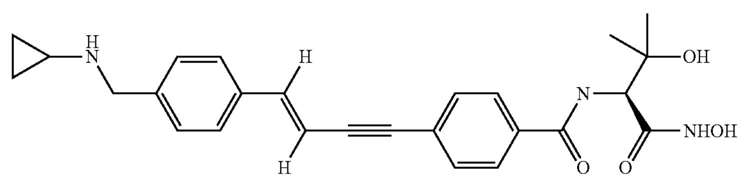 | 448.5 | 4.69 | B |
| 102-6 | 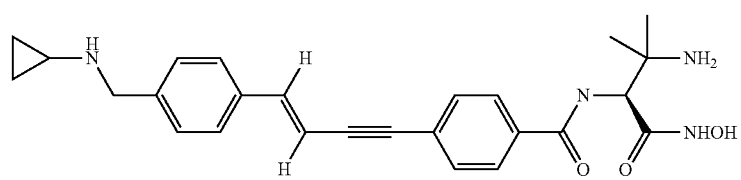 | 447.9 | 2.74 | A |
*Methyl ester of di-Me-Ser was prepared according to general procedure.
**Boc-protecting group before hydroxamate formation was removed by 2N HCl/dioxane
Example 103
N—[(S)-2-(2-Cyclopropylamino-acetylamino)-1-hydroxycarbamoyl-ethyl]-4-[(E)-4-(4-hydroxymethyl-phenyl)-but-3-en-1-ynyl]-benzamide (103-1)
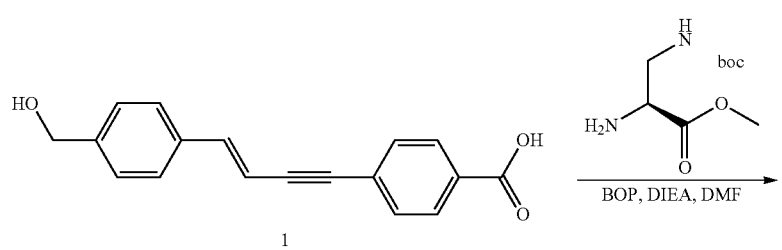

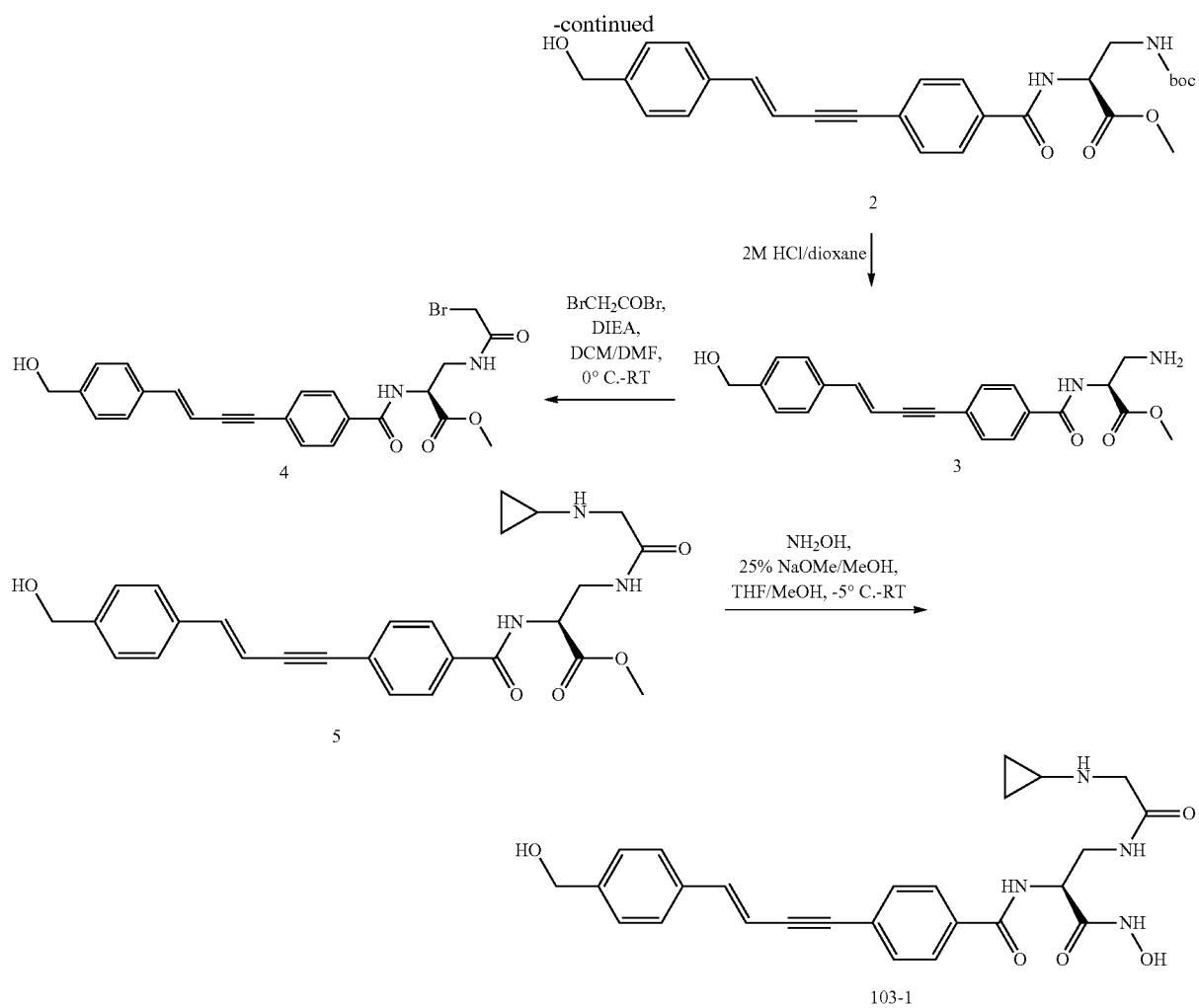

Synthesis of (S)-3-tert-butoxycarbonylamino-2-{4-[(E)-4-(4-hydroxymethyl-phenyl)-but-3-en-1-ynyl]-benzoylamino}-propionic acid methyl ester (2)

| Reagent | MW | Eq. | mg/mL | mmol |
|---|---|---|---|---|
| Compound 1 × sodium salt | 300.28 | 1.0 | 120 mg | 0.40 |
| H-(S)-DAP(Boc)-OMe × HCl | 254.7 | 1.2 | 122 mg | 0.48 |
| BOP | 442.28 | 1.3 | 230 mg | 0.52 |
| DIEA | 129.24 | 3.0 | 210 µl | 1.2 |
| DMF | | | 3 mL | |

The compound 2 (191 mg, 100%) as off-white solid was prepared using procedure of the BOP coupling described in Example 96 as for the synthesis of the compound 2. LC-MS [M+H] 479.3 (C27H30N2O6+H, requires 479.5). Compound was used in next synthetic step without additional purification.

Synthesis of (S)-3-amino-2-{4-[(E)-4-(4-hydroxymethyl-phenyl)-but-3-en-1-ynyl]-benzoylamino}-propionic acid methyl ester (3)

| Reagent | MW | Eq. | mg/mL | mmol |
|---|---|---|---|---|
| Compound 2 | 478.5 | 1.0 | 191 mg | 0.4 |
| 4N HCl/dioxane | | 30 | 3 mL | 12 |
| Dioxane/MeOH (1:1) | | | 3 mL | |

The product 3 (165 mg, 100%) as white solid was made using the General Method for Boc deprotection. LC-MS [M+H] 379.1 (C22H22N2O4+H, requires 379.4).

Synthesis of ((S)-3-(2-bromo-acetylamino)-2-{4-[(E)-4-(4-hydroxymethyl-phenyl)-but-3-en-1-ynyl]-benzoylamino}-propionic acid methyl ester (4)

| Reagent | MW | Eq. | mg/mL | mmol |
|---|---|---|---|---|
| Compound 3 × HCl | 414.9 | 1.0 | 165 mg | 0.40 |
| Bromoacetyl bromide | 201.86 | 1.0 | 35 µl | 0.40 |
| DIEA | 129.24 | 2.5 | 180 µl | 1.0 |

-continued

| Reagent | MW | Eq. | mg/mL | mmol |
|---|---|---|---|---|
| CH$_2$Cl$_2$ | | | 4 mL | |
| DMF | | | 1 mL | |

The target product 4 (199 mg, 100%), as yellow solid, was prepared using the method described in compound 4 of Example 100. LC-MS [M+H] 501.3 (C24H23BrN2O5+H, requires 500.4). Compound was used in next synthetic step without additional purification.

Synthesis of (S)-3-(2-cyclopropylamino-acetylamino)-2-{4-[(E)-4-(4-hydroxymethyl-phenyl)-but-3-en-1-ynyl]-benzoylamino}-propionic acid methyl ester (5)

| Reagent | MW | Eq. | g/mL | mmol |
|---|---|---|---|---|
| Compound 4 | 499.35 | 1.0 | 199 mg | 0.40 |
| Cyclopropylamine | 57.09 | 3.7 | 100 μl | 1.48 |
| CH$_2$Cl$_2$ | | | 4 mL | |

The target compound 5 (124 mg, 65%) as solid was prepared using the method described in compound 5 of Example 100. LC-MS [M+H] 476.3 (C27H29N3O5+H, requires 476.6).

Synthesis of N—[(S)-2-(2-cyclopropylamino-acetylamino)-1-hydroxycarbamoyl-ethyl]-4-[(E)-4-(4-hydroxymethyl-phenyl)-but-3-en-1-ynyl]-benzamide (103-1)

| Reagent | MW | Eq. | mg/mL | mmol |
|---|---|---|---|---|
| Compound 5 | 475.6 | 1.0 | 124 mg | 0.26 |
| NH$_2$OH × HCl | 69.49 | 7.4 | 135 mg | 1.94 |
| 25% NaOMe/MeOH | | 10.0 | 600 μl | 2.64 |
| MeOH | | | 4 mL | |
| THF | | | 1.5 mL | |

The product 6 (12.2 mg) as white solid was made using the General Method for hydroxamate formation. LC-MS [M+H] 477.3 (C26H28N4O5+H, requires 477.5).

| Compound | Scale (mmol)* | Yield (mg) | Yield (%)* | Purity (%) | [M + H] | Retention time (min)** |
|---|---|---|---|---|---|---|
| 103-1 | 0.4 | 12.2 | 5.2 | 98.9 | 477.3 | 4.8 |

*Based on the amount of carboxylic acid used in the coupling reaction
**HPLC-MS Method B Example 104

Synthesis of (E)-4-(4-Phenylbut-3-en-1-ynyl)benzoic acid (I-3)

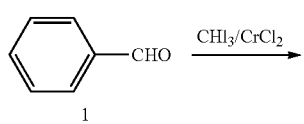

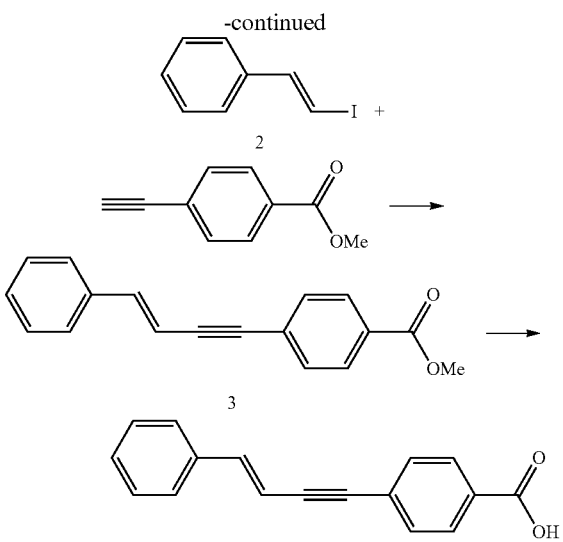

(E)-(2-Iodovinyl)benzene (2)

Chromium chloride anhydrous (37.1 g, 302 mmol, 8 eq) was added to THF (400 mL) under nitrogen at room temperature. A solution of triiodomethane (59.7 g, 151 mmol, 4 eq) in THF (500 mL) was added dropwise at 0° C. under nitrogen. Then a solution of benzaldehyde 1 (4.0 g, 37.7 mmol, 1 eq) in THF (100 mL) was added dropwise. The mixture was stirred at 0° C. for 2 hrs and then at room temperature for 2 more hours. The mixture was poured into ice water and extracted with EtOAc (800 mL×2). The organic phase was washed with 20% aq. Na$_2$S$_2$O$_3$ (300 mL), water (800 mL), brine (300 mL) dried (MgSO$_4$), filtered and concentrated under reduced pressure. The residue was triturated with EtOAc and hexanes. After filtration, the filtrates were concentrated to give the title compound 2 (7.2 g, 83%). $^1$H NMR (300 MHz, CDCl$_3$): δ ppm, 6.83 (d, J=15.1 Hz, 1H), 7.29-7.32 (m, 5H), 7.43 (d, J=14.8 Hz, 1H).

(E)-4-(4-Phenylbut-3-en-1-ynyl)benzoic acid methyl ester (3)

To a mixture of compound 2 (3.77 g, 16.4 mmol, 1.0 eq), 4 (2.62 g, 16.4 mmol, 1.0 eq), PdCl$_2$(PPh$_3$)$_2$ (0.58 mg, 0.82 mmol, 0.05 eq) and Et$_3$N (10 mL) in THF (100 mL) was added CuI (0.32 g, 1.64 mmol, 0.1 eq) under nitrogen at room temperature. The mixture was stirred at room temperature for 12 hrs. The reaction mixture was diluted with EtOAc (50 mL), filtered and concentrated. The residue was dissolved into EtOAc (300 mL) washed with water (300 mL) and brine (150 mL), and dried (MgSO$_4$). After filtration and concentration, the residue was purified by chromatography on silica gel (0 to 15% EtOAc/Hexanes) to give the title compound 3 (2.56 g, 60%). $^1$H NMR (300 MHz, DMSO-d$_6$): δ ppm, 3.87 (s, 3H), 6.70 (d, J=16.2 Hz, 1H), 7.19 (d, J=16.2 Hz, 1H), 7.35-7.43 (m, 3H), 7.59-7.64 (m, 4H), 7.97 (d, J=8.22 Hz, 2H)

(E)-4-(4-Phenylbut-3-en-1-ynyl)benzoic acid (I-3)

The product I-3 (1.45 g, 61%) was made and separated using the General Method for basic hydrolysis. MS (m/z): [M−H]$^+$=247, $^1$H NMR (300 MHz, DMSO-d$_6$) δ ppm, 6.70

(d, J=16.2 Hz, 1H), 7.19 (d, J=16.2 Hz, 1H), 7.32-7.42 (m, 3H), 7.58-7.61 (m, 4H), 7.95 (d, J=8.5 Hz, 2H).

N-((1S,2R)-2-Hydroxy-1-hydroxycarbamoyl-propyl)-4-((E)-4-phenyl-but-3-en-1-ynyl)-benzamide (104-1)

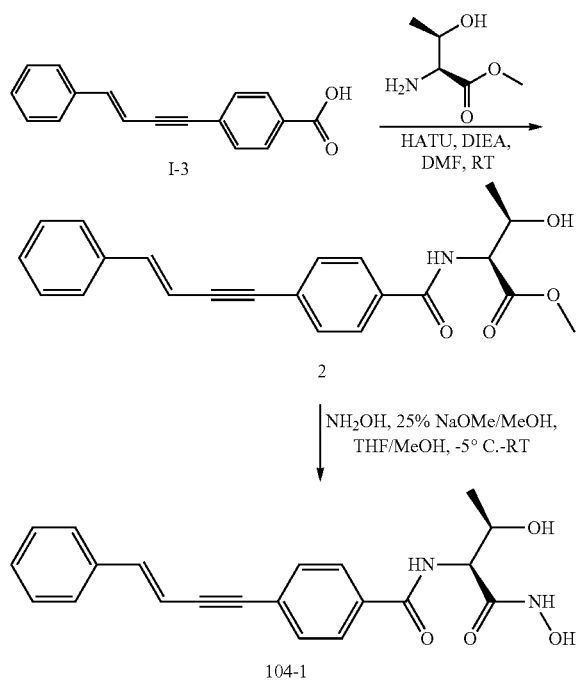

Synthesis of (2S,3R)-3-hydroxy-2-[4-((E)-4-phenyl-but-3-en-1-ynyl)-benzoylamino]-butyric acid methyl ester (2)

| Reagent | MW | Eq. | mg/mL | mmol |
|---|---|---|---|---|
| Compound 1 (Ach-Tr-Db-OH) | 248.28 | 1.0 | 85 mg | 0.34 |
| H-(S)-Thr-OMe × HCl | 169.6 | 1.1 | 63 mg | 0.37 |

-continued

| Reagent | MW | Eq. | mg/mL | mmol |
|---|---|---|---|---|
| HATU | 380.2 | 1.2 | 155 mg | 0.41 |
| DIEA | 129.24 | 3.0 | 178 μl | 1.0 |
| DMF | | | 2 mL | |

The product 2 (123 mg, 100%) as white solid was prepared using the General Method for HATU coupling. LC-MS [M+H] 364.7 (C22H21NO4+H, requires 364.42). Compound was used in next synthetic step without additional purification.

Synthesis of N-((1S,2R)-2-hydroxy-1-hydroxycarbamoyl-propyl)-4-((E)-4-phenyl-but-3-en-1-ynyl)-benzamide (23)

| Reagent | MW | Eq. | mg/mL | mmol |
|---|---|---|---|---|
| Compound 2 | 363.4 | 1.0 | 123 mg | 0.34 |
| NH2OH × HCl | 69.49 | 8.0 | 188 mg | 2.7 |
| 25% NaOMe/MeOH | | 10.0 | 777 μl | 3.4 |
| MeOH | | | 4 mL | |
| THF | | | 1.5 mL | |

The product 104-1 (58.7 mg, 48%) as white solid was made using the General Method for hydroxamate formation. LC-MS [M+H] 365.4 (C21H20N2O4+H, requires 365.4).

| Compound | Scale (mmol)* | Yield (mg) | Yield (%)* | Purity (%) | [M + H] | Retention time (min)** |
|---|---|---|---|---|---|---|
| 104-1 | 0.34 | 58.7 | 48 | 98.0 | 365.4 | 7.28 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 104-2 | 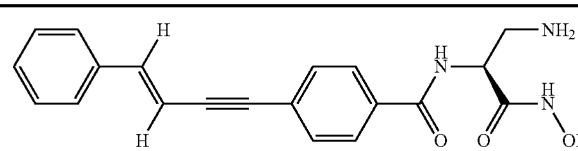 | 350.7 | 6.38 | B |
| 104-3* | 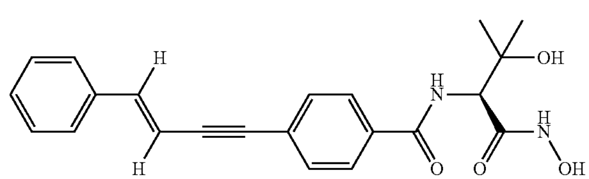 [SMILES: CC(C)(O)[C@H](NC(=O)c1ccc(C#C/C=C/c2ccccc2)cc1)C(=O)NO] | 379.7 | 7.58 | B |

| Compound # | Structure | MH+ (m/z) | Ret. Time (min) | HPLC-MS Method |
|---|---|---|---|---|
| 104-4 | 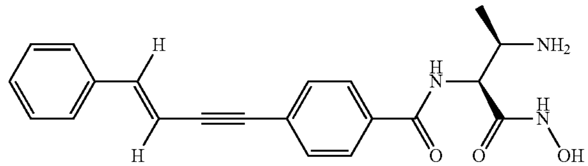 [SMILES: C[C@@H](N)[C@H](NC(=O)c1ccc(C#C/C=C/c2ccccc2)cc1)C(=O)NO] | 364.7 | 6.46 | B |
| 104-5** | 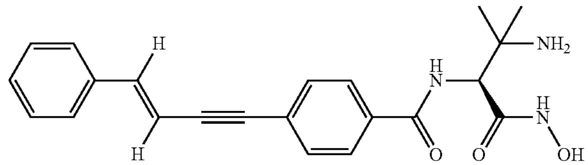 [SMILES: CC(C)(N)[C@H](NC(=O)c1ccc(C#C/C=C/c2ccccc2)cc1)C(=O)NO] | 378.5 | 4.55 | A |

*Methyl ester of diMeSer was prepared according to general procedure.
**Boc-protecting group before hydroxamate formation was removed by 4N HCl/dioxane.

Example 105

N—[(S)-2-(2-Cyclopropylamino-acetylamino)-1-hydroxy-carbamoyl-ethyl]-4-((E)-4-phenyl-but-3-en-1-ynyl)-benzamide (105-1)

N—{(S)-1-Hydroxycarbamoyl-2-[2-((S)-1-phenyl-ethylamino)-acetylamino]-ethyl}-4-((E)-4-phenyl-but-3-en-1-ynyl)-benzamide (105-2)

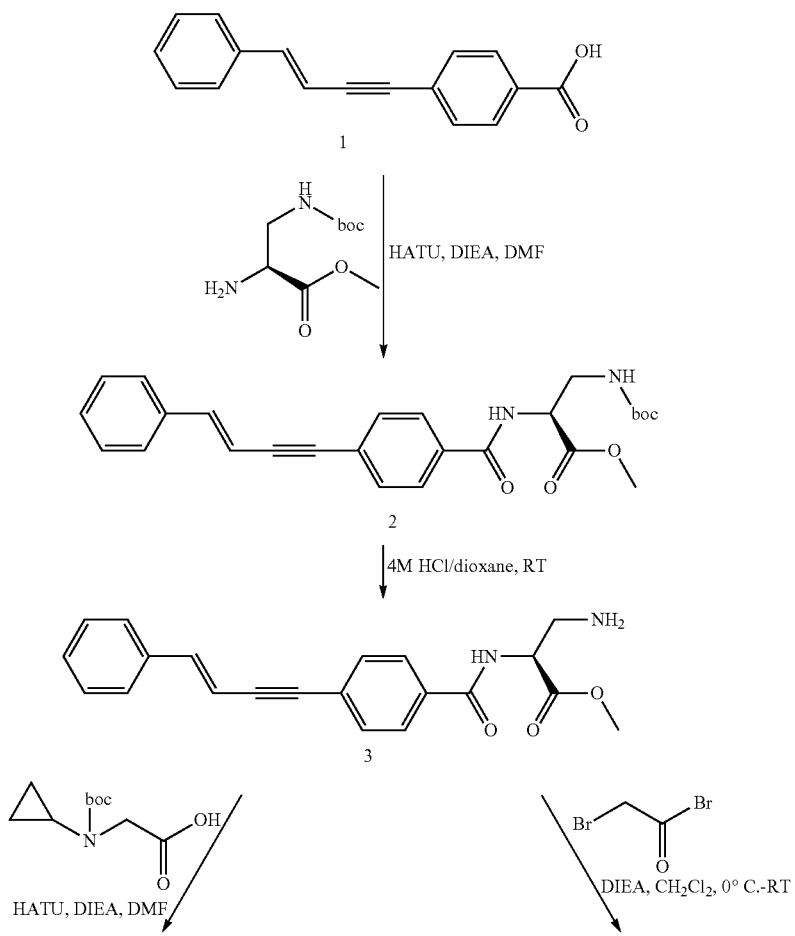

-continued

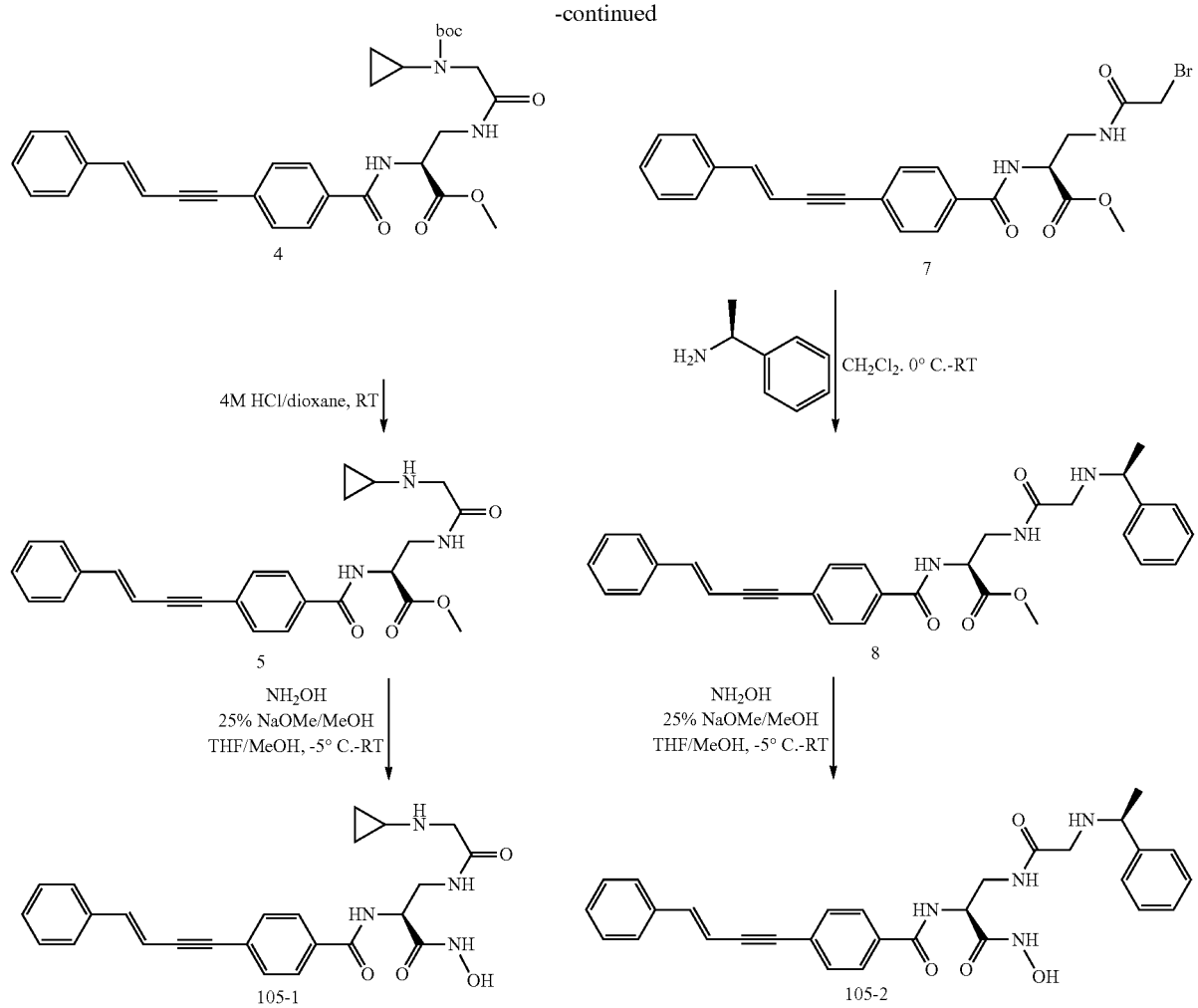

Synthesis of (S)-3-tert-butoxycarbonylamino-2-[4-((E)-4-phenyl-but-3-en-1-ynyl)-benzoylamino]-propionic acid methyl ester (2)

| Reagent | MW | Eq. | mg/mL | mmol |
|---|---|---|---|---|
| Compound 1 (Ach-Tr-Db-OH) | 248.3 | 1.0 | 189 mg | 0.76 |
| H-(S)-DAP(Boc)-OMe × HCl | 254.7 | 1.2 | 232 mg | 0.91 |
| HATU | 380.2 | 1.2 | 346 mg | 0.91 |
| DIEA | 129.2 | 3.0 | 397 µl | 2.28 |
| DMF | | | 4 mL | |

The product 2 (328 mg, 100%) as off-white solid was prepared using the General Method for HATU coupling. LC-MS [M+H] 433.8 (C26H28N2O4+H, requires 433.52). Compound was used in next synthetic step without additional purification.

Synthesis of ((S)-3-amino-2-[4-((E)-4-phenyl-but-3-en-1-ynyl)-benzoylamino]-propionic acid methyl ester (3)

| Reagent | MW | Eq. | mg/mL | mmol |
|---|---|---|---|---|
| Compound 2 | 432.5 | 1.0 | 328 mg | 0.76 |
| 4N HCl/dioxane | | 31.6 | 6 mL | 24.0 |

The product 3 (292 mg, 100%) as white solid was made using the General Method for Boc deprotection. LC-MS [M+H] 349.7 (C21H20N2O3+H, requires 349.41).

Synthesis of (S)-3-[2-(tert-butoxycarbonyl-cyclopropyl-amino)-acetylamino]-2-[4-((E)-4-phenyl-but-3-en-1-ynyl)-benzoylamino]-propionic acid methyl ester (4)

| Reagent | MW | Eq. | mg/mL | mmol |
|---|---|---|---|---|
| Compound 3 × HCl | 384.9 | 1.0 | 146 mg | 0.38 |
| N-Boc-N-Cyclopropyl-Gly-OH | 215.25 | 1.1 | 90 mg | 0.42 |

-continued

| Reagent | MW | Eq. | mg/mL | mmol |
|---|---|---|---|---|
| HATU | 380.2 | 1.2 | 175 mg | 0.46 |
| DIEA | 129.2 | 3.0 | 198 µl | 1.14 |
| DMF | | | 3 mL | |

The product 4 (207 mg, 100%) as light yellow oil was prepared using the General Method for HATU coupling. LC-MS [M+H] 546.4 (C31H35N3O6+H, requires 546.64). Compound was used in next synthetic step without additional purification.

Synthesis of (S)-3-(2-cyclopropylamino-acetylamino)-2-[4-((E)-4-phenyl-but-3-en-1-ynyl)-benzoylamino]-propionic acid methyl ester (5)

| Reagent | MW | Eq. | mg/mL | mmol |
|---|---|---|---|---|
| Compound 4 | 545.6 | 1.0 | 207 mg | 0.38 |
| 4N HCl/dioxane | | 31.6 | 3 mL | 12.0 |

The product 5 (183 mg, 100%) as white solid was made using the General Method for Boc deprotection. LC-MS [M+H] 446.3 (C26H27N3O4+H, requires 446.52).

Synthesis of N—[(S)-2-(2-cyclopropylamino-acetylamino)-1-hydroxycarbamoyl-ethyl]-4-((E)-4-phenyl-but-3-en-1-ynyl)-benzamide (105-1)

| Reagent | MW | Eq. | mg/mL | mmol |
|---|---|---|---|---|
| Compound 5 × HCl | 481.97 | 1.0 | 183 mg | 0.38 |
| NH2OH × HCl | 69.49 | 8.0 | 211 mg | 3.0 |
| 25% NaOMe/MeOH | | 10.0 | 868 µl | 3.8 |
| MeOH | | | 4 mL | |
| THF | | | 1.5 mL | |

The product 105-1 (21.7 mg, 10%) as white solid was made using the General Method for hydroxamate formation. LC-MS [M+H] 447.3 (C25H26N4O4+H, requires 447.52).

| Compound | Scale (mmol)* | Yield (mg) | Yield (%)* | Purity (%) | [M + H] | Retention time (min)** |
|---|---|---|---|---|---|---|
| 105-1 | 0.38 | 21.7 | 10 | 99.0 | 447.3 | 6.49 |

*Based on the amount of carboxylic acid used in the coupling reaction
**HPLC-MS Method B

Synthesis of (S)-3-(2-bromo-acetylamino)-2-[4-((E)-4-phenyl-but-3-en-1-ynyl)-benzoylamino]-propionic acid methyl ester (7)

| Reagent | MW | Eq. | mg/mL | mmol |
|---|---|---|---|---|
| Compound 3 × HCl | 384.9 | 1.0 | 146 mg | 0.38 |
| Bromoacetyl bromide | 201.86 | 1.08 | 36 µl | 0.41 |
| DIEA | 129.24 | 2.6 | 174 µl | 1.0 |
| CH2Cl2 | | | 3 mL | |

The target product 7 (150 mg, 85%), as yellow solid, was prepared using the method described in compound 4 of Example 19. LC-MS [M+H] 470.7 (C23H21BrN2O4+H, requires 470.34).

Synthesis of (S)-2-[4-((E)-4-phenyl-but-3-en-1-ynyl)-benzoylamino]-3-[2-((S)-1-phenyl-ethylamino)-acetylamino]-propionic acid methyl ester (8)

| Reagent | MW | Eq. | g/mL | mmol |
|---|---|---|---|---|
| Compound 7 | 469.3 | 1.0 | 150 mg | 0.32 |
| (S)-(−)-alpha-Methylbenzylamine | 121.18 | 3.0 | 124 µl | 0.96 |
| CH2Cl2 | | | 3 mL | |

The target compound 8 (155 mg, 95%) as a solid, was prepared using the method described in compound 5 of Example 19. LC-MS [M+H] 510.3 (C31H31N3O4+H, requires 510.61).

N—{(S)-1-Hydroxycarbamoyl-2-[2-((S)-1-phenyl-ethylamino)-acetylamino]-ethyl}-4-((E)-4-phenyl-but-3-en-1-ynyl)-benzamide (105-2)

| Reagent | MW | Eq. | mg/mL | mmol |
|---|---|---|---|---|
| Compound 8 | 509.61 | 1.0 | 155 mg | 0.30 |
| NH2OH × HCl | 69.49 | 8.0 | 167 mg | 2.4 |
| 25% NaOMe/MeOH | | 10.0 | 685 µl | 3.0 |
| MeOH | | | 3 mL | |
| THF | | | 1.2 mL | |

The product 105-2 (41.7 mg) as white solid was made using the General Method for hydroxamate formation. LC-MS [M+H] 511.8 (C30H30N4O4+H, requires 511.61).

| Compound | Scale (mmol)* | Yield (mg) | Yield (%)* | Purity (%) | [M + H] | Retention time (min)** |
|---|---|---|---|---|---|---|
| 105-2 | 0.38 | 41.7 | 17.5 | 97.3 | 511.8 | 7.38 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 105-3 | 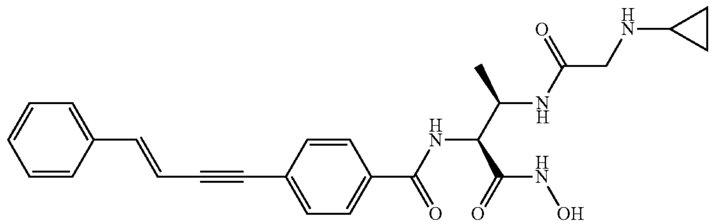 [SMILES: C[C@@H](NC(=O)CNC1CC1)[C@H](NC(=O)c1ccc(C#C/C=C/c2ccccc2)cc1)C(=O)NO] | 460.4 | 7.79 | B |
| 105-4 | 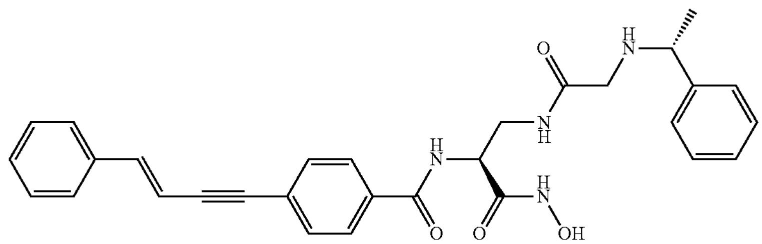 [SMILES: C[C@@H](NCC(=O)NC[C@H](NC(=O)c1ccc(C#C/C=C/c2ccccc2)cc1)C(=O)NO)c1ccccc1] | 511.8 | 7.37 | B |
| 105-5 | 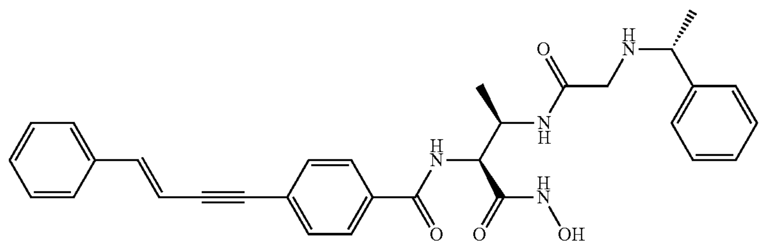 [SMILES: C[C@@H](NCC(=O)N[C@H](C)[C@H](NC(=O)c1ccc(C#C/C=C/c2ccccc2)cc1)C(=O)NO)c1ccccc1] | 525.2 | 7.56 | B |

Example 106

Methyl 4-[(3E)-4-chlorobut-3-en-1-yn-1-yl]benzoate

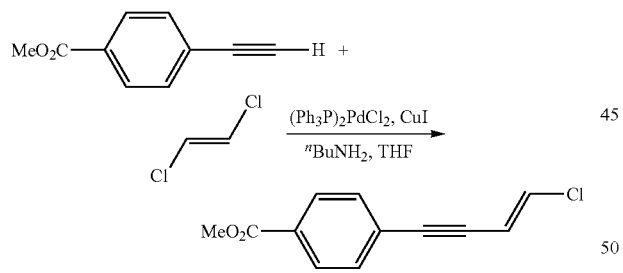

Methyl 4-[(3E)-4-chlorobut-3-en-1-yn-1-yl]benzoate

Methyl 4-ethynylbenzoate (2.0 g, 12.5 mmol, 1 eq) was dissolved in 200 mL anhydrous THF under nitrogen. n-Butylamine (2.5 mL, 25.3 mmol, 2 eq) was added followed by trans-1,2-dichloroethylene (1.95 mL, 25.3 mmol, 2 eq). Bis(triphenylphosphine)palladium(II) dichloride (0.44 g, 0.63 mmol, 0.05 eq) was added as a solid, and the reaction mixture was stirred for 20-30 minutes under nitrogen. Copper iodide (0.26 g, 1.4 mmol, 0.11 eq) was added as a solid to the clear amber solution, which became very dark within ten minutes. Stirring under nitrogen at room temperature was continued overnight. The reaction mixture was filtered through Celite and THF passed through the filtercake until the filtrate was colorless. The volatiles were removed via rotary and the dark red-brown residue partitioned between ethyl acetate and water. The layers were separated and the organic layer washed with brine, dried over Na$_2$SO$_4$, and stripped to give the product as a dark brown solid. The crude material was purified by chromatography on silica gel using 2.5% ethyl acetate in hexanes as eluent. Yield: 1.55 g, 56%. TLC R$_f$=0.46 (1:9 ethyl acetate:hexanes). APCI(−) m/z=219 amu as a minor signal. $^1$H NMR (CDCl$_3$, 300 MHz) δ ppm: 7.99 (d, J=8.5 Hz, 2H), 7.48 (d, J=8.5 Hz, 2H), 6.67 (d, J=13.8 Hz, 2H), 6.16 (d, J=13.5 Hz, 2H), 3.92 (s, 3H).

Methyl 4-[(3E)-4-pyridin-4-ylbut-3-en-1-yn-1-yl]benzoate

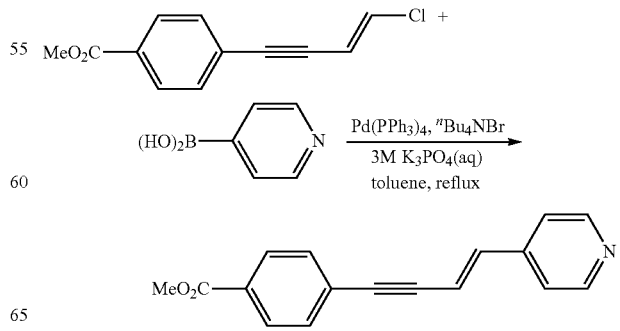

Methyl 4-[(3E)-4-pyridin-4-ylbut-3-en-1-yn-1-yl]benzoate

Methyl 4-[(3E)-4-chlorobut-3-en-1-yn-1-yl]benzoate (47 mg, 0.21 mmol, 1 eq), 4-pyridylboronic acid (28 mg, 0.23 mmol, 1.1 eq) and tetra-n-butylammonium bromide (58 mg, 0.21 mmol, 1 eq) were placed in a flask and dissolved in 5 mL toluene. Aqueous $K_3PO_4$ (3 M, 0.20 mL, 0.60 mmol, 2.8 eq) was added, followed by tetrakis(triphenylphosphine)palladium(O) (18 mg, 0.016 mmol, 0.08 eq). The reaction mixture was heated at reflux for three hours, then stirred at room temperature overnight. TLC in 1:9 ethyl acetate:hexanes confirmed the absence of starting material. The reaction mixture was diluted with ethyl acetate and washed sequentially with water and brine, then the volatiles were removed via rotary. The residue was plated onto silica and eluted with 33% ethyl acetate/hexanes to give the product as a yellow solid. Yield: 26 mg (46%). TLC $R_f$=0.20 (40% ethyl acetate/hexanes). APCI(+) m/z=246 amu. $^1$H NMR (CDCl$_3$, 300 MHz) δ ppm: 8.60 (d, J=6.1 Hz, 2H), 8.02 (d, J=8.3 Hz, 2H), 7.54 (d, J=8.5 Hz, 2H), 7.28 (d, J=6.3 Hz, 2H), 6.99 (d, J=16.2 Hz, 2H), 6.59 (d, J=16.2 Hz, 2H), 3.93 (s, 3H).

N-((1S,2R)-2-Hydroxy-1-hydroxycarbamoyl-propyl)-4-((E)-4-pyridin-4-yl-but-3-en-1-ynyl)-benzamide (106-1)

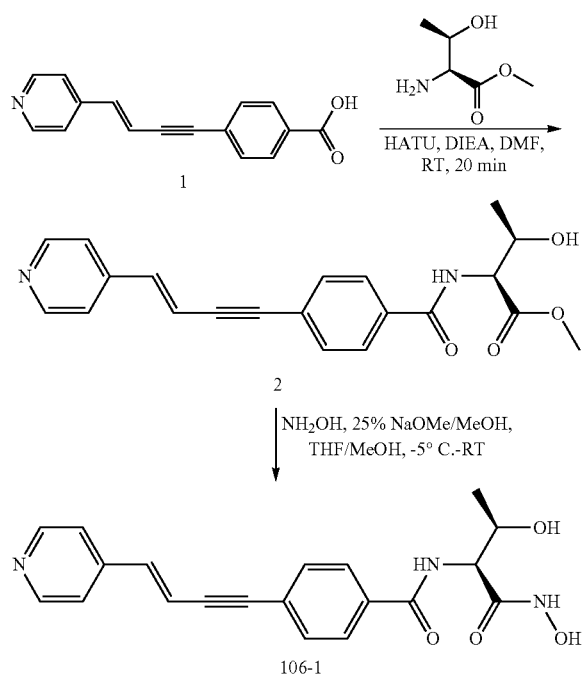

Synthesis of (2S,3R)-3-hydroxy-2-[4-((E)-4-pyridin-4-yl-but-3-en-1-ynyl)-benzoylamino]-butyric acid methyl ester (2)

| Reagent | MW | Eq. | mg/mL | mmol |
|---|---|---|---|---|
| Compound 1 × sodium salt | 271.25 | 1.0 | 109 mg | 0.4 |
| H-(S)-Thr-OMe × HCl | 169.6 | 1.2 | 82 mg | 0.48 |
| HATU | 380.2 | 1.2 | 183 mg | 0.48 |
| DIEA | 129.24 | 3.0 | 209 µl | 1.2 |
| DMF | | | 2.5 mL | |

The compound 2 (146 mg, 100%) as light yellow solid was prepared using the General Method for HATU coupling. LC-MS [M+H] 365.7 (C21H20N2O4+H, requires 365.4). Compound was used in next synthetic step without additional purification.

Synthesis of N-((1S,2R)-2-hydroxy-1-hydroxycarbamoyl-propyl)-4-((E)-4-pyridin-4-yl-but-3-en-1-ynyl)-benzamide (106-1)

| Reagent | MW | Eq. | mg/mL | mmol |
|---|---|---|---|---|
| Compound 2 | 364.4 | 1.0 | 146 mg | 0.4 |
| NH$_2$OH × HCl | 69.49 | 8.0 | 222 mg | 3.2 |
| 25% NaOMe/MeOH | | 10.0 | 914 µl | 4.0 |
| MeOH | | | 5 mL | |
| THF | | | 2 mL | |

The product 106-1 (52 mg) as off-white solid was made using the General Method for hydroxamate formation. LC-MS [M+H] 366.8 (C20H19N3O4+H, requires 366.4).

| Compound | Scale (mmol)* | Yield (mg) | Yield (%)* | Purity (%) | [M + H] | Retention time (min)** |
|---|---|---|---|---|---|---|
| 106-1 | 0.4 | 52 mg | 27.2% | 99.2 | 366.8 | 2.30 |

*Based on the amount of carboxylic acid used in the coupling reaction
**HPLC-MS Method A Each of the following compounds was synthesized as described above.

| Compound # | Structure | MH+ (m/z) | Ret. Time (min) | HPLC-MS Method |
|---|---|---|---|---|
| 106-2* | 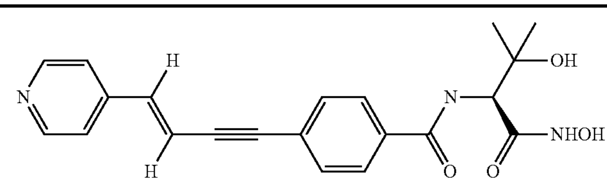 | 380.6 | 3.22 | B |

-continued
| Compound # | Structure | MH+ (m/z) | Ret. Time (min) | HPLC-MS Method |
|---|---|---|---|---|
| 106-3** | 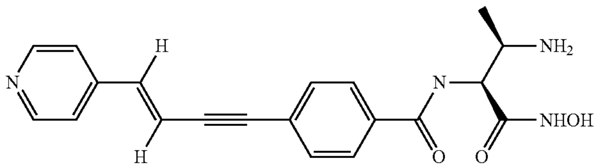 | 365.8 | 1.97 | B |
| 106-4 | 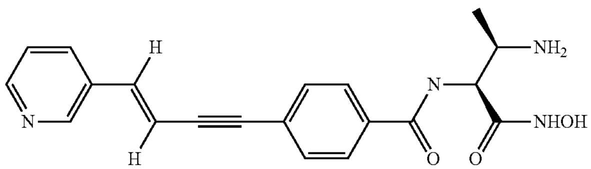 | 365.9 | 1.98 | A |
| 106-5 | 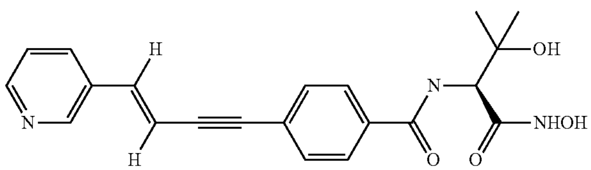 | 380.8 | 3.22 | B |
| 106-6 | 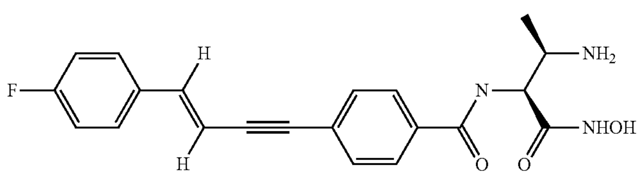 | 382.8 | 4.46 | A |
| 106-7 | 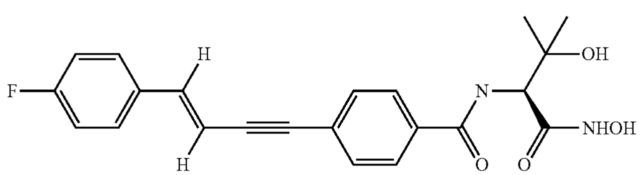 | 397.7 | 5.14 | A |
*Methyl ester of di-Me-Ser was prepared according to general procedure.
**Fmoc-protecting group before hydroxamate formation was removed by 20% piperidine/EtOAc.
Example 107
4-((E)-4-Cyclopropyl-but-3-en-1-ynyl)-N—((S)-2-hydroxy-1-hydroxycarbamoyl-2-methyl-propyl)-benzamide (107-1)
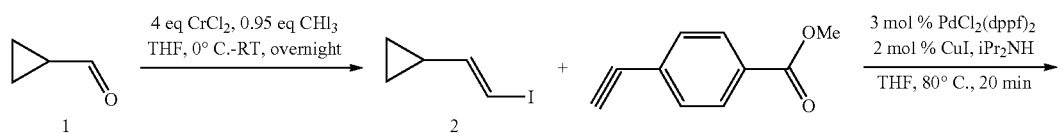

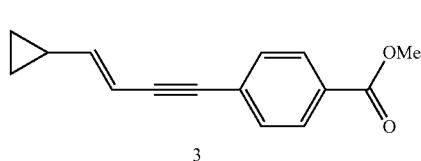
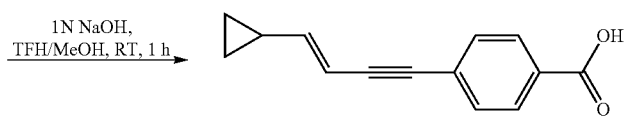
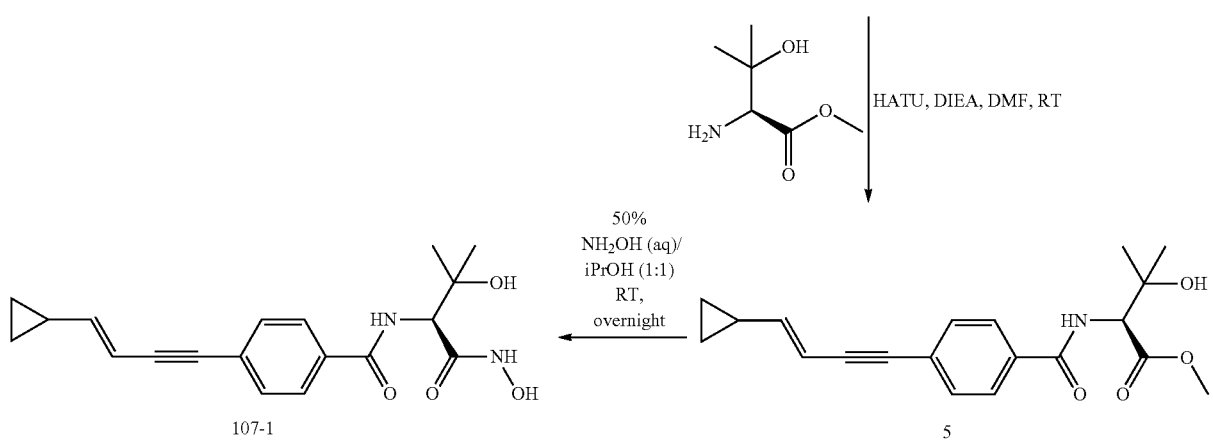

Synthesis of ((E)-2-Iodo-vinyl)-cyclopropane (2)

The chromium (II) chloride (15.0 g, 122.1 mmol) was placed in a flask in the glove box with a stir bar and capped with a septum. With good stirring, the THF (anh., 120 mL) was added quickly at ambient temperature. After stirring for 15-30 min under nitrogen, the flask was immersed in an ice bath for 30 min. To the cold suspension was added dropwise a solution of iodoform (11.42 g, 29.0 mmol) in THF (anh., 75 mL). After 5 min, the solution of cyclopropylaldehyde 1 (2.43 mL, 30.5 mmol) in THF (anh., 60 mL) was added neat dropwise to the vigorously stirred suspension. After stirring at 0° C. for 2 h, the reaction was allowed to warm to room temperature overnight. The reaction mixture was poured into and ice water and extracted with pentane (300 mL×2). The organic phase was washed with 20% aq. $Na_2S_2O_3$ (150 mL), water (300 mL), brine (300 mL), then dried over MgSO4 (anh.), filtered and pentane was concentrated in vacuo at 220 mbar to minimum volume (20 mL). The residue was used in the next synthetic step without additional purification (caution: cyclopropyl vinyl iodide is volatile material).

Synthesis of 4-((E)-4-cyclopropyl-but-3-en-1-ynyl)-benzoic acid methyl ester (3)

A solution of 4-ethynyl-benzoic acid methyl ester (1.76 g, 11.0 mmol), diisopropylamine (4.7 mL, 33 mmol), the catalysts $PdCl_2(dppf)_2$ (302 mg, 0.37 mmol) and the copper (I) iodide (46 mg, 0.24 mmol) in THF (anh., 30 mL) was purged for 10 min with dry nitrogen. Then, this mixture was added to a pentane solution of compound 1 (13.5 mL, C=~200 mg/mL, ~2.7 g, 14 mmol). Reaction mixture was heated at 80° C. for 20 min and cooled to ambient temperature. The reaction mixture was then dissolved in EtOAc (200 mL), washed with water (150 mL), 0.5 N HCl (150 mL) and brine (150 mL×2). Organic phase was dried over anh. Na2SO4, evaporated in vacuo. Residue was subjected to flash chromatography on CombiFlash® Companion unit equipped with RediSep® flash column (normal phase, 35-60 micron average particle size silica gel, 40 g, Teledyne Isco); flow rate=40 mL/min; mobile phase A: hexane; mobile phase B: EtOAc; gradient 0-30% B in 60 min. Fractions containing the desired material were combined and concentrated in vacuo to provide target material 3 (1 g, 40%) as yellow oil. LC-MS [M+H] 227.7 (C15H14O2+H, requires 227.29).

Synthesis of 4-((E)-4-cyclopropyl-but-3-en-1-ynyl)-benzoic acid (4)

| Reagent | MW | Eq. | g/mL | mmol |
|---|---|---|---|---|
| Compound 3 | 226.28 | 1.0 | 1.0 g | 4.41 |
| 1N NaOH | | 4.0 | 18 mL | 18.0 |
| THF/MeOH (1:1) | | | 18 mL | |

The compound 4 (800 mg, 85%) as a white solid was made and separated using the General Method for basic hydrolysis. LC-MS [M+H] 213.5 (C14H12O2+H, requires 213.3). Compound was used in next synthetic step without additional purification. Check of a sample by LC-MS showed a major product peak (Rt=5.10 min, E-isomer) with ~12% of the cis-isomer (Rt=4.96 min) (HPLC-MS Method A).

Synthesis of (S)-2-[4-((E)-4-cyclopropyl-but-3-en-1-ynyl)-benzoylamino]-3-hydroxy-3-methyl-butyric acid methyl ester (5)

| Reagent | MW | Eq. | mg/mL | mmol |
|---|---|---|---|---|
| Compound 4 | 212.25 | 1.0 | 85 mg | 0.4 |
| H-(S)-diMe-Ser-OMe × HCl* | 169.6 | 1.13 | 76 mg | 0.45 |
| HATU | 380.2 | 1.2 | 183 mg | 0.48 |

-continued

| Reagent | MW | Eq. | mg/mL | mmol |
|---|---|---|---|---|
| DIEA | 129.24 | 3.0 | 209 µl | 1.2 |
| DMF | | | 2 mL | |

*Methyl ester of di-Me-Ser was prepared according to general procedure.

The compound 5 (130 mg, 96%) as white solid was prepared using the General Method for HATU coupling. LC-MS [M+H] 342.8 (C20H23NO4+H, requires 342.4).

Synthesis of 4-((E)-4-cyclopropyl-but-3-en-1-ynyl)-N—((S)-2-hydroxy-1-hydroxycarbamoyl-2-methyl-propyl)-benzamide (107-1)

Isopropyl alcohol (2 mL) was added to triple-double ester 5 (130 mg, 0.38 mmol) and the mixture was cooled in an ice bath for 5 min. NH$_2$OH (50% aq, 2 mL, 32.8 mmol) was added to the mixture. After 5 min, the ice bath was removed and the reaction mixture was stirred until reaction was complete (~16 h, as determined by LC-MS analysis). Solvent volume was reduced by half using a nitrogen stream and water (8 mL) was added. The suspension was thoroughly agitated (vibro mixer and sonication), centrifuged and the supernatant was discarded. Water (8 mL) was added to the solid and the suspension was thoroughly agitated, centrifuged and the supernatant was discarded. Solid was dissolved in DMSO (600 µl) and subjected to HPLC purification. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophilized to provide the target product (66.3 mg) as white solid. LC-MS [M+H] 343.7 (C$_{19}$H$_{22}$N$_2$O$_4$+H, requires 343.4).

| Compound | Scale (mmol)* | Yield (mg) | Yield (%)* | Purity (%) | [M + H] | Retention time (min)** |
|---|---|---|---|---|---|---|
| 107-1 | 0.4 | 66.3 mg | 48.4% | 97.5 | 343.7 | 6.41 |

*Based on the amount of carboxylic acid used in the coupling reaction
**HPLC-MS Method B Each of the following compounds was synthesized as described above.

| Compound # | Structure | MH+ (m/z) | Ret. Time (min) | HPLC-MS Method |
|---|---|---|---|---|
| 107-2 | 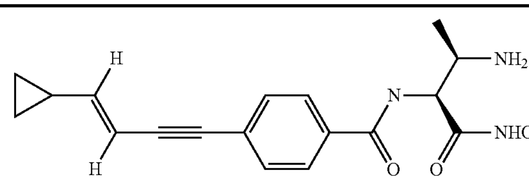 | 328.7 | 3.86 | A |
| 107-3 | 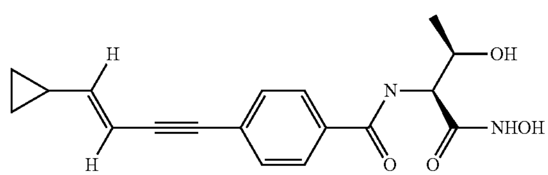 | 329.8 | 4.32 | B |
| 107-4* | 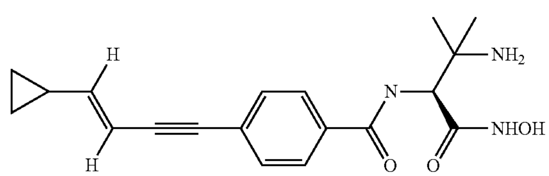 | 342.7 | 5.59 | B |
| 107-5* | 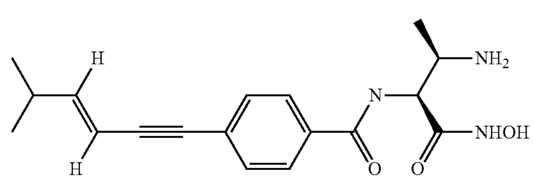 | 330.7 | 6.01 | A |
| 107-6* | 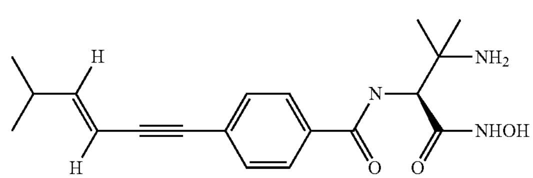 | 344.8 | 6.14 | B |

*Boc-protecting group before hydroxamate formation was removed by 2N HCl/dioxane.
**Desired scaffold for this product was prepared starting from isobutyraldehyde

Example 108

Synthesis of (E)-4-(hex-3-en-1-ynyl)benzoic acid (IC-10)

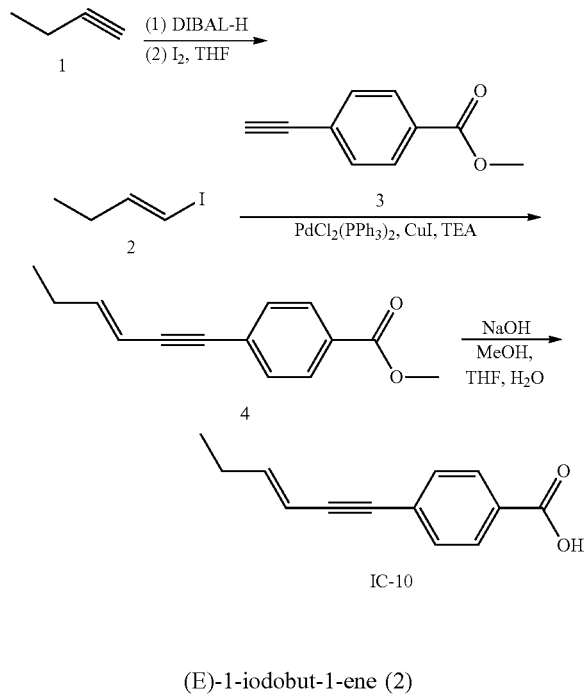

(E)-1-iodobut-1-ene (2)

To but-1-yne (1.5 g, 27.78 mmol) in a sealable tube at 0° C. was added DIBAL-H in hexane (1M; 28 mL, 28 mmol). The tube was sealed and allowed to stand for 30 min at R.T. before being heated to 55-60° C. for 4 h. After cooling down, the reaction mixture was evaporated in vacuo (using a vacuum manifold) and the residue was dissolved in THF (15 mL) at 0° C. The resultant solution was cooled to −78° C. and $I_2$ (8.47 g, 33.3 mmol) in THF (30 mL) was added dropwise. The mixture was allowed to warm to 0° C. And transferred via cannula to a stirred mixture of 1 M HCl (70 mL) and $Et_2O$ (40 mL). the layers were separated and the aqueous layer was extracted with saturated aqueous sodium thiosulfate (40 mL), 1M NaOH (40 mL), distilled water (40 mL) and brine (40 ml), dried over $Na_2SO_4$, filtered, and rotary evaporated at 0° C. to give compound 2 as a brown liquid and to next step without purification.

(E)-Methyl 4-(hex-3-en-1-ynyl)benzoate (4)

| Reagent | MW | Eq. | mmol | g, mL |
|---|---|---|---|---|
| Compound 2 | 182.00 | 1.0 | 16.2 | 2.94 g |
| Methyl 4-ethynylbenzoate | 160.17 | 1.0 | 16.2 | 2.58 g |
| PdCl₂(PPh₃)₂ | 701.90 | 0.1 | 1.62 | 1.13 g |
| CuI | 190.45 | 0.1 | 1.62 | 0.216 g |
| TEA | 101.19 | 13.0 | 220 | 30 mL |
| THF | | | | 150 mL |

The compound 4 (1.8 g, 52%) as a light yellow liquid was prepared by using the method described in compound 5 of Example 96. ¹H NMR (500 MHz, CDCl₃): δ ppm, 1.06 (t, J=15 Hz, 3H), 2.2 (m, 2H), 3.91 (s, 3H), 5.70 (d, J=15.5 Hz, 1H), 6.35 (m, 1H), 7.46 (d, J=8 Hz, 2H), 7.97 (d, J=8.5 Hz, 2H).

(E)-4-(hex-3-en-1-ynyl)benzoic acid (IC-10)

| Reagent | MW | Eq. | mmol | g, mL |
|---|---|---|---|---|
| Compound 4 | 214.26 | 1.0 | 8.41 | 1.8 g |
| NaOH(2N solution) | | | | 9 mL |
| THF | | | | 9 mL |
| Methanol | | | | 9 mL |

The compound IC-10 (1.5 g, 89%) as a white solid was made and separated using the General Method for basic hydrolysis. ¹H NMR (500 MHz, DMSO-d₆): δ ppm, 1.0 (t, J=15 Hz, 3H), 2.18 (m, 2H), 5.83 (d, J=16 Hz, 1H), 6.37 (m, 1H), 7.53 (d, J=8.5 Hz, 2H), 7.92 (d, J=8.5 Hz, 2H), 13.12 (s, 1H)

Synthesis of (E)-4-(4-(1-methyl-1H-pyrazol-4-yl)but-3-en-1-ynyl)benzoic acid (IC-11)

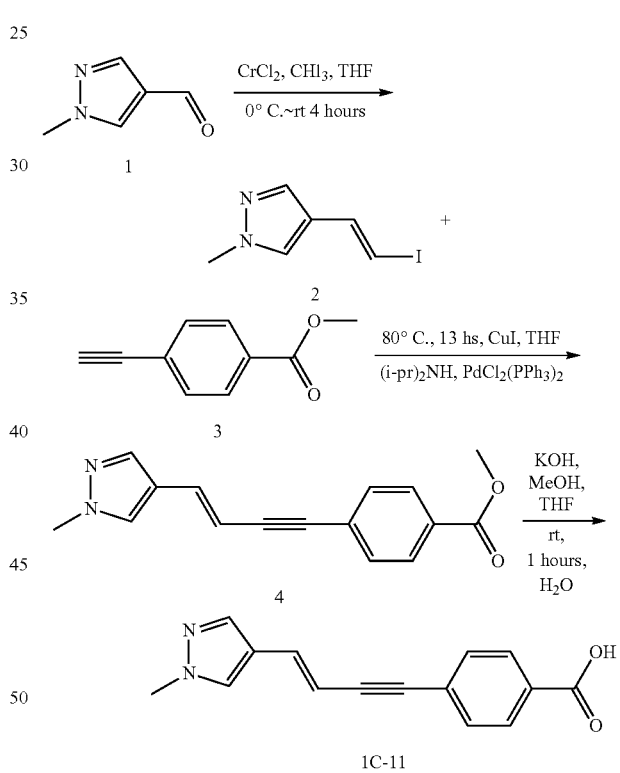

(E)-4-(2-iodovinyl)-1-methyl-1H-pyrazole (2)

| Reagent | MW | Eq. | mmol | g, mL |
|---|---|---|---|---|
| Compound 1 | 110.11 | 1.0 | 8.2 | 900 mg |
| Chromium chloride | 122.90 | 6.0 | 49.2 | 5.555 g |
| triiodomethane | 393.73 | 4.0 | 32.8 | 12.914 g |
| THF | | | | 185 mL |

The target compound 2 (635 mg, 33%) was prepared by using the method described in compound 5 of Example 96.

[M+1]: 234.9. ¹H-NMR: (400 MHz, DMSO-d₆): δ 3.87 (s, 3H), 6.43 (d, J=14.8 Hz, 1H), 7.21 (s, J=14.8 Hz, 1H), 7.34 (s, 1H), 7.49 (s, 1H).

(E)-methyl 4-(4-(1-methyl-1H-pyrazol-4-yl)but-3-en-1-ynyl)benzoate (4)

To a mixture of compound (E)-4-(2-iodovinyl)-1-methyl-1H-pyrazole (635 mg, 2.7 mmol, 1.0 equiv), methyl 4-ethynylbenzoate (434 g, 2.7 mmol, 1.0 equiv), PdCl₂(PPh₃)₂ (190 mg, 0.3 mmol, 0.1 equiv) and (i-Pr)₂NH (546 mg, 5.4 mmol, 2 equiv) in THF (100 mL) was added CuI (51 mg, 0.3 mmol, 0.1 equiv) under nitrogen at room temperature. The mixture was stirred at room temperature for 12 hours. The reaction mixture was diluted with EtOAc (50 mL), filtered and concentrated. The residue was dissolved into EtOAc (100 mL) and washed with water (100 mL) and brine (50 mL) and dried (MgSO₄). After filtration and concentration, the residue was purified by chromatography on silica gel (0 to 5% EtOAc/Hexanes) to give the title compound 4 (532 mg, 74%). [M+H]⁺: 267.0

(E)-4-(4-(1-methyl-1H-pyrazol-4-yl)but-3-en-1-ynyl)benzoic acid (IC-11)

| Reagent | MW | Eq. | g/ml | mmol |
|---|---|---|---|---|
| ACHL059-4 | 266.29 | 1.0 | 1.00 g | 3.74 |
| 2M NaOH aq. | 40.00 | 2.0 | 2.4 mL | 4.8 |
| THF | | | 25 mL | |
| MeOH | | | 25 mL | |

The product (650 mg, 71%) was made and separated using the General Method for basic hydrolysis. [M+1]⁺: 369.0. ¹H-NMR: (400 MHz, DMSO-d₆): δ 3.83 (s, 3H), 6.29 (d, J=16.0 Hz, 1H), 7.00 (s, J=16.0 Hz, 1H), 7.55 (d, J=8.4 Hz, 2H), 7.75 (s, 1H), 7.92~7.96 (m, 3H).

Synthesis of 4-(4-methylpent-3-en-1-ynyl)benzoic acid (IC-12)

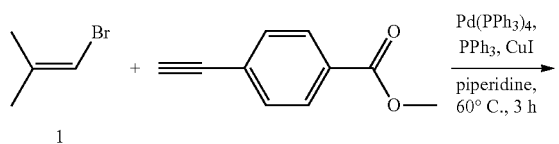

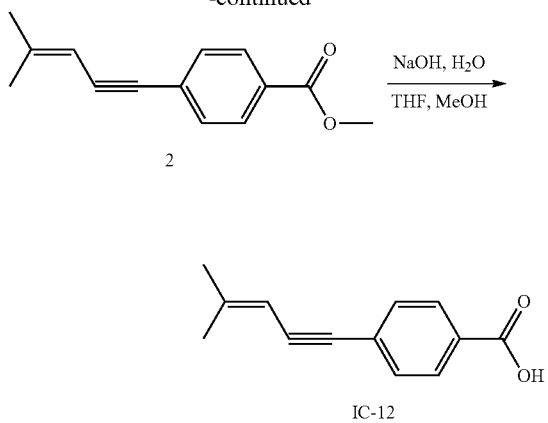

IC-12

Methyl 4-(4-methylpent-3-en-1-ynyl)benzoate (2)

To a solution of methyl 4-ethynylbenzoate (3.84 g, 24 mmol), Pd(PPh₃)₄ (2.22 g, 1.92 mmol), CuI (0.32 g, 1.68 mmol) and PPh₃ (1.13 g, 4.32 mmol) in degassed piperidine (160 mL) was added 1-bromo-2-methylprop-1-ene (6.38 g, 47.26 mmol) at room temperature. After the mixture was heated at 60° C. for 3 h, the reaction was quenched by sat. NH₄Cl solution and then was extracted with ethyl acetate twice. The combined organic layer was washed with brine and dried over anhydrous sodium sulfate. After filtration of the drying agent, the filtrate was evaporated, and the residue was purified by silica-gel column (1% ethyl acetate in petroleum) to give compound 2 (1.9 g, the yield was 37%) as a light yellow solid. ¹H NMR (400 MHz, CDCl₃): δ ppm, 1.88 (s, 3H), 1.99 (s, 3H), 3.91 (s, 3H), 5.49 (s, 1H), 7.46 (d, J=8.4 Hz, 2H), 7.96 (d, J=8.4 Hz, 2H).

4-(4-methylpent-3-en-1-ynyl)benzoic acid (IC-12)

The compound (1C-12)(1.45 g, 82%) as a white solid was made and separated using the General Method for basic hydrolysis. ¹H NMR (400 MHz, DMSO-d₆): δ ppm, 1.87 (s, 3H), 1.96 (s, 3H), 5.59 (s, 1H), 7.52 (d, J=8.8 Hz, 2H), 7.91 (d, J=8 Hz, 2H), 13.01 (s, 1H)

The following compounds were prepared by using the corresponding intermediate acids synthesized as described above.

| Compound # | Structure | MH⁺ (m/z) | Ret. Time (min) | HPLC-MS Method |
|---|---|---|---|---|
| 108-1 | 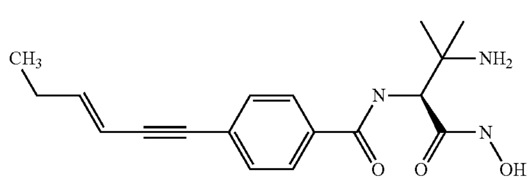 [SMILES: CC/C=C/C#Cc1ccc(C(=O)N[C@H](C(=O)NO)C(C)(C)N)cc1] | 329 | | |

-continued
| Compound # | Structure | MH+ (m/z) | Ret. Time (min) | HPLC-MS Method |
|---|---|---|---|---|
| 108-2 | 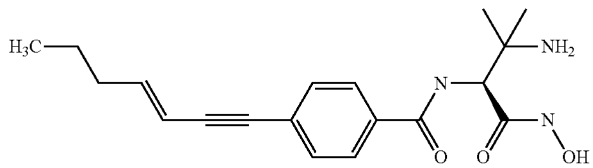 [SMILES: CCC/C=C/C#Cc1ccc(C(=O)N[C@H](C(=O)NO)C(C)(C)N)cc1] | 343 | | |
| 108-3 | 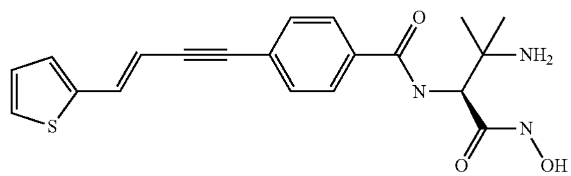 [SMILES: CC(C)(N)[C@H](NC(=O)c1ccc(C#C/C=C/c2cccs2)cc1)C(=O)NO] | 383 | | |
| 108-4 | 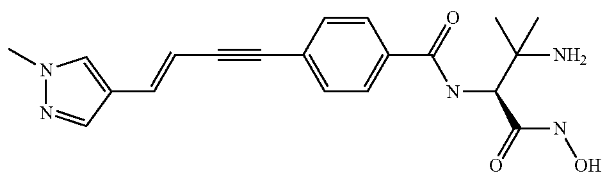 [SMILES: Cn1cc(/C=C/C#Cc2ccc(C(=O)N[C@H](C(=O)NO)C(C)(C)N)cc2)cn1] | 381 | | |
| 108-5 | 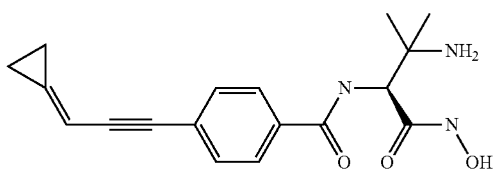 [SMILES: CC(C)(N)[C@H](NC(=O)c1ccc(C#CC=C2CC2)cc1)C(=O)NO] | 327 | | |
| 108-6 | 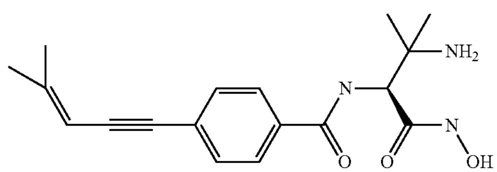 [SMILES: CC(C)=CC#Cc1ccc(C(=O)N[C@H](C(=O)NO)C(C)(C)N)cc1] | 329 | | |
Example 109
Synthesis of 4-(2-fluoro-4-(4-(morpholinomethyl)phenyl)but-1-en-3-ynyl)-N-((2S,3R)-3-hydroxy-1-(hydroxyamino)-1-oxobutan-2-yl)benzamide (109-1)
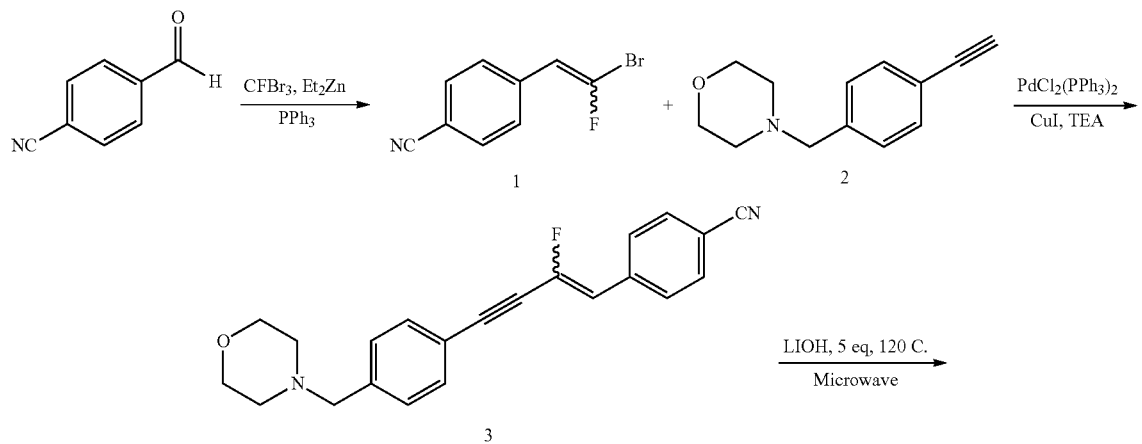

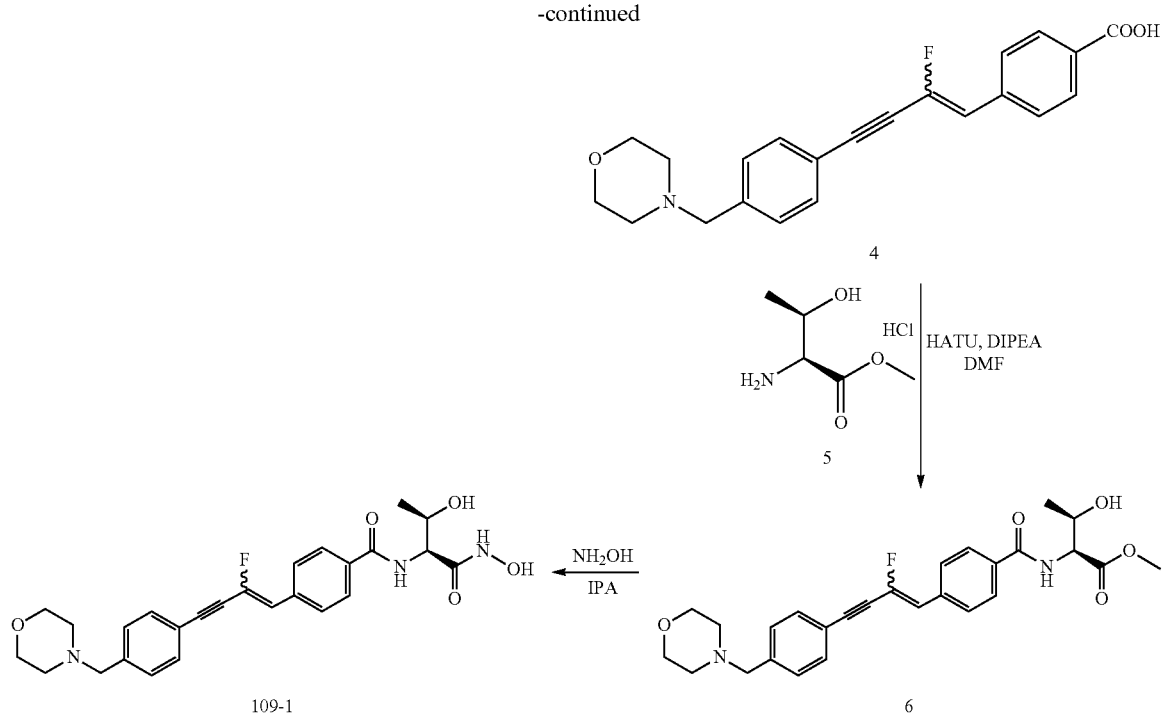

Synthesis of 4-(2-bromo-2-fluorovinyl)benzonitrile (1)

The THF solution (10 ml) of p-cyanobenzaldehyde (1.31 g, 10.0 mmol), triphenylphosphine (3.14 g, 12 mmol) and Tribromofluoromethane (3.25 g, 12 mmol) was cooled to 0° C. The THF solution (1 ml) of Diethyl zinc (1.47 g, 12 mmol) was added drop wise over 20 min. The reaction was warmed to r.t and stirred overnight. The reaction mixture was cooled to 0° C. and aqueous NH$_4$Cl (Sta'd, 20 ml) was added to quench the reaction. The mixture was extracted with Ethyl Acetate (100 ml×3). The combined organic layers was washed with HCl (1N, 100 ml), H$_2$O (100 ml×2) and brine (100 ml). The crude product was purified with ISCO normal phase silica gel column (0-10% EtOAc/Hex) to give desired 1.33 g product 1 as a trans/cis mixture (1:1) in the yield of 58.8%.

Synthesis of 4-(2-fluoro-4-(4_(morpholinomethyl) phenyl)-but-1-en-3-ynyl)benzonitrile The THF solution (5 ml) of compound 1 (226 mg, 1.0 mmol) and 2 (201 mg, 1.0 mmol) was charged N$_2$ gas for 15 min. PdCl$_2$(PPh$_3$)$_2$ (21 mg, 0.03 mmol), CuI (19.0 mg, 0.1 mmol) and TEA (0.5 mml) were added to reaction sequentially at r.t. The reaction was stirred at r.t. overnight. Diluted with EtOAc, the reaction mixture was filtered through celite. The filtrate was washed with brine (50 ml) and concentrated. The crude product was purified with ISCO normal phase silica gel column (0-50% EtOAc/Hex) to give 300 mg compound 3 in the yield of 86.7% as a 1:1 mixture of trans and cis against F-double bond.

Synthesis of 4-(2-fluoro-4-(4_(morpholinomethyl) phenyl)-but-1-en-3-ynyl)benzoic acid (4)

Compound 3 (300 mg, 0.87 mmol) was dissolved in 10 ml Dioxin and 5 ml H$_2$O. LiOH (104 mg, 4.3 mmol) was added to the solution. The reaction was heated to 120° C. under microwave for 2 hr. after cooling to r.t, the reaction mixture was acidified with 1N HCl to pH=3~4. Diluted with H$_2$O, the mixture was extracted with EtOAc to give 240 mg compound 4 as crude product in the yield of 75.5%.

Synthesis of 4-(2-fluoro-4-(4-(morpholinomethyl) phenyl)but-1-en-3-ynyl)-N-((2S,3R)-3-hydroxy-1-(hydroxyamino)-1-oxobutan-2-yl)benzamide (6)

DIPEA (0.67 ml, 3.85 mmol) was added to the DMF solution (5 ml) of compound 4 (240 mg, 0.77 mmol) and 5 (211 mg, 1.15 mmol) and HATU (380 mg, 1.0 mmol) at r.t. the reaction was stirred at r.t overnight. H$_2$O was added to quench the reaction. The reaction mixture was extracted with EtOAc (50 ml×3). The combined organic layers was washed with H$_2$O (50 ml×2) and brine (50 ml) then dried with Na$_2$SO$_4$. The crude product was purified with ISCO normal phase silica gel column (0-10% MeOH/DCM) to give compound 6 (140 mg, 37.8%) as a 1:1 mixture of trans and cis against F-double bond

Synthesis of 4-(2-fluoro-4-(4-(morpholinomethyl) phenyl)but-1-en-3-ynyl)-N-((2S,3R)-3-hydroxy-1-(hydroxyamino)-1-oxobutan-2-yl)benzamide (109-1)

Aqueous NH2OH (50% in H$_2$O, 0.5 ml) was added to the IPA solution (4 ml) of compound 6 (140 mg, 0.29 mmol) at r.t. The reaction was stirred overnight at r.t. After removing the reaction solvent, the crude product was purified by prep. HPLC to give compound (109-1), a mixture of trans and cis against double bond, (13 mg, 7.4%, m+z=482.2) as TFA salt.

| Compound | Scale (mmol)* | Yield (mg) | Yield (%)* | Purity (%) | [M + H] | Retention time (min)** |
|---|---|---|---|---|---|---|
| 109-1 | 0.29 | 13 mg | 7.4% | 94.4 | 492.2 | 1.508/1.634 |

Synthesis of (2S,3R)-methyl 2-(4-((Z)-3-fluoro-4-(4-(morpholinomethyl)phenyl)but-3-en-1-ynyl)benzamido)-3-hydroxybutanoate 109-2
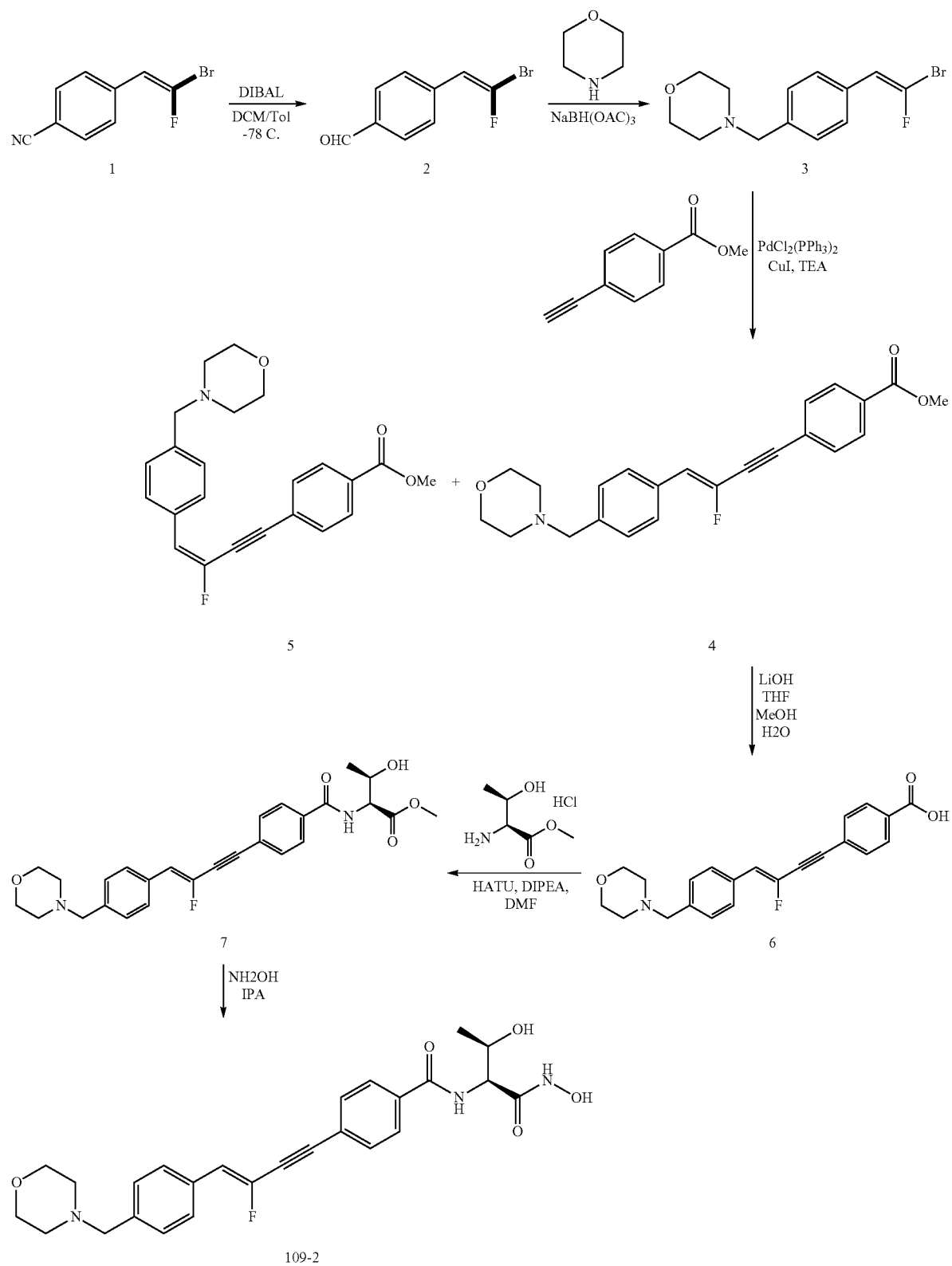

Synthesis of 4-(2-bromo-2-fluorovinyl)benzaldehyde (2)

Compound 1 (417 mg, 1.85 mmol) was dissolved in DCM/Tol mixed solvent (6 ml, 1:1). The solution was cooled to −78 C. DIBAL (2.2 ml, 2.21 mmol, 1.0M in DCM) was added dropwise. The reaction was stirred at −78 C for 2 hrs. $NH_4Cl$ (50 ml, aq. sta'd) was added to quench the reaction and the mixture was stirred at r.t. for 2 hrs. The reaction mixture was extracted with EtOAc (50 ml×3). The combined organic layers was washed with $H_2O$ (50 ml×2) and brine (50 ml). The crude product was purified with ISCO normal phase silica gel column (0-20% EtOAc/Hex) to give 250 mg compound 2 (250 mg, 59%) as 1:1 trans/cis mixture against double bond.

Synthesis of (E)-4-(4-(2-bromo-2-fluorovinyl)benzyl)morpholine (3)

$NaBH(OAc)_3$ (693 mg, 3.27 mmol) was added to the THF solution (5 ml) of compound 2 (250 mg, 1.09 mmol) and morphline (190 mg, 2.18 mmol). The reaction was stirred at r.t. overnight. THF was removed and the residue was dissolved in 50 ml EtOAc and 50 ml $H_2O$. After separation, the water layer was extracted with EtOAc (50 ml×2). The combined organic layers was washed with $H_2O$ (50 ml×2) and brine (50 ml) and dried with $Na_2SO4$. the crude the product was purified with ISCO normal phase silica gel column (0-50% EtOAc/DCM) to give compound 3 (209 mg, 63.9%) as a mixture of trans/cis in the ration of 7:1 based on NMR.

Synthesis of methyl 4-(3-fluoro-4-(4-(morpholinomethyl)phenyl)but-3-en-1-ynyl)benzoate (4 & 5)

Compound 3 (210 mg, 0.67 mmol) and methyl 4-ethynylbenzoate (119 mg, 0.75 mmol) were dissolved in 5 ml degassed THF. $PdCl_2(PPh_3)_2$ (14 mg, 0.02 mmol), CuI (13 mg, 0.07 mmol) and TEA (0.3 ml, 2.0 mmol) were added sequentially to the reaction at r.t. The reaction was stirred at R.T. for 4 hrs. The reaction mixture was filtered. The filtered solid was washed with EtOAc (100 ml). The organic solution was washed with $H_2O$ (50 ml×2) and brine (50 ml) and dried with $Na_2SO_4$. The crude product was purified with ISCO normal phase silica gel column (0-50% EtOAc/DCM) to give compound 4 (197 mg) and 5 (33 mg) in 81.4% total yield.

Synthesis of (Z)-4-(3-fluoro-4-(4-(morpholinomethyl)phenyl)but-3-en-1-ynyl)benzoic acid (6)

Compound 4 (197 mg, 0.52 mmol) was dissolved in THF/MeOH (4 ml, 1:1). The aq. solution (2 ml) of LiOH (25 mg, 1.04 mmol) was added to the reaction. Reaction was stirred at r.t overnight. Diluted with $H_2O$ (10 ml), the reaction mixture was neutralized with HOAc to pH=7 and extracted with EtOAc (20 ml×5) to give 180 mg crude product 6 in the yield of 94.8%.

Synthesis of (2S,3R)-methyl 2-(4-((Z)-3-fluoro-4-(4-(morpholinomethyl)phenyl)but-3-en-1-ynyl)benzamido)-3-hydroxybutanoate 7

| Reagent | MW | Eq. | g/ml | mmol |
|---|---|---|---|---|
| Compound 6 | 365.4 | 1 | 180 mg | 0.493 |
| Threonine | 169.61 | 1.1 | 99.3 mg | 0.54 |
| HATU | 380 | 1.2 | 225 mg | 0.59 |
| DIPEA | 129 | 4.5 | 0.38 ml | 2.2 |
| DMF | | | 5 ml | |

The compound 7 in the yield of 86.6% was prepared using the General Method for HATU coupling.

Synthesis of (2S,3R)-methyl 2-(4-((Z)-3-fluoro-4-(4-(morpholinomethyl)phenyl)but-3-en-1-ynyl)benzamido)-3-hydroxybutanoate 109-2

| Reagent | MW | Eq. | g/ml | Mmol |
|---|---|---|---|---|
| Compound 7 | 480.53 | 1 | 221 mg | 0.44 |
| $NH_2OH$ (50% in $H_2O$) | | | 1.1 ml | |
| IPA | | | 2 ml | |

The compound 109-2 (70 mg, 30.7%, m+z=482.2) as HCl salt was made using the General Method for hydroxamate formation.

The following compound was synthesized as described above.

| Compound # | Structure | Amount obtained | Yield | M + Z |
|---|---|---|---|---|
| 109-3 | 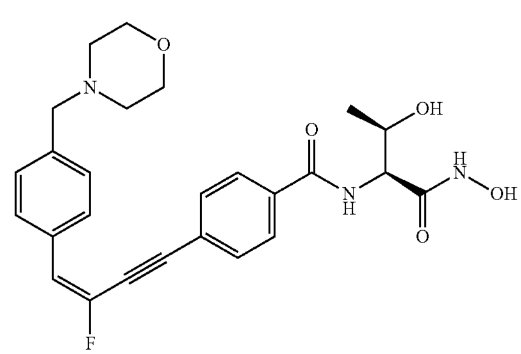 [SMILES: C[C@@H](O)[C@H](NC(=O)c1ccc(C#C/C(F)=C\c2ccc(CN3CCOCC3)cc2)cc1)C(=O)NO] | 0.7 mg TFA salt | 0.1% | 482.2 |

Example 110

Synthesis of (E)-4-(4-(4-(morpholinomethyl)phenyl)but-1-en-3-ynyl)benzoic acid (1)

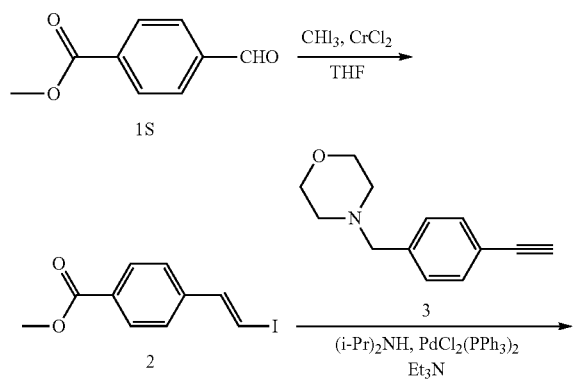

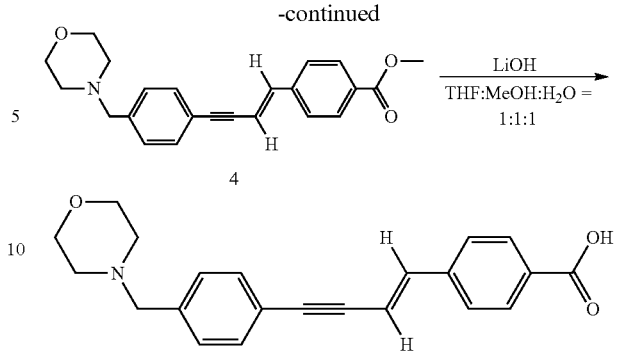

The detail procedure refers to Example 30 for synthesis of alternative intermediate 009

Each of the following compounds were prepared by the same synthetic route as described in Example 96 and as for compound 110-12 as described in Example 97

| Compound # | Structure | MH+ (m/z) | Ret. Time (min) | HPLC-MS Method |
|---|---|---|---|---|
| 110-1 (same as 30-12a) | 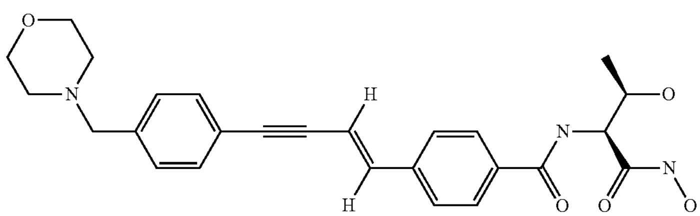 [SMILES: C[C@@H](O)[C@H](NC(=O)c1ccc(/C=C/C#Cc2ccc(CN3CCOCC3)cc2)cc1)C(=O)NO] | 464.5 | 3.62 | A |
| 110-2 | 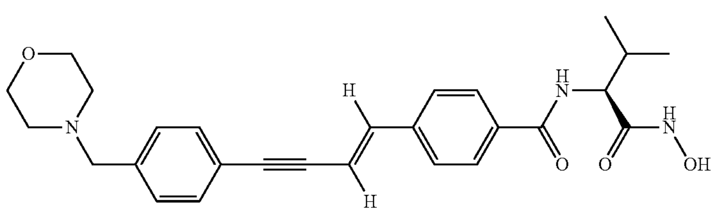 | 462.4 | 5.19 | B |
| 110-3 | 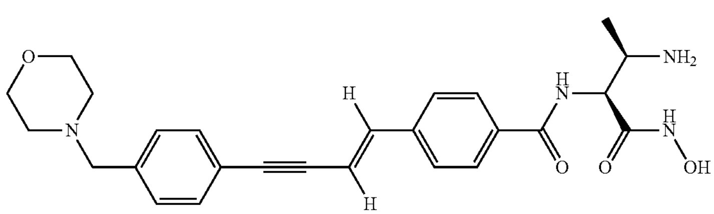 [SMILES: C[C@@H](N)[C@H](NC(=O)c1ccc(/C=C/C#Cc2ccc(CN3CCOCC3)cc2)cc1)C(=O)NO] | 463.4 | 6.11 | B |
| 110-4 | 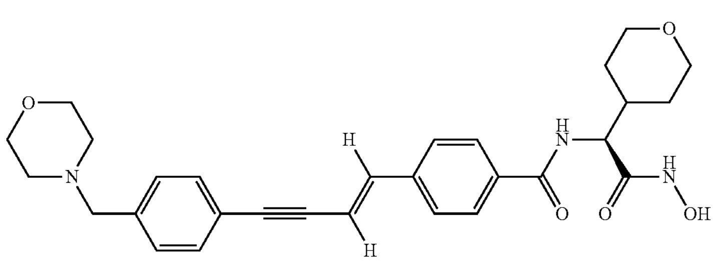 [SMILES: O=C(N[C@H](C(=O)NO)C1CCOCC1)c1ccc(/C=C/C#Cc2ccc(CN3CCOCC3)cc2)cc1] | 504.4 | 4.67 | B |

-continued

| Compound # | Structure | MH+ (m/z) | Ret. Time (min) | HPLC-MS Method |
|---|---|---|---|---|
| 110-5 | 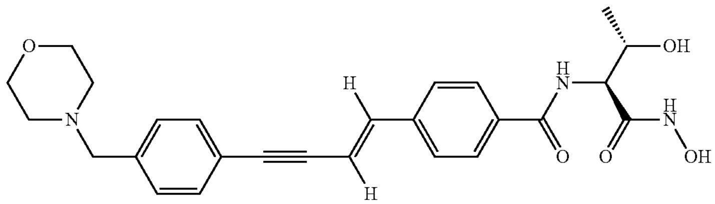 [SMILES: C[C@H](O)[C@H](NC(=O)c1ccc(/C=C/C#Cc2ccc(CN3CCOCC3)cc2)cc1)C(=O)NO] | 464.4 | 3.61 | A |
| 110-6 | 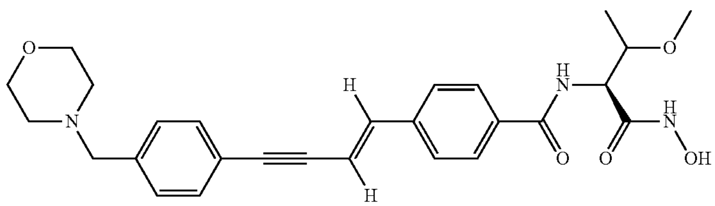 | 478.5 | 4.79 | B |
| 110-7 | 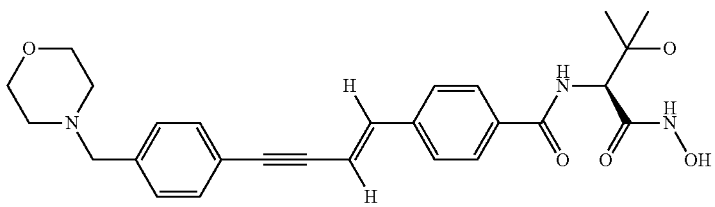 [SMILES: CC(C)(O)[C@H](NC(=O)c1ccc(/C=C/C#Cc2ccc(CN3CCOCC3)cc2)cc1)C(=O)NO] | 478.5 | 4.79 | B |
| 110-8 | 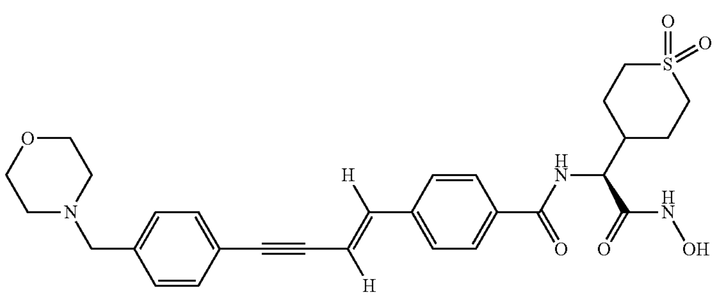 [SMILES: O=C(N[C@H](C(=O)NO)C1CCS(=O)(=O)CC1)c1ccc(/C=C/C#Cc2ccc(CN3CCOCC3)cc2)cc1] | 552.5 | 4.50 | B |
| 110-9 | 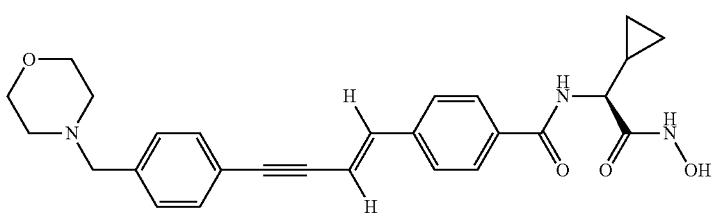 [SMILES: O=C(N[C@H](C(=O)NO)C1CC1)c1ccc(/C=C/C#Cc2ccc(CN3CCOCC3)cc2)cc1] | 460.3 | 4.84 | B |
| 110-10 | 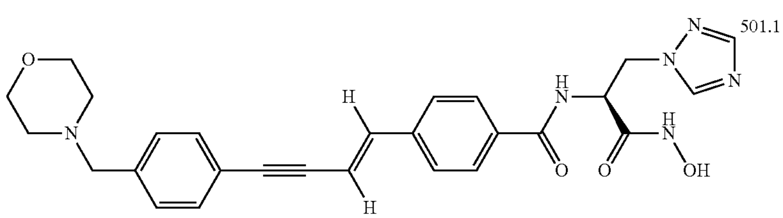 | 501.1 | 4.23 | B |

-continued

| Compound # | Structure | MH+ (m/z) | Ret. Time (min) | HPLC-MS Method |
|---|---|---|---|---|
| 110-11 | 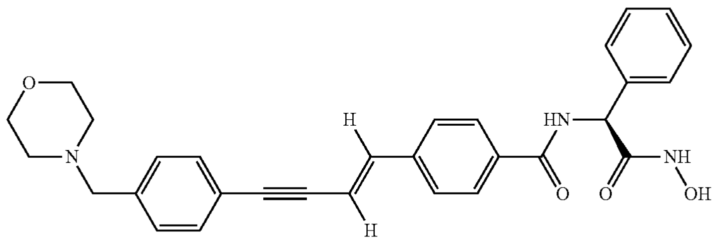 [SMILES: O=C(N[C@H](C(=O)NO)c1ccccc1)c1ccc(/C=C/C#Cc2ccc(CN3CCOCC3)cc2)cc1] | 496.4 | 5.57 | B |
| 110-12 | 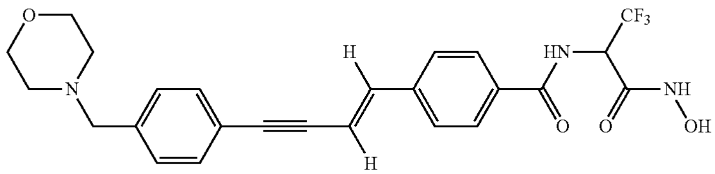 [SMILES: O=C(NC(C(=O)NO)C(F)(F)F)c1ccc(/C=C/C#Cc2ccc(CN3CCOCC3)cc2)cc1] | 488.4 | 5.41 | B |

Example 111

N-[2-Amino-1-((S)-hydroxycarbamoyl)-ethyl]-4-[(E)-4-(4-morpholin-4-ylmethyl-phenyl)-but-1-en-3-ynyl]-benzamide (111-1)

N-[2-(2-dimethylamino-acetylamino)-1-(S)-hydroxycarbamoyl)-ethyl]-4-[(E)-4-(4-morpholin-4-ylmethyl-phenyl)-but-1-en-3-ynyl]-benzamide (111-2)

N-[2-acetylamino-1-((S)-hydroxycarbamoyl)-ethyl]-4-[(E)-4-(4-morpholin-4-ylmethyl-phenyl)-but-1-en-3-ynyl]-(111-3)

N-[1-((S)-Hydroxycarbamoyl)-2-methylamino-ethyl]-4-[(E)-4-(4-morpholin-4-ylmethyl-phenyl)-but-1-en-3-ynyl]-benzamide (111-4)

The following compounds were prepared by the same synthetic route as described in Examples 98 and 99.

| Compound # | Structure | MH+ (m/z) | Ret. Time (min) | HPLC-MS Method |
|---|---|---|---|---|
| 111-1 | 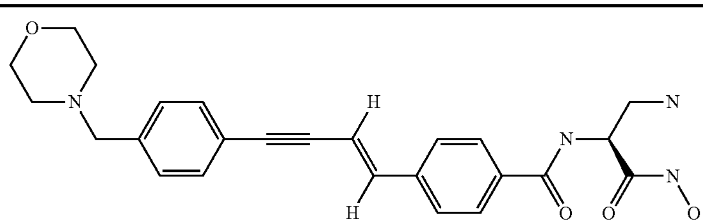 | 449.4 | 3.46 | B |
| 111-2 | 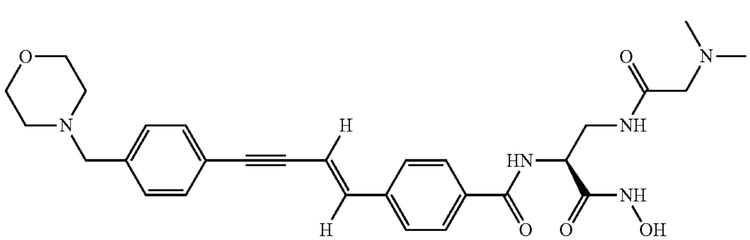 [SMILES: CN(C)CC(=O)NC[C@H](NC(=O)c1ccc(/C=C/C#Cc2ccc(CN3CCOCC3)cc2)cc1)C(=O)NO] | 534.3 | 3.64 | B |

| Compound # | Structure | MH+ (m/z) | Ret. Time (min) | HPLC-MS Method |
|---|---|---|---|---|
| 111-3 | 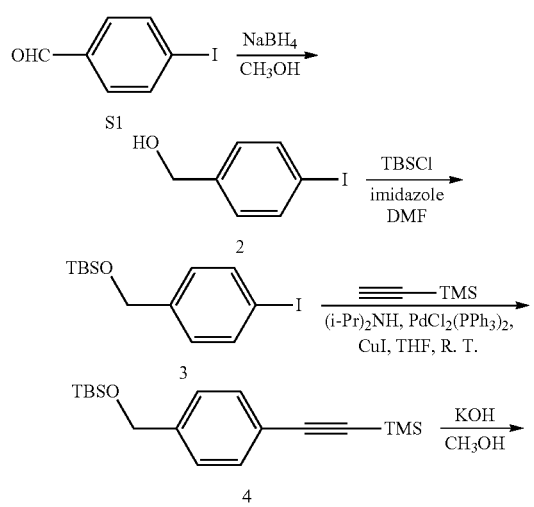 | 491.4 | 4.17 | B |
| 111-4 | 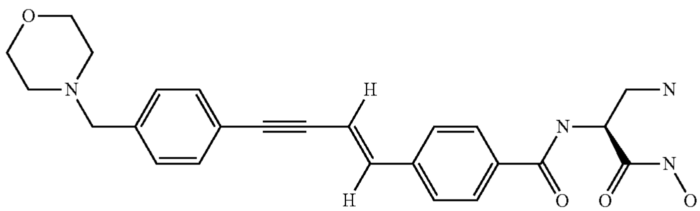 [SMILES: NC[C@H](NC(=O)c1ccc(/C=C/C#Cc2ccc(CN3CCOCC3)cc2)cc1)C(=O)NO] | 463.5 | 3.59 | B |

Example 112

Synthesis of (E)-methyl 4-(4-(4-(hydroxymethyl)phenyl)but-1-en-3-ynyl)benzoate (1)

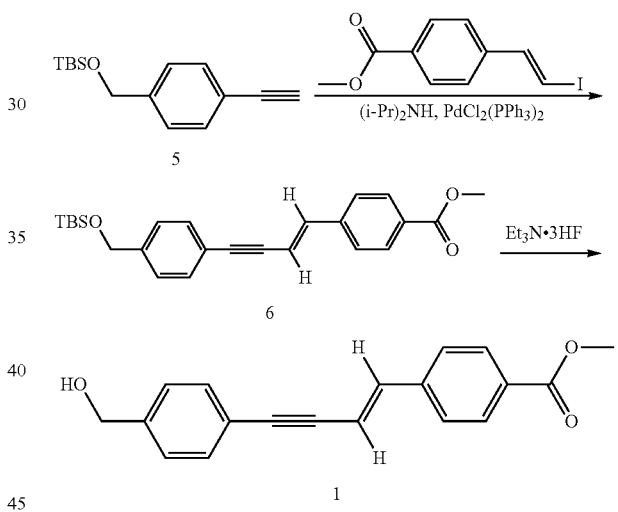

The detail procedure refers to Example 30 for synthesis of alternative intermediate 011

Each of the following compounds was synthesized using the synthetic route as described in Example 101.

| Compound # | Structure | MH+ (m/z) | Ret. Time (min) | HPLC-MS Method |
|---|---|---|---|---|
| 112-1 | 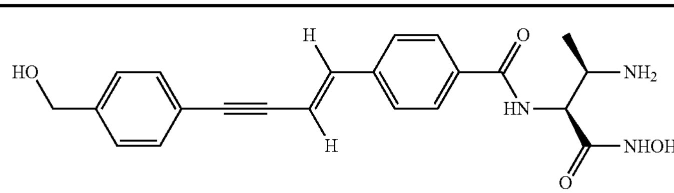 | 394.5 | 4.59 | B |

-continued

| Compound # | Structure | MH+ (m/z) | Ret. Time (min) | HPLC-MS Method |
|---|---|---|---|---|
| 112-2 | (structure) | 380.0 | 4.53 | B |
| 112-3 | (structure) | 395.2 | 5.29 | B |
| 112-4 | (structure) | 409.4 | 5.99 | B |
| 112-5 | (structure) | 409.4 | 5.57 | B |

Example 113

Each of the following compounds was synthesized using the synthetic route as described in Example 102 and for compound 113-11 as described in Example 103

| Compound # | Structure | MH+ (m/z) | Ret. Time (min) | HPLC-MS Method |
|---|---|---|---|---|
| 113-1 | (structure) | 419.4 | 3.86 | B |
| 113-2 | (structure) | 433.4 | 3.79 | B |
| 113-3 | (structure) | 434.5 | 4.49 | B |

-continued

| Compound # | Structure | MH+ (m/z) | Ret. Time (min) | HPLC-MS Method |
|---|---|---|---|---|
| 113-4 | 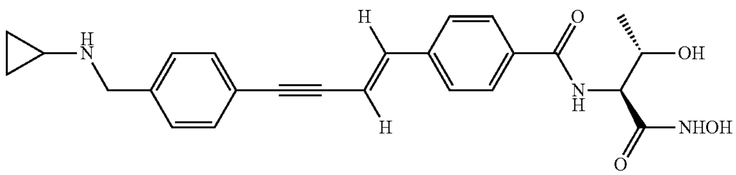 | 434.4 | 4.56 | B |
| 113-5 | 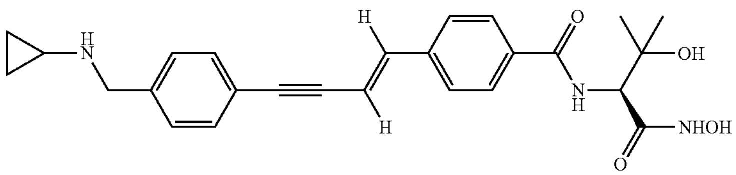 | 449.0 | 4.98 | A |
| 113-6 | 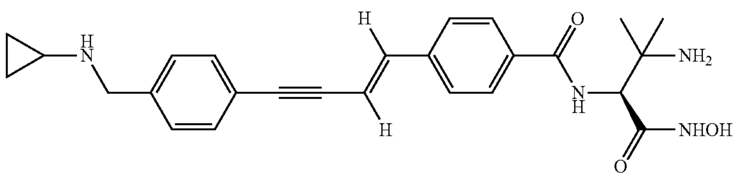 | 447.1 | 3.95 | B |
| 113-7 | 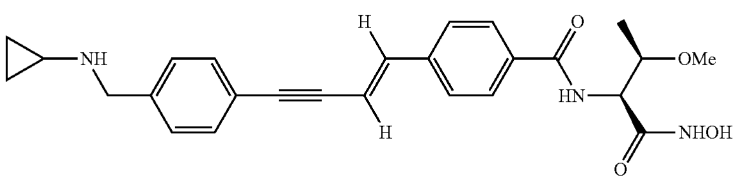 | 448.3 | 5.01 | B |
| 113-8 | 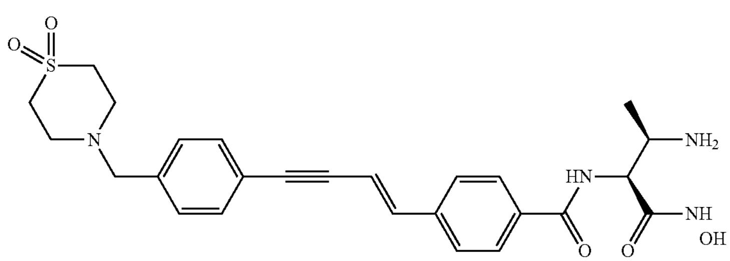 | 511.3 | 3.88 | B |
| 113-9 | 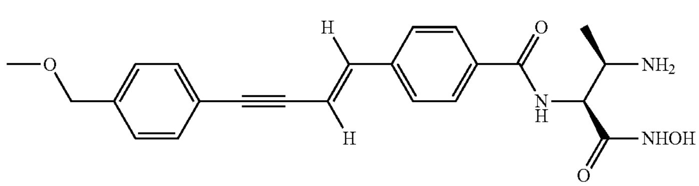 | 408.3 | 6.22 | B |
| 113-10 | 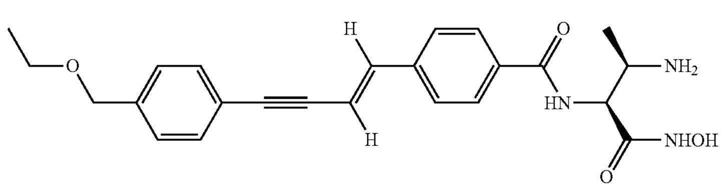 | 422.4 | 6.65 | B |

| Compound # | Structure | MH+ (m/z) | Ret. Time (min) | HPLC-MS Method |
|---|---|---|---|---|
| 113-11 | 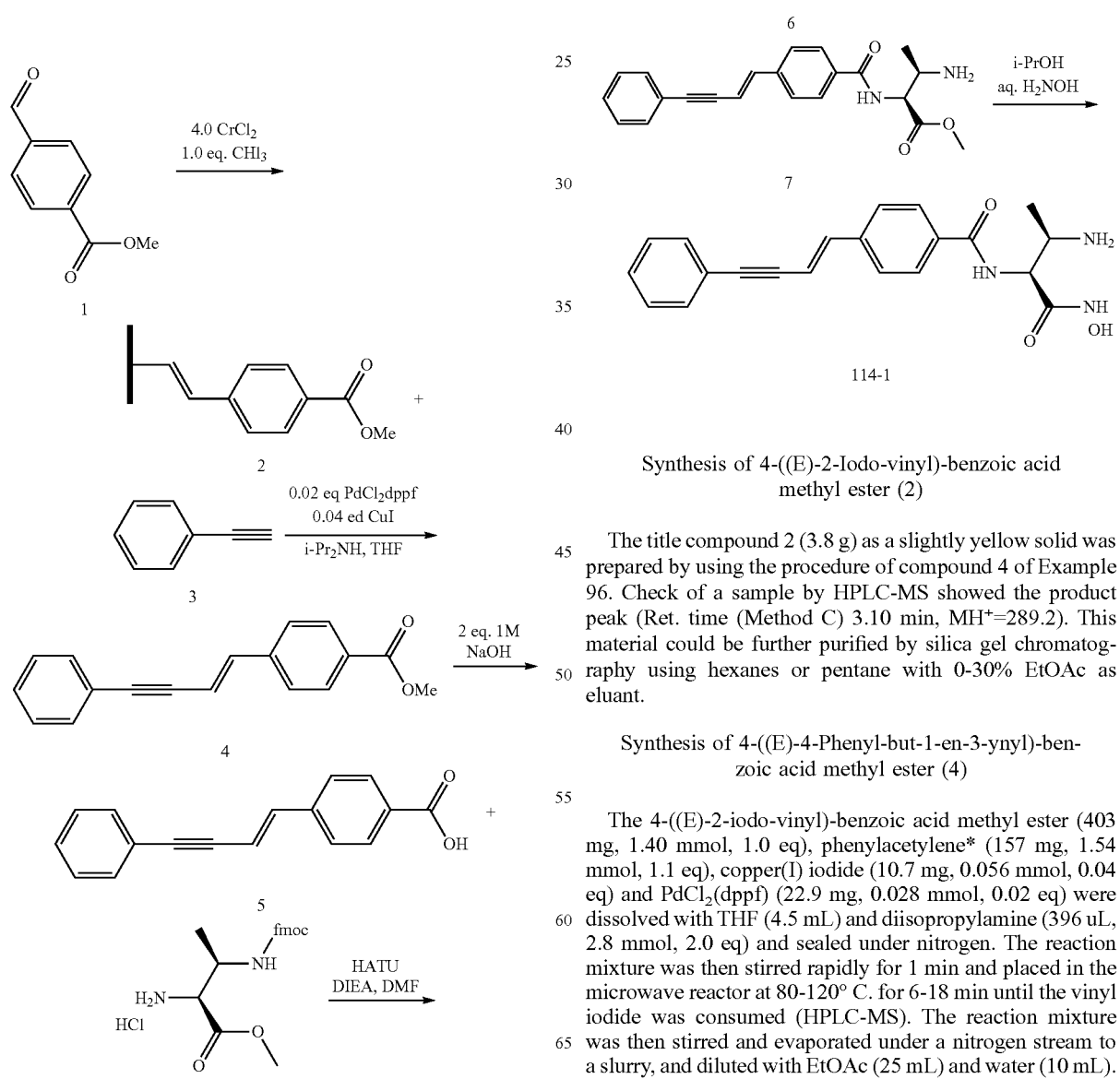 | 477.5 | 4.74 | B |

Example 114

Synthesis of N-((1S,2R)-2-Amino-1-hydroxycarbamoyl-propyl)-4-((E)-4-phenyl-but-1-en-3-ynyl)-benzamide

Synthesis of 4-((E)-2-Iodo-vinyl)-benzoic acid methyl ester (2)

The title compound 2 (3.8 g) as a slightly yellow solid was prepared by using the procedure of compound 4 of Example 96. Check of a sample by HPLC-MS showed the product peak (Ret. time (Method C) 3.10 min, MH+=289.2). This material could be further purified by silica gel chromatography using hexanes or pentane with 0-30% EtOAc as eluant.

Synthesis of 4-((E)-4-Phenyl-but-1-en-3-ynyl)-benzoic acid methyl ester (4)

The 4-((E)-2-iodo-vinyl)-benzoic acid methyl ester (403 mg, 1.40 mmol, 1.0 eq), phenylacetylene* (157 mg, 1.54 mmol, 1.1 eq), copper(I) iodide (10.7 mg, 0.056 mmol, 0.04 eq) and PdCl$_2$(dppf) (22.9 mg, 0.028 mmol, 0.02 eq) were dissolved with THF (4.5 mL) and diisopropylamine (396 uL, 2.8 mmol, 2.0 eq) and sealed under nitrogen. The reaction mixture was then stirred rapidly for 1 min and placed in the microwave reactor at 80-120° C. for 6-18 min until the vinyl iodide was consumed (HPLC-MS). The reaction mixture was then stirred and evaporated under a nitrogen stream to a slurry, and diluted with EtOAc (25 mL) and water (10 mL). After mixing and adjusting to pH~5 with 3 M HCl, the aqueous phase was removed. The organic phase was washed with 0.3 M HCl (15 mL, 2×), and satd aq NaCl (10 mL). Filtration of the brown solution through $Na_2SO_4$ and evaporation of the solvents yielded the title compound as a crude product (~450 mg). This material could be further purified by silica gel chromatography using hexanes or pentane with 0-100% EtOAc as eluant, and evaporation of the title compound as a yellow glass. Check of a sample by HPLC-MS showed a major product peak (Ret. time (Method C) 3.53 min, $MH^+$=263.3).

*—For aliphatic alkynes, using 3 eq of alkyne is required to obtain similar yields.

Synthesis of 4-((E)-4-Phenyl-but-1-en-3-ynyl)-benzoic acid (5)

| Reagent | MW | Eq. | mmol | mg, ml |
|---|---|---|---|---|
| 4-((E)-4-Phenyl-but-1-en-3-ynyl)-benzoic acid methyl ester (4) | 262.31 | 1.0 | ~1.4 | ~367 mg |
| THF | | | | 3.6 mL |
| MeOH | | | | 1.2 mL |
| 1M aq NaOH | | 2.0 | 2.8 | 2.8 mL |

The 4-((E)-4-phenyl-but-1-en-3-ynyl)-benzoic acid methyl ester was hydrolyzed and the acid precipitated using the "General Method for basic hydrolysis". Check of a sample by HPLC-MS showed a major product peak (Ret. time (Method A) 5.79 min, $[MH+DMSO]^+$=327.1).

Synthesis of (2S,3R)-3-(9H-Fluoren-9-ylmethoxycarbonylamino)-2-[4-((E)-4-phenyl-but-1-en-3-ynyl)-benzoylamino]-butyric acid methyl ester (6)

| Reagent | MW, d | Eq. | mmol | mg, ml |
|---|---|---|---|---|
| 4-((E)-4-Phenyl-but-1-en-3-ynyl)-benzoic acid (5) | 248.28 | 1.0 | 0.30 | 74.5 mg |
| DIEA | 129.24, 0.742 | 3.0 | 0.90 | 157 ul |
| HATU | 380.23 | 1.25 | 0.375 | 157 mg |
| DMF | | | | 1.2 ml |

| Reagent | MW, d | Eq. | mmol | mg, ml |
|---|---|---|---|---|
| N-Fmoc-(S)-MeDAP-OMe × HCl | 390.87 | 1.12 | 0.336 | 131 mg |

The 4-((E)-4-phenyl-but-1-en-3-ynyl)-benzoic acid was coupled to Fmoc-Me-DAP using the "General Method for HATU coupling". Check of a sample by HPLC-MS showed a major product peak (Ret. time (Method C) 3.57 min, $MH^+$=585.4).

Synthesis of (2S,3R)-3-Amino-2-[4-((E)-4-phenyl-but-1-en-3-ynyl-benzoylamino]-butyric acid methyl ester (7)

The FMOC group of (2S,3R)-3-(9H-fluoren-9-ylmethoxycarbonyl amino)-2-[4-((E)-4-phenyl-but-1-en-3-ynyl)-benzoylamino]-butyric acid methyl ester was deprotected by dissolving in 50% piperidine in THF (6 mL), stirring for 1-8 h, and evaporating the volatiles under vacuum or a nitrogen stream to yield the desired product residue which may be optionally purified by silica gel chromatography using hexanes with 0-100% EtOAc as eluant. Check of a sample by HPLC-MS showed a major product peak (Ret. time (Method C) 2.51 min, $MH^+$=363.2).

Synthesis of N-((1S,2R)-2-Amino-1-hydroxycarbamoyl-propyl)-4-((E)-4-phenyl-but-1-en-3-ynyl)-benzamide (114-1)

The (2S,3R)-3-amino-2-[4-((E)-4-phenyl-but-1-en-3-ynyl)-benzoyl amino]butyric acid methyl ester was dissolved in dioxane (0.6 mL), isopropanol (2.4 mL) and 50% aq hydroxylamine (3 mL), and optionally a catalytic amount of potassium cyanide (2 mg) was added at room temperature and stirred for 8-24 h until disappearance of the methyl ester (HPLC-MS). The reaction mixture was diluted in dichloromethane (8 mL), and the organic layer separated, dried ($Na_2SO_4$), and evaporated on the rotovap to yield a slurry that was dissolved in DMSO. After subjecting the sample to preparative HPLC, a major peak was collected which showed an HPLC-MS of the desired product (Ret. time (Method A) 4.10 min, $MH^+$=364.2). A second minor peak from preparative HPLC could also be collected as an isomer of the hydroxamic acid.

Each of the following compounds was synthesized as described above using the appropriate alkyne.

| Compound # | Structure | $MH^+$ (m/z) | Ret. Time (min) | HPLC-MS Method |
|---|---|---|---|---|
| 114-1 | 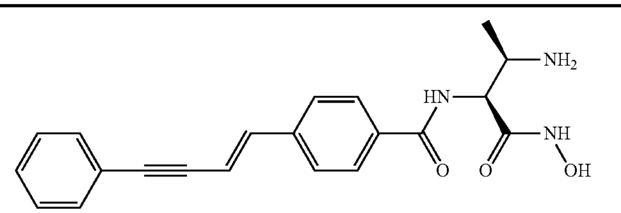 | 363.4 | 6.2 | B |
| 114-2 | 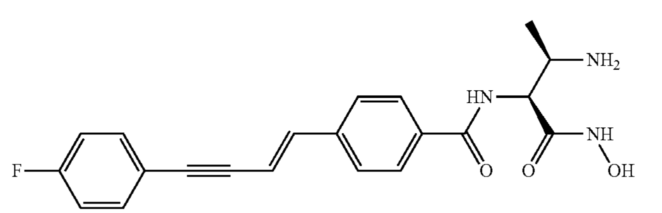 [SMILES: C[C@@H](N)[C@H](NC(=O)c1ccc(/C=C/C#Cc2ccc(F)cc2)cc1)C(=O)NO] | 382.3 | 6.59 | B |

-continued

| Compound # | Structure | MH+ (m/z) | Ret. Time (min) | HPLC-MS Method |
|---|---|---|---|---|
| 114-3 | 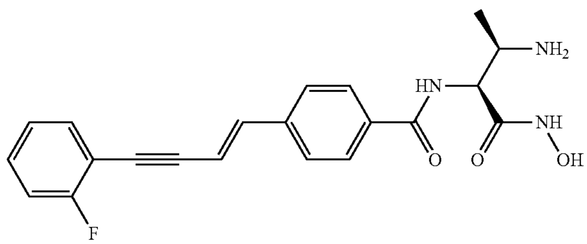 | 382.3 | 6.23 | B |
| 114-4 | 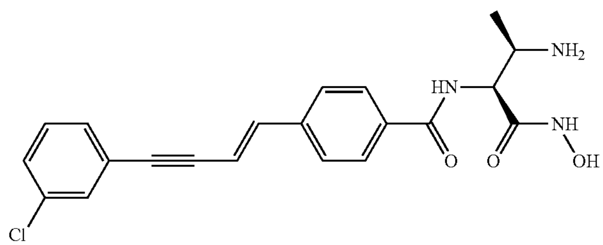 [SMILES: C[C@@H](N)[C@H](NC(=O)c1ccc(/C=C/C#Cc2cccc(Cl)c2)cc1)C(=O)NO] | 397.9 | 7.13 | B |
| 114-5 | 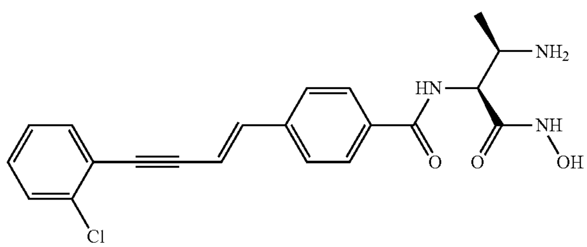 | 397.9 | 6.73 | B |
| 114-6 | 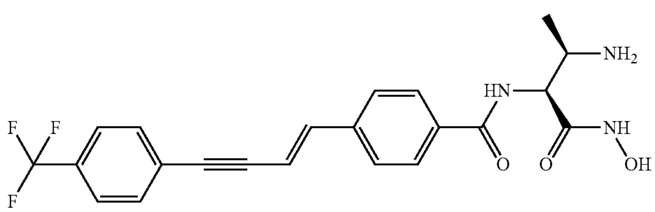 [SMILES: C[C@@H](N)[C@H](NC(=O)c1ccc(/C=C/C#Cc2ccc(C(F)(F)F)cc2)cc1)C(=O)NO] | 432.3 | 7.54 | B |
| 114-7 | 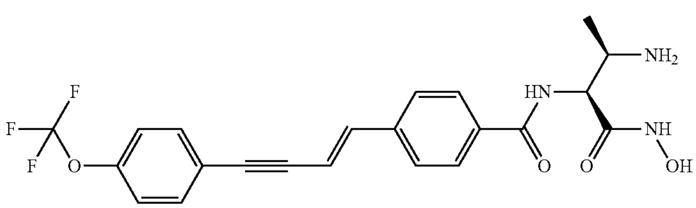 [SMILES: C[C@@H](N)[C@H](NC(=O)c1ccc(/C=C/C#Cc2ccc(OC(F)(F)F)cc2)cc1)C(=O)NO] | 447.9 | 7.71 | B |
| 114-8 | 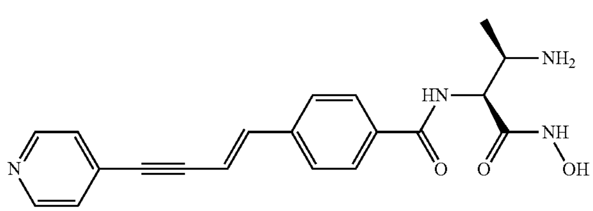 [SMILES: C[C@@H](N)[C@H](NC(=O)c1ccc(/C=C/C#Cc2ccncc2)cc1)C(=O)NO] | 365.1 | 2.38 | B |

-continued

| Compound # | Structure | MH+ (m/z) | Ret. Time (min) | HPLC-MS Method |
|---|---|---|---|---|
| 114-9 | 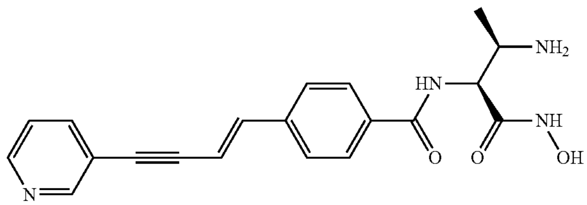 | 365.1 | 2.67 | B |
| 114-10 | 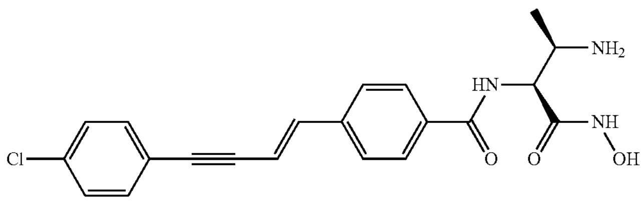 [SMILES: C[C@@H](N)[C@H](NC(=O)c1ccc(/C=C/C#Cc2ccc(Cl)cc2)cc1)C(=O)NO] | 398.4 | 4.56 | A |

Each of the following compounds of was synthesized as described above using the appropriate alkyne, threonine methyl ester hydrochloride or (S)-Me$_2$-BOC-DAP-OMe and BOC deprotection.

| Compound # | Structure | MH+ (m/z) | Ret. Time (min) | HPLC-MS Method |
|---|---|---|---|---|
| 114-11 | 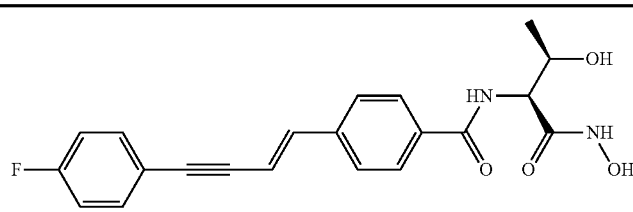 | 383.1 | 7.21 | B |
| 114-12 | 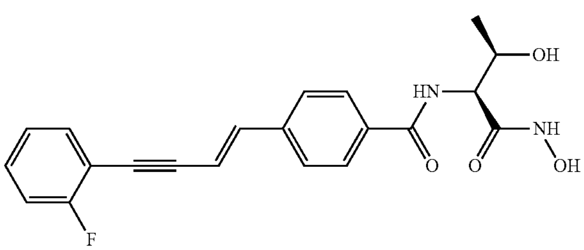 | 383.1 | 7.01 | B |
| 114-13 | 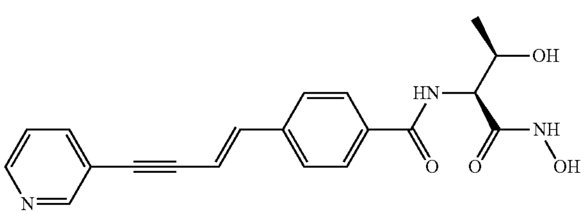 [SMILES: C[C@@H](O)[C@H](NC(=O)c1ccc(/C=C/C#Cc2cccnc2)cc1)C(=O)NO] | 366.3 | 3.30 | B |
| 114-14 | 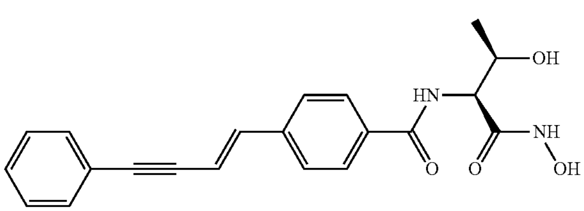 [SMILES: C[C@@H](O)[C@H](NC(=O)c1ccc(/C=C/C#Cc2ccccc2)cc1)C(=O)NO] | 365.3 | 7.01 | B |

-continued

| Compound # | Structure | MH+ (m/z) | Ret. Time (min) | HPLC-MS Method |
|---|---|---|---|---|
| 114-15 | 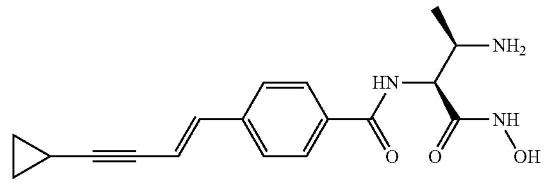 [SMILES: C[C@@H](N)[C@H](NC(=O)c1ccc(/C=C/C#CC2CC2)cc1)C(=O)NO] | 328.7 | 3.27 | A |
| 114-16 | 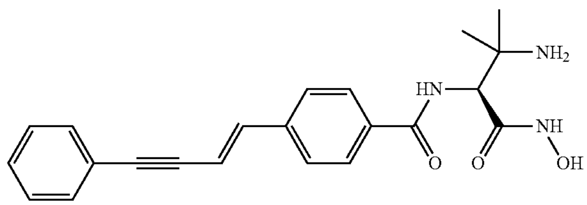 [SMILES: CC(C)(N)[C@H](NC(=O)c1ccc(/C=C/C#Cc2ccccc2)cc1)C(=O)NO] | 378.8 | 6.48 | B |
| 114-17 | 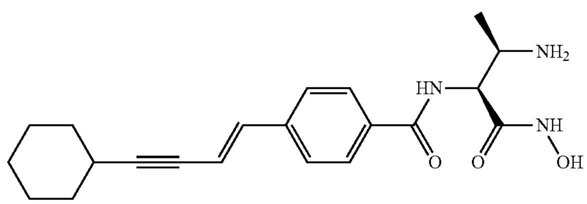 [SMILES: C[C@@H](N)[C@H](NC(=O)c1ccc(/C=C/C#CC2CCCCC2)cc1)C(=O)NO] | 370.3 | 6.99 | B |
| 114-18 | 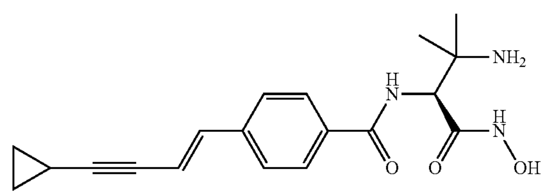 [SMILES: CC(C)(N)[C@H](NC(=O)c1ccc(/C=C/C#CC2CC2)cc1)C(=O)NO] | 342.3 | 5.54 | B |
| 114-19 | 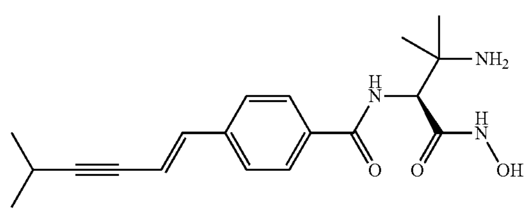 [SMILES: CC(C)C#C/C=C/c1ccc(C(=O)N[C@H](C(=O)NO)C(C)(C)N)cc1] | 344.3 | 6.09 | B |
| 114-20 | 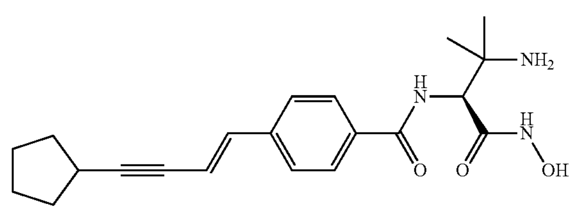 [SMILES: CC(C)(N)[C@H](NC(=O)c1ccc(/C=C/C#CC2CCCC2)cc1)C(=O)NO] | 370.3 | 6.88 | B |

General Procedure for Following Examples

Method 6 (Sonogashira Coupling)

A microwave tube was charged with bromo- or iodophenyl derivative (1.9 mmol), 4-ethynyl-benzoic acid methyl ester or acid (2.0 mmol), PdCl$_2$(dppf).CH$_2$Cl$_2$ (0.038 mmol, 2 mol %), CuI (0.076 mmol, 4 mol %), DIPA (4 mL), and THF (12 mL). The tube was backfilled with nitrogen, sealed, and irradiated in a microwave reactor (max. power 250 W) at 100-125° C. for 10-20 min. THF was removed in vacuo and the residue was taken up in EtOAc (100 mL). The organic layer was washed with water (2×50 mL) and brine (50 mL), dried over anhydrous Na$_2$SO$_4$, and concentrated in vacuo. Crude product was purified by normal phase flash chromatography on a CombiFlash® Companion™ unit using hexanes-EtOAc gradient elution. Fractions containing the desired product were combined and concentrated to give the target compound (Fmoc protecting groups are cleaved during the reaction).

Example 115

N-((2S,3R)-3-amino-1-(hydroxyamino)-1-oxobutan-2-yl)-4-((4-((4-fluoropiperidin-1-yl)methyl)phenyl)ethynyl)benzamide (115-1)

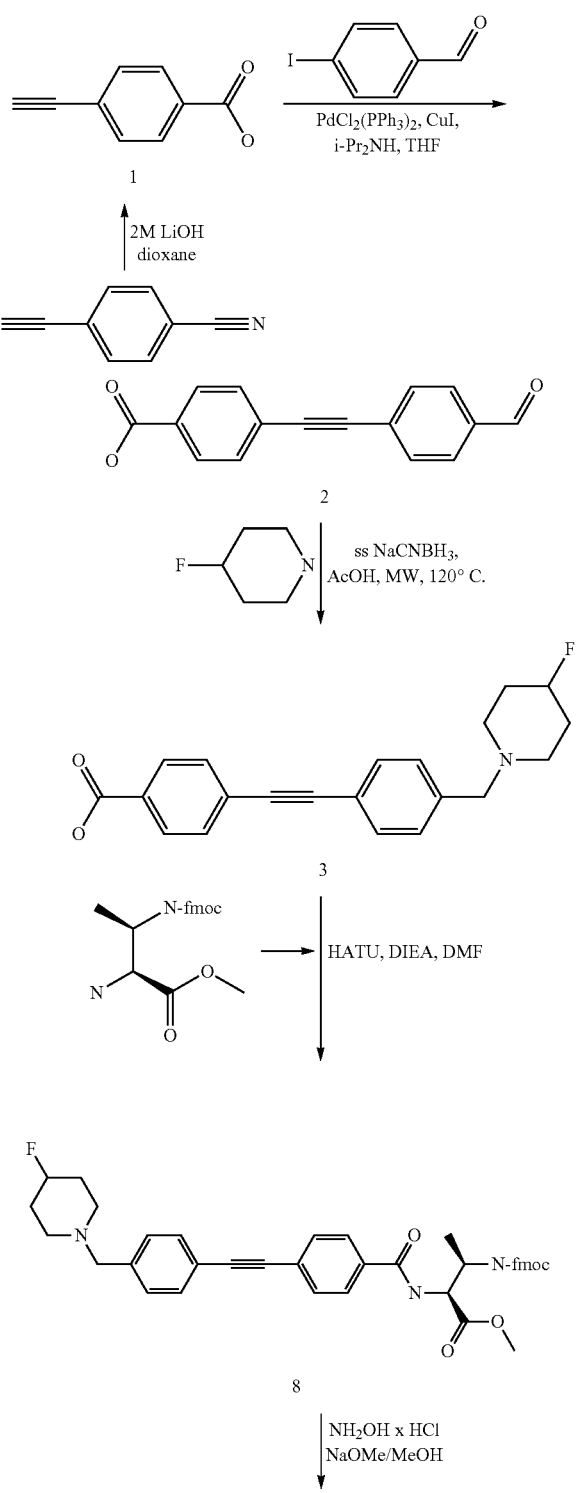

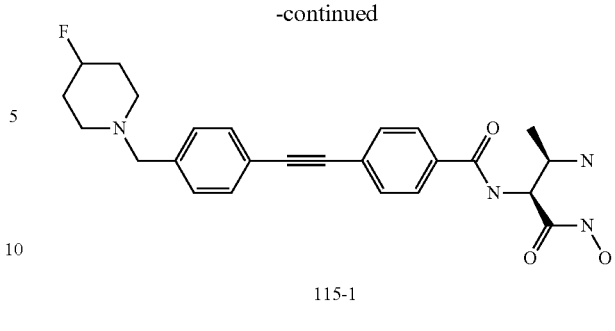

115-1

Synthesis of 4-ethynyl-benzoic acid (1)

A mixture of 4-ethynylbenzonitrile (1.27 g, 10 mmol) and 2M aq. LiOH (25 ml, 50 mmol) in dioxane (20 ml) was irradiated in microwave oven (max. power 250 W, 120° C.) for 30 min and cooled to ambient temperature. Reaction mixture was diluted with water (300 ml) and acidified with 1 M aq. HCl to pH~3. Formed precipitate was filtrated and washed with water and ether and dried in vacuum overnight to produce hydrochloric salt of target material (2.30 g, 63%) as yellow solid.

Synthesis of 4-(4-formyl-phenylethynyl)-benzoic acid (2)

A solution of compound 1 (1.46 g, 10 mmol), 4-iodobenzaldehyde (2.32 g, 10 mmol) and diisopropylamine (3 ml) in THF (6 ml) was purged for 10 min with dry nitrogen. A mixture of $PdCl_2(PPh_3)_2$ (210 mg, 0.03 mmol), and CuI (114 mg, 0.06 mmol) was added and reaction mixture was stirred at ambient temperature overnight. Formed precipitate was filtrated. Filtrate was evaporated in vacuum. Residue was dissolved in EtOAc (100 ml) and stirred with 5% aq. $NaHCO_3$ (30 ml). Formed precipitate was filtrated, washed with water, EtOAc, ether and dried in vacuum to provide target product (2.4 g, 96%) as off-white solid.

Synthesis of 4-[4-(4-fluoro-piperidin-1-ylmethyl)-phenylethynyl]-benzoic acid (3)

A mixture of compound 2 (150 mg, 0.6 mmol), 4-fluoropiperidine hydrochloride (84 mg, 0.6 mmol), AcOH (30 µl) and silica-supported $NaCNBH_3$ (120 mg, 0.12 mmol) in EtOH (1 ml) was irradiated in microwave oven (max. power 250 W, 120° C.) for 25 min and cooled to ambient temperature. Solids were filtrated. Filtrate was evaporated. Residue was dissolved in EtOAc (100 ml), washed with 5% aq. $NaHCO_3$ (30 ml) and brine (30 ml), dried over anh. $Na_2SO_4$ and evaporated in vacuum. Residue was dried in vacuum overnight to provide target material (68 mg, 34%) as white solid. LC-MS [M+H] 338.4.

Synthesis of (2S,3R)-3-azido-2-tert-butoxycarbonylamino-butyric acid methyl ester (4)

A solution of di-tert-butyl dicarbonate (810 mg, 3.7 mmol), (2S,3R)-2-amino-3-azido-butyric acid methyl ester hydrochloride (660 mg, 3.38 mmol) and DIEA (645 µl, 3.7 mmol) in i-PrOH (10 ml) was maintained at ambient temperature for 10 h. Reaction mixture was evaporated in vacuum. Residue was dissolved in water and extracted with hexane/ether (1:1). Combined organics were dried over anhydrous MgSO$_4$ and concentrated in vacuum. Residue was subjected to flash chromatography on CombiFlash® Companion unit equipped with RediSep® flash column (normal phase, 35-60 micron average particle size silicagel, 40 g, Teledyne Isco); flow rate=35 ml/min; injection volume 2 ml; mobile phase A: hexane; mobile phase B: EtOAc; gradient 0-50% B in 1 h. Fractions containing the desired product were combined and concentrated in vacuum to provide target compound (564 mg, 65%) as colorless oil. LC-MS [M+H] 259.0.

Synthesis of (2S,3R)-3-amino-2-tert-butoxycarbonylamino-butyric acid methyl ester (5)

Compound 4 (786 mg, 3.05 mmol) was dissolved in methanol (20 ml) followed by the addition of Pd/C (5% wt, 200 mg). Reaction mixture was subjected to hydrogenation (Parr apparatus, 80 psi) at ambient temperature for 40 min. Catalyst was filtered and washed with methanol. Filtrate was evaporated in vacuum to provide 3 (682 mg, 96%) as colorless oil. LC-MS [M+H] 233.0.

Synthesis of (2S,3R)-2-tert-butoxycarbonylamino-3-(9H-Fluoren-9-ylmethoxycarbonyl-amino)-butyric acid methyl ester (6)

A mixture of 5 (682 mg, 2.94 mmol) and Fmoc-OSu (1.04 g, 3.08 mmol) in acetone (5 ml) was stirred at ambient temperature for 2 h. Solvent was evaporated in vacuum. Residue was dissolved in EtOAc (50 ml) and washed with 5% NaHCO$_3$, and brine. Organic layer was dried over Na$_2$SO$_4$ and evaporated in vacuum. Residue was subjected to flash chromatography on CombiFlash® Companion unit equipped with RediSep® flash column (normal phase, 35-60 micron average particle size silicagel, 40 g, Teledyne Isco); flow rate=35 ml/min; injection volume 2 ml; mobile phase A: hexane; mobile phase B: EtOAc; gradient 0-45% B in 1 h. Fractions containing the desired product were combined and concentrated in vacuum to provide 6 (1.10 g, 82%) as colorless oil that was solidified during vacuum drying. LC-MS [M+H] 455.3.

Synthesis of (2S,3R)-2-amino-3-(9H-fluoren-9-ylmethoxycarbonylamino)-butyric acid methyl ester hydrochloride (7)

Compound 6 (1.10 g, 2.42 mmol) was dissolved in 4 N HCl/dioxane (8 ml) and solution was maintained at ambient temperature for 20 min. The resulting suspension was diluted with ether and the precipitate was filtered and washed with ether. Compound was dried in vacuum to provide the hydrochloride of 7 (840 mg, 89%) as white solid. LC-MS [M+H] 355.2.

Synthesis of (2S,3R)-3-(9H-fluoren-9-ylmethoxy-carbonylamino)-2-{4-[4-(4-fluoro-piperidin-1-ylm-ethyl)-phenylethynyl]-benzoylamino}-butyric acid methyl ester (8)

A solution of 3 (31 mg, 0.09 mmol), HATU (34 g, 0.09 mmol) and DIEA (50 µl, 0.27 mmol) in DMF (1 ml) was maintained at ambient temperature for 10 min followed by the addition of compound 7 hydrochloride (35 mg, 0.09 mmol). Reaction mixture was stirred at ambient temperature overnight followed by the dilution with EtOAc (100 ml). Solution was extracted with water (20 ml×2) and brine (20 ml). Organic layer was dried over MgSO$_4$ and evaporated. Residue was dried in vacuum to provide target compound (41 mg, 67%) as brown solid. LC-MS [M+H] 674.6.

Synthesis of N-((1S,2R)-2-Amino-1-hydroxycar-bamoyl-propyl)-4-[4-(4-fluoro-piperidin-1-ylm-ethyl)-phenylethynyl]-benzamide (115-1)

A solution of hydroxylamine hydrochloride (26 mg, 0.36 mmol) in MeOH (2 ml) was cooled to −5° C. followed by the addition of 25% NaOMe/MeOH (125 µl, 0.55 mmol) under nitrogen. Reaction mixture was stirred at −5° C. for additional 5 min, cooled to −20° C., and solution of 8 (41 mg, 0.061 mmol) in THF/MeOH (1:1, 2 ml) was added dropwise over the period of 5 min. Temperature of reaction mixture was raised to ambient. Completion of the reaction was monitored by LC-MS. Reaction mixture was acidified with 1 N aq. HCl to pH~7 and evaporated in vacuum. Residue was dissolved in DMSO (500 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 8% B to 28% B in 60 min., detection 254 nm]. Fractions containing the desired product were combined and lyophylised to provide the trifluoracetate salt of 115-1 as white solid. LC-MS [M+H] 452.9.

| Compound | Scale (mmol) | Yield (mg) | Yield (%) | Purity (%) | [M + H] | Retention time (min)* |
|---|---|---|---|---|---|---|
| 115-1 | 0.061 | 15.6 | 37 | 99.1 | 452.9 | 2.58 |

*[Chromolith SpeedRod RP-18e C18 column (4.6 x 50 mm); flow rate 1.5 ml/min; mobile phase A: 0.1% TFA/water; mobile phase B 0.1% TFA/ACN; gradient elution from 5% B to 100% B over 9.6 min, detection 254 nm]

The following compounds were made as described for 115-1 above.

| Compound # | Structure | RT (min) | [M + H] |
|---|---|---|---|
| 115-2 | 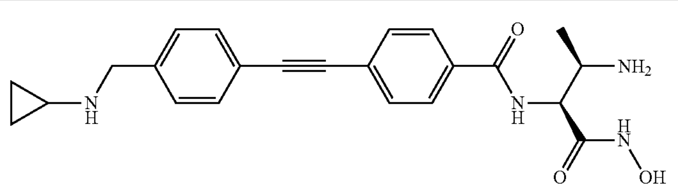 [SMILES: C[C@@H](N)[C@H](NC(=O)c1ccc(C#Cc2ccc(CNC3CC3)cc2)cc1)C(=O)NO] | 5.11[1] | 407.1 |

-continued

| Compound # | Structure | RT (min) | [M + H] |
|---|---|---|---|
| 115-3 | 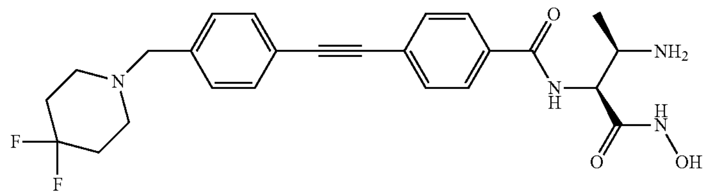 [SMILES: C[C@@H](N)[C@H](NC(=O)c1ccc(C#Cc2ccc(CN3CCC(F)(F)CC3)cc2)cc1)C(=O)NO] | 5.61[1] | 471.5 |
| 115-4 | 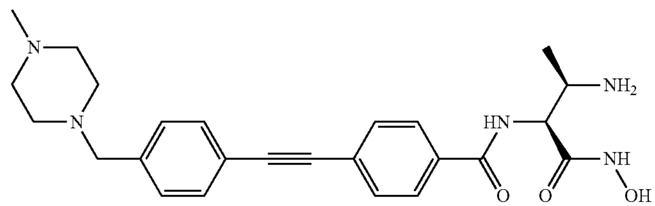 [SMILES: C[C@@H](N)[C@H](NC(=O)c1ccc(C#Cc2ccc(CN3CCN(C)CC3)cc2)cc1)C(=O)NO] | 2.59[2] | 450.3 |
| 115-5 | 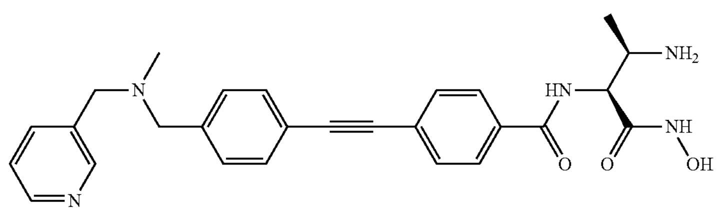 [SMILES: C[C@@H](N)[C@H](NC(=O)c1ccc(C#Cc2ccc(CN(C)Cc3cccnc3)cc2)cc1)C(=O)NO] | 2.67[2] | 472.3 |
| 115-6 | 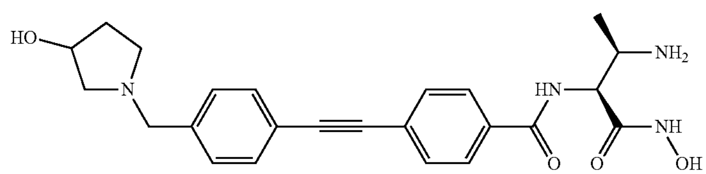 [SMILES: C[C@@H](N)[C@H](NC(=O)c1ccc(C#Cc2ccc(CN3CCC(O)C3)cc2)cc1)C(=O)NO] | 3.01[2] | 437.1 |
| 115-7 | 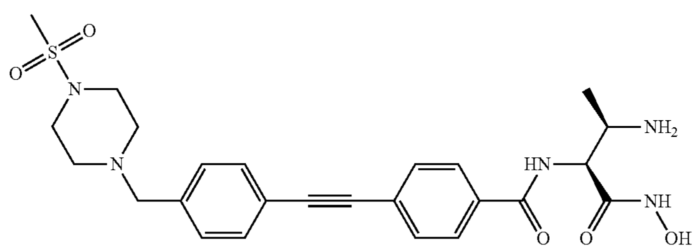 [SMILES: C[C@@H](N)[C@H](NC(=O)c1ccc(C#Cc2ccc(CN3CCN(S(C)(=O)=O)CC3)cc2)cc1)C(=O)NO] | 3.31[2] | 514.3 |
| 115-8 | 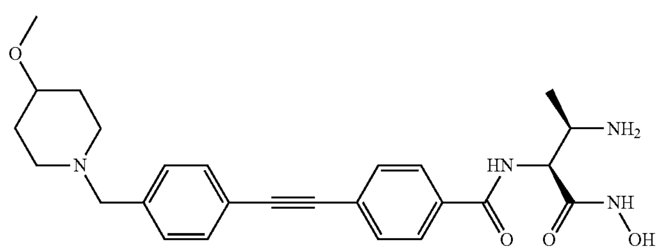 [SMILES: COC1CCN(Cc2ccc(C#Cc3ccc(C(=O)N[C@H](C(=O)NO)[C@@H](C)N)cc3)cc2)CC1] | 3.54[2] | 465.1 |

[1] Using LC-MS Analytical Method D.
[2] Using LC-MS Analytical Method B.

Example 116

(S)—N-(3-amino-1-(hydroxyamino)-1-oxopropan-2-yl)-4-((4-((2-aminoacetamido)methyl)phenyl)ethynyl)benzamide (116-1)

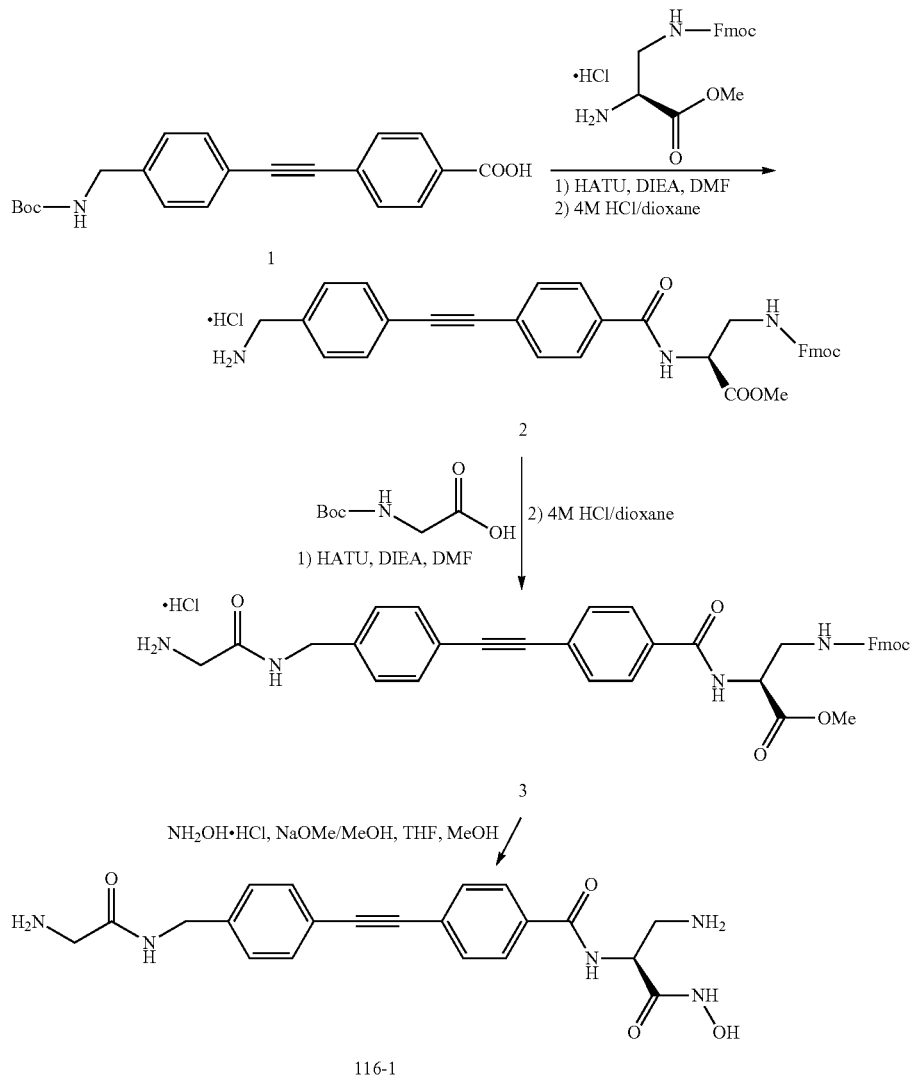

Synthesis of (S)-2-[4-(4-Aminomethyl-phenylethynyl)-benzoylamino]-3-(9H-fluoren-9-ylmethoxycarbonylamino)-propionic acid methyl ester hydrochloride (2)

Compound 1 (500 mg, 1.42 mmol), DAP (Fmoc, OMe) .HCl (589 mg, 1.56 mmol), HATU (597 mg, 1.57 mmol), DIEA (0.791 mL, 4.54 mmol) and DMF (2 mL) were combined and the mixture was stirred at ambient temperature for 30 min. Reaction mixture was diluted with EtOAc (100 mL), washed with water (2×50 mL) and brine (50 mL), dried over anhydrous MgSO$_4$, and concentrated in vacuo. LC-MS: RT (Method A) 7.37 min; [M+H] 674.4. The residue was dissolved in dioxane (10 mL) and 4 M HCl/dioxane (25 mL, 100 mmol) was added. Reaction mixture was stirred at ambient temperature for 1 h, and volatiles were removed in vacuo to give target compound 2 (1.134 g, 131%). LC-MS: RT (Method A) 5.07 min; [M+H] 574.5.

Synthesis of (S)-2-(4-{4-[(2-tert-Butoxycarbonylamino-acetylamino)-methyl]-phenylethynyl}-benzoylamino)-3-(9H-fluoren-9-ylmethoxycarbonylamino)-propionic acid methyl ester hydrochloride (3)

Compound 2 (365 mg, 0.598 mmol), Boc-Gly-OH (126 mg, 0.719 mmol), HATU (274 mg, 0.721 mmol), DIEA (0.365 mL, 2.09 mmol) and DMF (1 mL) were combined and the mixture was stirred at ambient temperature for 1 h. Reaction mixture was diluted with EtOAc (100 mL), washed with water (2×50 mL) and brine (50 mL), dried over anhydrous MgSO$_4$, and concentrated in vacuo. LC-MS: RT (Method A) 6.36 min; [M+H] 731.5 ($C_{42}H_{42}N_4O_8$+H, requires 731.84). The residue was dissolved in dioxane (5 mL) and 4 M HCl/dioxane (15 mL, 60 mmol) was added. Reaction mixture was stirred at ambient temperature for 1 h, and volatiles were removed in vacuo to give target compound 3 (489 mg, 122%). LC-MS: RT (Method A) 5.23 min; [M+H] 631.5.

(S)—N-(3-amino-1-(hydroxyamino)-1-oxopropan-2-yl)-4-((4-((2-aminoacetamido methyl)phenyl)ethynyl)benzamide (116-1)

| Reagent | MW | Eq. | mg/mL | mmol |
|---|---|---|---|---|
| Compound 3 | 667.17 | 1.0 | 147 mg | 0.220 |
| Hydroxylamine hydrochloride | 69.49 | 6 | 92 mg | 1.32 |
| 25% NaOMe/MeOH | 54.02 | 12 | 0.607 mL | 2.66 |
| THF | | | 2 mL | |
| MeOH | | | 2 mL | |

The target compound 116-1 (3.1 mg, 2.2% yield) as a white solid was prepared by following General Method for hydroxamate. LC-MS: RT (Method A) 2.39 min; [M+H] 410.5.

| Compound | Scale (mmol)[1] | Yield (mg) | Yield (%)[1] | Purity (%)[2] | [M + H] | Retention time (min)[2] |
|---|---|---|---|---|---|---|
| 116-1 | 0.220 | 3.1 | 2.2 | 99.1 | 410.4 | 2.39 |

[1]Based on the amount of compound used in the last step of the reaction.
[2]Using LC-MS Analytical Method A.

Example 117

N-((1S,2R)-2-Amino-1-methylcarbamoyl-propyl)-4-(4-morpholin-4-ylmethyl-phenylethynyl)-benzamide (117-1) and (2S,3R)-3-Amino-2-[4-(4-morpholin-4-ylmethyl-phenylethynyl)-benzoylamino]-butyric acid (117-2)

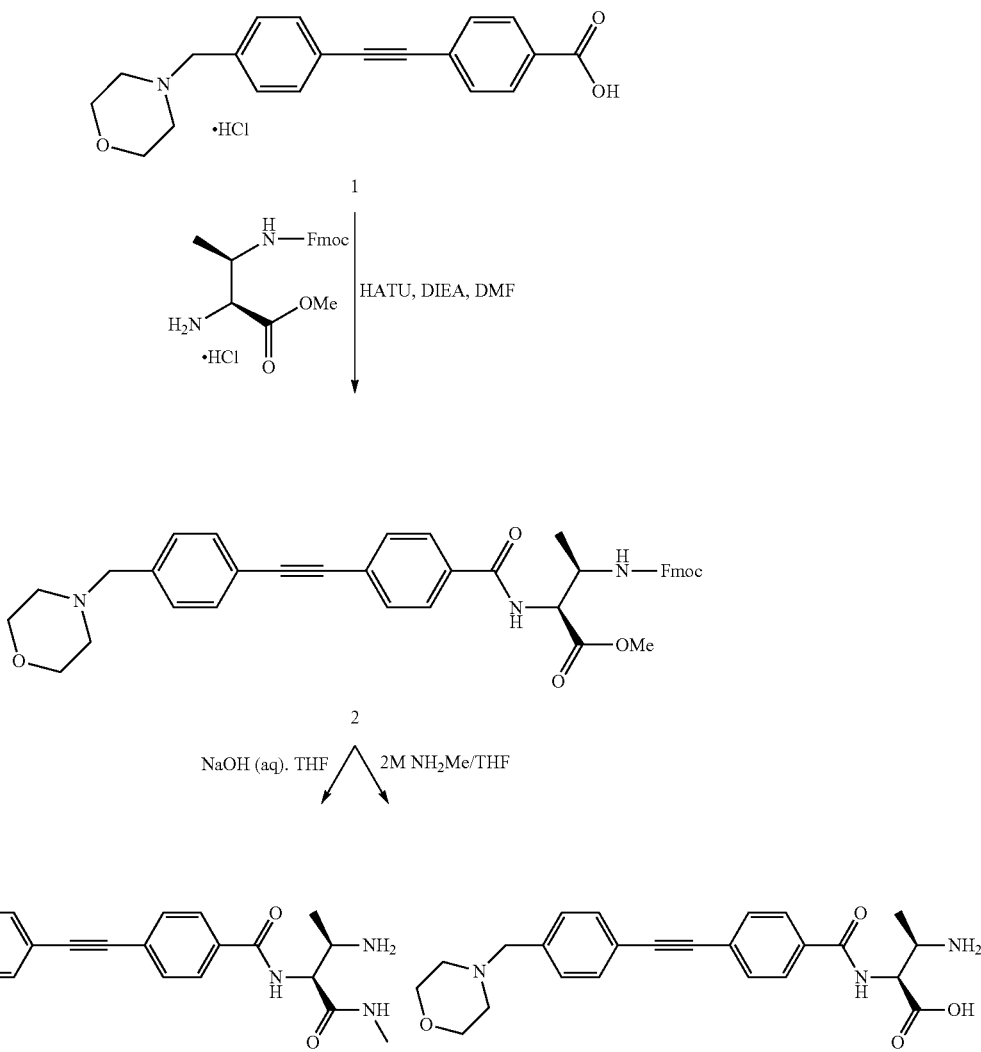

Synthesis of (2S,3R)-3-(9H-Fluoren-9-ylmethoxy-carbonylamino)-2-[4-(4-morpholin-4-ylmethyl-phenylethynyl)-benzoylamino]-butyric acid methyl ester (2)

Compound 1 (137 mg, 0.383 mmol), MeDAP (Fmoc, OMe).HCl (150 mg, 0.384 mmol), HATU (173 mg, 0.455 mmol), DIEA (0.298 mL, 1.71 mmol) and DMF (1 mL) were combined and the mixture was stirred at ambient temperature for 1 h. Reaction mixture was diluted with EtOAc (50 mL), washed with water (2×30 mL) and brine (30 mL), dried over anhydrous MgSO$_4$, and concentrated in vacuo to give target compound 2 (314 mg, 125%). LC-MS: RT (Method A) 5.35 min; [M+H] 658.4.

Synthesis of N-((1S,2R)-2-Amino-1-methylcarbamoyl-propyl)-4-(4-morpholin-4-ylmethyl-phenylethynyl)-benzamide (117-1)

A solution of compound 2 (~0.19 mmol) in 2 M NH$_2$Me/THF (2 mL) was stirred at 80° C. in a sealed reaction vessel for 16 h. Reaction mixture was concentrated in vacuo and the residue was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 5% B to 40% B over 90 min, MS detection). Fractions containing the desired product were combined and lyophilized to provide the trifluoroacetate salt of target compound 117-1 (10.8 mg, 8.58% yield) as a white solid. LC-MS: RT (Method A) 2.80 min; [M+H] 435.4.

| Compound | Scale (mmol)[1] | Yield (mg) | Yield (%)[1] | Purity (%)[2] | [M + H] | Retention time (min)[2] |
|---|---|---|---|---|---|---|
| 117-1 | 0.19 | 10.8 | 8.58 | 98.5 | 435.4 | 2.80 |

[1]Based on the amount of compound used in the last step.
[2]Using LC-MS Analytical Method A.

Synthesis of (2S,3R)-3-Amino-2-[4-(4-morpholin-4-ylmethyl-phenylethynyl)-benzoylamino]-butyric acid (117-2)

To a solution of compound 2 (~0.19 mmol) in THF (1 mL), was added 2 M NaOH (aq) (0.475 mL, 0.950 mmol), and the mixture was stirred at ambient temperature for 1 h. Reaction mixture was neutralized with 1 M HCl (aq) and concentrated in vacuo. The residue was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 5% B to 40% B over 60 min, MS detection). Fractions containing the desired product were combined and lyophilized to provide the trifluoroacetate salt of target compound 117-2 (26.7 mg, 21.6% yield) as a white solid. LC-MS: RT (Method A) 2.42 min; [M+H] 422.1.

| Compound | Scale (mmol)[1] | Yield (mg) | Yield (%)[1] | Purity (%)[2] | [M + H] | Retention time (min)[2] |
|---|---|---|---|---|---|---|
| 117-2 | 0.19 | 26.7 | 21.6 | 98.9 | 422.1 | 2.42 |

[1]Based on the amount of compound used in the last step.
[2]Using LC-MS Analytical Method A.

Example 118

N-((1S,2R)-2-Amino-1-hydroxycarbamoyl-propyl)-4-(4-azetidin-1-ylmethyl-phenylethynyl)-benzamide (118-1)

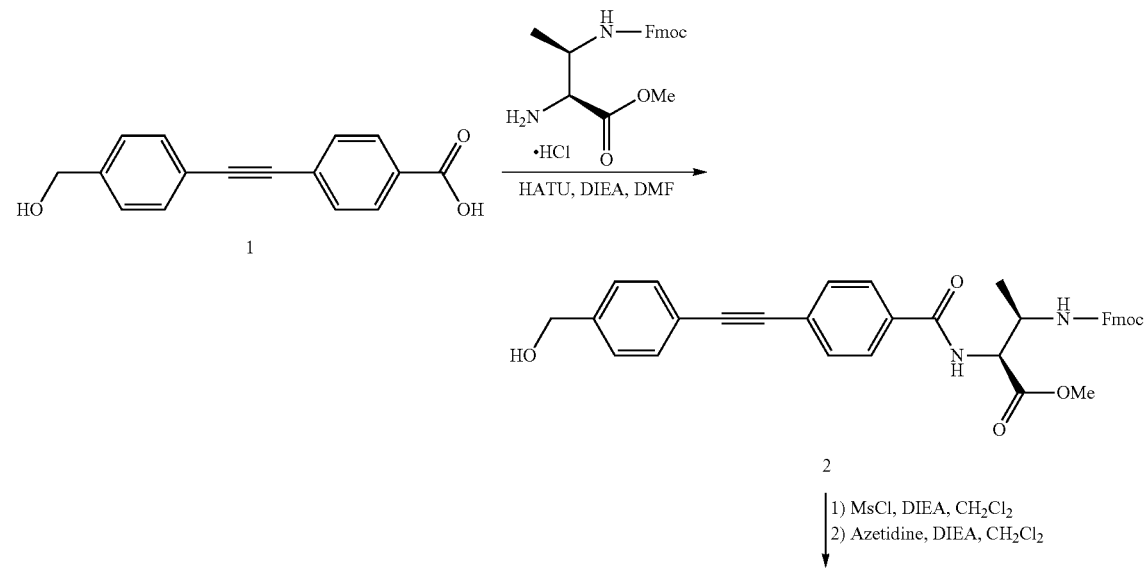

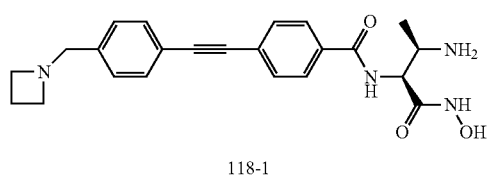 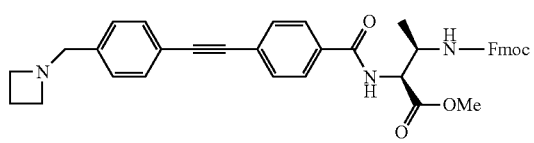

Synthesis of (2S,3R)-3-(9H-Fluoren-9-ylmethoxycarbonylamino)-2-[4-(4-hydroxymethyl-phenylethynyl)-benzoylamino]-butyric acid methyl ester (2)

Compound 1 (615 mg, 2.44 mmol), MeDAP (Fmoc, OMe).HCl (954 mg, 2.44 mmol), HATU (928 mg, 2.93 mmol), DIEA (1.4 mL, 8.04 mmol) and DMF (5 mL) were combined and the mixture was stirred at ambient temperature for 1 h. Reaction mixture was diluted with EtOAc (100 mL), washed with water (2×50 mL) and brine (50 mL), dried over anhydrous $Na_2SO_4$, and concentrated in vacuo to give target compound 2 (1.429 g, 99.6%). LC-MS: RT (Method A) 6.19 min; [M+H] 589.3.

Synthesis of (2S,3R)-2-[4-(4-Azetidin-1-ylmethyl-phenylethynyl)-benzoylamino]-3-(9H-fluoren-9-ylmethoxycarbonylamino)-butyric acid methyl ester (3)

To a stirred solution of compound 2 (1.429 g, 2.43 mmol) and DIEA (1.27 mL, 7.29 mmol) in DCM (10 mL), cooled in ice/salt bath, was added dropwise methanesulfonyl chloride (0.571 mL, 7.38 mmol). Reaction mixture was allowed to attain ambient temperature and stir for 30 min. One sixth of the reaction mixture (~1.8 mL, ~0.41 mmol) was added dropwise to a solution of azetidine (0.111 mL, 1.64 mmol) and DIEA (0.286 mL, 1.64 mmol) in DCM (1 mL). Reaction mixture was stirred at ambient temperature for 16 h, then diluted with EtOAc (100 mL), washed with water (2×50 mL) and brine (50 mL), dried over anhydrous $Na_2SO_4$, and concentrated in vacuo to give target compound 3 (247 mg, 96%). LC-MS: RT (Method A) 2.90 min; [M+H] 628.4.

Synthesis of N-((1S,2R)-2-Amino-1-hydroxycarbamoyl-propyl)-4-(4-azetidin-1-ylmethyl-phenylethynyl)-benzamide (118-1)

| Reagent | MW | Eq. | mg/mL | mmol |
|---|---|---|---|---|
| Compound 3 | 627.75 | 1.0 | 247 mg | 0.393 |
| Hydroxylamine hydrochloride | 69.49 | 6 | 164 mg | 2.36 |
| 25% NaOMe/MeOH | 54.02 | 12 | 1.08 mL | 4.72 |
| THF | | | 2 mL | |
| MeOH | | | 2 mL | |

The target compound 118-1 (3.0 mg, 1.2% yield) as a white solid was prepared by following General Method for hydroxamate. LC-MS: RT (Method A) 2.54 min; [M+H] 407.3.

| Compound | Scale (mmol)[1] | Yield (mg) | Yield (%)[1] | Purity (%)[2] | [M + H] | Retention time (min)[2] |
|---|---|---|---|---|---|---|
| 118-1 | 0.393 | 3.0 | 1.2 | 97.1 | 407.3 | 2.54 |

[1]Based on the amount of compound used in the last step of the reaction.
[2]Using LC-MS Analytical Method A.

Each of the following compounds was synthesized as described above.

| Compound # | Structure | RT[1] (min) | [M + H] |
|---|---|---|---|
| 118-2 | 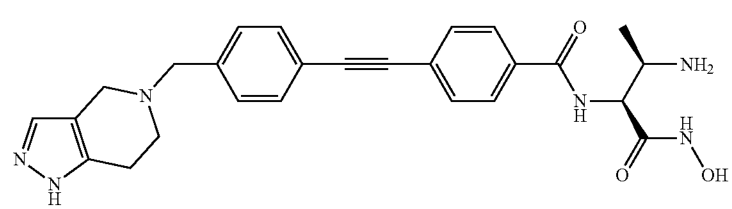 [SMILES: C[C@@H](N)[C@H](NC(=O)c1ccc(C#Cc2ccc(CN3CCc4[nH]ncc4C3)cc2)cc1)C(=O)NO] | 2.56 | 473.2 |
| 118-3 | 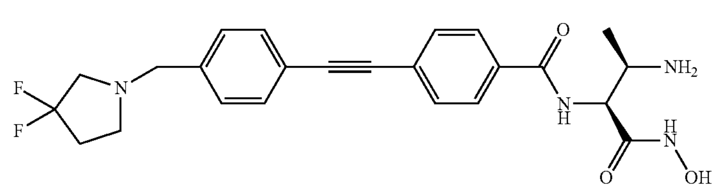 [SMILES: C[C@@H](N)[C@H](NC(=O)c1ccc(C#Cc2ccc(CN3CCC(F)(F)C3)cc2)cc1)C(=O)NO] | 2.76 | 457.1 |

-continued

| Compound # | Structure | RT¹ (min) | [M + H] |
|---|---|---|---|
| 118-4 | 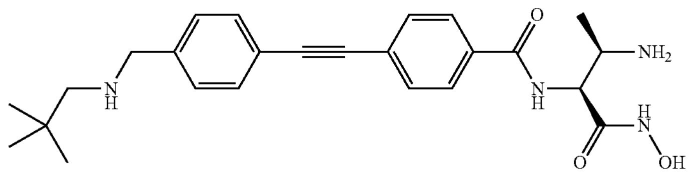 [SMILES: C[C@@H](N)[C@H](NC(=O)c1ccc(C#Cc2ccc(CNCC(C)(C)C)cc2)cc1)C(=O)NO] | 2.90 | 437.4 |
| 118-5 | 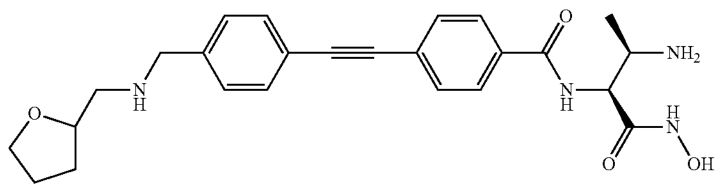 [SMILES: C[C@@H](N)[C@H](NC(=O)c1ccc(C#Cc2ccc(CNCC3CCCO3)cc2)cc1)C(=O)NO] | 2.61 | 451.5 |
| 118-6 | 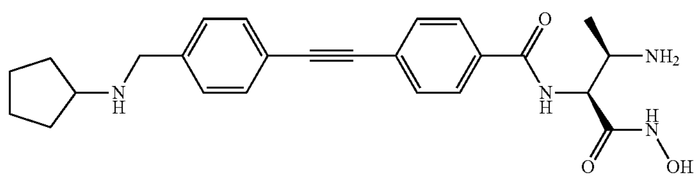 [SMILES: C[C@@H](N)[C@H](NC(=O)c1ccc(C#Cc2ccc(CNC3CCCC3)cc2)cc1)C(=O)NO] | 2.82 | 435.3 |
| 118-7 | 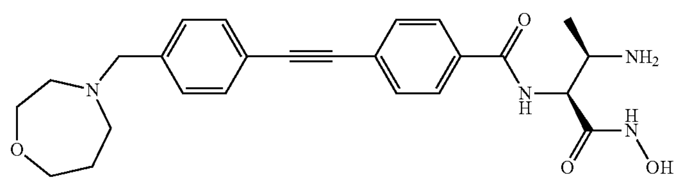 [SMILES: C[C@@H](N)[C@H](NC(=O)c1ccc(C#Cc2ccc(CN3CCCOCC3)cc2)cc1)C(=O)NO] | 2.38 | 451.3 |
| 118-8 | 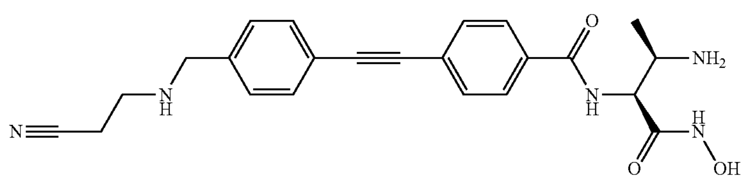 [SMILES: C[C@@H](N)[C@H](NC(=O)c1ccc(C#Cc2ccc(CNCCC#N)cc2)cc1)C(=O)NO] | 2.25 | 420.3 |
| 118-9 | 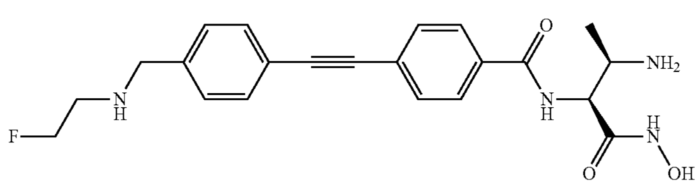 [SMILES: C[C@@H](N)[C@H](NC(=O)c1ccc(C#Cc2ccc(CNCCF)cc2)cc1)C(=O)NO] | 2.27 | 412.9 |
| 118-10 | 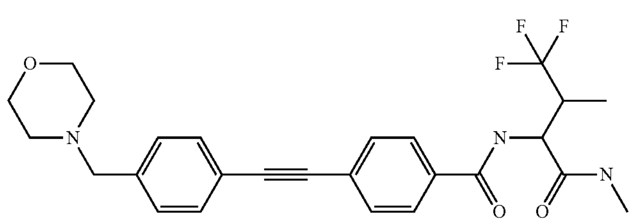 [SMILES: CNC(=O)C(NC(=O)c1ccc(C#Cc2ccc(CN3CCOCC3)cc2)cc1)C(C)C(F)(F)F] | 5.18 | 490.3 |

[1]Using LC-MS Analytical Method A.

Example 119

N-((1S,2R)-2-Amino-1-hydroxycarbamoyl-propyl)-4-{4-[(2,2-difluoro-ethylamino)-methyl]-phenylethynyl}-benzamide (119-1)

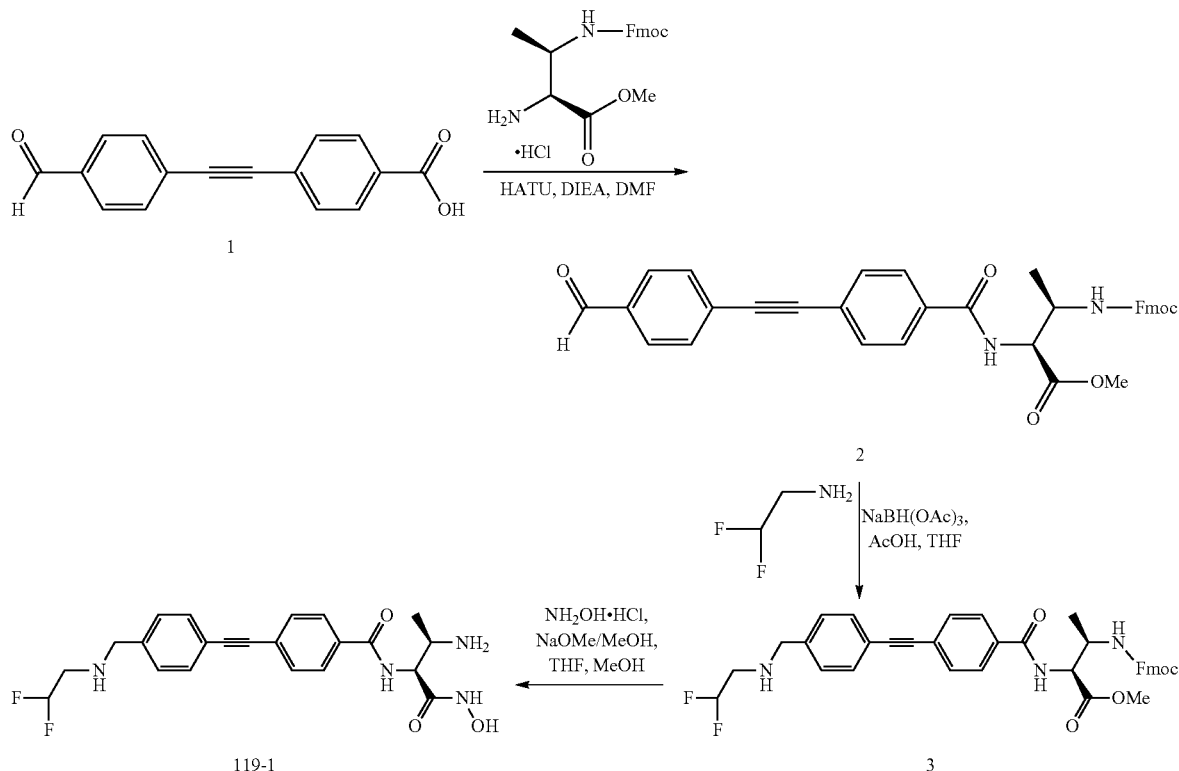

Synthesis of (3S,4R)-3-(9H-Fluoren-9-ylmethoxycarbonylamino)-2-[4-(4-formyl-phenylethynyl)-benzoylamino]-butyric acid methyl ester (2)

Compound 1 (448 mg, 1.79 mmol; see Example A), MeDAP (Fmoc, OMe)·HCl (700 mg, 1.79 mmol), HATU (816 mg, 2.15 mmol), DIEA (1.09 mL, 6.26 mmol) and DMF (3 mL) were combined and the mixture was stirred at ambient temperature for 1 h. Reaction mixture was diluted with EtOAc (50 mL), washed with water (2×30 mL) and brine (30 mL), dried over anhydrous MgSO₄, and concentrated in vacuo to give target compound 2 (1.533 g, 146%). LC-MS: RT (Method A) 7.06 min; [M+H] 587.2.

Synthesis of (2S,3R)-2-(4-{-4-[(2,2-Difluoro-ethylamino)-methyl]-phenylethynyl}-benzoylamino)-3-(9H-fluoren-9-ylmethoxycarbonylamino)-butyric acid methyl ester (3)

To a stirred solution of compound 2 (147 mg, 0.251 mmol) and 2,2-difluoroethylamine (27 mg, 0.337 mmol) in THF (2 mL), was added NaBH(OAc)₃ (74 mg, 0.349 mmol), and the mixture was stirred at ambient temperature for 72 h. LC-MS analysis of the reaction mixture showed only 10% conversion to desired product. 2,2-Difluoroethylamine (20 mg, 0.251 mmol), acetic acid (0.1 mL, 1.75 mmol) and NaBH(OAc)₃ (100 mg, 0.472 mmol) were added, and the reaction mixture was stirred at ambient temperature for 2 h. LC-MS analysis of the reaction mixture showed complete conversion to desired product. Reaction mixture was quenched with 5% NaHCO₃ (aq) (50 mL) and extracted with EtOAc (3×20 mL) Combined organic layers were washed with water (30 mL) and brine (30 mL), dried over anhydrous MgSO₄, and concentrated in vacuo to give target compound 3 (178 mg, 109%). LC-MS: RT (Method A) 5.60 min; [M+H] 652.3.

Synthesis of N-((1S,2R)-2-Amino-1-hydroxycarbamoyl-propyl)-4-{4-[(2,2-difluoro-ethylamino)-methyl]-phenylethynyl}-benzamide (119-1)

| Reagent | MW | Eq. | mg/mL | mmol |
| --- | --- | --- | --- | --- |
| Compound 3 | 627.75 | 1.0 | — | ~0.251 |
| Hydroxylamine hydrochloride | 69.49 | 6 | 105 mg | 1.51 |
| 25% NaOMe/MeOH | 54.02 | 12 | 0.685 mL | 3.00 |
| THF | | | 2 mL | |
| MeOH | | | 2 mL | |

The target compound 119-1 (20.1 mg, 12.2% yield) as a white solid was prepared by following General Method for hydroxamate. LC-MS: RT (Method A) 2.38 min; [M+H] 431.1 ($C_{22}H_{24}F_2N_4O_3$+H, requires 431.47).

| Compound | Scale (mmol)[1] | Yield (mg) | Yield (%)[1] | Purity (%)[2] | [M + H] | Retention time (min)[2] |
|---|---|---|---|---|---|---|
| 119-1 | 0.251 | 20.1 | 12.2 | 99.2 | 431.1 | 2.38 |

[1]Based on the amount of compound used in the reductive amination.
[2]Using LC-MS Analytical Method A.

The following compounds were made as described above.

| Compound # | Structure | RT (min) | [M + H] |
|---|---|---|---|
| 119-2 | 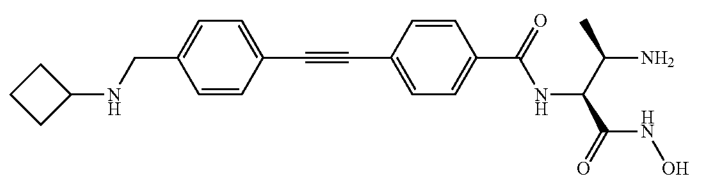 | 2.81[1] | 421.2 |
| 119-3 | 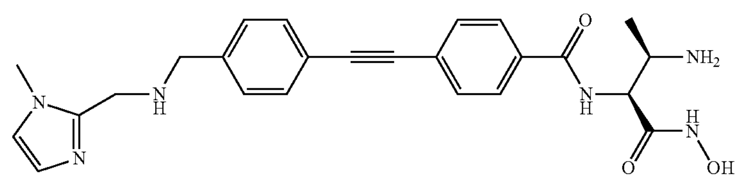 [SMILES: C[C@@H](N)[C@H](NC(=O)c1ccc(C#Cc2ccc(CNCc3nccn3C)cc2)cc1)C(=O)NO] | 2.35[1] | 461.2 |
| 119-4 | 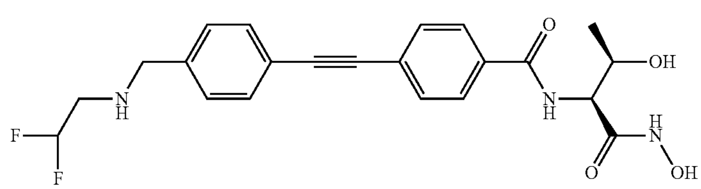 [SMILES: CC(C)(O)[C@H](NC(=O)c1ccc(C#Cc2ccc(CNCC(F)F)cc2)cc1)C(=O)NO] | 3.51[2] | 432.3 |
| 119-5 | 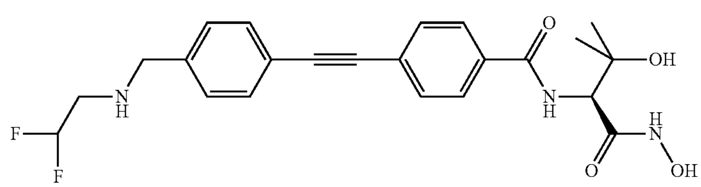 | 3.78[2] | 446.3 |
| 119-6 | 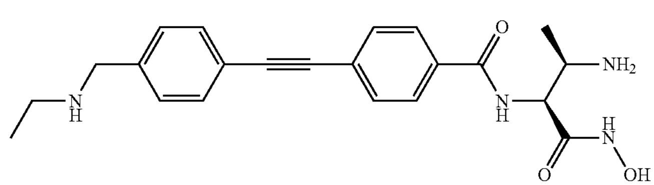 [SMILES: C[C@@H](N)[C@H](NC(=O)c1ccc(C#Cc2ccc(CCO)cc2)cc1)C(=O)NO] | 2.91[2] | 395.1 |

[1]Using LC-MS Analytical Method A.
[2]Using LC-MS Analytical Method B.

Example 120

N-((1S,2R)-2-Amino-1-hydroxycarbamoyl-propyl)-4-(4-ethoxymethyl-phenylethynyl)-benzamide (120-1)

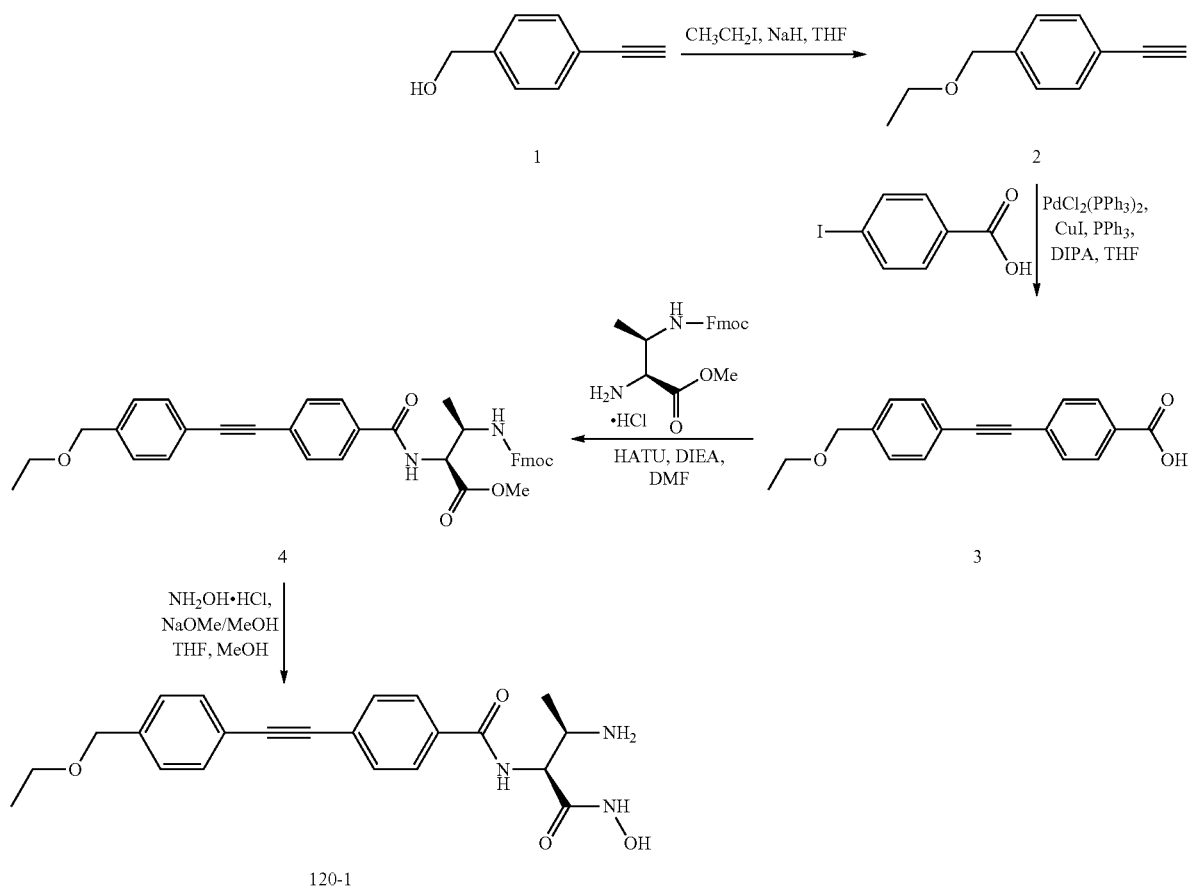

Synthesis of 1-Ethoxymethyl-4-ethynyl-benzene (2)

To a solution of 4-ethynylbenzyl alcohol (436 mg, 3.30 mmol) in THF (2 mL) was added NaH (101 mg, 4.21 mmol) and iodoethane (0.486 mL, 6.08 mmol). Reaction mixture was stirred at ambient temperature for 16 h. Reaction mixture was diluted with brine (50 mL) and extracted with EtOAc (2×50 mL). Combined organic layers were washed with brine (50 mL), dried over anhydrous $MgSO_4$, and concentrated in vacuo. Residue was purified by normal phase flash chromatography on a CombiFlash® Companion™ unit equipped with Luknova flash column (80 g silica gel, 40-60 μm average particle size, 60 Å pore size); flow rate: 60 mL/min; mobile phase A: hexane; mobile phase B: EtOAc; gradient elution from 0% B to 30% B over 60 min. Fractions containing the desired product were combined and concentrated in vacuo to give target compound 2 (290 mg, 55%). LC-MS: RT (Method A) 5.16 min; compound not significantly ionizable.

Synthesis of 4-(4-Ethoxymethyl-phenylethynyl)-benzoic acid (3)

Compound 2 (271 mg, 1.69 mmol), 4-iodobenzoic acid (419 mg, 1.69 mmol), $PdCl_2(PPh_3)_2$ (36 mg, 0.051 mmol), CuI (19 mg, 0.100 mmol), DIPA (4 mL, 28.3 mmol), and THF (12 mL) were combined in a microwave tube. The tube was backfilled with nitrogen, sealed, and irradiated in a microwave reactor (max. power 250 W) at 120° C. for 10 min. Reaction mixture was diluted with EtOAc (200 mL), washed with 2% $H_2SO_4$ (75 mL) and water (75 mL), dried over $MgSO_4$ and concentrated in vacuo to give target compound 3 (470 mg, 99%). LC-MS: RT (Method A) 5.79 min; compound not significantly ionizable.

Synthesis of (2S,3R)-2-[4-(4-Ethoxymethyl-phenylethynyl)-benzoylamino]-3-(9H-fluoren-9-yl-methoxycarbonylamino)-butyric acid methyl ester (4)

Compound 3 (115 mg, 0.410 mmol), MeDAP (Fmoc, OMe).HCl (161 mg, 0.412 mmol), HATU (187 mg, 0.492 mmol), DIEA (0.235 mL, 1.34 mmol) and DMF (0.8 mL) were combined and the mixture was stirred at ambient temperature for 1 h. Reaction mixture was diluted with EtOAc (50 mL), washed with water (2×30 mL) and brine (30 mL), dried over anhydrous $MgSO_4$, and concentrated in vacuo to give target compound 4 (230 mg, 91%). LC-MS: RT (Method A) 7.45 min; [M+H] 617.2.

Synthesis of N-((1S,2R)-2-Amino-1-hydroxycarbamoyl-propyl)-4-(4-ethoxymethyl-phenylethynyl)-benzamide (120-1)

| Reagent | MW | Eq. | mg/mL | mmol |
|---|---|---|---|---|
| Compound 4 | 616.72 | 1.0 | 230 mg | 0.372 |
| Hydroxylamine hydrochloride | 69.49 | 6 | 157 mg | 2.26 |
| 25% NaOMe/MeOH | 54.02 | 12 | 1.023 mL | 4.48 |
| THF | | | 2 mL | |
| MeOH | | | 2 mL | |

The target compound 120-1 (28.7 mg, 15.1% yield) as a white solid was prepared by following General Method for hydroxamate. LC-MS: RT (Method A) 4.06 min; [M+H] 396.2 ($C_{22}H_{25}N_3O_4$+H, requires 396.47).

| Compound | Scale (mmol)[1] | Yield (mg) | Yield (%)[1] | Purity (%)[2] | [M + H] | Retention time (min)[2] |
|---|---|---|---|---|---|---|
| 120-1 | 0.372 | 28.7 | 15.1 | 99.7 | 396.2 | 4.06 |

[1]Based on the amount of compound used in the last step.
[2]Using LC-MS Analytical Method A.

The following compounds were synthesized according to procedures for compound 5.

| Compound # | Structure | RT (min) | [M + H] |
|---|---|---|---|
| 120-2 | ![structure] | 2.95[1] | 430.1 |
| 120-3 | ![structure] | 4.22[2] | 382.3 |

[1]Using LC-MS Analytical Method A.
[2]Using LC-MS Analytical Method B.

Example 121

N—((S)-2-Amino-1-hydroxycarbamoyl-2-methyl-propyl)-4-(4-cyclopropylaminomethyl-phenylethynyl)-benzamide (121-1)

Scheme I

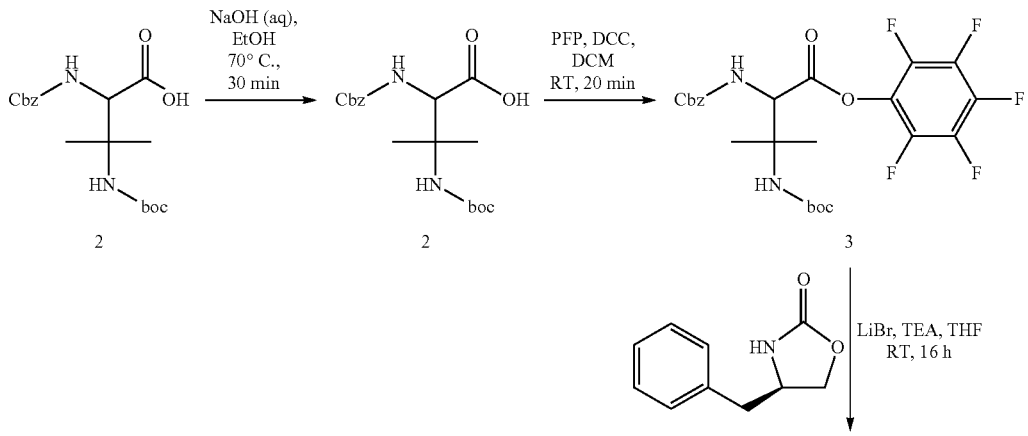

-continued
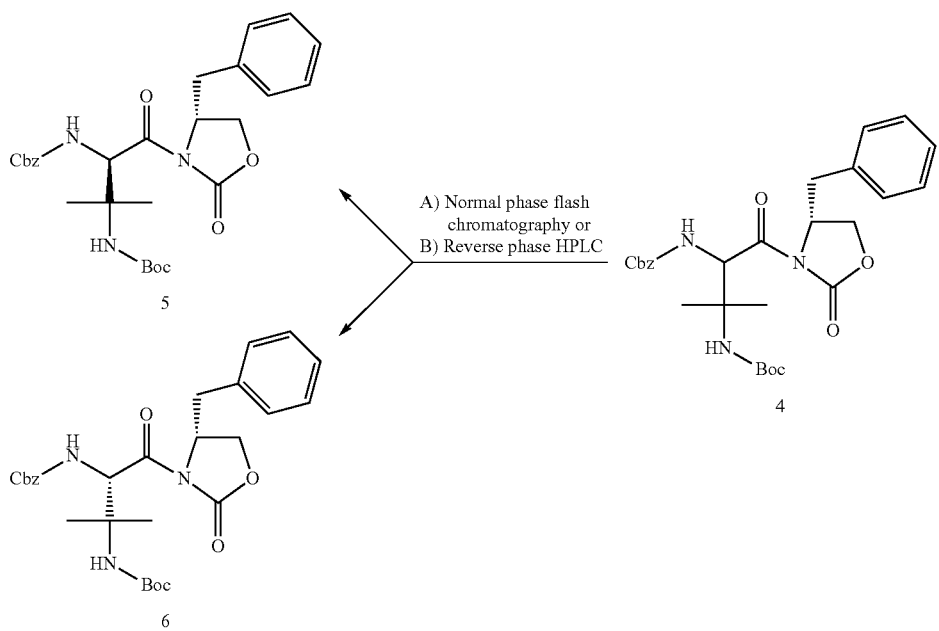
Scheme II
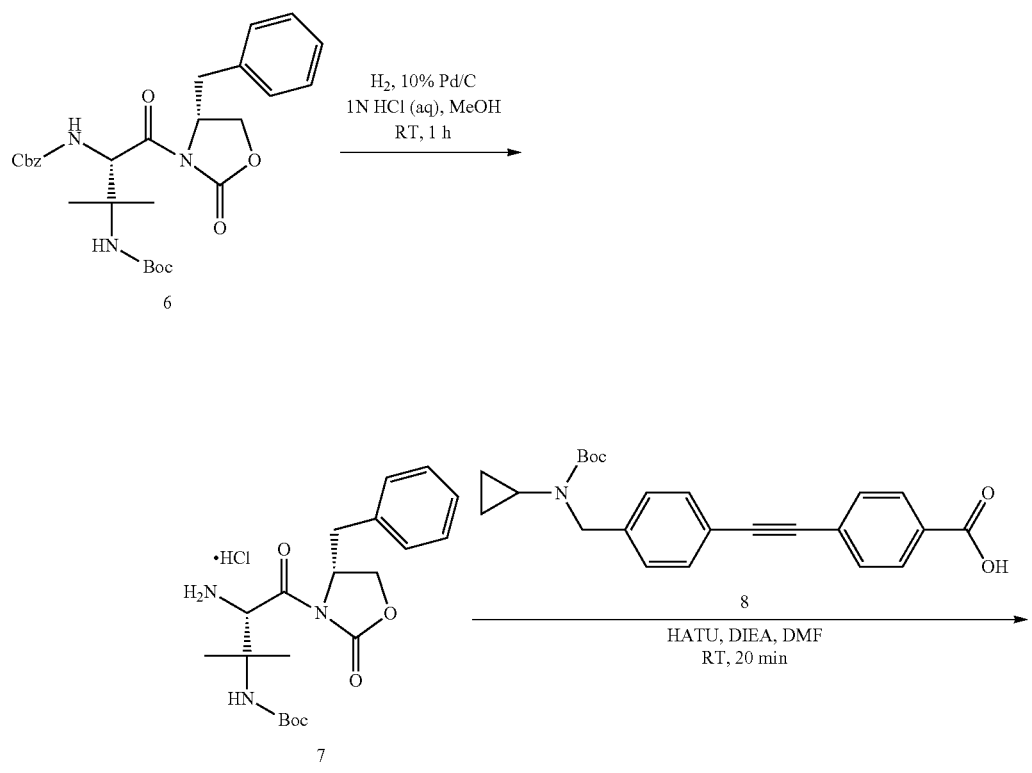

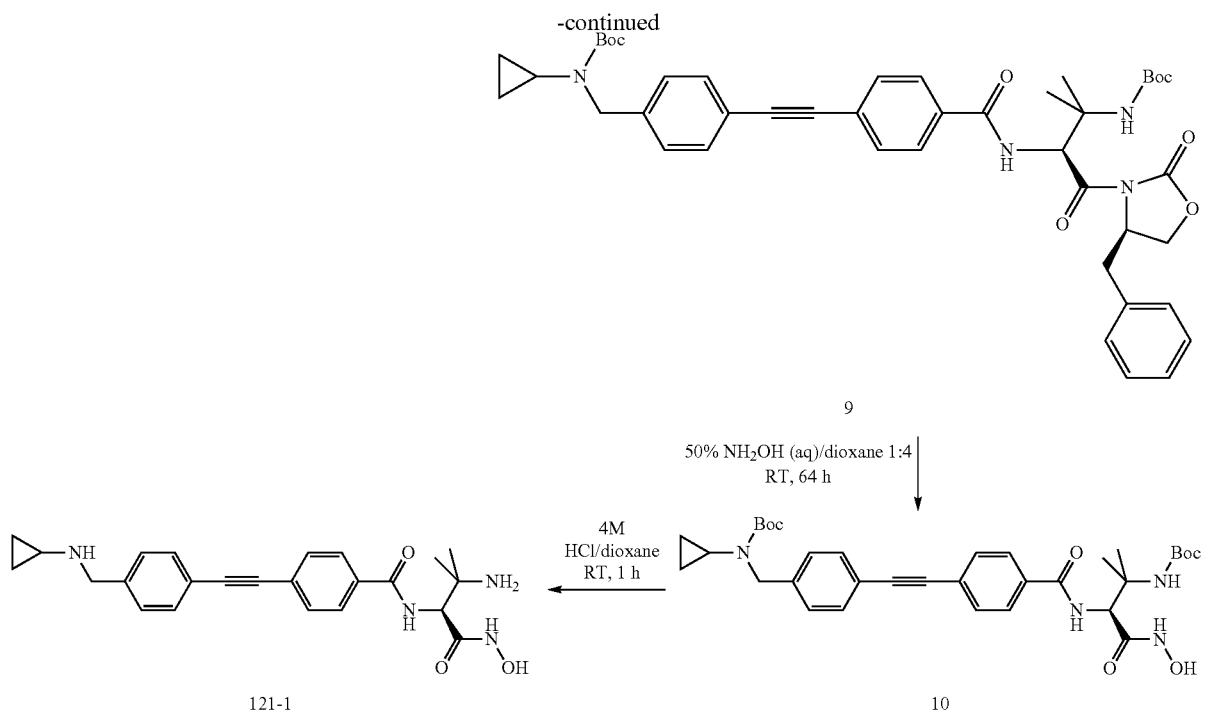

Synthesis of 2-Benzyloxycarbonylamino-3-tert-butoxycarbonylamino-3-methyl-butyric acid (2)

Compound 1 (1.467, 3.86 mmol) was dissolved in EtOH (10 mL), 3 M NaOH (aq) (10 mL, 30 mmol) was added, and the mixture was heated at 70° C. for 1 h. Reaction mixture was concentrated in vacuo and residue was dissolved in water (50 mL), cooled in ice/water bath, and acidified to pH 2 with 10% $H_3PO_4$ (aq). Mixture was extracted with EtOAc (30 mL, 2×20 mL). Combined organic layers were washed with water (30 mL) and brine (30 mL), dried over anhydrous $Na_2SO_4$, and concentrated in vacuo to give target compound 2 (0.977 g, 69.1%) as a viscous clear oil. LC-MS: RT (Method A) 4.96 min; [M+H] 367.3 ($C_{18}H_{26}N_2O_6$+H, requires 367.43). Crude product was used in next synthetic step without additional purification.

Synthesis of 2-Benzyloxycarbonylamino-3-tert-butoxycarbonylamino-3-methyl-butyric acid pentafluorophenyl ester (3)

To a solution of compound 2 (967 mg, 2.64 mmol) and PFP (680 mg, 3.69 mmol) in DCM (15 mL) was added DCC (653 mg, 3.16 mmol). Reaction mixture was allowed to stir at ambient temperature for 3 h. Reaction mixture was filtered, and solids (DCU) were washed with DCM (3×5 mL). Combined filtrate and washes were concentrated in vacuo, and the residue was purified by normal phase flash chromatography on a CombiFlash® Companion™ unit equipped with Luknova flash column (40 g silica gel, 40-60 µm average particle size, 60 Å pore size); flow rate: 40 mL/min; mobile phase A: hexane; mobile phase B: EtOAc; gradient elution from 0% B to 40% B over 60 min. Fractions containing the desired product were combined and concentrated in vacuo to give target compound 3 (1.025 g, 72.9%) as a viscous clear oil. LC-MS: RT (Method A) 7.25 min; [M+H] 533.2.

Synthesis of [3-((R)-4-Benzyl-2-oxo-oxazolidin-3-yl)-2-benzyloxycarbonylamino-1,1-dimethyl-3-oxo-propyl]-carbamic acid tert-butyl ester (4)

Compound 3 (1.025 g, 1.92 mmol), (R)-(+)-4-benzyl-2-oxazolidinone (0.5117 g, 2.89 mmol), LiBr (0.3344 g, 3.85 mmol), TEA (0.5366 mL, 3.85 mmol), and THF (10 mL) were combined and allowed to stir at ambient temperature for 14 h. Reaction mixture was concentrated in vacuo, and residue was partitioned between water (50 mL) and EtOAc (30 mL). Aqueous layer was extracted with EtOAc (2×20 mL). Combined organic layers were washed with water (30 mL) and brine (30 mL), dried over anhydrous $Na_2SO_4$, and concentrated in vacuo to give target compound 4 (1.153 g, 115%) as an off-white solid foam. LC-MS analysis (Method A) showed diastereomers, compounds 5 and 6, with retention times $RT_5$=6.60 min, $RT_6$=6.78 min. Both with [M+H] 526.3 ($C_{28}H_{35}N_3O_7$+H, requires 526.62).

Separation of diastereomers, [(R)-1-((R)-4-Benzyl-2-oxo-oxazolidine-3-carbonyl)-2-tert-butoxycarbonylamino-2-methyl-propyl]-carbamic acid benzyl ester (5) and [(S)-1-((R)-4-Benzyl-2-oxo-oxazolidine-3-carbonyl)-2-tert-butoxycarbonylamino-2-methyl-propyl]carbamic acid benzyl ester (6)

Method 1:
Crude compound 4 (1.153 g) was purified and its component diastereomers were separated by normal phase flash column chromatography on a CombiFlash® Companion™ unit equipped with Luknova flash column (80 g silica gel, 40-60 µm average particle size, 60 Å pore size); flow rate: 50 mL/min; mobile phase A: hexane; mobile phase B: EtOAc; gradient elution from 0% B to 10% B over 5 min, then 10% B to 25% B over 90 min. 25 mL fractions. Fractions containing target compound with diastereomeric excess (d.e.) greater than 95% were combined and concentrated in vacuo to give products as white solid foams (789.9 mg total yield, 78.1% from 3). F104-110: compound 6, 106.3 mg, 96% d.e. F111-127: overlap, mixture of 5 and 6, 580.9 mg. F128-140: compound 5, 102.7 mg, ~96% d.e.

Method 2:

The residue from combined fractions 111-127 (580.9 mg), overlap from purification by Method A, was subjected to preparative scale reverse-phase HPLC (Varian Microsorb 100-10 C-18 column (50×300 mm), flow rate: 50 mL/min, mobile phase A: 0.1% TFA/water, mobile phase B: 0.1% TFA/ACN, gradient elution from 20% B to 95% B over 90 min, UV 254 nm monitor, 50 mL fractions). Fractions containing target compound with d.e. greater than 95% were combined, neutralized with $NaHCO_3$ (aq), concentrated in vacuo to approximately one half of original volume, and extracted with EtOAc (3×1:2 vol. EtOAc:vol. aq). The combined organic layers were washed with water (1:2 vol. $H_2O$:vol. organics) and brine (1:2 vol. brine:vol. organics), dried over anhydrous $Na_2SO_4$, and concentrated in vacuo to give products as white solid foams (441 mg total yield, 75.9% recovery). F56-58: compound 5, 153 mg, 99.7% d.e. F59+60: overlap, mixture of 5 and 6, 181 mg. F61-63: compound 6, 107 mg, 97.7% d.e.

Synthesis of [(S)-2-Amino-3-((R)-4-benzyl-2-oxo-oxazolidin-3-yl)-1,1-dimethyl-3-oxo-propyl]-carbamic acid tert-butyl ester hydrochloride (7)

To a solution of compound 6 (207 mg, 0.394 mmol) (combined portions from separation methods 1 and 2, 96.7% d.e.) in MeOH (2.5 mL), were added 1 N HCl (0.394 mL) and 10% Pd/C (22.3 mg). Reaction vessel was evacuated and backfilled with $H_2$ three times, and reaction mixture was allowed to stir under an atmosphere of $H_2$ at ambient temperature for 1 h. Reaction mixture was filtered and concentrated in vacuo to give target compound 7 (174.6 mg, 103%) as a viscous clear oil which crystallized upon standing. LC-MS: RT (Method A) 4.11 min; [M+H] 392.4.

Synthesis of [(S)-3-((R)-4-Benzyl-2-oxo-oxazolidin-3-yl)-2-(4-{4-[(tert-butoxycarbonyl-cyclopropyl-amino)-methyl]-phenylethynyl}-benzoylamino)-1,1-dimethyl-3-oxo-propyl]-carbamic acid tert-butyl ester (9)

To a solution of compound 8 (167.7 mg, 0.428 mmol) and DIEA (0.355 mL, 2.04 mmol) in DMF (5 mL) was added HATU (162.9 mg, 0.428 mmol), and the mixture was stirred at ambient temperature for 5 min. Compound 7 (174.6 mg, 0.408 mmol) was added, and the mixture was stirred at ambient temperature for 20 min. Reaction mixture was added to 0.1 M HCl (aq) (80 mL), and extracted with EtOAc (3×25 mL). Combined organic layers were washed with water (40 mL) and brine (40 mL), dried over anhydrous $Na_2SO_4$, and concentrated in vacuo to give target compound 9 (351 mg, 112%) as a sticky amber solid foam. LC-MS: RT (Method A) 8.60 min; [M+H] 765.7.

Synthesis of [(S)-2-(4-{4-[(tert-Butoxycarbonyl-cyclopropyl-amino)-methyl]-phenylethynyl}-benzoylamino)-2-hydroxycarbamoyl-1,1-dimethyl-ethyl]-carbamic acid tert-butyl ester (10)

Compound 9 (0.408 mmol) was dissolved in dioxane (8 mL) with sonication, and 50% $NH_2OH$ (aq) (2 mL) was added. Reaction mixture was allowed to stir at ambient temperature for 64 h. Reaction mixture was reduced to approximately ⅓ of original volume by concentration in vacuo, diluted with water (50 mL), neutralized with 1 M HCl (aq), and extracted with EtOAc (3×30 mL). Combined organic layers were washed with water (40 mL) and brine (40 mL), dried over anhydrous $Na_2SO_4$, and concentrated in vacuo to give target compound 10 as an amber solid foam. LC-MS: RT (Method A) 6.72 min; [M+H] 621.6.

Synthesis of N—((S)-2-Amino-1-hydroxycarbamoyl-2-methyl-propyl)-4-(4-cyclopropylaminomethyl-phenylethynyl)-benzamide (121-1)

To compound 10 was added 4 M HCl/dioxane (5 mL), and the mixture was stirred at ambient temperature for 1 h. Volatiles were removed in vacuo to give a sticky amber solid residue. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 5% B to 20% B over 90 min, MS detection). Fractions containing the desired product were combined and lyophilized to provide the trifluoroacetate salt of target compound 121-1 (44.6 mg, 20.1% yield from 7) as a white solid. LC-MS: RT (Method A) 2.61 min; [M+H] 421.3.

| Compound | Scale (mmol)[1] | Yield (mg) | Yield (%)[1] | Purity (%)[2] | [M + H] | Retention time (min)[2] |
|---|---|---|---|---|---|---|
| 121-1 | 0.408 | 44.6 | 20.1 | 99.7 | 421.3 | 2.61 |

[1]Based on the amount of carboxylic acid used in the coupling reaction.
[2]Using LC-MS Analytical Method A.

The following compound was synthesized as described above for 121-1.

| Compound # | Structure | RT (min)[1] | [M + H] |
|---|---|---|---|
| 121-2 | (structure shown) | 2.61 | 421.2 |

[1]Using LC-MS Analytical Method A.

Example 122

N-((1S,2R)-2-Amino-1-hydroxycarbamoyl-propyl)-4-{4-[(2-methoxy-ethylamino)-methyl]-phenylethynyl}-benzamide (122-1)

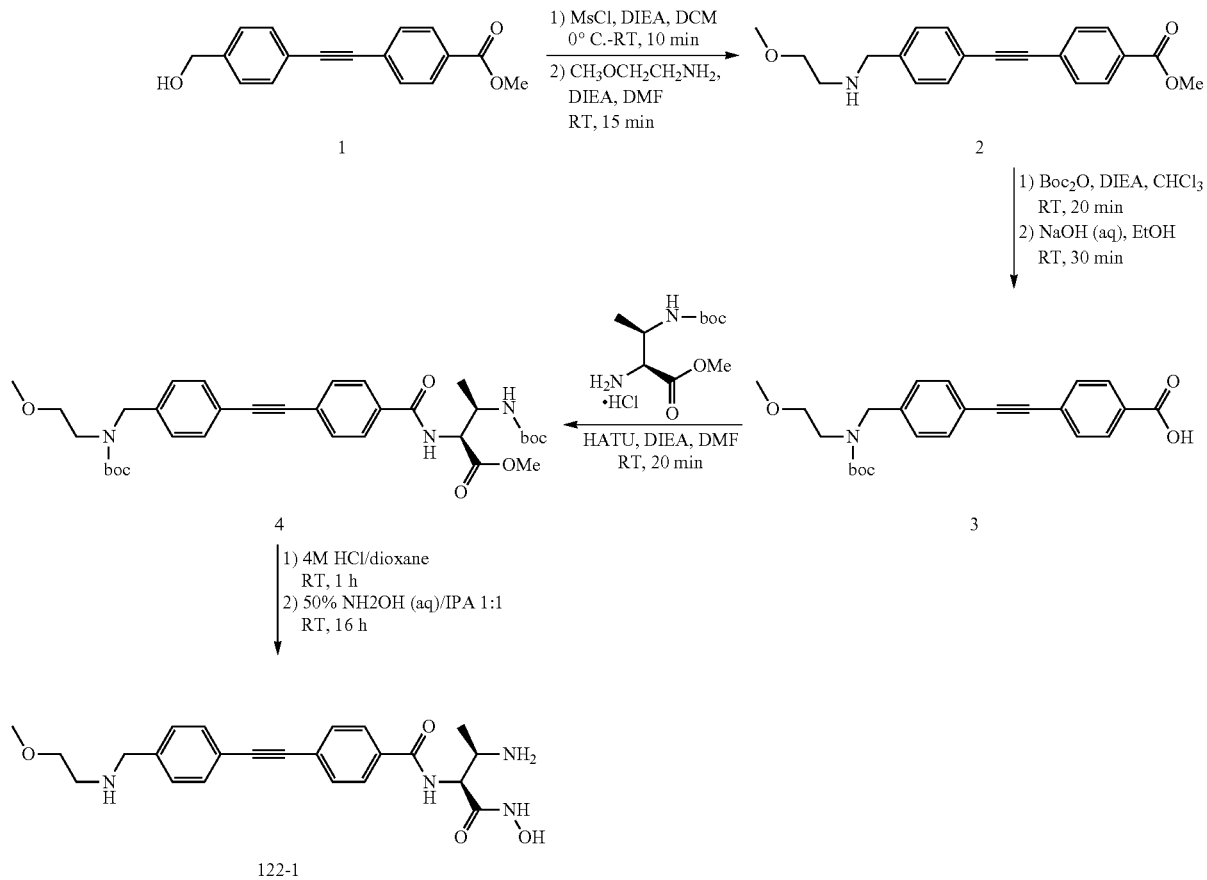

Synthesis of 4-{4-[(2-Methoxy-ethylamino)-methyl]-phenylethynyl}-benzoic acid methyl ester (2)

To a stirred suspension of compound 1 (200 mg, 0.751 mmol) and DIEA (0.654 mL, 3.76 mmol) in DCM (3 mL), cooled in ice/water bath, was added dropwise methanesulfonyl chloride (0.070 mL, 0.901 mmol). After 5 min the ice/water bath was removed and reaction mixture was stirred at ambient temperature for 5 min. LC-MS: RT (Method A) 6.03 min; compound not significantly ionizable. Reaction mixture was added dropwise to a solution of 2-methoxyethylamine (0.5 mL, 5.83 mmol) in DMF (5 mL), and the mixture was stirred at ambient temperature for 15 min. Reaction mixture was concentrated in vacuo, and residue was partitioned between water (100 mL) and EtOAc (50 mL). Layers were separated and aqueous layer was extracted with EtOAc (2×30 mL). Combined organic layers were washed with water (50 mL) and brine (50 mL), dried over anhydrous $Na_2SO_4$, and concentrated in vacuo to give target compound 2 (257 mg, 106%) as a viscous amber oil. LC-MS: RT (Method A) 4.19 min; [M+H] 324.3. Crude product was used in next synthetic step without additional purification.

Synthesis of 4-(4-{[tert-Butoxycarbonyl-(2-methoxy-ethyl)-amino]-methyl}-phenylethynyl)-benzoic acid (3)

To compound 2 (0.751 mmol) dissolved in $CHCl_3$ (15 mL) were added DIEA (0.262 mL, 1.50 mmol) and $Boc_2O$ (197 mg, 0.903 mmol), and the mixture was stirred at ambient temperature for 20 min.* LC-MS analysis of the reaction mixture showed complete reaction. LC-MS: RT (Method A) 7.48 min; [M+H] 424.4. Reaction mixture was concentrated in vacuo, and residue was dissolved in EtOH (5 mL). NaOH (3M, aq) (2 mL, 6 mmol) was added, and the mixture was stirred at ambient temperature for 30 min. Reaction mixture was diluted with water (75 mL), cooled in ice/water bath, acidified to pH 2 with 10% $H_3PO_4$ (aq), and extracted with EtOAc (40 mL, 2×20 mL). Combined organic layers were washed with water (40 mL) and brine (40 mL), dried over anhydrous $Na_2SO_4$, and concentrated in vacuo to give target compound 3 (326 mg, 106% from 1) as an off-white solid. LC-MS: RT (Method A) 6.20 min; [M+H] 410.2. Crude product was used in next synthetic step without additional purification.

*Boc protection was omitted for secondary amines.

Synthesis of (2S,3R)-3-tert-Butoxycarbonylamino-2-[4-(4-{[tert-butoxycarbonyl-(2-methoxy-ethyl)-amino]-methyl}-phenylethynyl)-benzoylamino]-butyric acid methyl ester (4)

To a solution of compound 3 (100 mg, 0.244 mmol) and DIEA (0.128 mL, 0.735 mmol) in DMF (2 mL) was added HATU (111.4 mg, 0.293 mmol), and the mixture was stirred at ambient temperature for 5 min. Methyl DAP.HCl (72.2 mg, 0.269 mmol) was added, and the mixture was stirred at ambient temperature for 20 min. Reaction mixture was added to 0.1 M HCl (aq) (80 mL), and extracted with EtOAc (3×25 mL). Combined organic layers were washed with water (40 mL) and brine (40 mL), dried over anhydrous $Na_2SO_4$, and concentrated in vacuo to give target compound 4 (207.8 mg, 136%) as a sticky amber solid. LC-MS: RT (Method A) 7.00 min; [M+H] 624.4 ($C_{34}H_{45}N_3O_8$+H, requires 624.76). Crude product was used in next synthetic step without additional purification.

Synthesis of N-((1S,2R)-2-Amino-1-hydroxycarbamoyl-propyl)-4-{4-[(2-methoxy-ethylamino)-methyl]-phenylethynyl}-benzamide (122-1)

| Reagent | MW | Eq. | mg/mL | mmol |
|---|---|---|---|---|
| Compound 4 | 623.75 | 1.0 | — | 0.244 |
| HCl, 4.0M solution in 1,4-dioxane | 36.46 | 82 | 5 mL | 20 |
| Isopropyl alcohol (IPA) | | | 2 mL | |
| Hydroxylamine, 50 wt. % solution in water | 33.03 | 133 | 2 mL | 32.6 |

The target compound 122-1 (11.0 mg, 8.37% yield from 3) as a white solid was prepared by following General Method for hydroxamate. LC-MS: RT (Method A) 2.35 min; [M+H] 425.2.

| Compound | Scale (mmol)[1] | Yield (mg) | Yield (%)[1] | Purity (%)[2] | [M + H] | Retention time (min)[2] |
|---|---|---|---|---|---|---|
| 122-1 | 0.244 | 11.0 | 8.37 | 96.7 | 425.2 | 2.35 |

[1] Based on the amount of carboxylic acid used in the coupling reaction.
[2] Using LC-MS Analytical Method A.

The following compounds were synthesized as described for 122-1.

| Compound # | Structure | RT (min) | [M + H] |
|---|---|---|---|
| 122-2 | 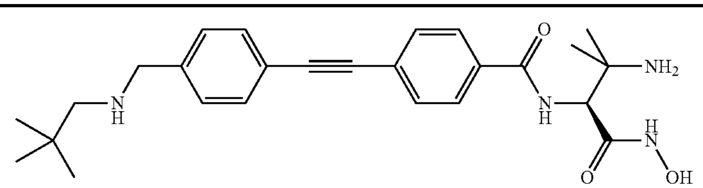 | 2.96[1] | 451.5 |
| 122-3 | 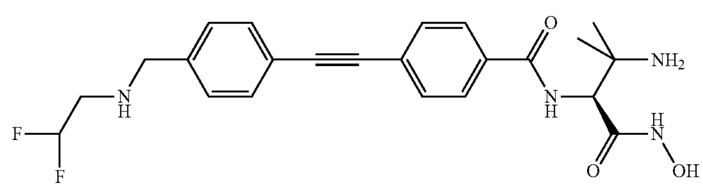 [SMILES: CC(C)(N)[C@H](NC(=O)c1ccc(C#Cc2ccc(CNCC(F)F)cc2)cc1)C(=O)NO] | 2.41[1] | 445.1 |
| 122-4 | 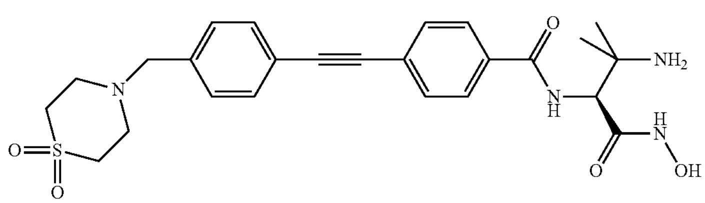 [SMILES: CC(C)(N)[C@H](NC(=O)c1ccc(C#Cc2ccc(CN3CCS(=O)(=O)CC3)cc2)cc1)C(=O)NO] | 2.58[1] | 499.2 |
| 122-5 | 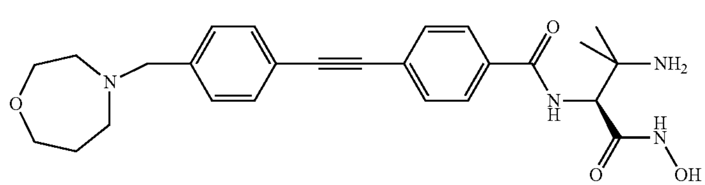 [SMILES: CC(C)(N)[C@H](NC(=O)c1ccc(C#Cc2ccc(CN3CCCOCC3)cc2)cc1)C(=O)NO] | 3.21[2] | 465.6 |

| Compound # | Structure | RT (min) | [M + H] |
|---|---|---|---|
| 122-6 | 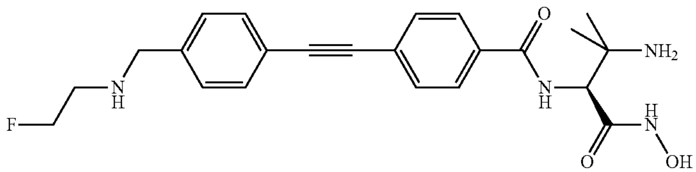 [SMILES: CC(C)(N)[C@H](NC(=O)c1ccc(C#Cc2ccc(CNCCF)cc2)cc1)C(=O)NO] | 2.94[2] | 427.6 |
| 122-7 (same as 121-1) | 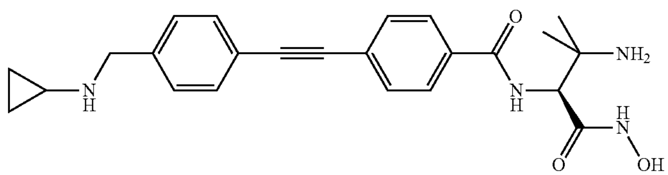 [SMILES: CC(C)(N)[C@H](NC(=O)c1ccc(C#Cc2ccc(CNC3CC3)cc2)cc1)C(=O)NO] | 3.20[2] | 421.1 |
| 122-8 | 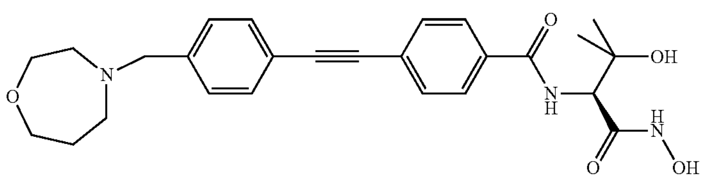 | 3.77[2] | 466.3 |
[1]Using LC-MS Analytical Method A.
[2]Using LC-MS Analytical Method B.
Example 123
N-((1S,2R)-2-Amino-1-hydroxycarbamoyl-propyl)-4-(4-cyclopropoxymethyl-phenylethynyl)-benzamide (123-1)
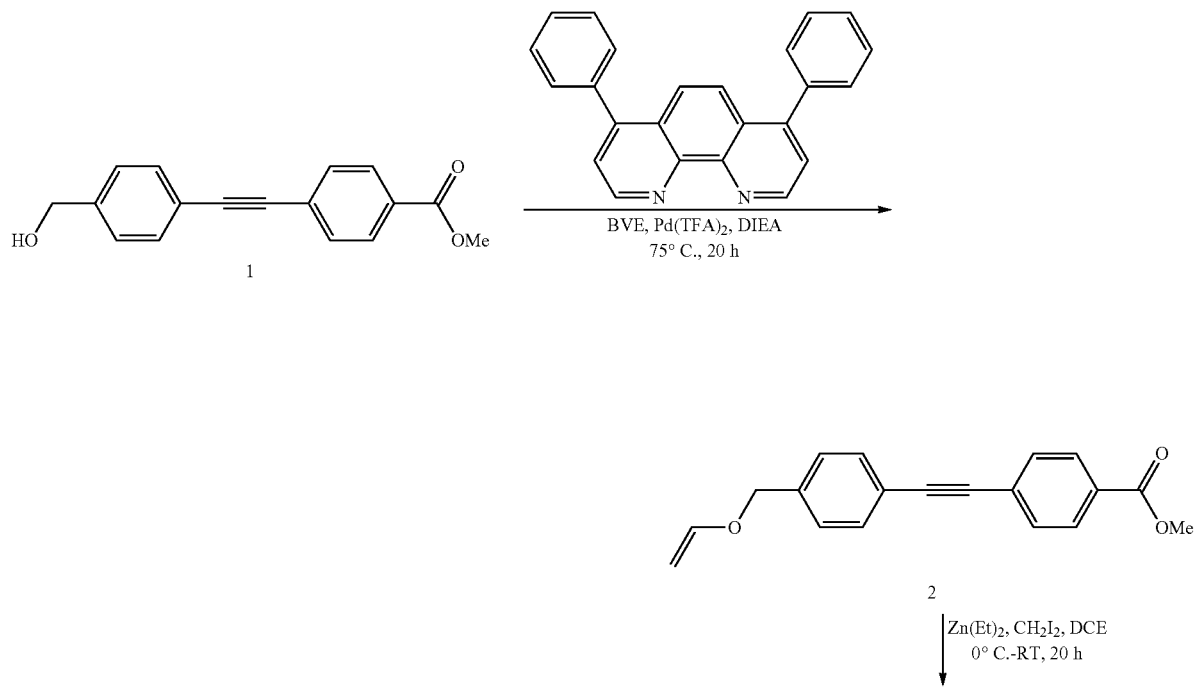

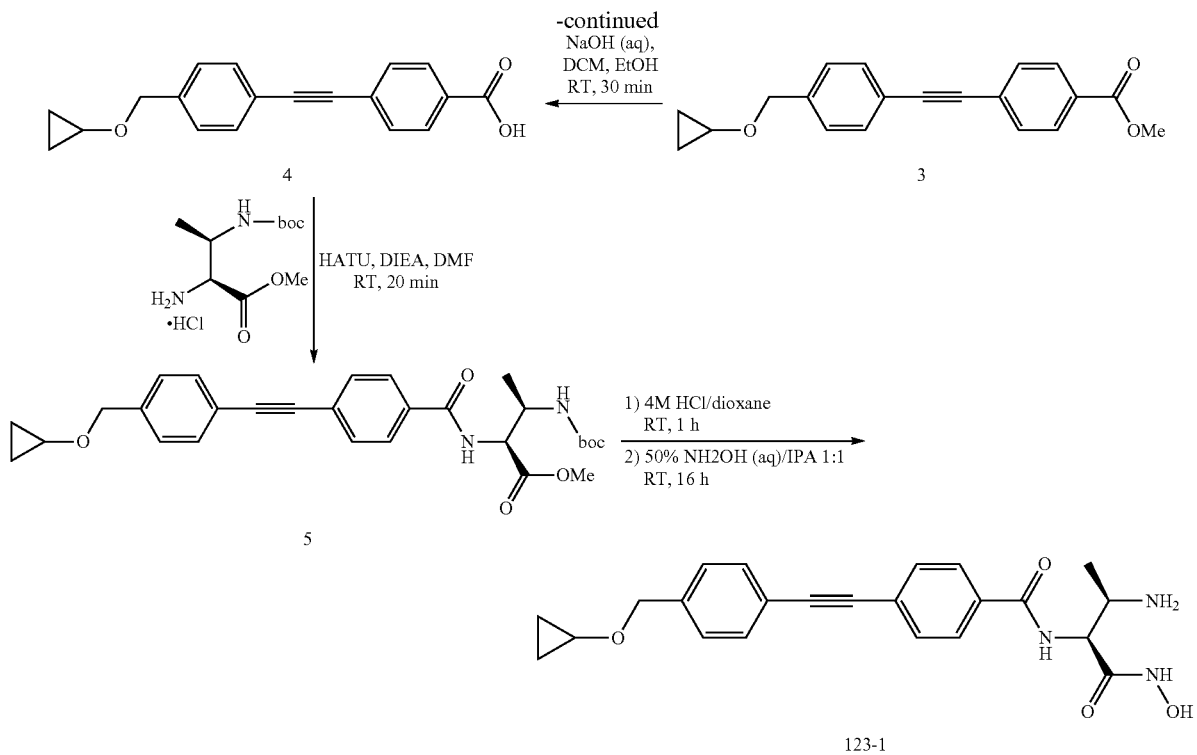

Synthesis of 4-(4-Vinyloxymethyl-phenylethynyl)-benzoic acid methyl ester (1)

Pd(TFA)$_2$ (3.1 mg, 0.5 mol %) and bathophenanthroline (3.1 mg, 0.5 mol %) were dissolved in BVE (5 mL, 38.8 mmol) in a vial, and the mixture was stirred at ambient temperature for 5 min. Compound 1 (500 mg, 1.88 mmol) and DIEA (0.0164 mL, 0.094 mmol) were added, vial was backfilled with nitrogen, capped, and heated at 75° C. for 20 h. Reaction mixture was concentrated in vacuo, and the residue was purified by normal phase flash chromatography on a CombiFlash® Companion™ unit equipped with Luknova flash column (40 g silica gel, 40-60 μm average particle size, 60 Å pore size); flow rate: 40 mL/min; mobile phase A: hexane; mobile phase B: EtOAc; gradient elution from 0% B to 40% B over 60 min. Fractions containing the desired product were combined and concentrated in vacuo to give target compound 2 (0.394 g, 71.8%) as an off-white solid. LC-MS: RT (Method A) 7.28 min; compound not significantly ionizable.

Synthesis of 4-(4-Cyclopropoxymethyl-phenylethynyl)-benzoic acid methyl ester (3)

To a stirred solution of compound 2 (150 mg, 0.513 mmol) and CH$_2$I$_2$ (0.100 mL, 1.24 mmol) in anhydrous DCE (3 mL), under a nitrogen atmosphere, cooled in an ice/water bath, was cautiously added diethylzinc (1.0 M in hexanes; 1.13 mL, 1.13 mmol). After 5 min the ice/water bath was removed and reaction mixture was allowed to stir at ambient temperature for 20 h. Reaction mixture was added cautiously to saturated NH$_4$Cl (aq) (50 mL) and extracted with DCM (3×20 mL). Combined organic layers were washed with 1 N HCl (30 mL), water (30 mL), saturated NaHCO$_3$ (aq) (30 mL) and brine (20 mL), dried over anhydrous Na$_2$SO$_4$, and concentrated in vacuo to give target compound 3 (180 mg, 115%) as an off-white solid. LC-MS: RT (Method A) 7.30 min; compound not significantly ionizable. $^1$H NMR (250 MHz, CDCl$_3$) δ 0.5-0.65 (4H, m), 3.3 (1H, m), 3.9 (3H, s), 4.55 (2H, s), 7.3 (2H, d), 7.5-7.6 (4H, m), 8.0 (2H, d).

Synthesis of 4-(4-Cyclopropoxymethyl-phenylethynyl)-benzoic acid (4)

To compound 3 (~0.513 mmol) were added EtOH (5 mL), DCM (2 mL), and 3 M NaOH (aq) (2 mL, 6 mmol), and the mixture was stirred at ambient temperature for 30 min. Reaction mixture was diluted with water (150 mL), cooled in ice/water bath, acidified to pH 3 with 10% H$_3$PO$_4$ (aq), and extracted with EtOAc (3×30 mL). Combined organic layers were washed with water (30 mL) and brine (30 mL), dried over anhydrous Na$_2$SO$_4$, and concentrated in vacuo to give to give target compound 4 (113.9 mg, 76% from 2) as a slightly off-white solid. LC-MS: RT (Method A) 6.06 min; compound not significantly ionizable.

Synthesis of (2S,3R)-3-tert-Butoxycarbonylamino-2-[4-(4-cyclopropoxymethyl-phenylethynyl)-benzoylamino]-butyric acid methyl ester (5)

To a solution of compound 4 (111 mg, 0.382 mmol) and DIEA (0.200 mL, 1.15 mmol) in DMF (5 mL) was added HATU (174 mg, 0.458 mmol), and the mixture was stirred at ambient temperature for 5 min. Methyl DAP.HCl (113 mg, 0.420 mmol) was added, and the mixture was stirred at ambient temperature for 20 min. Reaction mixture was added to water (100 mL), and extracted with EtOAc (3×30 mL). Combined organic layers were washed with water (50 mL) and brine (50 mL), dried over anhydrous Na₂SO₄, and concentrated in vacuo to give target compound 5 (239.2 mg, 123%) as a sticky amber solid foam. LC-MS: RT (Method A) 6.87 min; [M+H] 507.0 (C$_{29}$H$_{34}$N$_2$O$_6$+H, requires 507.61). Crude product was used in next synthetic step without additional purification.

Synthesis of N-((1S,2R)-2-Amino-1-hydroxycarbamoyl-propyl)-4-(4-cyclopropoxymethyl-phenylethynyl)-benzamide (123-1)

| Reagent | MW | Eq. | mg/mL | mmol |
|---|---|---|---|---|
| Compound 5 | 506.60 | 1.0 | — | ~0.382 |
| HCl, 4.0M solution in 1,4-dioxane | 36.46 | 31.4 | 3 mL | 12 |
| Isopropyl alcohol (IPA) | | | 4 mL | |
| Hydroxylamine, 50 wt. % solution in water | 33.03 | 171 | 4 mL | 65.3 |

The target compound 123-1 (67.5 mg, 33.9% yield from 4) as a white solid was prepared by following General Method for hydroxamate. LC-MS: RT (Method A) 4.19 min; [M+H] 408.3.

| Compound | Scale (mmol)[1] | Yield (mg) | Yield (%)[1] | Purity (%)[2] | [M + H] | Retention time (min)[2] |
|---|---|---|---|---|---|---|
| 123-1 | 0.382 | 67.5 | 33.9 | 97.7 | 408.3 | 4.19 |

[1]Based on the amount of carboxylic acid used in the coupling reaction.
[2]Using LC-MS Analytical Method A.

Example 124

N-((1S,2R)-2-Amino-1-hydroxycarbamoyl-propyl)-4-[4-(2,2,2-trifluoro-ethoxymethyl)-phenylethynyl]-benzamide (124-1)

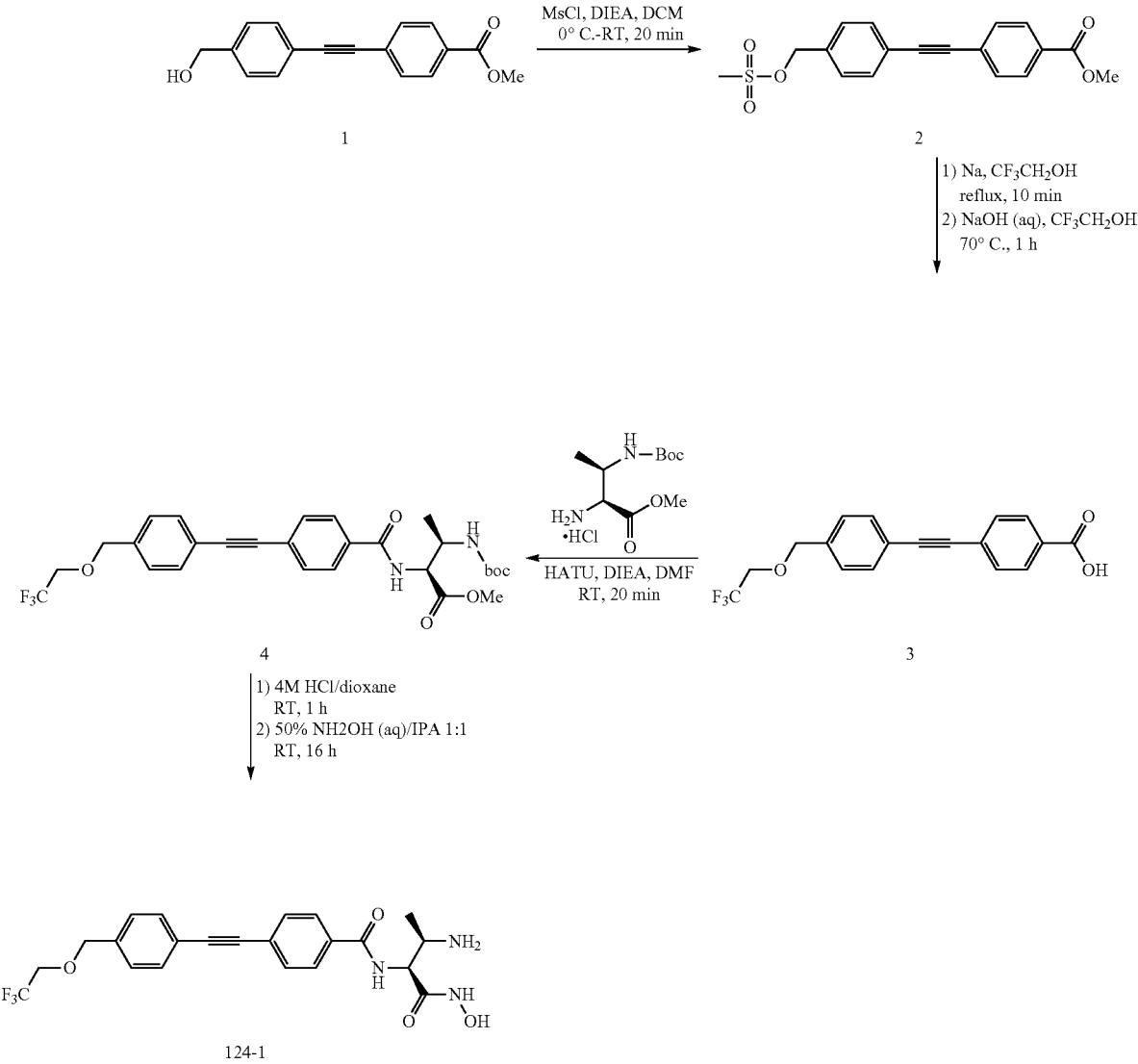

Synthesis of 4-(4-Methanesulfonyloxymethyl-phenylethynyl)-benzoic acid methyl ester To a suspension of compound 1 (200 mg, 0.751 mmol) and DIEA (0.262 mL, 1.5 mmol) in DCM (5 mL), cooled in ice/water bath, was added dropwise methanesulfonyl chloride (0.070 mL, 0.901 mmol) and the mixture was stirred in ice/water bath for 5 min. Reaction mixture was allowed to attain ambient temperature and stir for 10 min. Reaction mixture was diluted with DCM (40 mL), and washed with water (2×30 mL). Combined aqueous layers were back-extracted with DCM (2×20 mL). Combined organic layers were dried over anhydrous $Na_2SO_4$, and concentrated in vacuo to give target compound 2 (254.5 mg, 98.4%) as an off-white solid. LC-MS: RT (Method A) 6.05 min; compound not significantly ionizable.

Synthesis of 4-[4-(2,2,2-Trifluoro-ethoxymethyl)-phenylethynyl]-benzoic acid (3)

Sodium (25 mg, 1.09 mmol) was dissolved completely in 2,2,2-trifluoroethanol (8 mL, 111 mmol). Compound 2 (254.5 mg, 0.739 mmol) was added, and the mixture was heated to reflux for 5 min. NaOH (3M, aq) (6 mL, 18 mmol) was added, and the mixture was heated at 70° C. for 1 h. Reaction mixture was diluted with water (150 mL), cooled in ice/water bath, acidified to pH 3 with 10% $H_3PO_4$ (aq), and filtered. Solids were washed with water (3×50 mL) and dried by lyophilization to give target compound 3 (238.9 mg, 96.7%) as a slightly off-white solid. LC-MS: RT (Method A) 6.01 min; compound not significantly ionizable.

Synthesis of (2S,3R)-3-tert-Butoxycarbonylamino-2-{4-[4-(2,2,2-trifluoro-ethoxymethyl)-phenylethynyl]-benzoylamino}-butyric acid methyl ester (4)

To a solution of compound 3 (100 mg, 0.299 mmol) and DIEA (0.156 mL, 0.897 mmol) in DMF (2 mL) was added HATU (136 mg, 0.359 mmol), and the mixture was stirred at ambient temperature for 5 min. Methyl DAP.HCl (88.4 mg, 0.329 mmol) was added, and the mixture was stirred at ambient temperature for 20 min. Reaction mixture was added to 0.1 M HCl (aq) (80 mL), and extracted with EtOAc (3×25 mL). Combined organic layers were washed with water (40 mL) and brine (40 mL), dried over anhydrous $Na_2SO_4$, and concentrated in vacuo to give target compound 4 (192 mg, 117%) as a sticky light amber solid. LC-MS: RT (Method A) 6.81 min; [M+H] 549.5. Crude product was used in next synthetic step without additional purification.

Synthesis of N-((1S,2R)-2-Amino-1-hydroxycarbamoyl-propyl)-4-[4-(2,2,2-trifluoro-ethoxymethyl)-phenylethynyl]-benzamide (124-1)

| Reagent | MW | Eq. | mg/mL | mmol |
|---|---|---|---|---|
| Compound 4 | 548.56 | 1.0 | — | 0.299 |
| HCl, 4.0M solution in 1,4-dioxane | 36.46 | 53.5 | 4 mL | 16 |
| Isopropyl alcohol (IPA) | | | 2 mL | |
| Hydroxylamine, 50 wt. % solution in water | 33.03 | 109 | 2 mL | 32.6 |

The target compound 124-1 (38.1 mg, 22.6% yield from 3) as a white solid was prepared by following General Method for hydroxamate. LC-MS: RT (Method A) 4.35 min; [M+H] 449.9.

| Compound | Scale (mmol)[1] | Yield (mg) | Yield (%)[1] | Purity (%)[2] | [M + H] | Retention time (min)[2] |
|---|---|---|---|---|---|---|
| 124-1 | 0.299 | 38.1 | 22.6 | 95.8 | 449.9 | 4.35 |

[1]Based on the amount of carboxylic acid used in the coupling reaction.
[2]Using LC-MS Analytical Method A.

The following compounds were synthesized according to procedures above for 124-1.

| Compound # | Structure | RT (min)[1] | [M + H] |
|---|---|---|---|
| 124-2 | 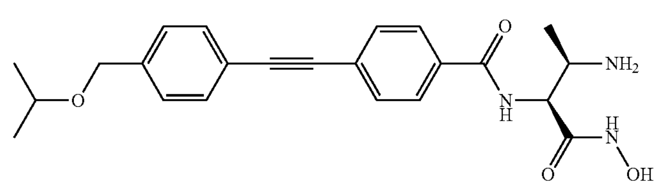 | 4.25 | 410.1 |
| 124-3 | 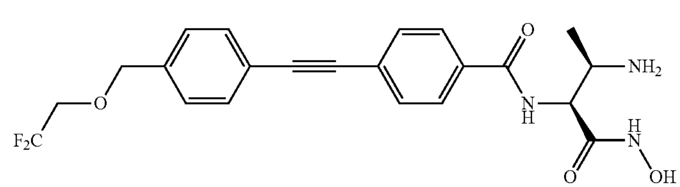 | 3.98 | 432.3 |

[1]Using LC-MS Analytical Method A.

Example 125

N-((1S,2R)-2-Amino-1-hydroxycarbamoyl-propyl)-4-(4-cyclopropoxy-phenylethynyl)-benzamide (125-1)

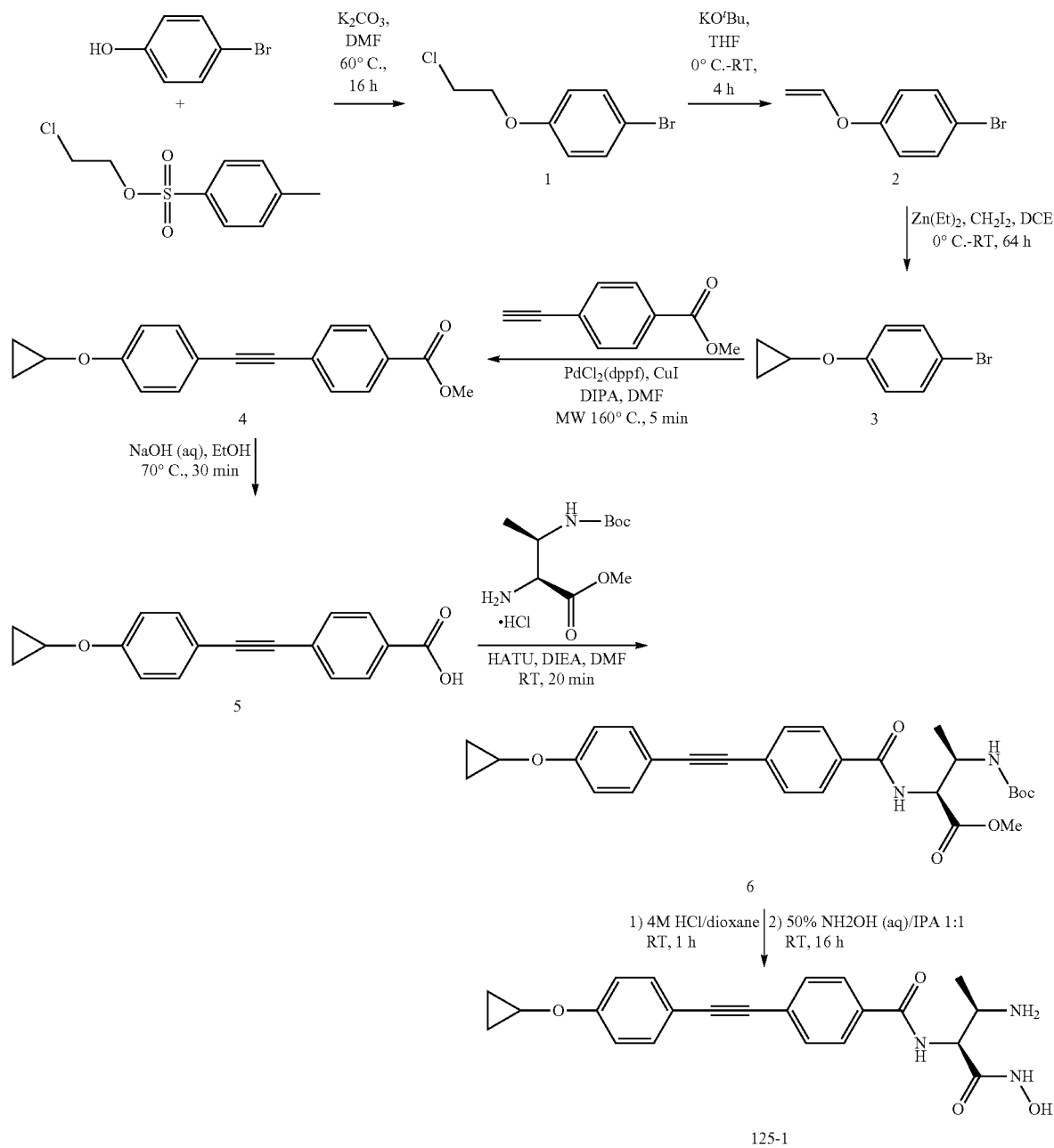

Synthesis of 1-Bromo-4-(2-chloro-ethoxy)-benzene (1)

To a mixture of 4-bromophenol (2.0 g, 11.6 mmol) and $K_2CO_3$ (3.20 g, 23.2 mmol) in DMF (50 mL) was added 3-chloroethyl p-toluenesulfonate (2.52 mL, 13.9 mmol), and the mixture was stirred at 60° C. for 16 h. Reaction mixture was concentrated in vacuo, and the residue was partitioned between water (200 mL) and DCM (50 mL). Aqueous layer was further extracted with DCM (3×20 mL). Combined organic layers were washed with water (30 mL) and brine (30 mL), dried over anhydrous $Na_2SO_4$, and concentrated in vacuo to give target compound 1 (3.12 g, 115%) as a light amber oil. LC-MS: RT (Method A) 5.83 min; compound not significantly ionizable. $^1$H NMR (250 MHz, CDCl$_3$) δ 3.8

(2H, t), 4.2 (2H, t), 6.8 (2H, d), 7.4 (2H, d). Crude product was used in next synthetic step without additional purification.

Synthesis of 1-Bromo-4-vinyloxy-benzene (2)

To a stirred solution of compound 1 (~11.6 mmol) in THF (30 mL), cooled in an ice/water bath, was added potassium tert-butoxide (1.95 g, 17.3 mmol) in three portions. After 10 min the ice/water bath was removed and reaction mixture was stirred at ambient temperature for 16 h. Reaction mixture was concentrated in vacuo and partitioned between water (150 mL) and DCM (50 mL). Aqueous layer was further extracted with DCM (3×30 mL). Combined organic layers were washed with water (40 mL) and brine (40 mL), dried over anhydrous $Na_2SO_4$, and concentrated in vacuo. Residue was purified by normal phase flash chromatography on a CombiFlash® Companion™ unit equipped with Luknova flash column (40 g silica gel, 40-60 μm average particle size, 60 Å pore size); flow rate: 40 mL/min; mobile phase: hexane. Fractions containing the desired product were combined and concentrated in vacuo to give target compound 2 (1.702 g, 74% from 4-bromophenol) as a clear oil. LC-MS: RT (Method A) 5.95 min; compound not significantly ionizable. $^1$H NMR (250 MHz, $CDCl_3$) δ 4.45 (1H, dd), 4.75 (1H, dd), 6.6 (1H, dd), 6.85 (2H, d), 7.4 (2H, d).

Synthesis of 1-Bromo-4-cyclopropoxy-benzene (3)

To a stirred solution of compound 2 (1.702 g, 8.55 mmol) and $CH_2I_2$ (5.52 mL, 68.4 mmol) in anhydrous DCE (75 mL), under a nitrogen atmosphere, cooled in an ice/water bath, was cautiously added diethylzinc (1.0 M in hexanes; 68.4 mL, 68.4 mmol). After 30 min the ice/water bath was removed and reaction mixture was allowed to stir at ambient temperature for 64 h. Reaction mixture was added cautiously to saturated $NH_4Cl$ (aq) (200 mL), mixture was shaken and layers separated, and aqueous layer was extracted with DCM (3×30 mL). Combined organic layers were washed with 1 N HCl (100 mL), water (100 mL), saturated $NaHCO_3$ (aq) (100 mL) and brine (80 mL), dried over anhydrous $Na_2SO_4$, and concentrated in vacuo to give a light amber oil. Crude product was purified by normal phase flash chromatography on a CombiFlash® Companion™ unit equipped with Luknova flash column (40 g silica gel, 40-60 μm average particle size, 60 Å pore size); flow rate: 40 mL/min; mobile phase: hexane. Fractions containing the desired product were combined and concentrated in vacuo to give target compound 3 (1.310 mg, 71.9%) as a clear oil. LC-MS: RT (Method A) 5.87 min; compound not significantly ionizable. $^1$H NMR (250 MHz, $CDCl_3$) δ 0.75 (4H, m), 3.7 (1H, m), 6.9 (2H, d), 7.4 (2H, d).

Synthesis of 4-(4-Cyclopropoxy-phenylethynyl)-benzoic acid methyl ester (4)

A microwave tube was charged with compound 3 (400 mg, 1.88 mmol), 4-ethynyl-benzoic acid methyl ester (330 mg, 2.06 mmol), $PdCl_2(dppf) \cdot CH_2Cl_2$ (30.7 mg, 2 mol %), CuI (14.3 mg, 4 mol %), DIPA (0.40 mL, 2.83 mmol), and DMF (6 mL). Tube was backfilled with nitrogen, sealed, and irradiated in a microwave reactor (max. power 250 W) at 160° C. for 5 min. Reaction mixture was diluted with water (100 mL) and extracted with EtOAc (3×30 mL). Combined organic layers were washed with water (50 mL) and brine (50 mL), dried over anhydrous $Na_2SO_4$, and concentrated in vacuo to give a sticky brown solid. Crude product was purified by normal phase flash chromatography on a CombiFlash® Companion™ unit equipped with Luknova flash column (40 g silica gel, 40-60 μm average particle size, 60 Å pore size); flow rate: 40 mL/min; mobile phase A: hexane; mobile phase B: EtOAc; gradient elution from 0% B to 40% B over 60 min. Fractions containing the desired product were combined and concentrated in vacuo to give target compound 4 (47.7 mg, 8.7%) as a light brown solid. LC-MS: RT (Method A) 7.32 min; compound not significantly ionizable. $^1$H NMR (250 MHz, $CDCl_3$) δ 0.75 (4H, m), 3.7 (1H, m), 3.85 (3H, s), 7.0 (2H, d), 7.5 (2H, d), 7.6 (2H, d), 8.0 (2H, d).

Synthesis of 4-(4-Cyclopropoxy-phenylethynyl)-benzoic acid (5)

To compound 4 (47.7 mg, 0.163 mmol) were added EtOH (5 mL) and 3 M NaOH (aq) (2 mL, 6 mmol). Reaction mixture was heated at 70° C. for 30 min. Reaction mixture was diluted with water (150 mL), cooled in ice/water bath, acidified to pH 3 with 10% $H_3PO_4$ (aq), and extracted with EtOAc (3×30 mL). Combined organic layers were washed with water (30 mL) and brine (30 mL), dried over anhydrous $Na_2SO_4$, and concentrated in vacuo to give to give target compound 5 (44.7 mg, 98.8%) as a slightly off-white solid. LC-MS: RT (Method A) 6.11 min; compound not significantly ionizable.

Synthesis of (2S,3R)-3-tert-Butoxycarbonylamino-2-[4-(4-cyclopropoxy-phenylethynyl)-benzoylamino]-butyric acid methyl ester (6)

To a solution of compound 5 (44.7 mg, 0.161 mmol) and DIEA (0.084 mL, 0.482 mmol) in DMF (2 mL) was added HATU (73.5 mg, 0.193 mmol), and the mixture was stirred at ambient temperature for 5 min. Methyl DAP.HCl (47.6 mg, 0.177 mmol) was added, and the mixture was stirred at ambient temperature for 20 min. Reaction mixture was added to water (100 mL), and extracted with DCM (3×30 mL). Combined organic layers were washed with water (30 mL), dried over anhydrous $Na_2SO_4$, and concentrated in vacuo to give target compound 6 (159.7 mg, 201%) as a viscous amber oil. LC-MS: RT (Method A) 6.89 min; [M+H] 493.2. Crude product was used in next synthetic step without additional purification.

Synthesis of N-((1S,2R)-2-Amino-1-hydroxycarbamoyl-propyl)-4-(4-cyclopropoxy-phenylethynyl)-benzamide (125-1)

To compound 6 (~0.161 mmol) was added 4 M HCl/dioxane (3 mL), and the mixture was stirred at ambient temperature for 1 h. Volatiles were removed in vacuo, and the residue was washed with diethyl ether (2×10 mL), centrifuging and removing supernatant after each wash, to give a light amber powdery solid. LC-MS: RT (Method A) 4.91 min; [M+H] 393.2 ($C_{23}H_{24}N_2O_4$+H, requires 393.47). Isopropyl alcohol (4 mL) was added to the solid and the mixture was cooled in an ice/water bath for 5 min. $NH_2OH$ (50%, aq) (4 mL) was added to the mixture, dropwise for the first 2 mL. Reaction mixture was allowed to stir in ice bath for 5 min, and then allowed to stir at ambient temperature for 16 h. Solvent volume was reduced approximately by half under a stream of nitrogen, and water (10 mL) was added. The suspension was thoroughly agitated (vibro mixer and sonication), centrifuged and the supernatant was discarded. Water (10 mL) was added to the solid and the suspension was thoroughly agitated, centrifuged and the supernatant was discarded. Wet solid was dried by lyophilization to give crude product (41.7 mg, 69.3% crude yield from 5) as an off-white solid. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 15% B to 40% B over 60 min, MS detection). Fractions containing the desired product were combined and lyophilized to provide the trifluoroacetate salt of target compound 125-1 (30.2 mg, 37.0% yield from 5, 56.1% recovery from crude product) as a white solid. LC-MS: RT (Method A) 4.39 min; [M+H] 394.3.

| Compound | Scale (mmol)[1] | Yield (mg) | Yield (%)[1] | Purity (%)[2] | [M + H] | Retention time (min)[2] |
|---|---|---|---|---|---|---|
| 125-1 | 0.161 | 30.2 | 37.0 | 100 | 394.3 | 4.39 |

[1]Based on the amount of carboxylic acid used in the coupling reaction.
[2]Using LC-MS Analytical Method A.

Example 126

N—((S)-2-Amino-1-hydroxycarbamoyl-2-methyl-propyl)-4-(4-ethoxymethyl-phenylethynyl)-benzamide (126-1)

Synthesis of 4-(4-Ethoxymethyl-phenylethynyl)-benzoic acid (2)

To a solution of compound 1 (1.5 g, 5.63 mmol) in dry DMSO (30 mL) was added sodium hydride (2.25 g, 56.3 mmol), and the mixture was stirred at ambient temperature for 10 min. Iodoethane (0.591 mL, 7.32 mmol) was added, and the mixture was stirred at ambient temperature for 1 h. Reaction mixture was diluted with water (150 mL), cooled in ice/water bath, acidified to pH 3 with 1 M HCl (aq), and extracted with EtOAc (80 mL, 2×50 mL). Combined organic layers were washed with water (80 mL) and brine (80 mL), dried over anhydrous Na$_2$SO$_4$, and concentrated in vacuo to give a yellow solid. Crude product was purified by normal phase flash chromatography on CombiFlash® Companion™ unit equipped with Luknova flash column (80 g silica gel, 40-60 μm average particle size, 60 Å pore size); flow rate: 50 mL/min; mobile phase A: CH$_2$Cl$_2$; mobile phase B: MeOH; gradient elution from 0% B to 8% B over 60 min. Fractions containing the desired product were combined and concentrated in vacuo to give target compound 2 (995 mg, 63%) as an off-white solid. LC-MS: RT (Method A) 5.89 min; compound not significantly ionizable. $^1$H NMR (250 MHz, DMSO-d6) δ 1.1 (3H, t), 3.6 (2H, q), 4.5 (2H, s), 7.4-8.0 (8H, m).

Synthesis of (S)-3-tert-Butoxycarbonylamino-2-[4-(4-ethoxymethyl-phenylethynyl)-benzoylamino]-3-methyl-butyric acid methyl ester (3)

To a solution of compound 2 (150 mg, 0.535 mmol) and DIEA (0.280 mL, 1.61 mmol) in DMF (5 mL) was added HATU (244 mg, 0.642 mmol), and the mixture was stirred at ambient temperature for 5 min. Chiral dimethyl DAP (145 mg, 0.589 mmol) was added, and the mixture was stirred at ambient temperature for 20 min. Reaction mixture was added to 0.1 M HCl (aq) (100 mL), and extracted with EtOAc (3×30 mL). Combined organic layers were washed with water (50 mL) and brine (50 mL), dried over anhydrous Na$_2$SO$_4$, and concentrated in vacuo to give target compound 3 (386 mg, 142%) as a viscous amber oil. LC-MS: RT (Method A) 7.20 min; [M+H] 509.3. Crude product was used in next synthetic step without additional purification.

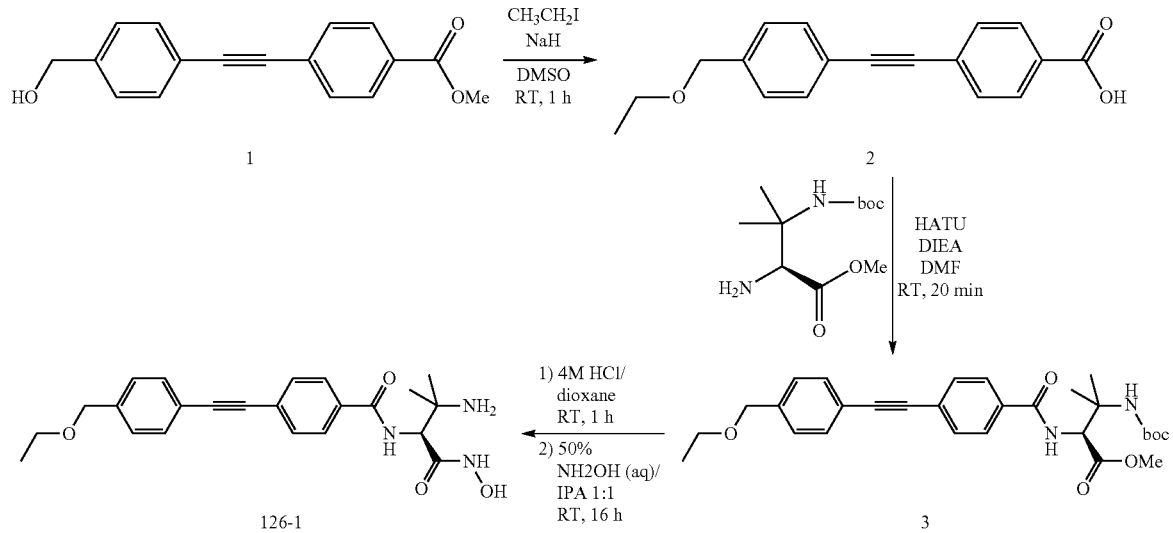

Synthesis of N—((S)-2-Amino-1-hydroxycarbamoyl-2-methyl-propyl)-4-(4-ethoxymethyl-phenylethynyl)-benzamide (126-1)

To compound 3 was added 4 B: 0.1% TFA/ACN, gradient elution from 20% B to 55% B over 90 min, MS detection M HCl/dioxane (4 mL), and the mixture was stirred at ambient temperature for 1 h. Volatiles were removed in vacuo to give a sticky amber solid. LC-MS: RT (Method A) 4.70 min; [M+H] 408.9 (C$_{24}$H$_{28}$N$_2$O$_4$+H, requires 409.51). Isopropyl alcohol (4 mL) was added to the solid and the mixture was cooled in an ice/water bath for 5 min. NH$_2$OH (50%, aq) (4 mL) was added to the mixture, dropwise for the first 2 mL.

Reaction mixture was allowed to stir in ice bath for 5 min, and then allowed to stir at ambient temperature for 16 h. Solvent volume was reduced approximately by half under a stream of nitrogen, and water (10 mL) was added. The suspension was thoroughly agitated (vibro mixer and sonication), centrifuged and the supernatant was discarded. Water (10 mL) was added to the solid and the suspension was thoroughly agitated, centrifuged and the supernatant was discarded. Wet solid was dried by lyophilization to give crude product (160.7 mg, 73.3% crude yield from 2) as an off-white solid. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase). Fractions containing the desired product were combined and lyophilized to provide the trifluoroacetate salt of target compound 126-1 (44.7 mg, 16% yield from 2, 22% recovery from crude product) as a white solid. LC-MS: RT (Method A) 4.07 min; [M+H] 410.5 ($C_{23}H_{27}N_3O_4$+H, requires 410.50).

| Compound | Scale (mmol)[1] | Yield (mg) | Yield (%)[1] | Purity (%)[2] | [M + H] | Retention time (min)[2] |
|---|---|---|---|---|---|---|
| 126-1 | 0.535 | 44.7 | 16 | 99.5 | 410.5 | 4.07 |

[1]Based on the amount of carboxylic acid used in the coupling reaction.
[2]Using LC-MS Analytical Method A.

Each of the following compounds was synthesized as described above for compound 4.

| Compound # | Structure | RT (min)[1] | [M + H] |
|---|---|---|---|
| 126-2 | (structure shown) | 4.24 | 410.3 |

[1]Using LC-MS Analytical Method A.

Example 127

N-[2-(Formyl-hydroxyamino)-ethyl]-4-(4-morpholin-4-ylmethyl-phenylethynyl)-benzamide (127-1)

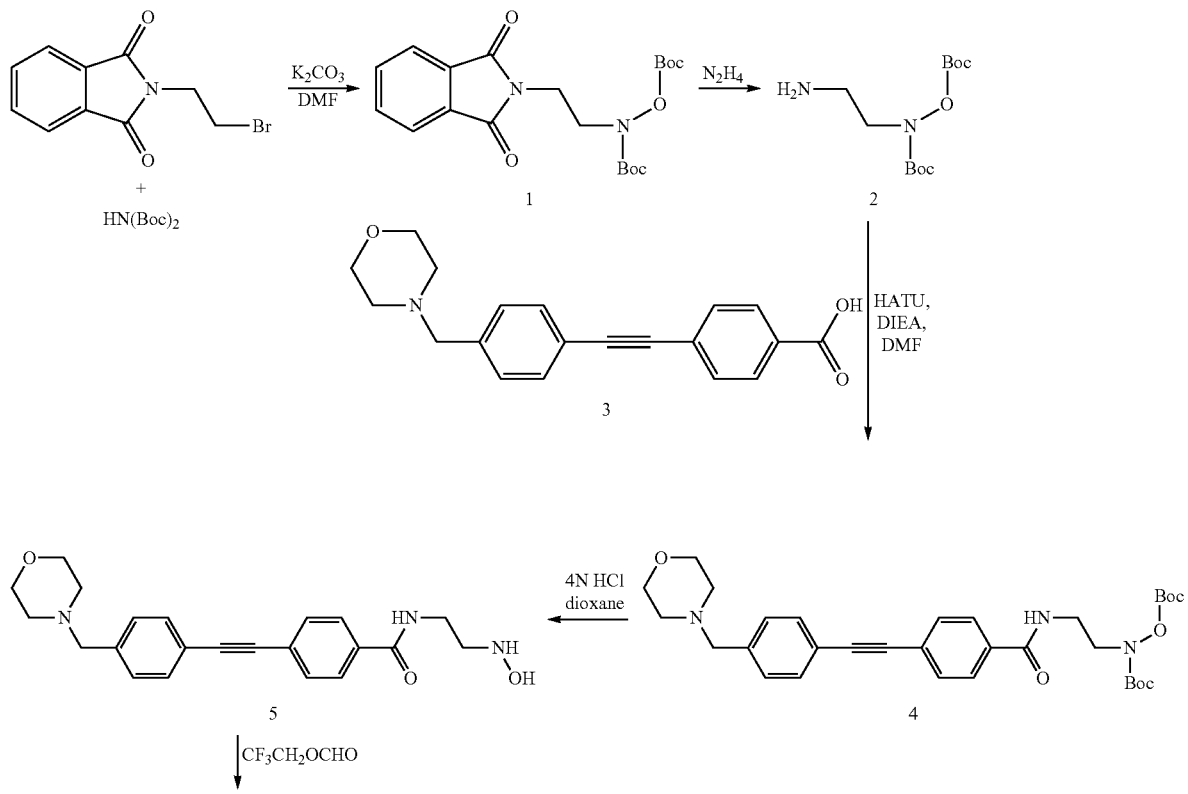

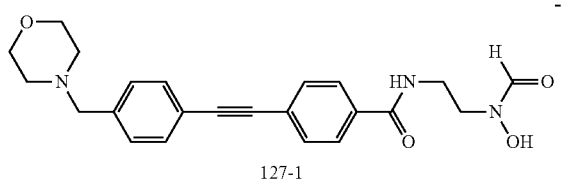

127-1

Synthesis of N-(2-N,O-Di-Boc-hydroxyaminoethyl)phthalimide (1)

To the mixture of N-(2-bromoethyl)-phthalimide (473 mg, 1.86 mmol) and N,O-di-Boc-hydroxylamine (500 mg, 2.14 mmol) in DMF (5 ml) was added $K_2CO_3$ (483 mg, 3.49 mmol). Reaction mixture was stirred at 65° C. overnight followed by the dilution with EtOAc (50 ml). Solution was extracted with water (15 ml×2) and brine (30 ml). Organic layer was dried over $Na_2SO_4$ and evaporated in vacuum. Residue was subjected to flash chromatography on Combi-Flash® Companion unit equipped with RediSep® flash column (normal phase, 35-60 micron average particle size silicagel, 12 g, Teledyne Isco); flow rate=30 ml/min; injection volume 2 ml; mobile phase A: hexane; mobile phase B: EtOAc; gradient 0-50% B in 25 min. Fractions containing the desired product were combined and concentrated in vacuum to provide target compound 450 mg (59.2%) as colorless oil. LC-MS [M+H] 407.0.

Synthesis of 2-N,O-DiBoc-Hydroxyaminoethylamine (2)

A solution of compound 2 (450 mg, 1.11 mmol) and $N_2H_4 \times H_2O$ (250 mg, 5.00 mmol) in EtOH (5 ml) was heated at 80° C. for 1 h. The reaction mixture was cooled to r.t., the formed white precipitant was filtrated and washed with EtOH (5 ml). Filtrate was concentrated in vacuum and dried in vacuum for 4 h. Compound 2 was used as is for the next chemical transformation with no additional purification. LC-MS [M+H] 277.4.

Synthesis of N-(2-N,O-di-Boc-hydroxyamino-ethyl)-4-(4-morpholin-4-ylmethyl-phenylethynyl)-benzamide (4)

A mixture of compound 2 (0.55 mmol), compound 3 (160 mg, 0.5 mmol), DIEA (330 μl, 2.0 mmol) and HATU (230 mg, 0.6 mmol) was stirred at ambient temperature overnight followed by the dilution with EtOAc (50 ml) and extraction extracted with water (15 ml×2) and brine (30 ml). Organic layer was dried over $Na_2SO_4$ and evaporated in vacuum. Residue was subjected to flash chromatography on Combi-Flash® Companion unit equipped with RediSep® flash column (normal phase, 35-60 micron average particle size silicagel, 4 g, Teledyne Isco); flow rate=18 ml/min; injection volume 2 ml; mobile phase A: hexane; mobile phase B: EtOAc; gradient 0-30% B in 30 min. Fractions containing the desired product were combined and concentrated in vacuum to provide target compound 250 mg (86.2%) as white solid. LC-MS [M+H] 480.2 (-Boc).

Synthesis of N-(2-hydroxyamino-ethyl)-4-(4-morpholin-4-ylmethyl-phenylethynyl)-benzamide (5)

A solution of compound 4 (250 mg, 0.43 mmol) in of 4 M HCl/dioxane (5 ml) was stirred at RT for 1 h. Solvents were evaporated in vacuum. Residue was dried in vacuum to provide dihydrochloride of compound 5 (184 mg, 95%) as yellow solid. LC-MS [M+H] 380.1.

N-[2-(Formyl-hydroxyamino)-ethyl]-4-(4-morpholin-4-ylmethyl-phenylethynyl)-benzamide (127-1)

A mixture of compound 5 (184 mg, 0.43 mmol), 2,2,2-trifluoroethyl formate (74 mg, 0.58 mmol), DIEA (165 μl, 1.0 mmol) in THF (5 ml) was stirred at 65° C. for 2 h. The reaction mixture was concentrated in vacuum, the residue was dissolved in DMSO (600 μl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 10% B to 40% B in 60 min., detection 254 nm]. Fractions containing the desired product were combined and lyophilized to provide trifluoroacetic salt of target compound (40.3 mg, 17.9%) as white solid. LC-MS [M+H] 408.4.

| Compound | Scale (mmol) | Yield (mg) | Yield (%) | Purity (%) | [M + H] | Retention time (min)* |
|---|---|---|---|---|---|---|
| 127-1 | 0.43 | 40.3 | 17.9 | 95.7 | 408.4 | 3.15 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.5 min, detection 254 nm]

Example 128

N-[2-(Formyl-hydroxy-amino)-1-hydroxymethyl-ethyl]-4-(4-morpholin-4-yl-methyl-phenylethynyl)-benzamide (128-1)

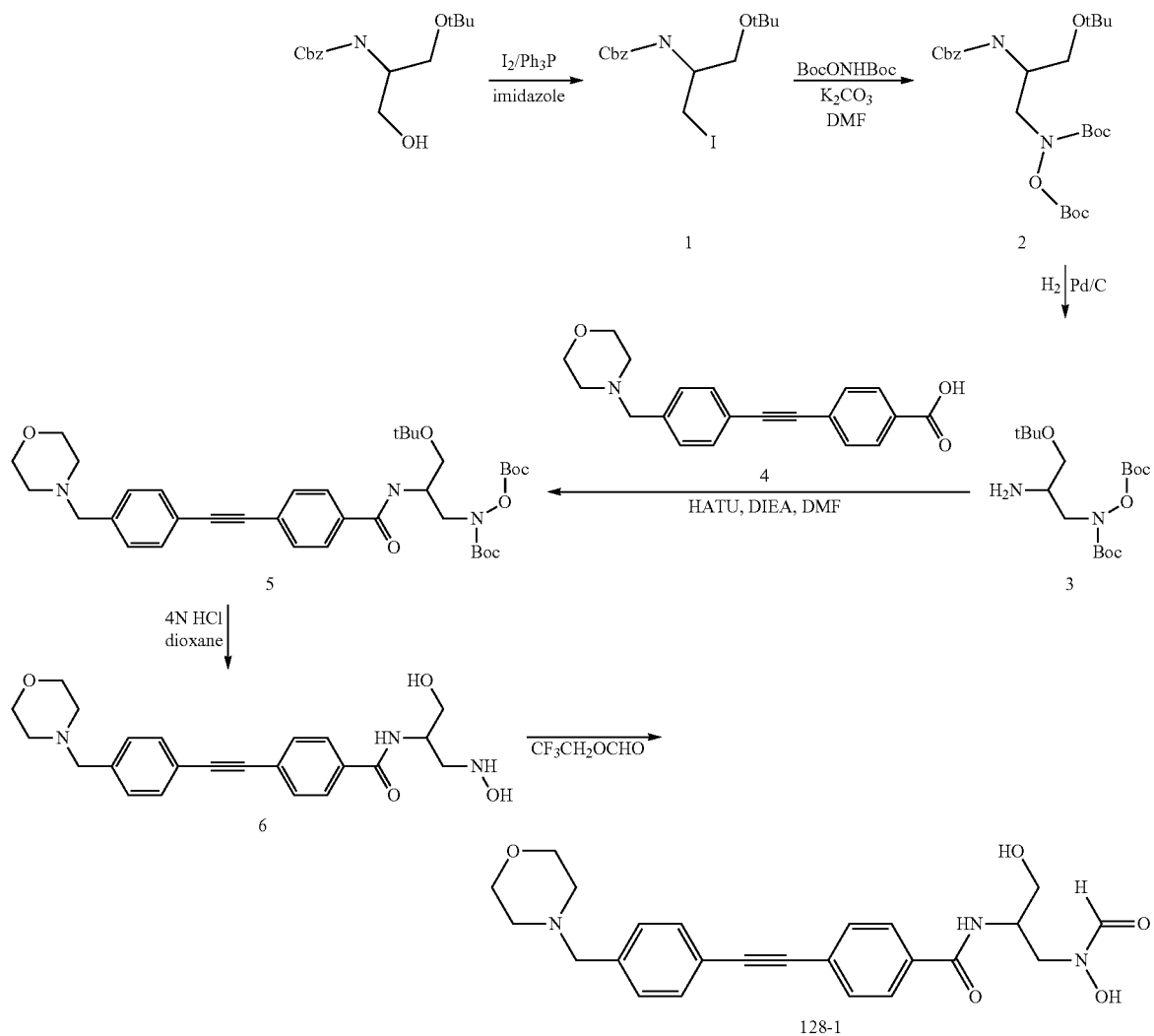

Synthesis of (2-tert-Butoxy-1-iodomethyl-ethyl)-carbamic acid benzyl ester (1)

A mixture of N-Cbz-O-tert-Bu-serinol (420 mg, 1.5 mmol), Ph₃P (487 mg, 1.86 mmol) and imidazole (150 mg, 2.2 mmol) was dissolved in THF (10 ml) followed by the addition of I₂ (483 mg, 3.49 mmol) portion wise during 3 min. The reaction mixture was stirred at ambient temperature overnight followed by the dilution with EtOAc (100 ml), and extraction with water (50 ml×3) and brine (30 ml). The organic layer was dried over Na₂SO₄ and evaporated in vacuum. The residue was used as is for the next chemical transformation with no additional purification. LC-MS [M+H⁺] 392.0.

Synthesis of (2-tert-Butoxy-1-(N,O-di-Boc-hydroxyaminomethyl-ethyl)-carbamic acid benzyl ester (2)

A mixture of compound 1 (1.5 mmol), N,O-di-Boc-hydroxylamine (350 mg, 1.5 mmol) and K₂CO₃ (483 mg, 3.49 mmol) in DMF (5 ml) was stirred at 65° C. for 2 h. The reaction mixture was diluted with EtOAc (50 ml), and extracted with water (15 ml×2) and brine (30 ml). The organic layer was dried over Na₂SO₄ and solvent was removed in vacuum. Residue was subjected to flash chromatography on CombiFlash® Companion unit equipped with RediSep® flash column (normal phase, 35-60 micron average particle size silicagel, 12 g, Teledyne Isco); flow rate=30 ml/min; injection volume 2 ml; mobile phase A: hexane; mobile phase B: EtOAc; gradient 0-95% B in 60 min. Fractions containing the desired product were combined and concentrated in vacuum to provide target compound (518 mg, 73.3% overall for 2 steps) as colorless oil. LC-MS [M+H⁺] 497.2.

Synthesis of (2-tert-Butoxy-1-(N,O-di-Boc-hydroxyaminomethyl)-ethylamine (3)

A mixture of solution of compound 2 (518 mg, 1.04 mmol) in 15 ml of MeOH and 5% Pd/C (200 mg) was subjected to hydrogenation in Parr shaker at 65 psi overnight. Pd/C was removed by filtration and filtrate was concentrated in vacuum to yield colorless oil, which was used on the next step with no additional purification. LC-MS [M+H⁺] 363.4.

Synthesis of N-(2-tert-Butoxy-1-(N,O-di-Boc-hydroxyaminomethyl)-ethyl)-4-(4-morpholin-4-ylmethyl-phenylethynyl)-benzamide (5)

A mixture of compound 3 (1.04 mmol), compound 4 (250 mg, 0.71 mmol), DIEA (496 µl, 3.0 mmol) and HATU (380 mg, 1.0 mmol) was stirred at ambient temperature for 45 min followed by the dilution with EtOAc (50 ml) and extraction with water (15 ml×2) and brine (30 ml). Organic layer was dried over Na₂SO₄ and evaporated in vacuum. Residue was subjected to flash chromatography on CombiFlash® Companion unit equipped with RediSep® flash column (normal phase, 35-60 micron average particle size silicagel, 4 g, Teledyne Isco); flow rate=18 ml/min; injection volume 2 ml; mobile phase A: hexane; mobile phase B: EtOAc; gradient 0-60% B in 60 min. Fractions containing the desired product were combined and concentrated in vacuum to provide target compound 5 250 mg (48.2%) as white solid. LC-MS [M+H] 666.1.

Synthesis of N-(2-Hydroxyamino-1-hydroxymethyl-ethyl)-4-(4-morpholin-4-ylmethyl-phenylethynyl)-benzamide (6)

The mixture of compound 5 (0.37 mmol, 250 mg) and 4 N HCl/dioxane (6 ml, 24 mmol) was stirred at r.t. for 1.5 h. Solvents were removed in vacuum and HCl salt was dissolved in a THF/DIEA mixture (10 ml/220 µl). A half of resulting solution was used on next step. LC-MS [M+H⁺] 410.0.

N-[2-(Formyl-hydroxyamino)-ethyl]-4-(4-morpholin-4-ylmethyl-phenylethynyl)-benzamide (128-1)

| Reagent | MW | Eq. | mg/ml | mmol |
|---|---|---|---|---|
| Compound 6 (as a solution, see pr. step.) | 276.34 | 1.0 | — | 0.18 |
| Trifluoroethyl formate | 128.05 | 11.1 | 195 mg | 2.00 |
| DIEA (as a solution, see pr. step.) | 129.24 | 3.6 | 110 µl | 0.65 |
| THF (as a solution, see pr. step.) | | | 5 ml | |

Trifluoroethyl formate (20 mg, 2 mmol) was added to the solution (~5 ml) from previous step and the reaction mixture was stirred at 55° C. for 1 h. The reaction mixture was concentrated in vacuum. Residue was dissolved in DMSO (600 µl) and subjected to HPLC purification. [Phenomenex Gemini C-18 column, 110 Å (30×100 mm); flow rate=20 ml/min; mobile phase A: 100% water, 0.1% TFA; mobile phase B: 100% ACN, 0.1% TFA; gradient elution from 10% B to 40% B in 60 min., detection 254 nm]. Fractions containing the desired product were combined and lyophilized to provide trifluoroacetic salt of target compound (10.6 mg, 10.7%) as white solid.

| Compound | Scale (mmol) | Yield (mg) | Yield (%) | Purity (%) | [M + H] | Retention time (min)* |
|---|---|---|---|---|---|---|
| 128-1 | 0.18 | 10.6 | 10.7 | 97.7 | 438.1 | 2.94 |

*[Chromolith SpeedRod RP-18e C18 column (4.6 × 50 mm); flow rate 1.5 ml/min; mobile phase A: 0.1% TFA/water; mobile phase B 0.1% TFA/ACN; gradient elution from 5% B to 100% B over 9.5 min, detection 254 nm]

Example 129

3-Amino-N-hydroxy-3-methyl-2-[3-(4-morpholin-4-ylmethyl-phenyl)-propynoylamino]-butyramide (129-1)

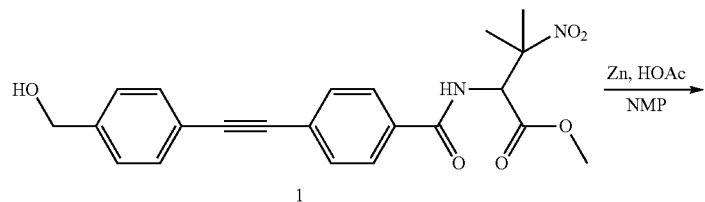

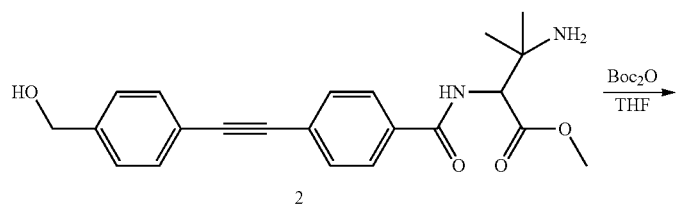

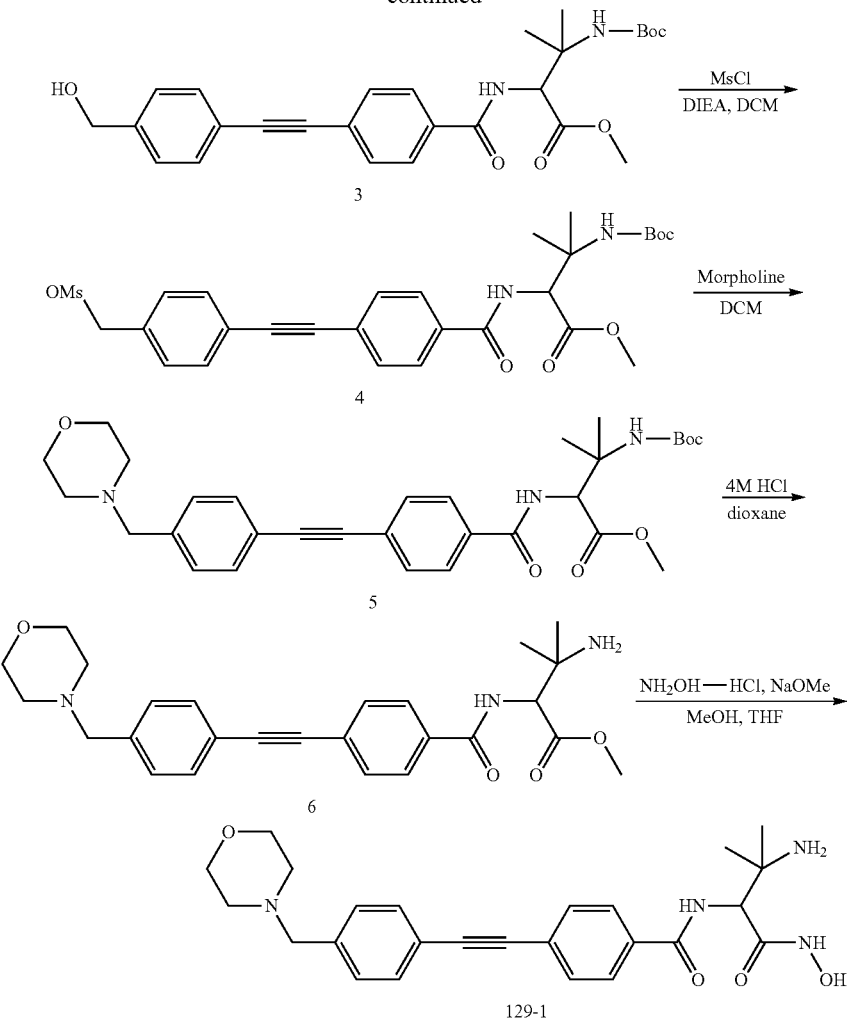

Synthesis of 3-Amino-2-[4-(4-hydroxymethyl-phenylethynyl)-benzoylamino]-3-methyl-butyric acid methyl ester (2)

To a cold solution of compound 1 (700 mg, 1.7 mmol) in 6 mL NMP and 10 mL AcOH of at 0° C., Zn dust (1.2 g, 18 mmol.) was added. The reaction mixture was vigorously stirred for 2 h at 25° C., monitored by LC-MS until there was no start material left. The reaction mixture was filtered though a celite pad, the solid was washed with DCM (3×10 mL) and MeOH (2×10 mL), combined the filtrate and washing liquid, and then concentrated to give 420 mg (65%) pure compound 2 as colorless oil. LC-MS: RT (Method A) 3.36 min; [M+H] 638.7.

Synthesis of 3-tert-Butoxycarbonylamino-2-[4-(4-hydroxymethyl-phenylethynyl)-benzoylamino]-3-methyl-butyric acid methyl ester (3)

To a cold solution of compound 2 (320 mg, 0.84 mmol) in THF (4 mL) at 0° C., di-tert-butyl dicarbonate (200 mg, 0.92 mmol) was added. The reaction mixture was stirred at ambient temperature for 2 h, until TLC (30% EtOAc in hexanes) indicated the disappearance of starting material. The reaction mixture was diluted with DCM (20 mL), washed with saturated NaHCO₃, brine, dried over Na₂SO₄, and then concentrated to give the crude compound 3 370 mg (92%).

Synthesis of 3-tert-Butoxycarbonylamino-3-methyl-2-[4-(4-morpholin-4-ylmethyl-phenylethynyl)-benzoylamino]-butyric acid methyl ester (5)

To a cold solution of compound 3 (370 mg, 0.77 mmol.) and DIEA (0.30 mL, 1.6 mmol) was added MsCl (0.12 mL, 1.54 mmol.) at 0° C. The reaction mixture was stirred at ambient temperature for 30 min. until TLC (30% EtOAc in Hexanes) indicated the disappearance of starting material. The reaction mixture was diluted with DCM (20 mL), washed with brine (2×20 mL), dried over Na₂SO₄, concentrated to give the crude product 4 (400 mg, 90%). The methanesulfonate 4 was re-dissolve in DCM (10 mL). To the solution at 0° C., morpholine (0.35 mL, 4.0 mmol) was added dropwise. The mixture was stirred at ambient temperature for 30 min. Reaction mixture was concentrated in vacuo, and residue was partitioned between water (30 mL) and EtOAc (30 mL). Layers were separated and aqueous layer was extracted with EtOAc (2×10 mL). Combined organic layers were washed with water (10 mL) and brine (10 mL), dried over anhydrous Na₂SO₄, and concentrated in vacuo to give compound 5 (439 mg, 100%) as a off-white solid.

Synthesis of N-(2-Amino-1-hydroxycarbamoyl-2-methyl-propyl)-4-(4-morpholin-4-ylmethyl-phenylethynyl)-benzamide (6)

To a mixture of compound 5 (148 mg) in dioxane (4 mL), HCl (4 M in dioxane, 4 mL) was added at 0° C. The reaction mixture was stirred at ambient temperature for 1 h, until LC-MS indicated the disappearance of starting material. HCl and solvent were removed by vacuum; the residue was dissolve in DCM, washed with sat. NaHCO₃, and brine, concentrated to give crude compound 6.

Synthesis of N-((1S,2R)-2-Amino-1-hydroxycarbamoyl-propyl)-4-[4-(2-cyclopropylamino-acetylamino)-phenylethynyl]-benzamide (129-1)

Compound 7 was made using the General Method for hydroxamate formation. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 15% B to 40% B over 60 min, MS detection). Fractions containing the desired product were combined and lyophilized to provide the trifluoroacetate salt of target compound 129-1 (11.4 mg, 6.2% yield) as a white solid. LC-MS: RT (Method A) 2.79 min; [M+H] 451.1.

| Compound | Scale (mmol)[1] | Yield (mg) | Yield (%)[1] | Purity (%)[2] | [M + H] | Retention time (min)[2] |
|---|---|---|---|---|---|---|
| 129-1 | 1 | 11.4 | 6.2 | 99.5 | 451.1 | 2.79 |

[1]Based on compound 5.
[2]Using LC-MS Analytical Method A.

Example 130

N-((1S,2R)-2-Amino-1-hydroxycarbamoyl-propyl)-4-[4-(2-cyclopropylamino-acetylamino)-phenylethynyl]-benzamide (130-1)

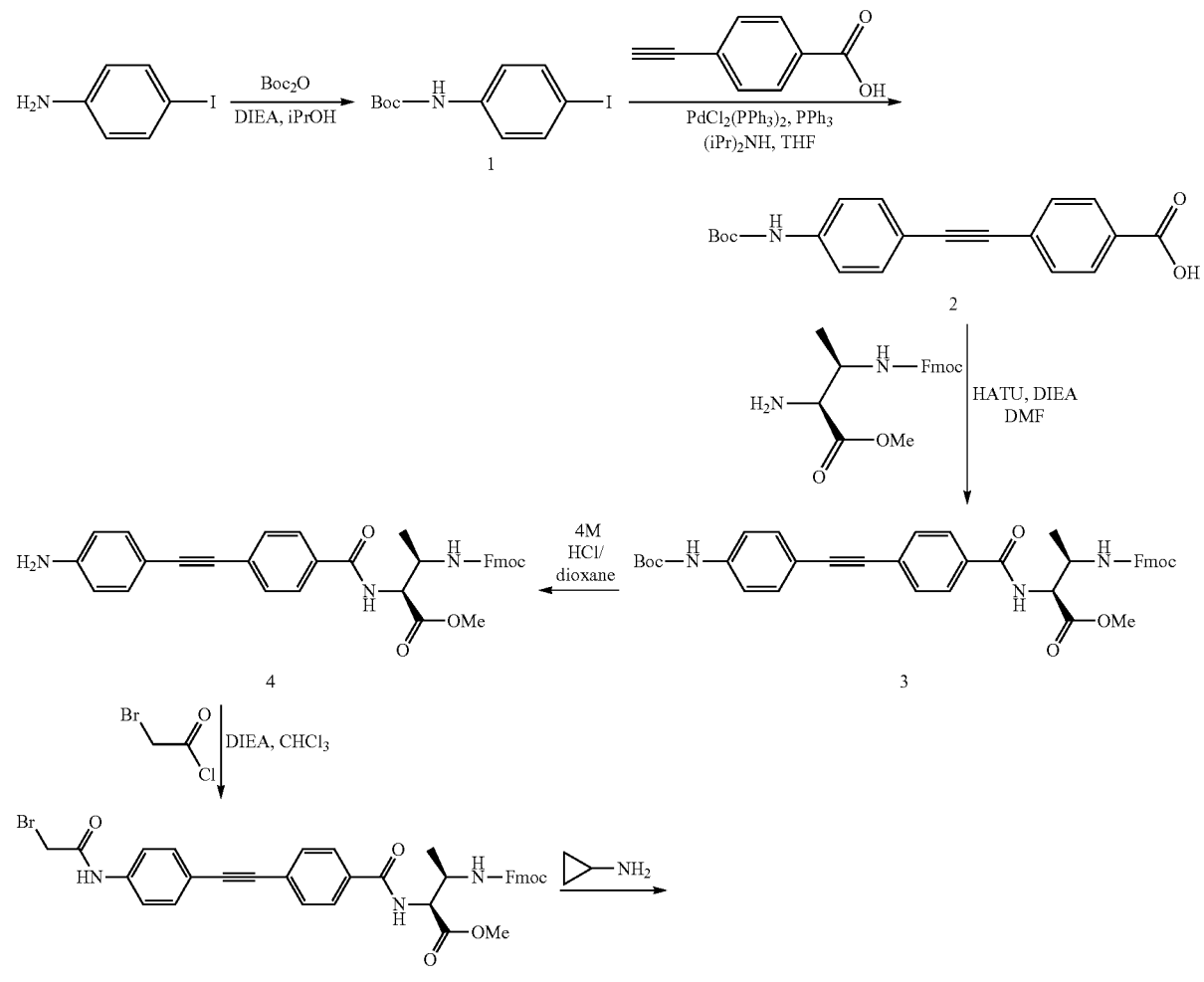

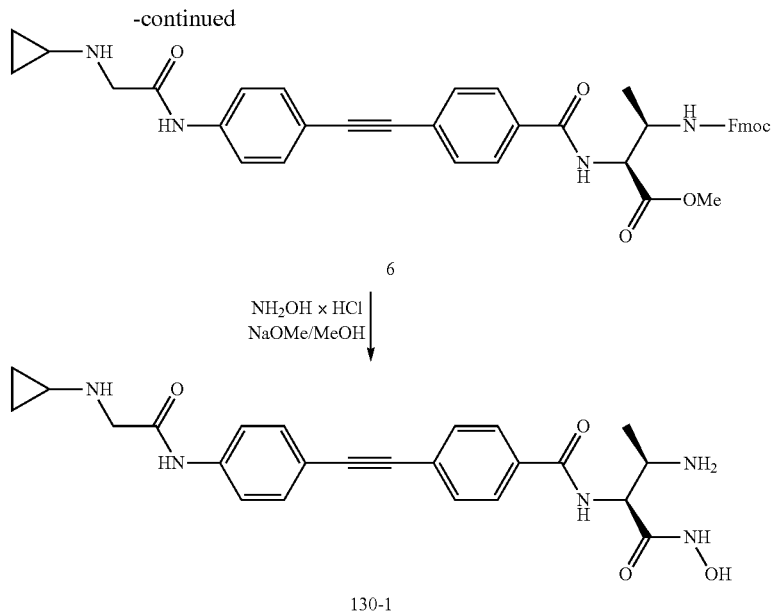

6

130-1

Synthesis of (4-Iodo-benzyl)-carbamic acid tert-butyl ester (1)

To a solution of 4-iodoaniline (1.95 g, 5.0 mmol) in iPrOH (10 mL) was added Boc₂O (1.199 g, 5.5 mmol), and the mixture was stirred at ambient temperature for 16 h. iPrOH was removed in vacuo and the residue was crystallized from Et₂O/hexanes mixture to give target compound 1 (1.219 g, 76%) as a off-white solid. LC-MS: RT (Method A) 6.14 min; [2M+H] 638.7.

Synthesis of 4-(4-tert-Butoxycarbonylamino-phenylethynyl)-benzoic acid (2)

| Reagent | MW | Eq. | mg, ml | mmol |
|---|---|---|---|---|
| 4-Ethynyl benzoic acid | 146.15 | 1.0 | 146 mg | 1.0 |
| Compound 1 | 319.14 | 1.0 | 319 mg | 1.0 |
| PdCl₂(PPh₃)₂ | 703.91 | 0.03 | 21 mg | 0.03 |
| CuI | 190.45 | 0.06 | 12 mg | 0.06 |
| (iPr)₂NH | 101.19 | | 0.6 mL | 0.3 |
| THF | | | 1.2 mL | |

The compound 2 was made using the General Method for Sonogashira coupling, but without PPh₃. Yield: 355 mg. Crude product was used in next synthetic step without additional purification. LC-MS: RT (Method A) 6.05 min, [M+H] 338.6.

Synthesis of (2S,3R)-2-[4-(4-tert-Butoxycarbonylamino-phenylethynyl)-benzoylamino]-3-(9H-fluoren-9-ylmethoxycarbonylamino)-butyric acid methyl ester (3)

| Reagent | MW | Eq. | mg/mL | mmol |
|---|---|---|---|---|
| Compound 2 | 337.38 | 1.0 | 355 mg | 1.0 |
| Fmoc-Methyl DAP•HCl | 390.87 | 1.0 | 390 mg | 1.0 |

| Reagent | MW | Eq. | mg/mL | mmol |
|---|---|---|---|---|
| HATU | 380.2 | 1.2 | 456 mg | 1.2 |
| DIEA | 129.25 | 3.5 | 0.609 mL | 3.5 |
| DMF | | | 1 mL | |

Compound 3 was made using the General Method for HATU coupling. LC-MS: RT (Method A) 7.49 min, [M+H] 674.2. Crude product was used in next synthetic step without additional purification.

Synthesis of (2S,3R)-2-[4-(4-Amino-phenylethynyl)-benzoylamino]-3-(9H-fluoren-9-ylmethoxycarbonylamino)-butyric acid methyl ester (4)

| Reagent | MW | Eq. | mg/mL | mmol |
|---|---|---|---|---|
| Compound 3 | 673.77 | 1.0 | — | 1.0 |
| HCl, 4.0M solution in 1,4-dioxane | | | 4 mL | |
| Dioxane | | | 2 mL | |

Compound 4 was made using the General Method for Boc deprotection. Crude product was used in next synthetic step without additional purification.

Synthesis of (2S,3R)-2-{4-[4-(2-Bromo-acetylamino)-phenylethynyl]-benzoylamino}-3-(9H-fluoren-9-ylmethoxycarbonylamino)-butyric acid methyl ester (5)

To a suspension of compound 5 (137 mg, 0.22 mmol) and DIEA (96 uL, 0.55 mmol) in CHCl₃ (1 mL), cooled in ice/water bath, was added dropwise bromoacetyl chloride (24 μL, 0.29 mmol) and the mixture was stirred in ice/water bath for 5 min. Reaction mixture was allowed to attain ambient temperature and stirred for 1.5 h. The reaction mixture was used on next step. LC-MS: RT (Method A) 6.91 min, MH⁺=695.5.

Synthesis of (2S,3R)-2-{4-[4-(2-Cyclopropylamino-acetylamino)-phenylethynyl]-benzoylamino}-3-(9H-fluoren-9-ylmethoxycarbonylamino)-butyric acid methyl ester (6)

Cyclopropyl amine (24 µL, 0.35 mmol) was added to the reaction mixture of compound 6 and resulting mixture was stirred for 1 h at ambient temperature. The reaction mixture was diluted with EtOAc (80 mL) and organic layer was washed with water (2×40 mL) and brine (40 mL), dried over anhydrous $Na_2SO_4$, and concentrated in vacuo to give target compound 6 (133 mg, 90%) as a brown solid. LC-MS: RT (Method A) 6.82 min, $MH^+$=671.3.

Synthesis of N-((1S,2R)-2-Amino-1-hydroxycarbamoyl-propyl)-4-[4-(2-cyclopropylamino-acetylamino)-phenylethynyl]-benzamide (130-1)

| Reagent | MW, d | Eq. | mg, ml | mmol |
|---|---|---|---|---|
| Compound 6 | 670.77 | 1.0 | 133 mg | 0.2 |
| $NH_2OH \times HCl$ | 69.49 | 6.0 | 92 mg | 0.78 |
| 25% MeONa in MeOH | | 12 | 0.6 mL | 1.56 |
| THF | | | 2 mL | |
| MeOH | | | 2 mL | |

Compound 130-1 was made using the General Method for hydroxamate formation. LC-MS: RT (Method A) 2.48 min, $MH^+$=450.2. Crude product was purified by preparative scale reverse-phase HPLC (Phenomenex Gemini C-18 column, 110 Å, 30×100 mm, flow rate: 20 mL/min, mobile phase A: 0.1% TFA/water, mobile phase B: 0.1% TFA/ACN, gradient elution from 15% B to 40% B over 60 min, MS detection). Fractions containing the desired product were combined and lyophilized to provide the trifluoroacetate salt of target compound 130-1 (3.7 mg, 0.54% yield) as a white solid. LC-MS: RT (Method A) 3.08 min; [M+H] 449.9.

| Compound | Scale (mmol)[1] | Yield (mg)[1] | Yield (%)[1] | Purity (%)[2] | [M + H] | Retention time (min)[2] |
|---|---|---|---|---|---|---|
| 130-1 | 1 | 3.7 | 0.54 | 95.0 | 449.9 | 3.08 |

[1]Based on the amount of carboxylic acid used in the coupling reaction.
[2]Using LC-MS Analytical Method A.

Example 131

N-((1S,2R)-2-Amino-1-hydroxycarbamoyl-propyl)-4-(4-aminomethyl-phenylethynyl)-benzamide (131-1), N-((1S,2R)-2-Amino-1-hydroxycarbamoyl-propyl)-4-[4-methanesulfonylamino-methyl)-phenylethynyl]-benzamide (131-2) and N-((1S,2R)-2-Amino-1-hydroxycarbamoyl-propyl)-4-(4-guanidinomethyl-phenylethynyl)-benzamide (131-3)

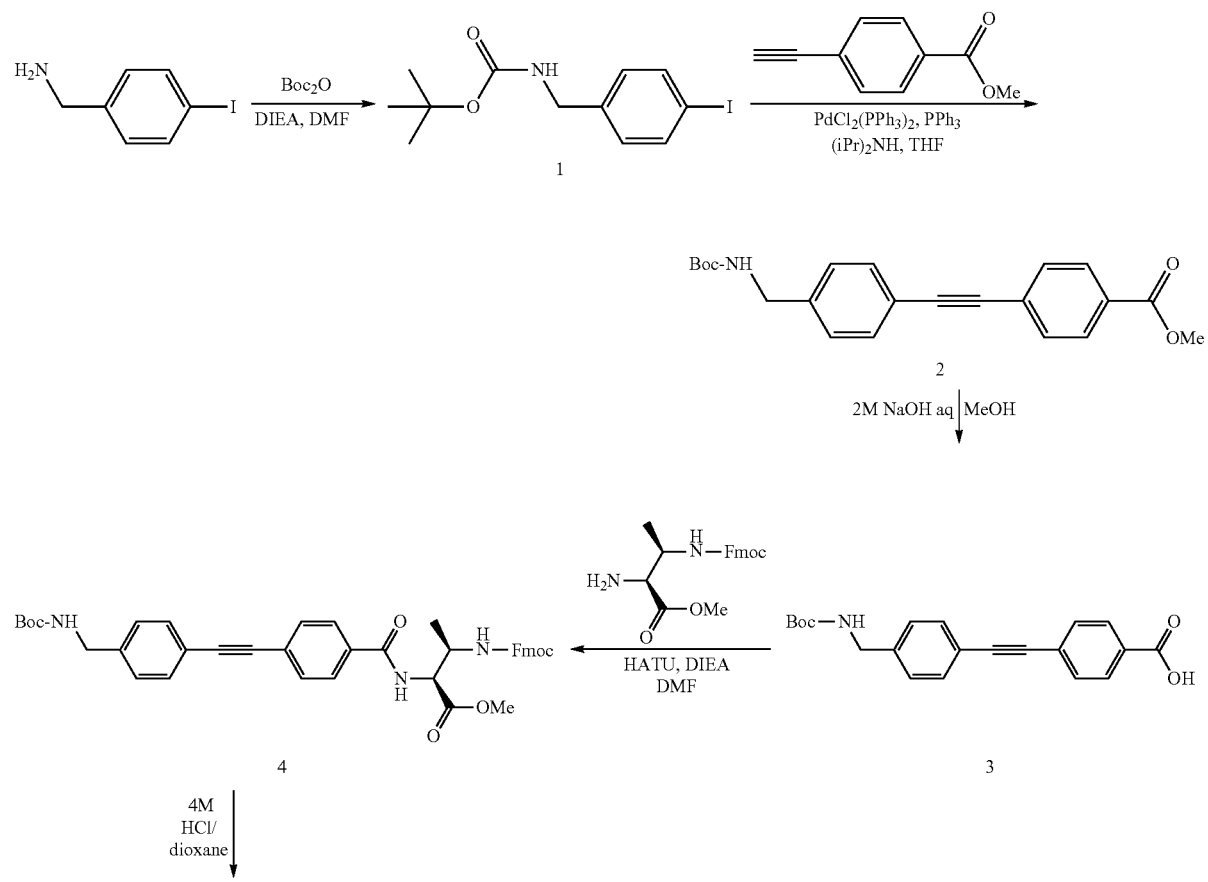

483

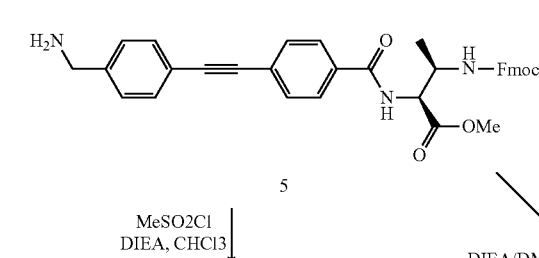

5

MeSO2Cl
DIEA, CHCl3

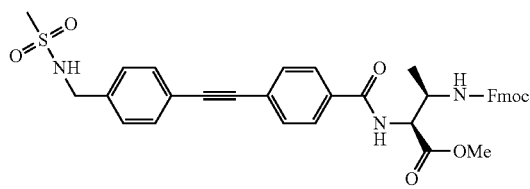

7

NH2OH × HCl
NaOMe/MeOH

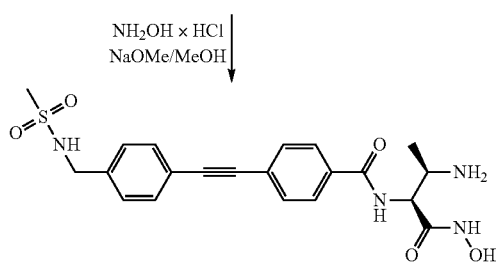

131-2

Synthesis of (4-Iodo-benzyl)-carbamic acid tert-butyl ester (1)

To a solution of 4-iodobenzylamine (1.35 g, 5.0 mmol) and DIEA (0.96 mL, 5.5 mmol) in DMF (5 mL) was added Boc$_2$O (1.09 g, 5.0 mmol), and the mixture was stirred at ambient temperature for 1 h. The reaction mixture was diluted with EtOAc (125 mL) and organic layer was washed with water (2×40 mL) and brine (40 mL), dried over anhydrous Na$_2$SO$_4$, and concentrated in vacuo to give target compound 1 (1.635 g, 98%) as a off-white solid. LC-MS: RT (Method A) 6.02 min; [2M+H] 667.0. Crude product was used in next synthetic step without additional purification.

Synthesis of 4-[4-(tert-Butoxycarbonylamino-methyl)-phenylethynyl]-benzoic acid methyl ester (2)

| Reagent | MW | Eq. | mg, ml | mmol |
|---|---|---|---|---|
| Methyl 4-Ethynyl benzoate | 160.17 | 1.0 | 1635 mg | 4.9 |
| Compound 1 | 333.17 | 1.1 | 864 mg | 5.4 |
| PdCl$_2$(PPh$_3$)$_2$ | 703.91 | 0.03 | 104 mg | 0.15 |
| PPh$_3$ | 262.29 | 0.1 | 129 mg | 0.49 |
| CuI | 190.45 | 0.06 | 56 mg | 0.3 |
| (iPr)$_2$NH | 101.19 |  | 3 mL |  |
| THF |  |  | 6 mL |  |

The compound 2 was made using the General Method for Sonogashira coupling. Crude product was used in next synthetic step without additional purification. LC-MS: RT (Method A) 5.92 min, [M+H] 366.2).

484

-continued
NH2OH × HCl
NaOMe/MeOH

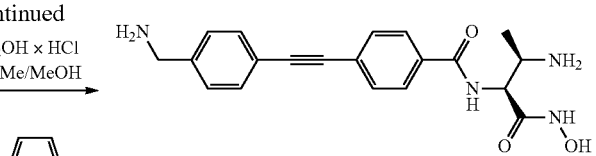

131-1

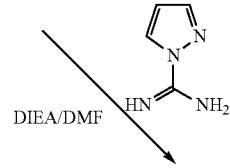

DIEA/DMF

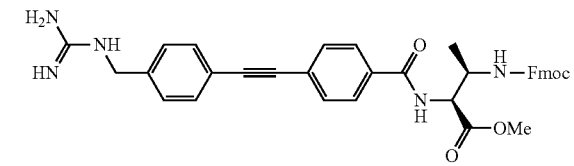

9

NH2OH × HCl
NaOMe/MeOH

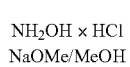

131-3

Synthesis of 4-[4-(tert-Butoxycarbonylamino-methyl)-phenylethynyl]-benzoic acid (3)

| Reagent | MW | Eq. | mg, ml | mmol |
|---|---|---|---|---|
| Compound 2 | 365.43 | 1.0 | 1.79 g | 4.91 |
| 2N NaOH aq. | 160.17 | 6.0 | 15 mL | 30 |
| MeOH |  |  | 100 mL |  |
| THF |  |  | 50 mL |  |

All components were stirred for 16 h at room temperature. Most of solvent was removed in vacuo. Water (100 mL) was added to residue. The aqueous solution was acidified with 2% H$_2$SO$_4$ aq. to pH=2-3 and extracted with EtOAc (2×50 mL) The combined organic layer was washed with water (2×40 mL), brine (50 mL) and dried over Na$_2$SO$_4$. EtOAc was removed in vacuo to give desired compound 3 (1.650 g, 96% based on compound 1) as an off-white solid. LC-MS: RT (Method A) 5.76 min; low ionization.

Synthesis of (2S,3R)-2-{4-[4-(tert-Butoxycarbo-nylamino-methyl)-phenylethynyl]-benzoylamino}-3-(9H-fluoren-9-ylmethoxycarbonylamino)-butyric acid methyl ester (4)

| Reagent | MW | Eq. | mg/mL | mmol |
|---|---|---|---|---|
| Compound 3 | 351.41 | 1.0 | 235 mg | 0.67 |
| Fmoc-Methyl DAP•HCl | 390.87 | 1.0 | 200 mg | 0.67 |
| HATU | 380.2 | 1.2 | 306 mg | 0.8 |
| DIEA | 129.25 | 3.5 | 0.408 mL | 2.35 |
| DMF |  |  | 1 mL |  |

Compound 4 was made using the General Method for HATU coupling. LC-MS: RT (Method A) 7.54 min, [M+H]

688.2). Crude product was used in next synthetic step without additional purification.

Synthesis of (2S,3R)-2-[4-(4-Aminomethyl-phenylethynyl)-benzoylamino]-3-(9H-fluoren-9-yl-methoxycarbonylamino)-butyric acid methyl ester (5)

| Reagent | MW | Eq. | mg/mL | mmol |
| --- | --- | --- | --- | --- |
| Compound 4 | 687.8 | 1.0 | — | 0.67 |
| HCl, 4.0M solution in 1,4-dioxane | | | 15 mL | |
| Dioxane | | | 5 mL | |

Compound 5 was made using the General Method for Boc deprotection. LC-MS: RT (Method A) 5.47 min, [M+H] 588.3. Crude product was used in next synthetic step without additional purification.

Synthesis of N-((1S,2R)-2-Amino-1-hydroxycarbamoyl-propyl)-4-(4-aminomethyl-phenylethynyl)-benzamide (131-1)

| Reagent | MW, d | Eq. | mg, ml | mmol |
| --- | --- | --- | --- | --- |
| Compound 5 HCl | 624.14 | 1.0 | 137 mg | 0.22 |
| NH$_2$OH × HCl | 69.49 | 6.0 | 92 mg | 1.32 |
| 25% MeONa in MeOH | | 12 | 0.63 mL | 2.64 |
| THF | | | 2 mL | |
| MeOH | | | 2 mL | |

Compound 131-1 was made using the General Method for hydroxamate formation. LC-MS: RT (Method A) 2.17 min, MH$^+$=367.0.

Synthesis of (2S,3R)-3-(9H-Fluoren-9-ylmethoxycarbonylamino)-2-{-4-[4-(methanesulfonylamino-methyl)-phenylethynyl]-benzoylamino}-butyric acid methyl ester (7)

To a suspension of compound 5 (137 mg, 0.22 mmol) and DIEA (77 μL, 0.44 mmol) in CHCl$_3$ (0.5 mL), cooled in ice/water bath, was added dropwise methanesulfonyl chloride (22 μL, 0.29 mmol) and the mixture was stirred in ice/water bath for 5 min. Reaction mixture was allowed to attain ambient temperature and stir for 30 min. Reaction mixture was diluted with EtOAc (100 mL), washed with water (2×30 mL) and brine (25 mL). Combined organic layers were dried over anhydrous Na$_2$SO$_4$, and concentrated in vacuo to give target compound 7 (141 mg, 97%) as an off-white solid. LC-MS: RT (Method A) 6.37 min, M+H$^+$=666.4.

N-((1S,2R)-2-Amino-1-hydroxycarbamoyl-propyl)-4-[4-methanesulfonyl-amino-methyl)-phenylethynyl]-benzamide (131-2)

| Reagent | MW, d | Eq. | mg, ml | mmol |
| --- | --- | --- | --- | --- |
| Compound 7 | 665.77 | 1.0 | 141 mg | 0.21 |
| NH$_2$OH × HCl | 69.49 | 6.0 | 92 mg | 1.32 |
| 25% MeONa in MeOH | | 12 | 0.63 mL | 2.64 |
| THF | | | 2 mL | |
| MeOH | | | 2 mL | |

Compound 131-2 was made using the General Method for hydroxamate formation. LC-MS: RT (Method A) 3.13 min, MH$^+$=445.3.

Synthesis of (2S,3R)-3-(9H-Fluoren-9-ylmethoxycarbonylamino)-2-[4-(4-guanidino-methyl-phenylethynyl)-benzoylamino]-butyric acid methyl ester (9)

To a suspension of compound 5 (137 mg, 0.22 mmol) and DIEA (191 μL, 1.1 mmol) in DMF (0.5 mL), was added 1H-pyrazole-1-carboxamidine HCl (71 mg, 0.48 mmol) and the mixture was stirred at 60° C. for 1 h. The reaction mixture was diluted with EtOAc (80 mL), washed with water (2×30 mL) and brine (25 mL). Combined organic layers were dried over anhydrous Na$_2$SO$_4$, and concentrated in vacuo to give target compound 9 (82 mg, 65%) as an off-white solid. LC-MS: RT (Method A) 5.48 min, MH$^+$=630.3.

Synthesis of N-((1S,2R)-2-Amino-1-hydroxycarbamoyl-propyl)-4-(4-guanidinomethyl-phenylethynyl)-benzamide (131-3)

| Reagent | MW, d | Eq. | mg, ml | mmol |
| --- | --- | --- | --- | --- |
| Compound 9 | 629.72 | 1.0 | 82 mg | 0.13 |
| NH$_2$OH × HCl | 69.49 | 6.0 | 55 mg | 0.78 |
| 25% MeONa in MeOH | | 12 | 0.35 mL | 1.56 |
| THF | | | 2 mL | |
| MeOH | | | 2 mL | |

Compound 131-3 was made using the General Method for hydroxamate formation. LC-MS: RT (Method A) 2.72 min, MH$^+$=409.2.

The following compounds were made as described above.

| Compound # | Structure | Ret. Time (min) | MH$^+$ (m/z) | HPLC-MS Method |
| --- | --- | --- | --- | --- |
| 131-1 | (structure) | 2.58 | 367.1 | A |

| Compound # | Structure | Ret. Time (min) | MH+ (m/z) | HPLC-MS Method |
|---|---|---|---|---|
| 131-2 | 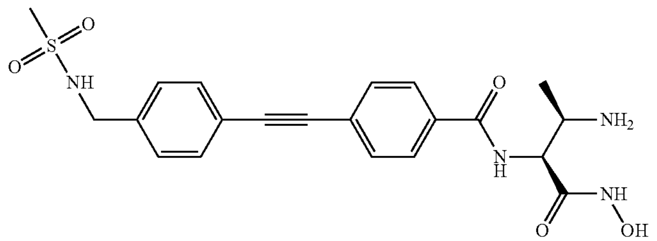 [SMILES: C[C@@H](N)[C@H](NC(=O)c1ccc(C#Cc2ccc(CNS(C)(=O)=O)cc2)cc1)C(=O)NO] | 4.23 | 445.5 | A |
| 131-3 | 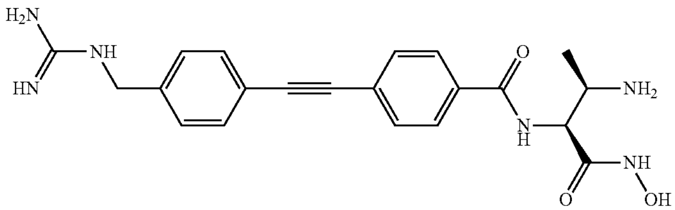 [SMILES: C[C@@H](N)[C@H](NC(=O)c1ccc(C#Cc2ccc(CNC(=N)N)cc2)cc1)C(=O)NO] | 2.99 | 409.1 | A |
Example 132
N—[(S)-2-(2-Cyclopropylamino-acetylamino)-1-hydroxycarbamoyl-ethyl]-4-phenylethynyl-benzamide (132-1)
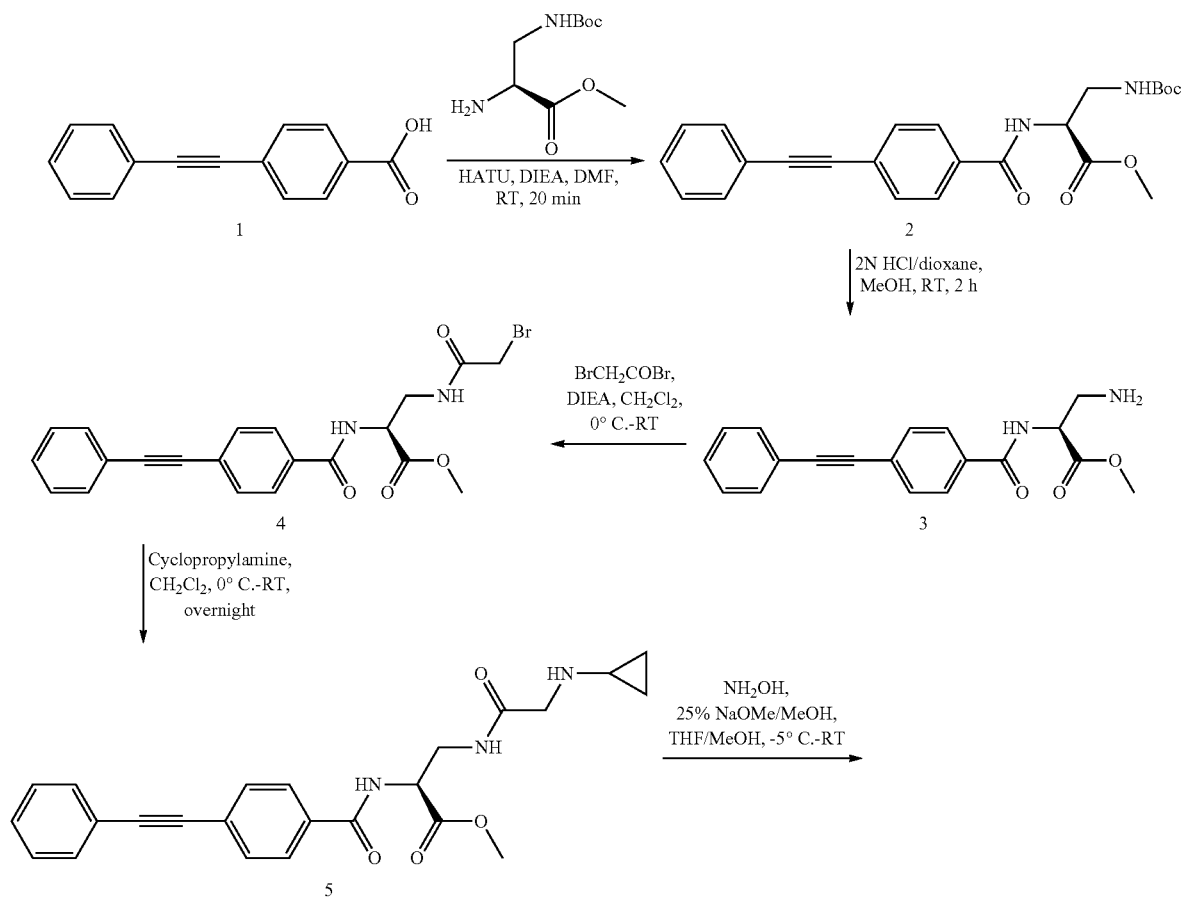

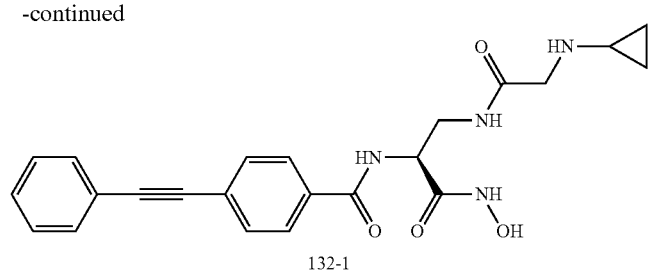

132-1

Synthesis of (S)-3-tert-butoxycarbonylamino-2-(4-phenylethynyl-benzoylamino)-propionic acid methyl ester (2)

To the mixture of compound 1 (210 mg, 0.94 mmol) and H—(S)-DAP(N'-Boc)-OMe hydrochloride (275 mg, 1.08 mmol) in DMF (5 mL) was added HATU (429 mg, 1.13 mmol) followed by DIEA (491 µl, 2.82 mmol). Reaction mixture was stirred at ambient temperature for 20 min, diluted with 0.1 M HCl$_{aq}$ (50 mL) and extracted with EtOAc (60 mL×2). Combined organic layers were washed with water (60 mL) and brine (60 mL), dried over anh. Na$_2$SO$_4$ and evaporated in vacuo to give target compound 2 (397 mg, 100%) as an yellow oil. LC-MS [M+H] 424.0. Compound was used in next synthetic step without additional purification.

Synthesis of (S)-3-amino-2-(4-phenylethynyl-benzoylamino)-propionic acid methyl ester (3)

To the solution of compound 2 (397 mg, 0.94 mmol) in dioxane (2 mL) and MeOH (2 mL) was added solution of 4 N HCl in dioxane (4 mL, 16 mmol). Reaction mixture was stirred at ambient temperature. Completion of the reaction was monitored by LC-MS. After completion (in 2 h) solvent was evaporated in vacuo. Residue was dissolved in i-PrOH (10 mL) and evaporated in vacuo. The aforementioned procedure was repeated twice to provide hydrochloride salt of target product 3 (337 mg, 100%) as a light yellow solid. LC-MS [M+H] 323.7.

Synthesis of (S)-3-(2-bromo-acetylamino)-2-(4-phenylethynyl-benzoylamino)-propionic acid methyl ester (4)

To the mixture of compound 3 hydrochloride (337 mg, 0.94 mmol) and DIEA (410 µl, 2.35 mmol) in CH$_2$Cl$_2$ (8 mL) was added bromoacetyl bromide (82 µl, 0.94 mmol) at 0° C. Reaction mixture was allowed to warm to ambient temperature and stirred for 30 min. CH$_2$Cl$_2$ was evaporated in vacuo. The residue was dissolved in EtOAc (100 mL), washed with water (50 mL) and brine (50 mL×2). Organic phase was dried over anh. Na$_2$SO$_4$ and evaporated in vacuo. The crude product was purified by flash column chromatography on silica gel utilizing a 5% MeOH/CH$_2$Cl$_2$ as an gradient to give the target product 4 (270 mg, 65%) as a white solid. LC-MS [M+H] 445.9.

Synthesis of (S)-3-(2-cyclopropylamino-acetylamino)-2-(4-phenylethynyl-benzoylamino)-propionic acid methyl ester (5)

To a solution of compound 4 (67 mg, 0.15 mmol) in CH$_2$Cl$_2$ (2 mL) was added cyclopropylamine (36 µl, 0.53 mmol) at 0° C. Reaction mixture was maintained at 0° C. for 10 min, mixture was then allowed to warm to ambient temperature and stirred overnight. After completion the solvent was removed in vacuo. The residue was diluted with water (40 mL), acidified with 1 N HCl to pH 4 and extracted with EtOAc (40 mL×2). Combined organic layers were washed with water (50 mL) and brine (50 mL), dried over anh. Na$_2$SO$_4$ and evaporated in vacuo to provide the target product 5 (63 mg, 100%) as a light yellow oil. LC-MS [M+H] 420.9.

Synthesis of N—[(S)-2-(2-cyclopropylamino-acetylamino)-1-hydroxycarbamoyl-ethyl]-4-phenylethynyl-benzamide (132-1)

To a stirred suspension of compound 5 (63 mg, 0.15 mmol) and hydroxylamine hydrochloride (83 mg, 1.2 mmol) in MeOH (anh, 2 mL) and THF (anh, 0.8 mL) was added dropwise 25% NaOMe/MeOH (343 µl, 1.5 mmol) at −5° C. under nitrogen. Reaction mixture was stirred at −5° C. for additional 5 min. Temperature of reaction mixture was raised to ambient. Completion of the reaction was monitored by LC-MS. After completion (in 20 min) reaction mixture was acidified with 1 N HCl in MeOH to pH~5 at low temperature and evaporated in vacuo. Residue was dissolved in DMSO (400 µl) and subjected to HPLC purification. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 8% B to 60% B in 60 min., detection 254 nm]. Fractions containing the desired product were combined and lyophilized to provide trifluoroacetate salt of target product 132-1 (32.4 mg) as a white solid. LC-MS [M+H] 421.1.

| Compound | Scale (mmol)* | Yield (mg) | Yield (%)* | Purity (%) | [M+H] | Retention time (min)** |
|---|---|---|---|---|---|---|
| 132-1 | 0.15 | 32.4 | 40.5 | 97.9 | 421.1 | 5.63 |

*Based on the amount of compound 4
**HPLC-MS Method B

Each of the following compounds was synthesized as described above using (S)-DAP(N'-Boc)-OMe×HCl or (S)-Me-DAP(N'-Boc)-OMe×HCl and the appropriate amine.

| Compound # | Structure | MH+ (m/z) | Ret. Time (min) | HPLC-MS Method |
|---|---|---|---|---|
| 132-2 | 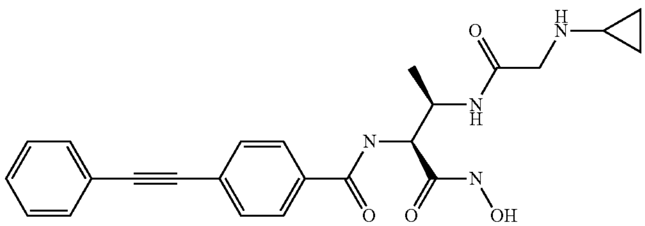 [SMILES: C[C@@H](NC(=O)CNC1CC1)[C@H](NC(=O)c1ccc(C#Cc2ccccc2)cc1)C(=O)NO] | 435.1 | 4.04 | A |
| 132-3 | 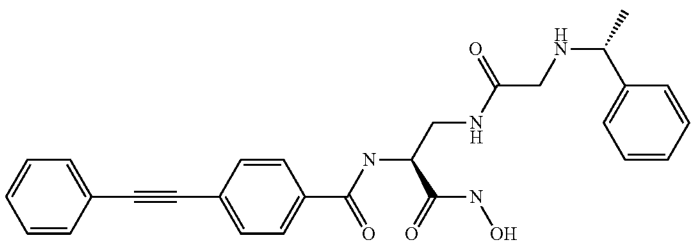 [SMILES: C[C@@H](NCC(=O)NC[C@H](NC(=O)c1ccc(C#Cc2ccccc2)cc1)C(=O)NO)c1ccccc1] | 485.1 | 6.55 | B |
| 132-4 | 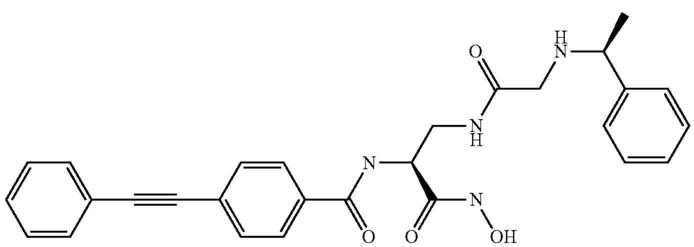 [SMILES: C[C@H](NCC(=O)NC[C@H](NC(=O)c1ccc(C#Cc2ccccc2)cc1)C(=O)NO)c1ccccc1] | 485.1 | 4.49 | A |
| 132-5 | 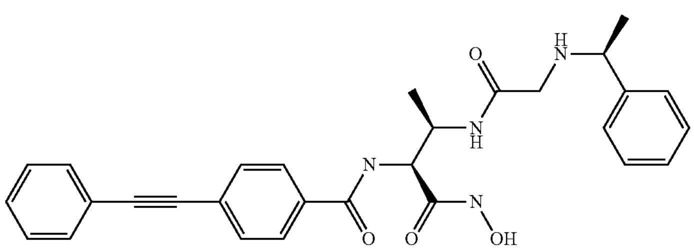 [SMILES: C[C@H](NCC(=O)N[C@H](C)[C@H](NC(=O)c1ccc(C#Cc2ccccc2)cc1)C(=O)NO)c1ccccc1] | 499.1 | 4.60 | A |
| 132-6 | 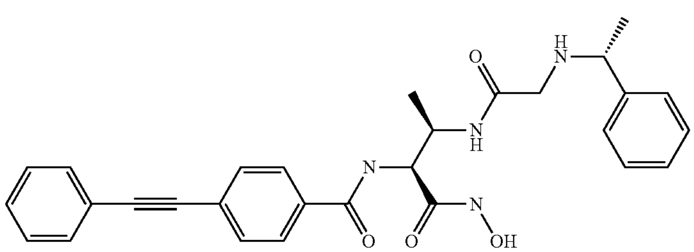 [SMILES: C[C@@H](NCC(=O)N[C@H](C)[C@H](NC(=O)c1ccc(C#Cc2ccccc2)cc1)C(=O)NO)c1ccccc1] | 499.1 | 4.61 | A |

Example 133

N-((1S,2S)-2-Amino-1-hydroxycarbamoyl-propyl)-4-phenylethynyl-benzamide (133-1)

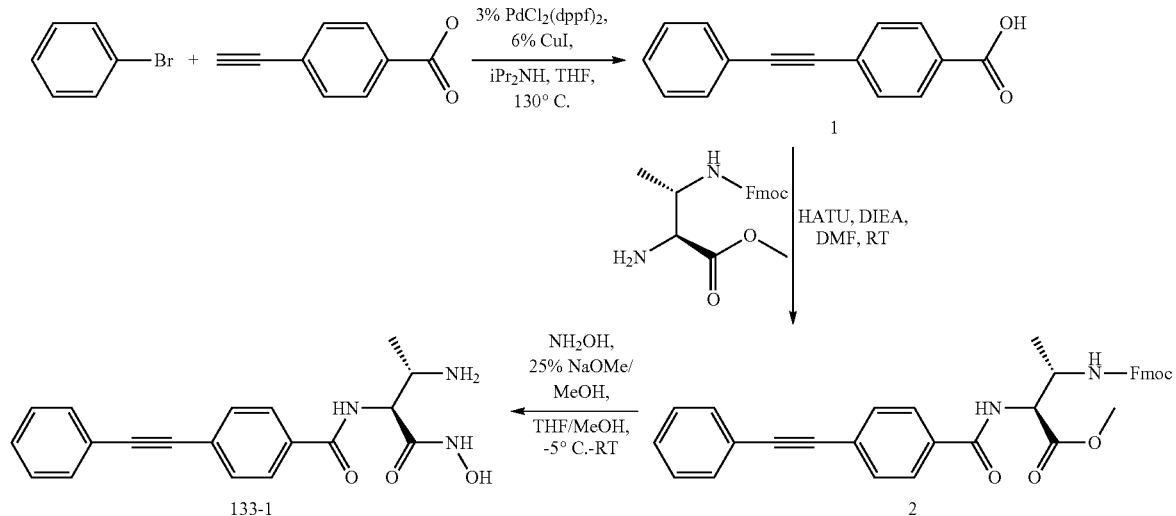

Synthesis of 4-phenylethynyl-benzoic acid (1)

The 4-ethynyl-benzoic acid (146 mg, 1.0 mmol), bromobenzene (116 µl, 1.1 mmol), PdCl$_2$(dppf)$_2$ (24.5 mg, 0.03 mmol) and copper(I) iodide (11 mg, 0.06 mmol), and diisopropylamine (7.0 mL, 2.3 mmol) were dissolved in THF (2 mL) and sealed under nitrogen. The reaction mixture was then stirred rapidly for 1 min and placed in the microwave reactor at 130° C. for 15 min. Then, mixture was diluted with EtOAc (50 mL) and water (40 mL). After mixing and adjusting to pH~5 with 3 M HCl, the aqueous phase was removed. The organic phase was washed with 0.3 M HCl (20 mL×2), and brine (30 mL). Filtration of the brown solution through anh Na$_2$SO$_4$ and evaporation of the solvents yielded the target crude product, which was purified by HPLC purification. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 30% B to 70% B in 60 min., detection 254 nm]. Fractions containing the desired product were combined and ACN was concentrated in vacuo. Product was extracted with EtOAc (50 mL), washed with brine (50 mL×2), dried over anh. Na$_2$SO$_4$ and solvent was evaporated in vacuo. Residue was dried in vacuo overnight to provide target compound 2 (160 mg, 72%) as white solid. LC-MS [M+H] 223.3.

Synthesis of (2S,3S)-3-(9H-fluoren-9-ylmethoxycarbonylamino)-2-(4-phenylethynyl-benzoylamino)-butyric acid methyl ester (2)

| Reagent | MW | Eq. | g/mL | mmol |
|---|---|---|---|---|
| Compound 1 | 222.25 | 1.0 | 53 mg | 0.24 |
| H-(Allo)-Me-DAP-(N'-Fmoc)-OMe × HCl* | 390.86 | 1.2 | 113 mg | 0.29 |
| HATU | 380.23 | 1.2 | 110 mg | 0.29 |
| DIEA | 129.24 | 3 | 125 µl | 0.72 |
| DMF | | | 1.5 mL | |

*amino acid was synthesized according to Scheme 2

Compound 2 was prepared by reaction with H-(Allo)-Me-DAP-(N'-Fmoc)-OMe×HCl according to General Method for HATU coupling in quantitative yield. LC-MS [M+H] 559.5 (C$_{35}$H$_{30}$N$_2$O$_5$+H, requires 559.64). Compound was used in next synthetic step without additional purification.

Synthesis of N-((1S,2S)-2-amino-1-hydroxycarbamoyl-propyl)-4-phenylethynyl-benzamide (133-1)

| Reagent | MW | Eq. | mg/mL | mmol |
|---|---|---|---|---|
| Compound 2 | 558.64 | 1.0 | 134 mg | 0.24 |
| NH$_2$OH × HCl | 69.49 | 10 | 167 mg | 2.40 |
| 25% NaOMe/MeOH | | 12 | 658 µl | 2.88 |
| MeOH | | | 3 mL | |
| THF | | | 1.2 mL | |

Compound 133-1 was prepared by following General Method for hydroxamate formation, anhydrous. Crude compound was purified by HPLC. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 15% B to 40% B over 60 min., detection 254 nm]. Fractions containing the desired product were combined and lyophilized to provide the trifluoroacetate salt of target compound 133-1 (21.1 mg) as a white solid. LC-MS: [M+H] 338.3.

| Compound | Scale (mmol)* | Yield (mg) | Yield (%)* | Purity (%) | [M + H] | Retention time (min)* |
|---|---|---|---|---|---|---|
| 133-1 | 0.24 | 21.1 mg | 23.4 | 98.6 | 338.3 | 5.62 |

*Based on the amount of carboxylic acid used in the coupling reaction
**HPLC-MS Method B Each of the following compounds was synthesized as described above starting from appropriate carboxylic acid.

| Compound # | Structure | MH+ (m/z) | Ret. Time (min) | HPLC-MS Method |
|---|---|---|---|---|
| 133-2 | 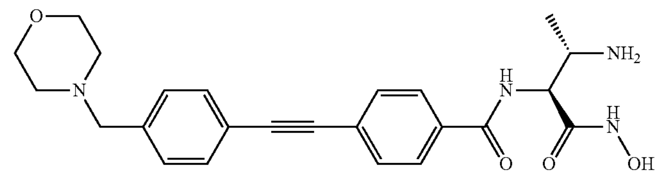 [SMILES: C[C@H](N)[C@H](NC(=O)c1ccc(C#Cc2ccc(CN3CCOCC3)cc2)cc1)C(=O)NO] | 437.1 | 2.88 | B |
| 133-3 | 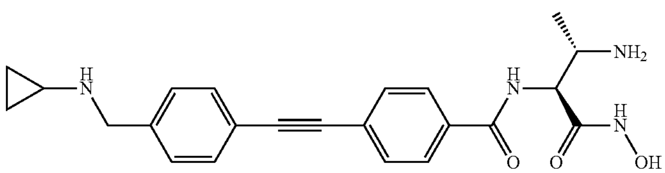 [SMILES: C[C@H](N)[C@H](NC(=O)c1ccc(C#Cc2ccc(CNC3CC3)cc2)cc1)C(=O)NO] | 407.1 | 3.24 | B |
| 133-4 | 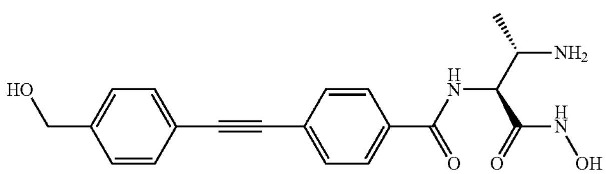 [SMILES: C[C@H](N)[C@H](NC(=O)c1ccc(C#Cc2ccc(CO)cc2)cc1)C(=O)NO] | 368.3 | 3.41 | B |

The following compound was synthesized as described for synthesis of compound 132-1 in Example 132 using H-(Allo)-Me-DAP-(N'-Fmoc)-OMe×HCl and Fmoc deprotection (20% piperidine in EtOAc).

| Compound # | Structure | MH+ (m/z) | Ret. Time (min) | HPLC-MS Method |
|---|---|---|---|---|
| 133-5 | 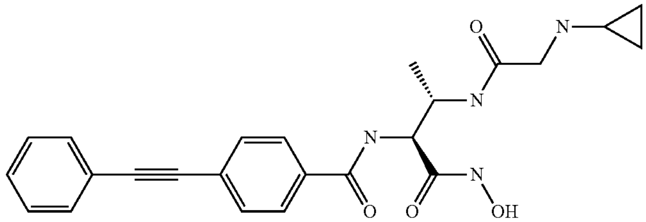 [SMILES: C[C@H](NC(=O)CNC1CC1)[C@H](NC(=O)c1ccc(C#Cc2ccccc2)cc1)C(=O)NO] | 453.1 | 5.89 | B |

Each of the following compounds was synthesized as described above starting from appropriate carboxylic acid.

| Compound # | Structure | MH+ (m/z) | Ret. Time (min) | HPLC-MS Method |
|---|---|---|---|---|
| 133-6 | 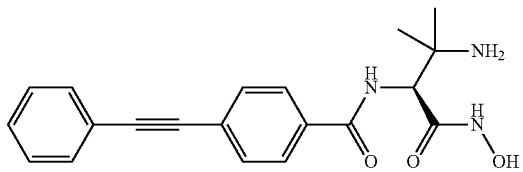 [SMILES: CC(C)(N)[C@H](NC(=O)c1ccc(C#Cc2ccccc2)cc1)C(=O)NO] | 352.3 | 5.68 | B |
| 133-7 | 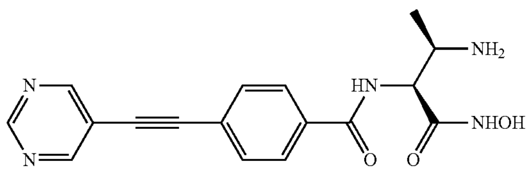 | 339 | | |
| 133-8 | 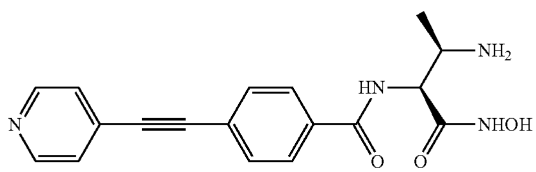 | 338 | | |
| 133-9 | 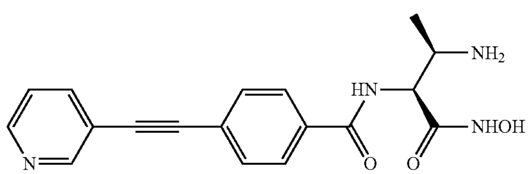 | 338 | | |
| 133-10 | 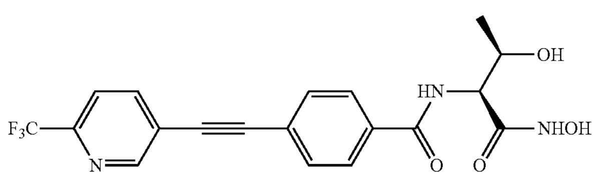 | 408.1 | | |
| 133-11 | 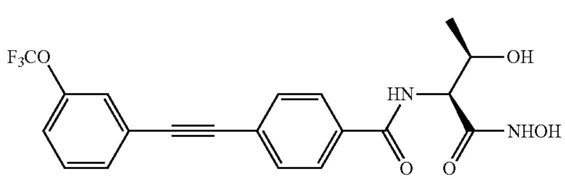 | 423.1 | | |
| 133-12 | 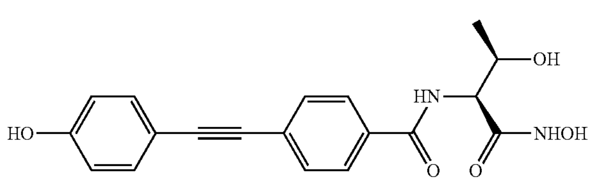 | 355.1 | | |
| 133-13 | 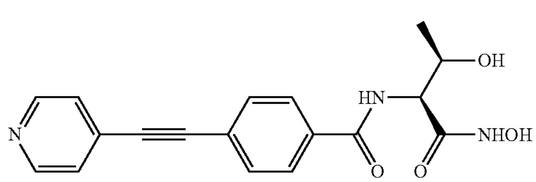 | 340.1 | | |

-continued
| Com-pound # | Structure | MH+ (m/z) | Ret. Time (min) | HPLC-MS Method |
|---|---|---|---|---|
| 133-14 | 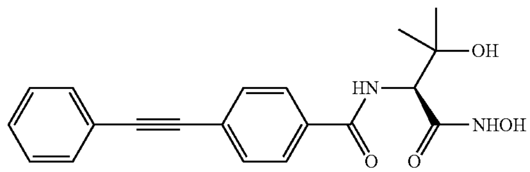 | 353.1 | | |
| 133-15 | 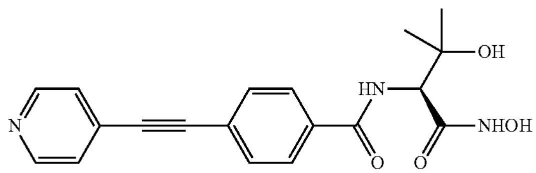 | 354.1 | | |
Example 134
N—((S)-2-Amino-1-hydroxycarbamoyl-2-methyl-propyl)-4-(2-phenyl-cyclopropylethynyl)-benzamide (134-1)
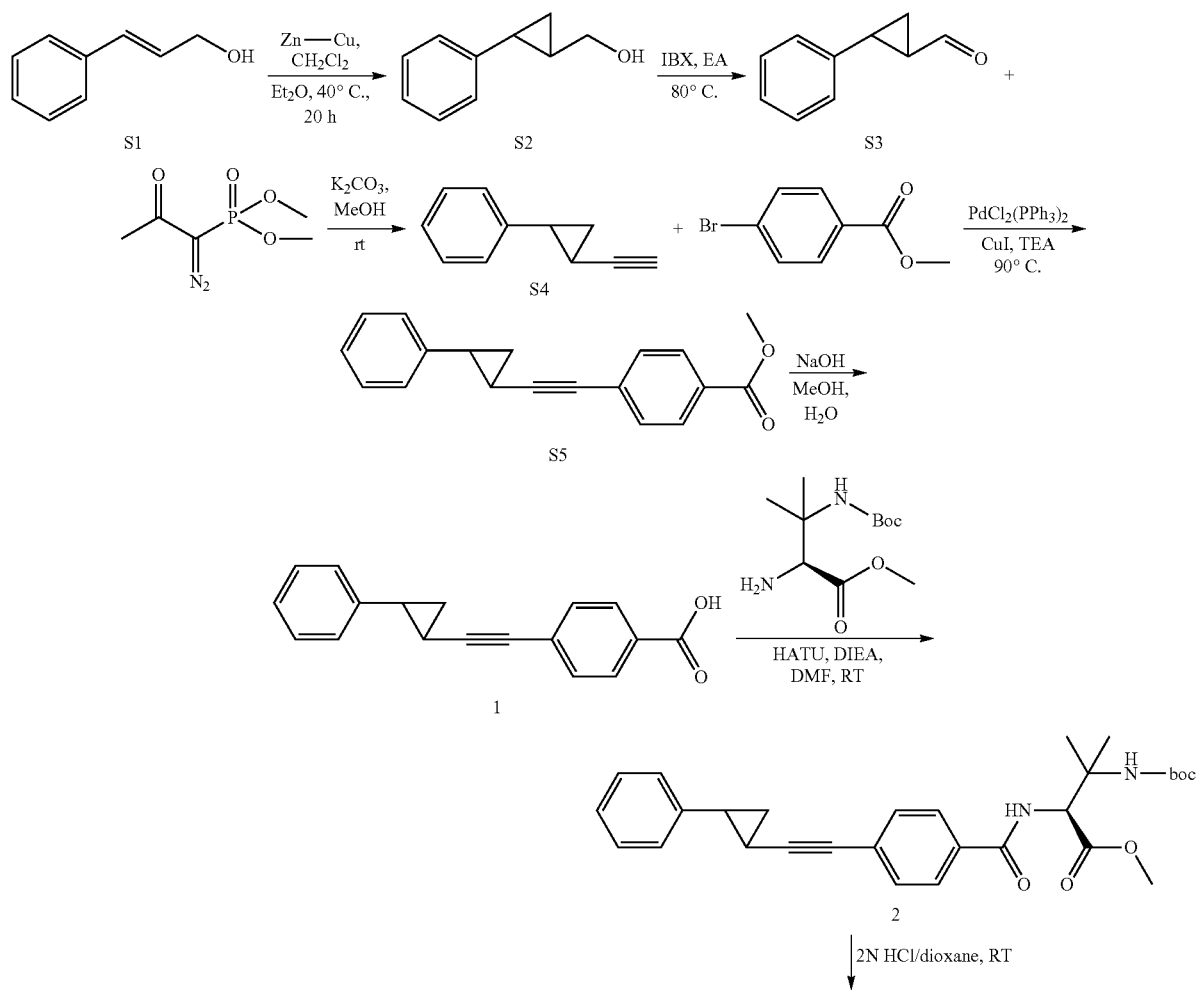

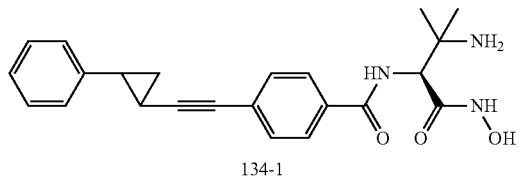

134-1

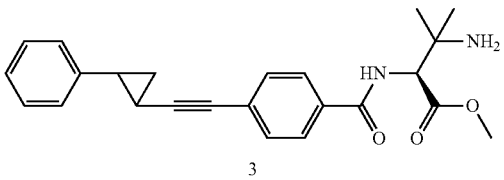

3

50% NH₂OH(aq)/ iPrOH (1:1) RT, overnight

(2-phenylcyclopropyl)methanol (S2)

3.5 g Me₃SiCl (32 mmol) was added dropwise to the mixture of 53 g Zn/Cu powder and 50 ml Et₂O at stirring under N₂. The mixture was stirred for 10 min and the solution of 1.6 ml CH₂I₂ and 10 ml Et₂O was added. The mixture was warmed to reflux and the solution of 26.7 ml CH₂I₂ (320 mmol), 21.5 g ACHL025-1 (160 mmol) and 160 ml Et₂O was added dropwise at refluxing. After the addition, the solution of 13.6 ml CH₂I₂ (160 mmol) and 30 ml Et₂O was added. The reaction mixture was stirred for 15 h. After the reaction, 300 ml Sat. NH₄Cl was added and the mixture was filtered. The organic layer was washed with Sat. NH₄Cl, brine, dried by MgSO₄, concentrated. The residue was purified by column chromatography to give 9.7 g ACHL025-2 (41% yield). 1H-NMR (400 MHz, CDCl₃): δ ppm: 0.91-0.99 (m, 2H), 1.43 (m, 1H), 1.81 (m, 1H), 3.52-3.62 (m, 2H), 4.78 (s, 1H), 7.07-7.28 (m, 5H).

2-phenylcyclopropanecarbaldehyde (S3)

18.7 g IBX (66.9 mmol, 3.0 eq.) was added to the solution of 3.3 g ACHL025-2 (22.3 mmol) in 60 ml EA. The mixture was warmed to 80° C. overnight. TLC showed the material was consumed completely. The reaction mixture was filtered, and the filtrate was concentrated to give 3.5 g crude ACHL025-3. ¹H-NMR (400 MHz, DMSO): δ ppm, 1.53-1.56 (m, 1H), 1.66-1.71 (m, 1H), 2.08-2.10 (m, 1H), 2.63-2.68 (m, 1H), 7.16-7.29 (m, 5H), 9.07 (s, 1H).

(2-ethynylcyclopropyl)benzene (S4)

To a solution of diazophoaphonate (9.56 g, 50 mmol) and ACHL015-3 (8 g, 54.8 mmol, 1.1 eq) in MeOH (200 ml) was added K₂CO₃ (13.8 g, 100 mmol). The mixture was stirred overnight at rt. The mixture was filtered and the filtrate was concentrated to give crude. The crude was purified by column chromatography on silica gel (PE/EA=50/0-50/1) to give 4.1 g ACHL025-4 (57% yield). ¹H-NMR (400 MHz, DMSO): δ ppm, 1.23 (m, 2H), 1.59 (m, 1H), 2.21 (m, 1H), 2.79 (s, 1H), 7.10-7.26 (m, 5H)

Methyl 4-((2-phenylcyclopropyl)ethynyl)benzoate (S5)

To a solution of 4.1 g ACHL025-4 (28.9 mmol) and 6.2 g methyl 4-bromobenzoate (28.9 mmol) in 100 ml TEA was added 2 g PdC₂l(PPh₃) (2.89 mmol) and 0.55 g CuI (2.89 mmol) under N₂. The mixture was warmed to 90° C. and stirred overnighte. The reaction mixture was filtered and concentrated to crude product. The crude product was purified by column chromatography (PE/EA=100/0-100-1) to give 3.4 g (S5) (42% yield). ¹H-NMR (400 MHz, CDCl₃): δ ppm, 1.40-1.47 (m, 2H), 1.72-1.74 (m, 1H), 2.39-2.42 (m, 1H), 3.92 (s, 3H), 7.13-7.32 (m, 5H), 7.45-7.47 (d, J=8 Hz, 2H), 7.96-7.98 (d, J=8 Hz, 2H).

Methyl 4-((2-phenylcyclopropyl)ethynyl)benzoate (1)

To a solution of 4.1 g ACHL025-5 (14.8 mmol) in 30 ml MeOH and 20 ml water was added 6 g NaOH. The mixture was stirred at rt for 4 h. 200 ml water was added and the mixture was adjusted to PH=4 with 1N HCl. The mixture was extracted with EA and the organic layer was washed by brine, dried by MgSO₄, concentrated to give 3.3 g ACHL025 (85% yield). ¹H-NMR (400 MHz, DMSO): δ ppm, 1.43 (m, 2H), 1.89 (m, 1H), 2.43 (m, 1H), 7.17-7.31 (m, 5H), 7.50-7.52 (d, J=8 Hz, 2H), 7.90-7.92 (d, J=8 Hz, 2H), 13.10 (s, 1H)

Synthesis of (S)-3-tert-butoxycarbonylamino-3-methyl-2-[4-(2-phenyl-cyclopropylethynyl)-benzoylamino]-butyric acid methyl ester (2)

| Reagent | MW | Eq. | mg/mL | mmol |
|---|---|---|---|---|
| Compound 1 | 262.3 | 1.0 | 150 mg | 0.57 |
| H-(S)-diMe-DAP-(N'-Boc)-OMe | 246.3 | 1.15 | 162 mg | 0.66 |
| HATU | 380.23 | 1.2 | 259 mg | 0.68 |
| DIEA | 129.24 | 3 | 298 µl | 1.71 |
| DMF | | | 3 mL | |

Compound 2 was prepared by coupling with H—(S)-diMe-DAP-(N'-Boc)-OMe according to General Method for HATU coupling in quantitative yield. LC-MS [M+H] 492.0 (C29H34N2O5+H, requires 491.60). Compound was used in next synthetic step without additional purification.

Synthesis of (S)-3-amino-3-methyl-2-[4-(2-phenyl-cyclopropylethynyl)-benzoylamino]-butyric acid methyl ester (3)

| Reagent | MW | Eq. | mg/mL | mmol |
|---|---|---|---|---|
| Compound 2 | 490.6 | 1.0 | 280 mg | 0.57 |
| 4N HCl/dioxane | | 14.0 | 2 mL | 8.0 |
| dioxane | | | 2 mL | |

Compound 3 was prepared using the General Method for Boc deprotection in quantitative yield. LC-MS [M+H] 392.0 (C24H26N2O3+H, requires 391.49). Compound was used in next synthetic step without additional purification.

Synthesis of N—((S)-2-amino-1-hydroxycarbamoyl-2-methyl-propyl)-4-(2-phenyl-cyclopropylethynyl)-benzamide (134-1)

| Reagent | MW | Eq. | mg/mL | mmol |
|---|---|---|---|---|
| Compound 3 × HCl | 426.94 | 1.0 | 243 mg | 0.57 |
| 50% aq NH$_2$OH | 33 | 57.5 | 2 mL | 32.8 |
| i-PrOH | | | 2 mL | |

Compound 134-1 was prepared by following General Method for hydroxamate formation, aqueous. Crude compound was purified by HPLC. [Phenomenex Gemini C-18 column, 110 Å (30×100 mm); flow rate=20 mL/min; mobile phase A: 100% water, 0.1% TFA; mobile phase B: 100% ACN, 0.1% TFA; gradient elution from 15% B to 60% B over 60 min., detection 254 nm]. Fractions containing the desired product were combined and lyophilized to provide the trifluoroacetate salt of target compound 134-1 (63.2 mg) as a white solid. LC-MS: [M+H] 392.3.

| Compound | Scale (mmol)* | Yield (mg) | Yield (%)* | Purity (%) | [M + H] | Retention time (min)* |
|---|---|---|---|---|---|---|
| 134-1 | 0.57 | 63.2 | 22.0 | 98.8 | 392.3 | 6.45 |

*Based on the amount of carboxylic acid used in the coupling reaction
**HPLC-MS Method B The following compound was synthesized as described above using H—(S)-Me-DAP-(N'-Boc)-OMe.

| Compound # | Structure | MH$^+$ (m/z) | Ret. Time (min) | HPLC-MS Method |
|---|---|---|---|---|
| 134-2 | 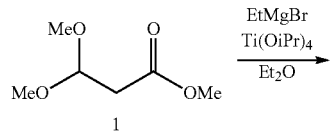 | 378.3 | 6.24 | B |

Example 135

Synthesis of N-(1-(1-aminocyclopropyl)-2-(hydroxyamino)-2-oxoethyl)-4-((4-(morpholinomethyl)phenyl)ethynyl)benzamide (135-1)

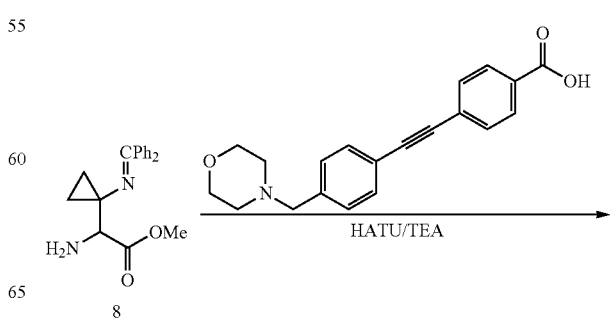

-continued

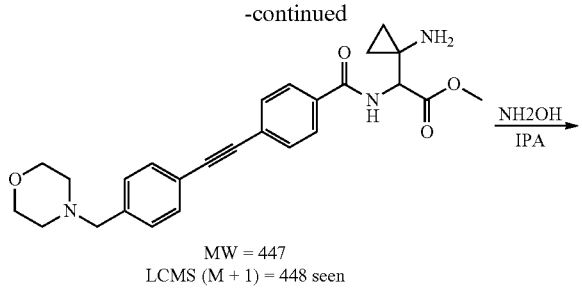

MW = 447
LCMS (M + 1) = 448 seen

NH2OH
IPA

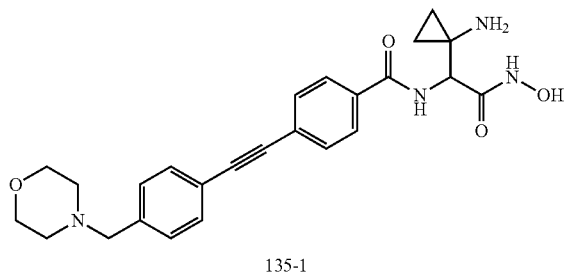 [SMILES: NC1(C(NC(=O)c2ccc(C#Cc3ccc(CN4CCOCC4)cc3)cc2)C(=O)NO)CC1]

135-1

Synthesis of 1-(2,2-dimethoxyethyl)cyclopropanol (2)

A solution of methyl 3,3-dimethoxypropanoate (28.2 g, 190 mmol) in a three-neck flask equipped with a overhead stirrer was cooled to 0° C. under $N_2$. The Ti(OiPr)$_4$ (11.3 mL, 38.1 mmol) was then slowly added and the solution was allowed to stir for 10 min at 0° C. To this cooled solution with vigorous stirring was then added the EtMgBr solution (158 mL, 475 mmol) via syringe pump at ~3 mL/min. After the addition was complete, the solution was allowed to slowly warm to ambient temperature and stirred for an additional 18 h. The solution was then cooled to 0° C. and deionized water (45 mL) was slowly added with vigorous stirring. After stirring for 20 min at 0° C. the mixture vacuum filtered through a pad of anhydrous MgSO$_4$. The clear, colorless solution was the concentrated in vacuo and purified by flash chromatography (0-50% EtOAc/Hex) to provide the desired product (2) as a clear, colorless oil (8.60 g, 31%). $^1$H NMR (DMSO) δ 5.04 (s, 1H), 4.62 (t, J=5.3, 1H), 3.22 (s, 6H), 1.69 (d, J=5.3, 2H) 0.50 (dd, J=4.9, 6.9, 2H), 0.37 (dd, J=4.2, 6.2, 2H).

Synthesis of 1-(2,2-dimethoxyethyl)cyclopropyl mesylate (3)

To a solution of compound 2 (8.60 g, 58.9 mmol) in CH$_2$Cl$_2$ was added TEA (12.6 mL, 124 mmol) sequentially. The solution was then cooled to 0° C. and methane sulfonyl chloride (8.09 g, 70.65 mmol) was added drop wise. After the addition was complete, the solution was stirred at 0° C. for 10 min then allowed to warm to ambient temperature and stirred for 4 h. The solution was then washed with aqueous NaHSO$_4$ (1.0 N, 2×100 mL), aqueous NaHCO$_3$ (sat., 2×100 mL), dried (MgSO$_4$), filtered and concentrated in vacuo. Isolated the desired product, (3) as a clear, colorless oil (13.62 g).

Synthesis of 2-(1-(methylsulfonyloxy)cyclopropyl)acetic acid (4)

Compound 3 (13.62 g, 60.8 mmol) was dissolved in THF (150 mL) and water (50 mL) and cooled to 0° C. To this cooled solution was added Oxone® (54.07 g, 88 mmol) in portions. After complete addition the slurry was allowed to stir at 0° C. for 10 min the warmed to ambient temperature. After 8 h at ambient temperature the slurry was diluted with deionized H2O (100 mL) and extracted with EtOAc (3×150 mL). The combined organics were dried (MgSO$_4$), filtered and concentrated in vacuo. The product (4) was isolated as a thick, colorless oil (8.4 g).

Synthesis of methyl 2-chloro-2-cyclopropylideneacetate (5)

Compound 4 (4 g, 20.6 mmol) was dissolved in anhydrous DCE (100 ml) under $N_2$ and cooled to 0° C. Thionyl chloride (1.8 ml, 30 mmol) was then added slowly and the solution was refluxed for 30 min. At ambient temperature, were added NCS (3.32 g, 25 mmol) and 4 drops of concentrated HCl and the solution was heated under reflux for 8 h. MeOH (50 ml) was added at room temperature and the solution was stirred at rt for 3 h, Followed by TEA (10 ml. 100 mmol) and stirring was continued for additional 1 h The solvent were removed under reduced pressure, water (100 ml) was added and product was extracted with ethyl acetate, dried (Na2SO4), and purified by flash chromatography (0-15% EA in Hex) to give 1.2 g of methyl 2-chloro-2-cyclopropylideneacetate 5. H$_1$NMR (DMSO-d6) 1.5 (t, 2H), 1.73 (t, 2H) 3.73 (s, 3H)

Synthesis of methyl 2-chloro-2-(1-(diphenylmethyleneamino)cyclopropyl)acetate (6)

To diphenyl imine (2.05 g, 11.37 mmol) in methanol (35 ml), the chloride product 5 (1.39 g, 9.48 mmol) was added in dry methanol (14 ml) and stirred at room temp for 24 h. The reaction mixture was concentrated to give 3.39 g of 6: 1H NMR (CDCl$_3$) 0.70-0.9 (m, 3H), 1.20-1.24 (m, 1H) 3.62 (s, 3H), 4.29, (s, 1H), 7.23-7.58 (m, 10H).

Synthesis of methyl 2-azido-2-(1-(diphenylmethyleneamino)cyclopropyl)acetate (7)

The chloride product 6 (3.24 g, 99 mmol) was redessolved in dry DMF (25 ml), NaN3 (1.3 g, 200 mmol) was added and heated at 85° C. for 18 h. The reaction mixture was diluted with ethyl acetate (100 ml) and water 5 ml was added. The organic layer was separated, dried and concentrated to give 2.8 g of 7. LCMS (M+1) 335, Chemical Formula: C19H18N4O2 MW: 334.37.

Synthesis of methyl 2-amino-2-(1-(diphenylmethyleneamino)cyclopropyl)acetate (8)

The compound 7 (480 mg, 1.43 mmol), PPh3 (278 mg, 1.06 mmol) in THF (5 ml) and water (1 ml) stirred for 18 h. The reaction mixture was diluted with ethyl acetate (100 ml) and water 5 ml was added. The organic layer was separated, dried and concentrated to give crude 8 which were used for the next step without any further purification.

Synthesis of methyl 2-(4-(cyclopropylbuta-1,3-diynyl)benzamido)-2-(1-hydroxycyclopropyl)acetate (9)

A solution of compound 4-((4-(morpholinomethyl)phenyl)ethynyl)benzoic acid (100 mg, 0.31 mmol), HATU (120 mg, 0.31 mmol) and DIEA (0.5 ml, excess) in CH3CN (15 mL) was maintained at ambient temperature for 10 min followed by the addition of compound 8 (408 mg, 1.31 mmol). Reaction mixture was stirred at ambient temperature 20 min and concentrated followed by the dilution with water (10 ml). Solution was extracted with ethyl acetate (20 ml×2) and brine (20 ml). Organic layer was dried over MgSO₄ and evaporated to give crude product 9, 160 mgs of methyl 2-(1-aminocyclopropyl)-2-(4-(4-(morpholinomethyl)phenyl)ethynyl)benzamido)acetate. LC-Ms (M+1) 448; Chemical Formula: C26H29N3O4; MW: 447.53.

Synthesis of N-(1-(1-aminocyclopropyl)-2-(hydroxyamino)-2-oxoethyl)-4-((4-(morpholinomethyl)phenyl)ethynyl)benzamide (135-1)

Aq. Hydroxylamine (2 ml, 50% aq.) was added to a stirred solution of ester 9, (0.16 g, 0.35 mmol) in isopropanol (15 ml), stirred for 18 h. Excess solvent was removed and the product was purified on a reverse phase HPLC to give compound (135-1) (6 mg). LC-MS (M+1) 449: Chemical Formula: C25H28N4O4; MW: 448.51.

Example 136

N-((2S,3R)-3-amino-1-(hydroxyamino)-1-oxobutan-2-yl)-4-(4-(morpholinomethyl)phenethyl)benzamide (137-1)

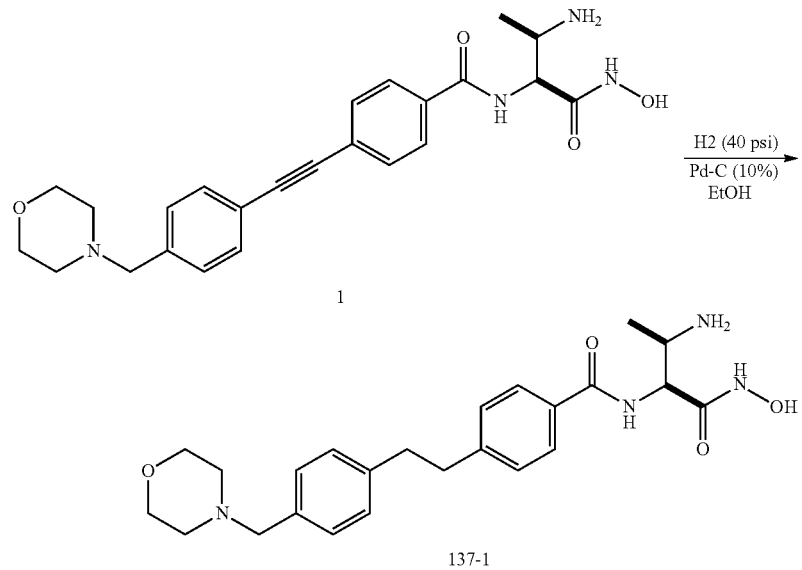

Compound 1 (200 mg, 0.45 mmol) was dissolved in methanol (20 ml) followed by the addition of Pd/C (10% wt, 46 mg). Reaction mixture was subjected to hydrogenation (Parr apparatus, 46 psi) at room temperature for 15 min. Catalyst was filtered and washed with methanol. Filtrate was evaporated in vacuum to provide target compound 136 (184 mg) as colorless oil. LC-MS [M+H] 441.0 (C10H20N2O4+H, requires 440.24).

Example 137

The following compounds were made according to the above synthetic procedures.

| Compound # | Structure | MH⁺ (m/z) |
|---|---|---|
| 137-1 | 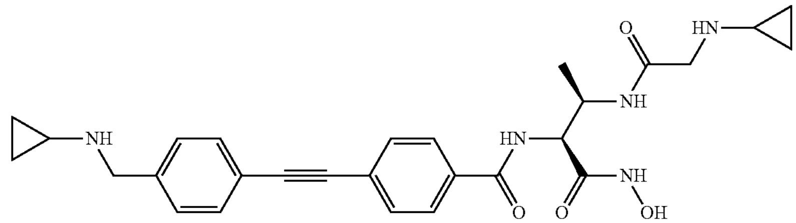 [SMILES: C[C@@H](NC(=O)CNC1CC1)[C@H](NC(=O)c1ccc(C#Cc2ccc(CNC3CC3)cc2)cc1)C(=O)NO] | 383.4 |

| Compound # | Structure | MH+ (m/z) |
|---|---|---|
| 137-2 | 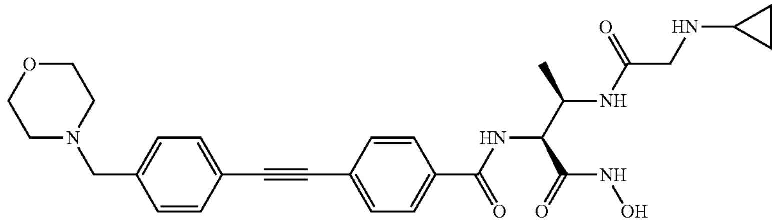 [SMILES: C[C@@H](NC(=O)CNC1CC1)[C@H](NC(=O)c1ccc(C#Cc2ccc(CN3CCOCC3)cc2)cc1)C(=O)NO] | 534.6 |
| 137-3 | 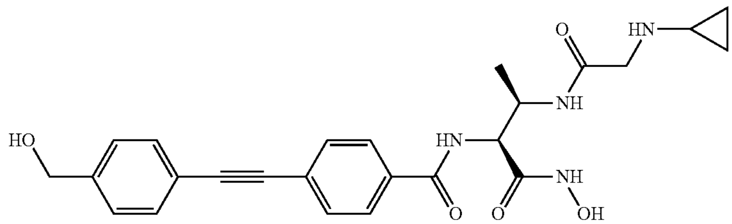 [SMILES: C[C@@H](NC(=O)CNC1CC1)[C@H](NC(=O)c1ccc(C#Cc2ccc(CO)cc2)cc1)C(=O)NO] | 465.5 |
| 137-4 | 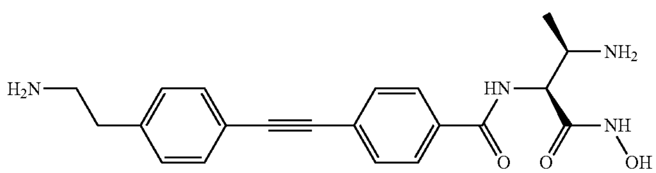 [SMILES: C[C@@H](N)[C@H](NC(=O)c1ccc(C#Cc2ccc(CCN)cc2)cc1)C(=O)NO] | 381.4 |
| 137-5 | 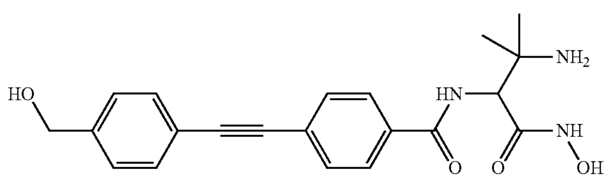 [SMILES: CC(C)(N)C(NC(=O)c1ccc(C#Cc2ccc(CO)cc2)cc1)C(=O)NO] | 382.4 |
| 137-6 | 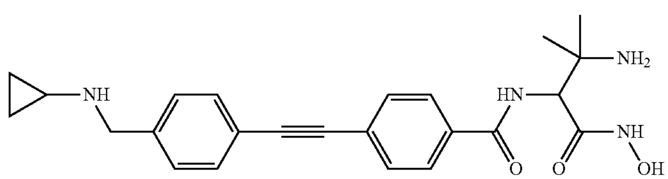 [SMILES: CC(C)(N)C(NC(=O)c1ccc(C#Cc2ccc(CNC3CC3)cc2)cc1)C(=O)NO] | 421.5 |
| 137-7 | 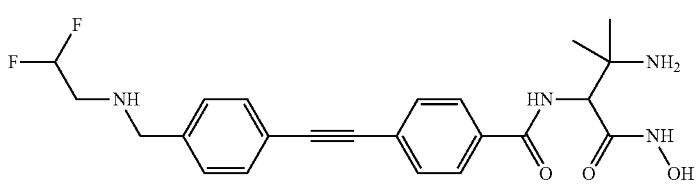 [SMILES: CC(C)(N)C(NC(=O)c1ccc(C#Cc2ccc(CNCC(F)F)cc2)cc1)C(=O)NO] | 445.5 |
| 137-8 | 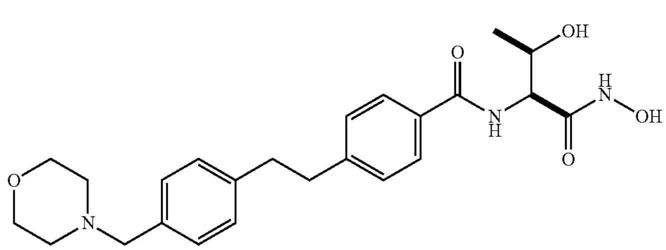 [SMILES: C[C@@H](O)[C@H](NC(=O)c1ccc(CCc2ccc(CN3CCOCC3)cc2)cc1)C(=O)NO] | 442.5 |

-continued

| Compound # | Structure | MH+ (m/z) |
|---|---|---|
| 137-9 | 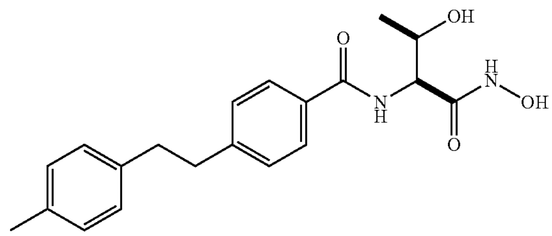 [SMILES: Cc1ccc(CCc2ccc(C(=O)N[C@H](C(=O)NO)[C@@H](C)O)cc2)cc1] | 358.4 |
| 137-10 | 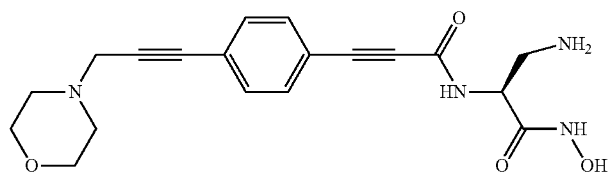 [SMILES: NC[C@H](NC(=O)C#Cc1ccc(C#CCN2CCOCC2)cc1)C(=O)NO] | 370.4 |
| 137-11 | 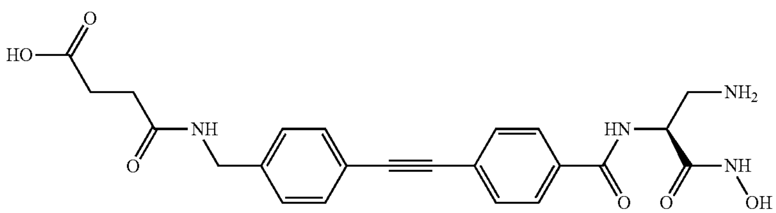 [SMILES: NC[C@H](NC(=O)c1ccc(C#Cc2ccc(CNC(=O)CCC(=O)O)cc2)cc1)C(=O)NO] | 452.4 |
| 137-12 | 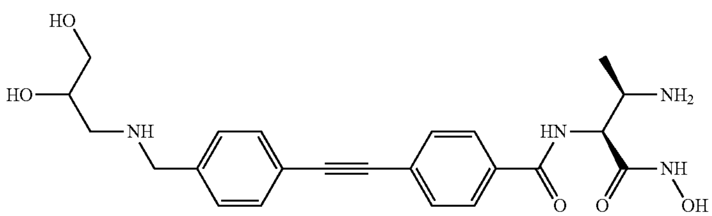 [SMILES: C[C@@H](N)[C@H](NC(=O)c1ccc(C#Cc2ccc(CNCC(O)CO)cc2)cc1)C(=O)NO] | 365.4 |
| 137-13 | 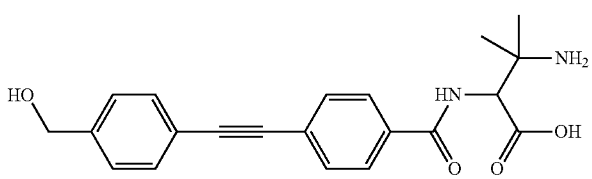 [SMILES: CC(C)(N)C(NC(=O)c1ccc(C#Cc2ccc(CO)cc2)cc1)C(=O)O] | 441.5 |
| 137-14 | 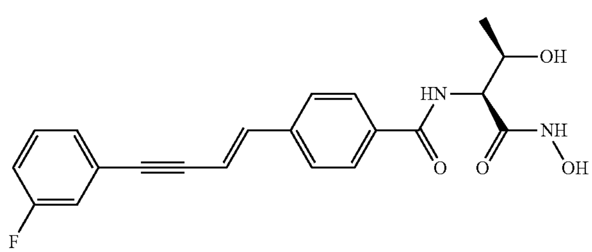 [SMILES: C[C@@H](O)[C@H](NC(=O)c1ccc(/C=C/C#Cc2cccc(F)c2)cc1)C(=O)NO] | 383.4 |
| 137-15 | 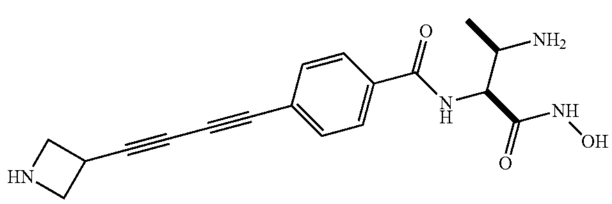 [SMILES: C[C@@H](N)[C@H](NC(=O)c1ccc(C#CC#CC2CNC2)cc1)C(=O)NO] | 341.4 |

-continued
| Compound # | Structure | MH+ (m/z) |
|---|---|---|
| 137-16 | 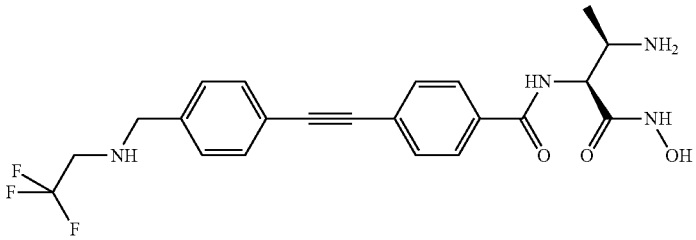 [SMILES: C[C@@H](N)[C@H](NC(=O)c1ccc(C#Cc2ccc(CNCC(F)(F)F)cc2)cc1)C(=O)NO] | 449.4 |
| 137-17 | 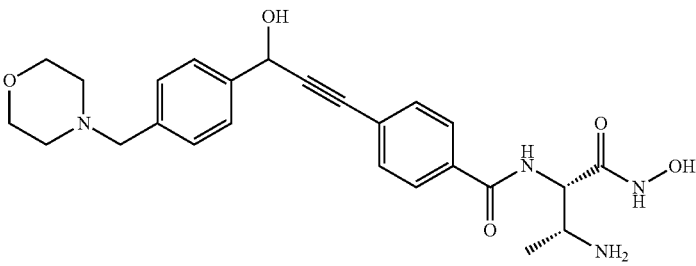 [SMILES: C[C@@H](N)[C@H](NC(=O)c1ccc(C#CC(O)c2ccc(CN3CCOCC3)cc2)cc1)C(=O)NO] | 467.5 |
| 137-18 | 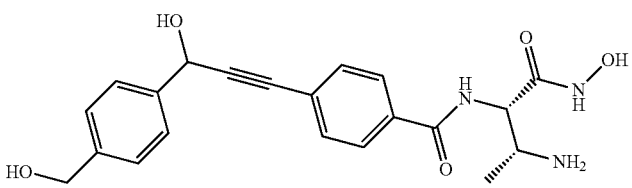 [SMILES: C[C@@H](N)[C@H](NC(=O)c1ccc(C#CC(O)c2ccc(CO)cc2)cc1)C(=O)NO] | 398.4 |
| 137-19 | 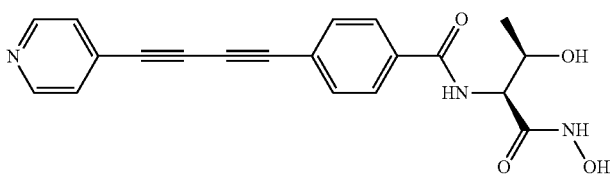 [SMILES: C[C@@H](O)[C@H](NC(=O)c1ccc(C#CC#Cc2ccncc2)cc1)C(=O)NO] | 364.4 |
| 137-20 | 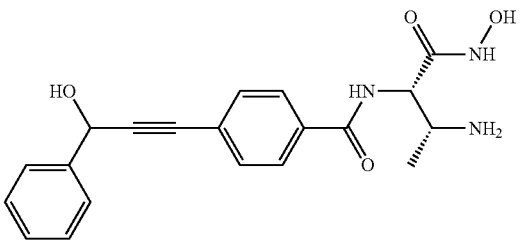 [SMILES: C[C@@H](N)[C@H](NC(=O)c1ccc(C#CC(O)c2ccccc2)cc1)C(=O)NO] | 368.4 |
| 137-21 | 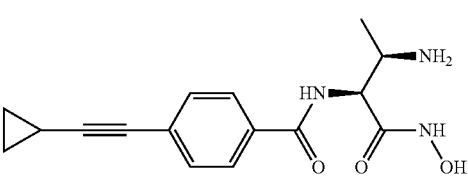 [SMILES: C[C@@H](N)[C@H](NC(=O)c1ccc(C#CC2CC2)cc1)C(=O)NO] | 302.3 |
| 137-22 | 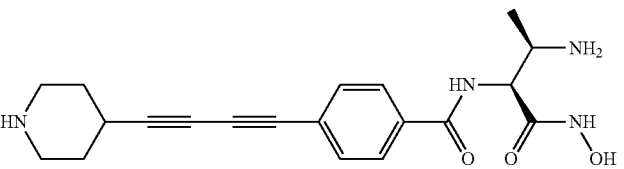 [SMILES: C[C@@H](N)[C@H](NC(=O)c1ccc(C#CC#CC2CCNCC2)cc1)C(=O)NO] | 369.4 |

-continued
| Compound # | Structure | MH+ (m/z) |
|---|---|---|
| 137-23 | 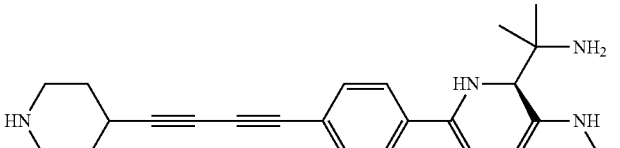 | 383.5 |
| 137-24 | 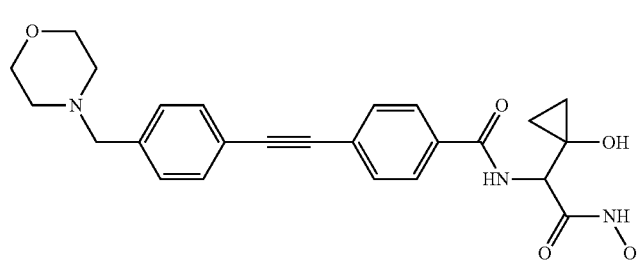 | 450.5 |
| 137-25 | 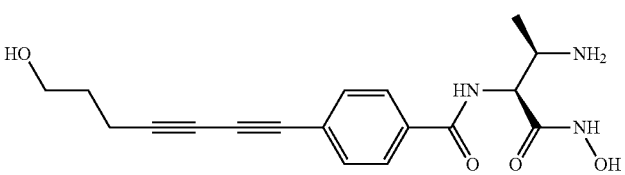 [SMILES: C[C@@H](N)[C@H](NC(=O)c1ccc(C#CC#CCCCO)cc1)C(=O)NO] | 344.4 |
| 137-26 | 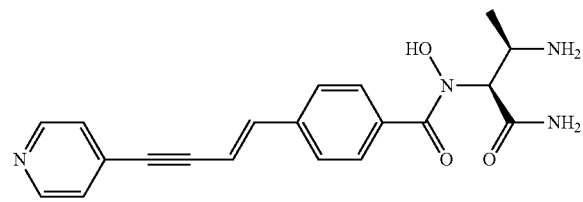 [SMILES: C[C@@H](N)[C@@H](C(N)=O)N(O)C(=O)c1ccc(/C=C/C#Cc2ccncc2)cc1] | 364.4 |
| 137-27 | 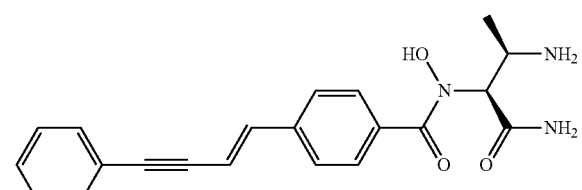 | 364.4 |
Example 138
The following compounds may be made according to the above synthetic procedures.
| Compound # | Structure | MH+ (m/z) |
|---|---|---|
| 138-1 | 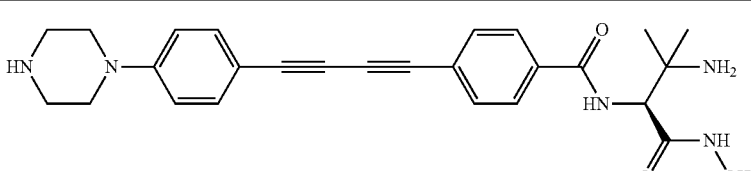 | 460.5 |

-continued

| Compound # | Structure | MH+ (m/z) |
|---|---|---|
| 138-2 | 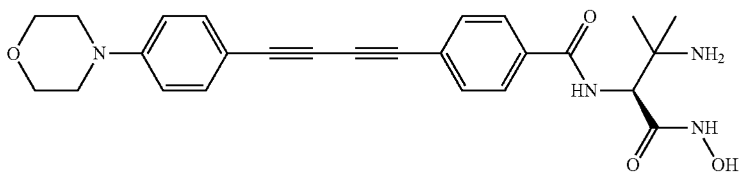 [SMILES: CC(C)(N)[C@H](NC(=O)c1ccc(C#CC#Cc2ccc(N3CCOCC3)cc2)cc1)C(=O)NO] | 461.6 |
| 138-3 | 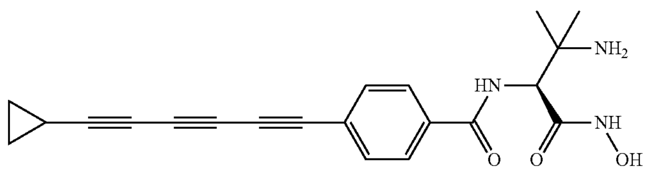 [SMILES: CC(C)(N)[C@H](NC(=O)c1ccc(C#CC#CC#CC2CC2)cc1)C(=O)NO] | 363.4 |
| 138-4 | 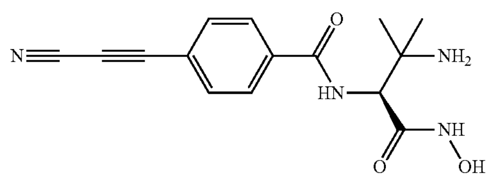 [SMILES: CC(C)(N)[C@H](NC(=O)c1ccc(C#CC#N)cc1)C(=O)NO] | 300.3 |
| 138-5 | 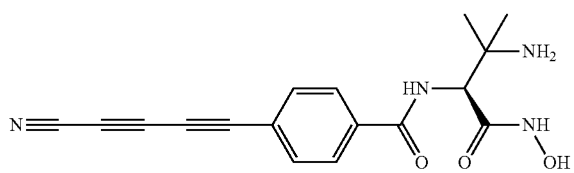 [SMILES: CC(C)(N)[C@H](NC(=O)c1ccc(C#CC#CC#N)cc1)C(=O)NO] | 324.3 |
| 138-6 | 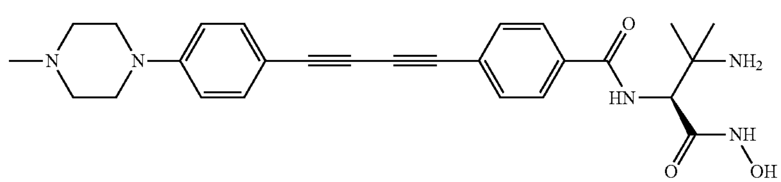 [SMILES: CN1CCN(c2ccc(C#CC#Cc3ccc(C(=O)N[C@H](C(=O)NO)C(C)(C)N)cc3)cc2)CC1] | 473.6 |
| 138-7 | 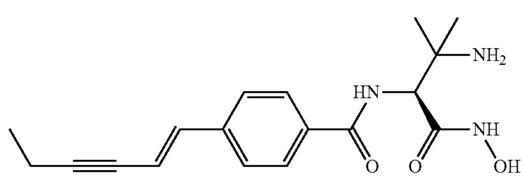 [SMILES: CCC#C/C=C/c1ccc(C(=O)N[C@H](C(=O)NO)C(C)(C)N)cc1] | 329.4 |
| 138-8 | 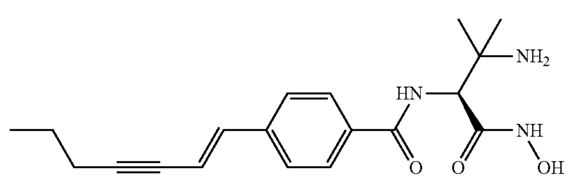 [SMILES: CCCC#C/C=C/c1ccc(C(=O)N[C@H](C(=O)NO)C(C)(C)N)cc1] | 343.3 |
| 138-9 | 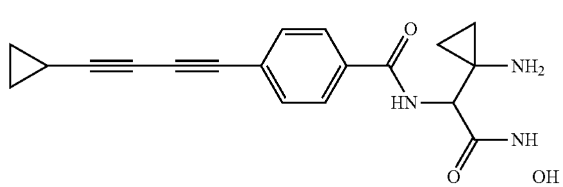 | 338.4 |

| Compound # | Structure | MH+ (m/z) |
|---|---|---|
| 138-10 | 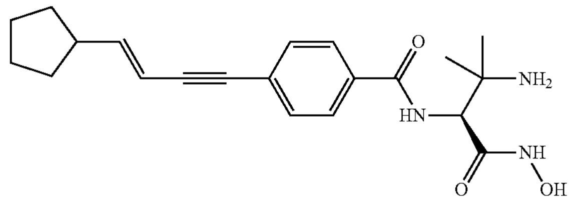 [SMILES: CC(C)(N)[C@H](NC(=O)c1ccc(C#C/C=C/C2CCCC2)cc1)C(=O)NO] | 344.4 |
| 138-11 | 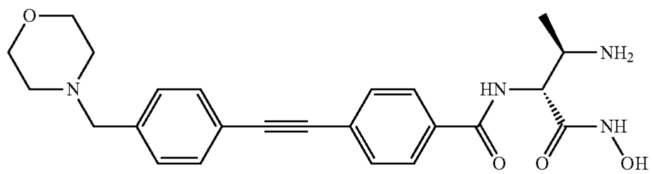 [SMILES: C[C@@H](N)[C@@H](NC(=O)c1ccc(C#Cc2ccc(CN3CCOCC3)cc2)cc1)C(=O)NO] | 437.5 |
| 138-12 | 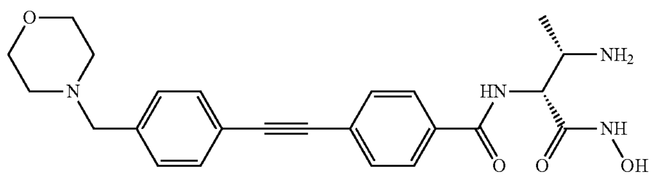 [SMILES: C[C@H](N)[C@@H](NC(=O)c1ccc(C#Cc2ccc(CN3CCOCC3)cc2)cc1)C(=O)NO] | 437.5 |

LC-MS Analytical Methods

All LC-MS spectra were acquired using HPLC (Column: Phenomenex, Onyx Monolithic C18, 4.6×50 mm. Flow rate: 1.5 mL/min. Mobile phase A: 0.1% trifluoroacetic acid in water. Mobile phase B: 0.1% trifluoroacetic acid in acetonitrile.) with an ion spray MS detector (PE SCIEX API 365 LC/MS/MS), and UV/VIS (254 nm) detection (Shimadzu SPD-10A) under the following gradients:

Method A (12 minute method): 5% B to 100% B over 9.6 min.

Method B (Analytical 5-60): 5% B to 60% B over 9.1 min.

Method C (6 minute method): 5% B to 100% B over 4.6 min.

Method D (Analytical 5-35): 5% B to 35% B over 9.1 min.

NMR Data

All NMR spectra were taken on a Bruker 250 NMR (250 MHz) or Varian 400 (400 MHz), using DMSO-$d_6$ or CDCl$_3$

Biological Protocols and Data

Bacterial Screens and Cultures

Bacterial isolates were cultivated from −70° C. frozen stocks by overnight passages at 35° C. in ambient air on Mueller-Hinton agar (Beckton Dickinson, Franklin Lakes, N.J.). Clinical isolates tested were obtained from various geographically diverse hospitals in the US and abroad (Focus Diagnostics, Herndon, Va. and JMI, North Liberty, Iowa). Quality control strains were from the American Type Culture Collection (ATCC; Rockville, Md.). Additional primary panel strains were generated using standard molecular biology techniques. Strain AECO063 does not express the principal multidrug efflux pump for *E. coli* and is hypersusceptible to many antibacterials. Target enzyme replacement strains (AECO061—*E. coli*, AECO062—*P. aeruginosa* and AECO065—*A. baumannii*) possess a non-functional genomic copy of the *E. coli* lpxC gene complemented by a plasmid-borne sequence from the species indicated under the control of the native *E. coli* lpxC promoter (*E. coli* strain background MG1655).

Susceptibility Testing

Minimum Inhibitory Concentrations (MICs) were determined by the broth microdilution method in accordance with the Clinical and Laboratory Standards Institute (CLSI) guidelines. In brief, organism suspensions were adjusted to a 0.5 McFarland standard to yield a final inoculum between $3\times10^5$ and $7\times10^5$ colony-forming units (CFU)/mL. Drug dilutions and inocula were made in sterile, cation adjusted Mueller-Hinton Broth (Beckton Dickinson). An inoculum volume of 100 µL was added to wells containing 100 µL of broth with 2-fold serial dilutions of drug. All inoculated microdilution trays were incubated in ambient air at 35° C. for 18-24 hours. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines. Typically, compounds of the present invention have MIC values of 0.03-64 mic/mL. To this end, data for certain representative compounds is shown in Table 1 below.

Efficacy in Mouse Model of Systemic *Pseudomonas aeruginosa* and *Eschericia Coli* Infection Male CD-1 mice weighing 22-26 g were infected intraperitoneally with 0.5 mL of a bacterial suspension of *P. aeruginosa* strain ATCC27853 or *E. coli* ATCC25922 in blood heart infusion broth (BHI, DIFCO, USA) plus 5% Mucin (Sigma, USA). The number of bacterial cells used was approximately 2 times the dose that would kill 90% of animals (LD$_{90}$, $6.5\times10^4$ CFU for *P. aeruginosa*, $4.5\times10^5$ CFU for *E. coli*). At one hour (1 hr) post infection, the test compound was injected intravenously in doses ranging from 0.3 mg/kg to 50 mg/kg, ten mice per dosing group. Survival of the mice was observed daily for 7 days, and the dose of compound resulting in survival of 50% of mice ($ED_{50}$) was calculated. Example 3/12a demonstrated an ED50<20 mg/kg in the *E. coli* septicemia model.

Efficacy in Neutropenic Thigh Model

Mice were rendered neutropenic prior to infection with 2 doses of cyclophosphamide, and then infected intramuscularly in the thigh with $10^5$-$10^6$ CFU of bacteria. See Gudmundsson S., Erlensdottir H., "Murine Thigh Infection Model" *Handbook of Animal Models of Infection*, M. A. Sande and O. Zak, Eds.; London: Academic Press, 1999, pp 137-144. Antibiotics or vehicle alone as a negative control were administered twice at 2 hrs and 14 hrs post-infection. At 24 hrs post-infection, thighs were harvested, homogenized, and plated to measure the number of CFUs surviving per thigh. Thighs from a subset of animals were also harvested 2 hrs post-infection to record the CFUs present just prior to the first antibiotic treatment (pre-treatment). The static dose, defined as the dose required to result in a CFU load at 24 hours that is identical to that measured at 0 hours post infection, was calculated by standard methods in Prizm from a dose response curve.

TABLE 1

| Compound # | AECO001 | AECO001 HSA AGP | AECO063 | APAE001 | APAE006 | APAE006 + PMBN | AABA1060 | ASAU001 |
|---|---|---|---|---|---|---|---|---|
| 62-6 | C | | | D | B | | | D |
| 62-7 | C | C | B | D | B | | C | D |
| 62-10 | B | | | D | A | | | D |
| 62-8 | C | | | D | C | | | D |
| 62-11 | B | | | D | A | | | D |
| 62-9 | C | | | D | B | | | D |
| 62-4 | B | | | D | B | | | D |
| 62-5 | B | | | D | C | | | D |
| 48-5 | D | D | D | D | D | | D | D |
| 47-5 | D | D | D | D | C | | D | D |
| 46-4 | C | C | B | C | A | | D | D |
| 41-5 | D | D | C | C | A | A | D | D |
| 43-7 | D | D | C | C | A | A | D | D |
| 42-7 | C | C | C | C | A | A | C | D |
| 60-5 | C | D | C | D | C | B | D | D |
| 115-2 | A | B | A | A | A | A | B | D |
| 115-3 | A | A | A | B | A | A | B | D |
| 66-5 | A | B | A | B | A | A | B | D |
| 67-9 | B | C | A | C | A | A | D | D |
| 67-7 | A | B | A | B | A | A | B | D |
| 67-8 | A | B | A | B | A | A | B | D |
| 65-6 | C | D | B | C | B | A | C | D |
| 64-7 | B | C | A | B | A | A | C | D |
| 59-8 | C | D | C | D | C | C | D | D |
| 67-5 | A | B | A | B | A | A | C | D |
| 68-6 | A | B | A | B | A | A | C | D |
| 66-6 | A | B | A | C | A | A | C | D |
| 30-12a | A | A | A | A | A | A | B | D |
| 30-12b | B | C | A | B | A | A | C | D |
| 30-11a | B | C | B | C | B | A | C | D |
| 115-4 | B | C | A | A | A | A | C | D |
| 115-5 | A | B | A | B | A | A | B | D |
| 115-6 | B | B | A | A | A | A | C | D |
| 115-7 | A | B | A | B | A | A | B | D |
| 115-8 | A | B | A | A | A | A | B | D |
| 96-1 | A | A | A | B | A | A | B | D |
| 110-3 | A | B | A | A | A | A | B | D |
| 110-6 | A | B | A | B | A | A | B | D |
| 111-3 | A | B | A | B | A | A | B | D |
| 110-7 | A | B | A | B | A | A | A | D |
| 111-2 | B | B | A | B | A | A | B | C |
| 111-4 | A | C | A | B | A | A | C | D |
| 110-4 | A | B | A | B | A | A | C | C |
| 110-2 | A | B | A | B | A | A | B | D |
| 118-10 | A | B | A | C | B | A | B | D |
| 96-4 | A | B | A | B | A | A | B | D |
| 132-4 | A | B | A | B | A | A | B | C |
| 113-2 | A | B | A | A | A | A | B | D |
| 113-1 | A | B | A | B | A | A | C | D |
| 113-3 | A | B | A | B | A | A | B | D |
| 113-4 | A | B | A | B | A | A | B | D |
| 110-5 | A | B | A | B | A | A | B | D |
| 112-1 | A | C | A | A | A | A | B | D |
| 112-2 | B | C | A | B | A | A | D | D |
| 112-3 | A | C | A | B | A | A | C | C |
| 110-8 | A | C | A | B | A | A | C | D |
| 110-9 | A | B | A | B | A | A | B | D |
| 110-10 | A | B | A | B | A | A | C | C |
| 110-11 | A | B | A | C | A | A | C | C |
| 110-12 | A | A | A | B | A | A | A | C |

TABLE 1-continued

| Compound # | AECO001 | AECO001 HSA AGP | AECO063 | APAE001 | APAE006 | APAE006 + PMBN | AABA1060 | ASAU001 |
|---|---|---|---|---|---|---|---|---|
| 112-4 | A | B | A | A | A | A | A | C |
| 112-5 | A | B | A | A | A | A | A | C |
| 127-1 | C | C | B | D | C | C | D | D |
| 97-1 | A | A | A | B | A | A | B | C |
| 97-2 | A | A | A | A | A | A | A | C |
| 98-1 | A | A | A | A | A | A | C | C |
| 116-1 | C | C | C | B | A | A | C | C |
| 117-1 | D | D | D | D | D | D | D | D |
| 117-2 | D | D | D | D | D | C | D | D |
| 118-1 | C | C | B | B | A | A | C | C |
| 118-2 | A | C | A | A | A | A | B | C |
| 118-3 | A | B | A | B | A | A | B | C |
| 128-1 | C | C | C | C | C | C | C | C |
| 113-11 | A | C | A | B | A | A | C | D |
| 96-2 | A | B | A | B | A | A | B | C |
| 96-3 | A | B | A | B | A | A | B | C |
| 98-3 | A | A | A | B | A | A | C | D |
| 98-2 | A | B | A | B | A | A | C | C |
| 99-1 | A | B | A | B | A | A | C | C |
| 100-1 | A | B | A | B | A | A | C | C |
| 119-1 | A | B | A | A | A | A | B | C |
| 119-2 | B | C | B | A | A | A | D | D |
| 119-3 | B | B | A | B | A | A | C | D |
| 131-1 | C | D | C | B | A | A | D | D |
| 131-2 | B | C | A | A | A | A | C | D |
| 131-3 | C | C | C | B | A | A | C | C |
| 82-2 | A | C | A | A | A | A | C | C |
| 82-3 | A | C | A | A | A | A | B | C |
| 86-2 | A | A | A | B | A | A | B | C |
| 82-4 | A | B | A | B | A | A | B | B |
| 101-2 | A | C | A | B | A | A | C | C |
| 102-3 | A | B | A | A | A | A | C | C |
| 101-3 | A | B | A | A | A | A | B | C |
| 101-1 | A | B | A | B | A | A | C | C |
| 101-4 | A | B | A | B | A | A | C | C |
| 102-2 | A | B | A | B | A | A | B | C |
| 102-1 | A | B | A | B | A | A | C | C |
| 102-4 | A | B | A | B | A | A | C | D |
| 133-7 | A | B | A | A | A | A | A | B |
| 133-8 | C | C | B | B | A | A | C | D |
| 133-9 | C | C | B | B | A | A | C | D |
| 86-3 | A | A | A | A | A | A | B | C |
| 82-5 | A | B | A | A | A | A | B | B |
| 82-6 | A | B | A | B | B | A | C | C |
| 113-9 | A | B | A | A | A | A | A | C |
| 113-10 | A | B | A | B | A | A | B | C |
| 103-1 | A | B | A | B | A | A | D | D |
| 137-1 | A | B | A | B | A | A | D | D |
| 137-2 | A | B | A | B | A | A | C | D |
| 137-3 | A | B | A | B | A | A | C | C |
| 120-3 | A | B | A | A | A | A | B | D |
| 113-8 | A | B | A | B | A | A | A | C |
| 104-2 | A | B | A | B | A | A | C | C |
| 104-1 | A | B | A | B | A | A | B | C |
| 104-3 | A | B | A | A | A | A | A | C |
| 104-4 | A | B | A | A | A | A | B | C |
| 113-7 | A | B | A | B | A | A | B | D |
| 113-5 | A | A | A | A | A | A | A | C |
| 101-5 | A | B | A | A | A | A | A | C |
| 137-4 | D | D | C | D | C | C | D | D |
| 82-7 | A | B | A | A | A | A | A | B |
| 82-8 | A | B | A | C | A | A | D | D |
| 82-9 | A | B | A | B | A | A | B | B |
| 82-10 | A | B | A | B | A | A | B | B |
| 82-11 | B | B | A | C | B | A | C | C |
| 88-3 | A | B | A | A | A | A | B | D |
| 88-4 | B | C | A | A | A | A | C | D |
| 91-2 | A | B | A | A | A | A | A | B |
| 82-12 | A | B | A | B | A | A | B | C |
| 102-5 | A | A | A | A | A | A | B | D |
| 88-2 | A | B | A | A | A | A | B | B |
| 133-2 | A | C | A | A | A | A | C | D |
| 109-1 | A | B | A | B | A | A | B | D |
| 137-5 | A | B | A | A | A | A | B | C |
| 129-1 | A | B | A | A | A | A | B | D |
| 137-6 | A | B | A | A | A | A | B | C |

TABLE 1-continued

| Compound # | AECO001 | AECO001 HSA AGP | AECO063 | APAE001 | APAE006 | APAE006 + PMBN | AABA1060 | ASAU001 |
|---|---|---|---|---|---|---|---|---|
| 137-7 | A | B | A | A | A | A | B | C |
| 120-1 | A | B | A | A | A | A | B | C |
| 82-13 | A | A | A | A | A | A | A | C |
| 133-4 | B | C | A | A | A | A | D | D |
| 136-1 | B | C | A | B | A | A | C | C |
| 137-8 | B | C | A | B | A | A | C | C |
| 137-9 | A | B | A | B | A | A | B | C |
| 118-4 | A | B | A | A | A | A | C | D |
| 118-5 | B | B | A | A | A | A | C | D |
| 118-6 | B | B | A | A | A | A | C | C |
| 118-7 | A | B | A | A | A | A | B | C |
| 85-2 | A | B | A | B | A | A | C | C |
| 85-1 | A | B | A | B | A | A | C | C |
| 87-2 | A | A | A | A | A | A | C | C |
| 87-3 | A | A | A | A | A | A | A | C |
| 133-3 | A | B | A | A | A | A | C | D |
| 133-1 | A | B | A | A | A | A | A | C |
| 133-10 | B | B | A | C | A | A | C | C |
| 133-11 | A | C | A | C | B | A | C | C |
| 118-8 | A | B | A | A | A | A | B | C |
| 88-1 | A | B | A | B | A | A | C | C |
| 133-5 | A | B | A | C | A | A | A | C |
| 114-2 | A | B | A | B | A | A | B | C |
| 105-1 | A | B | A | B | A | A | C | C |
| 105-3 | C | C | B | C | B | A | C | C |
| 109-2 | A | B | A | B | A | A | B | C |
| 133-12 | A | B | A | A | A | A | C | C |
| 118-9 | A | B | A | A | A | A | B | C |
| 119-6 | B | B | A | A | A | A | C | C |
| 114-3 | A | B | A | A | A | A | A | C |
| 114-4 | A | B | A | B | A | A | B | B |
| 114-5 | A | B | A | B | A | A | A | B |
| 114-6 | A | B | A | B | B | A | B | B |
| 114-7 | B | B | A | B | B | A | B | B |
| 114-8 | A | B | A | A | A | A | B | C |
| 114-9 | B | B | A | A | A | A | B | C |
| 114-1 | A | B | A | A | A | A | A | B |
| 88-9 | A | B | A | B | A | A | C | C |
| 88-10 | A | B | A | B | A | A | B | C |
| 114-10 | A | B | A | B | A | A | B | C |
| 137-26 | C | C | B | C | B | A | C | C |
| 137-27 | C | C | B | C | A | A | C | C |
| 82-14 | A | C | A | A | A | A | A | C |
| 82-15 | A | C | A | A | A | A | A | C |
| 88-5 | A | A | A | B | A | N/A | A | C |
| 137-12 | B | C | B | B | A | A | C | C |
| 91-3 | A | B | A | A | A | A | B | B |
| 91-4 | A | B | A | B | A | A | B | B |
| 120-2 | B | C | A | B | A | A | C | C |
| 82-16 | A | B | A | A | A | A | A | C |
| 105-2 | A | A | A | B | A | A | C | C |
| 105-4 | A | B | A | C | B | A | C | C |
| 105-5 | B | B | A | C | B | A | C | C |
| 91-5 | A | A | A | A | A | A | B | C |
| 82-17 | A | A | A | A | A | A | A | B |
| 119-4 | A | A | A | A | A | A | B | C |
| 119-5 | A | A | A | A | A | A | A | C |
| 133-13 | C | C | B | C | A | A | C | C |
| 133-15 | B | B | A | B | A | A | B | C |
| 133-14 | A | A | A | B | A | A | A | C |
| 137-13 | C | C | B | C | A | A | C | C |
| 91-30 | C | C | B | A | A | A | C | C |
| 130-1 | B | C | A | A | A | A | B | C |
| 82-18 | A | B | A | B | A | A | C | C |
| 82-19 | A | B | A | B | A | A | A | C |
| 91-6 | A | A | A | A | A | A | A | C |
| 114-11 | A | C | A | C | A | A | B | C |
| 137-14 | A | C | A | B | A | A | B | C |
| 114-12 | A | B | A | B | A | A | A | C |
| 114-13 | A | B | A | B | A | A | B | C |
| 114-14 | A | B | A | B | A | A | A | C |
| 82-20 | A | B | A | B | A | A | B | C |
| 82-21 | A | B | A | B | A | A | A | C |
| 132-1 | A | B | A | B | A | A | B | C |
| 132-3 | A | B | A | C | A | A | B | C |
| 88-12 | A | B | A | A | A | A | A | B |

TABLE 1-continued

| Compound # | AECO001 | AECO001 HSA AGP | AECO063 | APAE001 | APAE006 | APAE006 + PMBN | AABA1060 | ASAU001 |
|---|---|---|---|---|---|---|---|---|
| 92-2 | C | C | B | C | B | B | C | C |
| 91-17 | A | B | A | A | A | A | B | C |
| 82-22 | A | C | A | C | C | A | C | C |
| 91-10 | A | A | A | A | A | A | A | C |
| 87-1 | A | B | A | A | A | A | A | C |
| 88-6 | A | B | A | B | A | A | B | C |
| 104-5 | A | A | A | B | A | A | A | B |
| 126-2 | A | A | A | B | A | A | A | C |
| 121-1 | A | A | A | A | A | A | B | C |
| 121-2 | B | C | B | C | A | A | C | C |
| 101-6 | A | C | A | A | A | A | B | C |
| 92-1 | B | C | B | B | A | A | C | C |
| 122-1 | B | B | A | B | A | A | C | C |
| 123-1 | A | B | A | B | A | A | B | C |
| 137-16 | A | B | A | B | A | A | B | C |
| 106-6 | A | C | A | B | A | A | B | C |
| 106-7 | A | B | A | B | A | A | B | C |
| 137-17 | C | C | C | C | B | A | C | C |
| 137-18 | C | C | C | C | B | B | C | C |
| 137-19 | A | B | A | B | A | A | C | C |
| 124-1 | A | B | A | B | A | A | C | C |
| 91-11 | A | C | A | B | A | A | C | C |
| 88-7 | A | B | A | B | A | A | B | C |
| 91-12 | A | A | A | A | A | A | A | B |
| 124-2 | A | B | A | B | A | A | B | C |
| 124-3 | A | B | A | B | A | A | B | C |
| 132-5 | C | C | N/A | C | A | N/A | C | C |
| 132-2 | A | B | A | B | A | A | C | C |
| 132-6 | B | C | A | C | A | A | C | C |
| 106-4 | B | C | A | B | A | A | C | C |
| 91-13 | A | B | A | A | A | A | B | B |
| 82-23 | A | C | A | C | A | A | C | C |
| 114-15 | B | C | A | A | A | A | B | C |
| 86-4 | A | B | A | B | A | A | B | C |
| 82-24 | A | B | A | B | A | A | A | B |
| 107-2 | A | B | A | A | A | A | A | B |
| 106-1 | A | B | A | C | A | A | C | C |
| 107-3 | A | B | A | A | A | A | B | C |
| 106-5 | A | B | A | B | A | A | B | C |
| 107-1 | A | B | A | A | A | A | B | C |
| 106-3 | A | C | A | A | A | A | C | C |
| 137-20 | C | C | C | C | B | A | B | C |
| 133-6 | A | A | A | A | A | A | A | B |
| 91-14 | A | B | A | A | A | A | A | B |
| 82-25 | A | A | A | A | A | A | A | C |
| 82-26 | A | C | A | B | B | A | B | B |
| 91-1 | A | A | A | A | A | A | A | B |
| 106-2 | A | B | A | B | A | A | B | C |
| 91-7 | A | B | A | A | A | A | B | B |
| 91-8 | A | B | A | A | A | A | B | B |
| 89-1 | A | B | A | A | A | A | B | C |
| 93-1 | A | C | A | A | A | A | A | C |
| 137-21 | C | C | C | B | A | A | B | C |
| 114-16 | A | A | A | B | A | A | A | C |
| 107-4 | A | A | A | A | A | A | A | B |
| 122-5 | A | A | A | A | A | A | A | C |
| 88-8 | A | A | A | A | A | A | B | C |
| 122-6 | A | A | A | A | A | A | B | C |
| 91-15 | A | B | A | A | A | A | A | B |
| 125-1 | A | B | A | B | A | A | A | C |
| 86-1 | A | B | A | A | A | A | B | C |
| 137-22 | C | C | C | B | B | B | C | C |
| 137-23 | C | C | C | B | A | B | C | C |
| 137-24 | A | B | A | B | A | A | B | C |
| 94-1 | A | B | A | A | A | A | B | C |
| 82-1 | A | B | A | B | A | A | B | C |
| 84-1 | A | B | A | C | B | A | C | C |
| 86-5 | A | C | A | A | A | A | B | C |
| 114-17 | A | B | A | B | A | A | B | B |

TABLE 1-continued

| Compound # | AECO001 | AECO001 HSA AGP | AECO063 | APAE001 | APAE006 | APAE006 + PMBN | AABA1060 | ASAU001 |
|---|---|---|---|---|---|---|---|---|
| 91-9 | A | A | A | A | A | A | A | B |
| 137-25 | C | C | B | C | A | A | C | C |
| 107-5 | A | B | A | B | A | A | A | B |
| 88-13 | A | A | A | A | A | A | A | B |
| 88-15 | A | A | A | A | A | A | A | B |
| 83-2 | A | C | A | A | A | A | B | C |
| 91-16 | A | A | A | A | A | A | A | B |
| 83-1 | A | B | A | A | A | A | A | C |
| 88-11 | A | A | A | A | A | N/A | A | C |
| 88-14 | A | B | A | A | A | A | A | C |
| 107-6 | A | B | A | B | A | A | A | C |
| 134-1 | B | B | A | B | A | A | A | C |
| 134-2 | B | C | B | B | A | A | B | C |
| 122-8 | A | A | A | A | A | A | B | C |
| 126-1 | A | A | A | A | A | A | A | C |
| 82-27 | A | B | A | B | A | A | B | C |
| 89-2 | A | B | A | A | A | A | A | C |
| 114-18 | A | B | A | A | A | A | A | C |
| 122-2 | A | B | A | A | A | A | B | C |
| 122-3 | A | A | A | A | A | A | A | C |
| 122-4 | A | B | A | A | A | A | A | C |
| 102-6 | A | B | A | A | A | A | B | C |
| 89-3 | A | A | A | A | A | A | B | C |
| 91-21 | A | B | A | B | A | A | B | B |
| 91-22 | A | B | A | B | A | A | B | B |
| 91-23 | A | B | A | B | A | A | B | B |
| 138-10 | A | B | A | B | A | A | B | B |
| 87-4 | A | B | A | A | A | A | A | C |
| 88-16 | A | B | A | A | A | A | A | C |
| 89-4 | C | C | B | B | A | A | C | C |
| 89-5 | B | B | A | A | A | A | B | C |
| 82-28 | A | B | A | B | A | A | A | B |
| 113-6 | A | A | A | A | A | A | A | C |
| 91-18 | A | A | A | B | B | A | B | C |
| 91-19 | A | A | A | B | A | A | B | C |
| 91-20 | A | B | A | B | B | A | B | C |
| 89-6 | B | B | A | A | A | A | B | C |
| 89-7 | B | B | A | B | A | A | C | C |
| 114-19 | A | B | A | A | A | A | A | B |
| 114-20 | A | B | A | B | A | A | A | B |
| 82-29 | A | A | N/A | A | A | N/A | A | B |
| 86-6 | A | B | A | B | A | A | B | C |
| 86-7 | A | B | A | B | A | A | A | C |
| 91-24 | A | B | A | A | A | N/A | B | B |
| 91-25 | C | C | C | C | B | B | C | C |
| 91-26 | A | A | A | A | A | N/A | A | C |
| 91-27 | A | B | A | A | A | N/A | B | C |
| 91-28 | A | B | A | B | A | A | B | B |
| 88-17 | A | C | A | A | A | A | B | C |
| 115-1 | A | B | A | B | A | A | B | D |
| 137-11 | D | D | C | C | B | B | D | D |
| 137-10 | D | D | D | D | C | C | D | D |

MIC Key
MIC's of 2.0 μg/mL or less = A
MIC's of greater than 2.0 μg/mL to 16.0 μg/mL = B
MIC's of greater than 16.0 μg/mL to 64.0 μg/mL = C
MIC's of greater than 64.0 μg/mL = D

*AECO001 is ATCC25922, AECO063 is ATCC25922 bearing an acrAB mutation, APAE001 is ATCC27853, APAE006 is a strain of *P. aeruginosa* in which all efflux pumps are inactivated, APAE006+PMBN indicates MICs with the indicated strain in the presence of 8 micrograms per milliliter of polymyxin B nonapeptide, AABA1060 is a clinical isolate of *Acinetobacter baumannii*, ASAU001 is a laboratory strain of *S. aureus* (ATCC29213).

As shown in the following Table 2, the MICs on AECO001 for fourteen pairs of compounds were compared (n=2 data). For each pair of compounds, the compounds were identical in structure except for the A moiety. More specifically, A is —C(CH$_3$)$_2$NH$_2$ in one compound and A is —CHCH$_3$NH$_2$ in the other compound. As shown, for each pair of compounds, the compound wherein A is —C(CH$_3$)$_2$NH$_2$ was more potent.

TABLE 2

| Compound # (A = —CHCH$_3$NH$_2$) | Compound # (A = —C(CH$_3$)$_2$NH$_2$) | Ratio of MICs on AECO001 [Cpd (A = —CHCH$_3$NH$_2$)/ Cpd (A = —C(CH$_3$)$_2$NH$_2$)] |
|---|---|---|
| 91-2 | 91-12 | 5.6 |
| 91-3 | 91-14 | 3.3 |

TABLE 2-continued

| Compound # (A = —CHCH$_3$NH$_2$) | Compound # (A = —C(CH$_3$)$_2$NH$_2$) | Ratio of MICs on AECO001 [Cpd (A = —CHCH$_3$NH$_2$)/ Cpd (A = —C(CH$_3$)$_2$NH$_2$)] |
|---|---|---|
| 82-16 | 82-25 | 1.6 |
| 91-7 | 91-1 | 7.2 |
| 88-3 | 88-8 | 5.1 |
| 91-13 | 91-15 | 6.5 |
| 91-8 | 91-9 | 5.2 |
| 88-12 | 88-13 | 4.1 |
| 91-17 | 91-16 | 2.6 |
| 89-1 | 89-2 | 1.6 |
| 115-2 | 121-1 | 4.0 |
| 133-7 | 133-6 | 20.8 |
| 118-7 | 122-5 | 2.4 |
| 118-9 | 122-6 | 2.1 |

As shown in the following Table 3, three pairs of compounds were tested in the neutropenic thigh efficacy model. For each pair of compounds, the compounds were identical in structure except for the A moiety. More specifically, A is —C(CH$_3$)$_2$NH$_2$ in one compound and A is —C(CH$_3$)$_2$OH in the other compound. A ratio of >1 indicates that the compound wherein A is —C(CH$_3$)$_2$NH$_2$ had a lower static dose and is therefore a more potent compound in vivo. For all three pairs of compounds, the compound wherein A is —C(CH$_3$)$_2$NH$_2$ had superior in vivo efficacy to that of the compound wherein A is —C(CH$_3$)$_2$OH. In addition, the ratios of the MICs of each pair of compounds on the infecting strain (ATCC43816) was calculated. A ratio of >1 indicates that the compound wherein A is —C(CH$_3$)$_2$NH$_2$ had a lower MIC and was therefore more potent on this strain. When the ratio of neutropenic thigh potencies was normalized to reflect the differences in MICs, it was found that the compounds wherein A is —C(CH$_3$)$_2$NH$_2$ still have superior activity relative to the compounds wherein A is —C(CH$_3$)$_2$OH, demonstrating that the functional group —C(CH$_3$)$_2$NH$_2$ confers advantageous properties for in vivo antibacterial activity that is not readily predictable from the MICs.

TABLE 3

| Compound # (A = —C(CH$_3$)$_2$NH$_2$) | Compound # (A = —C(CH$_3$)$_2$OH) | Ratio of thigh static doses | Ratio of MICs on ATCC43816 [Cpd (A = —CH(CH$_3$)$_2$OH/Cpd (A = —C(CH$_3$)$_2$NH$_2$)] | Ratio of thigh static dose normalized to MICs |
|---|---|---|---|---|
| 88-13 | 88-11 | >7x | 1.6 | >4.4x |
| 91-12 | 91-6 | >3x | 1.0 | >3x |
| 122-5 | 122-8 | >2x | 0.5 | >4x |

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Furthermore, while particular embodiments of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

What is claimed is:

1. A compound having the following formula (I):

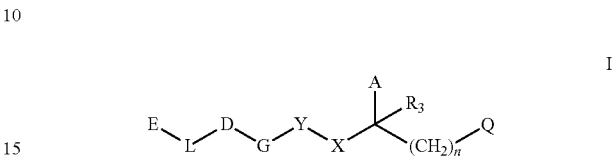

or a stereoisomer, pharmaceutically acceptable salt, ester, or prodrug thereof, wherein:

E is selected from the group consisting of:
(1) $C_1$-$C_6$-alkyl optionally substituted with $C_1$-$C_6$-alkoxy, halogen, —O—$C_3$-$C_6$-alkyl, $C_3$-$C_6$-alkyl, or 5- or 6-membered heterocyclyl,
(2) $C_3$-$C_6$-cycloalkyl,
(3) 3- to 6-membered heterocyclyl optionally substituted with C(O)H, and
(4) 5- or 6-membered heteroaryl optionally substituted with $C_1$-$C_6$-alkyl or NH$_2$;

L is absent;

D is absent;

G is selected from the group consisting of:
(1) —C≡C—,
(2) —C≡C—C≡C—,
(3) —CR$^{3G}$=CR$^{3G}$—C≡C—,
(4) —C≡C—CR$^{3G}$=CR$^{3G}$—,
wherein:
each R$^{3G}$ is independently selected from the group consisting of H, a halogen atom, and substituted or unsubstituted $C_1$-$C_6$-alkyl;

Y is unsubstituted phenyl

X is —(C=O)NR$_4$—;

R$_3$ is H;

R$_4$ is H;

n is 0;

A is selected from the group consisting of:
(1) —C(CH$_3$)$_2$NH$_2$; and
(2) —CH(CH$_3$)NH$_2$;
and Q is (C=O)NHOH.

2. The compound of claim 1, wherein G is selected from the group consisting of:
(1) —C≡C—,
(2) —C≡C—C≡C—,
(3) —CH=CH—C≡C—, and
(4) —C≡C—CH=CH—.

3. The compound of claim 2, wherein G is —C≡C—.

4. The compound of claim 2, wherein G is —C≡C—C≡C—.

5. The compound of claim 2, wherein G is —CH=CH—C≡C—.

6. The compound of claim 2, wherein G is —C≡C—CH=CH—.

7. A pharmaceutical composition comprising a compound of claim 1 and a pharmaceutically acceptable carrier or diluent.

\* \* \* \* \*